(12) United States Patent
Axten et al.

(10) Patent No.: US 8,697,685 B2
(45) Date of Patent: Apr. 15, 2014

(54) CHEMICAL COMPOUNDS

(75) Inventors: Jeffrey Michael Axten, Collegeville, PA (US); Charles William Blackledge, Jr., Collegeville, PA (US); Gerald Patrick Brady, Jr., Collegeville, PA (US); Yanhong Feng, Collegeville, PA (US); Seth W. Grant, Collegeville, PA (US); Jesus Raul Medina, Collegeville, PA (US); William H. Miller, Collegeville, PA (US); Stuart P. Romeril, Collegeville, PA (US)

(73) Assignee: GlaxoSmithKline LLC, Wilmington, DE (US)

( * ) Notice: Subject to any disclaimer, the term of this patent is extended or adjusted under 35 U.S.C. 154(b) by 246 days.

(21) Appl. No.: 13/130,368

(22) PCT Filed: Nov. 18, 2009

(86) PCT No.: PCT/US2009/064891
§ 371 (c)(1),
(2), (4) Date: Jul. 27, 2011

(87) PCT Pub. No.: WO2010/059658
PCT Pub. Date: May 27, 2010

(65) Prior Publication Data
US 2011/0275611 A1 Nov. 10, 2011

Related U.S. Application Data

(60) Provisional application No. 61/116,508, filed on Nov. 20, 2008.

(51) Int. Cl.

| | | |
|---|---|---|
| A61K 31/33 | (2006.01) |
| A61K 31/54 | (2006.01) |
| A61K 31/505 | (2006.01) |
| A61K 31/55 | (2006.01) |
| C07D 401/08 | (2006.01) |
| C07D 417/02 | (2006.01) |
| C07D 413/06 | (2006.01) |
| C07D 239/02 | (2006.01) |

(52) U.S. Cl.
USPC ............. 514/210.21; 514/217; 514/228.2; 514/234.5; 514/272; 514/275; 540/599; 544/62; 544/122; 544/321; 544/324; 544/331

(58) Field of Classification Search
USPC ............ 514/210.21, 228.2, 272, 275, 234.5, 514/217.06; 540/599; 544/62, 321, 324, 544/331, 122
See application file for complete search history.

(56) References Cited

U.S. PATENT DOCUMENTS

| | | |
|---|---|---|
| 2006/0142345 A1 | 6/2006 | Kephart et al. |
| 2008/0081809 A1 | 4/2008 | Duggan et al. |
| 2008/0132501 A1 | 6/2008 | Sun et al. |

FOREIGN PATENT DOCUMENTS

| | | | |
|---|---|---|---|
| ES | 2385276 | * | 7/2012 |
| WO | WO 03/097610 A1 | | 11/2003 |
| WO | WO 2005/073219 A1 | | 8/2005 |
| WO | WO 2005/123688 A2 | | 12/2005 |
| WO | WO 2006/044732 A2 | | 4/2006 |

OTHER PUBLICATIONS

Nykanen, et al., "VEGFR-3 Signalling Mediates Lymphangiogenesis and Alloimune Reactions in Cardiac Allografts," *The Journal of Heart and Lung Transplantation*, vol. 25 (2, Supplement 1): S159; p. S159, left col. (2006).

Valtola, et al., "VEGFR-3 and its Ligand VEGF-C Are Associated with Angiogenesis in Breast Cancer," *American Journal of Pathology*, vol. 154, No. 5, pp. 1381-90, Abstract (1999).

Peifer, et al., "Small-Molecule Inhibitors of PDK1" *ChemMedChem*, vol. 3, No. 12, pp. 1810-1838 (2008).

* cited by examiner

*Primary Examiner* — James O Wilson
*Assistant Examiner* — Ebenezer O Sackey
(74) *Attorney, Agent, or Firm* — Andrea V. Lockenour; Edward R. Gimmi; Carl W. Battle

(57) ABSTRACT

The invention is directed to 6-(4-pyrimidinyl)-1H-indazole derivatives. Specifically, the invention is directed to compounds according to Formula (I) wherein $R^1$-$R^4$ are defined herein. The compounds of the invention axe inhibitors of PDK1 and can be useful in the treatment of immune and metabolic diseases and disorders characterized by constitutively activated ACG kinases such as cancer and more specifically cancers of the breast, colon, and lung. Accordingly, the invention is further directed to pharmaceutical compositions comprising a compound of the invention. The invention is still further directed to methods of inhibiting PDK1 activity and treatment of disorders associated therewith using a compound of the invention or a pharmaceutical composition comprising a compound of the invention.

8 Claims, No Drawings

CHEMICAL COMPOUNDS

This application is a 371 of International Application No. PCT/US2009/064891, filed 18 Nov. 2009, which is incorporated herein by reference. This application also claims the benefit of U.S. Provisional Application No. 61/116,508, filed 20 Nov. 2008.

FIELD OF THE INVENTION

The present invention relates to 6-(4-pyrimidinyl)-1H-indazole derivatives that are inhibitors of the activity of the serine/threonine kinase, PDK1. The present invention also relates to pharmaceutical compositions comprising such compounds and methods of using such compounds in the treatment of cancer, metabolic and immune diseases.

BACKGROUND OF THE INVENTION

The phosphoinositide-3 kinase (PI3K) pathway regulates critical cellular functions such as cell cycle progression, growth, survival, and differentiation as well as the metabolic actions of insulin (Hennessy et al. *Nature Rev. Drug Dis.* 4:988-1004 (2005)). Modulation of the activity of kinases downstream of PI3K is mediated by 3-phosphoinositide dependent kinase 1 (PDK1), a 63-kD serine/threonine kinase that is ubiquitously expressed in human tissues (Storz and Toker, *Front. Biosci.* 7:886-902 (2002). PDK1 contains an amino-terminal kinase domain, a linker region and a pleckstrin-homology (PH) domain at the carboxyl-terminus. The PH domain binds to the lipid products of PI3K (phosphatidylinositol 3,4,5-triphosphate, PIP3) with high affinity, and facilitates co-localization of the kinase with its PH-domain-containing substrates. Substrates of PDK1 include many of the AGC family of protein kinases (the cAMP-dependent, cGMP-dependent, and protein kinase C), including AKT/PKB, p70S6K, cyclic AMP-dependent protein kinase (PKA), protein kinase C (PKC), serum and glucocorticoid-inducible kinase (SGK), p90 ribosomal protein kinase (RSK), p21-activated kinase-1 (PAK1), PRK1/2, and others (Wick and Liu, *Curr. Drug Targets Immune Endocr. Metabol. Disord.* 1:209-221 (2001); Mora et al., *Semin. Cell Dev. Biol.* 15:161-170 (2004)). Recent in vivo studies with PDK1(−/−) and PDK1(−/+) mice showed that AKT, p70S6K, RSK and protein kinase C are key mediators of PDK1 function, regulating diverse cellular functions (Lawlor et al *EMBO J.* 21:3728-3738 (2002); Williams et al., *Curr. Biol.* 10:439-448 (2000); Storz and Toker, *Front. Biosci.* 7:886-902 (2002)). Activation of these substrates by PDK1 leads to an increase in glucose uptake, protein synthesis, and inhibition of pro-apoptotic proteins.

Dysregulation of the PI-3 kinase pathway is seen in a variety of cancers. A significant number of cancers possess mutations in genes that result in elevation of cellular levels of PIP3. Increased levels of PIP3 leads to activation of AKT and p70S6K kinases, which promote the proliferation and enhanced survival of these tumor cells. For example, genetic alterations of the PI3K gene including amplifications and activating mutations have been observed in various cancers (Hennessey et al., *Nature Rev. Cancer* 4, 988-1004 (2005)). One of the most common mutations giving rise to elevated levels of PIP3 is in the PIP3 3-phosphatase PTEN gene (Leslie and Downes, *Cell Signal.* 14:285-295 (2002); Cantley, *Science* 296:1655-1657 (2002)). Germline mutations of PTEN are responsible for human cancer syndromes such as Cowden disease (Liaw et al., *Nature Genetics* 16:64-67 (1997)). PTEN is deleted in a large percentage of human tumors and tumor cell lines without functional PTEN show elevated levels of activated AKT (Li et al. supra, Guldberg et al., *Cancer Research* 57:3660-3663 (1997), Risinger et al., *Cancer Research* 57:4736-4738 (1997)).

AKT/PKB (consisting of 3 family members, AKT1, AKT2, AKT3) is a substrate for PDK1 and is an important mediator of the physiological effects of insulin and several growth factors including EGF, PDGF, and IGF-1 (Manning and Cantley, *Cell* 129:1261-1274 (2007)). AKT is activated by phosphorylation events occurring in response to PI3K signaling. PI3K phosphorylates membrane inositol phospholipids, generating the second messengers PIP3 and phosphatidylinositol 3,4-diphosphate, which have been shown to bind to the PH domain of AKT. The current model of AKT activation proposes recruitment of the enzyme to the membrane by PIP3 through the PH domain of PDK1. Co-localization of AKT and PDK1 at the membrane allows for AKT modification and activation by PDK1 and possibly other kinases (Hemmings, *Science* 275:628-630 (1997); Hemmings, *Science* 276:534 (1997); Downward, *Science* 279:673-674 (1998)). Phosphorylation of AKT1 occurs on two regulatory sites, Thr308 by PDK1 in the catalytic domain activation loop and Ser473 (most probably by TORC2 mTOR complex) near the carboxy terminus (Alessi et al., *EMBO J.* 15:6541-6551 (1996); Meier et al., *J. Biol. Chem.* 272:30491-30497 (1997)). Analysis of AKT levels in human tumors revealed that AKT is overexpressed in a significant number of ovarian (Cheung et al., *Proc. Natl. Acad. Sci. U.S.A.* 89:9267-9271 (1992)) and pancreatic cancers (Cheung et al., *Proc. Natl. Acad. Sci. U.S.A.* 93:3636-3641 (1996)). AKT was also found to be overexpressed in breast and prostate cancer cell lines (Nakatani et al. *J. Biol. Chem.* 274:21528-21532 (1999)). More recently, a transforming mutation in the PH domain of AKT1 was detected in human breast, colorectal and ovarian cancers (Carpten et al., *Nature* 448:439-444 (2007)). Specific inhibitors of PI3K or dominant negative AKT mutants abolish survival-promoting activities of growth factors or cytokines. It has been previously described that inhibitors of PI3K (LY294002 or wortmannin) blocked the activation of AKT. In addition, introduction of constitutively active PI3K or AKT mutants promotes cell survival under conditions in which cells normally undergo apoptotic cell death (Kulik et al., *Mol. Cell Biol.* 17(3):1595-1606 (1997); Dudek et al, *Science* 275 (5300):661-665 (1997)).

PDK1 modulates affects the activity of a variety of substrates besides AKT. These substrates lack the PH domain seen in AKT and are therefore not dependent on co-localization with PDK1 on cell membranes. Important PH-domain-independent substrates of PDK1 are PKC, RSK and p70 S6K. RSKs have been recently implicated in promoting FGFR3-mediated hematopoetic transformation (Kang et al., *Cancer Cell* 12:201-214 (2007)). PDK1 activates RSK by phosphorylating its amino terminal kinase domain in an ERK-dependent manner (Cohen et al., *Nature Chem. Biol.* 3(3):156-160 (2007)). Also, recent studies revealed additional roles of PDK1 that could be important during tumorigenesis and metastasis, such as cell motility and migration (Primo et al., *J. Cell Biol.* 176(7):1035-1047 (2007); Pinner and Sahai, *Nature Cell Biol.* 10(2):127-137 (2008)).

Taken together, these observations suggest a beneficial role for an inhibitor of PDK1 in the treatment of cancer cells. Consistent with this, a hypomorphic mutation of PDK1 suppresses tumorigenesis in PTEN+/− mice (Bayascas et al., *Curr. Biol.* 15, 1839-1846 (2005)). Furthermore, antisense-based reduction of PDK1 levels in tumor cells leads to decreased tumor cell proliferation and increased apoptosis (Flynn et al. *Curr. Biol.* 10: 1439-1442 (2000)), and small molecule kinase inhibitors of PDK1 inhibit the growth of tumors cells in vitro and in vivo (Feldman et al., *J. Biol. Chem.* 280: 19867-19874 (2005); Gopalsamy et al. (*J. Med. Chem.* 50, 5547-5549 (2007); Tamguney et al. *Exp. Cell Res.* 314: 2299-2312 (2008)). Finally, since knockdown of PDK1 by siRNA was shown to sensitise breast cancer cells to tamoxifen (Irons et al., *Biochem. J.* 417:361-370 (2009)), inhibition of PDK1 may have a therapeutic benefit in combination with other anticancer treatments.

PDK1 is reported to be a mediator of T-cell activation through NF-kB activation (Lee et al. *Science* 308: 114-118 (2005)) and also a regulator of T-cell development (Hinton et. al. *Nat. Immunol.* 5(5), 539-545 (2004)). Literature data also suggests that a PDK1 inhibitor may be useful for the treatment of autoimmune disease and transplant rejection (e.g. Park et al. *Nat. Immunol.* 10(2), 158-666 (2009)).

Given the close association of PDK1 with the AKT and PI3K pathways, and inhibitor of PDK1 may have beneficial use in treating diseases related to metabolism and aging, for example through the downstream inhibition of S6K1 signaling (Selman et al. Science 326: 140-144 (2009)).

It is an object of the instant invention to provide novel compounds that are inhibitors of PDK1.

It is also an object of the present invention to provide pharmaceutical compositions that comprise a pharmaceutical carrier and compounds useful in the methods of the invention.

It is also an object of the present invention to provide a method for treating cancer, immune and metabolic diseases that comprises administering such inhibitors of PDK1 activity.

SUMMARY OF THE INVENTION

The invention is directed to 6-(4-pyrimidinyl)-1H-indazole derivatives. Specifically, the invention is directed to compounds according to Formula I:

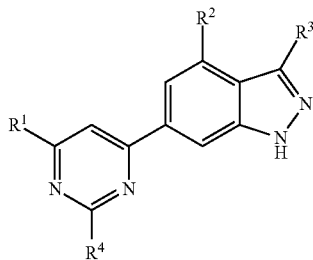

(I)

wherein $R^1$-$R^4$ are defined below.

The compounds of the invention are inhibitors of PDK1 and can be useful in the treatment of disorders characterized by constitutively activated ACG kinases such as metabolic, immune diseases and cancer, and suitably cancers of the breast, colon, and lung. Accordingly, the invention is further directed to pharmaceutical compositions comprising a compound of the invention. The invention is further directed to methods of inhibiting PDK1 activity and treatment of disorders associated therewith using a compound of the invention or a pharmaceutical composition comprising a compound of the invention. The invention is further directed to novel processes and novel intermediates useful in preparing the presently invented Akt/PKB inhibiting compounds. The invention is further directed to methods of co-administering the presently invented PDK1 inhibiting compounds with further active ingredients.

DETAILED DESCRIPTION OF THE INVENTION

This invention relates to novel compounds of Formula (I):

(I)

wherein:
$R^1$ is selected from: hydrogen, $C_1$-$C_6$alkyl, $C_3$-$C_7$cycloalkyl, $C_3$-$C_7$cycloalkyl substituted with from one to three $R^8$, $C_1$-$C_6$alkoxy, $C_1$-$C_6$mercapto, —N($R^5$)($R^6$), aryl, aryl substituted with from one to three $R^8$, heteroaryl, heteroaryl substituted with from one to three $R^8$, heterocycloalkyl and heterocycloalkyl substituted with from one to three $R^8$,
where,
$R^5$ is hydrogen or $C_1$-$C_3$alkyl,
$R^6$ is selected from: hydrogen, aryl, aryl substituted with from one to three $R^7$, $C_3$-$C_7$cycloalkyl, $C_3$-$C_7$cycloalkyl substituted with from one to three $R^8$, $C_1$-$C_6$alkyl and $C_1$-$C_6$alkyl substituted with one $R^9$,
where,
$R^9$ is selected from: phenyl, phenyl substituted with from one to three $R^7$, heteroaryl, heteroaryl substituted with one to three $R^7$, $C_3$-$C_7$ cycloalkyl, $C_3$-$C_7$ cycloalkyl substituted with one or three $R^8$;
$R^2$ is selected from: hydrogen, halo, —N($R^{10}$)—$(CH_2)_n$—$R^{11}$, —O—$(CH_2)_n$—$R^{11}$, —S—$(CH_2)_n$—$R^{11}$; aryl, aryl substituted with from one to three $R^7$, heteroaryl, heteroaryl substituted with from one to three $R^7$, $C_3$-$C_7$cycloalkyl, $C_3$-$C_7$cycloalkyl substituted with from one to three $R^7$, heterocycloalkyl, and heterocycloalkyl substituted with from one to three $R^7$,
where,
$R^{10}$ is hydrogen or $C_1$-$C_3$ alkyl,
$R^{11}$ is selected from: hydrogen, $C_1$-$C_3$alkyl, $C_1$-$C_3$alkyl substituted with from one to three $R^7$, $C_3$-$C_7$cycloalkyl, $C_3$-$C_7$cycloalkyl substituted with from one to three $R^7$, aryl, aryl substituted with from one to three $R^7$, heteroaryl, heteroaryl substituted with one to three $R^7$, —O—$C_3$-$C_7$cycloalkyl, —O—$C_3$-$C_7$cycloalkyl substituted with from one to three $R^7$, —O-aryl, —O-aryl substituted with from one to three $R^7$, —O-heteroaryl and —O-heteroaryl substituted with one to three $R^7$, and
n is 0, 1, 2, or 3
provided that when $R^{11}$ is —O—$C_3$-$C_7$cycloalkyl, —O— aryl or —O-heteroaryl,
n is not 0;
$R^3$ is selected from: hydrogen, —$NH_2$, $C_1$-$C_3$alkyl, and $C_3$-$C_7$cycloalkyl; and
$R^4$ is selected from: hydrogen, $NH_2$ and $NHC_1$-$C_3$alkyl;
where,
each $R^8$ is independently selected from: hydroxy, $C_1$-$C_6$alkyl, $C_1$-$C_6$alkyl substituted with from one to three $R^7$, —C(O)$C_1$-$C_6$alkyl, $C_3$-$C_7$cycloalkyl, $C_1$-$C_6$alkoxy, amino, $C_1$-$C_4$alkylamino, di$C_1$-$C_4$alkylamino, —$C_1$-$C_4$alkyl $NR^{200}R^{201}$, aryl, aryl substituted with from one to three $R^7$, —$C_1$-$C_4$alkylaryl, —$C_1$-$C_4$alkylaryl substituted with from one to three R$^7$, phenylheteroaryl, phenylheteroaryl substituted with from one to three R$^7$, heterocycloalkyl, heterocycloalkyl substituted with from one to three R$^7$, heteroaryl, heteroaryl substituted with from one to three R$^7$, nitro, cyano, oxo, halo, —CO$_2$R$^{120}$, —C(O)NR$^{200}$R$^{201}$, —C$_1$-C$_4$alkylOC(O)NR$^{200}$R$^{201}$, —OC(O)NR$^{200}$R$^{201}$, —OC(O)R$^{200}$, —NR$^{200}$C(O)OR$^{301}$, —C$_1$-C$_4$alkylNR$^{200}$C(O)OR$^{301}$, —NR$^{200}$C(O)R$^{302}$, —NR$^{200}$S(O)$_2$R$^{302}$, —C$_1$-C$_4$alkylNR$^{200}$C(O)R$^{302}$ and —C$_1$-C$_4$alkylNR$^{200}$S(O)$_2$R$^{302}$, where, R$^{120}$ is selected form: hydrogen, C$_1$-C$_4$alkyl and C$_3$-C$_7$cycloalkyl, R$^{200}$ is hydrogen or C$_1$-C$_3$alkyl, R$^{201}$ is selected from: hydrogen, C$_1$-C$_6$alkyl, C$_1$-C$_6$alkyl substituted with from one to three R$^7$, C$_3$-C$_7$cycloalkyl, C$_3$-C$_7$cycloalkyl substituted with from one to three R$^7$, —C$_1$-C$_4$alkylC$_3$-C$_7$cycloalkyl, —C$_1$-C$_4$alkylC$_3$-C$_7$cycloalkyl substituted with from one to three R$^7$, aryl, aryl substituted with from one to three R$^7$, —C$_1$-C$_4$alkylaryl, —C$_1$-C$_4$alkylaryl substituted with from one to three R$^7$, heteroaryl, heteroaryl substituted with from one to three R$^7$, —C$_1$-C$_4$alkylheteroaryl, —C$_1$-C$_4$alkylheteroaryl substituted with from one to three R$^7$, heterocycloalkyl, heterocycloalkyl substituted with from one to three R$^7$, —C$_1$-C$_4$alkylheterocycloalkyl, —C$_1$-C$_4$alkylheterocycloalkyl substituted with from one to three R$^7$, R$^{301}$ is selected from: C$_1$-C$_6$alkyl, C$_1$-C$_6$alkyl substituted with from one to three R$^7$, C$_3$-C$_7$cycloalkyl, C$_3$-C$_7$cycloalkyl substituted with from one to three R$^7$, —C$_1$-C$_4$alkylaryl, —C$_1$-C$_4$alkylaryl substituted with from one to three R$^7$, —C$_1$-C$_4$alkylC$_3$-C$_7$cycloalkyl, —C$_1$-C$_4$alkylC$_3$-C$_7$cycloalkyl substituted with from one to three R$^7$, and R$^{302}$ is selected from: hydrogen, C$_1$-C$_6$alkyl, C$_1$-C$_6$alkyl substituted with from one to three R$^7$, C$_3$-C$_7$cycloalkyl, C$_3$-C$_7$cycloalkyl substituted with from one to three R$^7$, —C$_1$-C$_4$alkylC$_3$-C$_7$cycloalkyl, —C$_1$-C$_4$alkylC$_3$-C$_7$cycloalkyl substituted with from one to three R$^7$, aryl, aryl substituted with from one to three R$^7$, —C$_1$-C$_4$alkylaryl, —C$_1$-C$_4$alkylaryl substituted with from one to three R$^7$, heteroaryl, heteroaryl substituted with from one to three R$^7$, —C$_1$-C$_4$alkylheteroaryl, —C$_1$-C$_4$alkylheteroaryl substituted with from one to three R$^7$, heterocycloalkyl, heterocycloalkyl substituted with from one to three R$^7$, —C$_1$-C$_4$alkylheterocycloalkyl, —C$_1$-C$_4$alkylheterocycloalkyl substituted with from one to three R$^7$; and each R$^7$ is independently selected from: halo, cyano, hydroxy, amino, C$_1$-C$_4$alkylamino, diC$_1$-C$_4$alkylamino, C$_1$-C$_3$ alkyl and C$_1$-C$_3$ alkoxy;

or a salt thereof.

This invention also relates to pharmaceutically acceptable salts of the compounds of Formula (I).

Suitably the compound of Formula (I) is not (3S,6R)-1-[6-(3-Amino-1H-indazol-6-yl)-2-(methylamino)-4-pyrimidinyl]-N-cyclohexyl-6-methyl-3-piperidinecarboxamide.

Suitably the compound of Formula (I) is not (3S,6R)-1-[2-Amino-6-(3-amino-1H-indazol-6-yl)-4-pyrimidinyl]-6-methyl-N-phenyl-3-piperidinecarboxamide.

Suitably R$^1$ is C$_1$-C$_6$ alkyl. Suitably R$^1$ is methyl, ethyl, propyl, isopropyl, tert-butyl, sec-butyl Suitably R$^1$ is C$_3$-C$_7$ cycloalkyl. Suitably R$^1$ is cyclopropyl, cyclobutyl, cyclopentyl and cyclohexyl.

Suitably R$^1$ is C$_1$-C$_6$ alkoxy. Suitably R$^1$ is methoxy, ethoxy and isopropoxy.

Suitably R$^1$ is C$_1$-C$_6$ mercapto. Suitably R$^1$ is thiomethyl.

Suitably R$^1$ is —N(R$^5$)(R$^6$) wherein R$^5$ is H and R$^6$ is as defined in Formula (I) above. Suitably R$^6$ is phenyl, ethyl, propyl, isopropyl, tert-butyl, cyclopropyl, cyclobutyl, cyclopentyl, cyclohexyl, or C$_1$-C$_6$ alkyl optionally substituted by phenyl or cyclohexyl.

Suitably R$^1$ is NH$_2$.

Suitably R$^1$ is phenyl optionally substituted with one to three R$^7$. Suitably R$^1$ is unsubstituted phenyl.

Suitably R$^1$ is heteroaryl. Suitably R$^1$ is thiazolyl, thienyl, furanyl and pyridyl.

Suitably R$^1$ is heterocycloalkyl optionally substituted with one to three R$^8$. Suitably R$^1$ is azetidinyl, pyrrolidinyl, piperidinyl, morpholinyl, thiomorpholinyl, pyranyl or hexahydro-1H-azepine each of which is optionally substituted with one to three R$^8$.

Suitably R$^2$ is H, —NH—(CH$_2$)$_n$—R$^{11}$, or —O—(CH$_2$)$_n$—R$^{11}$;

wherein:

R$^{11}$ is H, CF$_3$, phenyl optionally substituted with one to three R$^7$, phenoxy optionally substituted with one to three R$^7$, or heteroaryl optionally substituted with one to three R$^7$; and n is 1, 2, or 3.

Suitably R$^2$ is —NH—(CH$_2$)$_n$—R$^{11}$ wherein; R$^{11}$ is H, CF$_3$, phenyl optionally substituted with one to three R$^7$, unsubstituted phenoxy, or heteroaryl optionally substituted with one to three R$^7$; and n is 1, 2, or 3. Suitably R$^{11}$ is phenyl optionally substituted with one to three R$^7$, unsubstituted phenoxy, pyrazolyl optionally substituted with one to three R$^7$, or pyridinyl optionally substituted with one to three R$^7$; and n is 1, 2, or 3.

Suitably R$^2$ is —O—(CH$_2$)$_n$—R$^{11}$ wherein R$^{11}$ is H, CF$_3$, phenyl optionally substituted with one to three R$^7$, or phenoxy optionally substituted with one to three R$^7$; and n is 1, 2, or 3.

Suitably R$^2$ is methoxy, ethoxy, methylamino or ethylamino.

Suitably R$^2$ is heteroaryl. Suitably R$^2$ is furanyl.

Suitably R$^8$ is hydroxy, cyano, oxo, fluoro or trifluoromethyl.

Suitably R$^8$ is trifluoromethyl.

Suitably R$^8$ is C$_1$-C$_4$ alkyl. Suitably R$^8$ is methyl, ethyl or isopropy.

Suitably R$^8$ is C$_3$-C$_8$ cycloalkyl. Suitably R$^8$ is cyclopropyl.

Suitably R$^8$ is heteroaryl. Suitably R$^8$ is pyrazolyl, imidazolyl, azabenzimidazolyl and benzimidazolyl optionally substituted with up to three R$^7$ groups as defined in Formula (I) above. Suitably R$^8$ is 1H-benzimidazol-2-yl, 4,5,6,7-tetrahydro-1H-benzimidazol-2-yl, 5-chloro-1H-benzimidazol-2-yl, 5-fluoro-1H-benzimidazol-2-yl, 5-methyl-1H-benzimidazol-2-yl, 5-methoxy-1H-benzimidazol-2-yl 1H-imidazo[4,5-c]pyridin-2-yl, 1H-imidazo[4,5-b]pyridin-2-yl, 4-(1,1-dimethylethyl)-1H-imidazol-2-yl, 4-phenyl-1H-imidazol-2-yl, 4-methyl-5-phenyl-1H-imidazol-2-yl, 4-(2-chlorophenyl)-1H-imidazol-2-yl, 4-(3-chlorophenyl)-1H-imidazol-2-yl, 4-(4-chlorophenyl)-1H-imidazol-2-yl, 4-(3-methoxyphenyl)-1H-imidazol-2-yl, 4-(4-methoxyphenyl)-1H-imidazol-2-yl.

Suitably $R^8$ is hydroxy$C_1$-$C_4$alkyl. Suitably $R^8$ is hydroxylmethyl or hydroxyethyl.

Suitably $R^8$ is —C(O)NR$^{200}$R$^{201}$. Suitably $R^8$ is —C(O)NH$_2$, —C(O)NHCH$_3$ or —C(O)N(CH$_3$)$_2$ Suitably $R^8$ is —C(O)NR$^{200}$R$^{201}$ wherein R$^{200}$ is hydrogen, and R$^{201}$ is as defined in Formula (I) above. Suitably R$^{201}$ is methyl, ethyl, propyl, isopropyl, butyl, sec-butyl, isopentyl, cyclopentyl, cyclohexyl, 2-methylcyclohexyl, 3-methylcyclohexyl, 4-methylcyclohexyl, 4-ethylcyohexyl, 4-hydroxycyclohexyl, (1R)-1-cyclohexylethyl, phenyl, 4-fluorophenyl, 2-methylphenyl, 3-methylphenyl, 4-methylphenyl, 2-fluorophenyl, 3-fluorophenyl, 3,4-difluorophenyl, 4-chlorophenyl, 3-chlorophenyl, 3-methoxyphenyl, 4-methoxyphenyl, pyranyl, phenylethyl, benzyl, (1S)-1-phenylethyl, (1R)-1-phenylethyl, 1-methyl-1-phenylethyl, 2-methoxybenzyl, 3-methoxybenzyl, 4-methoxylbenzyl, 2-fluorobenzyl, 3-fluorobenzyl, 4-methylbenzyl, 4-fluorobenzyl, 4-pyridinylmethyl, 1-methyl-1H-pyrazol-5-yl, 1,3-dimethyl-1H-pyrazol-5-yl.

Suitably $R^8$ is —OC(O)NHR$^{200}$ where R$^{200}$ is as defined in Formula (I) above. Suitably R$^{200}$ is as defined in Formula (I) above. Suitably R$^{200}$ is isopropyl, cyclobutyl, tert-butyl, cyclopentyl, cyclohexyl, phenyl and benzyl.

Suitably $R^8$ is —NHC(O)OR$^{301}$ where R$^{301}$ is as defined in Formula (I) above. Suitably R$^{301}$ is isopropyl, cyclobutyl, tert-butyl, cyclopentyl, cyclohexyl benzyl.

Included in the presently invented compounds of Formula (I) are compounds of Formula (II):

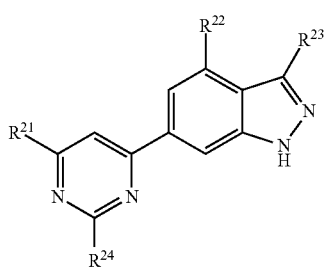

(II)

wherein:
$R^{21}$ is selected from: hydrogen, $C_1$-$C_6$alkyl, $C_3$-$C_7$cycloalkyl, $C_1$-$C_6$alkoxy, $C_1$-$C_6$mercapto, —N(R$^{25}$)(R$^{26}$), aryl, aryl substituted with from one to three R$^{28}$, heterocycloalkyl and heterocycloalkyl substituted with from one to three R$^{28}$,
where,
$R^{25}$ is hydrogen or $C_1$-$C_3$alkyl,
$R^{26}$ is selected from: hydrogen, aryl, aryl substituted with from one to three R$^{27}$, $C_3$-$C_7$cycloalkyl, $C_3$-$C_7$cycloalkyl substituted with from one to three R$^{28}$, $C_1$-$C_6$alkyl and $C_1$-$C_6$alkyl substituted with one R$^{29}$,
where,
$R^{29}$ is selected from: phenyl, phenyl substituted with from one to three R$^{27}$ and $C_3$-$C_7$ cycloalkyl;
$R^{22}$ is selected from: hydrogen, hydroxy, halo, —N(R$^{30}$)—(CH$_2$)$_n$—R$^{31}$, —O—(CH$_2$)$_n$—R$^{31}$, —S—(CH$_2$)$_n$—R$^{31}$; heteroaryl, heterocycloalkyl, and heterocycloalkyl substituted with from one to three R$^{27}$,
where,
$R^{30}$ is hydrogen,
$R^{31}$ is selected from: hydrogen, $C_1$-$C_3$alkyl, $C_1$-$C_3$alkyl substituted with from one to three R$^{27}$, $C_3$-$C_7$cycloalkyl, aryl, aryl substituted with from one to three R$^{27}$, heteroaryl, heteroaryl substituted with one to three R$^{27}$, —O-aryl and —O-aryl substituted with from one to three R$^{27}$, and n is 0, 1, 2, or 3
provided that when R$^{31}$ is —O-aryl,
n is not 0;
$R^{23}$ is selected from: hydrogen, —NH$_2$ and $C_1$-$C_3$alkyl; and
$R^{24}$ is selected from: hydrogen, NH$_2$ and NHC$_1$-$C_3$alkyl;
where,
each $R^{28}$ is independently selected from: hydroxy, $C_1$-$C_6$alkyl, $C_1$-$C_6$alkyl substituted with from one to three R$^{27}$, $C_3$-$C_7$cycloalkyl, amino, $C_1$-$C_4$alkylamino, diC$_1$-$C_4$alkylamino, —C$_1$-C$_4$alkylNR$^{500}$R$^{501}$,
—C$_1$-C$_4$alkylaryl, —C$_1$-C$_4$alkylaryl substituted with from one to three R$^{27}$, phenylheteroaryl, phenylheteroaryl substituted with from one to three R$^{27}$, heterocycloalkyl, heterocycloalkyl substituted with from one to three R$^{27}$, heteroaryl, heteroaryl substituted with from one to three R$^{27}$, nitro, cyano, oxo, halo, —CO$_2$R$^{420}$, —C(O)NR$^{500}$R$^{501}$,
—C$_1$-C$_4$alkylOC(O)NR$^{500}$R$^{501}$, —OC(O)NR$^{500}$R$^{501}$, —OC(O)R$^{500}$, —NR$^{500}$C(O)OR$^{601}$, —C$_1$-C$_4$alkylNR$^{500}$C(O)OR$^{601}$, —NR$^{500}$C(O)R$^{602}$, —NR$^{500}$S(O)$_2$R$^{602}$, —C$_1$-C$_4$alkylNR$^{500}$C(O)R$^{602}$ and —C$_1$-C$_4$alkylNR$^{500}$S(O)$_2$R$^{602}$,
where,
$R^{420}$ is selected form: hydrogen, $C_1$-$C_4$alkyl and $C_3$-$C_7$cycloalkyl,
$R^{500}$ is hydrogen or $C_1$-$C_3$alkyl,
$R^{501}$ is selected from: hydrogen, $C_1$-$C_6$alkyl, $C_3$-$C_7$cycloalkyl,
$C_3$-$C_7$cycloalkyl substituted with from one to three R$^{27}$,
—C$_1$-C$_4$alkylC$_3$-C$_7$cycloalkyl, aryl, aryl substituted with from one to three R$^{27}$, —C$_1$-C$_4$alkylaryl, —C$_1$-C$_4$alkylaryl substituted with from one to three R$^{27}$, heteroaryl, heteroaryl substituted with from one to three R$^{27}$ and C$_1$-C$_4$alkylheteroaryl,
$R^{601}$ is selected from: $C_1$-$C_6$alkyl, $C_3$-$C_7$cycloalkyl, and —C$_1$-C$_4$alkylaryl, and
$R^{602}$ is selected from: hydrogen, $C_1$-$C_6$alkyl, $C_1$-$C_6$alkyl substituted with from one to three R$^{27}$, $C_3$-$C_7$cycloalkyl, $C_3$-$C_7$cycloalkyl substituted with from one to three R$^{27}$, —C$_1$-C$_4$alkylC$_3$-C$_7$cycloalkyl,
—C$_1$-C$_4$alkylC$_3$-C$_7$cycloalkyl substituted with from one to three R$^{27}$, aryl, aryl substituted with from one to three R$^{27}$, —C$_1$-C$_4$alkylaryl, and
—C$_1$-C$_4$alkylaryl substituted with from one to three R$^{27}$; and
each $R^{27}$ is independently selected from: halo, cyano, hydroxy, amino, $C_1$-$C_4$alkylamino, diC$_1$-C$_4$alkylamino, $C_1$-$C_3$ alkyl and $C_1$-$C_3$ alkoxy;
or a salt thereof.

This invention also relates to pharmaceutically acceptable salts of the compounds of Formula (II).

Suitably the compound of Formula (II) is not (3S,6R)-1-[6-(3-Amino-1H-indazol-6-yl)-2-(methylamino)-4-pyrimidinyl]-N-cyclohexyl-6-methyl-3-piperidinecarboxamide.

Suitably the compound of Formula (II) is not (3S,6R)-1-[2-Amino-6-(3-amino-1H-indazol-6-yl)-4-pyrimidinyl]-6-methyl-N-phenyl-3-piperidinecarboxamide.

Included in the presently invented compounds of Formula (I) are compounds of Formula (III):

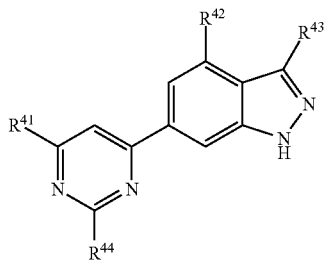

(III)

wherein:
$R^{41}$ is selected from the group consisting of:
  hydrogen,
  methyl,
  trifluoromethyl,
  ethyl,
  propyl,
  isopropyl,
  tert-butyl,
  sec-butyl,
  cyclopropyl,
  cyclobutyl,
  cyclopentyl,
  cyclohexyl,
  methoxy,
  ethoxy,
  isopropoxy,
  thiomethyl,
  thioethyl,
  —N($R^{55}$)($R^{56}$), where $R^{55}$ is H and $R^{56}$ are selected from: phenyl, ethyl, propyl, isopropyl, tert-butyl, cyclopropyl, cyclobutyl, cyclopentyl, cyclohexyl, $C_1$-$C_6$ alkyl, and $C_1$-$C_6$alkyl optionally substituted by phenyl or cyclohexyl,
  amino,
  phenyl,
  phenyl substituted with one to three $R^{47}$,
  thiazolyl,
  thienyl,
  furanyl,
  pyridyl,
  azetidinyl,
  pyrrolidinyl,
  piperidinyl,
  morpholinyl,
  thiomorpholinyl, pyranyl,
  hexahydro-1H-azepine,
  heterocycloalkyl substituted with one to three $R^{48}$, where heterocycloalkyl is selected from: azetidinyl, pyrrolidinyl, piperidinyl, morpholinyl, thiomorpholinyl, pyranyl and hexahydro-1H-azepine;
$R^{42}$ is selected from the group consisting of:
  hydrogen,
  halo,
  furanyl,
  —NH—$(CH_2)_n$—$R^{61}$, where $R^{61}$ is selected from: hydrogen, trifluoromethyl, phenyl, phenyl substituted with one to three $R^{47}$, phenoxy, phenoxy substituted with one to three $R^{47}$, heteroaryl and heteroaryl substituted with one to three $R^{47}$, and n is 1, 2, or 3,
  —O—$(CH_2)_n$—$R^{61}$, where $R^{61}$ is selected from: hydrogen, trifluoromethyl, phenyl, phenyl substituted with one to three $R^{47}$, phenoxy, phenoxy substituted with one to three $R^{47}$, heteroaryl and heteroaryl substituted with one to three $R^{47}$, and n is 1, 2, or 3,
$R^{43}$ is selected from: hydrogen, —$NH_2$ and $C_1$-$C_3$alkyl; and
$R^{44}$ is selected from: hydrogen, $NH_2$ and $NHC_1$-$C_3$alkyl;
where,
each $R^{48}$ is independently selected from:
  hydroxy,
  cyano,
  oxo,
  fluoro,
  chloro,
  trifluoromethyl,
  $C_1$-$C_4$ alkyl,
  $C_3$-$C_7$ cycloalkyl
  pyrazolyl,
  imidazolyl,
  azabenzimidazolyl,
  benzimidazolyl,
  benzimidazolyl substituted with one to three $R^{47}$,
  1H-benzimidazol-2-yl,
  4,5,6,7-tetrahydro-1H-benzimidazol-2-yl,
  5-chloro-1H-benzimidazol-2-yl,
  5-fluoro-1H-benzimidazol-2-yl,
  5-methyl-1H-benzimidazol-2-yl,
  5-methoxy-1H-benzimidazol-2-yl,
  1H-imidazo[4,5-c]pyridin-2-yl,
  1H-imidazo[4,5-b]pyridin-2-yl,
  4-(1,1-dimethylethyl)-1H-imidazol-2-yl,
  4-phenyl-1H-imidazol-2-yl,
  4-methyl-5-phenyl-1H-imidazol-2-yl,
  4-(2-chlorophenyl)-1H-imidazol-2-yl,
  4-(3-chlorophenyl)-1H-imidazol-2-yl,
  4-(4-chlorophenyl)-1H-imidazol-2-yl,
  4-(3-methoxyphenyl)-1H-imidazol-2-yl,
  4-(4-methoxyphenyl)-1H-imidazol-2-yl,
  hydroxy$C_1$-$C_4$alkyl,
  —C(O)$NH_2$,
  —C(O)$NHCH_3$,
  —C(O)N$(CH_3)_2$,
  —C(O)N$R^{800}R^{801}$, wherein $R^{800}$ is hydrogen and $R^{801}$ is selected from: ethyl, propyl, isopropyl, butyl, sec-butyl, isopentyl, cyclopentyl, cyclohexyl, 2-methylcyclohexyl, 3-methylcyclohexyl, 4-methylcyclohexyl, 4-ethylcycohexyl, 4-hydroxycyclohexyl, (1R)-1-cyclohexylethyl, phenyl, 4-fluorophenyl, 2-methylphenyl, 3-methylphenyl, 4-methylphenyl, 2-fluorophenyl, 3-fluorophenyl, 3,4-difluorophenyl, 4-chlorophenyl, 3-chlorophenyl, 3-methoxyphenyl, 4-methoxyphenyl, pyranyl, phenylethyl, benzyl, (1S)-1-phenylethyl, (1R)-1-phenylethyl, 1-methyl-1-phenylethyl, 2-methoxybenzyl, 3-methoxybenzyl, 4-methoxybenzyl, 2-fluorobenzyl, 3-fluorobenzyl, 4-methylbenzyl, 4-fluorobenzyl, 4-pyridinylmethyl, 1-methyl-1H-pyrazol-5-yl and 1,3-dimethyl-1H-pyrazol-5-yl,
  —OC(O)$NHR^{810}$, where $R^{810}$ is selected from: methyl, ethyl, isopropyl, cyclobutyl, tert-butyl, cyclopentyl, cyclohexyl, phenyl and benzyl, and
  —NHC(O)$OR^{901}$, where $R^{901}$ is selected from: methyl, .ethyl. isopropyl, cyclobutyl, tert-butyl, cyclopentyl, cyclohexyl and benzyl; and
each $R^{47}$ is independently selected from:
  halo,
  cyano,
  hydroxy, amino,
C$_1$-C$_4$alkylamino,
diC$_1$-C$_4$alkylamino,
C$_1$-C$_3$ alkyl and
C$_1$-C$_3$ alkoxy;
or a salt thereof.

This invention also relates to pharmaceutically acceptable salts of the compounds of Formula (III).

Suitably the compound of Formula (III) is not (3S,6R)-1-[6-(3-Amino-1H-indazol-6-yl)-2-(methylamino)-4-pyrimidinyl]-N-cyclohexyl-6-methyl-3-piperidinecarboxamide.

Suitably the compound of Formula (III) is not (3S,6R)-1-[2-Amino-6-(3-amino-1H-indazol-6-yl)-4-pyrimidinyl]-6-methyl-N-phenyl-3-piperidinecarboxamide.

Included in the presently invented compounds of Formula (I) are:

6-(3-Amino-1H-indazol-6-yl)-N$^4$-phenyl-2,4-pyrimidinediamine;
6-(3-Amino-1H-indazol-6-yl)-N$^4$-(phenylmethyl)-2,4-pyrimidinediamine;
6-[2-Amino-6-(methylthio)-4-pyrimidinyl]-1H-indazol-3-amine;
6-[2-Amino-6-(4-thiomorpholinyl)-4-pyrimidinyl]-1H-indazol-3-amine;
6-(3-Amino-1H-indazol-6-yl)-2,4-pyrimidinediamine;
6-[2-Amino-6-(4-morpholinyl)-4-pyrimidinyl]-1H-indazol-3-amine;
6-(3-Amino-1H-indazol-6-yl)-N$^4$-ethyl-2,4-pyrimidinediamine;
6-(3-Amino-1H-indazol-6-yl)-N$^4$-(1-methylethyl)-2,4-pyrimidinediamine;
6-[2-Amino-6-(1-piperidinyl)-4-pyrimidinyl]-1H-indazol-3-amine;
6-(3-Amino-1H-indazol-6-yl)-N$^4$-cyclopentyl-2,4-pyrimidinediamine;
6-(3-Amino-1H-indazol-6-yl)-N$^4$-cyclohexyl-2,4-pyrimidinediamine;
6-[2-Amino-6-(1-azetidinyl)-4-pyrimidinyl]-1H-indazol-3-amine;
6-[2-(Methylamino)-6-(1-piperidinyl)-4-pyrimidinyl]-1H-indazol-3-amine;
6-(2-Amino-6-methyl-4-pyrimidinyl)-1H-indazol-3-amine;
6-(2-Amino-6-phenyl-4-pyrimidinyl)-1H-indazol-3-amine;
6-(2-Amino-4-pyrimidinyl)-N$^4$-(2-phenylethyl)-1H-indazole-3,4-diamine;
6-(2-Amino-4-pyrimidinyl)-N$^4$-(3-phenylpropyl)-1H-indazole-3,4-diamine;
6-(2-Amino-4-pyrimidinyl)-N$^4$-[2-(phenyloxy)ethyl]-1H-indazole-3,4-diamine;
6-(2-Amino-4-pyrimidinyl)-N$^4$-[3-(5-methyl-1H-pyrazol-4-yl)propyl]-1H-indazole-3,4-diamine;
2-(3-{[3-Amino-6-(2-amino-4-pyrimidinyl)-1H-indazol-4-yl]amino}propyl)phenol;
6-(2-Amino-4-pyrimidinyl)-N$^4$-[3-(2-fluorophenyl)propyl]-1H-indazole-3,4-diamine;
6-(2-Amino-4-pyrimidinyl)-N$^4$-[3-(4-fluorophenyl)propyl]-1H-indazole-3,4-diamine;
6-(2-Amino-4-pyrimidinyl)-N$^4$-[3-(4-pyridinyl)propyl]-1H-indazole-3,4-diamine;
6-(2-Amino-4-pyrimidinyl)-N$^4$-[3-(3,5-dimethyl-1H-pyrazol-4-yl)propyl]-1H-indazole-3,4-diamine;
6-(2-Amino-4-pyrimidinyl)-N$^4$-[3-(phenyloxy)propyl]-1H-indazole-3,4-diamine;
6-(2-Amino-4-pyrimidinyl)-N$^4$-[3-(3-fluorophenyl)propyl]-1H-indazole-3,4-diamine;
6-(2-Amino-4-pyrimidinyl)-4-(methyloxy)-1H-indazol-3-amine;
6-(2-Amino-4-pyrimidinyl)-4-[(3-phenylpropyl)oxy]-1H-indazol-3-amine;
6-(2-Amino-4-pyrimidinyl)-4-{[3-(phenyloxy)propyl]oxy}-1H-indazol-3-amine;
6-(2-Amino-4-pyrimidinyl)-4-(ethyloxy)-1H-indazol-3-amine;
6-(2-Amino-4-pyrimidinyl)-4-[(2,2,2-trifluoroethyl)oxy]-1H-indazol-3-amine;
6-[2-Amino-6-(4-morpholinyl)-4-pyrimidinyl]-N$^4$-(2-phenylethyl)-1H-indazole-3,4-diamine;
6-[2-Amino-6-(4-morpholinyl)-4-pyrimidinyl]-4-(methyloxy)-1H-indazol-3-amine;
6-[2-Amino-6-(dimethylamino)-4-pyrimidinyl]-N$^4$-(2-phenylethyl)-1H-indazole-3,4-diamine;
6-[3-Amino-4-(methyloxy)-1H-indazol-6-yl]-N$^4$-ethyl-2,4-pyrimidinediamine;
6-(2-Amino-6-methyl-4-pyrimidinyl)-N$^4$-(3-phenylpropyl)-1H-indazole-3,4-diamine;
6-(2-amino-6-methyl-4-pyrimidinyl)-N$^4$-(2-phenylethyl)-1H-indazole-3,4-diamine;
6-(3-Amino-1H-indazol-6-yl)-N$^4$-(cyclohexylmethyl)-2,4-pyrimidinediamine;
6-{2-Amino-6-[2-(methyloxy)phenyl]-4-pyrimidinyl}-1H-indazol-3-amine;
6-{2-Amino-6-[2-(phenylmethyl)-1-pyrrolidinyl]-4-pyrimidinyl}-1H-indazol-3-amine;
6-{2-Amino-6-[2-(1-methylethyl)-1-pyrrolidinyl]-4-pyrimidinyl}-1H-indazol-3-amine;
6-[2-Amino-6-(2-methyl-1-pyrrolidinyl)-4-pyrimidinyl]-1H-indazol-3-amine;
6-(3-Amino-1H-indazol-6-yl)-N$^4$-(2-phenylethyl)-2,4-pyrimidinediamine'
6-[2-Amino-6-(hexahydro-1H-azepin-1-yl)-4-pyrimidinyl]-1H-indazol-3-amine;
6-[2-Amino-6-(methyloxy)-4-pyrimidinyl]-1H-indazol-3-amine;
6-{2-Amino-6-[(2R)-2-ethyl-1-pyrrolidinyl]-4-pyrimidinyl}-1H-indazol-3-amine;
6-[2-Amino-6-(2-cyclopropyl-1-pyrrolidinyl)-4-pyrimidinyl]-1H-indazol-3-amine;
Cis-1-[2-Amino-6-(3-amino-1H-indazol-6-yl)-4-pyrimidinyl]-N-cyclohexyl-6-(trifluoromethyl)-3-piperidinecarboxamide;
Cis-1-[6-(3-Amino-1H-indazol-6-yl)-2-(methylamino)-4-pyrimidinyl]-N-cyclohexyl-6-(trifluoromethyl)-3-piperidinecarboxamide;
6-(3-Amino-1H-indazol-6-yl)-N$^4$-[(2-chlorophenyl)methyl]-2,4-pyrimidinediamine;
6-(3-Amino-1H-indazol-6-yl)-N$^4$-cyclopropyl-2,4-pyrimidinediamine;
6-(3-Amino-1H-indazol-6-yl)-N$^4$-(3-phenylpropyl)-2,4-pyrimidinediamine;
6-(3-Amino-1H-indazol-6-yl)-N$^4$-[2-(2-fluorophenyl)ethyl]-2,4-pyrimidinediamine;
6-(3-Amino-1H-indazol-6-yl)-N$^4$-{2-[2-(methyloxy)phenyl]ethyl}-2,4-pyrimidinediamine;
6-(3-Amino-1H-indazol-6-yl)-N$^4$-[2-(3-chlorophenyl)ethyl]-2,4-pyrimidinediamine;
6-(3-Amino-1H-indazol-6-yl)-N$^4$-methyl-N$^4$-(2-phenylethyl)-2,4-pyrimidinediamine;
6-(3-Amino-1H-indazol-6-yl)-N$^4$-[2-(3-fluorophenyl)ethyl]-2,4-pyrimidinediamine;
6-(3-Amino-1H-indazol-6-yl)-N$^4$-[2-(2-chlorophenyl)ethyl]-2,4-pyrimidinediamine;
6-(3-Amino-1H-indazol-6-yl)-N$^4$-[2-(2-methylphenyl)ethyl]-2,4-pyrimidinediamine;

6-(3-Amino-1H-indazol-6-yl)-N$^4$-[2-(3-methylphenyl)ethyl]-2,4-pyrimidinediamine;
6-(3-Amino-1H-indazol-6-yl)-N$^4$-[1-(phenylmethyl)cyclopropyl]-2,4-pyrimidinediamine;
6-(3-Amino-1H-indazol-6-yl)-N$^4$-(1,1-dimethyl-2-phenylethyl)-2,4-pyrimidinediamine;
1-[2-Amino-6-(3-amino-1H-indazol-6-yl)-4-pyrimidinyl]-N-phenyl-3-pyrrolidinecarboxamide;
6-(3-Amino-1H-indazol-6-yl)-N$^4$-methyl-N$^4$-[(1R)-1-methyl-2-phenylethyl]-2,4-pyrimidinediamine;
6-(3-Amino-1H-indazol-6-yl)-N$^4$-(2,3-dihydro-1H-inden-1-yl)-2,4-pyrimidinediamine;
4-[2-Amino-6-(3-amino-1H-indazol-6-yl)-4-pyrimidinyl]benzamide;
(2S,5R)-4-[2-Amino-6-(3-amino-1H-indazol-6-yl)-4-pyrimidinyl]-5-methyl-N-phenyl-2-morpholinecarboxamide;
1,1-Dimethylethyl{1-[2-amino-6-(3-amino-1H-indazol-6-yl)-4-pyrimidinyl]-3-piperidinyl}carbamate;
N-{1-[2-Amino-6-(3-amino-1H-indazol-6-yl)-4-pyrimidinyl]-3-piperidinyl}benzamide;
6-{2-Amino-6-[2-(trifluoromethyl)-1-pyrrolidinyl]-4-pyrimidinyl}-1H-indazol-3-amine;
6-{2-Amino-6-[(3R)-3-ethyl-4-morpholinyl]-4-pyrimidinyl}-1H-indazol-3-amine;
6-(3-Amino-1H-indazol-6-yl)-N$^4$-(1,1-dimethylethyl)-2,4-pyrimidinediamine;
6-(3-Amino-1H-indazol-6-yl)-N$^4$-(2-methylpropyl)-2,4-pyrimidinediamine;
6-(3-Amino-1H-indazol-6-yl)-N$^4$-propyl-2,4-pyrimidinediamine;
6-{2-Amino-6-[(3R)-3-methyl-4-morpholinyl]-4-pyrimidinyl}-1H-indazol-3-amine;
4-[2-Amino-6-(3-amino-1H-indazol-6-yl)-4-pyrimidinyl]-N-phenyl-2-morpholinecarboxamide;
(3S,6R)-1-[6-(3-amino-1H-indazol-6-yl)-2-(methylamino)-4-pyrimidinyl]-6-methyl-N-phenyl-3-piperidinecarboxamide;
(3S,6R)-1-[6-(3-Amino-1H-indazol-6-yl)-2-(methylamino)-4-pyrimidinyl]-N-cyclohexyl-6-methyl-3-piperidinecarboxamide;
(3S,6R)—N-Cyclohexyl-1-[6-(1H-indazol-6-yl)-2-(methylamino)-4-pyrimidinyl]-6-methyl-3-piperidinecarboxamide;
(3S,6R)-1-[6-(3-Amino-1H-indazol-6-yl)-2-(methylamino)-4-pyrimidinyl]-6-methyl-N-(phenylmethyl)-3-pipendinecarboxamide;
(3S,6R)-1-[6-(1H-Indazol-6-yl)-2-(methylamino)-4-pyrimidinyl]-6-methyl-N-(phenylmethyl)-3-pipendinecarboxamide;
(3S,6R)-6-Methyl-1-[2-(methylamino)-6-(3-methyl-1H-indazol-6-yl)-4-pyrimidinyl]-N-phenyl-3-pipendinecarboxamide;
(3S,6R)—N-Cyclohexyl-6-methyl-1-[2-(methylamino)-6-(3-methyl-1H-indazol-6-yl)-4-pyrimidinyl]-3-piperidinecarboxamide;
(3S,6R)-6-Methyl-1-[2-(methylamino)-6-(3-methyl-1H-indazol-6-yl)-4-pyrimidinyl]-N-(phenylmethyl)-3-piperidinecarboxamide;
(3S,6R)-1-[6-(3-Amino-4-fluoro-1H-indazol-6-yl)-2-(methylamino)-4-pyrimidinyl]-N-cyclohexyl-6-methyl-3-pipendinecarboxamide;
(3S,6R)-1-[6-(3-Amino-4-fluoro-1H-indazol-6-yl)-2-(methylamino)-4-pyrimidinyl]-6-methyl-N-(phenylmethyl)-3-pipendinecarboxamide;
cis-1-[6-(3-amino-1H-indazol-6-yl)-2-(methylamino)-4-pyrimidinyl]-5-methyl-N-(phenylmethyl)-3-pyrrolidinecarboxamide;
4-[2-Amino-6-(3-amino-1H-indazol-6-yl)-4-pyrimidinyl]-3-morpholinecarboxamide;
N-({(2R,5R)-4-[2-Amino-6-(3-amino-1H-indazol-6-yl)-4-pyrimidinyl]-5-methyl-2-morpholinyl}methyl)benzamide;
N-({(2S,5R)-4-[2-Amino-6-(3-amino-1H-indazol-6-yl)-4-pyrimidinyl]-5-methyl-2-morpholinyl}methyl)benzenesulfonamide;
N-({(2R,5R)-4-[2-Amino-6-(3-amino-1H-indazol-6-yl)-4-pyrimidinyl]-5-methyl-2-morpholinyl}methyl)-2,2-dimethylpropanamide;
Methyl({(2R,5R)-4-[2-amino-6-(3-amino-1H-indazol-6-yl)-4-pyrimidinyl]-5-methyl-2-morpholinyl}methyl)carbamate;
N-({(2S,5R)-4-[2-Amino-6-(3-amino-1H-indazol-6-yl)-4-pyrimidinyl]-5-methyl-2-morpholinyl}methyl)methanesulfonamide;
N-({(2S,5R)-4-[2-Amino-6-(3-amino-1H-indazol-6-yl)-4-pyrimidinyl]-5-methyl-2-morpholinyl}methyl)cyclohexanesulfonamide;
6-(2-Amino-6-{2-[4-(4-chlorophenyl)-1H-imidazol-2-yl]-4-morpholinyl}-4-pyrimidinyl)-1H-indazol-3-amine;
6-{2-Amino-6-[2-(4,5,6,7-tetrahydro-1H-benzimidazol-2-yl)-4-morpholinyl]-4-pyrimidinyl}-1H-indazol-3-amine;
6-{2-Amino-6-[2-(4-phenyl-1H-imidazol-2-yl)-4-morpholinyl]-4-pyrimidinyl}-1H-indazol-3-amine;
6-(2-Amino-6-{2-[4-(3-chlorophenyl)-1H-imidazol-2-yl]-4-morpholinyl}-4-pyrimidinyl)-1H-indazol-3-amine;
6-[2-Amino-6-(2-{4-[4-(methyloxy)phenyl]-1H-imidazol-2-yl}-4-morpholinyl)-4-pyrimidinyl]-1H-indazol-3-amine;
(3S)-1-[2-Amino-6-(3-amino-4-fluoro-1H-indazol-6-yl)-4-pyrimidinyl]-N-phenyl-3-piperidinecarboxamide;
(3S)-1-[2-Amino-6-(3-amino-4-fluoro-1H-indazol-6-yl)-4-pyrimidinyl]-N-cyclohexyl-3-piperidinecarboxamide;
6-(3-Amino-1H-indazol-6-yl)-N$^4$-methyl-N$^4$-phenyl-2,4-pyrimidinediamine;
6-{2-Amino-6-[2-(1H-imidazo[4,5-c]pyridin-2-yl)-4-morpholinyl]-4-pyrimidinyl}-1H-indazol-3-amine;
6-[2-Amino-6-(2-{4-[3-(methyloxy)phenyl]-1H-imidazol-2-yl}-4-morpholinyl)-4-pyrimidinyl]-1H-indazol-3-amine;
6-(2-Amino-6-{2-[5-(methyloxy)-1H-benzimidazol-2-yl]-4-morpholinyl}-4-pyrimidinyl)-1H-indazol-3-amine;
{(2S,5R)-4-[2-Amino-6-(3-amino-1H-indazol-6-yl)-4-pyrimidinyl]-5-methyl-2-morpholinyl}methyl phenylcarbamate;
6-{2-Amino-6-[2-(4-methyl-5-phenyl-1H-imidazol-2-yl)-4-morpholinyl]-4-pyrimidinyl}-1H-indazol-3-amine;
6-{2-Amino-6-[2-(5-chloro-1H-benzimidazol-2-yl)-4-morpholinyl]-4-pyrimidinyl}-1H-indazol-3-amine;
6-{2-Amino-6-[2-(5-fluoro-1H-benzimidazol-2-yl)-4-morpholinyl]-4-pyrimidinyl}-1H-indazol-3-amine;
(3S,6R)-1-[2-Amino-6-(3-amino-1H-indazol-6-yl)-4-pyrimidinyl]-6-methyl-N-phenyl-3-piperidinecarboxamide;
Cis-1,1-dimethylethyl{(1-[2-amino-6-(3-amino-1H-indazol-6-yl)-4-pyrimidinyl]-6-methyl-3-piperidinyl}carbamate;
Phenylmethyl{(3S,6R)-1-[2-amino-6-(3-amino-1H-indazol-6-yl)-4-pyrimidinyl]-6-methyl-3-piperidinyl}carbamate;
N-{(3S,6R)-1-[2-Amino-6-(3-amino-1H-indazol-6-yl)-4-pyrimidinyl]-6-methyl-3-pipendinyl}benzamide;
N-{(3S,6R)-1-[2-Amino-6-(3-amino-1H-indazol-6-yl)-4-pyrimidinyl]-6-methyl-3-piperidinyl}-2-phenylacetamide;

cis-1-[6-(3-amino-1H-indazol-6-yl)-2-(methylamino)-4-pyrimidinyl]-N-cyclopentyl-6-(trifluoromethyl)-3-piperidinecarboxamide;

Cis-1-[6-(3-amino-1H-indazol-6-yl)-2-(methylamino)-4-pyrimidinyl]-N-(phenylmethyl)-6-(trifluoromethyl)-3-pipendinecarboxamide;

(3S)-1-[2-Amino-6-(3-amino-1H-indazol-6-yl)-4-pyrimidinyl]-N-cyclohexyl-3-piperidinecarboxamide;

(3S)-1-[2-Amino-6-(3-amino-1H-indazol-6-yl)-4-pyrimidinyl]-N-phenyl-3-pipendinecarboxamide;

(3R)-1-[2-Amino-6-(3-amino-1H-indazol-6-yl)-4-pyrimidinyl]-N-phenyl-3-pipendinecarboxamide;

Cis-cyclopentyl{1-[2-amino-6-(3-amino-1H-indazol-6-yl)-4-pyrimidinyl]-6-methyl-3-pipendinyl}carbamate;

(3S,6R)-1-[2-Amino-6-(3-amino-1H-indazol-6-yl)-4-pyrimidinyl]-N-cyclohexyl-6-methyl-3-pipendinecarboxamide;

(3S)-1-[2-Amino-6-(3-amino-1H-indazol-6-yl)-4-pyrimidinyl]-N-(4-fluorophenyl)-3-piperidinecarboxamide;

(3S)-1-[2-Amino-6-(3-amino-1H-indazol-6-yl)-4-pyrimidinyl]-N-(3-methylphenyl)-3-pipendinecarboxamide;

(3S)-1-[2-Amino-6-(3-amino-1H-indazol-6-yl)-4-pyrimidinyl]-N-(3,4-difluorophenyl)-3-pipendinecarboxamide;

(3S)-1-[2-Amino-6-(3-amino-1H-indazol-6-yl)-4-pyrimidinyl]-N-(4-methylphenyl)-3-pipendinecarboxamide;

(3S)-1-[2-Amino-6-(3-amino-1H-indazol-6-yl)-4-pyrimidinyl]-N-(2-fluorophenyl)-3-pipendinecarboxamide;

(3S)-1-[2-Amino-6-(3-amino-1H-indazol-6-yl)-4-pyrimidinyl]-N-(3-fluorophenyl)-3-pipendinecarboxamide;

(3S)-1-[2-Amino-6-(3-amino-1H-indazol-6-yl)-4-pyrimidinyl]-N-(2-methylphenyl)-3-pipendinecarboxamide;

(3S)-1-[2-Amino-6-(3-amino-1H-indazol-6-yl)-4-pyrimidinyl]-N-(4-chlorophenyl)-3-piperidinecarboxamide;

(3S)-1-[2-Amino-6-(3-amino-1H-indazol-6-yl)-4-pyrimidinyl]-N-[4-(methyloxy)phenyl]-3-pipendinecarboxamide;

(3S)-1-[2-Amino-6-(3-amino-1H-indazol-6-yl)-4-pyrimidinyl]-N-[3-(methyloxy)phenyl]-3-pipendinecarboxamide;

(3S)-1-[2-Amino-6-(3-amino-1H-indazol-6-yl)-4-pyrimidinyl]-N-(3-chlorophenyl)-3-pipendinecarboxamide;

(3S)-1-[2-Amino-6-(3-amino-1H-indazol-6-yl)-4-pyrimidinyl]-N-(phenylmethyl)-3-pipendinecarboxamide;

(3S)-1-[2-Amino-6-(3-amino-1H-indazol-6-yl)-4-pyrimidinyl]-N-(4-pyridinylmethyl)-3-piperidinecarboxamide;

(3S)-1-[2-Amino-6-(3-amino-1H-indazol-6-yl)-4-pyrimidinyl]-N-(4-methylcyclohexyl)-3-pipendinecarboxamide;

(3S)-1-[2-Amino-6-(3-amino-1H-indazol-6-yl)-4-pyrimidinyl]-N-(1-methyl-1H-pyrazol-5-yl)-3-piperidinecarboxamide;

(3S)-1-[2-Amino-6-(3-amino-1H-indazol-6-yl)-4-pyrimidinyl]-N-(1,3-dimethyl-1H-pyrazol-5-yl)-3-pipendinecarboxamide;

(3S,6R)-1-[2-Amino-6-(3-methyl-1H-indazol-6-yl)-4-pyrimidinyl]-6-methyl-N-(phenylmethyl)-3-pipendinecarboxamide;

(3S,6R)-1-[2-Amino-6-(1H-indazol-6-yl)-4-pyrimidinyl]-N-cyclohexyl-6-methyl-3-piperidinecarboxamide;

(3S,6R)-1-[2-amino-6-(3-amino-1H-indazol-6-yl)-4-pyrimidinyl]-N-(cyclohexylmethyl)-6-methyl-3-piperidinecarboxamide;

(3S,6R)-1-[2-amino-6-(3-amino-1H-indazol-6-yl)-4-pyrimidinyl]-6-methyl-N-{[4-(methyloxy)phenyl]methyl}-3-piperidinecarboxamide;

(3S,6R)-1-[2-Amino-6-(3-amino-1H-indazol-6-yl)-4-pyrimidinyl]-N-cyclopentyl-6-methyl-3-piperidinecarboxamide;

(3S,6R)-1-[2-Amino-6-(3-amino-1H-indazol-6-yl)-4-pyrimidinyl]-N-[(1R)-1-cyclohexylethyl]-6-methyl-3-piperidinecarboxamide;

(3S,6R)-1-[2-Amino-6-(3-amino-1H-indazol-6-yl)-4-pyrimidinyl]-N-[(3-fluorophenyl)methyl]-6-methyl-3-piperidinecarboxamide;

(3S,6R)-1-[2-Amino-6-(3-amino-1H-indazol-6-yl)-4-pyrimidinyl]-6-methyl-N-(phenylmethyl)-3-piperidinecarboxamide;

(3S,6R)-1-[2-Amino-6-(3-amino-1H-indazol-6-yl)-4-pyrimidinyl]-6-methyl-N-[(4-methylphenyl)methyl]-3-piperidinecarboxamide;

(3S,6R)-1-[2-Amino-6-(3-amino-1H-indazol-6-yl)-4-pyrimidinyl]-N-[(4-fluorophenyl)methyl]-6-methyl-3-piperidinecarboxamide;

(3S,6R)-1-[2-Amino-6-(3-amino-1H-indazol-6-yl)-4-pyrimidinyl]-6-methyl-N-(3-methylcyclohexyl)-3-piperidinecarboxamide;

(3S,6R)-1-[2-Amino-6-(3-amino-1H-indazol-6-yl)-4-pyrimidinyl]-6-methyl-N-(2-phenylethyl)-3-piperidinecarboxamide;

(3S,6R)-1-[2-Amino-6-(3-amino-1H-indazol-6-yl)-4-pyrimidinyl]-6-methyl-N-(4-methylcyclohexyl)-3-piperidinecarboxamide;

6-{2-(Methylamino)-6-[(3R)-3-(1-methylethyl)-4-morpholinyl]-4-pyrimidinyl}-4-(methyloxy)-1H-indazol-3-amine;

4-(Ethyloxy)-6-{2-(methylamino)-6-[(3R)-3-(1-methylethyl)-4-morpholinyl]-4-pyrimidinyl}-1H-indazol-3-amine;

6-{2-(Methylamino)-6-[(3R)-3-(1-methylethyl)-4-morpholinyl]-4-pyrimidinyl}-4-(methylthio)-1H-indazol-3-amine;

1,1-Dimethylethyl{(3R,6S)-1-[2-amino-6-(3-amino-1H-indazol-6-yl)-4-pyrimidinyl]-6-methyl-3-piperidinyl}carbamate;

1,1-Dimethylethyl{(3R,6S)-1-[6-(3-amino-1H-indazol-6-yl)-2-(methylamino)-4-pyrimidinyl]-6-methyl-3-piperidinyl}carbamate;

6-{2-Amino-6-[(2R,5R)-2-(aminomethyl)-5-methyl-4-morpholinyl]-4-pyrimidinyl}-1H-indazol-3-amine;

6-[2-Amino-6-((2R,5R)-5-methyl-2-{[(phenylmethyl)amino]methyl}-4-morpholinyl)-4-pyrimidinyl]-1H-indazol-3-amine;

{(2S,5R)-4-[6-(3-Amino-1H-indazol-6-yl)-2-(methylamino)-4-pyrimidinyl]-5-methyl-2-morpholinyl}methanol;

(2S,5R)-4-[6-(3-amino-1H-indazol-6-yl)-2-(methylamino)-4-pyrimidinyl]-5-methyl-N-phenyl-2-morpholinecarboxamide;

(2S,5R)-4-[6-(3-amino-1H-indazol-6-yl)-2-(methylamino)-4-pyrimidinyl]-N-cyclohexyl-5-methyl-2-morpholinecarboxamide;

(2S,5R)-4-[6-(3-Amino-1H-indazol-6-yl)-2-(methylamino)-4-pyrimidinyl]-5-methyl-N-(phenylmethyl)-2-morpholinecarboxamide;

6-[6-{(2R,5R)-2-[(Dimethylamino)methyl]-5-methyl-4-morpholinyl}-2-(methylamino)-4-pyrimidinyl]-1H-indazol-3-amine;

6-(2-Amino-6-{2-[4-(2-chlorophenyl)-1H-imidazol-2-yl]-4-morpholinyl}-4-pyrimidinyl)-1H-indazol-3-amine;

4-Fluoro-6-{2-(methylamino)-6-[(3R)-3-methyl-4-morpholinyl]-4-pyrimidinyl}-1H-indazol-3-amine;

6-{2-(Methylamino)-6-[(3R)-3-methyl-4-morpholinyl]-4-pyrimidinyl}-1H-indazol-3-amine;

6-{2-(Methylamino)-6-[(3R)-3-methyl-4-morpholinyl]-4-pyrimidinyl}-4-(methyloxy)-1H-indazol-3-amine;

6-{2-(Methylamino)-6-[(3R)-3-methyl-4-morpholinyl]-4-pyrimidinyl}-4-(methylthio)-1H-indazol-3-amine;
$N^4$-Methyl-6-{2-(methylamino)-6-[(3R)-3-methyl-4-morpholinyl]-4-pyrimidinyl}-1H-indazole-3,4-diamine;
4-(2-Furanyl)-6-{2-(methylamino)-6-[(3R)-3-methyl-4-morpholinyl]-4-pyrimidinyl}-1H-indazol-3-amine;
6-{2-Amino-6-[(3R)-3-methyl-4-morpholinyl]-4-pyrimidinyl}-4-(ethyloxy)-1H-indazol-3-amine;
6-{2-Amino-6-[(3R)-3-methyl-4-morpholinyl]-4-pyrimidinyl}-4-[(1-methylethyl)oxy]-1H-indazol-3-amine;
(2S,5R)-4-[2-Amino-6-(3-amino-1H-indazol-6-yl)-4-pyrimidinyl]-5-ethyl-N-phenyl-2-morpholinecarboxamide;
(2S,5R)-4-[2-Amino-6-(3-amino-1H-indazol-6-yl)-4-pyrimidinyl]-N-cyclohexyl-5-ethyl-2-morpholinecarboxamide;
(2S,5R)-4-[6-(3-Amino-1H-indazol-6-yl)-2-(methylamino)-4-pyrimidinyl]-5-ethyl-N-phenyl-2-morpholinecarboxamide;
(2S,5R)-4-[6-(3-amino-1H-indazol-6-yl)-2-(methylamino)-4-pyrimidinyl]-N-cyclohexyl-5-ethyl-2-morpholinecarboxamide;
(2S,5R)-4-[6-(3-Amino-1H-indazol-6-yl)-2-(methylamino)-4-pyrimidinyl]-5-ethyl-N-(phenylmethyl)-2-morpholinecarboxamide;
6-[6-[(3R)-3-Ethyl-4-morpholinyl]-2-(methylamino)-4-pyrimidinyl]-1H-indazol-3-amine;
6-[6-[(3R)-3-Ethyl-4-morpholinyl]-2-(methylamino)-4-pyrimidinyl]-4-fluoro-1H-indazol-3-amine;
6-[6-[(3R)-3-Ethyl-4-morpholinyl]-2-(methylamino)-4-pyrimidinyl]-4-(methyloxy)-1H-indazol-3-amine;
6-[6-[(3R)-3-Ethyl-4-morpholinyl]-2-(methylamino)-4-pyrimidinyl]-4-(methylthio)-1H-indazol-3-amine;
$N^4$-Cyclopentyl-6-[6-[(3R)-3-ethyl-4-morpholinyl]-2-(methylamino)-4-pyrimidinyl]-1H-indazole-3,4-diamine;
6-[6-[(3R)-3-Ethyl-4-morpholinyl]-2-(methylamino)-4-pyrimidinyl]-$N^4$-methyl-1H-indazole-3,4-diamine;
6-[6-[(3R)-3-Ethyl-4-morpholinyl]-2-(methylamino)-4-pyrimidinyl]-4-(1-pyrrolidinyl)-1H-indazol-3-amine;
6-[6-[(3R)-3-Ethyl-4-morpholinyl]-2-(methylamino)-4-pyrimidinyl]-4-(ethyloxy)-1H-indazol-3-amine;
6-{2-(Methylamino)-6-[(2R)-2-methyl-1-pyrrolidinyl]-4-pyrimidinyl}-4-(methyloxy)-1H-indazol-3-amine;
6-{2-(methylamino)-6-[(2R)-2-methyl-1-pyrrolidinyl]-4-pyrimidinyl}-4-(methylthio)-1H-indazol-3-amine;
4-(Ethyloxy)-6-{2-(methylamino)-6-[(2R)-2-methyl-1-pyrrolidinyl]-4-pyrimidinyl}-1H-indazol-3-amine;
(3S,6R)-1-[2-Amino-6-(3-amino-1H-indazol-6-yl)-4-pyrimidinyl]-6-methyl-N-[(1S)-1-phenylethyl]-3-piperidinecarboxamide;
(3S,6R)-1-[2-Amino-6-(3-amino-1H-indazol-6-yl)-4-pyrimidinyl]-6-methyl-N-{[2-(methyloxy)phenyl]methyl}-3-piperidinecarboxamide;
(3S,6R)-1-[2-Amino-6-(3-amino-1H-indazol-6-yl)-4-pyrimidinyl]-6-methyl-N-{[3-(methyloxy)phenyl]methyl}-3-piperidinecarboxamide;
(3S,6R)-1-[2-Amino-6-(3-amino-1H-indazol-6-yl)-4-pyrimidinyl]-N-[(2-fluorophenyl)methyl]-6-methyl-3-piperidinecarboxamide;
(3S,6R)-1-[2-Amino-6-(3-amino-1H-indazol-6-yl)-4-pyrimidinyl]-6-methyl-N-[(1R)-1-phenylethyl]-3-piperidinecarboxamide;
(3S,6R)-1-[2-Amino-6-(3-amino-1H-indazol-6-yl)-4-pyrimidinyl]-6-methyl-N-(1-methyl-1-phenylethyl)-3-piperidinecarboxamide;
(3S,6R)-1-[2-Amino-6-(3-amino-1H-indazol-6-yl)-4-pyrimidinyl]-N-(4-ethylcyclohexyl)-6-methyl-3-piperidinecarboxamide;
(3S,6R)-1-[2-Amino-6-(3-amino-1H-indazol-6-yl)-4-pyrimidinyl]-6-methyl-N-(2-methylcyclohexyl)-3-piperidinecarboxamide;
6-[6-[(2R,5R)-2,5-Dimethyl-4-morpholinyl]-2-(methylamino)-4-pyrimidinyl]-1H-indazol-3-amine;
6-{2-Amino-6-[(3R)-3-(1-methylethyl)-4-morpholinyl]-4-pyrimidinyl}-1H-indazol-3-amine;
6-{2-Amino-6-[(3R)-3-(1-methylethyl)-4-morpholinyl]-4-pyrimidinyl}-4-(methyloxy)-1H-indazol-3-amine;
6-{2-Amino-6-[(3R)-3-(1-methylethyl)-4-morpholinyl]-4-pyrimidinyl}-4-(ethyloxy)-1H-indazol-3-amine;
6-{2-Amino-6-[(3R)-3-methyl-4-morpholinyl]-4-pyrimidinyl}-4-(methyloxy)-1H-indazol-3-amine;
1,1-Dimethylethyl{(3R)-1-[2-amino-6-(3-amino-1H-indazol-6-yl)-4-pyrimidinyl]-3-piperidinyl}carbamate;
1,1-Dimethylethyl{(3R)-1-[6-(3-amino-1H-indazol-6-yl)-2-(methylamino)-4-pyrimidinyl]-3-piperidinyl}carbamate;
1,1-Dimethylethyl{(3R)-1-[6-[3-amino-4-(methyloxy)-1H-indazol-6-yl]-2-(methylamino)-4-pyrimidinyl]-3-piperidinyl}carbamate;
6-{2-(Methylamino)-6-[(2S)-2-(trifluoromethyl)-1-pyrrolidinyl]-4-pyrimidinyl}-4-(methyloxy)-1H-indazol-3-amine;
6-{2-(Methylamino)-6-[(2S)-2-(trifluoromethyl)-1-pyrrolidinyl]-4-pyrimidinyl}-1H-indazol-3-amine;
N-{(3R)-1-[6-(3-Amino-1H-indazol-6-yl)-2-(methylamino)-4-pyrimidinyl]-3-pipendinyl}benzamide;
Phenylmethyl{(3R)-1-[2-amino-6-(3-amino-1H-indazol-6-yl)-4-pyrimidinyl]-3-piperidinyl}carbamate;
Cyclopentyl{(3R)-1-[2-amino-6-(3-amino-1H-indazol-6-yl)-4-pyrimidinyl]-3-piperidinyl}carbamate;
Cyclobutyl{(3R)-1-[2-amino-6-(3-amino-1H-indazol-6-yl)-4-pyrimidinyl]-3-piperidinyl}carbamate;
Cyclohexyl{(3R)-1-[2-amino-6-(3-amino-1H-indazol-6-yl)-4-pyrimidinyl]-3-piperidinyl}carbamate;
3-{(3R)-1-[2-Amino-6-(3-amino-1H-indazol-6-yl)-4-pyrimidinyl]-3-piperidinyl}-1,3-oxazolidin-2-one;
1,1-Dimethylethyl{(3R,5R)-1-[2-amino-6-(3-amino-1H-indazol-6-yl)-4-pyrimidinyl]-5-methyl-3-piperidinyl}carbamate;
3-{(3R,5R)-1-[2-Amino-6-(3-amino-1H-indazol-6-yl)-4-pyrimidinyl]-5-methyl-3-piperidinyl}-1,3-oxazolidin-2-one;
1,1-Dimethylethyl((3R,5R)-1-{2-amino-6-[3-amino-4-(methyloxy)-1H-indazol-6-yl]-4-pyrimidinyl}-5-methyl-3-piperidinyl)carbamate;
1,1-Dimethylethyl{(3R,5R)-1-[6-(3-amino-1H-indazol-6-yl)-2-(methylamino)-4-pyrimidinyl]-5-methyl-3-piperidinyl}carbamate;
1,1-Dimethylethyl{(3R,5R)-1-[6-[3-amino-4-(methyloxy)-1H-indazol-6-yl]-2-(methylamino)-4-pyrimidinyl]-5-methyl-3-piperidinyl}carbamate;
1-Methylethyl{(3R)-1-[2-amino-6-(3-amino-1H-indazol-6-yl)-4-pyrimidinyl]-3-piperidinyl}carbamate;
6-[6-[(2R)-2-Ethyl-1-pyrrolidinyl]-2-(methylamino)-4-pyrimidinyl]-4-(methyloxy)-1H-indazol-3-amine;
6-[6-[(2R)-2-Ethyl-1-pyrrolidinyl]-2-(methylamino)-4-pyrimidinyl]-4-(methylthio)-1H-indazol-3-amine;
4-(Ethyloxy)-6-[6-[(2R)-2-ethyl-1-pyrrolidinyl]-2-(methylamino)-4-pyrimidinyl]-1H-indazol-3-amine;
1,1-Dimethylethyl{(3R,5R)-1-[2-amino-6-(3-amino-1H-indazol-6-yl)-4-pyrimidinyl]-5-methyl-3-piperidinyl}methylcarbamate; and
1-[2-amino-6-(3-amino-1H-indazol-6-yl)-4-pyrimidinyl]-L-prolinamide;
or a salt thereof including a pharmaceutically acceptable salt thereof.

Included among the presently invented compounds of Formula (I) are:
6-(2-Amino-6-methyl-4-pyrimidinyl)-1H-indazol-3-amine;
6-{2-Amino-6-[(2R)-2-ethyl-1-pyrrolidinyl]-4-pyrimidinyl}-1H-indazol-3-amine;
or a salt thereof including a pharmaceutically acceptable salt thereof.

Included among the presently invented compounds of Formula (I) are:
(2S,5R)-4-[2-Amino-6-(3-amino-1H-indazol-6-yl)-4-pyrimidinyl]-5-methyl-N-phenyl-2-morpholinecarboxamide;
6-{2-Amino-6-[(3R)-3-ethyl-4-morpholinyl]-4-pyrimidinyl}-1H-indazol-3-amine;
6-{2-Amino-6-[(3R)-3-methyl-4-morpholinyl]-4-pyrimidinyl}-1H-indazol-3-amine;
(3S,6R)-1-[6-(3-Amino-1H-indazol-6-yl)-2-(methylamino)-4-pyrimidinyl]-N-cyclohexyl-6-methyl-3-piperidinecarboxamide;
(3S,6R)-1-[6-(3-Amino-1H-indazol-6-yl)-2-(methylamino)-4-pyrimidinyl]-6-methyl-N-(phenylmethyl)-3-piperidinecarboxamide;
(3S,6R)—N-Cyclohexyl-6-methyl-1-[2-(methylamino)-6-(3-methyl-1H-indazol-6-yl)-4-pyrimidinyl]-3-piperidinecarboxamide;
(3S,6R)-1-[6-(3-Amino-4-fluoro-1H-indazol-6-yl)-2-(methylamino)-4-pyrimidinyl]-N-cyclohexyl-6-methyl-3-piperidinecarboxamide;
Cis-1,1-dimethylethyl{(1-[2-amino-6-(3-amino-1H-indazol-6-yl)-4-pyrimidinyl]-6-methyl-3-piperidinyl}carbamate;
Cis-cyclopentyl{1-[2-amino-6-(3-amino-1H-indazol-6-yl)-4-pyrimidinyl]-6-methyl-3-piperidinyl}carbamate;
(3S,6R)-1-[2-amino-6-(3-amino-1H-indazol-6-yl)-4-pyrimidinyl]-N-cyclopentyl-6-methyl-3-piperidinecarboxamide;
(3S,6R)-1-[2-Amino-6-(3-amino-1H-indazol-6-yl)-4-pyrimidinyl]-6-methyl-N-(2-phenylethyl)-3-piperidinecarboxamide;
1,1-Dimethylethyl{(3R,6S)-1-[2-amino-6-(3-amino-1H-indazol-6-yl)-4-pyrimidinyl]-6-methyl-3-piperidinyl}carbamate;
(2S,5R)-4-[6-(3-Amino-1H-indazol-6-yl)-2-(methylamino)-4-pyrimidinyl]-5-methyl-N-(phenylmethyl)-2-morpholinecarboxamide;
(2S,5R)-4-[2-Amino-6-(3-amino-1H-indazol-6-yl)-4-pyrimidinyl]-N-cyclohexyl-5-ethyl-2-morpholinecarboxamide;
6-[6-[(3R)-3-Ethyl-4-morpholinyl]-2-(methylamino)-4-pyrimidinyl]-1H-indazol-3-amine;
N⁴-Cyclopentyl-6-[6-[(3R)-3-ethyl-4-morpholinyl]-2-(methylamino)-4-pyrimidinyl]-1H-indazole-3,4-diamine;
6-[6-[(3R)-3-Ethyl-4-morpholinyl]-2-(methylamino)-4-pyrimidinyl]-4-(ethyloxy)-1H-indazol-3-amine;
6-{2-Amino-6-[(3R)-3-(1-methylethyl)-4-morpholinyl]-4-pyrimidinyl}-4-(ethyloxy)-1H-indazol-3-amine;
6-{2-Amino-6-[(3R)-3-methyl-4-morpholinyl]-4-pyrimidinyl}-4-(methyloxy)-1H-indazol-3-amine;
1,1-Dimethylethyl{(3R)-1-[6-[3-amino-4-(methyloxy)-1H-indazol-6-yl]-2-(methylamino)-4-pyrimidinyl]-3-piperidinyl}carbamate;
Cyclobutyl{(3R)-1-[2-amino-6-(3-amino-1H-indazol-6-yl)-4-pyrimidinyl]-3-piperidinyl}carbamate;
3-{(3R)-1-[2-Amino-6-(3-amino-1H-indazol-6-yl)-4-pyrimidinyl]-3-piperidinyl}-1,3-oxazolidin-2-one;
1,1-Dimethylethyl{(3R,5R)-1-[2-amino-6-(3-amino-1H-indazol-6-yl)-4-pyrimidinyl]-5-methyl-3-piperidinyl}carbamate;
1,1-Dimethylethyl((3R,5R)-1-{2-amino-6-[3-amino-4-(methyloxy)-1H-indazol-6-yl]-4-pyrimidinyl}-5-methyl-3-piperidinyl)carbamate;
1-Methylethyl{(3R)-1-[2-amino-6-(3-amino-1H-indazol-6-yl)-4-pyrimidinyl]-3-piperidinyl}carbamate; and
1,1-Dimethylethyl{(3R,5R)-1-[2-amino-6-(3-amino-1H-indazol-6-yl)-4-pyrimidinyl]-5-methyl-3-piperidinyl}methylcarbamate;
or a salt thereof including a pharmaceutically acceptable salt thereof.

Included in the presently invented compounds of Formula (I) are compounds of Formula (IA):

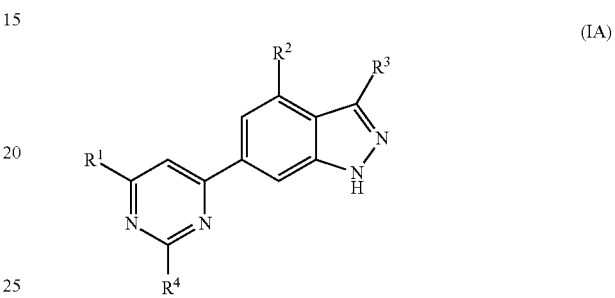

(IA)

wherein:
$R^1$ is H, $C_1$-$C_6$ alkyl, $C_1$-$C_6$ alkoxy, $C_1$-$C_6$ mercapto, —N($R^5$)($R^6$), phenyl optionally substituted with one to three $R^7$, heteroaryl optionally substituted with one to three $R^7$, or heterocycloalkyl optionally substituted with one to three $R^8$;
$R^5$ is H or $C_1$-$C_3$ alkyl;
$R^6$ is H, phenyl optionally substituted by one to three $R^7$, $C_3$-$C_7$ cycloalkyl optionally substituted with one to three $R^8$, or $C_1$-$C_6$ alkyl optionally substituted with one $R^9$;
$R^9$ is phenyl optionally substituted with one to three $R^7$, heteroaryl optionally substituted with one to three $R^7$, or $C_3$-$C_7$ cycloalkyl optionally substituted with one or three $R^8$;
$R^2$ is H, halo, —N($R^{10}$)—($CH_2$)$_n$—$R^{11}$, —O—($CH_2$)$_n$—$R^{11}$, or —S—($CH_2$)$_n$—$R^{11}$;
$R^{10}$ is H or $C_1$-$C_3$ alkyl;
$R^{11}$ is H, $CF_3$, phenyl optionally substituted with one to three $R^7$, phenoxy optionally substituted with one to three $R^7$, or heteroaryl optionally substituted with one to three $R^7$;
n is 1, 2, or 3;
$R^3$ is H, $NH_2$, or $C_1$-$C_3$ alkyl;
$R^4$ is $NH_2$ or $NHCH_3$;
each $R^7$ is independently selected from the group consisting of halo, cyano, hydroxy, $C_1$-$C_3$ alkyl, and $C_1$-$C_3$ alkoxy; and
each $R^8$ is independently selected from the group consisting of hydroxy, $C_1$-$C_6$ alkyl, C(O)—$C_1$-$C_6$ alkyl, and benzyl.

This invention also relates to salts including pharmaceutically acceptable salts of the compounds of Formula (IA).

According to the compounds of Formula (IA) suitably $R^1$ is $C_1$-$C_6$ alkyl. Suitably $R^1$ is methyl.
According to the compounds of Formula (IA) suitably $R^1$ is $C_1$-$C_6$ alkoxy. Suitably $R^1$ is methoxy.
According to the compounds of Formula (IA) suitably $R^1$ is $C_1$-$C_6$ mercapto. Suitably $R^1$ is thiomethyl.
According to the compounds of Formula (IA) suitably $R^1$ is —N($R^5$)($R^6$) wherein $R^5$ is H and $R^6$ is as defined in Formula (IA) above. Suitably $R^6$ is phenyl, cyclopropyl, cyclobutyl, cyclopentyl, cyclohexyl, or $C_1$-$C_6$ alkyl optionally substituted by phenyl or cyclohexyl.

According to the compounds of Formula (IA) suitably $R^1$ is $NH_2$.

According to the compounds of Formula (IA) suitably $R^1$ is phenyl optionally substituted with one to three $R^7$. Suitably $R^1$ is unsubstituted phenyl.

According to the compounds of Formula (IA) suitably $R^1$ is heterocycloalkyl optionally substituted with one to three $R^8$. Suitably $R^1$ is azetidinyl, pyrrolidinyl, piperidinyl, morpholinyl, thiomorpholinyl, or hexahydro-1H-azepine each of which is optionally substituted with one to three $R^8$.

According to the compounds of Formula (IA) suitably $R^2$ is H, —N($R^{10}$)—($CH_2$)$_n$—$R^{11}$, or —O—($CH_2$)$_n$—$R^{11}$;
wherein:
$R^{10}$ is H or $C_1$-$C_3$ alkyl;
$R^{11}$ is H, $CF_3$, phenyl optionally substituted with one to three $R^7$, phenoxy optionally substituted with one to three $R^7$, or heteroaryl optionally substituted with one to three $R^7$; and
n is 1, 2, or 3.

According to the compounds of Formula (IA) suitably $R^2$ is —N($R^{10}$)—($CH_2$)$_n$—$R^{11}$ wherein $R^{10}$ is H; $R^{11}$ is H, $CF_3$, phenyl optionally substituted with one to three $R^7$, unsubstituted phenoxy, or heteroaryl optionally substituted with one to three $R^7$; and n is 1, 2, or 3. Suitably $R^{11}$ is phenyl optionally substituted with one to three $R^7$, unsubstituted phenoxy, pyrazolyl optionally substituted with one to three $R^7$, or pyridinyl optionally substituted with one to three $R^7$; and n is 1, 2, or 3.

According to the compounds of Formula (IA) suitably $R^2$ is or —O—($CH_2$)$_n$—$R^{11}$ wherein $R^{11}$ is H, $CF_3$, phenyl optionally substituted with one to three $R^7$, or phenoxy optionally substituted with one to three $R^7$; and n is 1, 2, or 3.

The skilled artisan will appreciate that salts, including pharmaceutically acceptable salts, of the compounds according to Formula I may be prepared. Indeed, in certain embodiments of the invention, salts including pharmaceutically-acceptable salts of the compounds according to Formula I may be preferred over the respective free base. Accordingly, the invention is further directed to salts, including pharmaceutically-acceptable salts, of the compounds according to Formula I.

The salts of the compounds of the invention are readily prepared by those of skill in the art.

The pharmaceutically acceptable salts of the compounds of the invention are readily prepared by those of skill in the art.

The compounds according to Formula I may contain one or more asymmetric center (also referred to as a chiral center) and may, therefore, exist as individual enantiomers, diastereomers, or other stereoisomeric forms, or as mixtures thereof. Chiral centers, such as chiral carbon atoms, may also be present in a substituent such as an alkyl group. Where the stereochemistry of a chiral center present in Formula I, or in any chemical structure illustrated herein, if not specified the structure is intended to encompass all individual stereoisomers and all mixtures thereof. Thus, compounds according to Formula I containing one or more chiral center may be used as racemic mixtures, enantiomerically enriched mixtures, or as enantiomerically pure individual stereoisomers.

The compounds according to Formula I may also contain double bonds or other centers of geometric asymmetry. Where the stereochemistry of a center of geometric asymmetry present in Formula I, or in any chemical structure illustrated herein, is not specified, the structure is intended to encompass the trans (E) geometric isomer, the cis (Z) geometric isomer, and all mixtures thereof. Likewise, all tautomeric forms are also included in Formula I whether such tautomers exist in equilibrium or predominately in one form.

The compounds of Formula I or salts, including pharmaceutically acceptable salts, thereof may exist in solid or liquid form. In the solid state, the compounds of the invention may exist in crystalline or noncrystalline form, or as a mixture thereof. For compounds of the invention that are in crystalline form, the skilled artisan will appreciate that pharmaceutically acceptable solvates may be formed wherein solvent molecules are incorporated into the crystalline lattice during crystallization. Solvates may involve nonaqueous solvents such as ethanol, isopropanol, DMSO, acetic acid, ethanolamine, and ethyl acetate, or they may involve water as the solvent that is incorporated into the crystalline lattice. Solvates wherein water is the solvent that is incorporated into the crystalline lattice are typically referred to as "hydrates." Hydrates include stoichiometric hydrates as well as compositions containing vaiable amounts of water. The invention includes all such solvates.

The skilled artisan will further appreciate that certain compounds of Formula I or salts, including pharmaceutically acceptable salts, thereof that exist in crystalline form, including the various solvates thereof, may exhibit polymorphism (i.e. the capacity to occur in different crystalline structures). These different crystalline forms are typically known as "polymorphs." The invention includes all such polymorphs. Polymorphs have the same chemical composition but differ in packing, geometrical arrangement, and other descriptive properties of the crystalline solid state. Polymorphs, therefore, may have different physical properties such as shape, density, hardness, deformability, stability, and dissolution properties. Polymorphs typically exhibit different melting points, IR spectra, and X-ray powder diffraction patterns, which may be used for identification. The skilled artisan will appreciate that different polymorphs may be produced, for example, by changing or adjusting the reaction conditions or reagents, used in making the compound. For example, changes in temperature, pressure, or solvent may result in polymorphs. In addition, one polymorph may spontaneously convert to another polymorph under certain conditions.

Another embodiment of the present invention is a compound according to Formula (IIIA)

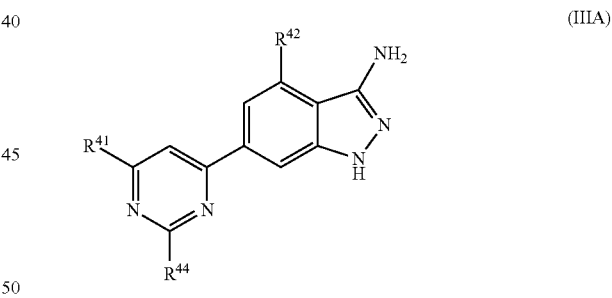

wherein $R^{41}$, $R^{42}$, and $R^{44}$ are as defined in Formula (III) above.

Another embodiment of the present invention is a compound according to Formula (IIIB)

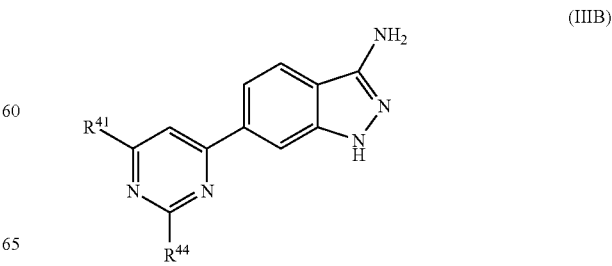

wherein $R^{41}$ and $R^{44}$ are as defined in Formula (III) above.

Another embodiment of the present invention is a compound according to Formula (IIIC)

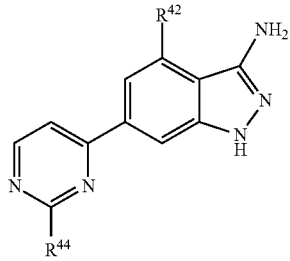

(IIIC)

wherein $R^{42}$ and $R^{44}$ are as defined in Formula (III) above.

Another embodiment of the present invention is a compound according to Formula (IIID)

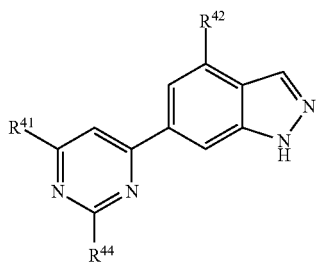

(IIID)

wherein $R^{41}$, $R^{42}$ and $R^{44}$ are as defined in Formula (III) above.

Another embodiment of the present invention is a compound according to Formula (IIIE)

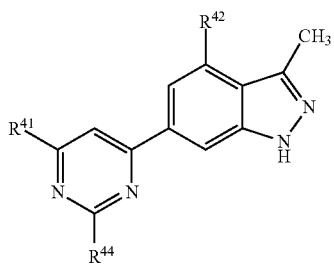

(IIIE)

wherein $R^{41}$, $R^{42}$ and $R^{44}$ are as defined in Formula (III) above.

Another embodiment of the present invention is a compound according to Formula (IIIF)

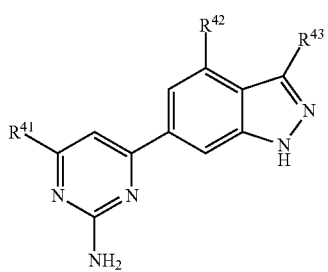

(IIIF)

wherein $R^{41}$, $R^{42}$, and $R^{43}$ are as defined in Formula III above.

Another embodiment of the present invention is a compound according to Formula (IIIG)

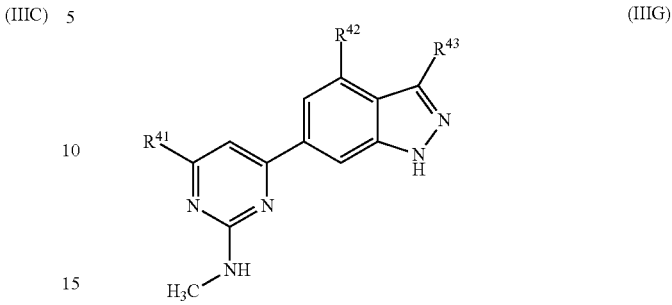

(IIIG)

wherein $R^{41}$, $R^{42}$, and $R^{43}$ are as defined in Formula III above.

DEFINITIONS

"Alkyl" refers to a hydrocarbon chain having the specified number of member atoms. For example, $C_1$-$C_6$ alkyl refers to an alkyl group having from 1 to 6 member atoms. Alkyl groups may be optionally substituted with one or more substituents as defined herein. Alkyl groups may be saturated, unsaturated, straight or branched. Representative branched alkyl groups have one, two, or three branches. Alkyl includes methyl, ethyl, ethylene, propyl (n-propyl and isopropyl), butene, butyl (n-butyl, isobutyl, and t-butyl), pentyl (n-pentyl, isopentyl, and neopentyl), and hexyl.

"Alkoxy" refers to an —O-alkyl group wherein alkyl is a saturated hydrocarbon chain having the specified number of member atoms. For example, $C_1$-$C_6$ alkoxy refers to an alkoxy group having from 1 to 6 member atoms. Alkoxy groups may be straight or branched. Representative branched alkoxy groups have one, two, or three branches. Examples of such groups include methoxy, ethoxy, propoxy, butoxy, pentoxy and hexoxy.

"Aryl and Ar" refers to an aromatic hydrocarbon ring. Aryl groups are monocyclic ring systems or bicyclic ring systems. Monocyclic aryl ring refers to phenyl. Bicyclic aryl rings refer to napthyl and rings wherein phenyl is fused to a cycloalkyl or cycloalkenyl ring having 5, 6, or 7 member atoms. Aryl groups may be optionally substituted with one or more substituents as defined herein.

"Cycloalkyl" refers to a saturated or unsaturated non aromatic hydrocarbon ring having the specified number of member atoms. Cycloalkyl groups are monocyclic ring systems or a monocyclic ring fused with an aryl ring. For example, $C_3$-$C_7$ cycloalkyl refers to a cycloalkyl group having from 3 to 7 member atoms. For example, 2,3-dihydro-1H-indene would be a $C_5$cycloalkyl ring fused with an aryl ring. Cycloalkyl groups may be optionally substituted with one or more substituents as defined herein. Examples of cycloalkyl as used herein includes cyclopropyl, cyclobutyl, cyclopentyl, cyclohexyl, 2,3-dihydro-1H-indene, cyclobutenyl, cyclopentenyl and cyclohexenyl.

"Halo" refers to the halogen radicals fluoro, chloro, bromo, and iodo.

"Heteroaryl" refers to an aromatic ring containing from 1 to 4 heteroatoms as member atoms in the ring. Heteroaryl groups containing more than one heteroatom may contain different heteroatoms. Heteroaryl groups may be optionally substituted with one or more substituents as defined herein. Heteroaryl groups are monocyclic ring systems or are fused, spiro, or bridged bicyclic ring systems. Monocyclic heteroaryl rings have 5 or 6 member atoms. Bicyclic heteroaryl rings have from 8 to 11 member atoms. Bicyclic heteroaryl rings include those rings wherein a monocyclic heteroaryl ring and a phenyl, or a monocyclic cycloalkyl, heterocycloalkyl, or heteroaryl ring are attached forming a fused, spiro, or bridged bicyclic ring system. Heteroaryl includes pyrrolyl, pyrazolyl, imidazolyl, oxazolyl, isoxazolyl, thiazolyl, isothiazolyl, furanyl, furazanyl, thienyl, triazolyl, pyridinyl, pyrimidinyl, pyridazinyl, pyrazinyl, triazinyl, tetrazinyl, indolyl, isoindolyl, indolizinyl, indazolyl, purinyl, quinolinyl, isoquinolinyl, quinoxalinyl, quinazolinyl, pteridinyl, cinnolinyl, azabenzimidazolyl, tetrahydrobenzimidazolyl, benzimidazolyl, benopyranyl, benzoxazolyl, benzofuranyl, isobenzofuranyl, benzothiazolyl, benzothienyl, imidazo[4.5-c]pyridine, imidazo[4.5-b]pyridine, furopyridinyl and napthyridinyl.

"Heteroatom" refers to a nitrogen, sulphur or oxygen atom.

"Heterocycloalkyl" refers to a saturated or unsaturated ring containing from 1 to 4 heteroatoms as member atoms in the ring. However, heterocycloalkyl rings are not aromatic. Heterocycloalkyl groups containing more than one heteroatom may contain different heteroatoms. Heterocycloalkyl groups may be optionally substituted with one or more substituents as defined herein. Heterocycloalkyl groups are monocyclic ring systems or a monocyclic ring fused with and aryl ring or to a heteroaryl ring having from 4 to 11 member atoms. In certain embodiments, heterocycloalkyl is saturated. In other embodiments, heterocycloalkyl is unsaturated but not aromatic. Heterocycloalkyl includes pyrrolidinyl, tetrahydrofuranyl, dihydrofuranyl, pyranyl, tetrahydropyranyl, dihydropyranyl, tetrahydrothienyl, pyrazolidinyl, oxazolidinyl, thiazolidinyl, piperidinyl, homopiperidinyl, piperazinyl, morpholinyl, thiamorpholinyl, 1,3-dioxolanyl, 1,3-dioxanyl, 1,4-dioxanyl, 1,3-oxathiolanyl, 1,3-oxathianyl, 1,3-dithianyl, 1,3oxazolidin-2-one, hexahydro-1H-azepin, 4,5,6,7,tetrahydro-1H-benzimidazol and azetidinyl.

"Mercapto" refers to the group —S-alkyl group wherein alkyl is a saturated hydrocarbon chain having the specified number of member atoms. For example, $C_1$-$C_6$ mercapto refers to an mercapto group having from 1 to 6 member atoms. Mercapto groups may be straight or branched. Representative branched alkoxy groups have one, two, or three branches. Examples of mercapto groups include thiomethyl, thioethyl, methylthio and ethylthio.

"Pharmaceutically acceptable" refers to those compounds, materials, compositions, and dosage forms which are, within the scope of sound medical judgment, suitable for use in contact with the tissues of human beings and animals without excessive toxicity, irritation, or other problem or complication, commensurate with a reasonable benefit/risk ratio.

As used herein the symbols and conventions used in these processes, schemes and examples are consistent with those used in the contemporary scientific literature, for example, the *Journal of the American Chemical Society* or the *Journal of Biological Chemistry*. Standard single-letter or three-letter abbreviations are generally used to designate amino acid residues, which are assumed to be in the L-configuration unless otherwise noted. Unless otherwise noted, all starting materials were obtained from commercial suppliers and used without further purification. Specifically, the following abbreviations may be used in the examples and throughout the specification:

Ac (acetyl);
$Ac_2O$ (acetic anhydride);
ACN (acetonitrile);
AIBN (azobis(isobutyronitrile));
BINAP (2,2'-bis(diphenylphosphino)-1,1'-binaphthyl);
BMS (borane-dimethyl sulphide complex);
Bn (benzyl);
Boc (tert-Butoxycarbonyl);
$Boc_2O$ (di-tert-butyl dicarbonate);
BOP (Benzotriazole-1-yl-oxy-tris-(dimethylamino)-phosphonium hexafluorophosphate);
CAN (cerric ammonium nitrate);
Cbz (benzyloxycarbonyl);
CSI (chlorosulfonyl isocyanate);
DABCO (1,4-Diazabicyclo[2.2.2]octane);
DAST ((Diethylamino)sulfur trifluoride);
DBU (1,8-Diazabicyclo[5.4.0]undec-7-ene);
DCC (Dicyclohexyl Carbodiimide);
DDQ (2,3-Dichloro-5,6-dicyano-1,4-benzoquinone);
ATP (adenosine triphosphate);
Bis-pinacolatodiboron (4,4,4',4',5,5,5',5'-Octamethyl-2,2'-bi-1,3,2-dioxaborolane);
BSA (bovine serum albumin);
C18 (refers to 18-carbon alkyl groups on silicon in HPLC stationary phase)
$CH_3CN$ (acetonitrile);
Cy (cyclohexyl);
DCM (dichloromethane);
DIPEA (Hünig's base, N-ethyl-N-(1-methylethyl)-2-propanamine);
DMAP (4-dimethylaminopyridine);
DME (1,2-dimethoxyethane);
DMF (N,N-dimethylformamide);
DMSO (dimethylsulfoxide);
DPPA (diphenyl phosphoryl azide);
EDC (N-(3-dimethylaminopropyl)-N' ethylcarbodiimide);
EDTA (ethylenediaminetetraacetic acid);
EtOAc (ethyl acetate);
EtOH (ethanol);
$Et_2O$ (diethyl ether);
HEPES (4-(2-hydroxyethyl)-1-piperazine ethane sulfonic acid);
HATU (O-(7-Azabenzotriazol-1-yl)-N,N,N',N'-tetramethyluronium hexafluorophosphate);
HOAt (1-hydroxy-7-azabenzotriazole);
HOBt (1-hydroxybenzotriazole);
HOAc (acetic acid);
HPLC (high pressure liquid chromatography);
HMDS (hexamethyldisilazide);
Hunig's Base (N,N-Diisopropylethylamine);
IPA (isopropyl alcohol);
KHMDS (potassium hexamethyldisilazide);
LAH (lithium aluminum hydride);
LDA (lithium diisopropylamide);
LHMDS (lithium hexamethyldisilazide)
MeOH (methanol);
MTBE (methyl tert-butyl ether);
mCPBA (m-chloroperbezoic acid);
NaHMDS (sodium hexamethyldisilazide);
NBS (N-bromosuccinimide);
PE (petroleum ether);
$Pd_2(dba)_3$ (Tris(dibenzylideneacetone)dipalladium(0);
$Pd(dppf)Cl_2$ ([1,1'-Bis(diphenylphosphino)ferrocene]dichloropalladium(II));
PyBOP (benzotriazol-1-yl-oxytripyrrolidinophosphonium hexafluorophosphate);

PyBrOP (bromotripyrrolidinophosphonium hexafluorophosphate);
RPHPLC (reverse phase high pressure liquid chromatography);
SFC (supercritical fluid chromatography);
SGC (silica gel chromatography);
TEA (triethylamine);
TEMPO (2,2,6,6-Tetramethylpiperidine 1-oxyl, free radical);
TFA (trifluoroacetic acid); and
THF (tetrahydrofuran).
All references to ether are to diethyl ether and brine refers to a saturated aqueous solution of NaCl.

Compound Preparation

The compounds according to Formula I are prepared using conventional organic syntheses. A suitable synthetic route is depicted below in the following general reaction schemes.

The skilled artisan will appreciate that if a substituent described herein is not compatible with the synthetic methods described herein, the substituent may be protected with a suitable protecting group that is stable to the reaction conditions. The protecting group may be removed at a suitable point in the reaction sequence to provide a desired intermediate or target compound. Suitable protecting groups and the methods for protecting and de-protecting different substituents using such suitable protecting groups are well known to those skilled in the art. In some instances, a substituent may be specifically selected to be reactive under the reaction conditions used. Under these circumstances, the reaction conditions convert the selected substituent into another substituent that is either useful as an intermediate compound or is a desired substituent in a target compound. All of the starting materials are commercially available or are readily made from commercially available starting materials by those of skill in the art unless otherwise noted in the experimental section.

Dichloropyrimidines 2 are commercially available or may be synthesized using techniques well known in the art. For instance, reaction of commercially available sulfone 1 with a suitable amine such as methylamine in a suitable solvent such as EtOAc and THF from about 0° C. to room temperature provides intermediate 2. Chloropyrimidines 3 are commercially available or may be synthesized using techniques well known in the art. Reaction of dichloropyrimidines 2 with a suitable nucleophile such as a primary or secondary amine in the presence of a suitable base (such as $K_2CO_3$ or DIPEA) at a suitable temperature (typically from about room temperature to about 120° C.) provides intermediate 3. Alternatively, the reaction can be run under microwave condition at temperatures as high as 200° C. This reaction can be performed in a wide variety of solvents such as DMF, THF, EtOH, $CH_3OH$, 1,4-dioxane, etc. In the case of poorly nucleophilic amines such as 2-trifluoromethylamines, their reactivity might not be enough to displace the chloro group on the dichloropyrimidine 2 and an alternative approach to the synthesis of chloropyrimidines 3 might be necessary. An alternative approach for the synthesis of intermediate 3 is also illustrated in Scheme 1. Formation of an amine anion by the reaction of the respective amine with a strong base such as LiHMDS in a suitable solvent such as THF followed by addition of commercially available 2-thiomethyl-4,6-dichloropyrimidine 4 provides intermediate 5. Oxidation of the thiomethyl group with a suitable oxidation agent such as mCPBA or oxone in a suitable solvent such as $CH_2Cl_2$ or $CH_3OH$ respectively provides intermediate 6. Selective displacement of the sulfone functionality with a suitable nucleophile such as methylamine in the presence of a suitable base such as Hunig's base in a solvent such as THF can provide chloropyrimidine intermediate 3.

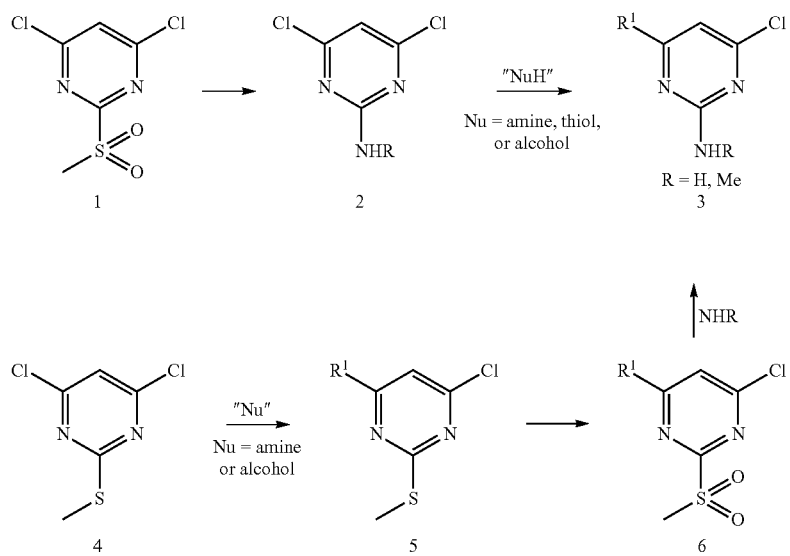

Scheme 1

Scheme 2

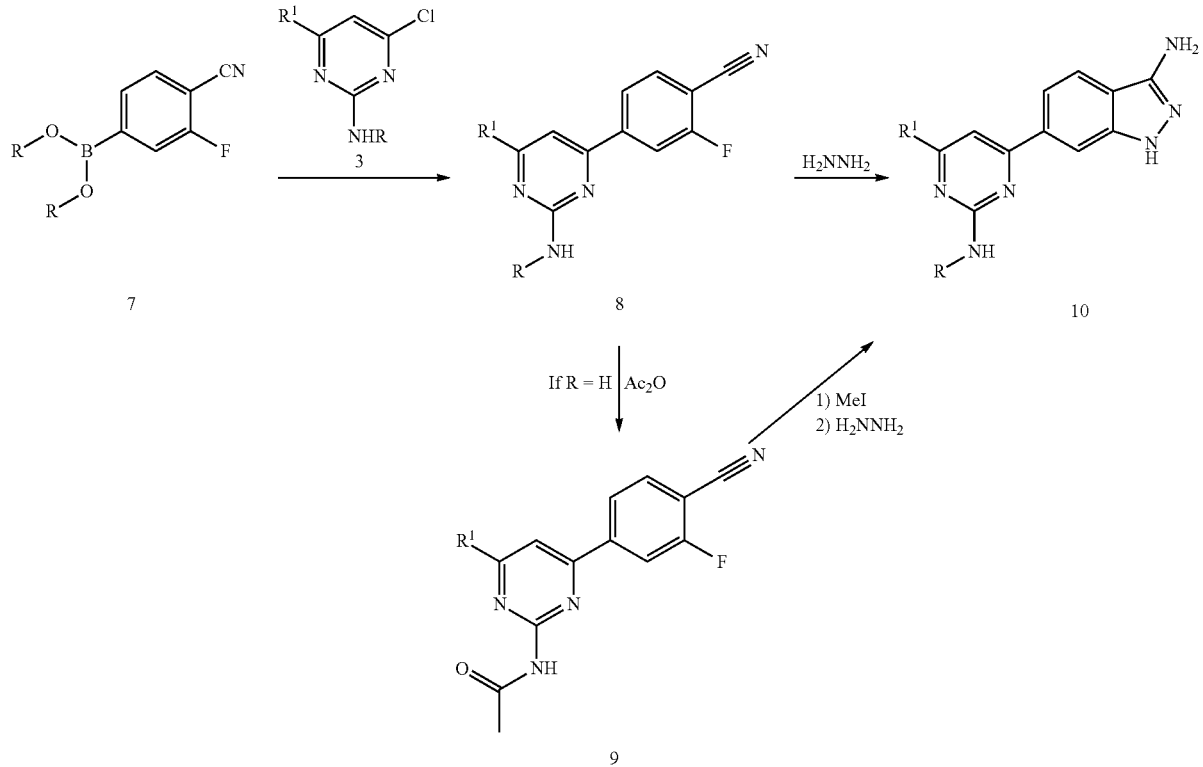

Boron reagent 7 which is commercially available or may be synthesized using techniques well known in the art, can be reacted with chloropyrimidine intermediate 3 under Suzuki coupling conditions to produce intermediate 8, using a palladium catalyst such as Pd(PPh$_3$)$_4$, a base such as saturated aqueous NaHCO$_3$, and a suitable solvent such as dioxane. This coupling reaction is advantageously carried out at elevated temperatures (typically from about 80 to about 100° C., or under microwave conditions). Reaction of intermediate 8 with hydrazine in a suitable solvent such as dioxane or ethanol at an elevated temperature (typically from about 80 to about 120° C.) provides final product 10. Alternatively, the reactions can be performed under microwave conditions. When R=H in compound 8 and the desired final product 10 requires R=Me, an alternative synthetic route can be pursued from intermediate 8. Reaction of intermediate 8 with acetic anhydride as the solvent under reflux conditions provides intermediate 9. If products containing two acetyl groups on the amine are observed, a selective removal of one of the acetyl groups can be done using techniques well known in the art. Alternatively, a separation of the desired intermediate 9 from the by-products can be achieved by purification methods conventional in the art. Methylation of intermediate 9 followed by reaction with hydrazine in a suitable solvent such as dioxane or ethanol at an elevated temperature (typically from about 80 to about 120° C., or under microwave heating up to 200° C.) provides final product 10.

Scheme 3

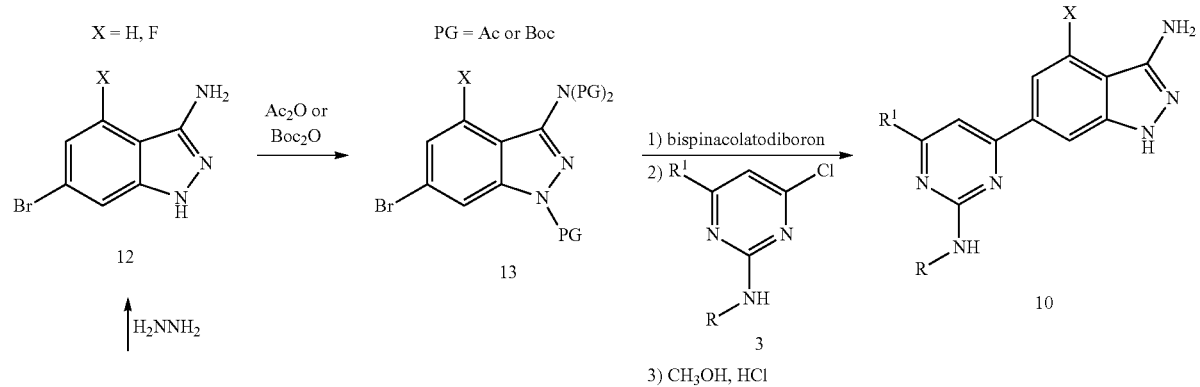

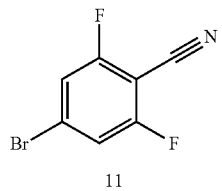

11

An alternative method for preparing final product 10 is illustrated in Scheme 3. 6-Bromoindazoles 12 are commercially available or can be synthesized using techniques well known in the art. For instance, 4-fluoro-6-bromoindazole can be prepared from the reaction of commercially available difluoronitrile 11 with hydrazine at high temperatures or under microwave conditions (about 150° C.) in a suitable solvent such as ethanol. Bromoindazole 12 can be acetylated using acetic anhydride as the solvent under reflux conditions to provide intermediate 13. Alternatively, bromoindazole 12 can be protected with the Boc group instead of the acetyl group using techniques well known in the art such as using $Boc_2O$ in a suitable solvent such as $CH_3CN$ and a suitable catalyst such as DMAP at an elevated temperature (about 80° C.). Bispinacolatodiboron coupling to form the intermediate boronate ester followed by in-situ Suzuki coupling with chloropyrimidine 3 provides an acetylated version or Boc version of final product 10. A final de-acetylation or Boc-deprotection process using techniques well known in the art such as refluxing the intermediate in methanolic HCl provides final product 10. The bispinacolatodiboron coupling can be advantageously carried out at elevated temperatures (typically from about 80 to about 100° C., or under microwave conditions) in the presence of a suitable base such as potassium acetate using a palladium catalyst such as $Pd(dppf)Cl_2$—$CH_2Cl_2$ in a suitable solvent such as dioxane. The boronate intermediate can be either isolated or used directly into the Suzuki coupling by subsequent addition to the reaction mixture of the corresponding chloropyrimidine 3 and a suitable base such as saturated aqueous $NaHCO_3$.

solvent provides the respective sulfoxide and/or sulfone intermediates. Suitable nucleophiles such as primary and secondary amines can then be reacted with the sulfoxide and/or sulfone intermediates at elevated temperatures (~100° C. or higher) in a suitable solvent such as dioxane to provide the final product 15.

Scheme 5

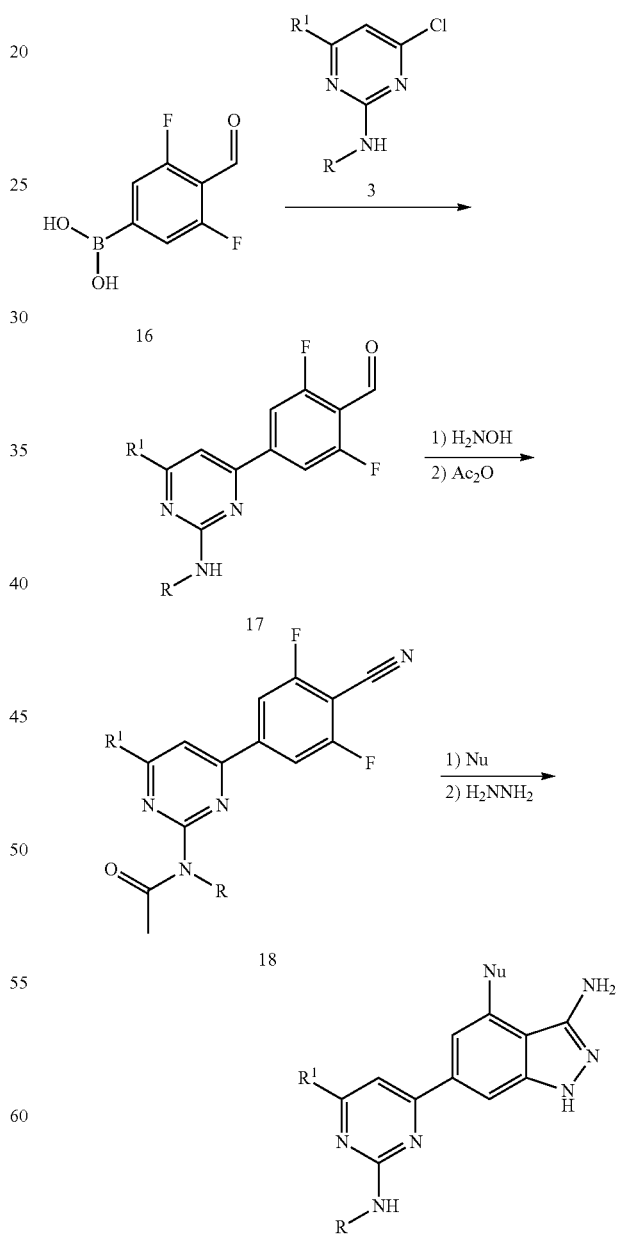

Scheme 4

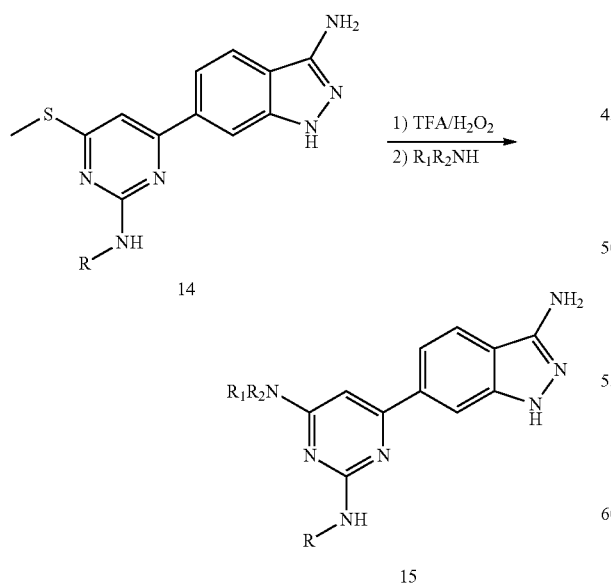

Alternatively, final products of Formula 15 can be prepared from intermediate 14, a compound which can be prepare in a similar fashion by the methods describe in Scheme 2. Reaction of intermediate 14 with hydrogen peroxide in TFA as the Commercially available compound 16 and chloropyrimidine 3 may be advantageously reacted under Suzuki coupling conditions to produce intermediate 17, using a palladium catalyst such as Pd(PPh$_3$)$_4$, a base such as saturated aqueous NaHCO$_3$, and a suitable solvent such as dioxane. This coupling reaction is advantageously carried out at elevated temperatures (typically from about 80 to about 100° C.). Reaction of intermediate 17 with hydroxylamine generates the respective oxime which, upon exposure to acetic anhydride as the solvent under reflux conditions, provides intermediate nitrile 18. Displacement of a fluoride with a suitable nucleophile (Nu) followed by reaction with hydrazine in a suitable solvent such as dioxane or ethanol at an elevated temperature (typically from about 80 to about 120° C., or under microwave conditions) provides final product 19.

aqueous NaHCO$_3$, and a suitable solvent such as dioxane at an elevated temperature (typically from about 80 to about 130° C., or under microwave conditions). Displacement of one fluoride with a suitable nucleophile (Nu) followed reaction with hydrazine in a suitable solvent such as dioxane or ethanol at an elevated temperature (typically from about 80 to about 120° C.) provides final product 19.

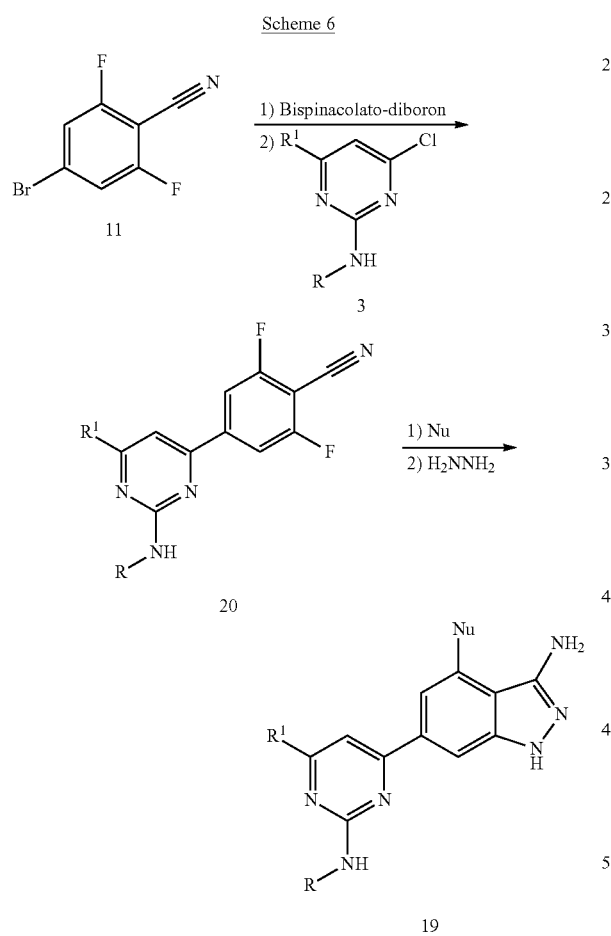

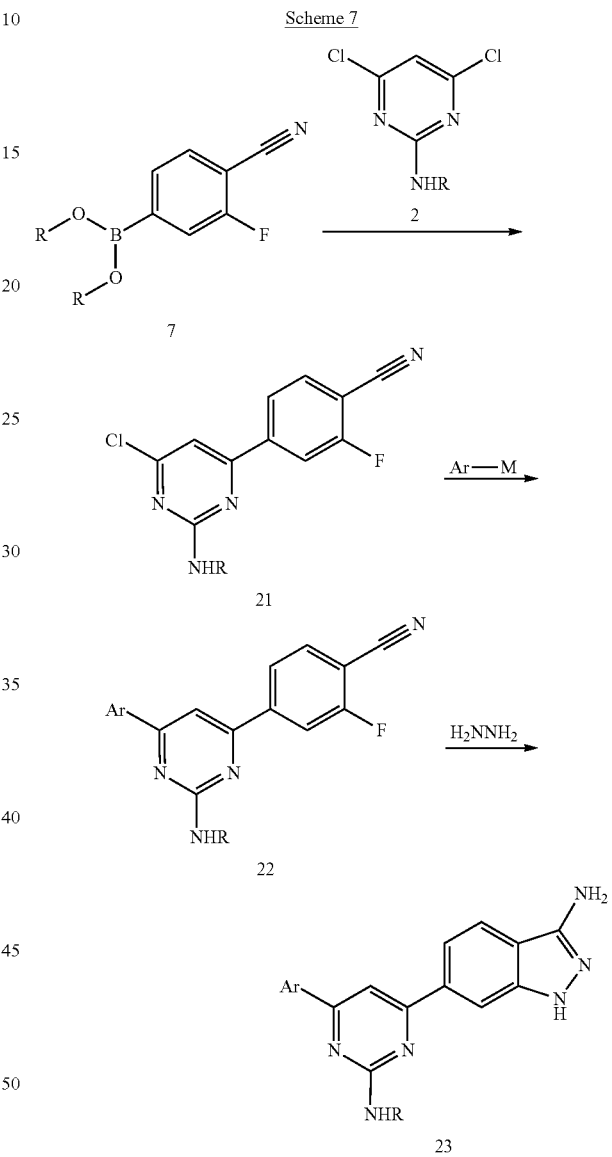

Alternatively, as shown in Scheme 6, final product 19 can be prepared from compound II which is commercially available or may be synthesized using techniques well known in the art. Bispinacolatodiboron coupling to form the intermediate boronate ester followed by Suzuki coupling with chloropyrimidine 3 provides intermediate 20. The bispinacolatodiboron coupling can be advantageously carried out at elevated temperatures (typically from about 80 to about 100° C., or under microwave conditions) in the presence of a suitable base such as potassium acetate using a palladium catalyst such as Pd(dppf)Cl$_2$·CH$_2$Cl$_2$ in a suitable solvent such as dioxane. The Suzuki coupling can be carried out by using a palladium catalyst such as Pd(PPh$_3$)$_4$, a base such as saturated According to Scheme 7, compound 7 and dichloropyrimidine 2 may be advantageously reacted under Suzuki coupling conditions to produce intermediate 21, using a palladium catalyst such as Pd(PPh$_3$)$_4$, a base such as saturated aqueous NaHCO$_3$, and a suitable solvent such as dioxane. This coupling reaction is advantageously carried out at elevated temperatures (typically from about 80 to about 100° C., or under microwave conditions). Metal catalyzed cross coupling reactions with intermediate 21 can be used to generate compounds of Formula 22 which, upon reaction with hydrazine in a suitable solvent such as dioxane or ethanol at an elevated temperature (typically from about 80 to about 120° C., or under microwave conditions), provides final product 23.

Scheme 8

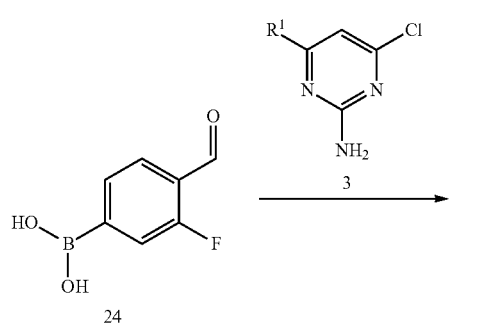

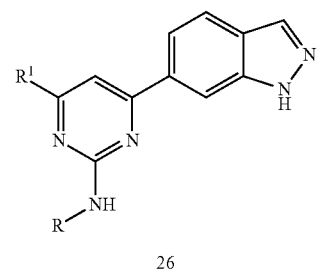

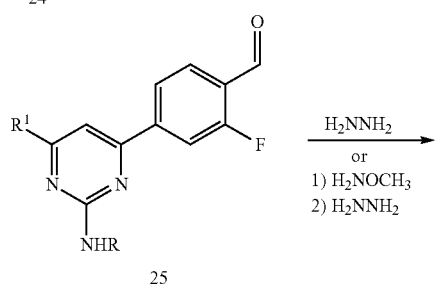

Alternatively, final product 26 can be prepared from the Suzuki coupling of commercially available compound 27 with intermediate 3. The Suzuki coupling can be carried out by using a palladium catalyst such as $Pd_2(dba)_3$, a ligand such as tricyclohexylphosphine, a base such as $K_3PO_4$, and a suitable solvent system such as dioxane/water at elevated temperatures (typically from about 80 to about 160° C.) or microwave conditions.

Scheme 10

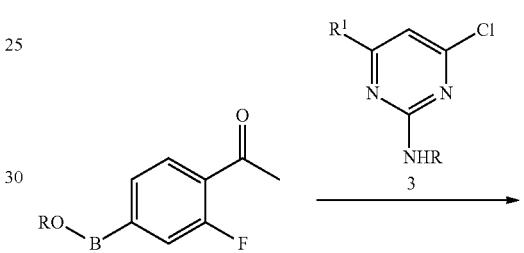

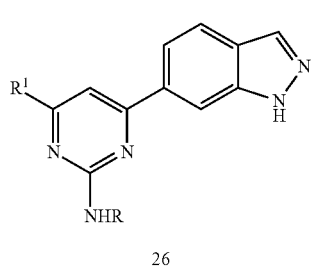

Commercially available compound 24 and chloropyrimidine 3 may be advantageously reacted under Suzuki coupling conditions to produce intermediate 25, using a palladium catalyst such as $Pd(PPh_3)_4$, a base such as saturated aqueous $NaHCO_3$, and a suitable solvent such as dioxane as shown in Scheme 8. This coupling reaction is advantageously carried out at elevated temperatures (typically from about 80 to about 100° C., or under microwave conditions). Reaction of intermediate 25 with hydrazine in a suitable solvent such as dimethoxyethane at an elevated temperature (typically from about 80 to about 120° C.) provides final product 26. Alternatively, intermediate 25 can be reacted with methoxylamine to afford the respective oxime intermediate which, upon treatment with hydrazine in a suitable solvent such as dimethoxyethane at an elevated temperature (typically from about 80 to about 120° C.), provides final product 26.

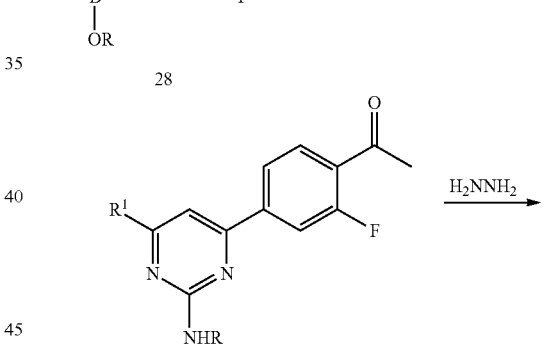

Scheme 9

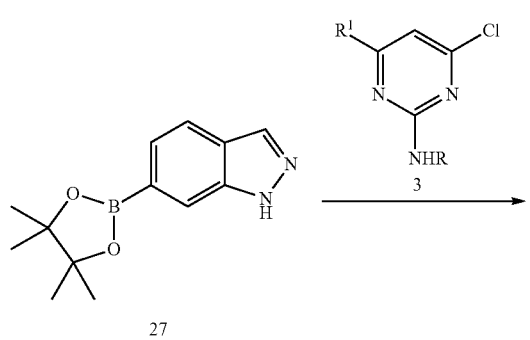

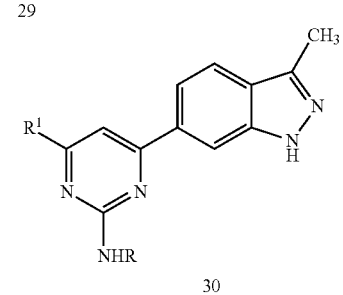

Boron reagent 28 is commercially available or may be synthesized using techniques well known in the art. Suzuki coupling with intermediate 3, using a palladium catalyst such as $Pd(PPh_3)_4$, a base such as saturated aqueous $NaHCO_3$, and a suitable solvent such as dioxane at elevated temperatures (typically from about 80 to about 100° C.) provides intermediate 29. Reaction of 29 with hydrazine in a suitable solvent such as ethanol at an elevated temperature (typically from about 120 to about 180° C.) provides final product 30.

Scheme 11

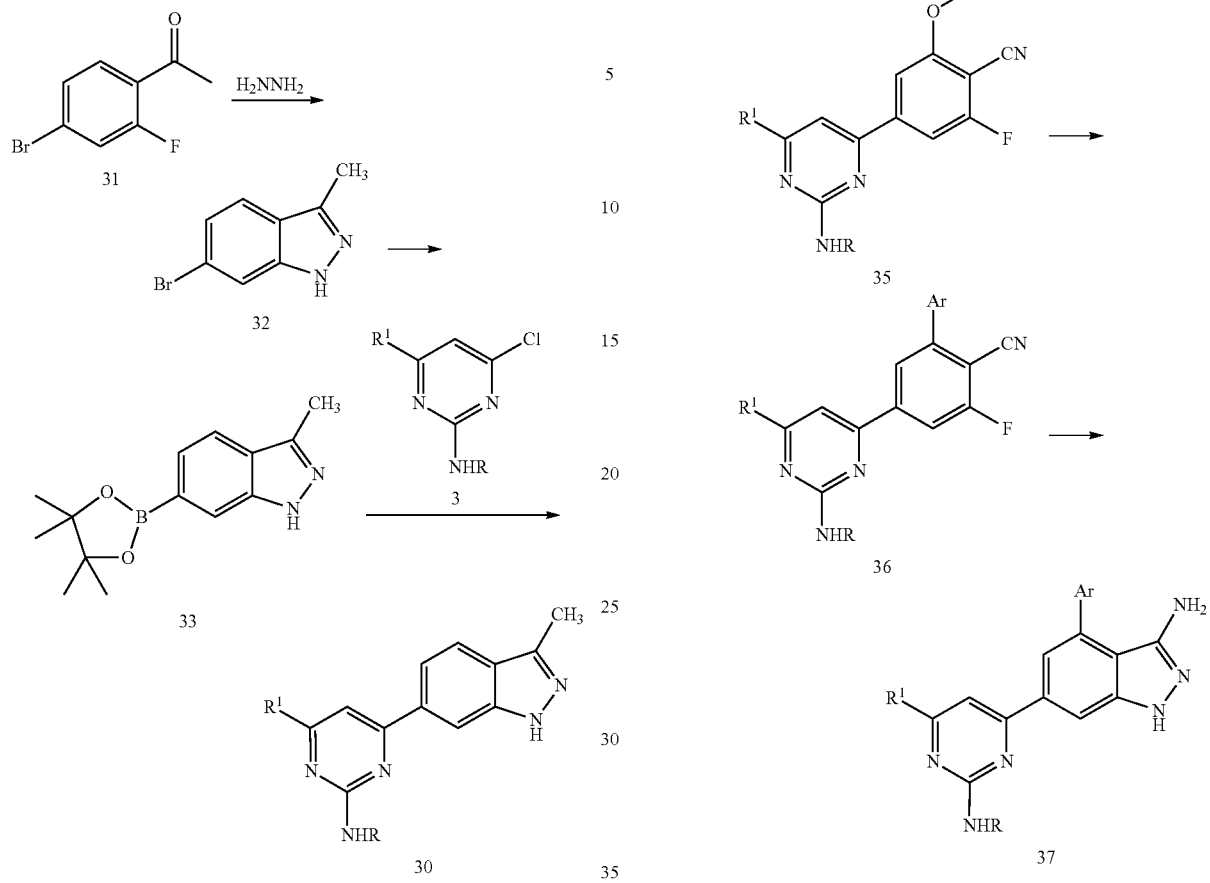

Alternatively, as shown in Scheme 11, final product 30 can be prepared from the Suzuki coupling of chloropyrimidine intermediate 3 with boronate ester intermediate 33, a compound which can be prepared from commercially available compound 31. Reaction of 31 with hydrazine at an elevated temperature (typically from about 120 to about 180° C.) provides compound 32. Bispinacolatodiboron coupling to form the intermediate boronate ester 33 followed by Suzuki coupling with chloropyrimidine 3 provides final product 30. The bispinacolatodiboron coupling can be advantageously carried out at elevated temperatures (typically from about 80 to about 100° C.) in the presence of a suitable base such as potassium acetate using a palladium catalyst such as Pd(dppf)Cl$_2$.CH$_2$Cl$_2$ in a suitable solvent such as dioxane. The Suzuki coupling can be carried out by using a palladium catalyst such as Pd$_2$(dba)$_3$, a ligand such as tricyclohexylphosphine, a base such as K$_3$PO$_4$, and a suitable solvent system such as dioxane/water at elevated temperatures (typically from about 80 to about 120° C., or under microwave conditions).

Scheme 12

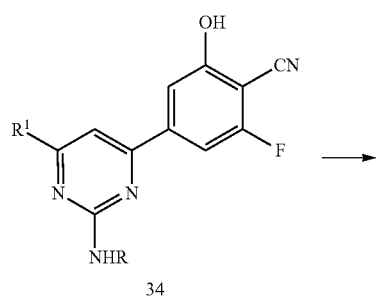

As shown in Scheme 12, intermediate 34 can be prepared in a similar way as described in Scheme 6. Reaction of 34 with triflic anhydride in a suitable solvent such as CH$_2$Cl$_2$ and a suitable base such as pyridine provides intermediate 35. Metal catalyzed coupling such as Suzuki coupling with a suitable arylboronic acid, using a palladium catalyst such as PdCl$_2$(dppf).CH$_2$Cl$_2$, a base such K$_3$PO$_4$, and a suitable solvent such as dioxane at elevated temperatures (typically from about 80 to about 100° C.) provides intermediate 36. Reaction of 36 with hydrazine in a suitable solvent such as ethanol at an elevated temperature (typically from about 80 to about 150° C., or performed under microwave conditions) provides final product 37.

The skilled artisan will appreciate that if further manipulation of functionality present in the R$^1$ substituent is necessary, it might be performed at different stages during the indazole synthesis. Highlighted in the schemes below are the syntheses of selected amines amines used in the examples.

Scheme 13 illustrates the synthesis of disubstituted piperidines from pyridines. 2,5-Bis-substituted pyridines 38 are commercially available or may be synthesized using techniques well known in the art. Hydrogenation in a suitable solvent such as CH$_3$OH in the presence of a suitable acid such as HCl and a suitable catalyst such as PtO$_2$ provides intermediate 39. This intermediate is normally obtained as a mixture of diastereomers, cis being the predominant one. Intermediate 39 can be used directly or derivatized and purified by chromatography to give pure diastereomers. Additionally, racemic intermediate 39 can be resolved into its pure enantiomers using techniques well known in the art such as chiral HPLC or recrystallization with optically pure acids.

Scheme 13

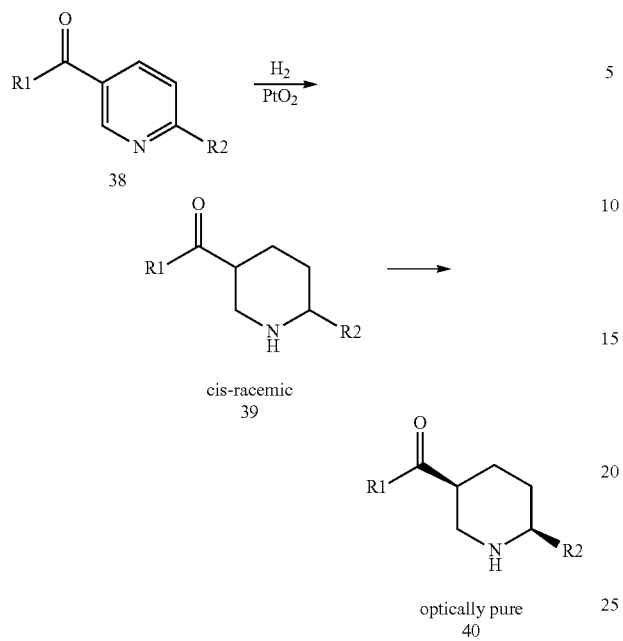

cis-racemic
39 optically pure
40

Intermediate 41, which can be prepared as described in Scheme 13 can be converted to Cbz protected intermediate 42 as shown in Scheme 14 using techniques well known in the art. For instance, intermediate 41 can be Cbz protected by reaction with CbzCl in a suitable solvent such as $CH_2Cl_2$, and a suitable base such as triethylamine and a suitable catalyst such as DMAP. The ester functionality can be hydrolyzed using a suitable hydroxide source such as $LiOH \cdot H_2O$ in a suitable solvent mixture such as $THF/H_2O/CH_3OH$ to give 42. Intermediate 42 can be converted to 43 using techniques well known in the art such as a Curtius rearrangement using DPPA in t-BuOH in the presence of a suitable base such as triethylamine at an elevated temperature (around 100° C.). The Cbz group can be removed using techniques well known in the art to generate the desired unprotected amine.

Scheme 14

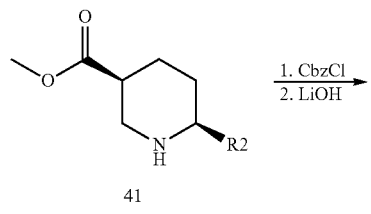

41

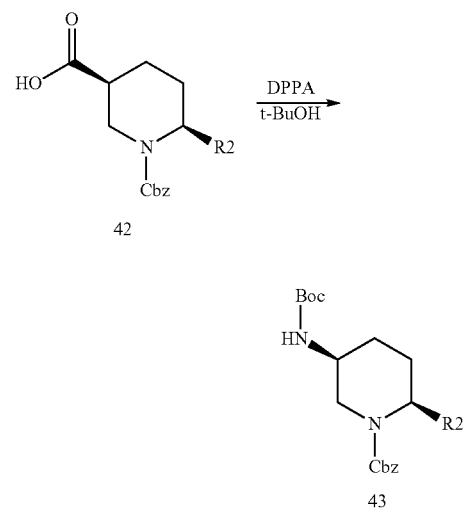

42

43

Compounds of the invention that contain morpholines with imidazole or benzimidazole substituents can be prepared according to methods in Scheme 15. Morpholine acid reagent 44 is commercially available or may be synthesized using techniques well known in the art. Amide coupling with a suitable aminoketone derivative using techniques well known in the art provides intermediate 46. The skilled artisan will appreciate that if a suitable aminoketone is not available and/or accessible, then the respective aminoalcohol can be used in the amine coupling reaction to provide intermediate 45. The alcohol functionality in intermediate 45 can then be oxidized to the ketone using techniques well known in the art to provide intermediate 46. Cyclization of 46 to the imidazole intermediate 47 can be performed using techniques well known in the art such as heating at elevated temperatured (around 150° C.) in the presence of ammonium trifluoroacetate. Additionally, intermediate 44 can be reacted with 1,2-diaminoaryl or heteroaryl systems under acidic conditions such as refluxing in polyphosphoric acid to provide intermediate 48. Both intermediates 47 and 48 can then be deprotected by removal of the benzyl functionality using techniques well known in the art to provide the required secondary amine.

Scheme 15

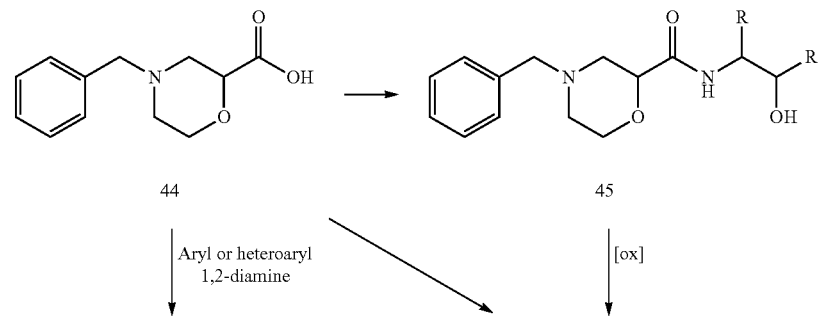

44                              45

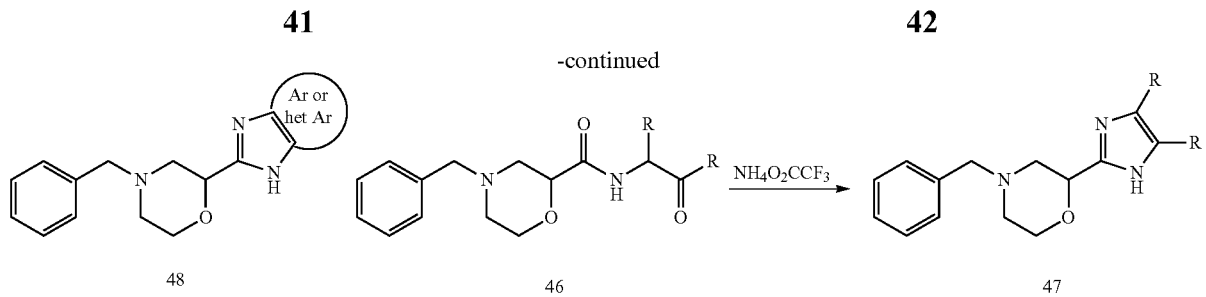

2,5-bis-Substituted morphilines 49 illustrated in Scheme 16 were made according to the reported method (Breuning et al, *Eur. J. Org. Chem.* 2007, 2100-2106). Compound 49 can be further elaborated into a variety of disubstituted morpholines using common functional group transformations to give intermediate 50. Monosubstituted morpholines at the 2-position were either commercially available or synthesized using techniques well known in the art. For instance, intermediate 48 can be reacted with chloroacetyl chloride using techniques well known in the art to provide intermediate 51. Reduction of the lactam functionality to the amine using reducing agents well known in the art such as Red-Al in toluene, borane or LiAlH$_4$ in THF provides intermediate 52. Final debenzylation provides the desired secondary amine. The skill artisan will appreciate that this synthetic sequence might be performed without the presence of the benzyl group. In such a case, the non-benzylated aminoalcohol version of 48 can be used for reaction with chloroacetyl chloride.

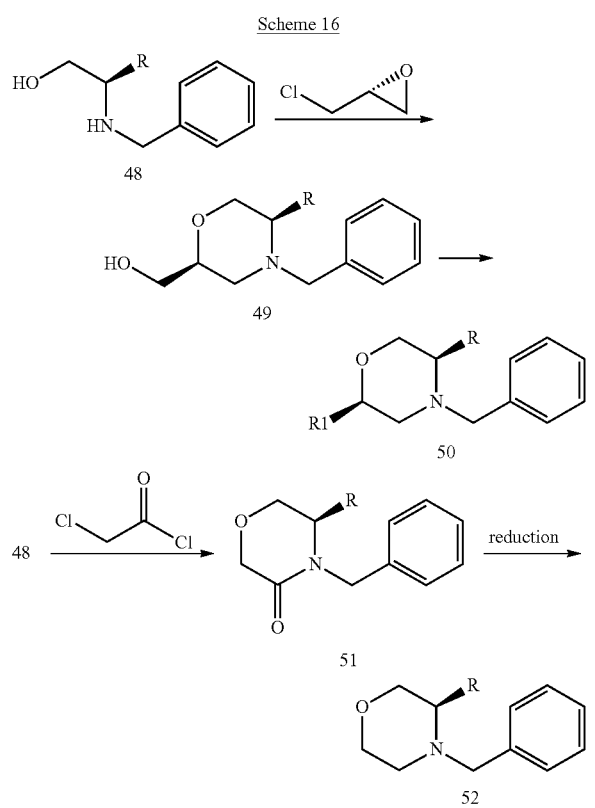

Compound 53 was made according to the reported synthesis of its respective enantiomer (Lee et. al PCT Int. Appl. (2009), WO 2009023473 A2 20090219). Compound 53 can be debenzylated using techniques well known in the art to provide the desired secondary amine, or it can be functionalized prior to the benzyl group deprotection step. For instance, compound 53 can be methylated using a suitable base such as NaH and a suitable methylating agent such as methyl iodide in a suitable solvent such as DMF to provide intermediate 54.

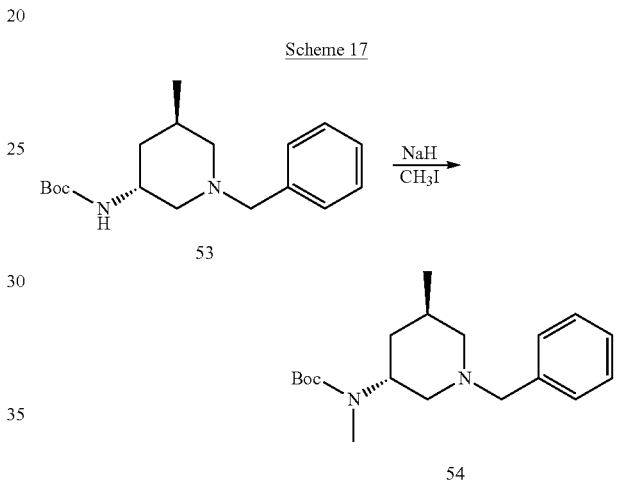

Methods of Use

The compounds according to Formula I and pharmaceutically acceptable salts thereof are inhibitors of PDK1. These compounds are potentially useful in the treatment of conditions wherein the underlying pathology is attributable to (but not limited to) constitutively activated ACG kinases, for example, metabolic and immune diseases, cancer and more specifically cancers of the breast, colon, and lung. Constitutively activated ACG kinases means that one or more ACG kinases are being produced at a constant rate regardless of physiological demand or concentration. Accordingly, another aspect the invention is directed to methods of treating such conditions.

Suitably, the present invention relates to a method for treating or lessening the severity of breast cancer, including inflammatory breast cancer, ductal carcinoma, and lobular carcinoma.

Suitably the present invention relates to a method for treating or lessening the severity of colon cancer.

Suitably the present invention relates to a method for treating or lessening the severity of lung cancer including small cell lung cancer, non-small cell lung cancer, squamous cell carcinoma, adenocarcinoma, and large cell carcinoma.

Suitably the present invention relates to a method for treating or lessening the severity of cancers selected from the group consisting of brain (gliomas), glioblastomas, Wilm's tumor, Ewing's sarcoma, Rhabdomyosarcoma, ependymoma, medulloblastoma, head and neck, kidney, liver, melanoma, ovarian, pancreatic, prostate, sarcoma, osteosarcoma, giant cell tumor of bone, thyroid, lymphoblastic T cell leukemia, chronic myelogenous leukemia, chronic lymphocytic leukemia, hairy-cell leukemia, acute lymphoblastic leukemia, acute myelogenous leukemia, chronic neutrophilic leukemia, acute lymphoblastic T cell leukemia, plasmacytoma, Immunoblastic large cell leukemia, mantle cell leukemia, multiple myeloma, megakaryoblastic leukemia, multiple myeloma, acute megakaryocytic leukemia, promyelocytic leukemia, erythroleukemia, malignant lymphoma, hodgkins lymphoma, non-hodgkins lymphoma, lymphoblastic T cell lymphoma, Burkitt's lymphoma, follicular lymphoma, neuroblastoma, bladder cancer, urothelial cancer, vulval cancer, cervical cancer, endometrial cancer, renal cancer, mesothelioma, esophageal cancer, salivary gland cancer, hepatocellular cancer, gastric cancer, nasopharangeal cancer, buccal cancer, cancer of the mouth, GIST (gastrointestinal stromal tumor) and testicular cancer.

Suitably the present invention relates to a method for treating or lessening the severity of metabolic and immune diseases including: diabetes, transplant/graft rejection, psoriasis and colitis.

The methods of treatment of the invention comprise administering an effective amount of a compound according to Formula I or a pharmaceutically acceptable salt, thereof to a patient in need thereof.

The invention also provides a compound according to Formula I or a pharmaceutically-acceptable salt thereof for use in medical therapy, and particularly in cancer therapy. Thus, in further aspect, the invention is directed to the use of a compound according to Formula I or a pharmaceutically acceptable salt thereof in the preparation of a medicament for the treatment of a disorder characterized by constitutively activated ACG kinases, such as cancer.

As used herein, "treat" and derivatives thereof, in reference to a condition means: (1) to ameliorate or prevent the condition or one or more of the biological manifestations of the condition, (2) to interfere with (a) one or more points in the biological cascade that leads to or is responsible for the condition or (b) one or more of the biological manifestations of the condition, (3) to alleviate one or more of the symptoms or effects associated with the condition, or (4) to slow the progression of the condition or one or more of the biological manifestations of the condition.

As indicated above, "treatment" and derivatives thereof, of a condition includes prevention of the condition. The skilled artisan will appreciate that "prevention" is not an absolute term. In medicine, "prevention" is understood to refer to the prophylactic administration of a drug to substantially diminish the likelihood or severity of a condition or biological manifestation thereof, or to delay the onset of such condition or biological manifestation thereof.

As used herein, "patient" or "subject" refers to a human or other animal. Suitably the patient or subject is a human.

The compounds of Formula I or pharmaceutically acceptable salts thereof may be administered by any suitable route of administration, including systemic administration. Systemic administration includes oral administration, and parenteral administration, Parenteral administration refers to routes of administration other than enteral, transdermal, or by inhalation, and is typically by injection or infusion. Parenteral administration includes intravenous, intramuscular, and subcutaneous injection or infusion.

The compounds of Formula I or pharmaceutically acceptable salts thereof may be administered once or according to a dosing regimen wherein a number of doses are administered at varying intervals of time for a given period of time. For example, doses may be administered one, two, three, or four times per day. Doses may be administered until the desired therapeutic effect is achieved or indefinitely to maintain the desired therapeutic effect. Suitable dosing regimens for a compound of the invention depend on the pharmacokinetic properties of that compound, such as absorption, distribution, and half-life, which can be determined by the skilled artisan. In addition, suitable dosing regimens, including the duration such regimens are administered, for a compound of the invention depend on the condition being treated, the severity of the condition being treated, the age and physical condition of the patient being treated, the medical history of the patient to be treated, the nature of concurrent therapy, the desired therapeutic effect, and like factors within the knowledge and expertise of the skilled artisan. It will be further understood by such skilled artisans that suitable dosing regimens may require adjustment given an individual patient's response to the dosing regimen or over time as individual patient needs change.

Additionally, the compounds of Formula I or pharmaceutically-acceptable salts thereof may be administered as prodrugs. As used herein, a "prodrug" of a compound of the invention is a functional derivative of the compound which, upon administration to a patient, eventually liberates the compound of the invention in vivo. Administration of a compound of the invention as a prodrug may enable the skilled artisan to do one or more of the following: (a) modify the onset of the compound in vivo; (b) modify the duration of action of the compound in vivo; (C) modify the transportation or distribution of the compound in vivo; (d) modify the solubility of the compound in vivo; and (e) overcome or overcome a side effect or other difficulty encountered with the compound. Typical functional derivatives used to prepare prodrugs include modifications of the compound that are chemically or enzymatically cleaved in vivo. Such modifications, which include the preparation of phosphates, amides, esters, thioesters, carbonates, and carbamates, are well known to those skilled in the art.

The compounds of Formula I and pharmaceutically acceptable salts thereof may be co-administered with at least one other active ingredient known to be useful in the treatment of cancer.

By the term "co-administration" as used herein is meant either simultaneous administration or any manner of separate sequential administration of a PDK1 inhibiting compound, as described herein, and a further active ingredient or ingredients, known to be useful in the treatment of cancer, including chemotherapy and radiation treatment. The term further active ingredient or ingredients, as used herein, includes any compound or therapeutic agent known to or that demonstrates advantageous properties when administered to a patient in need of treatment for cancer. Preferably, if the administration is not simultaneous, the compounds are administered in a close time proximity to each other. Furthermore, it does not matter if the compounds are administered in the same dosage form, e.g. one compound may be administered by injection and another compound may be administered orally.

Typically, any anti-neoplastic agent that has activity versus a susceptible tumor being treated may be co-administered in the treatment of cancer in the present invention. Examples of such agents can be found in Cancer Principles and Practice of Oncology by V. T. Devita and S. Hellman (editors), 6$^{th}$ edition (Feb. 15, 2001), Lippincott Williams & Wilkins Publishers. A person of ordinary skill in the art would be able to discern which combinations of agents would be useful based on the particular characteristics of the drugs and the cancer involved. Typical anti-neoplastic agents useful in the present invention include, but are not limited to, anti-microtubule agents such as diterpenoids and vinca alkaloids; platinum coordination complexes; alkylating agents such as nitrogen mustards, oxazaphosphorines, alkylsulfonates, nitrosoureas, and triazenes; antibiotic agents such as anthracyclins, actinomycins and bleomycins; topoisomerase II inhibitors such as epipodophyllotoxins; antimetabolites such as purine and pyrimidine analogues and anti-folate compounds; topoisomerase I inhibitors such as camptothecins; hormones and hormonal analogues; signal transduction pathway inhibitors; non-receptor tyrosine kinase angiogenesis inhibitors; immunotherapeutic agents; proapoptotic agents; and cell cycle signaling inhibitors.

Examples of a further active ingredient or ingredients (anti-neoplastic agent) for use in combination or co-administered with the presently invented PDK1 inhibiting compounds are chemotherapeutic agents.

Anti-microtubule or anti-mitotic agents are phase specific agents active against the microtubules of tumor cells during M or the mitosis phase of the cell cycle. Examples of anti-microtubule agents include, but are not limited to, diterpenoids and vinca alkaloids.

Diterpenoids, which are derived from natural sources, are phase specific anti-cancer agents that operate at the $G_2$/M phases of the cell cycle. It is believed that the diterpenoids stabilize the β-tubulin subunit of the microtubules, by binding with this protein. Disassembly of the protein appears then to be inhibited with mitosis being arrested and cell death following. Examples of diterpenoids include, but are not limited to, paclitaxel and its analog docetaxel.

Paclitaxel, 5β,20-epoxy-1,2α,4,7β,10β,13α-hexa-hydroxytax-11-en-9-one 4,10-diacetate 2-benzoate 13-ester with (2R,3S)—N-benzoyl-3-phenylisoserine; is a natural diterpene product isolated from the Pacific yew tree *Taxus brevifolia* and is commercially available as an injectable solution TAXOL®. It is a member of the taxane family of terpenes. It was first isolated in 1971 by Wani et al. J. Am. Chem, Soc., 93:2325. 1971), who characterized its structure by chemical and X-ray crystallographic methods. One mechanism for its activity relates to paclitaxel's capacity to bind tubulin, thereby inhibiting cancer cell growth. Schiff et al., Proc. Natl, Acad, Sci. USA, 77:1561-1565 (1980); Schiff et al., Nature, 277:665-667 (1979); Kumar, J. Biol, Chem, 256: 10435-10441 (1981). For a review of synthesis and anticancer activity of some paclitaxel derivatives see: D. G. I. Kingston et al., Studies in Organic Chemistry vol. 26, entitled "New trends in Natural Products Chemistry 1986", Attaur-Rahman, P. W. Le Quesne, Eds. (Elsevier, Amsterdam, 1986) pp 219-235.

Paclitaxel has been approved for clinical use in the treatment of refractory ovarian cancer in the United States (Markman et al., Yale Journal of Biology and Medicine, 64:583, 1991; McGuire et al., Ann. Intern, Med., 111:273, 1989) and for the treatment of breast cancer (Holmes et al., J. Nat. Cancer Inst., 83:1797, 1991.) It is a potential candidate for treatment of neoplasms in the skin (Einzig et. al., Proc. Am. Soc. Clin. Oncol., 20:46) and head and neck carcinomas (Forastire et. al., Sem. Oncol., 20:56, 1990). The compound also shows potential for the treatment of polycystic kidney disease (Woo et. al., Nature, 368:750. 1994), lung cancer and malaria. Treatment of patients with paclitaxel results in bone marrow suppression (multiple cell lineages, Ignoff, R. J. et. al, Cancer Chemotherapy Pocket Guide, 1998) related to the duration of dosing above a threshold concentration (50 nM) (Kearns, C. M. et. al., Seminars in Oncology, 3(6) p. 16-23, 1995).

Docetaxel, (2R,3S)—N-carboxy-3-phenylisoserine,N-tert-butyl ester, 13-ester with 5β-20-epoxy-1,2α,4,7β,10β, 13α-hexahydroxytax-11-en-9-one 4-acetate 2-benzoate, trihydrate; is commercially available as an injectable solution as TAXOTERE®. Docetaxel is indicated for the treatment of breast cancer. Docetaxel is a semisynthetic derivative of paclitaxel q.v., prepared using a natural precursor, 10-deacetyl-baccatin III, extracted from the needle of the European Yew tree. The dose limiting toxicity of docetaxel is neutropenia.

Vinca alkaloids are phase specific anti-neoplastic agents derived from the periwinkle plant. Vinca alkaloids act at the M phase (mitosis) of the cell cycle by binding specifically to tubulin. Consequently, the bound tubulin molecule is unable to polymerize into microtubules. Mitosis is believed to be arrested in metaphase with cell death following. Examples of vinca alkaloids include, but are not limited to, vinblastine, vincristine, and vinorelbine.

Vinblastine, vincaleukoblastine sulfate, is commercially available as VELBAN® as an injectable solution. Although, it has possible indication as a second line therapy of various solid tumors, it is primarily indicated in the treatment of testicular cancer and various lymphomas including Hodgkin's Disease; and lymphocytic and histiocytic lymphomas. Myelosuppression is the dose limiting side effect of vinblastine.

Vincristine, vincaleukoblastine, 22-oxo-, sulfate, is commercially available as ONCOVIN® as an injectable solution. Vincristine is indicated for the treatment of acute leukemias and has also found use in treatment regimens for Hodgkin's and non-Hodgkin's malignant lymphomas. Alopecia and neurologic effects are the most common side effect of vincristine and to a lesser extent myelosupression and gastrointestinal mucositis effects occur.

Vinorelbine, 3',4'-didehydro-4'-deoxy-C'-norvincaleukoblastine[R—(R*,R*)-2,3-dihydroxybutanedioate (1:2) (salt)], commercially available as an injectable solution of vinorelbine tartrate (NAVELBINE®), is a semisynthetic vinca alkaloid. Vinorelbine is indicated as a single agent or in combination with other chemotherapeutic agents, such as cisplatin, in the treatment of various solid tumors, particularly non-small cell lung, advanced breast, and hormone refractory prostate cancers. Myelosuppression is the most common dose limiting side effect of vinorelbine.

Platinum coordination complexes are non-phase specific anti-cancer agents, which are interactive with DNA. The platinum complexes enter tumor cells, undergo, aquation and form intra- and interstrand crosslinks with DNA causing adverse biological effects to the tumor. Examples of platinum coordination complexes include, but are not limited to, cisplatin and carboplatin.

Cisplatin, cis-diamminedichloroplatinum, is commercially available as PLATINOL® as an injectable solution. Cisplatin is primarily indicated in the treatment of metastatic testicular and ovarian cancer and advanced bladder cancer. The primary dose limiting side effects of cisplatin are nephrotoxicity, which may be controlled by hydration and diuresis, and ototoxicity.

Carboplatin, platinum, diammine[1,1-cyclobutane-dicarboxylate(2-)-O,O'], is commercially available as PARAPLATIN® as an injectable solution. Carboplatin is primarily indicated in the first and second line treatment of advanced ovarian carcinoma. Bone marrow suppression is the dose limiting toxicity of carboplatin.

Alkylating agents are non-phase anti-cancer specific agents and strong electrophiles. Typically, alkylating agents form covalent linkages, by alkylation, to DNA through nucleophilic moieties of the DNA molecule such as phosphate, amino, sulfhydryl, hydroxyl, carboxyl, and imidazole groups. Such alkylation disrupts nucleic acid function leading to cell death. Examples of alkylating agents include, but are not limited to, nitrogen mustards such as cyclophosphamide, melphalan, and chlorambucil; alkyl sulfonates such as busulfan; nitrosoureas such as carmustine; and triazenes such as dacarbazine.

Cyclophosphamide, 2-[bis(2-chloroethyl)amino]tetrahydro-2H-1,3,2-oxazaphosphorine 2-oxide monohydrate, is commercially available as an injectable solution or tablets as CYTOXAN®. Cyclophosphamide is indicated as a single agent or in combination with other chemotherapeutic agents, in the treatment of malignant lymphomas, multiple myeloma, and leukemias. Alopecia, nausea, vomiting and leukopenia are the most common dose limiting side effects of cyclophosphamide.

Melphalan, 4-[bis(2-chloroethyl)amino]-L-phenylalanine, is commercially available as an injectable solution or tablets as ALKERAN®. Melphalan is indicated for the palliative treatment of multiple myeloma and non-resectable epithelial carcinoma of the ovary. Bone marrow suppression is the most common dose limiting side effect of melphalan.

Chlorambucil, 4-[bis(2-chloroethyl)amino]benzenebutanoic acid, is commercially available as LEUKERAN® tablets. Chlorambucil is indicated for the palliative treatment of chronic lymphatic leukemia, and malignant lymphomas such as lymphosarcoma, giant follicular lymphoma, and Hodgkin's disease. Bone marrow suppression is the most common dose limiting side effect of chlorambucil.

Busulfan, 1,4-butanediol dimethanesulfonate, is commercially available as MYLERAN® TABLETS. Busulfan is indicated for the palliative treatment of chronic myelogenous leukemia. Bone marrow suppression is the most common dose limiting side effects of busulfan.

Carmustine, 1,3-[bis(2-chloroethyl)-1-nitrosourea, is commercially available as single vials of lyophilized material as BiCNU®. Carmustine is indicated for the palliative treatment as a single agent or in combination with other agents for brain tumors, multiple myeloma, Hodgkin's disease, and non-Hodgkin's lymphomas. Delayed myelosuppression is the most common dose limiting side effects of carmustine.

Dacarbazine, 5-(3,3-dimethyl-1-triazeno)-imidazole-4-carboxamide, is commercially available as single vials of material as DTIC-Dome®. Dacarbazine is indicated for the treatment of metastatic malignant melanoma and in combination with other agents for the second line treatment of Hodgkin's Disease. Nausea, vomiting, and anorexia are the most common dose limiting side effects of dacarbazine.

Antibiotic anti-neoplastics are non-phase specific agents, which bind or intercalate with DNA. Typically, such action results in stable DNA complexes or strand breakage, which disrupts ordinary function of the nucleic acids leading to cell death. Examples of antibiotic anti-neoplastic agents include, but are not limited to, actinomycins such as dactinomycin, anthrocyclins such as daunorubicin and doxorubicin; and bleomycins.

Dactinomycin, also know as Actinomycin D, is commercially available in injectable form as COSMEGEN®. Dactinomycin is indicated for the treatment of Wilm's tumor and rhabdomyosarcoma. Nausea, vomiting, and anorexia are the most common dose limiting side effects of dactinomycin.

Daunorubicin, (8S-cis-)-8-acetyl-10-[(3-amino-2,3,6-trideoxy-α-L-lyxo-hexopyranosyl)oxy]-7,8,9,10-tetrahydro-6,8,11-tri hydroxy-1-methoxy-5,12 naphthacenedione hydrochloride, is commercially available as a liposomal injectable form as DAUNOXOME® or as an injectable as CERUBIDINE®. Daunorubicin is indicated for remission induction in the treatment of acute nonlymphocytic leukemia and advanced HIV associated Kaposi's sarcoma. Myelosuppression is the most common dose limiting side effect of daunorubicin.

Doxorubicin, (8S,10S)-10-[(3-amino-2,3,6-trideoxy-α-L-lyxo-hexopyranosyl)oxy]-8-glycoloyl, 7,8,9,10-tetrahydro-6,8,11-trihydroxy-1-methoxy-5,12 naphthacenedione hydrochloride, is commercially available as an injectable form as RUBEX® or ADRIAMYCIN RDF®. Doxorubicin is primarily indicated for the treatment of acute lymphoblastic leukemia and acute myeloblastic leukemia, but is also a useful component in the treatment of some solid tumors and lymphomas. Myelosuppression is the most common dose limiting side effect of doxorubicin.

Bleomycin, a mixture of cytotoxic glycopeptide antibiotics isolated from a strain of *Streptomyces verticillus*, is commercially available as BLENOXANE®. Bleomycin is indicated as a palliative treatment, as a single agent or in combination with other agents, of squamous cell carcinoma, lymphomas, and testicular carcinomas. Pulmonary and cutaneous toxicities are the most common dose limiting side effects of bleomycin.

Topoisomerase II inhibitors include, but are not limited to, epipodophyllotoxins.

Epipodophyllotoxins are phase specific anti-neoplastic agents derived from the mandrake plant. Epipodophyllotoxins typically affect cells in the S and $G_2$ phases of the cell cycle by forming a ternary complex with topoisomerase II and DNA causing DNA strand breaks. The strand breaks accumulate and cell death follows. Examples of epipodophyllotoxins include, but are not limited to, etoposide and teniposide.

Etoposide, 4'-demethyl-epipodophyllotoxin 9[4,6-0-(R)-ethylidene-β-D-glucopyranoside], is commercially available as an injectable solution or capsules as VePESID® and is commonly known as VP-16. Etoposide is indicated as a single agent or in combination with other chemotherapy agents in the treatment of testicular and non-small cell lung cancers. Myelosuppression is the most common side effect of etoposide. The incidence of leucopenia tends to be more severe than thrombocytopenia.

Teniposide, 4'-demethyl-epipodophyllotoxin 9[4,6-0-(R)-thenylidene-β-D-glucopyranoside], is commercially available as an injectable solution as VUMON® and is commonly known as VM-26. Teniposide is indicated as a single agent or in combination with other chemotherapy agents in the treatment of acute leukemia in children. Myelosuppression is the most common dose limiting side effect of teniposide. Teniposide can induce both leucopenia and thrombocytopenia.

Antimetabolite neoplastic agents are phase specific anti-neoplastic agents that act at S phase (DNA synthesis) of the cell cycle by inhibiting DNA synthesis or by inhibiting purine or pyrimidine base synthesis and thereby limiting DNA synthesis. Consequently, S phase does not proceed and cell death follows. Examples of antimetabolite anti-neoplastic agents include, but are not limited to, fluorouracil, methotrexate, cytarabine, mercaptopurine, thioguanine, and gemcitabine.

5-fluorouracil, 5-fluoro-2,4-(1H,3H) pyrimidinedione, is commercially available as fluorouracil. Administration of 5-fluorouracil leads to inhibition of thymidylate synthesis and is also incorporated into both RNA and DNA. The result typically is cell death. 5-fluorouracil is indicated as a single agent or in combination with other chemotherapy agents in the treatment of carcinomas of the breast, colon, rectum, stomach and pancreas. Myelosuppression and mucositis are dose limiting side effects of 5-fluorouracil. Other fluoropyrimidine analogs include 5-fluoro deoxyuridine (floxuridine) and 5-fluorodeoxyuridine monophosphate.

Cytarabine, 4-amino-1-β-D-arabinofuranosyl-2 (1H)-pyrimidinone, is commercially available as CYTOSAR-U® and is commonly known as Ara-C. It is believed that cytarabine exhibits cell phase specificity at S-phase by inhibiting DNA chain elongation by terminal incorporation of cytarabine into the growing DNA chain. Cytarabine is indicated as a single agent or in combination with other chemotherapy agents in the treatment of acute leukemia. Other cytidine analogs include 5-azacytidine and 2',2'-difluorodeoxycytidine (gemcitabine). Cytarabine induces leucopenia, thrombocytopenia, and mucositis.

Mercaptopurine, 1,7-dihydro-6H-purine-6-thione monohydrate, is commercially available as PURINETHOL®. Mercaptopurine exhibits cell phase specificity at S-phase by inhibiting DNA synthesis by an as of yet unspecified mechanism. Mercaptopurine is indicated as a single agent or in combination with other chemotherapy agents in the treatment of acute leukemia. Myelosuppression and gastrointestinal mucositis are expected side effects of mercaptopurine at high doses. A useful mercaptopurine analog is azathioprine.

Thioguanine, 2-amino-1,7-dihydro-6H-purine-6-thione, is commercially available as TABLOID®. Thioguanine exhibits cell phase specificity at S-phase by inhibiting DNA synthesis by an as of yet unspecified mechanism. Thioguanine is indicated as a single agent or in combination with other chemotherapy agents in the treatment of acute leukemia. Myelosuppression, including leucopenia, thrombocytopenia, and anemia, is the most common dose limiting side effect of thioguanine administration. However, gastrointestinal side effects occur and can be dose limiting. Other purine analogs include pentostatin, erythrohydroxynonyladenine, fludarabine phosphate, and cladribine.

Gemcitabine, 2'-deoxy-2',2'-difluorocytidine monohydrochloride (β-isomer), is commercially available as GEMZAR®. Gemcitabine exhibits cell phase specificity at S-phase and by blocking progression of cells through the G1/S boundary. Gemcitabine is indicated in combination with cisplatin in the treatment of locally advanced non-small cell lung cancer and alone in the treatment of locally advanced pancreatic cancer. Myelosuppression, including leucopenia, thrombocytopenia, and anemia, is the most common dose limiting side effect of gemcitabine administration.

Methotrexate, N-[4[[(2,4-diamino-6-pteridinyl)methyl]methylamino]benzoyl]-L-glutamic acid, is commercially available as methotrexate sodium. Methotrexate exhibits cell phase effects specifically at S-phase by inhibiting DNA synthesis, repair and/or replication through the inhibition of dyhydrofolic acid reductase which is required for synthesis of purine nucleotides and thymidylate. Methotrexate is indicated as a single agent or in combination with other chemotherapy agents in the treatment of choriocarcinoma, meningeal leukemia, non-Hodgkin's lymphoma, and carcinomas of the breast, head, neck, ovary and bladder. Myelosuppression (leucopenia, thrombocytopenia, and anemia) and mucositis are expected side effect of methotrexate administration.

Camptothecins, including, camptothecin and camptothecin derivatives are available or under development as Topoisomerase I inhibitors. Camptothecins cytotoxic activity is believed to be related to its Topoisomerase I inhibitory activity. Examples of camptothecins include, but are not limited to irinotecan, topotecan, and the various optical forms of 7-(4-methylpiperazino-methylene)-10,11-ethylenedioxy-20-camptothecin described below.

Irinotecan HCl, (4S)-4,11-diethyl-4-hydroxy-9-[(4-piperidinopiperidino) carbonyloxy]-1H-pyrano[3',4',6,7]indolizino[1,2-b]quinoline-3,14(4H,12H)-dione hydrochloride, is commercially available as the injectable solution CAMPTOSAR®.

Irinotecan is a derivative of camptothecin which binds, along with its active metabolite SN-38, to the topoisomerase I-DNA complex. It is believed that cytotoxicity occurs as a result of irreparable double strand breaks caused by interaction of the topoisomerase I:DNA:irintecan or SN-38 ternary complex with replication enzymes. Irinotecan is indicated for treatment of metastatic cancer of the colon or rectum. The dose limiting side effects of irinotecan HCl are myelosuppression, including neutropenia, and GI effects, including diarrhea.

Topotecan HCl, (S)-10-[(dimethylamino)methyl]-4-ethyl-4,9-dihydroxy-1H-pyrano[3',4',6,7]indolizino[1,2-b]quinoline-3,14-(4H,12H)-dione monohydrochloride, is commercially available as the injectable solution HYCAMTIN®. Topotecan is a derivative of camptothecin which binds to the topoisomerase I-DNA complex and prevents religation of singles strand breaks caused by Topoisomerase I in response to torsional strain of the DNA molecule. Topotecan is indicated for second line treatment of metastatic carcinoma of the ovary and small cell lung cancer. The dose limiting side effect of topotecan HCl is myelosuppression, primarily neutropenia.

Also of interest, is the camptothecin derivative of Formula A following, currently under development, including the racemic mixture (R,S) form as well as the R and S enantiomers:

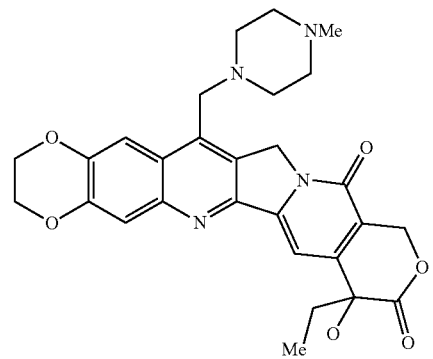

A known by the chemical name "7-(4-methylpiperazino-methylene)-10,11-ethylenedioxy-20(R,S)-camptothecin (racemic mixture) or "7-(4-methylpiperazino-methylene)-10,11-ethylenedioxy-20(R)-camptothecin (R enantiomer) or "7-(4-methylpiperazino-methylene)-10,11-ethylenedioxy-20(S)-camptothecin (S enantiomer). Such compound as well as related compounds are described, including methods of making, in U.S. Pat. Nos. 6,063,923; 5,342,947; 5,559,235; 5,491,237 and pending U.S. patent application Ser. No. 08/977,217 filed Nov. 24, 1997.

Hormones and hormonal analogues are useful compounds for treating cancers in which there is a relationship between the hormone(s) and growth and/or lack of growth of the cancer. Examples of hormones and hormonal analogues useful in cancer treatment include, but are not limited to, adrenocorticosteroids such as prednisone and prednisolone which are useful in the treatment of malignant lymphoma and acute leukemia in children; aminoglutethimide and other aromatase inhibitors such as anastrozole, letrazole, vorazole, and exemestane useful in the treatment of adrenocortical carcinoma and hormone dependent breast carcinoma containing estrogen receptors; progestrins such as megestrol acetate useful in the treatment of hormone dependent breast cancer and endometrial carcinoma; estrogens, androgens, and anti-androgens such as flutamide, nilutamide, bicalutamide, cyproterone acetate and 5α-reductases such as finasteride and dutasteride, useful in the treatment of prostatic carcinoma and benign prostatic hypertrophy; anti-estrogens such as tamoxifen, toremifene, raloxifene, droloxifene, iodoxyfene, as well as selective estrogen receptor modulators (SERMS) such those described in U.S. Pat. Nos. 5,681,835, 5,877,219, and 6,207,716, useful in the treatment of hormone dependent breast carcinoma and other susceptible cancers; and gonadotropin-releasing hormone (GnRH) and analogues thereof which stimulate the release of leutinizing hormone (LH) and/or follicle stimulating hormone (FSH) for the treatment prostatic carcinoma, for instance, LHRH agonists and antagagonists such as goserelin acetate and luprolide.

Signal transduction pathway inhibitors are those inhibitors, which block or inhibit a chemical process which evokes an intracellular change. As used herein this change is cell proliferation or differentiation. Signal tranduction inhibitors useful in the present invention include inhibitors of receptor tyrosine kinases, non-receptor tyrosine kinases, SH2/SH3 domain blockers, serine/threonine kinases, phosphotidylinositol-3 kinases, myo-inositol signaling, and Ras oncogenes.

Several protein tyrosine kinases catalyse the phosphorylation of specific tyrosyl residues in various proteins involved in the regulation of cell growth. Such protein tyrosine kinases can be broadly classified as receptor or non-receptor kinases.

Receptor tyrosine kinases are transmembrane proteins having an extracellular ligand binding domain, a transmembrane domain, and a tyrosine kinase domain. Receptor tyrosine kinases are involved in the regulation of cell growth and are generally termed growth factor receptors. Inappropriate or uncontrolled activation of many of these kinases, i.e. aberrant kinase growth factor receptor activity, for example by over-expression or mutation, has been shown to result in uncontrolled cell growth. Accordingly, the aberrant activity of such kinases has been linked to malignant tissue growth. Consequently, inhibitors of such kinases could provide cancer treatment methods. Growth factor receptors include, for example, epidermal growth factor receptor (EGFr), platelet derived growth factor receptor (PDGFr), erbB2, erbB4, vascular endothelial growth factor receptor (VEGFr), tyrosine kinase with immunoglobulin-like and epidermal growth factor homology domains (TIE-2), insulin growth factor-I (IGFI) receptor, macrophage colony stimulating factor (cfms), BTK, ckit, cmet, fibroblast growth factor (FGF) receptors, Trk receptors (TrkA, TrkB, and TrkC), ephrin (eph) receptors, and the RET protooncogene. Several inhibitors of growth receptors are under development and include ligand antagonists, antibodies, tyrosine kinase inhibitors and antisense oligonucleotides. Growth factor receptors and agents that inhibit growth factor receptor function are described, for instance, in Kath, John C., Exp. Opin. Ther. Patents (2000) 10(6):803-818; Shawver et al DDT Vol 2, No. 2 Feb. 1997; and Lofts, F. J. et al, "Growth factor receptors as targets", New Molecular Targets for Cancer Chemotherapy, ed. Workman, Paul and Kerr, David, CRC press 1994, London.

Tyrosine kinases, which are not growth factor receptor kinases are termed non-receptor tyrosine kinases. Non-receptor tyrosine kinases for use in the present invention, which are targets or potential targets of anti-cancer drugs, include cSrc, Lck, Fyn, Yes, Jak, cAbl, FAK (Focal adhesion kinase), Brutons tyrosine kinase, and Bcr-Abl. Such non-receptor kinases and agents which inhibit non-receptor tyrosine kinase function are described in Sinh, S, and Corey, S. J., (1999) Journal of Hematotherapy and Stem Cell Research 8 (5): 465-80; and Bolen, J. B., Brugge, J. S., (1997) Annual review of Immunology. 15: 371-404.

SH2/SH3 domain blockers are agents that disrupt SH2 or SH3 domain binding in a variety of enzymes or adaptor proteins including, PI3-K p85 subunit, Src family kinases, adaptor molecules (Shc, Crk, Nck, Grb2) and Ras-GAP. SH2/SH3 domains as targets for anti-cancer drugs are discussed in Smithgall, T. E. (1995), Journal of Pharmacological and Toxicological Methods. 34(3) 125-32.

Inhibitors of Serine/Threonine Kinases including MAP kinase cascade blockers which include blockers of Raf kinases (rafk), Mitogen or Extracellular Regulated Kinase (MEKs), and Extracellular Regulated Kinases (ERKs); and Protein kinase C family member blockers including blockers of PKCs (alpha, beta, gamma, epsilon, mu, lambda, iota, zeta). IkB kinase family (IKKa, IKKb), PKB family kinases, akt kinase family members, and TGF beta receptor kinases. Such Serine/Threonine kinases and inhibitors thereof are described in Yamamoto, T., Taya, S., Kaibuchi, K., (1999), Journal of Biochemistry. 126 (5) 799-803; Brodt, P, Samani, A., and Navab, R. (2000), Biochemical Pharmacology, 60. 1101-1107; Massague, J., Weis-Garcia, F. (1996) Cancer Surveys. 27:41-64; Philip, P. A., and Harris, A. L. (1995), Cancer Treatment and Research. 78: 3-27, Lackey, K. et al Bioorganic and Medicinal Chemistry Letters, (10), 2000, 223-226; U.S. Pat. No. 6,268,391; and Martinez-lacaci, L., et al, Int. J. Cancer (2000), 88(1), 44-52.

Suitably, the pharmaceutically active compounds of the invention are used in combination with a MEK inhibitor. Suitably, N-{3-[3-cyclopropyl-5-(2-fluoro-4-iodo-phenylamino)-6,8-dimethyl-2,4,7-trioxo-3,4,6,7-tetrahydro-2H-pyrido[4,3-d]pyrimidin-1-yl]phenyl}acetamide, or a pharmaceutically acceptable salt or solvate, suitably the dimethyl sulfoxide solvate, thereof, which is disclosed and claimed in International Application No. PCT/JP2005/011082, having an International filing date of Jun. 10, 2005; International Publication Number WO 2005/121142 and an International Publication date of Dec. 22, 2005, the entire disclosure of which is hereby incorporated by reference. N-{3-[3-cyclopropyl-5-(2-fluoro-4-iodo-phenylamino)-6,8-dimethyl-2,4,7-trioxo-3,4,6,7-tetrahydro-2H-pyrido[4,3-d]pyrimidin-1-yl]phenyl}acetamide, can be prepared as described in United States Patent Publication No. US 2006/0014768, Published Jan. 19, 2006, the entire disclosure of which is hereby incorporated by reference.

Suitably, the pharmaceutically active compounds of the invention are used in combination with a B-Raf inhibitor. Suitably, N-{3-[5-(2-Amino-4-pyrimidinyl)-2-(1,1-dimethylethyl)-1,3-thiazol-4-yl]-2-fluorophenyl}-2,6-difluorobenzenesulfonamide, or a pharmaceutically acceptable salt thereof, which is disclosed and claimed, in International Application No. PCT/US2009/042682, having an International filing date of May 4, 2009, the entire disclosure of which is hereby incorporated by reference. N-{3-[5-(2-Amino-4-pyrimidinyl)-2-(1,1-dimethylethyl)-1,3-thiazol-4-yl]-2-fluorophenyl}-2,6-difluorobenzenesulfonamide can be prepared as described in International Application No. PCT/US2009/042682.

Inhibitors of Phosphotidylinositol-3 Kinase family members including blockers of PI3-kinase, ATM, DNA-PK, and Ku may also be useful in the present invention. Such kinases are discussed in Abraham, R. T. (1996), Current Opinion in Immunology. 8 (3) 412-8; Canman, C. E., Lim, D. S. (1998), Oncogene 17 (25) 3301-3308; Jackson, S. P. (1997), International Journal of Biochemistry and Cell Biology. 29 (7):935-8; and Zhong, H. et al, Cancer res, (2000) 60(6), 1541-1545.

Also of interest in the present invention are Myo-inositol signaling inhibitors such as phospholipase C blockers and Myoinositol analogues. Such signal inhibitors are described in Powis, G., and Kozikowski A., (1994) New Molecular Targets for Cancer Chemotherapy ed., Paul Workman and David Kerr, CRC press 1994, London.

Another group of signal transduction pathway inhibitors are inhibitors of Ras Oncogene. Such inhibitors include inhibitors of farnesyltransferase, geranyl-geranyl transferase, and CAAX proteases as well as anti-sense oligonucleotides, ribozymes and immunotherapy. Such inhibitors have been shown to block ras activation in cells containing wild type mutant ras, thereby acting as antiproliferation agents. Ras oncogene inhibition is discussed in Scharovsky, O. G., Rozados, V. R., Gervasoni, S. I. Matar, P. (2000), Journal of Biomedical Science. 7(4) 292-8; Ashby, M. N. (1998), Current Opinion in Lipidology. 9 (2) 99-102; and BioChim. Biophys. Acta, (19899) 1423(3):19-30.

As mentioned above, antibody antagonists to receptor kinase ligand binding may also serve as signal transduction inhibitors. This group of signal transduction pathway inhibitors includes the use of humanized antibodies to the extracellular ligand binding domain of receptor tyrosine kinases. For example Imclone C225 EGFR specific antibody (see Green, M. C. et al, Monoclonal Antibody Therapy for Solid Tumors, Cancer Treat. Rev., (2000), 26(4), 269-286); Herceptin® erbB2 antibody (see Tyrosine Kinase Signalling in Breast cancer:erbB Family Receptor Tyrosine Kinases, Breast cancer Res., 2000, 2(3), 176-183); and 2CB VEGFR2 specific antibody (see Brekken, R. A. et al, Selective Inhibition of VEGFR2 Activity by a monoclonal Anti-VEGF antibody blocks tumor growth in mice, Cancer Res. (2000) 60, 5117-5124).

Non-receptor kinase angiogenesis inhibitors may also be useful in the present invention. Inhibitors of angiogenesis related VEGFR and TIE2 are discussed above in regard to signal transduction inhibitors (both receptors are receptor tyrosine kinases). Angiogenesis in general is linked to erbB2/EGFR signaling since inhibitors of erbB2 and EGFR have been shown to inhibit angiogenesis, primarily VEGF expression. Accordingly, non-receptor tyrosine kinase inhibitors may be used in combination with the compounds of the present invention. For example, anti-VEGF antibodies, which do not recognize VEGFR (the receptor tyrosine kinase), but bind to the ligand; small molecule inhibitors of integrin (alpha$_v$ beta$_3$) that will inhibit angiogenesis; endostatin and angiostatin (non-RTK) may also prove useful in combination with the disclosed compounds. (See Bruns C J et al (2000), Cancer Res., 60: 2926-2935; Schreiber A B, Winkler M E, and Derynck R. (1986), Science, 232: 1250-1253; Yen L et al. (2000), Oncogene 19: 3460-3469).

Agents used in immunotherapeutic regimens may also be useful in combination with the compounds of Formula (I). There are a number of immunologic strategies to generate an immune response. These strategies are generally in the realm of tumor vaccinations. The efficacy of immunologic approaches may be greatly enhanced through combined inhibition of signaling pathways using a small molecule inhibitor. Discussion of the immunologic/tumor vaccine approach against erbB2/EGFR are found in Reilly R T et al. (2000), Cancer Res. 60: 3569-3576; and Chen Y, Hu D, Eling D J, Robbins J, and Kipps T J. (1998), Cancer Res. 58: 1965-1971.

Agents used in proapoptotic regimens (e.g., bcl-2 antisense oligonucleotides) may also be used in the combination of the present invention. Members of the Bcl-2 family of proteins block apoptosis. Upregulation of bcl-2 has therefore been linked to chemoresistance. Studies have shown that the epidermal growth factor (EGF) stimulates anti-apoptotic members of the bcl-2 family (i.e., mcl-1). Therefore, strategies designed to downregulate the expression of bcl-2 in tumors have demonstrated clinical benefit and are now in Phase II/III trials, namely Genta's G3139 bcl-2 antisense oligonucleotide. Such proapoptotic strategies using the antisense oligonucleotide strategy for bcl-2 are discussed in Water J S et al. (2000), J. Clin. Oncol. 18: 1812-1823; and Kitada S et al. (1994), Antisense Res. Dev. 4: 71-79.

Cell cycle signalling inhibitors inhibit molecules involved in the control of the cell cycle. A family of protein kinases called cyclin dependent kinases (CDKs) and their interaction with a family of proteins termed cyclins controls progression through the eukaryotic cell cycle. The coordinate activation and inactivation of different cyclin/CDK complexes is necessary for normal progression through the cell cycle. Several inhibitors of cell cycle signalling are under development. For instance, examples of cyclin dependent kinases, including CDK2, CDK4, and CDK6 and inhibitors for the same are described in, for instance, Rosania et al, Exp. Opin. Ther. Patents (2000) 10(2):215-230.

Compositions

The pharmaceutically active compounds within the scope of this invention are useful as PDK1 inhibitors in mammals, particularly humans, in need thereof.

The compounds of Formula I or pharmaceutically acceptable salts thereof will normally, but not necessarily, be formulated into pharmaceutical compositions prior to administration to a patient. Accordingly, in another aspect the invention is directed to pharmaceutical compositions comprising a compounds of Formula I or pharmaceutically acceptable salts thereof and one or more pharmaceutically acceptable excipient.

Doses of the presently invented pharmaceutically active compounds in a pharmaceutical dosage unit as described above will be an efficacious, nontoxic quantity suitably selected from the range of 0.001-100 mg/kg of active compound, suitably 0.01-50 mg/kg, suitably 0.1-20 mg/kg. When treating a human patient in need of a PDK1 inhibitor, the selected dose is administered preferably from 1-6 times daily, orally or parenterally. Preferred forms of parenteral administration include topically, rectally, transdermally, by injection and continuously by infusion. Oral dosage units for human administration suitably contain from about 0.05 to 3500 mg of active compound, suitably 0.5 to 350 mg, suitably 5 to 200 mg. Oral administration, which uses lower dosages, is preferred. Parenteral administration, at high dosages, however, also can be used when safe and convenient for the patient.

The pharmaceutical compositions of the invention typically contain one compound of Formula I or pharmaceutically acceptable salt thereof. However, in certain embodiments, the pharmaceutical compositions of the invention contain more than one compound of Formula I. For example, in certain embodiments the pharmaceutical compositions of the invention contain two compounds of Formula I. In addition, the pharmaceutical compositions of the invention may optionally further comprise one or more additional pharmaceutically active compounds.

The compound of Formula I or pharmaceutically acceptable salt thereof and the pharmaceutically-acceptable excipient or excipients will typically be formulated into a dosage form adapted for administration to the patient by the desired route of administration. For example, dosage forms include those adapted for (1) oral administration such as tablets, capsules, caplets, pills, troches, powders, syrups, elixers, suspensions, solutions, emulsions, sachets, and cachets; and (2) parenteral administration such as sterile solutions, suspensions, and powders for reconstitution;

Suitable pharmaceutically acceptable excipients will vary depending upon the particular dosage form chosen. In addition, suitable pharmaceutically-acceptable excipients may be chosen for a particular function that they may serve in the composition. For example, certain pharmaceutically-acceptable excipients may be chosen for their ability to facilitate the production of uniform dosage forms. Certain pharmaceutically-acceptable excipients may be chosen for their ability to facilitate the production of stable dosage forms. Certain pharmaceutically-acceptable excipients may be chosen for their ability to facilitate the carrying or transporting the compound or compounds of the invention once administered to the patient from one organ, or portion of the body, to another organ, or portion of the body. Certain pharmaceutically-acceptable excipients may be chosen for their ability to enhance patient compliance.

Suitable pharmaceutically acceptable excipients include the following types of excipients: Diluents, fillers, binders, disintegrants, lubricants, glidants, granulating agents, coating agents, wetting agents, solvents, co-solvents, suspending agents, emulsifiers, sweetners, flavoring agents, flavor masking agents, coloring agents, anticaking agents, hemectants, chelating agents, plasticizers, viscosity increasing agents, antioxidants, preservatives, stabilizers, surfactants, and buffering agents. The skilled artisan will appreciate that certain pharmaceutically-acceptable excipients may serve more than one function and may serve alternative functions depending on how much of the excipient is present in the formulation and what other ingredients are present in the formulation.

Skilled artisans possess the knowledge and skill in the art to enable them to select suitable pharmaceutically acceptable excipients in appropriate amounts for use in the invention. In addition, there are a number of resources that are available to the skilled artisan which describe pharmaceutically-acceptable excipients and may be useful in selecting suitable pharmaceutically-acceptable excipients. Examples include *Remington's Pharmaceutical Sciences* (Mack Publishing Company), *The Handbook of Pharmaceutical Additives* (Gower Publishing Limited), and *The Handbook of Pharmaceutical Excipients* (the American Pharmaceutical Association and the Pharmaceutical Press).

The pharmaceutical compositions of the invention are prepared using techniques and methods known to those skilled in the art. Some of the methods commonly used in the art are described in Remington's *Pharmaceutical Sciences* (Mack Publishing Company).

In one aspect, the invention is directed to a solid oral dosage form such as a tablet or capsule comprising a safe and effective amount of a compound of Formula I or pharmaceutically acceptable salt thereof and a diluent or filler. Suitable diluents and fillers include lactose, sucrose, dextrose, mannitol, sorbitol, starch (e.g. corn starch, potato starch, and pre-gelatinized starch), cellulose and its derivatives (e.g. microcrystalline cellulose), calcium sulfate, and dibasic calcium phosphate. The oral solid dosage form may further comprise a binder. Suitable binders include starch (e.g. corn starch, potato starch, and pre-gelatinized starch), gelatin, acacia, sodium alginate, alginic acid, tragacanth, guar gum, povidone, and cellulose and its derivatives (e.g. microcrystalline cellulose). The oral solid dosage form may further comprise a disintegrant. Suitable disintegrants include crospovidone, sodium starch glycolate, croscarmelose, alginic acid, and sodium carboxymethyl cellulose. The oral solid dosage form may further comprise a lubricant. Suitable lubricants include stearic acid, magnesuim stearate, calcium stearate, and talc.

Where appropriate, dosage unit formulations for oral administration can be microencapsulated. The composition can also be prepared to prolong or sustain the release as for example by coating or embedding particulate material in polymers, wax or the like.

The compounds of the invention may also be coupled with soluble polymers as targetable drug carriers. Such polymers can include polyvinylpyrrolidone, pyran copolymer, polyhydroxypropylmethacrylamide-phenol, polyhydroxyethylaspartamidephenol, or polyethyleneoxidepolylysine substituted with palmitoyl residues. Furthermore, the compounds of the invention may be coupled to a class of biodegradable polymers useful in achieving controlled release of a drug, for example, polylactic acid, polepsilon caprolactone, polyhydroxy butyric acid, polyorthoesters, polyacetals, polydihydropyrans, polycyanoacrylates and cross-linked or amphipathic block copolymers of hydrogels.

In another aspect, the invention is directed to a liquid oral dosage form. Oral liquids such as solution, syrups and elixirs can be prepared in dosage unit form so that a given quantity contains a predetermined amount of a compound of the invention. Syrups can be prepared by dissolving the compound of the invention in a suitably flavored aqueous solution, while elixirs are prepared through the use of a non-toxic alcoholic vehicle. Suspensions can be formulated by dispersing the compound of the invention in a non-toxic vehicle. Solubilizers and emulsifiers such as ethoxylated isostearyl alcohols and polyoxy ethylene sorbitol ethers, preservatives, flavor additive such as peppermint oil or natural sweeteners or saccharin or other artificial sweeteners, and the like can also be added.

Other pharmaceutically-acceptable excipients may be added to the suspension or solution. The compound of the invention may be stabilized by the addition of an inorganic acid, e.g., hydrochloric acid, nitric acid, sulphuric acid and/or phosphoric acid; an organic acid, e.g., ascorbic acid, citric acid, acetic acid, and tartaric acid, etc., a complexing agent such as EDTA or citric acid and salts thereof; or an antioxidant such as antioxidant such as vitamin E or ascorbic acid. These may be used alone or together to stabilize the compound of the invention. Preservatives may be added such as benzalkonium chloride or benzoic acid and salts thereof. Surfactant may be added particularly to improve the physical stability of suspensions. These include lecithin, disodium dioctylsulphosuccinate, oleic acid and sorbitan esters.

Another aspect of the invention is directed to a pharmaceutical composition adapted for parenteral administration comprising a compound of Formula I or a pharmaceutically acceptable salt thereof. Pharmaceutical compositions adapted for parenteral administration include aqueous and non-aqueous sterile injection solutions which may contain anti-oxidants, buffers, bacteriostats and solutes which render the formulation isotonic with the blood of the intended recipient; and aqueous and non-aqueous sterile suspensions which may include suspending agents and thickening agents. The compositions may be presented in unit-dose or multi-dose containers, for example sealed ampoules and vials, and may be stored in a freeze-dried (lyophilized) condition requiring only the addition of the sterile liquid carrier, for example water for injections, immediately prior to use. Extemporaneous injection solutions and suspensions may be prepared from sterile powders, granules and tablets.

Optimal dosages to be administered may be readily determined by those skilled in the art, and will vary with the particular PDK1 inhibitor in use, the strength of the preparation, the mode of administration, and the advancement of the disease condition. Additional factors depending on the particular patient being treated will result in a need to adjust dosages, including patient age, weight, diet, and time of administration.

The method of this invention of inducing PDK1 inhibitory activity in mammals, including humans, comprises administering to a subject in need of such activity an effective PDK1 inhibiting amount of a pharmaceutically active compound of the present invention.

The invention also provides for the use of a compound of Formula (I) or a pharmaceutically acceptable salt thereof in the manufacture of a medicament for use as a PDK1 inhibitor.

The invention also provides for the use of a compound of Formula (I) or a pharmaceutically acceptable salt thereof in the manufacture of a medicament for use in therapy.

The invention also provides for the use of a compound of Formula (I) or a pharmaceutically acceptable salt thereof in the manufacture of a medicament for use in treating cancer.

The invention also provides for a pharmaceutical composition for use as a PDK1 inhibitor which comprises a compound of Formula (I) or a pharmaceutically acceptable salt thereof and a pharmaceutically acceptable carrier.

The invention also provides for a pharmaceutical composition for use in the treatment of cancer which comprises a compound of Formula (I) or a pharmaceutically acceptable salt thereof and a pharmaceutically acceptable carrier.

In addition, the pharmaceutically active compounds of the present invention can be co-administered with further active ingredients, such as other compounds known to treat cancer, or compounds known to have utility when used in combination with a PDK1 inhibitor.

Without further elaboration, it is believed that one skilled in the art can, using the preceding description, utilize the present invention to its fullest extent. The following Examples are, therefore, to be construed as merely illustrative and not a limitation of the scope of the present invention in any way.

EXAMPLES

The following examples illustrate the invention. These examples are not intended to limit the scope of the present invention, but rather to provide guidance to the skilled artisan to prepare and use the compounds, compositions, and methods of the present invention. While particular embodiments of the present invention are described, the skilled artisan will appreciate that various changes and modifications can be made without departing from the spirit and scope of the invention.

Intermediate 1

6-Chloro-N$^4$-phenyl-2,4-pyrimidinediamine

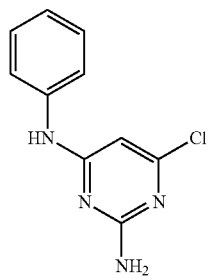 [SMILES: Nc1nc(Cl)cc(Nc2ccccc2)n1]

To 4,6-dichloro-2-pyrimidinamine (0.50 g, 3.05 mmol) in ethanol (EtOH) (10 mL) was added aniline (0.3 mL, 3.3 mmol) and the reaction mixture was stirred overnight at 100° C. The mixture was poured onto ethyl acetate (EtOAc) and saturated aqueous NaHCO$_3$. The layers were separated and the aqueous layer was further extracted with more EtOAc. The combined organic layers were washed with brine, dried (MgSO$_4$), filtered and concentrated to provide the crude title compound (620 mg) as a yellow solid. Product contains ~25% of bis-addition product. LC-MS (ES) m/z=221 [M+H]$^+$.

Intermediate 2

4-[2-Amino-6-(phenylamino)-4-pyrimidinyl]-2-fluorobenzonitrile

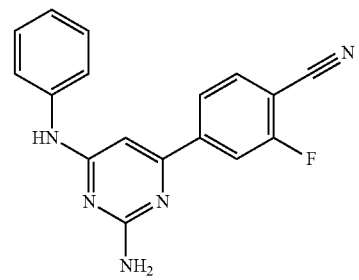 [SMILES: N#Cc1ccc(-c2cc(Nc3ccccc3)nc(N)n2)cc1F]

To (4-cyano-3-fluorophenyl)boronic acid (197 mg, 1.20 mmol) and 6-chloro-N$^4$-phenyl-2,4-pyrimidinediamine (330 mg, 1.50 mmol) in a sealable flask were added 1,4-dioxane (6 mL) and saturated aqueous NaHCO$_3$ (3 mL). The mixture was degassed with nitrogen gas for 10 minutes. Pd(Ph$_3$P)$_4$ (86 mg, 0.075 mmol) was added and the reaction mixture was stirred overnight at 100° C. The mixture was poured onto EtOAc and water. The organic layer was separated and the aqueous layer was further extracted with EtOAc. The combined organic layers were washed with brine, dried (MgSO$_4$), filtered and concentrated. The resulting residue was chromatographed on SiO$_2$ (gradient: 99:1:0.1 CHCl$_3$/CH$_3$OH/NH$_4$OH to 90:10:1 CHCl$_3$/CH$_3$OH/NH$_4$OH) to afford the title compound (366 mg). LC-MS (ES) m/z=306 [M+H]$^+$.

Example 1

6-(3-Amino-1H-indazol-6-yl)-N$^4$-phenyl-2,4-pyrimidinediamine

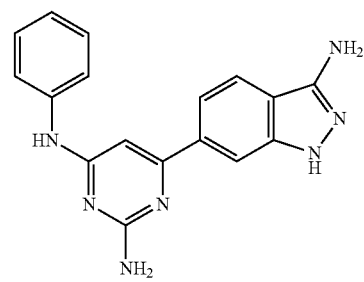 [SMILES: Nc1nc(Nc2ccccc2)cc(-c2ccc3c(N)n[nH]c3c2)n1]

To 4-[2-amino-6-(phenylamino)-4-pyrimidinyl]-2-fluorobenzonitrile (366 mg, 1.2 mmol) in EtOH (10 mL) was added hydrazine monohydrate (1.0 mL, 32 mmol) and the reaction mixture was stirred overnight at 100° C. The mixture was poured onto water and EtOAc. The layers were separated and the aqueous layer was further extracted with EtOAc. The combined organic layers were washed with brine, dried (MgSO$_4$), filtered and concentrated to afford crude product (230 mg). This material was dissolved in EtOH. Hexane was added until a precipitate began to form (a spatula was used to scratch the walls). The mixture was decanted and the solid was dried under vacuum to afford the title compound (100 mg, 26%) as a tan solid. LC-MS (ES) m/z=302, 304 [M+H]$^+$. $^1$H NMR (400 MHz, CD$_3$OD): δ 6.51 (s, 1H), 7.04 (m, 1H), 7.32 (m, 2H), 7.46 (dd, J=8.6, 1.3 Hz, 1H), 7.66 (m, 2H), 7.75 (dd, J=8.3, 0.8 Hz, 1H), 7.81 (s, 1H).

Intermediate 3

6-Chloro-N$^4$-(phenylmethyl)-2,4-pyrimidinediamine

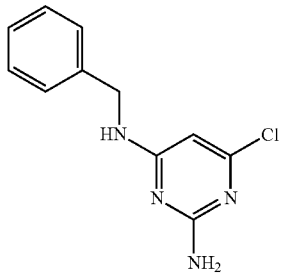 [SMILES: Nc1nc(Cl)cc(NCc2ccccc2)n1]

To 4,6-dichloro-2-pyrimidinamine (0.5 g, 3.1 mmol) in EtOH (10 mL) was added Hunig's base (1.1 mL, 6.1 mmol) followed by benzylamine (0.37 mL, 3.35 mmol) and the reaction mixture was stirred overnight at 100° C. The reaction mixture was poured onto water and EtOAc. The organic layer was separated and the aqueous layer was further extracted with EtOAc. The combined organic layers were washed with brine, dried (MgSO$_4$), filtered and concentrated to afford the crude title compound (670 mg) as a yellow solid. LC-MS (ES) m/z=235 [M+H]$^+$.

Intermediate 4

4-{2-Amino-6-[(phenylmethyl)amino]-4-pyrimidinyl}-2-fluorobenzonitrile

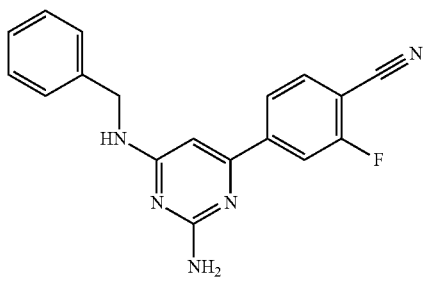 [SMILES: N#Cc1ccc(-c2cc(NCc3ccccc3)nc(N)n2)cc1F]

To (4-cyano-3-fluorophenyl)boronic acid (190 mg, 1.15 mmol) and 6-chloro-N$^4$-(phenylmethyl)-2,4-pyrimidinediamine (300 mg, 1.28 mmol) into a sealable flask were added 1,4-dioxane (6 mL) and saturated aqueous NaHCO$_3$ (3 mL). The mixture was degassed with nitrogen gas for 10 minutes. Pd(Ph$_3$P)$_4$ (74 mg, 0.064 mmol) was added and the reaction mixture was stirred overnight at 100° C. The mixture was poured onto EtOAc and water. The organic layer was separated and the aqueous layer was further extracted with EtOAc. The combined organic layers were filtered, then washed with brine, dried (MgSO$_4$), filtered and concentrated. The resulting residue was chromatographed on SiO$_2$ (gradient: 99:1:0.1 CHCl$_3$/CH$_3$OH/NH$_4$OH to 90:10:1 CHCl$_3$/CH$_3$OH/NH$_4$OH). The material (367 mg) was carried on as is into the next reaction.

Example 2

6-(3-Amino-1H-indazol-6-yl)-N$^4$-(phenylmethyl)-2,4-pyrimidinediamine

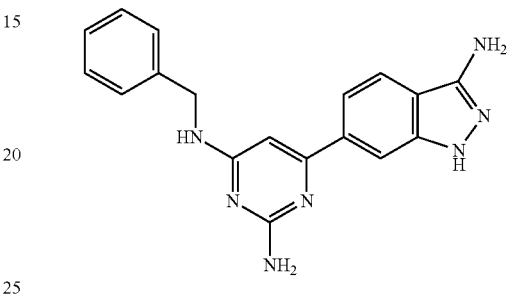

To 4-{2-amino-6-[(phenylmethyl)amino]-4-pyrimidinyl}-2-fluorobenzonitrile (367 mg, 1.15 mmol) in EtOH (10 mL) was added hydrazine monohydrate (1.0 mL, 20.4 mmol) and the reaction mixture was stirred overnight at 100° C. The mixture was poured onto water and EtOAc. The layers were separated and the aqueous layer was further extracted with EtOAc. The combined organic layers were washed with brine, dried (MgSO$_4$), filtered and concentrated to afford crude product (280 mg). This material was dissolved in EtOH. Hexane was added until a precipitate began to form (a spatula was used to scratch the walls). The mixture was decanted and the solid was dried under vacuum to afford the title compound (150 mg, 39%) as a tan solid. LC-MS (ES) m/z=332 [M+H]$^+$. $^1$H NMR (400 MHz, CD$_3$OD): δ 4.59 (s, 2H), 6.29 (s, 1H), 7.23 (m, 1H), 7.28-7.38 (m, 4H), 7.41 (d, J=8.3 Hz, 1H), 7.72 (d, J=8.6 Hz, 1H), 7.75 (s, 1H).

Intermediate 5

4-Chloro-6-(methylthio)-2-pyrimidinamine

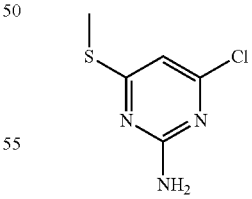

To 4,6-dichloro-2-pyrimidinamine (1.0 g, 6.1 mmol) in EtOH (15 ml) was added sodium thiomethoxide (0.43 g, 6.10 mmol) and the reaction mixture was stirred for 1 hour at room temperature. The mixture was poured onto water and EtOAc. The organic layer was separated and the aqueous layer was further extracted with EtOAc. The combined organic layers were washed with brine, dried (MgSO$_4$), filtered and concentrated to afford the crude title compound (910 mg) as a yellow solid. LC-MS (ES) m/z=176 [M+H]$^+$.

Example 3

6-[2-Amino-6-(methylthio)-4-pyrimidinyl]-1H-indazol-3-amine

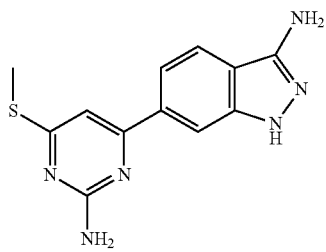 [SMILES: CSc1cc(-c2ccc3c(N)n[nH]c3c2)nc(N)n1]

To 2-fluoro-4-(4,4,5,5-tetramethyl-1,3,2-dioxaborolan-2-yl)benzonitrile (16.5 g, 66.6 mmol) and 4-chloro-6-(methylthio)-2-pyrimidinamine (11.7 g, 66.6 mmol) were added 1,4-dioxane (300 mL) and saturated aqueous NaHCO$_3$ (150 mL) and the mixture was degassed with nitrogen gas for 15 minutes into a sealable tube. Pd(Ph$_3$P)$_4$ (2.3 g, 2.0 mmol) was added, the tube was sealed, and the reaction mixture was stirred overnight at 100° C. The mixture was cooled to room temperature and poured onto water where a precipitate was formed. The mixture was filtered and the solid was transferred to a sealable tube. Dioxane (300 mL) was added followed by hydrazine monohydrate (32.7 mL, 666 mmol) and the reaction mixture was stirred overnight at 100° C. into the sealed tube. The reaction mixture was allowed to cool to room temperature and filtered. The filtrate was poured onto water and filtered again. The aqueous filtrate was poured onto a separatory funnel and extracted with EtOAc (3×). The combined organic layers were washed with brine, dried (MgSO$_4$), filtered and concentrated. To the resulting residue was added 1,4-dioxane (100 mL) and the mixture was sonicated for 30 minutes. The solids were filtered affording the crude title compound (11.5 g) as a yellow solid. The filtrate was concentrated and the resulting residue was dissolved in dioxane and purified via flash chromatography on SiO$_2$ (gradient: 99:1:0.1 CHCl$_3$/CH$_3$OH/NH$_4$OH to 90:10:1 CHCl$_3$/CH$_3$OH/NH$_4$OH) to afford the title compound (4.5 g) as a pale yellow solid. LC-MS (ES) m/z=273 [M+H]$^+$. $^1$H NMR (400 MHz, DMSO-d$_6$): δ 2.53 (s, 3H), 5.41 (s, 2H), 6.70 (s, 2H), 7.06 (s, 1H), 7.58 (dd, J=8.5, 1.1 Hz, 1H), 7.74 (d, J=8.6 Hz, 1H), 7.98 (s, 1H), 11.60 (s, 1H).

Example 4

6-[2-Amino-6-(4-thiomorpholinyl)-4-pyrimidinyl]-1H-indazol-3-amine

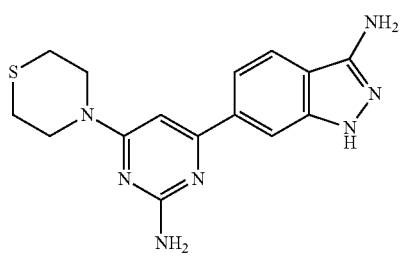 [SMILES: Nc1nc(-c2ccc3c(N)n[nH]c3c2)cc(N2CCSCC2)n1]

To 6-[2-amino-6-(methylthio)-4-pyrimidinyl]-1H-indazol-3-amine (0.43 g, 1.58 mmol) in trifluoroacetic acid (TFA) (15 mL) at 0° C. was added aqueous H$_2$O$_2$ (0.97 mL, 9.47 mmol, 30% (w/w)) dropwise. After 10 minutes, the reaction mixture was allowed to warm to room temperature and stirred at this temperature for 30 minutes. LCMS showed a mixture of sulfoxide and sulfone. The reaction mixture was cooled to 0° C. and quenched with dimethyl sulfide (1.0 mL, 13.5 mmol, dropwise addition) to ensure no hydrogen peroxide is left. The reaction mixture was warmed to room temperature and diluted with diethyl ether (Et$_2$O). When the oxidation converts all the starting material to the sulfone, this material precipitate out when Et$_2$O is added. However, this time the sulfoxide species was the dominant (~80%) as shown in the LCMS. Therefore, hexane was added to ensure complete precipitation of the sulfoxide and sulfone mixture. The material was filtered, and the solid was treated with 1,4-dioxane (10 mL) and thiomorpholine (1.21 mL, 12.6 mmol). The reaction mixture was stirred overnight at 100° C. The mixture was cooled to room temperature and poured onto water and EtOAc. The layers were separated and the aqueous layer was further extracted with EtOAc. The combined organic layers were washed with brine, dried (MgSO$_4$), filtered and concentrated. The crude mixture was purified via flash chromatography on SiO$_2$ (gradient: 99:1:0.1 CHCl$_3$/CH$_3$OH/NH$_4$OH to 90:10:1 CHCl$_3$/CH$_3$OH/NH$_4$OH). The fractions containing the desired product were combined and concentrated. Trituration with Et$_2$O afforded the title compound (205 mg, 40%) as a yellow solid. LC-MS (ES) m/z=328 [M+H]$^+$. $^1$H NMR (400 MHz, DMSO-d$_6$): δ 2.61 (m, 4H), 3.99 (m, 4H), 5.37 (s, 2H), 6.12 (s, 2H), 6.61 (s, 1H), 7.58 (dd, J=8.6, 1.3 Hz, 1H), 7.70 (d, J=8.6 Hz, 1H), 7.95 (s, 1H), 11.50 (s, 1H).

Intermediate 6

N-Acetyl-N-(1-acetyl-6-bromo-1H-indazol-3-yl)acetamide

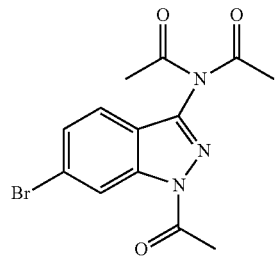 [SMILES: CC(=O)N(C(C)=O)c1nn(C(C)=O)c2cc(Br)ccc12]

In a 100 mL flask under argon were combined 6-bromo-1H-indazol-3-amine (2.47 g, 11.7 mmol), acetic anhydride (22.0 mL, 233 mmol), and DMAP (0.07 g, 0.58 mmol). The reaction mixture was heated at 120° C. for 5 hours after which time it was cooled to room temperature and stirred overnight. LCMS shows a mixture of 2 products, bis- and tris-acetylated. The reaction mixture was concentrated to dryness. The resulting residue was dry-loaded in acetone onto SiO$_2$ and chromatographed on 90 g SiO$_2$ (Analogix) using a EtOAc/Hexanes gradient. The first compound to elute is the desired tris-acetylated product. The fractions were combined and concentrated to afford the title compound (2.84 g, 68%) as a white solid. $^1$H NMR (400 MHz, DMSO-d$_6$): δ 2.31 (s, 6H), 2.70 (s, 3H), 7.67 (dd, J=8.6, 1.8 Hz, 1H), 7.83 (d, J=8.6 Hz, 1H), 8.53 (d, J=1.5 Hz, 1H).

Intermediate 7

N-[6-(2,6-Diamino-4-pyrimidinyl)-1H-indazol-3-yl]acetamide

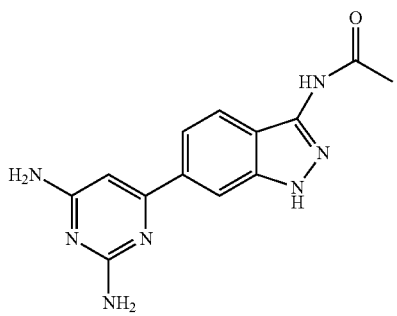 [SMILES: CC(=O)Nc1n[nH]c2cc(-c3cc(N)nc(N)n3)ccc12]

In a 25 mL sealable tube under argon were combine N-acetyl-N-(1-acetyl-6-bromo-1H-indazol-3-yl)acetamide (0.25 g, 0.74 mmol), bis(pinacolato)diboron (0.197 g, 0.776 mmol), potassium acetate (0.145 g, 1.48 mmol), and 1,4-dioxane (4.9 mL). The mixture was degassed with argon for 5 minutes. $PdCl_2(dppf)$-$CH_2Cl_2$ (0.024 g, 0.03 mmol) was added, the tube was sealed, and the reaction mixture was stirred overnight at 100° C. The mixture was cooled to room temperature, the tube was unsealed, and 4-chloro-2,6-diaminopyrimidine (0.12 g, 0.81 mmol), $NaHCO_3$ (0.248 g, 2.96 mmol), $PdCl_2(dppf)$-$CH_2Cl_2$ (0.024 g, 0.03 mmol), and water (1.64 mL) were added. The tube was resealed under argon and the reaction mixture was stirred overnight at 100° C., then over the weekend at room temperature. The mixture was diluted with $CH_3CN$ (15 mL) and filtered through a pad of Celite503. The filtrate was concentrated and the resulting dark brown solid was sonicated in 20 mL of a 3:1 mixture of water and $CH_3CN$ respectively containing TFA (1 mL). The resulting solution containing most of the material was filtered through a 300 mg plug of C18. The filtrate was concentrated to 50% volume, and then purified on a Varian RPHPLC ($CH_3CN/H_2O$ w/0.1% TFA) to afford a TFA salt of the title compound (83 mg) as a light tan solid. LC-MS (ES) m/z=284 $[M+H]^+$.

Example 5

6-(3-Amino-1H-indazol-6-yl)-2,4-pyrimidinediamine

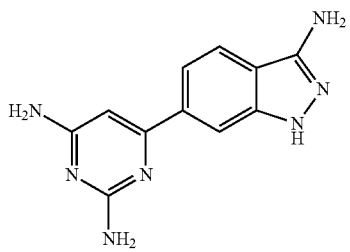 [SMILES: Nc1cc(-c2ccc3c(N)n[nH]c3c2)nc(N)n1]

In a 100 mL flask under argon were combined N-[6-(2,6-diamino-4-pyrimidinyl)-1H-indazol-3-yl]acetamide (0.083 g, 0.29 mmol) and HCl (0.28 mL, 9.4 mmol, 12 M) in $CH_3OH$ (20 mL). The reaction mixture was stirred at 60° C. for 8 hours and then cooled to room temperature overnight. The mixture was concentrated and the resulting yellow solid was dissolved in water (3 mL). NaOH (1M) was added to the solution until the pH was 12. The precipitated solid was filtered, washed with water, and dried under vacuum at 40° C. The solid (18 mg) was dissolved in hot DMSO (0.5 mL) and sonicated. The resulting precipitate was filtered. Since HPLC showed the material to be only 90% pure, everything was combined (solids and filtrate) and purified on a Gilson RPHPLC ($CH_3CN/H_2O$ w/0.1% $NH_4OH$) to afford the title compound (7 mg, 10%) as a white solid. LC-MS (ES) m/z=242 $[M+H]^+$. $^1H$ NMR (400 MHz, DMSO-$d_6$): δ 5.37 (s, 2H), 5.93 (s, 2H), 6.25 (s, 1H), 6.31 (s, 2H), 7.40 (dd, J=8.3, 1.3 Hz, 1H), 7.69 (d, J=8.3 Hz, 1H), 7.82 (s, 1H), 11.51 (s, 1H).

Intermediate 8

N-{6-[2-Amino-6-(4-morpholinyl)-4-pyrimidinyl]-1H-indazol-3-yl}acetamide

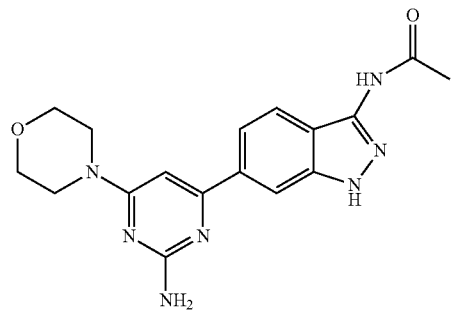 [SMILES: CC(=O)Nc1n[nH]c2cc(-c3cc(N4CCOCC4)nc(N)n3)ccc12]

In a 25 mL sealable tube under argon were combined N-acetyl-N-(1-acetyl-6-bromo-1H-indazol-3-yl)acetamide (0.25 g, 0.74 mmol), bis(pinacolato)diboron (0.197 g, 0.776 mmol), and potassium acetate (0.145 g, 1.48 mmol) in 1,4-dioxane (4.9 mL). The mixture was degassed with argon for 5 minutes. $PdCl_2(dppf)$-$CH_2Cl_2$ (0.024 g, 0.03 mmol) was added, the tube was sealed, and the reaction mixture was stirred for 5 hours at 100° C. The mixture was cooled to room temperature, the tube was unsealed, and 4-chloro-6-(4-morpholinyl)-2-pyrimidinamine (0.175 g, 0.813 mmol), $NaHCO_3$ (0.25 g, 2.96 mmol), water (1.64 mL), and $PdCl_2$(dppf)-$CH_2Cl_2$ (0.024 g, 0.03 mmol) were added. The tube was resealed under argon and the reaction mixture was stirred overnight at 100° C. The mixture was cooled to room temperature, dilute with $CH_3CN$ (10 mL), filtered through a pad of Celite503, and concentrated. The resulting brown solid was dissolved 10 mL of solvent (30/70 $CH_3CN/H_2O$ w/0.25 ml TFA), and the solution was filtered through a 0.45μ filter disk. Purification on a Varian RPHPLC ($CH_3CN/H_2O$ w/0.1% TFA) afforded a TFA salt of the title compound (151 mg) as a white solid. LC-MS (ES) m/z=354 $[M+H]^+$.

Example 6

6-[2-Amino-6-(4-morpholinyl)-4-pyrimidinyl]-1H-indazol-3-amine

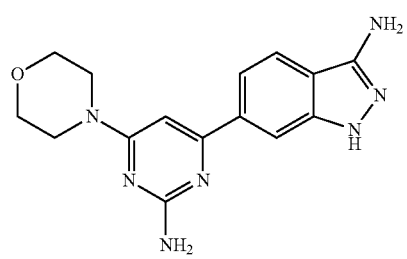 [SMILES: Nc1nc(-c2ccc3c(N)n[nH]c3c2)cc(N2CCOCC2)n1]

In a 100 mL flask under argon was dissolved N-{6-[2-amino-6-(4-morpholinyl)-4-pyrimidinyl]-1H-indazol-3-yl}acetamide (0.15 g, 0.26 mmol) in $CH_3OH$ (10 mL). HCl (0.69 mL, 8.3 mmol, 12 M) was added and the reaction mixture was stirred at 60° C. for 4 hours. The mixture was cooled to room temperature and filtered. The solid was washed with hexanes to afford a HCl salt of the title compound (75 mg) as a light yellow solid. LC-MS (ES) m/z=312 [M+H]$^+$. $^1$H NMR (400 MHz, DMSO-d$_6$): δ 3.73 (m, 4H), 3.89 (m, 4H), 6.98 (s, 1H), 7.66 (d, J=8.6 Hz, 1H), 8.08 (m, 2H).

Intermediate 9

6-Chloro-N$^4$-ethyl-2,4-pyrimidinediamine

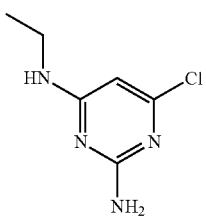

In a 50 mL flask under argon were combined 4,6-dichloro-2-pyrimidinamine (0.50 g, 3.05 mmol) and ethylamine (2.0 M in CH$_3$OH) (15.24 mL, 30.5 mmol) and the reaction mixture was stirred at 50° C. for 3 hours. The mixture was cooled to room temperature and concentrated. The resulting yellow solid was dissolved in EtOAc and the solution was washed with water. The organic layer was dried (MgSO$_4$), filtered and concentrated to afford the title compound (368 mg, 69%) as a yellow solid. LC-MS (ES) m/z=173 [M+H]$^+$.

Intermediate 10

4-[2-Amino-6-(ethylamino)-4-pyrimidinyl]-2-fluorobenzonitrile

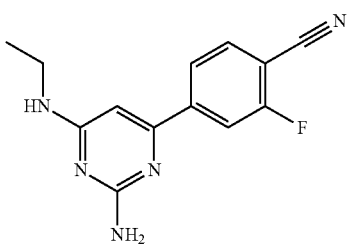 [SMILES: CCNc1cc(-c2ccc(C#N)c(F)c2)nc(N)n1]

In a 25 mL sealable tube under nitrogen were added (4-cyano-3-fluorophenyl)boronic acid (0.29 g, 1.74 mmol) and 6-chloro-N4-ethyl-2,4-pyrimidinediamine (0.30 g, 1.74 mmol) followed by in 1,4-dioxane (11.1 mL) and a saturated aqueous solution of NaHCO$_3$ (2.8 mL). The mixture was degassed with nitrogen for 10 minutes. Pd(Ph$_3$P)$_4$ (0.10 g, 0.087 mmol) was added, the vial was sealed, and the reaction mixture was stirred for 16 hours at 95° C. The reaction was cooled to room temperature, filtered, and concentrated. The resulting residue was partitioned between EtOAc and water. The organic layer was separated, dried (MgSO$_4$), filtered and concentrated. The resulting yellow oil was dissolved in CH$_3$CN (5 mL w/5 drops TFA). DMSO (3 drops) and water (0.5 mL) were added and the solution was purified on a Gilson RPHPLC (CH$_3$CN/H$_2$O w/0.1% TFA). The fractions containing the desired product were combined and concentrated until most of the CH$_3$CN was removed (half the original volume). The resulting precipitate was filtered, washed with water, and dried under vacuum to afford a TFA salt of the title compound (164 mg) as a white solid. LC-MS (ES) m/z=258 [M+H]$^+$.

Example 7

6-(3-Amino-1H-indazol-6-yl)-N$^4$-ethyl-2,4-pyrimidinediamine

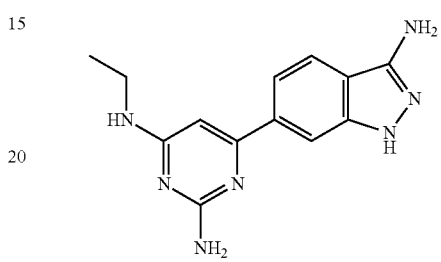

In a 25 mL flask under argon was added 4-[2-amino-6-(ethylamino)-4-pyrimidinyl]-2-fluorobenzonitrile (0.164 g, 0.442 mmol) followed by EtOH (3.5 mL). Hydrazine monohydrate (0.87 mL, 17.7 mmol) was added and the reaction mixture was stirred for 6 hours at 80° C. The reaction was cooled to room temperature and concentrated to near dryness. Water (3 mL) was added (orange oil was formed) followed by CH$_3$CN (8 drops), and the mixture was sonicated. A light yellow precipitate was formed. The suspension was cooled on an ice bath and the solid was filtered, washed with water and dried under vacuum at 40° C. to afford the title compound (82 mg, 68%) as a light yellow solid. LC-MS (ES) m/z=270 [M+H]$^+$. $^1$H NMR (400 MHz, DMSO-d$_6$): δ 1.13 (t, J=7.2 Hz, 3H), 3.20-3.40 (m, 2H), 5.36 (s, 2H), 5.97 (s, 2H), 6.25 (s, 1H), 6.82 (bs, 1H), 7.41 (d, J=8.3 Hz, 1H), 7.69 (d, J=8.3 Hz, 1H), 7.84 (s, 1H), 11.50 (s, 1H).

Intermediate 11

6-Chloro-N$^4$-(1-methylethyl)-2,4-pyrimidinediamine

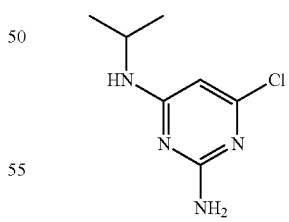

In a 25 mL sealable tube under argon were combined 4,6-dichloro-2-pyrimidinamine (0.50 g, 3.05 mmol) and isopropylamine (0.78 mL, 9.15 mmol) in CH$_3$OH (15 mL). The vial was sealed and the resulting mixture was stirred overnight at 50° C. The reaction was cooled to room temperature and stirred over the weekend. The reaction mixture was concentrated, and the resulting orange oil was partitioned between EtOAc and water. The organic layer was separated, washed with brine, dried (MgSO$_4$), filtered and concentrated

Intermediate 12

4-{2-Amino-6-[(1-methylethyl)amino]-4-pyrimidinyl}-2-fluorobenzonitrile

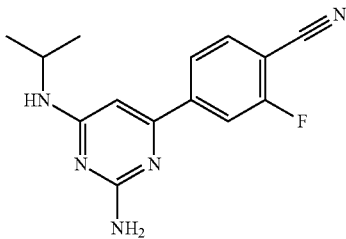 [SMILES: CC(C)Nc1cc(-c2ccc(C#N)c(F)c2)nc(N)n1]

In a 25 mL sealable tube under argon were added (4-cyano-3-fluorophenyl)boronic acid (0.40 g, 2.43 mmol) and 6-chloro-N4-(1-methylethyl)-2,4-pyrimidinediamine (0.45 g, 2.43 mmol) followed by 1,4-dioxane (9.7 mL) and saturated aqueous NaHCO$_3$ (2.4 mL). The mixture was degassed with argon for 5 minutes. Pd(Ph$_3$P)$_4$ (0.14 g, 0.12 mmol) was added, the vial was sealed, and the reaction mixture was stirred overnight at 95° C. The reaction was cooled to room temperature, decanted, and concentrated. The resulting orange oil was partitioned between EtOAc and water. The organic layer was separated, dried (MgSO$_4$), filtered and concentrated. To the resulting orange oil was added to water (1 mL), CH$_3$CN (3 mL), DMSO (2 mL) and TFA (10 drops). The mixture was filtered through a 0.2 μm frit and purified on a Gilson RPHPLC (CH$_3$CN/H$_2$O w/0.1% TFA). The fractions containing the desired product were combined and concentrated until most of the CH$_3$CN was removed. A white solid precipitated from the remaining water. The mixture was filtered, and the solid was washed with water and dried under vacuum at 40° C. to afford a TFA salt of the title compound as a white solid (208 mg). LC-MS (ES) m/z=272 [M+H]$^+$.

Example 8

6-(3-Amino-1H-indazol-6-yl)-N$^4$-(1-methylethyl)-2,4-pyrimidinediamine

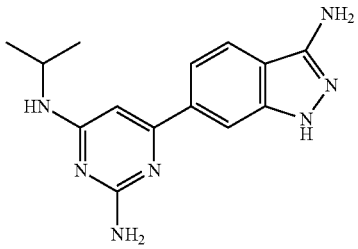 [SMILES: CC(C)Nc1cc(-c2ccc3c(N)n[nH]c3c2)nc(N)n1]

In a 25 mL sealable tube were combined 4-{2-amino-6-[(1-methylethyl)amino]-4-pyrimidinyl}-2-fluorobenzonitrile (0.21 g, 0.54 mmol), hydrazine monohydrate (1.06 mL, 21.6 mmol), and EtOH (10 mL). The tube was sealed and the reaction mixture was stirred overnight at 95° C. The mixture was concentrated and to the resulting solid was added to EtOH (2 mL) followed by hexanes (15 mL). The mixture was sonicated and filtered. The solid was washed with hexanes to afford the title compound (167 mg, 99%) as an off-white solid. LC-MS (ES) m/z=284 [M+H]$^+$. $^1$H NMR (400 MHz, DMSO-d$_6$): δ 1.15 (d, J=6.6 Hz, 6H), 4.12 (bs, 1H), 5.36 (s, 2H), 5.94 (s, 2H), 6.24 (s, 1H), 6.71 (d, J=7.6 Hz, 1H), 7.40 (d, J=8.6 Hz, 1H), 7.69 (d, J=8.3 Hz, 1H), 7.82 (s, 1H), 11.50 (bs, 1H).

Intermediate 13

4-Chloro-6(1-piperidinyl)-2-pyrimidinamine

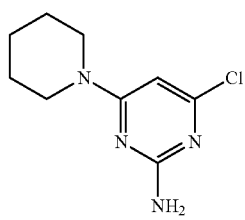 [SMILES: Nc1nc(Cl)cc(N2CCCCC2)n1]

In a 25 mL sealable tube under argon were combined 4,6-dichloro-2-pyrimidinamine (0.50 g, 3.05 mmol), piperidine (0.75 mL, 7.62 mmol) and CH$_3$OH (10 mL). The vial was sealed and the reaction mixture was stirred for 4 hours at 50° C. The reaction was cooled to room temperature and concentrated. The resulting solid was partitioned between EtOAc and water. The organic layer was separated, dried (MgSO$_4$), filtered and concentrated to afford the title compound (565 mg, 83%) as a yellow solid. LC-MS (ES) m/z=213 [M+H]$^+$.

Intermediate 14

4-[2-Amino-6-(1-piperidinyl)-4-pyrimidinyl]-2-fluorobenzonitrile

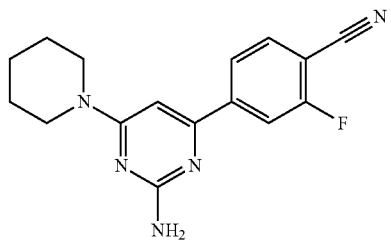 [SMILES: N#Cc1ccc(-c2cc(N3CCCCC3)nc(N)n2)cc1F]

In a 25 mL sealable tube under argon were combined 4-chloro-6-(1-piperidinyl)-2-pyrimidinamine (0.57 g, 2.66 mmol) and (4-cyano-3-fluorophenyl)boronic acid (0.44 g, 2.66 mmol) followed by in 1,4-dioxane (10.6 mL) and saturated aqueous NaHCO$_3$ (2.7 mL). The mixture was degassed for 5 minutes with argon. Pd(Ph$_3$P)$_4$ (0.15 g, 0.13 mmol) was added, the vial was sealed, and the reaction mixture was stirred for 15 hours at 95° C. The reaction was cooled to room temperature and the solution was decanted and concentrated. The resulting orange residue was partitioned between EtOAc and water. The organic layer was separated, dried (MgSO$_4$), filtered and concentrated. The resulting orange oil was dissolve in 90/10 CHCl$_3$/EtOAc and chromatographed on a 90 g SiO$_2$ column, using 90/10/1 CHCl$_3$/CH$_3$OH/NH$_4$OH as the solvent system. HPLC analysis showed a mixture of 2 products. Purification on a Gilson RPHPLC (CH₃CN/H₂O w/0.1% TFA) afforded a TFA salt of the title compound (286 mg) as a white solid. LC-MS (ES) m/z=298 [M+H]⁺.

Example 9

6-[2-Amino-6-(1-piperidinyl)-4-pyrimidinyl]-1H-indazol-3-amine

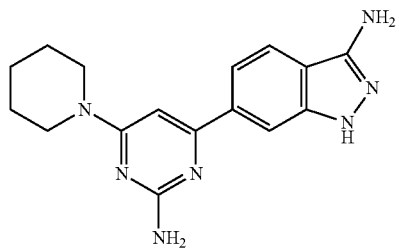 [SMILES: Nc1nc(-c2ccc3c(N)n[nH]c3c2)cc(N2CCCCC2)n1]

In a 25 mL sealable tube under argon were combined 4-[2-amino-6-(1-piperidinyl)-4-pyrimidinyl]-2-fluorobenzonitrile (0.106 g, 0.258 mmol), hydrazine monohydrate (0.51 mL, 10.3 mmol) and EtOH (5 mL). The vial was sealed and the reaction mixture was stirred overnight at 95° C. The reaction was cooled to room temperature and concentrated. The resulting solid was sonicated on a mixture of EtOH (1 mL) and water (9 mL). The mixture was filtered and the solid was washed with water and dried under vacuum at 40° C. to afford the title compound (66 mg, 80%) as a white solid. LC-MS (ES) m/z=310 [M+H]⁺. ¹H NMR (400 MHz, DMSO-d₆): δ 1.53 (m, 4H), 1.64 (m, 2H), 3.47-3.79 (m, 4H), 5.37 (s, 2H), 6.03 (s, 2H), 6.58 (s, 1H), 7.57 (dd, J=8.3, 1.3 Hz, 1H), 7.70 (d, J=8.6 Hz, 1H), 7.94 (s, 1H), 11.49 (s, 1H).

Intermediate 15

6-Chloro-N⁴-cyclopentyl-2,4-pyrimidinediamine

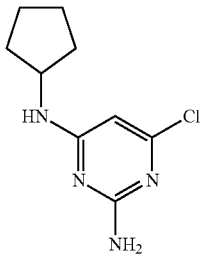 [SMILES: Nc1nc(Cl)cc(NC2CCCC2)n1]

In a 25 mL sealable tube under argon were combined 4,6-dichloro-2-pyrimidinamine (0.50 g, 3.05 mmol), cyclopentylamine (0.75 mL, 7.62 mmol) and CH₃OH (10 mL). The vial was sealed and the reaction mixture was stirred for 16 hours at 50° C. The reaction was concentrated, and the resulting oil was partitioned between EtOAc and water. The organic layer was separated, dried (MgSO₄), filtered and concentrated to afford the title compound (605 mg, 93%) as an orange oil. LC-MS (ES) m/z=213 [M+H]⁺.

Intermediate 16

4-[2-Amino-6-(cyclopentylamino)-4-pyrimidinyl]-2-fluorobenzonitrile

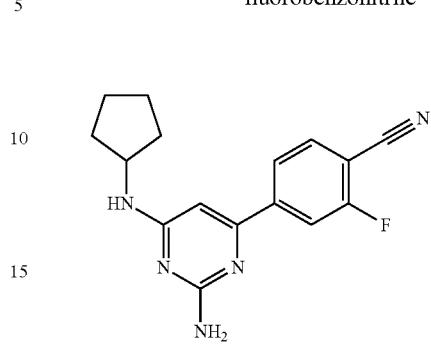

In a 25 mL sealable tube under nitrogen were combined 6-chloro-N4-cyclopentyl-2,4-pyrimidinediamine (0.60 g, 2.82 mmol) and (4-cyano-3-fluorophenyl)boronic acid (0.51 g, 3.10 mmol) followed by in 1,4-dioxane (11.3 mL) and saturated aqueous NaHCO₃ (2.8 mL). The mixture was degassed with nitrogen for 5 minutes. Pd(Ph₃P)₄ (0.16 g, 0.14 mmol) was added, the tube was sealed, and the reaction mixture was stirred overnight at 95° C. The solution was decanted and concentrated, and the resulting residue was partitioned between EtOAc and water. The organic layer was separated, dried (MgSO₄), filtered and concentrated. Purification on a Gilson RPHPLC (CH₃CN/H₂O w/0.1% TFA) afforded a TFA salt of the title compound (476 mg, 39%) as a white solid. LC-MS (ES) m/z=298 [M+H]⁺.

Example 10

6-(3-Amino-1H-indazol-6-yl)-N⁴-cyclopentyl-2,4-pyrimidinediamine

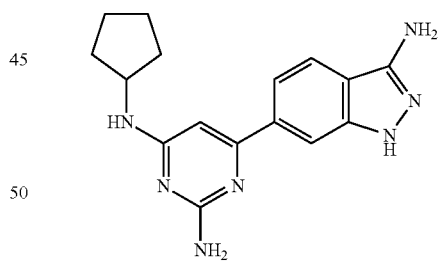

In a 25 mL sealable tube was dissolved 4-[2-amino-6-(cyclopentylamino)-4-pyrimidinyl]-2-fluorobenzonitrile (0.476 g, 1.16 mmol) in EtOH (10 mL). Hydrazine monohydrate (1.14 mL, 23.1 mmol) was added, the vial was sealed, and the reaction mixture was stirred for 16 hours at 95° C. The reaction was cooled to room temperature and concentrated. The resulting yellow solid was dissolved in EtOH (2 mL). Water (8 mL) was added, and the resulting mixture was sonicated for 10 minutes. The resulting white precipitate was filtered and dried to afford the title compound (177 mg, 47%) as a white solid. LC-MS (ES) m/z=310 [M+H]⁺. ¹H NMR (400 MHz, DMSO-d₆): δ 1.38-1.61 (m, 4H), 1.61-1.78 (m, 2H), 1.92 (m, 2H), 4.22 (bs, 1H), 5.37 (s, 2H), 5.97 (bs, 2H), 6.26 (s, 1H), 6.87 (bs, 1H), 7.40 (d, J=8.6 Hz, 1H), 7.70 (d, J=8.4 Hz, 1H), 7.82 (s, 1H), 11.51 (s, 1H).

Intermediate 17

6-Chloro-N⁴-cyclohexyl-2,4-pyrimidinediamine

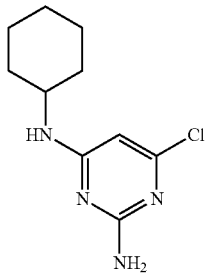 [SMILES: Nc1nc(Cl)cc(NC2CCCCC2)n1]

In a 25 mL sealable tube under argon were combined 4,6-dichloro-2-pyrimidinamine (0.50 g, 3.05 mmol) and cyclohexylamine (0.87 mL, 7.62 mmol) and $CH_3OH$ (10 mL). The vial was sealed, and the reaction mixture was stirred for 2 days at 50° C. The reaction was cooled to room temperature and concentrated. The resulting oil was partitioned between EtOAc and water. The organic layer was separated, washed with brine, dried ($MgSO_4$), filtered and concentrated to afford the title compound (750 mg, 99%) as an orange oil. LC-MS (ES) m/z=227 [M+H]⁺.

Intermediate 18

4-[2-Amino-6-(cyclohexylamino)-4-pyrimidinyl]-2-fluorobenzonitrile

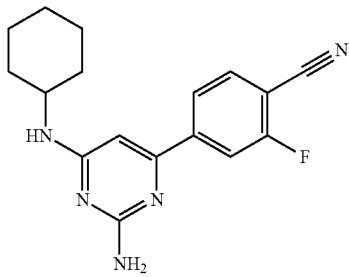 [SMILES: N#Cc1ccc(-c2cc(NC3CCCCC3)nc(N)n2)cc1F]

In a 25 mL sealable tube under nitrogen were combined 6-chloro-N4-cyclohexyl-2,4-pyrimidinediamine (0.75 g, 3.31 mmol) and (4-cyano-3-fluorophenyl)boronic acid (0.546 g, 3.31 mmol) followed by 1,4-dioxane (13.2 mL) and saturated aqueous $NaHCO_3$ (3.3 mL). The resulting mixture was degassed with nitrogen for 5 minutes. $Pd(Ph_3P)_4$ (0.19 g, 0.165 mmol) was added, the vial was sealed, and the reaction mixture was stirred for 16 hours at 95° C. The reaction was cooled to room temperature, decanted, and concentrated. The resulting orange oil was partitioned between EtOAc and water. The organic layer was separated, washed with brine, dried ($MgSO_4$), filtered and concentrated. To the resulting yellow solid was added $CH_3CN$ (5 mL), and the mixture was sonicated. Filtration of the solid and washing with minimal $CH_3CN$ afforded the title compound (387 mg, 36%) as a light tan solid. LC-MS (ES) m/z=312 [M+H]⁺.

Example 11

6-(3-Amino-1H-indazol-6-yl)-N⁴-cyclohexyl-2,4-pyrimidinediamine

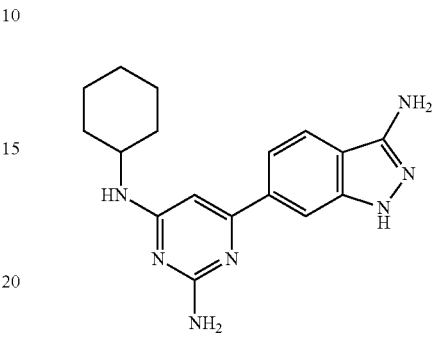

In a 25 mL sealable tube were combined 4-[2-amino-6-(cyclohexylamino)-4-pyrimidinyl]-2-fluorobenzonitrile (0.39 g, 1.24 mmol), hydrazine monohydrate (1.2 mL, 24.9 mmol) and EtOH (10 mL). The vial was sealed and the reaction mixture was stirred overnight at 95° C. The reaction was cooled to room temperature and filtered through a pad of Celite503. The filtrate was concentrated to dryness. The resulting yellow solid was diluted with EtOH (2 mL) followed by water (8 mL). The mixture was sonicated for 10 minutes, and then filtered. To the resulting solid was added 5 mL of a 90/10 mixture of $CH_3CN$ and water respectively. TFA (0.5 mL) was added and, after 2 minutes, a solid mass was observed. The mixture was diluted with $CH_3CN$ (15 mL) and filtered to afford a TFA salt of the title compound (100 mg) as a white solid. LC-MS (ES) m/z=324 [M+H]⁺. ¹H NMR (400 MHz, DMSO-$d_6$): δ 1.30 (m, 6H), 1.62 (m, 1H), 1.70-1.81 (m, 2H), 1.91 (m, 2H), 3.96 (bs, 1H), 6.36 (s, 1H), 7.17 (dd, J=8.5, 1.4 Hz, 1H), 7.57 (s, 1H), 7.89 (d, J=8.3 Hz, 1H), 8.66 (d, J=7.8 Hz, 1H), 11.87 (s, 1H), 11.94 (bs, 1H).

Intermediate 19

4-(1-Azetidinyl)-6-chloro-2-pyrimidinamine

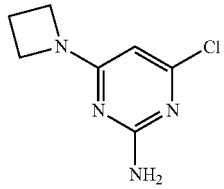 [SMILES: Nc1nc(Cl)cc(N2CCC2)n1]

In a 25 mL sealable tube were combined 4,6-dichloro-2-pyrimidinamine (0.50 g, 3.05 mmol), azetidine (0.21 mL, 3.05 mmol), and triethylamine (1.06 mL, 7.62 mmol) in $CH_3OH$ (10 mL). The vial was sealed and the reaction mixture was stirred overnight at 50° C. The reaction was concentrated and the resulting solid was partitioned between EtOAc and water. The organic layer was separated, dried ($MgSO_4$), filtered and concentrated to afford the title compound (314 mg, 53%) as a yellow solid. LC-MS (ES) m/z=185 [M+H]⁺.

Intermediate 20

4-[2-Amino-6-(1-azetidinyl)-4-pyrimidinyl]-2-fluorobenzonitrile

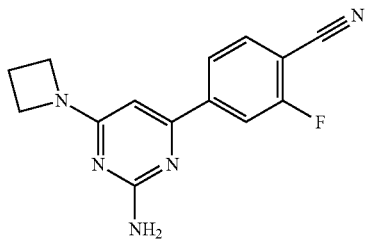 [SMILES: N#Cc1ccc(-c2cc(N3CCC3)nc(N)n2)cc1F]

In a 25 mL sealable tube under nitrogen were combined (4-cyano-3-fluorophenyl)boronic acid (0.28 g, 1.70 mmol) and 4-(1-azetidinyl)-6-chloro-2-pyrimidinamine (0.314 g, 1.70 mmol) in 1,4-dioxane (6.8 mL) and saturated aqueous NaHCO₃ (1.7 mL). The resulting mixture was degassed with nitrogen for 5 minutes. Pd(Ph₃P)₄ (0.098 g, 0.085 mmol) was added, the vial was sealed, and the reaction mixture was stirred overnight at 95° C. The reaction was concentrated and the resulting solid was partitioned between EtOAc and water. The organic layer was separated, dried (MgSO₄), filtered and concentrated. To the resulting yellow solid was added CH₃CN (3 mL), water (1 mL) and TFA (0.5 mL), and the mixture was sonicated for 2 minutes, and then concentrated. The solid was diluted with CH₃CN (2 mL), filtered, and washed with CH₃CN (1 mL) and Et₂O (2 mL) to afford a TFA salt of the title compound (212 mg) as an off-white solid. LC-MS (ES) m/z=270 [M+H]⁺.

Example 12

6-[2-Amino-6-(1-azetidinyl)-4-pyrimidinyl]-1H-indazol-3-amine

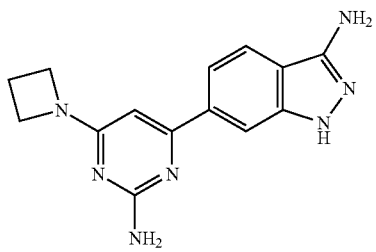 [SMILES: Nc1nc(-c2ccc3c(N)n[nH]c3c2)cc(N2CCC2)n1]

In a 25 mL sealable tube were combined 4-[2-amino-6-(1-azetidinyl)-4-pyrimidinyl]-2-fluorobenzonitrile (0.21 g, 0.79 mmol), hydrazine monohydrate (0.77 mL, 15.8 mmol) and CH₃OH (10 mL). The vial was sealed, and the reaction mixture was stirred overnight at 95° C. The reaction was concentrated, and the resulting yellow solid was diluted with EtOH (2 mL) and water (5 mL). The mixture was sonicated, and the solid was filtered, washed with water, and dried under vacuum to afford the title compound (99 mg, 43%) as a light yellow solid. LC-MS (ES) m/z=282 [M+H]⁺. ¹H NMR (400 MHz, DMSO-d₆): δ 2.33 (m, 2H), 4.02 (m, 4H), 5.38 (s, 2H), 6.13 (bs, 2H), 6.14 (s, 1H), 7.51 (dd, J=8.3, 1.3 Hz, 1H), 7.70 (d, J=8.3 Hz, 1H), 7.91 (s, 1H), 11.50 (s, 1H).

Intermediate 21

N-[4-(4-Cyano-3-fluorophenyl)-6-(1-piperidinyl)-2-pyrimidinyl]acetamide

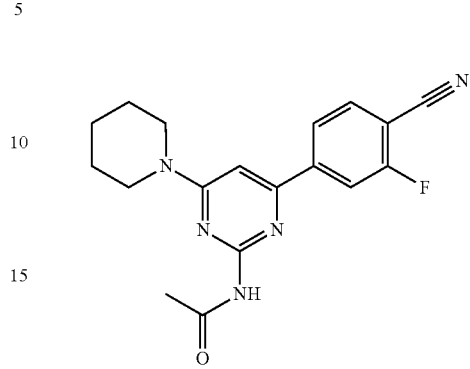

In a 25 mL sealable tube under argon were combined 4-[2-amino-6-(1-piperidinyl)-4-pyrimidinyl]-2-fluorobenzonitrile (0.18 g, 0.44 mmol) and acetic anhydride (5 mL). The vial was sealed and the reaction mixture was stirred at 95° C. After 16 hours, LCMS indicated a mixture of 2:1 bis:mono acetylated products. The reaction mixture was cooled to room temperature and concentrated. To the resulting crude mixture (192 mg) was added CH₃OH (10 mL) followed by DMAP (0.046 g, 0.38 mmol) and the reaction mixture was stirred overnight at 30° C. Additional DMAP (30 mg) was added and the reaction mixture was stirred for an additional 24 hours. The reaction was concentrated, and the resulting oil was partitioned between EtOAc and water. The organic layer was separated, dried (MgSO₄), filtered and concentrated to afford the title compound (150 mg, some DMAP is present) as a light yellow solid. LC-MS (ES) m/z=340 [M+H]⁺.

Intermediate 22

N-[4-(4-Cyano-3-fluorophenyl)-6-(1-piperidinyl)-2-pyrimidinyl]-N-methylacetamide

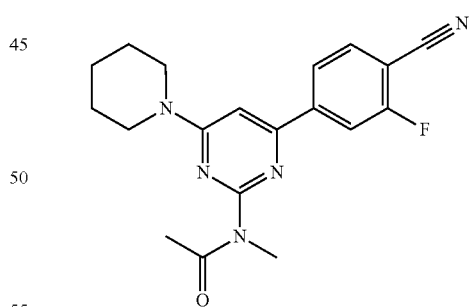

To N-[4-(4-cyano-3-fluorophenyl)-6-(1-piperidinyl)-2-pyrimidinyl]acetamide (0.15 g, 0.44 mmol) in DMF (4.4 mL) was added cesium carbonate (0.16 g, 0.49 mmol) followed by methyl iodide (0.03 mL, 0.49 mmol), and the reaction mixture was stirred overnight at room temperature. Additional cesium carbonate (300 mg) and methyl iodide (0.03 mL) were added, and the reaction mixture was stirred at room temperature over the weekend. The mixture was filtered through a 0.2 μM frit and purified on a Gilson RPHPLC (CH₃CN/H₂O w/0.1% TFA). The fractions containing the title compound and the de-acetylated title compound were combined and

Example 13

6-[2-(Methylamino)-6-(1-piperidinyl)-4-pyrimidinyl]-1H-indazol-3-amine

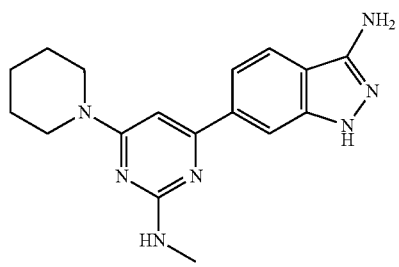 [SMILES: CNc1nc(-c2ccc3c(N)n[nH]c3c2)cc(N2CCCCC2)n1]

In a 25 mL sealable tube were combined N-[4-(4-cyano-3-fluorophenyl)-6-(1-piperidinyl)-2-pyrimidinyl]-N-methylacetamide (0.04 g, 0.11 mmol) and hydrazine monohydrate (0.11 mL, 2.21 mmol) in EtOH (10 mL). The tube was sealed, and the reaction mixture was stirred overnight at 95° C. The reaction was cooled to room temperature and concentrated. The resulting oil was dissolved in EtOH (3 mL) followed by the addition of water (6 mL). Since no solid was observed (a yellow oil was formed), the mixture was concentrated to dryness. The resulting oil was diluted with $CH_3CN$ (2 mL) and sonicated. The resulting yellow solid was filtered, washed with $CH_3CN$ (1 mL) and dried to afford the title compound (18 mg, 48%). LC-MS (ES) m/z=324 [M+H]$^+$. $^1$H NMR (400 MHz, DMSO-$d_6$): δ 1.60 (m, 4H), 1.68 (m, 2H), 2.92 (d, J=4.3 Hz, 3H), 3.84 (bs, 4H), 5.54 (bs, 2H), 6.81 (bs, 1H), 7.21 (bs, 1H), 7.40 (bs, 1H), 7.76 (bs, 1H), 7.85 (d, J=8.3 Hz, 1H), 11.83 (bs, 1H).

Intermediate 23

N-[6-(2-Amino-6-methyl-4-pyrimidinyl)-1H-indazol-3-yl]acetamida

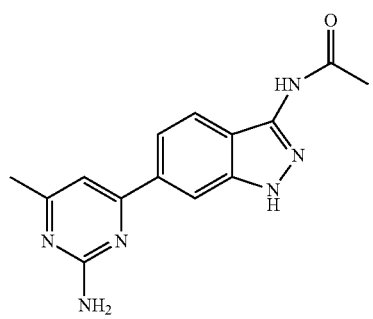 [SMILES: CC(=O)Nc1n[nH]c2cc(-c3cc(C)nc(N)n3)ccc12]

Into a 25 mL flask under argon were combined N-acetyl-N-(1-acetyl-6-bromo-1H-indazol-3-yl)acetamide (0.25 g, 0.74 mmol), bis(pinacolato)diboron (0.197 g, 0.78 mmol), and potassium acetate (0.145 g, 1.48 mmol) in 1,4-dioxane (4.9 mL). The mixture was degassed with argon for 5 minutes. $PdCl_2(dppf).CH_2Cl_2$ (0.024 g, 0.03 mmol) was added, the tube was sealed, and the reaction mixture was stirred overnight at 100° C. The reaction was cooled to room temperature and the tube was unsealed. 4-Chloro-6-methyl-2-pyrimidinamine (0.117 g, 0.813 mmol), sodium bicarbonate (0.25 g, 2.96 mmol), $PdCl_2(dppf).CH_2Cl_2$ (0.024 g, 0.03 mmol), and water (1.64 mL) were added, the tube was resealed under argon, and the reaction mixture was stirred overnight at 100° C. The reaction was cooled to room temperature, diluted with $CH_3CN$ (15 mL), filtered through a pad of Celite503, and concentrated. To the resulting brown solid were added a 70/30 mixture of water/$CH_3CN$ (12 mL) and TFA (0.5 mL). The resulting mixture was filtered through 0.45 μM filter disk and injected into a Varian RPHPLC ($CH_3CN/H_2O$ w/0.1% TFA). The fraction containing the desired product were combined and concentrated (material bumped on rotary evaporator and a significant amount of material was lost) to afford a TFA salt of the title compound as a yellow solid (21 mg). LC-MS (ES) m/z=283 [M+H]$^+$.

Example 14

6-(2-Amino-6-methyl-4-pyrimidinyl)-1H-indazol-3-amine

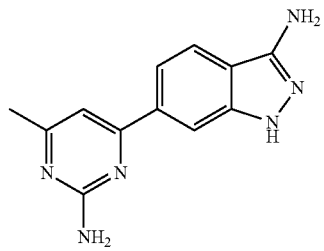 [SMILES: Cc1cc(-c2ccc3c(N)n[nH]c3c2)nc(N)n1]

In a 100 mL flask under argon was dissolved N-[6-(2-amino-6-methyl-4-pyrimidinyl)-1H-indazol-3-yl]acetamide (0.021 g, 0.074 mmol) in $CH_3OH$ (5 mL). HCl (2.26 μl, 0.074 mmol) was added and the solution was stirred for 8 hours at 60° C. The reaction was cooled to room temperature. The resulting precipitate was filtered and washed with minimal $CH_3OH$ to afford an HCl salt of the title compound (6 mg, 26%) as a white solid. LC-MS (ES) m/z=241 [M+H]$^+$. $^1$H NMR (400 MHz, DMSO-$d_6$): δ 2.51 (s, 3H {assumed to be hidden beneath DMSO peak}), 7.59 (s, 1H), 7.81 (dd, J=8.6, 1.3 Hz, 1H), 7.99 (d, J=8.6 Hz, 1H), 8.21 (s, 1H), 12.72 (bs, 1H).

Intermediate 24

4-(2-Amino-6-chloro-4-pyrimidinyl)-2-fluorobenzonitrile

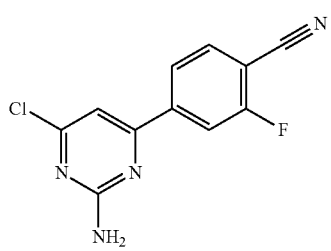 [SMILES: N#Cc1ccc(-c2cc(Cl)nc(N)n2)cc1F]

In a 25 mL sealable tube under argon were combined (4-cyano-3-fluorophenyl)boronic acid (0.50 g, 3.03 mmol), 4,6-dichloro-2-pyrimidinamine (0.497 g, 3.03 mmol), saturated aqueous $NaHCO_3$ (4.04 mL), and 1,4-dioxane (16.2 mL), and the mixture was degassed with argon for 5 minutes. $Pd(Ph_3P)_4$ (0.175 g, 0.152 mmol) was added, the vial was sealed, and the reaction mixture was stirred for 16 hours at 95° C. The reaction was cooled to room temperature, filtered through a plug of celite503, and concentrated. The resulting orange tar was partitioned between EtOAc and water. The organic layer was separated, washed with brine, dried (MgSO$_4$), filtered and concentrated. The resulting orange solid was sonicated in CHCl$_3$ (50 mL) for 2 minutes. The mixture was filtrated, the solid was washed with CHCl$_3$, and the filtrate was concentrated. Flash chromatography on SiO$_2$ (40 g) of the resulting residue (gradient: 100% CHCl$_3$ to 5% EtOAc/CHCl$_3$) afforded the title compound (267 mg, 32%) as a yellow solid. LC-MS (ES) m/z=249 [M+H]$^+$.

Intermediate 25

4-(2-Amino-6-phenyl-4-pyrimidinyl)-2-fluorobenzonitrile

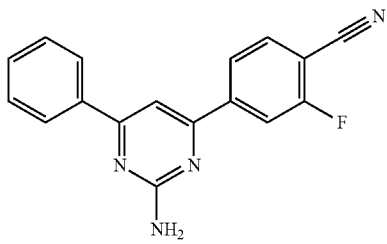 [SMILES: N#Cc1ccc(-c2cc(-c3ccccc3)nc(N)n2)cc1F]

In a 25 mL sealable tube under argon were combined 4-(2-amino-6-chloro-4-pyrimidinyl)-2-fluorobenzonitrile (0.196 g, 0.788 mmol) and phenylboronic acid (0.096 g, 0.79 mmol) in 1,4-dioxane (5.0 mL) and saturated aqueous NaHCO$_3$ (1.3 mL), and the mixture was degassed with argon for 5 minutes. Pd(Ph$_3$P)$_4$ (0.046 g, 0.04 mmol) was added, the vial was sealed, and the reaction mixture was stirred overnight at 95° C. The reaction was cooled to room temperature and filtered, and the filtrate was concentrated to dryness. The resulting solid was partitioned between EtOAc and water. The organic layer was separated, washed with brine, dried (MgSO$_4$), filtered and concentrated. Purification of the resulting solids on Gilson RPHPLC (CH$_3$CN/H$_2$O w/0.1% TFA) afforded a TFA salt of the title compound (52 mg) as a white solid. LC-MS (ES) m/z=291 [M+H]$^+$.

Example 15

6-(2-Amino-6-phenyl-4-pyrimidinyl)-1H-indazol-3-amine

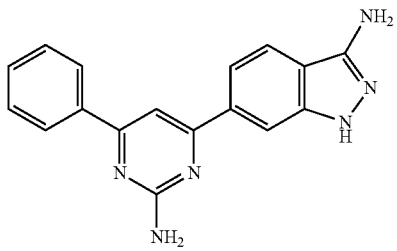 [SMILES: Nc1nc(-c2ccccc2)cc(-c2ccc3c(N)n[nH]c3c2)n1]

Into a 25 mL sealable tube under argon were added 4-(2-amino-6-phenyl-4-pyrimidinyl)-2-fluorobenzonitrile (0.052 g, 0.18 mmol) and EtOH (5 mL). Hydrazine monohydrate (0.35 mL, 7.17 mmol) was added, the vial was sealed, and the reaction mixture was stirred overnight at 95° C. The reaction was cooled to room temperature and concentrated. The resulting solid was sonicated in a mixture of EtOH (1 mL) and water (10 mL), filtered, washed with water, and dried under vacuum at 40° C. to afford the title compound as a yellow solid (44 mg, 77%). LC-MS (ES) m/z=303 [M+H]$^+$. $^1$H NMR (400 MHz, DMSO-d$_6$): δ 5.43 (s, 2H), 6.74 (s, 2H), 7.46-7.59 (m, 3H), 7.69-7.84 (m, 3H), 8.12 (s, 1H), 8.23 (m, 2H), 11.63 (s, 1H).

General Procedure A:

A solution of (3,5-difluoro-4-formylphenyl)boronic acid and the chloro-pyrimidine (1 eq) in a mixture of 1,4-dioxane/saturated aqueous NaHCO$_3$ (4:1 ratio) was degassed with nitrogen for ~20 minutes. Pd(Ph$_3$P)$_4$ (0.05 eq.) was added, and the resulting yellow solution was stirred at 100° C. until the starting materials were consumed as judged by LCMS or HPLC. The reaction mixture was diluted with EtOAc and water. The organic phase was separated and the aqueous phase was further extracted with EtOAc. The combined organic extracts were concentrated to a solid. Workup from here varies according to the compound.

Intermediate 26

4-(2-Amino-4-pyrimidinyl)-2,6-difluorobenzaldehyde

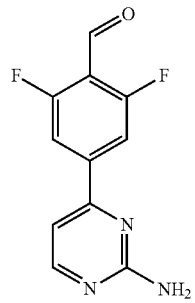 [SMILES: Nc1nccc(-c2cc(F)c(C=O)c(F)c2)n1]

The title compound was prepared following the General Procedure A using: (3,5-difluoro-4-formylphenyl)boronic acid (4.93 g, 26.5 mmol) and 4-chloro-2-pyrimidinamine (3.44 g, 26.5 mmol). Flash chromatography on SiO$_2$ (gradient: 100% CHCl$_3$ to 10% THF/90% CHCl$_3$) afforded the title compound (5.69 g, 75%) as an off-white solid. LC-MS (ES) m/z=236 [M+H]$^+$.

Intermediate 27

N-[4-(4-Cyano-3,5-difluorophenyl)-2-pyrimidinyl]acetamide

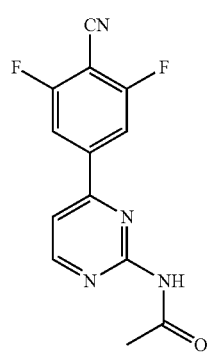

To a suspension of 4-(2-amino-4-pyrimidinyl)-2,6-difluorobenzaldehyde (5.69 g, 24.2 mmol) in EtOH (50 mL) and water (150 mL), were added sodium carbonate (2.82, 26.6 mmol) and hydroxylamine hydrochloride (1.85 g, 26.6 mmol), and the resulting mixture was stirred at 100° C. until the starting material was consumed as judged by LCMS (~2 hours). The reaction mixture was concentrated, and the resulting tan solid was washed with water and filtered. The aqueous washings were extracted with EtOAc, and the combined organic layers were concentrated. The concentrated organic extract and the filter cake were combined and suspended in acetic anhydride (used as solvent, ~150 mL), and the reaction mixture was stirred at 100° C. until the oxime intermediate was completely converted to the nitrile (~5 days). The reaction mixture was concentrated and co-evaporated with EtOH, and the resulting solid was triturated with $CH_3OH$ to afford the title compound (2.4 g, 36%) as a sandy tan solid. The filtrate was treated with saturated aqueous $NaHCO_3$ and $K_2CO_3$, and the basic solution was stirred overnight at room temperature converting the bis-acetyl by-product to the title compound. The basic solution was filtered, and the filtrate was concentrated. The resulting solid was triturated with $CH_3OH$ and washed with water to afford the title compound (1.05 g, 16%) as a sandy tan solid. LC-MS (ES) m/z=275 [M+H]$^+$.

General Procedure B:

To a slurry of the appropriate difluoro-nitrile in tetrahydrofuran (THF) or 1,4-dioxanes were added the appropriate amine (1.1 eq.) and Hunig's base (1.1 eq.) The resulting mixture was stirred at 85-90° C. until the starting material was consumed as judged by HPLC or LCMS (~12 hours). Hydrazine monohydrate (50 eq.) was added, and the reaction mixture was stirred at 85-90° C. until the intermediate was consumed as judged by LCMS or HPLC analysis (~12 hours). The reaction mixture was poured onto EtOAc and water, the organic layer was separated, and the aqueous layer was further extracted with EtOAc. The combined organic layers were concentrated. Work-up from here varies according to the compound.

Example 16

6-(2-Amino-4-pyrimidinyl)-$N^4$-(2-phenylethyl)-1H-indazole-3,4-diamine

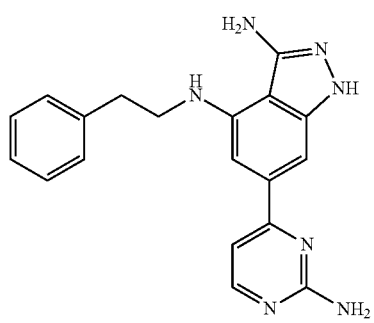 [SMILES: Nc1nccc(-c2cc(NCCc3ccccc3)c3c(N)n[nH]c3c2)n1]

The title compound was prepared following the General Procedure B using: N-[4-(4-cyano-3,5-difluorophenyl)-6-methyl-2-pyrimidinyl]acetamide (0.10 g, 0.37 mmol), (2-phenylethyl)amine (0.059 mL, 0.47 mmol) and tetrahydrofuran (THF) (3 mL). The residue was dry loaded onto a 12 g $SiO_2$ column eluting from 100% $CHCl_3$ to 90:10:1 $CHCl_3$:$CH_3OH$:$NH_4OH$. The clean fractions were concentrated to afford the title compound (43 mg, 29%) as yellow solid. LC-MS (ES) m/z=346 [M+H]$^+$. $^1$H NMR (400 MHz, $CD_3OD$): δ 3.04 (t, J=7.3 Hz, 2H), 3.56 (t, J=7.3 Hz, 2H), 6.74 (d, J=1.3 Hz, 1H), 7.11 (d, J=5.3 Hz, 1H), 7.24 (m, 2H), 7.33 (m, 2H), 7.34 (s, 2H), 8.27 (d, J=5.3 Hz, 1H).

Example 17

6-(2-Amino-4-pyrimidinyl)-$N^4$-(3-phenylpropyl)-1H-indazole-3,4-diamine

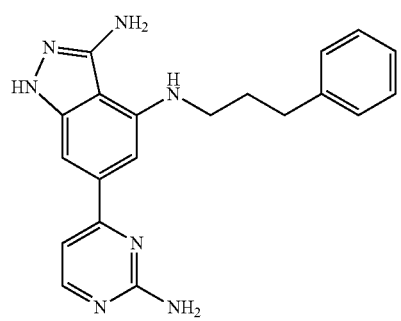 [SMILES: Nc1nccc(-c2cc(NCCCc3ccccc3)c3c(N)n[nH]c3c2)n1]

The title compound was prepared following the General Procedure B using: N-[4-(4-cyano-3,5-difluorophenyl)-6-methyl-2-pyrimidinyl]acetamide (0.30 g, 1.09 mmol), 3-phenyl-1-propanamine (0.17 mL, 1.20 mmol) and 1,4-dioxane (5 mL). The residue was dissolved in hot EtOH and precipitated with hexanes. The precipitate was collected via vacuum filtration to afford the title compound (0.14 g, 36%) as a light yellow solid. LC-MS (ES) m/z=360 [M+H]$^+$. $^1$H NMR (400 MHz, $CD_3OD$): δ 2.07-2.13 (m, 2H), 2.82 (t, J=7.5 Hz, 2H), 6.58 (s, 1H), 7.03 (d, J=5.3 Hz, 1H), 7.18 (m, 1H), 7.22 (m, 1H), 7.25-7.30 (m, 4H), 8.26 (d, J=5.6 Hz, 1H). NOTE the $NHCH_2$ protons are assumed to be hidden beneath the solvent residual peak.

Example 18

6-(2-Amino-4-pyrimidinyl)-$N^4$-[2-(phenyloxy)ethyl]-1H-indazole-3,4-diamine

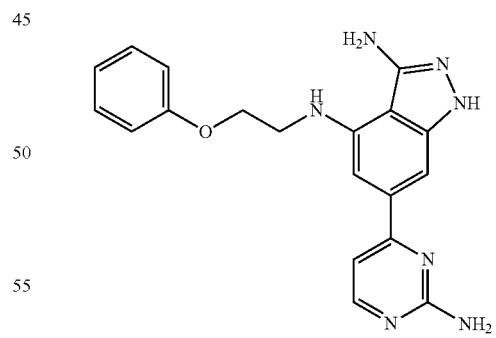

The title compound was prepared following the General Procedure B using: N-[4-(4-cyano-3,5-difluorophenyl)-2-pyrimidinyl]acetamide (0.10 g, 0.365 mmol), 2-(phenyloxy)ethanamine (0.053 mL, 0.40 mmol) and 1,4-dioxane (3 mL). The solid was dissolved in hot EtOH and precipitated with hexanes (just enough hexanes to start to turn the solution cloudy). The precipitate was collected via vacuum filtration to afford the title compound (57 mg, 43%) as a yellow solid. LC-MS (ES) m/z=362 [M+H]$^+$. $^1$H NMR (400 MHz, CD$_3$OD): δ 3.72 (t, J=5.6 Hz, 2H), 4.31 (t, J=5.6 Hz, 2H), 6.79 (d, J=1.3 Hz, 1H), 6.93 (m, 1H), 7.00 (m, 2H), 7.10 (d, J=5.3 Hz, 1H), 7.24-7.32 (m, 3H), 8.25 (d, J=5.6 Hz, 1H).

Example 19

6-(2-Amino-4-pyrimidinyl)-N$^4$-[3-(5-methyl-1H-pyrazol-4-yl)propyl]-1H-indazole-3,4-diamine

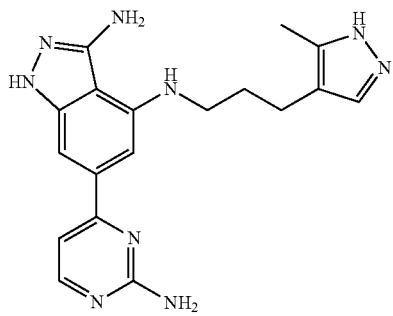 [SMILES: Cc1[nH]ncc1CCCNc1cc(-c2ccnc(N)n2)cc2[nH]nc(N)c12]

The title compound was prepared following the General Procedure B using: N-[4-(4-cyano-3,5-difluorophenyl)-6-methyl-2-pyrimidinyl]acetamide (0.10 g, 0.365 mmol), 3-(5-methyl-1H-pyrazol-4-yl)-1-propanamine (0.056 g, 0.40 mmol) and 1,4-dioxane (3 mL). The residue was dissolved in hot EtOH and precipitated with hexanes (just enough hexanes to start to turn the solution cloudy). The precipitate was collected via vacuum filtration to afford the title compound (47 mg, 36%) as a dark yellow solid. LC-MS (ES) m/z=364 [M+H]$^+$. $^1$H NMR (400 MHz, THF): δ 1.92-2.00 (m, 2H), 2.18 (s, 3H), 2.57 (t, J=7.2 Hz, 2H), 3.24-3.35 (m, 3H), 4.37 (bs, 2H), 5.28 (bs, 1H), 6.06 (bs, 2H), 6.71 (d, J=1.3 Hz, 1H), 6.94 (d, J=5.3 Hz, 1H), 7.21 (d, J=1.3 Hz, 1H), 7.33 (s, 1H), 8.17 (d, J=5.1 Hz, 1H), 10.79 (bs, 1H).

Example 20

2-(3-{[3-Amino-6-(2-amino-4-pyrimidinyl)-1H-indazol-4-yl]amino}propyl)phenol

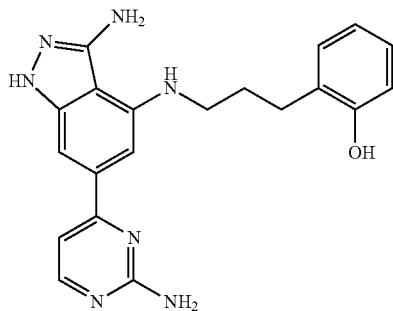 [SMILES: Nc1nccc(-c2cc(NCCCc3ccccc3O)c3c(N)n[nH]c3c2)n1]

The title compound was prepared following the General Procedure B using: N-[4-(4-cyano-3,5-difluorophenyl)-6-methyl-2-pyrimidinyl]acetamide (0.10 g, 0.365 mmol), 2-(3-aminopropyl)phenol (0.061 g, 0.40 mmol) and 1,4-dioxane (3 mL). The residue was dissolved in 2:1 CHCl$_3$: acetone (3 mL) and injected onto a 12 g SiO$_2$ column eluting from 100% CHCl$_3$ to 80:20:2 CHCl$_3$:CH$_3$OH:NH$_4$OH. The fractions containing the desired product were concentrated. The resulting yellow solid was dissolved in CH$_3$OH (1 mL) and injected onto a Gilson RPHPLC (CH$_3$CN/H$_2$O w/0.1% TFA). The appropriate fractions were concentrated to afford a TFA salt of the title compound (28 mg, 13%) as an orange solid. LC-MS (ES) m/z=376 [M+H]$^+$. $^1$H NMR (400 MHz, CD$_3$OD): δ 2.03-2.10 (m, 2H), 2.78 (t, J=7.3 Hz, 2H), 3.37 (t, J=7.2 Hz, 2H), 6.74-6.81 (m, 3H), 7.00-7.07 (m, 1H), 7.12 (d, J=7.3 Hz, 1H), 7.35 (d, J=6.6 Hz, 1H), 7.38 (s, 1H), 8.29 (d, J=6.8 Hz, 1H).

Example 21

6-(2-Amino-4-pyrimidinyl)-N$^4$-[3-(2-fluorophenyl)propyl]-1H-indazole-3,4-diamine

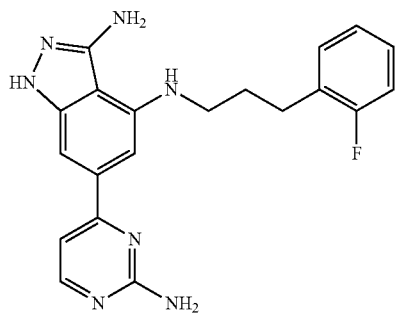 [SMILES: Nc1nccc(-c2cc(NCCCc3ccccc3F)c3c(N)n[nH]c3c2)n1]

The title compound was prepared following the General Procedure B using: N-[4-(4-cyano-3,5-difluorophenyl)-6-methyl-2-pyrimidinyl]acetamide (0.150 g, 0.547 mmol), 3-(2-fluorophenyl)-1-propanamine (0.114 g, 0.602 mmol) and 1,4-dioxane (3 mL). The solid was dissolved in hot EtOH and precipitated with hexanes. The precipitate was collected via vacuum filtration to afford the title compound (86 mg, 42%) as a tan solid. LC-MS (ES) m/z=378 [M+H]$^+$. $^1$H NMR (400 MHz, DMSO-d$_6$): δ 1.98 (m, 2H), 2.78 (t, J=7.7 Hz, 2H), 3.21-3.28 (m, 2H), 5.11 (s, 2H), 5.63 (m, 1H), 6.45 (s, 1H), 6.56 (s, 2H), 6.97 (d, J=5.3 Hz, 1H), 7.13-7.20 (m, 3H,) 7.24-7.30 (m, 1H), 7.37 (m, 1H), 8.25 (d, J=5.3 Hz, 1H), 11.49 (s, 1H).

Example 22

6-(2-Amino-4-pyrimidinyl)-N$^4$-[3-(4-fluorophenyl)propyl]-1H-indazole-3,4-diamine

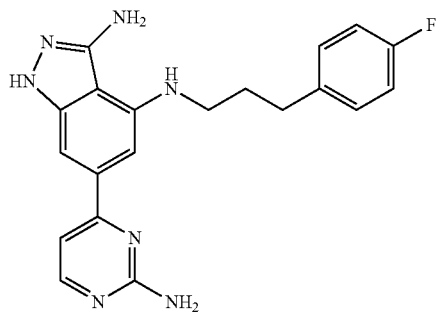 [SMILES: Nc1nccc(-c2cc(NCCCc3ccc(F)cc3)c3c(N)n[nH]c3c2)n1]

The title compound was prepared following the General Procedure B using: N-[4-(4-cyano-3,5-difluorophenyl)-6-methyl-2-pyrimidinyl]acetamide (0.150 g, 0.547 mmol), 3-(4-fluorophenyl)-1-propanamine (0.092 g, 0.602 mmol) and 1,4-dioxane (3 mL). The solid was dissolved in hot EtOH and precipitated with hexanes. The precipitate was collected via vacuum filtration to afford the title compound (109 mg, 53%) as a tan solid. LC-MS (ES) m/z=378 [M+H]+. 1H NMR (400 MHz, DMSO-d6): δ 1.95-2.01 (m, 2H), 2.74 (t, J=7.6 Hz, 2H), 3.18-3.25 (m, 2H), 5.12 (s, 2H), 5.60 (m, 1H), 6.44 (s, 1H), 6.57 (s, 2H), 6.97 (d, J=5.1 Hz, 1H), 7.09-7.16 (m, 2H), 7.18 (s, 1H), 7.28-7.34 (m, 2H), 8.25 (d, J=5.3 Hz, 1H), 11.49 (s, 1H).

Example 23

6-(2-Amino-4-pyrimidinyl)-N⁴-[3-(4-pyridinyl)propyl]-1H-indazole-3,4-diamine

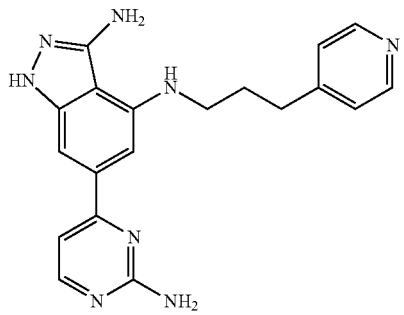 [SMILES: Nc1nccc(-c2cc(NCCCc3ccncc3)c3c(N)n[nH]c3c2)n1]

The title compound was prepared following the General Procedure B using: N-[4-(4-cyano-3,5-difluorophenyl)-6-methyl-2-pyrimidinyl]acetamide (0.10 g, 0.365 mmol), 3-(4-pyridinyl)-1-propanamine (0.138 g, 0.802 mmol) and 1,4-dioxane (3 mL). The residue was dissolved in 2:1 CHCl₃: acetone and injected onto a 12 g SiO₂ column eluting from 100% CHCl₃ to 90:10:1 CHCl₃:MeOH:NH₄OH. The fractions containing the desired product were concentrated, and the resulting solid was dissolved in CH₃OH and injected onto a Gilson RPHPLC (CH₃CN/H₂O w/0.1% TFA). The appropriate fractions were concentrated to afford a TFA salt of the title compound (15 mg, 6%) as a red solid. LC-MS (ES) m/z=361 [M+H]+. 1H NMR (400 MHz, CD₃OD): δ 2.23-2.30 (m, 2H), 3.15-3.21 (m, 2H), 3.52 (t, J=6.6 Hz, 2H), 6.92 (d, J=1.3 Hz, 1H), 7.46 (s, 1H), 7.53 (d, J=6.6 Hz, 1H), 7.99 (d, J=6.6 Hz, 2H), 8.34 (d, J=6.6 Hz, 1H), 8.68 (d, J=6.6 Hz, 2H).

Intermediate 28

4-(2-Amino-4-pyrimidinyl)-2-{[3-(3,5-dimethyl-1H-pyrazol-4-yl)propyl]amino}-6-fluorobenzonitrile

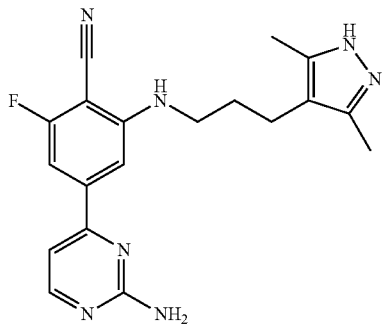 [SMILES: Cc1n[nH]c(C)c1CCCNc1cc(-c2ccnc(N)n2)cc(F)c1C#N]

To N-[4-(4-cyano-3,5-difluorophenyl)-2-pyrimidinyl]acetamide (0.10 g, 0.365 mmol) in 1,4-dioxane (3 ml) were added Hunig's base (0.07 mL, 0.40 mmol) and 3-(3,5-dimethyl-1H-pyrazol-4-yl)-1-propanamine (0.061 g, 0.40 mmol). The resulting mixture was stirred at 90° C. until the starting material was consumed as judged by LCMS (~12 hours). The reaction mixture was poured onto EtOAc and water. The organic phase was separated, the aqueous phase was further extracted with EtOAc, and the combined organic extracts were concentrated. The resulting yellow residue was dissolved in DMSO (1 mL) and injected onto a Gilson RPHPLC (CH₃CN/H₂O w/0.1% TFA). The appropriate fractions were concentrated to afford a TFA salt of the title compound (38 mg, 18%) as a yellow solid. LC-MS (ES) m/z=366 [M+H]+.

Example 24

6-(2-Amino-4-pyrimidinyl)-N⁴-[3-(3,5-dimethyl-1H-pyrazol-4-yl)propyl]-1H-indazole-3,4-diamine

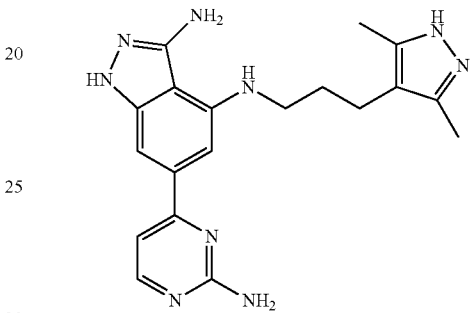

To a solution of 4-(2-amino-4-pyrimidinyl)-2-{[3-(3,5-dimethyl-1H-pyrazol-4-yl)propyl]amino}-6-fluorobenzonitrile (22 mg, 0.037 mmol) in EtOH (2 mL) was added hydrazine monohydrate (1 mL). The resulting solution was stirred at 90° C. until the starting material was consumed as judged by LCMS (~12 hours). The reaction mixture was concentrated, and the resulting yellow solid was dissolved in EtOH and precipitated with hexanes. The filtrate was decanted to afford the title compound (5 mg, 32%) as a light yellow solid. LC-MS (ES) m/z=378 [M+H]+. 1H NMR (400 MHz, CD₃OD): δ 1.91-1.98 (m, 2H), 2.16-2.23 (s, 6H), 2.59 (t, J=7.2 Hz, 2H), 3.24-3.31 (m, 2H), 6.60 (s, 1H), 7.04 (d, J=5.3 Hz, 1H), 7.23 (s, 1H), 8.27 (d, J=5.30 Hz, 1H).

Example 25

6-(2-Amino-4-pyrimidinyl)-N⁴-[3-(phenyloxy)propyl]-1H-indazole-3,4-diamine

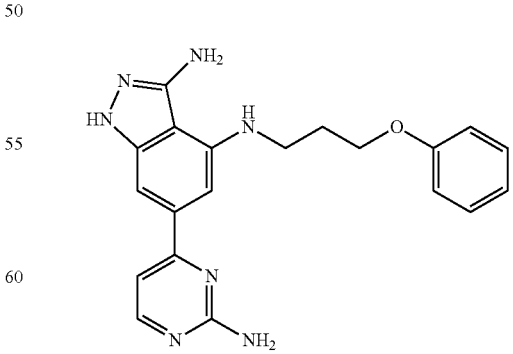

The title compound was prepared following the General Procedure B using: N-[4-(4-cyano-3,5-difluorophenyl)-6-methyl-2-pyrimidinyl]acetamide (0.150 g, 0.547 mmol), phenoxypropylamine (0.113 g, 0.602 mmol) and 1,4-dioxane (3 mL). The residue was dissolved in a CH$_3$OH:DMSO solution and injected onto a Gilson RPHPLC (CH$_3$CN/H$_2$O w/0.1% TFA). The appropriate fractions were concentrated to afford a TFA salt of the title compound (52 mg, 14%) as a red solid. LC-MS (ES) m/z=376 [M+H]$^+$. $^1$H NMR (400 MHz, CD$_3$OD): δ 2.23 (m, 2H), 3.61 (t, J=6.8 Hz, 2H), 4.15 (t, J=5.8 Hz, 2H), 6.88-6.95 (m, 3H), 7.21-7.28 (m, 2H), 7.39 (s, 1H), 7.41 (d, J=6.8 Hz, 1H), 8.26 (d, J=6.6 Hz, 1H). Note the proton of the "enamine" is exchangeable and not present in the NMR.

Example 26

6-(2-Amino-4-pyrimidinyl)-N$^4$-[3-(3-fluorophenyl) propyl]-1H-indazole-3,4-diamine

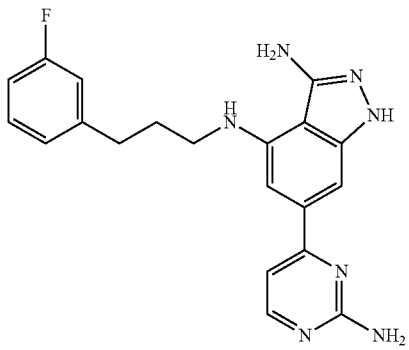 [SMILES: Nc1nccc(-c2cc(NCCCc3cccc(F)c3)c3c(N)n[nH]c3c2)n1]

The title compound was prepared following the General Procedure B using: N-[4-(4-cyano-3,5-difluorophenyl)-6-methyl-2-pyrimidinyl]acetamide (0.10 g, 0.365 mmol), 3-(3-fluorophenyl)-1-propanamine (0.069 g, 0.365 mmol) and 1,4-dioxane (3 mL). The solid was dissolved in hot EtOH and precipitated with hexanes. The precipitate was collected via vacuum filtration to afford the title compound (44 mg, 29%) as a yellow solid. LC-MS (ES) m/z=378 [M+H]$^+$. $^1$H NMR (400 MHz, DMSO-d$_6$): δ 2.00 (m, 2H), 2.78 (t, J=7.6 Hz, 2H), 3.18-3.26 (m, 2H), 5.12 (s, 2H), 5.61 (m, 1H), 6.45 (s, 1H), 6.57 (s, 2H), 6.98 (d, J=5.3 Hz, 1H), 6.99-7.06 (m, 1H), 7.12 (m, 2H), 7.18 (d, J=1.0 Hz, 1H), 7.31-7.38 (m, 1H), 8.25 (d, J=5.1 Hz, 1H), 11.50 (s, 1H).

Intermediate 29

4-(2-Amino-4-pyrimidinyl)-2-fluoro-6-(methyloxy) benzonitrile

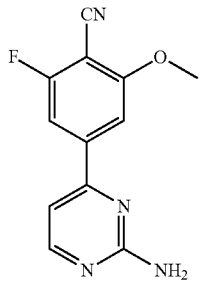 [SMILES: COc1cc(-c2ccnc(N)n2)cc(F)c1C#N]

To a slurry of 4-(2-amino-4-pyrimidinyl)-2,6-difluorobenzaldehyde (5.37 g, 22.8 mmol) in a mixture of EtOH and water were added sodium carbonate (2.66 g, 25.1 mmol) and hydroxylamine hydrochloride (1.75 g, 25.1 mmol). The resulting mixture was refluxed until the starting material was consumed (~2 hours). The reaction was allowed to cool to room temperature, and the insoluble oxime was filtered. The filtrate was extracted with EtOAc, and the organic layer was concentrated. The resulting gray solid was combined with the oxime precipitate and treated with excess acetic anhydride (solvent). The reaction mixture was stirred at 100° C. until LCMS confirms complete conversion to the desired nitrile (~5 days). The mixture was concentrated, and the resulting dark brown solid was co-evaporated with EtOH to removed excess acetic anhydride. The dark brown solid was triturated with CH$_3$OH to afford N-[4-(4-cyano-3,5-difluorophenyl)-2-pyrimidinyl]acetamide (2.44 g 39%) as a tan solid. The filtrate was treated with aqueous sodium bicarbonate and K$_2$CO$_3$ in CH$_3$OH, and the resulting mixture was stirred overnight at room temperature. The CH$_3$OH was evaporated, and the resulting tan solid was dissolved in EtOAc and water. The phases were separated and the aqueous phase was further extracted with EtOAc. The combined organic layers were concentrated, and the resulting tan solid was triturated with CH$_3$OH to afford the title compound (0.60 g 11%). LC-MS (ES) m/z=245 [M+H]$^+$.

Example 27

6-(2-Amino-4-pyrimidinyl)-4-(methyloxy)-1H-indazol-3-amine

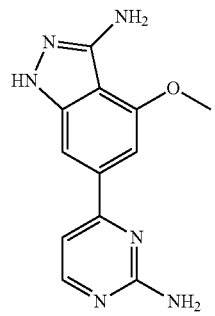 [SMILES: COc1cc(-c2ccnc(N)n2)cc2[nH]nc(N)c12]

To a slurry of 4-(2-amino-4-pyrimidinyl)-2-fluoro-6-(methyloxy)benzonitrile (0.20 g, 0.82 mmol) in THF (2 mL) was added hydrazine monohydrate (1.3 mL), and the resulting mixture was stirred at 90° C. until the starting material was consumed as judged by LCMS (~12 hours). The reaction mixture was concentrated to afford the title compound (102 mg, 49%) as a bright yellow solid. LC-MS (ES) m/z=257 [M+H]$^+$. $^1$H NMR (400 MHz, DMSO-d$_6$): δ 3.94 (s, 3H), 5.06 (s, 2H), 6.65 (s, 2H), 6.97 (s, 1H), 7.16 (d, J=5.3 Hz, 1H), 7.54 (d, J=1.0 Hz, 1H), 8.30 (d, J=5.3 Hz, 1H), 11.67 (bs, 1H). General Procedure C:

To a solution of N-[4-(4-cyano-3,5-difluorophenyl)-6-methyl-2-pyrimidinyl]acetamide in DMF (3 mL) was added sodium hydride (1.5 eq.). To the basic solution was added dropwise a solution of the appropriate alcohol (1 eq.) and sodium hydride (1 eq.) in DMF (3 mL). The vial that contained the alkoxide solution was rinsed with more DMF (1 mL). When the reaction was judged complete (HPLC, ~1 hour), the reaction mixture was poured onto saturated aqueous ammonium chloride. After standing for ~10-15 minutes, the precipitate formed was collected by vacuum filtration. To the resulting solid in EtOH was added hydrazine monohydrate (50 eq.), and the reaction mixture was stirred overnight at 90° C. The reaction was poured onto EtOAc and water. The organic phase was separated and the aqueous layer was further extracted with EtOAc. The combined organic layers were concentrated. Work-up from here varies according to the compound.

Example 28

6-(2-Amino-4-pyrimidinyl)-4-[(3-phenylpropyl)oxy]-1H-indazol-3-amine

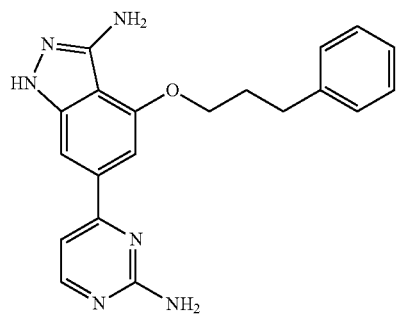 [SMILES: Nc1nccc(-c2cc(OCCCc3ccccc3)c3c(N)n[nH]c3c2)n1]

The title compound was prepared following the General Procedure C using: N-[4-(4-cyano-3,5-difluorophenyl)-6-methyl-2-pyrimidinyl]acetamide (0.10 g, 0.37 mmol) and 3-phenyl-propan-1-ol (0.044 mL, 0.33 mmol). The residue was dissolved in a 2:1 $CHCl_3$:acetone mixture (3 mL) and injected onto a 12 g $SiO_2$ column eluting from 100% $CHCl_3$ to 90:10:1 $CHCl_3$:$CH_3OH$:$NH_4OH$. The fractions containing the desired product were concentrated, and the resulting residue was dissolved in a mixture of $CH_3OH$ and DMSO (total volume ~0.7 mL). The solution was injected onto a Gilson RPHPLC ($CH_3CN/H_2O$ w/0.1% TFA). The appropriate fractions were concentrated to afford a TFA salt of the title compound (15 mg, 7%) as a yellow solid. LC-MS (ES) m/z=361 $[M+H]^+$. $^1$H NMR (400 MHz, $CD_3OD$): δ 2.23-2.31 (m, 2H), 2.89 (t, J=7.5 Hz, 2H), 4.28 (t, J=6.3 Hz, 2H), 7.15-7.21 (m, 1H), 7.22-7.30 (m, 5H), 7.52 (d, J=6.6 Hz, 1H), 7.81 (s, 1H), 8.31 (d, J=6.8 Hz, 1H).

Example 29

6-(2-Amino-4-pyrimidinyl)-4-{[3-(phenyloxy)propyl]oxy}-1H-indazol-3-amine

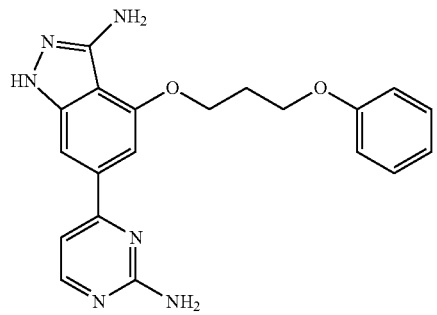 [SMILES: Nc1nccc(-c2cc(OCCCOc3ccccc3)c3c(N)n[nH]c3c2)n1]

The title compound was prepared following the General Procedure C using: N-[4-(4-cyano-3,5-difluorophenyl)-6-methyl-2-pyrimidinyl]acetamide (0.15 g, 0.55 mmol) and 3-(phenyloxy)-1-propanol (0.070 mL, 0.49 mmol). The tan residue was dissolved in hot EtOH and precipitated with hexanes. The precipitate was collected by vacuum filtration. The resulting solid was dissolved in DMSO and injected onto a Gilson RPHPLC ($CH_3CN/H_2O$ w/0.1% TFA). The appropriate fractions were concentrated to afford a TFA salt of the title compound (36 mg, 10%) as a golden solid. LC-MS (ES) m/z=377 $[M+H]^+$. $^1$H NMR (400 MHz, DMSO-$d_6$): δ 2.33 (m, 2H), 4.22 (t, J=6.1 Hz, 2H), 4.36 (t, J=6.1 Hz, 2H), 6.93-6.99 (m, 3H), 7.10 (s, 1H), 7.26-7.33 (m, 2H), 7.43 (m, 1H), 7.67 (s, 1H), 8.37 (d, J=5.8 Hz, 1H). NOTE: The 2 sets of amino protons are probably too broad to see.

Example 30

6-(2-Amino-4-pyrimidinyl)-4-(ethyloxy)-1H-indazol-3-amine

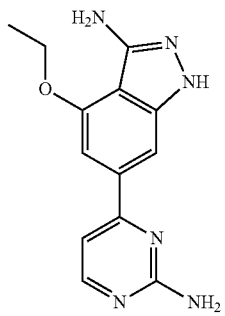 [SMILES: CCOc1cc(-c2ccnc(N)n2)cc2[nH]nc(N)c12]

The title compound was prepared following the General Procedure C using: N-[4-(4-cyano-3,5-difluorophenyl)-6-methyl-2-pyrimidinyl]acetamide (0.15 g, 0.55 mmol) and EtOH (0.032 mL, 0.55 mmol). The light tan solid was dissolved in DMSO (1 mL) and injected onto a Gilson RPHPLC ($CH_3CN/H_2O$ w/0.1% TFA). The appropriate fractions were concentrated to afford a TFA salt of the title compound (14 mg, 5%) as a yellow solid. LC-MS (ES) m/z=271 $[M+H]^+$. $^1$H NMR (400 MHz, $CD_3OD$): δ 1.58 (t, J=7.1 Hz, 3H), 4.38 (q, J=6.9 Hz, 2H), 7.32 (s, 1H), 7.58 (d, J=6.6 Hz, 1H), 7.83 (d, J=1.3 Hz, 1H), 8.35 (d, J=6.6 Hz, 1H).

Example 31

6-(2-Amino-4-pyrimidinyl)-4-[(2,2,2-trifluoroethyl)oxy]-1H-indazol-3-amine

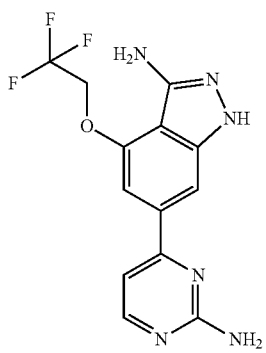 [SMILES: Nc1nccc(-c2cc(OCC(F)(F)F)c3c(N)n[nH]c3c2)n1]

The title compound was prepared following the General Procedure C using: N-[4-(4-cyano-3,5-difluorophenyl)-6- methyl-2-pyrimidinyl]acetamide (0.15 g, 0.55 mmol) and 2,2,2-trifluoroethanol (0.04 mL, 0.55 mmol). The yellow solid was dissolved in DMSO (1 mL) and injected onto a Gilson RPHPLC ($CH_3CN/H_2O$ w/0.1% TFA). The appropriate fractions were concentrated to afford a TFA salt of the title compound (38 mg, 13%) as a yellow solid. LC-MS (ES) m/z=325 [M+H]$^+$. $^1$H NMR (400 MHz, $CD_3OD$): δ 7.35 (s, 1H), 7.61 (d, J=6.6 Hz, 1H), 7.95 (d, J=1.0 Hz, 1H), 8.35 (d, J=6.6 Hz, 1H). NOTE: The —$OCH_2CF_3$ protons are assumed to be hidden beneath the water peak.

Intermediate 30

4-[2-Amino-6-(4-morpholinyl)-4-pyrimidinyl]-2,6-difluorobenzaldehyde

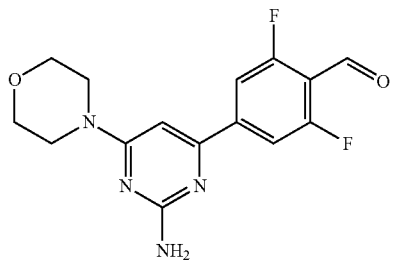 [SMILES: Nc1nc(-c2cc(F)c(C=O)c(F)c2)cc(N2CCOCC2)n1]

The title compound was prepared following the General Procedure A using: (3,5-difluoro-4-formylphenyl)boronic acid (2.17 g, 11.7 mmol) and 4-chloro-6-(4-morpholinyl)-2-pyrimidinamine (2.50 g, 11.7 mmol). The solid was dry loaded in 10 g of $SiO_2$. Flash chromatography on $SiO_2$ eluting from 100% $CHCl_3$ to 90:10 $CHCl_3$:$CH_3OH$ afforded the title compound (2.55 g, 51%) as a yellow solid. LC-MS (ES) m/z=321 [M+H]$^+$.

Intermediate 31

(A) N-[4-(4-cyano-3,5-difluorophenyl)-6-(4-morpholinyl)-2-pyrimidinyl]acetamide (B) N-acetyl-N-[4-(4-cyano-3,5-difluorophenyl)-6-(4-morpholinyl)-2-pyrimidinyl]acetamide A
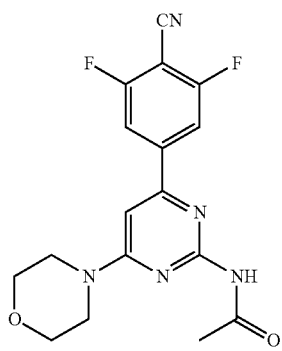

B
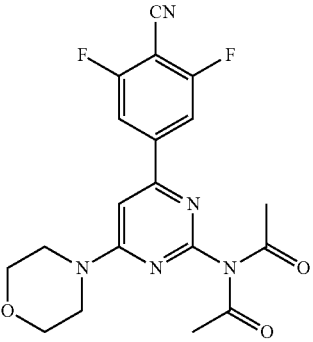

To a slurry of 4-[2-amino-6-(4-morpholinyl)-4-pyrimidinyl]-2,6-difluorobenzaldehyde (2.55 g, 7.96 mmol) in THF/EtOH/water, were added sodium carbonate (0.93 g, 8.8 mmol) and hydroxylamine hydrochloride (0.61 g, 8.8 mmol), and the resulting mixture was stirred at 100° C. until the starting material was consumed (~2 hours). The reaction mixture was concentrated, and the resulting yellow solid was dissolved in a mixture of EtOAc and water. The organic layer was separated, and the aqueous layer was further extracted with EtOAc. The combined organic layers were concentrated to afford a residue. The precipitate that formed in the aqueous layer was also collected via vacuum filtration. The combined residues were treated with acetic anhydride (used as solvent), and the reaction mixture was stirred at 100° C. until the oxime was completely converted to the nitrile as judge by LCMS (~5 days). The reaction mixture was diluted with EtOH, concentrated, and co-evaporated with EtOH (3×) to afford a tan orange solid. The solid was triturated with $CH_3OH$ and filtered to afford a mixture of the title compounds (2.4 g). (A) LC-MS (ES) m/z=360 [M+H]$^+$. (B) LC-MS (ES) m/z=402 [M+H]$^+$.

Example 32

6-[2-Amino-6-(4-morpholinyl)-4-pyrimidinyl]-N$^4$-(2-phenylethyl)-1H-indazole-3,4-diamine

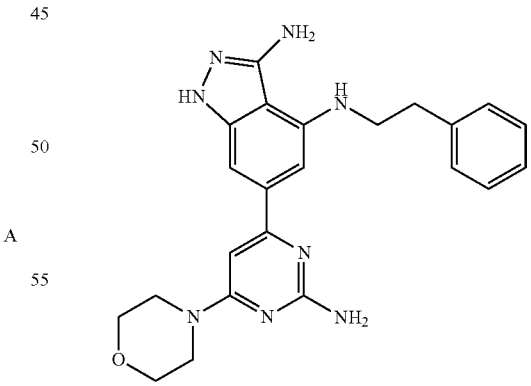

The title compound was prepared following the General Procedure B using: Intermediate 31 (0.15 g) and (2-phenylethyl)amine (0.066 mL, 0.52 mmol) in 1,4-dioxanes (3 mL). The residue was dissolved in EtOH (1.1 mL). Part of the solution (0.6 mL) was injected onto a Gilson RPHPLC ($CH_3CN/H_2O$ w/0.1% TFA), and the appropriate fractions were concentrated to afford impure product. The yellow solid was recrystallize from EtOH to afford a TFA salt of the title compound (42 mg) as a yellow solid. LC-MS (ES) m/z=431 [M+H]+. 1H NMR (400 MHz, CD3OD): δ 3.07 (t, J=7.3 Hz, 2H), 3.58 (t, J=7.3 Hz, 2H), 3.73-3.85 (m, 4H), 3.93 (bs, 4H), 6.30 (s, 1H), 6.67 (s, 1H), 6.94 (s, 1H) 7.15-7.51 (m, 5H).

Example 33

6-[2-Amino-6-(4-morpholinyl)-4-pyrimidinyl]-4-(methyloxy)-1H-indazol-3-amine

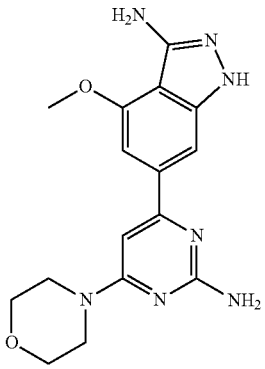 [SMILES: COc1cc(-c2cc(N3CCOCC3)nc(N)n2)cc2[nH]nc(N)c12]

To a solution of Intermediate 31 (0.15 g) in DMF (3 mL) was added sodium hydride (0.22 g, 0.56 mmol, 60% oil dispersion), followed by the dropwise addition of a solution of sodium methoxide (0.085 mL, 0.374 mmol, 25 wt. % in CH3OH) in DMF (3 mL). The vial that contained the sodium methoxide solution was rinsed with DMF (1 mL), and the resulting mixture was added to the reaction mixture. The reaction mixture was stirred at room temperature until the starting material was consumed (~1 hour). The mixture was poured onto saturated aqueous NH4Cl, and the resulting solid was filtered. To the solid was added EtOH followed by hydrazine monohydrate (0.59 mL), and the resulting mixture was stirred overnight at 90° C. The reaction mixture was cooled to room temperature and filtered. The filtrate was concentrated to a yellow solid. The solid was dissolved in DMSO and injected onto a Gilson RPHPLC (CH3CN/H2O w/0.1% TFA). The appropriate fractions were concentrated to afford a TFA salt of the title compound (14 mg, 6%) as an off-white solid. LC-MS (ES) m/z=342 [M+H]+. 1H NMR (400 MHz, CD3OD): δ 3.81 (m, 6H), 4.05 (bs, 2H), 4.11 (s, 3H), 6.79 (s, 1H), 6.85 (d, J=1.0 Hz, 1H), 7.37 (d, J=1.3 Hz, 1H).

Intermediate 32

6-Chloro-N4,N4-dimethyl-2,4-pyrimidinediamine

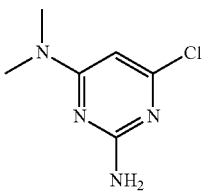

To a solution of 4,6-dichloropyrimidinamine (2.0 g, 12.2 mmol) in acetonitrile were added Hunig's base (2.34 mL, 13.4 mmol) and dimethylamine (6.7 mL, 13.4 mmol), and the reaction mixture was stirred for 1.5 hours at 50° C. The mixture was poured onto CH2Cl2 and water. The organic layer was separated, washed with brine, and concentrated to afford the title compound (2.2 g, 94%) as an off-white solid. LC-MS (ES) m/z=173, 175 [M+H]+.

Intermediate 33

4-[2-Amino-6-(dimethylamino)-4-pyrimidinyl]-2,6-difluorobenzaldehyde

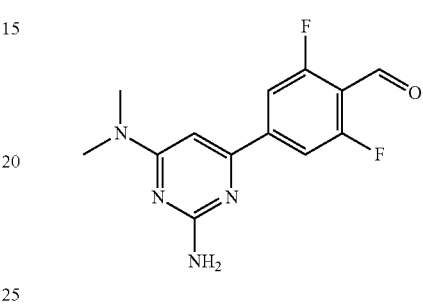

The title compound was prepared following the General Procedure A using: (3,5-difluoro-4-formylphenyl)boronic acid (2.37 g, 12.8 mmol) and 6-chloro-N4,N4-dimethyl-2,4-pyrimidinediamine (2.2 g, 12.8 mmol). The solid was dissolved in EtOAc and precipitated with hexanes. The resulting solid was collected via vacuum filtration to afford the title compound (2.82 g, 80%) as a yellow solid. LC-MS (ES) m/z=279 [M+H]+.

Intermediate 34

N-acetyl-N-[4-(4-cyano-3,5-difluorophenyl)-6-(dimethylamino)-2-pyrimidinyl]acetamide

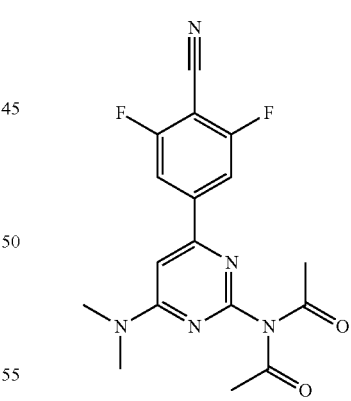

To a solution of 4-[2-amino-6-(dimethylamino)-4-pyrimidinyl]-2,6-difluorobenzaldehyde (2.86 g, 10.3 mmol) in a mixture of EtOH and water were added sodium carbonate (1.2 g, 11.3 mmol) and hydroxylamine hydrochloride (0.79 g, 11.3 mmol). The resulting mixture was refluxed until the starting material was consumed (~2 hours). The mixture was concentrated, and the resulting gray solid was washed with water. The filtrate was extracted with EtOAc, and the organic layer was combined with the gray solid and concentrated. The resulting residue was treated with excess acetic anhydride (solvent), and the reaction mixture was stirred at 100° C. until LCMS confirms complete conversion to the desired nitrile (~5 days). The reaction mixture was concentrated, and the resulting dark tan solid was triturated with CH₃OH to afford the title compound (0.624 g, 17%) as a gray solid. LC-MS (ES) m/z=360 [M+H]⁺. LCMS (M+1)=360 m/z.

Example 34

6-[2-Amino-6-(dimethylamino)-4-pyrimidinyl]-N⁴-(2-phenylethyl)-1H-indazole-3,4-diamine

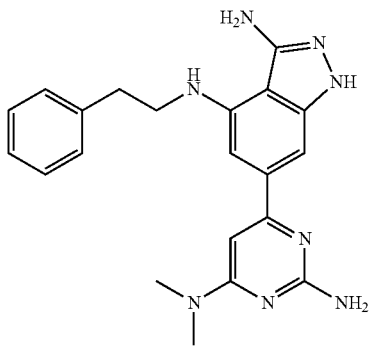 [SMILES: CN(C)c1cc(-c2cc(NCCc3ccccc3)c3c(N)n[nH]c3c2)nc(N)n1]

The title compound was prepared following the General Procedure B using: N-acetyl-N-[4-(4-cyano-3,5-difluorophenyl)-6-(dimethylamino)-2-pyrimidinyl]acetamide (0.145 g, 0.404 mmol), (2-phenylethyl)amine (0.056 mL, 0.44 mmol) and 1,4-dioxane (3 mL). NOTE: The EtOAc/water work-up was not necessary for this process. The reaction mixture was cooled to room temperature and a precipitate formed. The precipitate was filtered and washed with water to afford the title compound (70 mg, 40%) as a tan solid. LC-MS (ES) m/z=389 [M+H]⁺. ¹H NMR (400 MHz, DMSO-d₆): δ 2.99 (t, J=7.3 Hz, 2H), 3.06 (s, 6H), 3.38-3.46 (m, 2H), 5.03 (s, 2H), 5.63 (t, J=5.3 Hz, 1H), 5.96 (s, 2H), 6.32 (s, 1H), 6.55 (s, 1H), 7.13 (s, 1H), 7.19-7.26 (m, 1H), 7.34 (m, 4H), 11.38 (s, 1H).

Intermediate 35

4-[2-Amino-6-(ethylamino)-4-pyrimidinyl]-2,6-difluorobenzaldehyde

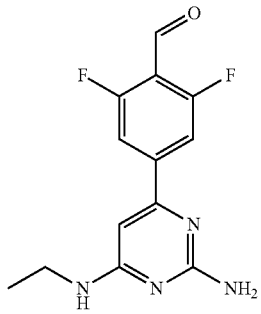 [SMILES: CCNc1cc(-c2cc(F)c(C=O)c(F)c2)nc(N)n1]

The title compound was prepared following the General Procedure A using: (3,5-difluoro-4-formylphenyl)boronic acid (2.54 g, 13.7 mmol) and 6-chloro-N4-ethyl-2,4-pyrimidinediamine (2.36 g, 13.7 mmol). The solid was triturated with EtOAc and filtered to afford the title compound (1.63 g, 43%) as a yellow solid. LC-MS (ES) m/z=279 [M+H]⁺.

Intermediate 36

N-Acetyl-N-[4-(4-cyano-3,5-difluorophenyl)-6-(ethylamino)-2-pyrimidinyl]acetamide

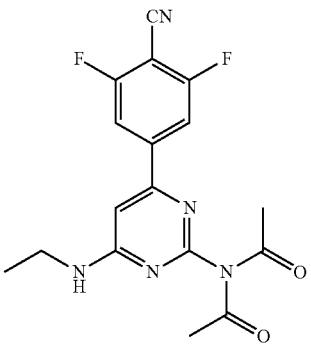 [SMILES: CCNc1cc(-c2cc(F)c(C#N)c(F)c2)nc(N(C(C)=O)C(C)=O)n1]

To a solution of 4-[2-amino-6-(ethylamino)-4-pyrimidinyl]-2,6-difluorobenzaldehyde (1.57 g, 5.64 mmol) in EtOH/water were added sodium carbonate (0.66 g, 6.21 mmol) and hydroxylamine hydrochloride (0.431 g, 6.21 mmol). The resulting mixture was refluxed until the starting material was consumed. The reaction mixture was concentrated to a dark solid. The solid was washed with water and the aqueous washings were extracted with EtOAc. The solid and EtOAc extractions were combined to afford a dark solid. The solid was treated with acetic anhydride (excess) and stirred at 100° C. until the oxime was converted to the nitrile (~5 days). The reaction mixture was concentrated and co-evaporated with EtOH. The resulting dark solid was triturated with CH₃OH to afford the title compound (0.2 g, 10%) as a dark brown solid. LC-MS (ES) m/z=360 [M+H]⁺.

Example 35

6-[3-Amino-4-(methyloxy)-1H-indazol-6-yl]-N⁴-ethyl-2,4-pyrimidinediamine

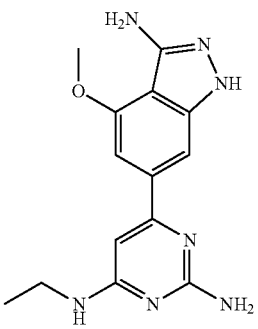 [SMILES: CCNc1cc(-c2cc(OC)c3c(N)n[nH]c3c2)nc(N)n1]

The title compound was prepared following the General Procedure C using: N-acetyl-N-[4-(4-cyano-3,5-difluorophenyl)-6-(ethylamino)-2-pyrimidinyl]acetamide (0.10 g, 0.28 mmol) and sodium methoxide (0.064 mL, 0.28 mmol, 25 wt. % in CH₃OH). NOTE: The EtOAc/water work-up was omitted for this process. The reaction mixture was cooled to room temperature and concentrated to a residue. The residue was dissolved in DMSO and injected onto a Gilson RPHPLC (CH₃CN/H₂O w/0.1% TFA). The appropriate fractions were concentrated to afford a TFA salt of the title compound (8 mg, 5%) as a tan solid. LC-MS (ES) m/z=300 [M+H]⁺. ¹H NMR (400 MHz, CD₃OD): δ 1.28 (t, J=7.3 Hz, 3H), 3.57 (q, J=7.33 Hz, 2H), 4.09 (s, 3H), 6.37 (s, 1H), 6.76 (d, J=1.0 Hz, 1H), 7.29 (d, J=1.3 Hz, 1H).

Intermediate 37

4-(2-Amino-6-methyl-4-pyrimidinyl)-2,6-difluorobenzaldehyde

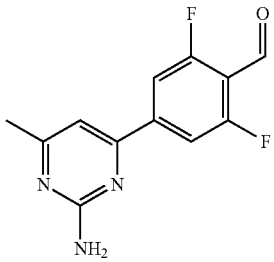 [SMILES: Cc1cc(-c2cc(F)c(C=O)c(F)c2)nc(N)n1]

To (3,5-difluoro-4-formylphenyl)boronic acid (5.0 g, 26.9 mmol) and 4-chloro-6-methyl-2-pyrimidinamine (3.86 g, 26.9 mmol) were added 1,4-dioxane (100 mL) and saturated aqueous NaHCO$_3$ (40 mL). The mixture was degassed with nitrogen for 10 minutes. Pd(Ph$_3$P)$_4$ (1.0 g, 0.87 mmol) was added and the reaction mixture was stirred overnight at 100° C. The reaction mixture was cooled to room temperature, poured onto water and filtered. The solid was washed with water and EtOAc to provide a pale yellow solid (2.4 g). The combined filtrates were poured into a separatory funnel. The organic layer was separated and the aqueous layer was further extracted with EtOAc. The combined organic layers were washed with brine, dried (MgSO$_4$), filtered and concentrated. The resulting residue was chromatographed on a SiO$_2$ column (gradient: 100% CHCl$_3$ to 90:10:1 CHCl$_3$/CH$_3$OH/NH$_4$OH). Loading of the material into the column was complicated by the poor solubility properties of the residue. Hot dioxane was used to help solubilize the residue. Part of the material co-eluted with the solvent front. All the fractions containing the product (including the ones that co-eluted with the solvent front) were combined, concentrated and triturated with ~1:1 mixture of EtOAc and hexanes to provide desired product as a yellow solid (1.6 g). This material was combined with the pale yellow solid obtained from the initial filtration and used without further purification. LC-MS (ES) m/z=250 [M+H]$^+$.

Intermediate 38

N-[4-(4-Cyano-3,5-difluorophenyl)-6-methyl-2-pyrimidinyl]acetamide

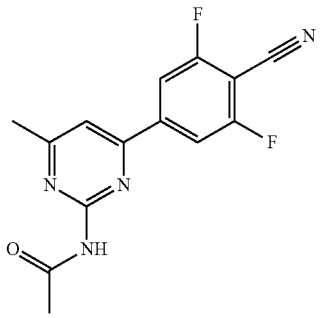 [SMILES: CC(=O)Nc1nc(C)cc(-c2cc(F)c(C#N)c(F)c2)n1]

To 4-(2-amino-6-methyl-4-pyrimidinyl)-2,6-difluorobenzaldehyde (4.0 g, 16.1 mmol) in water (150 mL) and EtOH (50 mL) were added hydroxylamine hydrochloride (1.23 g, 17.7 mmol) and sodium carbonate (1.87 g, 17.7 mmol). The mixture was stirred for 3 hours at 100° C. The reaction mixture was filtered and the solid was washed with water. The combined filtrate was extracted with EtOAc, and the organic layer was washed with brine, dried (MgSO$_4$), filtered and concentrated. The resulting solid was combined with the solid obtained after filtration of the reaction mixture and treated with acetic anhydride (used as solvent) into a sealable tube. The tube was sealed and the reaction mixture was stirred for 5 days at 100° C. LCMS analysis showed a mixture of mono and bis-acetylated desired product together with their respective acetylated oximes. The reaction mixture was heated for 2 more days at 110° C. The mixture was concentrated and the resulting residue was treated with CH$_3$OH. The mixture was filtered and the solid was washed with more CH$_3$OH to provide the title compound (1.3 g) as a tan solid. To the filtrate solution (150 mL) containing mostly bis-acetylated desired product was added K$_2$CO$_3$ (~1 g) and the reaction mixture was stirred overnight at room temperature. More K$_2$CO$_3$ (~1 g) was added followed by water (~50 mL) and the reaction mixture was stirred overnight at room temperature. LCMS analysis showed complete conversion to the mono-acetylated product. The reaction mixture was diluted with water and filtered. The resulting solid was washed with CH$_3$OH to provide the title compound (1.03 g) as a brown solid. LC-MS (ES) m/z=289 [M+H]$^+$.

Example 36

6-(2-Amino-6-methyl-4-pyrimidinyl)-N$^4$-(3-phenylpropyl)-1H-indazole-3,4-diamine

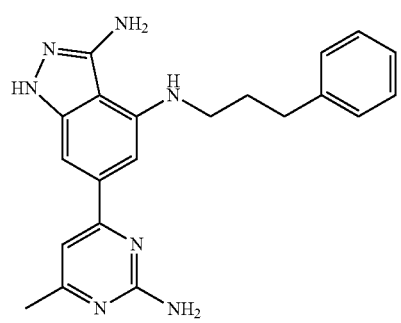 [SMILES: Cc1cc(-c2cc(NCCCc3ccccc3)c3c(N)n[nH]c3c2)nc(N)n1]

The title compound was prepared following the General Procedure B using: N-[4-(4-cyano-3,5-difluorophenyl)-6-methyl-2-pyrimidinyl]acetamide (0.15 g, 0.52 mmol), 3-phenyl-1-propanamine (0.081 mL, 0.57 mmol) and 1,4-dioxanes (3 mL). The residue was dissolved in CH$_3$OH (1.2 mL) and injected onto a Gilson RPHPLC (CH$_3$CN/H$_2$O w/0.1% TFA). The appropriate fractions were concentrated to afford a TFA salt of the title compound (60 mg, 19%) as a red solid. LC-MS (ES) m/z=374 [M+H]$^+$. $^1$H NMR (400 MHz, CD$_3$OD): δ 2.06-2.13 (m, 2H), 2.57 (s, 3H), 2.80 (t, J=7.6 Hz, 2H), 3.37 (t, J=7.2 Hz, 2H), 7.14-7.19 (m, 1H), 7.22-7.29 (m, 5H), 7.32 (s, 1H), 7.36 (s, 1H).

Example 37

6-(2-amino-6-methyl-4-pyrimidinyl)-$N^4$-(2-phenylethyl)-1H-indazole-3,4-diamine

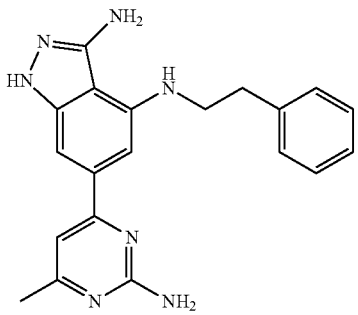 [SMILES: Cc1cc(-c2cc(NCCc3ccccc3)c3c(N)n[nH]c3c2)nc(N)n1]

The title compound was prepared following the General Procedure B using: N-[4-(4-cyano-3,5-difluorophenyl)-6-methyl-2-pyrimidinyl]acetamide (0.15 g, 0.52 mmol), (2-phenylethyl)amine (0.072 mL, 0.57 mmol) and 1,4-dioxane (3 mL). The residue was dissolved in DMSO (1 mL) and injected onto a Gilson RPHPLC (CH$_3$CN/H$_2$O w/0.1% TFA). The appropriate fractions were concentrated to afford a TFA salt of the title compound (40 mg, 13%) as a red solid. LC-MS (ES) m/z=360 [M+H]$^+$. $^1$H NMR (400 MHz, CD$_3$OD): δ 2.55 (s, 3H), 3.01-3.08 (m, 2H), 3.52-3.60 (m, 2H), 7.19-7.26 (m, 2H), 7.27-7.34 (m, 5H), 7.37 (s, 1H).

Intermediate 39

6-Chloro-$N^4$-(cyclohexylmethyl)-2,4-pyrimidinediamine

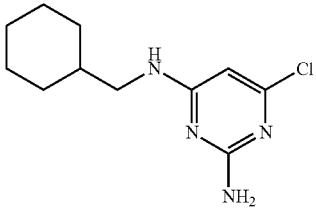 [SMILES: Nc1nc(Cl)cc(NCC2CCCCC2)n1]

To 4,6-dichloro-2-pyrimidinamine (1.64 g, 10 mmol) in CH$_3$OH (20 mL) were added triethylamine (2.02 g, 20 mmol) and cyclohexylmethanamine (1.36 g, 12 mmol), and the reaction mixture was stirred for 3 hours at 60° C. The mixture was evaporated under vacuum, and the resulting residue was subjected to SiO$_2$ chromatography (gradient: EtOAc/petroleum ether 1:4 to 1:2) to afford the title compound (1.6 g, 66%) as light yellow solid. LC-MS (ES) m/z=241, 243 [M+H]$^+$.

Intermediate 40

4-{2-Amino-6-[(cyclohexylmethyl)amino]-4-pyrimidinyl}-2-fluorobenzonitrile

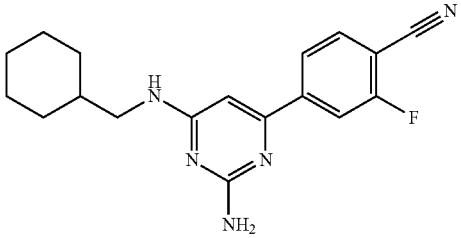 [SMILES: N#Cc1ccc(-c2cc(NCC3CCCCC3)nc(N)n2)cc1F]

To 6-chloro-$N^4$-(cyclohexylmethyl)-2,4-pyrimidinediamine_(1.2 g, 5 mmol), 2-fluoro-4-(4,4,5,5-tetramethyl-1,3,2-dioxaborolan-2-yl)benzonitrile (1.48 g, 6 mmol) and Pd(PPh$_3$)$_4$ (289 mg, 0.25 mmol) in 1,4-dioxane (40 mL) was added a solution of Na$_2$CO$_3$ (636 mg, 6 mmol) in water (10 mL), and the resulting mixture was degassed and then recharged with nitrogen (3×). The reaction mixture was stirred overnight at 100° C. The reaction was cooled to room temperature, and the organic layer was separated and concentrated. The resulting residue was purified by SiO$_2$ chromatography (eluent: 1/2 EtOAc/petroleum ether) to afford the title compound (0.7 g, 43%) as a white solid. LC-MS (ES) m/z=326 [M+H]$^+$.

Example 38

6-(3-Amino-1H-indazol-6-yl)-$N^4$-(cyclohexylmethyl)-2,4-pyrimidinediamine

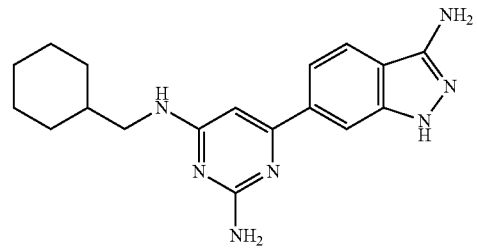 [SMILES: Nc1nc(NCC2CCCCC2)cc(-c2ccc3c(N)n[nH]c3c2)n1]

To a solution of 4-{2-amino-6-[(cyclohexylmethyl)amino]-4-pyrimidinyl}-2-fluorobenzonitrile (300 mg, 0.92 mmol) in EtOH (2 mL) was added hydrazine monohydrate (3.0 mL, 61.2 mmol), and the resulting suspension was stirred at 120° C. for 1 hour under microwave conditions. The clear reaction mixture was concentrated, and the resulting residue was purified by RPHPLC (CH$_3$CN/H$_2$O w/0.1% THF) to afford the title compound (160 mg, 48%) as a light yellow solid. LC-MS (ES) m/z=338 [M+H]$^+$. $^1$HNMR (400 MHz, DMSO-d$_6$): δ 0.92 (m, 2H), 1.19 (m, 3H), 1.51 (m, 1H), 1.68 (m, 5H), 3.14 (s, 2H), 5.37 (s, 2H), 5.95 (s, 2H), 6.29 (s, 1H), 6.85 (bs, 1H), 7.40 (bs, 1H), 7.69 (d, J=8.8 Hz, 1H), 7.83 (s, 1H), 11.5 (s, 1H).

Intermediate 41

4-{2-Amino-6-[2-(methyloxy)phenyl]-4-pyrimidinyl}-2-fluorobenzonitrile

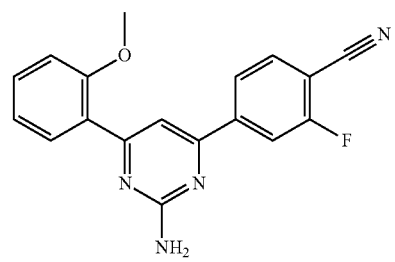 [SMILES: COc1ccccc1-c1cc(-c2ccc(C#N)c(F)c2)nc(N)n1]

A mixture of 4-(2-amino-6-chloro-4-pyrimidinyl)-2-fluorobenzonitrile (298 mg, 1.2 mmol), [2-(methyloxy)phenyl]boronic acid (273 mg, 1.8 mmol) and Na$_2$CO$_3$ (318 mg in 2 mL of water) in 1,4-dioxane (8 mL), was degassed with N$_2$. Pd(PPh$_3$)$_4$ (69 mg, 0.06 mmol) was added, and the reaction mixture was stirred overnight at 95° C. The reaction was poured onto water and EtOAc. The organic layer was separated, and the aqueous layer was further extracted with EtOAc (2×). The combined organic layers were dried (MgSO$_4$), filtered and concentrated to afford the crude title compound (306 mg). LC-MS (ES) m/z=321 [M+H]+.

Example 39

6-{2-Amino-6-[2-(methyloxy)phenyl]-4-pyrimidinyl}-1H-indazol-3-amine

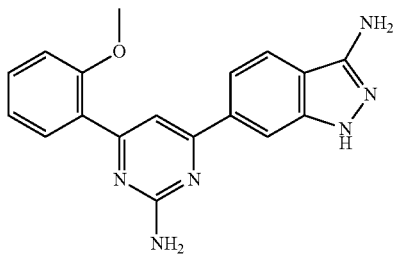 [SMILES: COc1ccccc1-c1cc(-c2ccc3c(N)n[nH]c3c2)nc(N)n1]

To the mixture of 4-{2-Amino-6-[2-(methyloxy)phenyl]-4-pyrimidinyl}-2-fluorobenzonitrile (306 mg) in 1,4-dioxane (30 mL) was added hydrazine monohydrate (2.5 mL), and the mixture was stirred overnight at 95° C. The reaction mixture was cooled to room temperature and filtered to remove some black solid (seemed to be Pd particle). Additional hydrazine monohydrate (1 mL) was added, and the resulting mixture was stirred for another 24 hours at 95° C. The solvent was evaporated, and the resulting residue was purified by RPHPLC ($CH_3CN/H_2O$ w/0.1% $NH_4HCO_3$) to afford the title compound (43 mg) as a yellow solid. LC-MS (ES) m/z=333 [M+H]+. 1HNMR (400 MHz, DMSO-$d_6$): δ 3.88 (s, 3H), 5.42 (s, 2H), 6.66 (s, 2H), 7.08 (m, 1H), 7.18 (d, J=8.4 Hz, 1H), 7.46 (m, 1H), 7.58 (m, 2H), 7.78 (m, 2H), 7.98 (s, 1H), 11.60 (s, 1H).

Intermediate 42

6-[2-Amino-6-(methylsulfonyl)-4-pyrimidinyl]-1H-indazol-3-amine

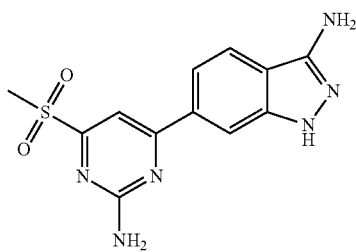 [SMILES: CS(=O)(=O)c1cc(-c2ccc3c(N)n[nH]c3c2)nc(N)n1]

To 6-[2-amino-6-(methylthio)-4-pyrimidinyl]-1H-indazol-3-amine (1.0 g, 3.7 mmol) in TFA (30 mL) at 0° C. was added aqueous $H_2O_2$ (1.5 mL, 14.7 mmol, 30% (w/w)) dropwise over 3 minutes. The reaction was allowed to warm to room temperature. After 2 hours, LCMS showed complete oxidation to the sulfone. The reaction mixture was cooled to 0° C. and quenched with dimethyl sulfide (1.36 mL, 18.4 mmol, dropwise addition). Upon completion of the addition, the reaction was warmed to room temperature. After 10 minutes, the mixture was cooled back to 0° C. and treated with $Et_2O$ (20 mL) and hexane (40 mL). The resulting solid was filtered and washed with hexane to afford a TFA salt of the title compound (1.01 g) as an orange solid. LC-MS (ES) m/z=305 [M+H]+.

Example 40

6-{2-Amino-6-[2-(phenylmethyl)-1-pyrrolidinyl]-4-pyrimidinyl}-1H-indazol-3-amine

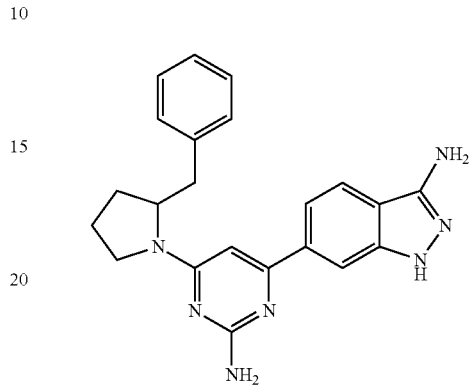

In a 10 mL sealable tube under nitrogen were combined 6-[2-amino-6-(methylsulfonyl)-4-pyrimidinyl]-1H-indazol-3-amine (0.20 g, 0.376 mmol), 1,4-dioxane (5 mL), 2-(phenylmethyl)pyrrolidine (0.151 g, 0.939 mmol), and triethylamine (0.16 mL, 1.13 mmol). The vial was sealed and the mixture was stirred overnight at 95° C. The reaction mixture was concentrated and the resulting residue was partially purify by flash chromatography on $SiO_2$ (90/10/1 $CHCl_3$/$CH_3OH/NH_4OH$). The fractions containing the desired product were combined and concentrated. The resulting material was purify on a Gilson RPHPLC ($CH_3CN/H_2O$ w/0.1% TFA) to afford a TFA salt of the title compound (9 mg) as a yellow solid as a mixture of rotamers. LC-MS (ES) m/z=386 [M+H]+. 1H NMR (400 MHz, DMSO-$d_6$): δ [1.86-2.11 (m) and 2.73-2.79 (m)] (5H), [2.89-3.01 (m) and 3.25-3.26 (m)] (1H), 3.60-3.81 (m, 2H), [4.50-4.55 (m) and 4.67-4.72 (m)] (1H), [6.11 (s) and 6.53 (s)] (1H), [7.13-7.33 (m) and 7.49-7.51 (m)] (6H), [7.62 (s) and 7.85 (s)] (1H), 7.97-8.03 (m, 1H).

Example 41

6-{2-Amino-6-[2-(1-methylethyl)-1-pyrrolidinyl]-4-pyrimidinyl}-1H-indazol-3-amine

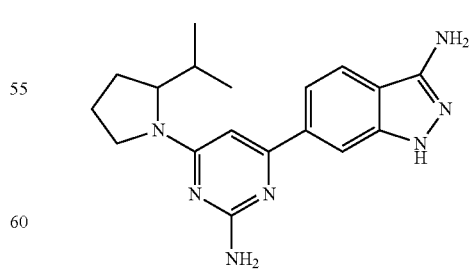

To 6-[2-amino-6-(methylthio)-4-pyrimidinyl]-1H-indazol-3-amine (0.25 g, 0.92 mmol) in TFA (8.74 mL) at 0° C. was added aqueous $H_2O_2$ (0.375 mL, 3.67 mmol, 30% (w/w)) dropwise over 2 minutes. Upon completion of the addition, the reaction was allowed to warm to room temperature. After 2 hours, the reaction mixture was cooled back to 0° C. and quenched with dimethyl sulfide (0.54 mL, 7.34 mmol, dropwise addition). The reaction was allowed to warm to room temperature and stirred for 1 hour. The mixture was cooled to 0° C. and diluted with Et$_2$O (5 mL) Et$_2$O and hexane (15 mL). The resulting orange precipitate was filtered and transferred to a 25 mL sealable tube under nitrogen. 1,4-Dioxane (5.83 mL), 2-(1-methylethyl)pyrrolidine hydrochloride (0.275 g, 1.84 mmol), and triethylamine (0.51 mL, 3.67 mmol) were added, and the tube was sealed, and the reaction mixture was stirred overnight at 95° C. Since LCMS showed a minimal amount of product, additional triethylamine (1 mL) was added, and the reaction mixture was stirred overnight at 95° C. The reaction was cooled to room temperature and decanted. The solution was concentrated, and the resulting oil was dissolved in a mixture of 50/50 CH$_3$CN/H$_2$O w/0.1 mL TFA. The resulting mixture was filtered through a 0.45µ frit and purified on a Gilson RPHPLC (CH$_3$CN/H$_2$O w/0.1% TFA) to afford a TFA salt of the title compound (12 mg) as a yellow solid as a mixture of rotamers. LC-MS (ES) m/z=338 [M+H]$^+$. $^1$H NMR (400 MHz, DMSO-d$_6$): δ 0.75-0.99 (m, 6H), 1.79-2.04 (m, 4H), 3.58-3.88 (m, 3H), 4.26 (m, 1H), 4-5 (bs), [6.59 (s) and 6.65 (s)] (1H), [7.33 (d, J=8.6 Hz) and 7.37 (d, J=8.6 Hz)] (1H), [7.69 (s) and 7.73 (s)] (1H), 7.91 (d, J=8.6 Hz, 1H), 12.04 (bs, 1H).

Example 42

6-[2-Amino-6-(2-methyl-1-pyrrolidinyl)-4-pyrimidinyl]-1H-indazol-3-amine

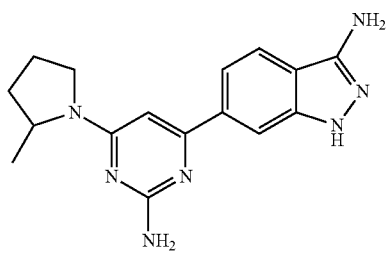 [SMILES: CC1CCCN1c1cc(-c2ccc3c(N)n[nH]c3c2)nc(N)n1]

To 6-[2-amino-6-(methylthio)-4-pyrimidinyl]-1H-indazol-3-amine (0.250 g, 0.918 mmol) in TFA (8.7 mL) at 0° C. was added aqueous H$_2$O$_2$ (0.375 mL, 3.67 mmol, 30% (w/w)) dropwise over 3 minutes. Upon completion of addition, the reaction was allowed to warm to room temperature. After 2 hours, LCMS showed complete conversion to the sulfone. The reaction was cooled to 0° C. and quenched with dimethyl sulfide (0.54 mL, 7.34 mmol). The reaction was allowed to warm to room temperature and stirred for 10 minutes. The mixture was cooled to 0° C. and diluted with Et$_2$O (10 mL) and hexane (5 mL). The resulting orange precipitate was filtered, washed with hexane and placed into a 25 mL sealable tube. 1,4-Dioxane (5.83 mL) and triethylamine (0.51 mL, 3.67 mmol) were added followed by 2-methylpyrrolidine (0.12 mL, 1.19 mmol). The tube was sealed, and the reaction mixture was stirred overnight at 95° C. LCMS analysis of the reaction mixture showed 60% desired product and 30% unreacted sulfone. More 2-methylpyrrolidine (0.1 mL) was added and the reaction mixture was stirred for 2 additional hours at 95° C. The reaction was cooled to room temperature and decanted. The solution was concentrated, and the resulting residue was dissolved in 3 mL of 50/50 CH$_3$CN/H$_2$O w/0.1% TFA. Purification on a Gilson RPHPLC (CH$_3$CN/H$_2$O w/0.1% TFA) afforded a TFA salt of the title compound (105 mg, 20%) as a yellow solid as a mixture of rotamers. LC-MS (ES) m/z=310 [M+H]$^+$. $^1$H NMR (400 MHz, DMSO-d$_6$): δ 1.22-1.26 (m, 3H), 1.65-1.87 (m, 1H), 1.93-2.16 (m, 3H), 3.47-3.64 (m, 1H), 3.65-3.87 (m, 1H), 4.31-4.54 (m, 1H), [6.54 (s) and 6.63 (s)] (1H), 7.36 (d, J=8.6 Hz, 1H), 7.72 (s, 1H), 7.91 (m, 1H), 11.99 (bs, 2H).

Intermediate 43

6-Chloro-N$^4$-(2-phenylethyl)-2,4-pyrimidinediamine

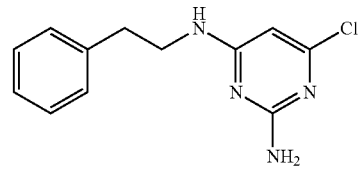 [SMILES: Nc1nc(Cl)cc(NCCc2ccccc2)n1]

A mixture of 4,6-dichloro-2-pyrimidinamine (815 mg, 5.0 mmol), (2-phenylethyl)amine (665 mg, 5.5 mmol) and triethylamine (1.0 g, 10 mmol) in CH$_3$OH (20 mL) was stirred at 60° C. for 2 hours. The reaction mixture was concentrated, and the resulting residue was subjected to flash chromatography on SiO$_2$ (eluent: 1/1 EtOAc/petroleum ether) to afford the title compound (1.0 g, 81%) as light yellow solid. LC-MS (ES) m/z=249 [M+H]$^+$.

Intermediate 44

4-{2-Amino-6-[(2-phenylethyl)amino]-4-pyrimidinyl}-2-fluorobenzonitrile

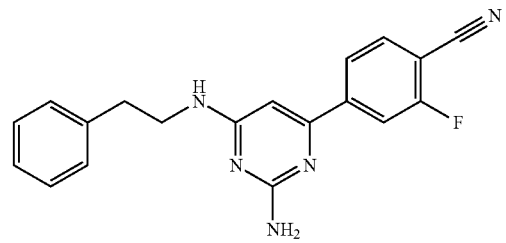

To a mixture of 6-chloro-N$^4$-(2-phenylethyl)-2,4-pyrimidinediamine_(0.9 g, 3.6 mmol), 2-fluoro-4-(4,4,5,5-tetramethyl-1,3,2-dioxaborolan-2-yl)benzonitrile (1.06 g, 4.3 mmol) and Pd(PPh$_3$)$_4$ (289 mg, 0.25 mmol) in 1,4-dioxane (200 mL) was added a solution of Na$_2$CO$_3$ (320 mg, 3 mmol) in water (20 mL), and the resulting mixture was degassed and re-charged with N$_2$ (3×). The resulting reaction mixture was stirred overnight at 95° C., then allowed to cool to room temperature. The organic layer was separated and concentrated, and the resulting crude product was purified by flash chromatography on SiO$_2$ (gradient: 1:5 to 2:1 EtOAc/petroleum ether) to afford the title compound (0.8 g, 66%) as light yellow solid. LC-MS (ES) m/z=334 [M+H]$^+$.

Example 43

6-(3-Amino-1H-indazol-6-yl)-N⁴-(2-phenylethyl)-2,4-pyrimidinediamine

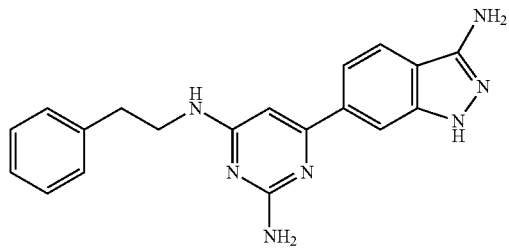 [SMILES: Nc1nc(NCCc2ccccc2)cc(-c2ccc3c(N)n[nH]c3c2)n1]

To a solution of 4-{2-amino-6-[(2-phenylethyl)amino]-4-pyrimidinyl}-2-fluorobenzonitrile (800 mg, 2.4 mmol) in EtOH (20 mL) was added hydrazine monohydrate (7 mL), and the resulting suspension was stirred overnight at 95° C. The clear reaction mixture was concentrated, and the resulting residue was purified by RPHPLC (CH$_3$CN/H$_2$O w/0.1% THF) to afford the title compound (500 mg, 42%) as a light yellow powder. LC-MS (ES) m/z=346 [M+H]⁺. ¹H NMR (400 MHz, DMSO-d$_6$): δ 2.85 (t, J=7.2 Hz, 2H), 3.53 (m, 2H), 5.37 (s, 2H), 6.02 (s, 2H), 6.28 (s, 1H), 6.94 (s, 1H), 7.18-7.23 (m, 1H), 7.28-7.33 (m, 4H), 7.42 (d, J=8.4 Hz, 1H), 7.70 (d, J=8.4 Hz, 1H), 7.85 (s, 1H), 11.5 (s, 1H).

Intermediate 45

4-Chloro-6-(hexahydro-1H-azepin-1-yl)-2-pyrimidinamine

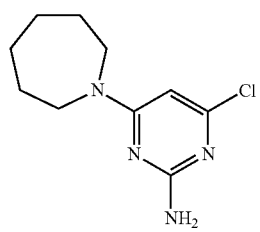 [SMILES: Nc1nc(Cl)cc(N2CCCCCC2)n1]

In a 25 mL sealable tube under nitrogen were combined 4,6-dichloro-2-pyrimidinamine (0.50 g, 3.05 mmol) and hexahydro-1H-azepine (0.34 mL, 3.05 mmol) in CH$_3$OH (10 mL). Triethylamine (0.47 mL, 3.35 mmol) was added, the vial was sealed, and the reaction mixture was stirred for 5 hours at 50° C. The reaction was cooled to room temperature and concentrated. The resulting yellow solid was partitioned between EtOAc and water. The organic layer was separated, dried (MgSO$_4$), filtered and concentrated to afford the title compound (600 mg, 82%) as a yellow solid. LC-MS (ES) m/z=227 [M+H]⁺.

Intermediate 46

4-[2-Amino-6-(hexahydro-1H-azepin-1-yl)-4-pyrimidinyl]-2-fluorobenzonitrile

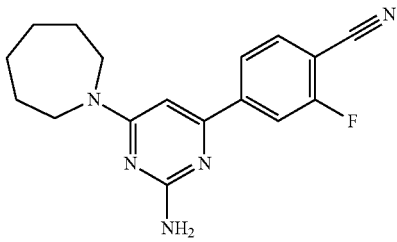 [SMILES: N#Cc1ccc(-c2cc(N3CCCCCC3)nc(N)n2)cc1F]

In a 25 mL sealable tube under nitrogen were combined 4-chloro-6-(hexahydro-1H-azepin-1-yl)-2-pyrimidinamine (600 mg, 2.65 mmol) and (4-cyano-3-fluorophenyl)boronic acid (0.437 g, 2.65 mmol) in 1,4-dioxane (10.6 mL). Saturated aqueous NaHCO$_3$ (2.65 mL) was added, and the resulting mixture was degassed with nitrogen for 5 minutes. Pd(Ph$_3$P)$_4$ (0.153 g, 0.13 mmol) was added, the vessel was sealed, and the reaction mixture was stirred overnight at 95° C. The reaction was cooled to room temperature, and the organic layer was separated and concentrated. The resulting solid was partitioned between EtOAc and water. The organic layer was separated, dried (MgSO$_4$), filtered and concentrated. Flash chromatography on SiO$_2$ (eluent: 90/10/1 CHCl$_3$/CH$_3$OH/NH$_4$OH) afforded the title compound (547 mg, 62%) as a yellow solid. LC-MS (ES) m/z=312 [M+H]⁺.

Example 44

6-[2-Amino-6-(hexahydro-1H-azepin-1-yl)-4-pyrimidinyl]-1H-indazol-3-amine

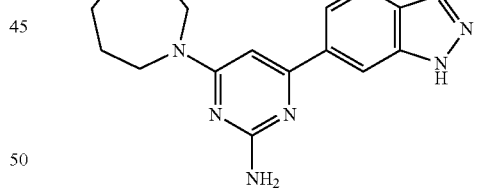

In a 25 mL sealable tube under nitrogen were combined 4-[2-amino-6-(hexahydro-1H-azepin-1-yl)-4-pyrimidinyl]-2-fluorobenzonitrile (0.547 g, 1.76 mmol) and hydrazine monohydrate (1.72 mL) in EtOH (8.8 mL). The vial was sealed, and the reaction mixture was stirred for 6 hours at 95° C. The reaction was filtered through a 0.2 μM frit to remove some precipitate and the filtrate was concentrated. The resulting oil was diluted with EtOH (5 mL) and the mixture was concentrated. The resulting solid was dissolved in a mixture of CH$_3$CN/H$_2$O/TFA and purified on a Gilson RPHPLC (CH$_3$CN/H$_2$O w/0.1% TFA) to afford a TFA salt of the title compound (90 mg, 9%) as a white solid. LC-MS (ES) m/z=324 [M+H]⁺. ¹H NMR (400 MHz, DMSO-d$_6$): δ 1.52-1.56 (m, 4H), 1.68-1.86 (m, 4H), 3.73-3.92 (m, 4H), 6.75 (s, 1H), 7.37 (dd, J=8.4, 1.6 Hz, 1H), 7.72 (s, 1H), 7.91 (d, J=8.3 Hz, 1H), 12.00 (s, 1H).

Intermediate 47

N-{6-[2-amino-6-(methyloxy)-4-pyrimidinyl]-1H-indazol-3-yl}acetamide

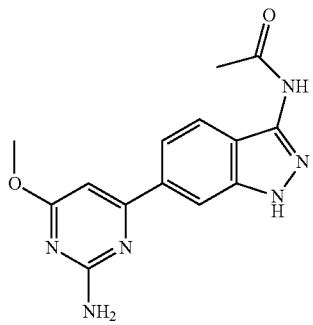 [SMILES: COc1cc(-c2ccc3c(NC(C)=O)n[nH]c3c2)nc(N)n1]

In a 25 mL sealable tube under argon were combined N-acetyl-N-(1-acetyl-6-bromo-1H-indazol-3-yl)acetamide (0.25 g, 0.74 mmol), bis(pinacolato)diboron (0.197 g, 0.776 mmol), potassium acetate (0.145 g, 1.48 mmol) and 1,4-dioxane (4.9 mL). The mixture was degassed with argon for 5 minutes. PdCl$_2$(dppf)-CH$_2$Cl$_2$ (0.024 g, 0.03 mmol) was added, the tube was sealed, and the reaction mixture was stirred overnight at 100° C. The mixture was cooled to room temperature, the tube was unsealed, and 4-chloro-6-(methyloxy)-2-pyrimidinamine (0.130 g, 0.813 mmol), NaHCO$_3$ (0.248 g, 2.96 mmol), PdCl$_2$(dppf)-CH$_2$Cl$_2$ (0.024 g, 0.03 mmol), and water (1.64 mL) were added. The tube was resealed under argon and the reaction mixture was stirred overnight at 100° C. The reaction was allowed to cool to room temperature, diluted with CH$_3$CN (20 mL), and filtered through a pad of Celite 503. The filtrate was concentrated, and the resulting brown solid was dissolved in a mixture of CH$_3$CN (5 mL), water (10 mL) and TFA (0.5 mL). The resulting mixture was filtered through a 300 mg plug of C18, washing with a mixture of 20% CH$_3$CN/80% H$_2$O. The filtrate was concentrated, and the resulting yellow foam was purified on a Varian RPHPLC (CH$_3$CN/H$_2$O w/0.1% TFA) to afford a TFA salt of the title compound (115 mg) as a yellow solid. LC-MS (ES) m/z=299 [M+H]$^+$.

Example 45

6-[2-Amino-6-(methyloxy)-4-pyrimidinyl]-1H-indazol-3-amine

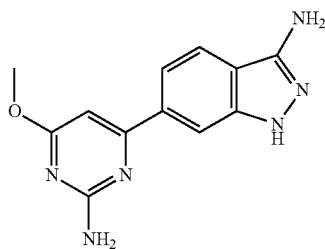 [SMILES: COc1cc(-c2ccc3c(N)n[nH]c3c2)nc(N)n1]

To N-{6-[2-amino-6-(methyloxy)-4-pyrimidinyl]-1H-indazol-3-yl}acetamide (115 mg, 0.218 mmol) in CH$_3$OH (20 mL) was added HCl (0.21 mL, 2.5 mmol, 12 M), and the reaction mixture was stirred for 12 hours at 60° C. The reaction was cooled to room temperature and stirred over the weekend. The mixture was concentrated, and the resulting yellow solid was purified on a Gilson RPHPLC(CH$_3$CN/H$_2$O w/0.1% TFA). The fractions containing the desired product were combined and concentrated. The resulting yellow solid was dissolved in water and treated with NaOH (1M). The resulting pink solid was filtered to afford the title compound (15 mg, 25%). LC-MS (ES) m/z=257 [M+H]$^+$. $^1$H NMR (400 MHz, DMSO-d$_6$): δ 3.86 (s, 3H), 5.40 (s, 2H), 6.58 (s, 1H), 6.64 (s, 2H), 7.54 (dd, J=8.6, 1.0 Hz, 1H), 7.72 (d, J=8.3 Hz, 1H), 7.95 (s, 1H), 11.57 (s, 1H).

Intermediate 48

Phenylmethyl(2S)-2-({[(4-methylphenyl)sulfonyl]oxy}methyl)-1-pyrrolidinecarboxylate]

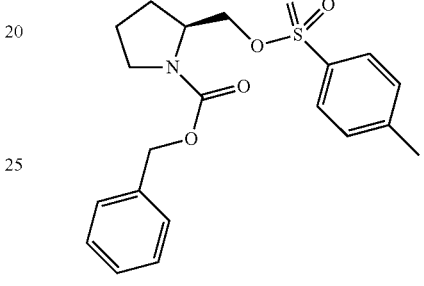

To phenylmethyl(2S)-2-(hydroxymethyl)-1-pyrrolidinecarboxylate (0.78 g, 3.32 mmol) in CH$_2$Cl$_2$ (10 mL) was added Et$_3$N (0.92 mL, 6.63 mmol) followed by TsCl (0.664 g, 3.48 mmol) and the reaction mixture was stirred overnight at room temperature. The mixture was poured onto water and diethyl ether (Et$_2$O). The aqueous layer was separated and the organic layer was washed with saturated aqueous NaHCO$_3$ followed by brine, dried (MgSO$_4$), filtered and concentrated. Flash chromatography on SiO$_2$ (gradient: 100% hexanes to 20% EtOAc/hexanes) afforded the title compound (0.85 g, 66%) as a colorless oil. LC-MS (ES) m/z=390 [M+H]$^+$.

Intermediate 49

Phenylmethyl(2R)-2-ethyl-1-pyrrolidinecarboxylate

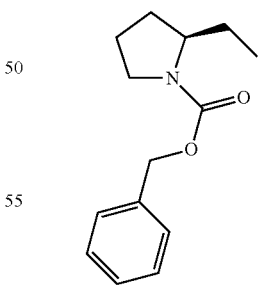

To copper(I) iodide (1.25 g, 6.55 mmol) in Et$_2$O (25 mL) was added methyllithium (8.2 mL, 13.1 mmol) at 0° C. A solution of phenylmethyl(2S)-2-({[(4-methylphenyl)sulfonyl]oxy}methyl)-1-pyrrolidinecarboxylate (0.85 g, 2.182 mmol) in CH$_2$Cl$_2$ (4 mL) was added next, and the reaction mixture was stirred for 2 hours at 0° C. The reaction was quenched with saturated aqueous NH$_4$Cl, and extracted with CH$_2$Cl$_2$ (3×). The combined organic layers were washed with brine, dried (MgSO$_4$), filtered and concentrated. Flash chromatography on SiO$_2$ (gradient: 100% hexanes to 20% EtOAc/hexanes) afforded the title compound (230 mg, 45%) as a colorless oil. LC-MS (ES) m/z=234 [M+H]$^+$.

Intermediate 50

(2R)-2-Ethyl pyrrolidine

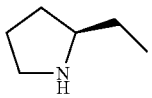

Into a sealable tube, phenylmethyl(2R)-2-ethyl-1-pyrrolidinecarboxylate (230 mg, 0.99 mmol) was dissolved in a mixture of 1,4-dioxane (6 mL) and concentrated HCl (4 mL). The tube was sealed, and the reaction mixture was stirred for 5 hours at 90° C. The solution was concentrated, evaporating the resulting residue from toluene (~20 mL). Et$_2$O was added, and the resulting mixture was sonicated and decanted. The resulting solid was dissolved in acetonitrile (CH$_3$CN) and treated with Et$_2$O until a precipitate was formed. The mixture was sonicated and decanted, and the solid was triturated with Et$_2$O to afford the HCl salt of the title compound (80 mg, 60%) as an off-white solid. $^1$H NMR (400 MHz, CD$_3$OD): δ 1.07 (t, J=7.5, 3H), 1.60-1.84 (m, 3H), 1.96-2.17 (m, 2H), 2.19-2.31 (m, 1H), 3.30 (m, 2H), 3.38-3.52 (m, 1H).

Intermediate 51

4-Chloro-6-[(2R)-2-ethyl-1-pyrrolidinyl]-2-pyrimidinamine

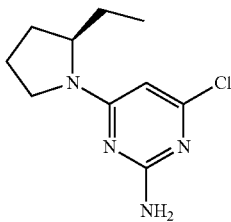

A mixture of (2R)-2-ethylpyrrolidine (80 mg, 0.59 mmol), 4,6-dichloro-2-pyrimidinamine (119 mg, 0.726 mmol) and Et$_3$N (0.25 mL, 1.77 mmol) in CH$_3$CN (6 mL) was stirred overnight at 80° C. The mixture was poured onto water (~150 mL), sonicated and filtered to afford the title compound (94 mg, 70%) as a white solid. LC-MS (ES) m/z=227, 229 [M+H]$^+$.

Intermediate 52

4-{2-Amino-6-[(2R)-2-ethyl-1-pyrrolidinyl]-4-pyrimidinyl}-2-fluorobenzonitrile

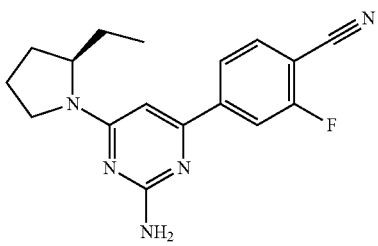 [SMILES: CC[C@@H]1CCCN1c1cc(-c2ccc(C#N)c(F)c2)nc(N)n1]

To 4-chloro-6-[(2R)-2-ethyl-1-pyrrolidinyl]-2-pyrimidinamine (40 mg, 0.176 mmol) and (4-cyano-3-fluorophenyl) boronic acid (29.1 mg, 0.176 mmol) was added 1,4-dioxane (3 mL) followed by sat. aq. NaHCO$_3$ (0.5 mL), and the mixture was purged with N$_2$ for 10 minutes into a sealable tube. Pd(Ph$_3$P)$_4$ (20.4 mg, 0.018 mmol) was added, the tube was sealed, and the reaction mixture was stirred overnight at 100° C. The mixture was poured onto water and EtOAc. The organic layer was separated, washed with brine, dried (MgSO$_4$), filtered and concentrated. Flash chromatography on SiO$_2$ (gradient: 100° ACHCl$_3$ to 95:5:0.5 CHCl$_3$:CH$_3$OH:NH$_4$OH) afforded the title compound (52 mg) as a solid. LC-MS (ES) m/z=312 [M+H]$^+$.

Example 46

6-{2-Amino-6-[(2R)-2-ethyl-1-pyrrolidinyl]-4-pyrimidinyl}-1H-indazol-3-amine

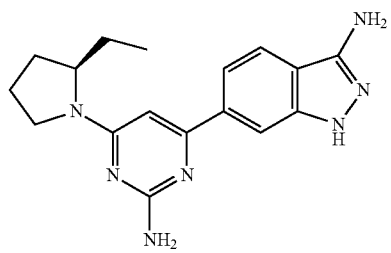 [SMILES: CC[C@@H]1CCCN1c1cc(-c2ccc3c(N)n[nH]c3c2)nc(N)n1]

To 4-{2-amino-6-[(2R)-2-ethyl-1-pyrrolidinyl]-4-pyrimidinyl}-2-fluorobenzonitrile (50 mg, 0.161 mmol) in ethanol (4 mL) was added hydrazine monohydrate (1 mL, 20.40 mmol), and the reaction mixture was stirred overnight at 100° C. into a sealed tube. The reaction was poured onto water and EtOAc, and the organic layer was separated, dried (MgSO$_4$), filtered and concentrated. The resulting solid was dissolved in ethanol (~2 mL), and treated with hexanes until the solution became cloudy. The mixture was roto-evaporated (~½ original volume) until a heavy precipitate was observed. The solution was decanted and the solid was dried under vacuum at 40° C. to afford the title compound (30 mg, 58%) as a pale yellow solid. LC-MS (ES) m/z=324 [M+H]$^+$. $^1$H NMR (400 MHz, DMSO-d$_6$): δ 0.89 (t, J=7.3 Hz, 3H), 1.37 (m, 1H), 1.7-2.0 (m, 5H), 3.40 (m, 1H), 3.50 (m, 1H), 4.00 (m, 1H), 5.38 (bs, 2H), 5.97 (bs, 2H), 6.23 (s, 1H), 7.51 (dd, J=8.6, 1.0 Hz, 1H), 7.70 (d, J=8.3 Hz, 1H), 7.89 (s, 1H), 11.49 (s, 1H).

Intermediate 53

1-(Phenylmethyl)-2,5-pyrrolidinedione

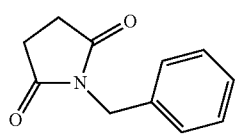 [SMILES: O=C1CCC(=O)N1Cc1ccccc1]

To 2,5-pyrrolidinedione (2.5 g, 25.2 mmol) in DMF (50 mL) was added K$_2$CO$_3$ (4.18 g, 30.3 mmol) followed by benzyl bromide (3.00 mL, 25.2 mmol), and the reaction mixture was stirred overnight at 55° C. Water was added to the reaction mixture (~200 mL) and a precipitate was immediately observed. The precipitate was filtered, and the white solid was washed with water and dried to afford the title compound (2.7 g, 57%). $^1$H NMR (400 MHz, CDCl$_3$): δ 2.73 (s, 4H), 4.68 (s, 2H), 7.28-7.37 (m, 3H), 7.39-7.44 (m, 2H).

Intermediate 54

5-Cyclopropyl-5-hydroxy-1-(phenylmethyl)-2-pyrrolidinone

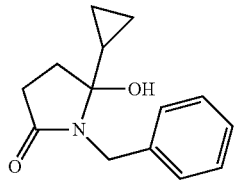 [SMILES: O=C1CCC(O)(C2CC2)N1Cc1ccccc1]

To 1-(phenylmethyl)-2,5-pyrrolidinedione (1 g, 5.29 mmol) in THF (50 mL) at −78° C. was added cyclopropylmagnesium bromide (42.3 mL, 21.1 mmol) dropwise. The reaction mixture was allowed to warm to 0° C. and stirred for an additional 2 hours. The reaction was quenched with a saturated aqueous solution of ammonium chloride and transferred to a separatory funnel. EtOAc was added, and the organic phase was separated. The aqueous layer was further extracted with EtOAc, and the combined organic layers were washed with brine, dried (MgSO$_4$), filtered and concentrated. Flash chromatography on SiO$_2$ (gradient: 100% hexanes to 80% EtOAc/hexanes) afforded the title compound (400 mg, 33%) as a yellow solid. LC-MS (ES) m/z=232 [M+H]$^+$.

Intermediate 55

5-Cyclopropyl-1-(phenylmethyl)-2-pyrrolidinone

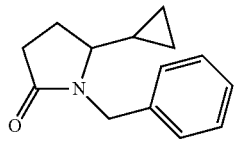 [SMILES: O=C1CCC(C2CC2)N1Cc1ccccc1]

To 5-cyclopropyl-5-hydroxy-1-(phenylmethyl)-2-pyrrolidinone (400 mg, 1.73 mmol) in CH$_2$Cl$_2$ (10 mL) at −78° C. was added a mixture of triethylsilane (2.76 mL, 17.3 mmol) and BF$_3$.OEt$_2$ (0.88 mL, 6.92 mmol) dropwise. The resulting reaction mixture was stirred for 2 hours at −78° C., then allowed to warm to room temperature and stirred overnight. The reaction was quenched by adding a saturated aqueous NaHCO$_3$ solution, and the aqueous layer was extracted with CH$_2$Cl$_2$ (2×). The combined organic layers were dried (MgSO$_4$), filtered and concentrated. Flash chromatography on SiO$_2$ (gradient: 100% hexanes to 100% EtOAc) afforded the title compound (240 mg, 65%) as a colorless oil. LC-MS (ES) m/z=216 [M+H]$^+$.

Intermediate 56

2-Cyclopropyl-1-(phenylmethyl)pyrrolidine

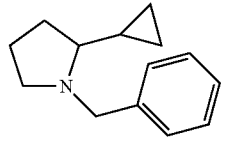 [SMILES: c1ccc(CN2CCCC2C2CC2)cc1]

To 5-cyclopropyl-1-(phenylmethyl)-2-pyrrolidinone (240 mg, 1.12 mmol) in THF (5 mL) was added BH$_3$.SMe$_2$ 2M in THF (5.6 mL, 11.2 mmol), and the reaction mixture was stirred over the weekend at room temperature. The reaction was quenched with the dropwise addition of CH$_3$OH (~2 mL, caution: vigorous H$_2$ evolution occurs). The solution was poured onto water (~50 mL) and EtOAc (~50 mL), and the mixture was stirred at 60° C. for 3 hours. A saturated aqueous solution of NaHCO$_3$ (~25 mL) and EtOAc (~50 mL) were added, and the organic layer was separated, washed with brine, dried (MgSO$_4$), filtered and concentrated. Flash chromatography on SiO$_2$ (gradient: 100% hexanes to 75% EtOAc/hexanes) afforded the title compound (100 mg, 45%) as a yellow oil. LC-MS (ES) m/z=202 [M+H]$^+$.

Intermediate 57

2-Cyclopropylpyrrolidine

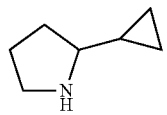

To a solution of 2-cyclopropyl-1-(phenylmethyl)pyrrolidine (100 mg, 0.50 mmol) in ethanol (5 mL) was added 1N HCl$_{(aq)}$ (0.50 mL, 0.50 mmol), and the resulting mixture was purged with N$_2$ for 10 minutes. Pd/C (10 mg, 10 wt %) was added and the reaction mixture was stirred overnight at room temperature under a H$_2$ atmosphere (balloon setup). LCMS analysis indicated ~20% desired product and ~70% starting material. More Pd/C was added (30 mg), and the reaction mixture was stirred under a H$_2$ atmosphere for an additional 24 hours. Additional 1N HCl$_{(aq)}$ (0.50 mL, 0.50 mmol) was added, and the mixture was filtered through an Acrodisk, washing with ethanol. The solution was evaporated, and the resulting residue was triturated with diethyl ether to afford the HCl salt of the title compound (74 mg) as a white solid. $^1$H NMR (400 MHz, CD$_3$OD): δ 0.37-0.54 (m, 2H), 0.67-0.80 (m, 2H), 0.98-1.15 (m, 1H), 1.77-1.93 (m, 1H), 1.96-2.18 (m, 2H), 2.18-2.30 (m, 1H), 2.84-2.98 (m, 1H), 3.20-3.30 (m, 1H), 3.30-3.43 (m, 1H).

Intermediate 58

4-Chloro-6-(2-cyclopropyl-1-pyrrolidinyl)-2-pyrimidinamine

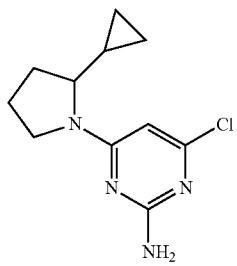 [SMILES: Nc1nc(Cl)cc(N2CCCC2C2CC2)n1]

To 4,6-dichloro-2-pyrimidinamine (95 mg, 0.576 mmol) in CH$_3$CN (5 mL) was added Et$_3$N (0.25 mL, 1.75 mmol) followed by 2-cyclopropylpyrrolidine (74 mg, 0.50 mmol), and the reaction mixture was stirred for 4 hours at 80° C. The reaction was poured onto water (a precipitate was formed), and filtered. Flash chromatography SiO$_2$ (gradient: EtOAc/hexanes) afforded the title compound (70 mg) as a white solid. LC-MS (ES) m/z=239, 241 [M+H]$^+$.

Example 47

6-[2-Amino-6-(2-cyclopropyl-1-pyrrolidinyl)-4-pyrimidinyl]-1H-indazol-3-amine

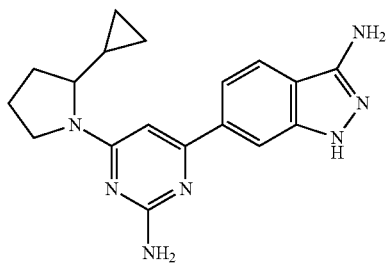 [SMILES: Nc1nc(-c2ccc3c(N)n[nH]c3c2)cc(N2CCCC2C2CC2)n1]

To 4-chloro-6-(2-cyclopropyl-1-pyrrolidinyl)-2-pyrimidinamine (26 mg, 0.11 mmol) and (4-cyano-3-fluorophenyl)boronic acid (17.96 mg, 0.11 mmol) were added 1,4-dioxane (3 mL) and saturated aqueous solution of NaHCO$_3$ (0.5 mL), and the resulting mixture was purged ("degassed") with N$_2$ into a sealable tube. Pd(Ph$_3$P)$_4$ (12.6 mg, 10.9 μmol) was added, the tube was sealed, and the reaction mixture was stirred overnight at 100° C. The mixture was poured onto water and filtered. Flash chromatography on SiO$_2$ of the filtrated solid (gradient: 100% CHCl$_3$ to 90:10:1 CHCl$_3$: CH$_3$OH:NH$_4$OH) afforded the desired Suzuki product. LC-MS (ES) m/z=324 [M+H]$^+$. This material was dissolved in ethanol (4 mL), treated with hydrazine monohydrate (1 mL, 20.4 mmol), and the resulting mixture was stirred overnight at 100° C. into a sealed tube. The mixture was poured onto water and EtOAc. The organic layer was separated, and the aqueous layer was further extracted with EtOAc. The combined organic layers were washed with brine, dried (MgSO$_4$), filtered and concentrated. The resulting residue was dissolved in ethanol (~2 mL) and treated with hexanes until the solution turned cloudy. The mixture was concentrated under vacuum until a precipitate was observed. The precipitate was filtered to afford the desired product (22 mg) as a pale yellow solid. LC-MS (ES) m/z=336 [M+H]$^+$. $^1$H NMR (400 MHz, CD$_3$OD): δ 0.29 (m, 1H), 0.47 (m, 1H), 0.60 (m, 1H), 0.71 (m, 1H), 1.05 (m, 1H), 1.92-2.10 (m, 3H), 2.19 (m, 1H), 3.47-3.59 (m, 1H), 3.65 (m, 1H), 4.00 (m, 1H), 6.36 (s, 1H), 7.46 (dd, J=8.6, 1.3 Hz, 1H), 7.76-7.81 (m, 2H).

Intermediate 59

N-Cyclohexyl-6-(trifluoromethyl)-3-pyridinecarboxamide

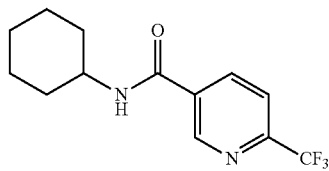 [SMILES: O=C(NC1CCCCC1)c1ccc(C(F)(F)F)nc1]

To 6-(trifluoromethyl)-3-pyridinecarboxylic acid (2.0 g, 10.5 mmol) in DMF (10 mL) was added HATU (4.18 g, 11.0 mmol) followed by Hunig's base (1.83 mL, 10.5 mmol). After 15 minutes, cyclohexylamine (2.40 mL, 20.9 mmol) was added, and the reaction mixture was stirred for 45 minutes at room temperature. The reaction was poured onto water (~300 mL). After 5 minutes, the resulting aqueous mixture was filtered, and the white solid was air dried for ~15 minutes to afford the title compound (2.57 g). LC-MS (ES) m/z=273 [M+H]$^+$.

Intermediate 60

Cis-N-Cyclohexyl-6-(trifluoromethyl)-3-piperidinecarboxamide

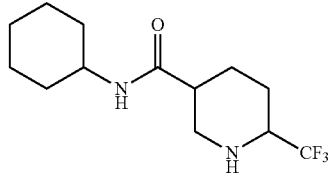 [SMILES: O=C(NC1CCCCC1)C1CCC(C(F)(F)F)NC1]

To a solution of N-cyclohexyl-6-(trifluoromethyl)-3-pyridinecarboxamide (2.57 g, 9.44 mmol) in CH$_3$OH (100 mL) was added platinum(IV) oxide (0.11 g, 0.47 mmol) followed by concentrated HCl (1 ml, 12.00 mmol) into a Parr Shaker. The mixture was degassed (3×) with nitrogen, and the reaction mixture was stirred overnight under a H$_2$ atmosphere (55 psi). The reaction mixture was degassed (3×) with N$_2$, filtered through an acrodisk, and concentrated. The resulting residue was co-evaporated from toluene (100 mL), followed by CH$_3$CN (100 mL) and dried under vacuum to afford the HCl salt of the title compound (2.91 g) as a white solid which contained a small amount of the trans isomer. $^1$H NMR (400 MHz, CD$_3$OD): δ 1.14-1.44 (m, 5H), 1.67 (m, 1H), 1.73-2.2 (m, 8H), 2.86 (m, 1H), 3.27 (dd, J=12.9, 3.3 Hz, 1H), 3.68 (m, 2H), 4.24 (m, 1H).

Intermediate 61

Cis-1-[6-Chloro-2-(methylthio)-4-pyrimidinyl]-N-cyclohexyl-6-(trifluoromethyl)-3-piperidinecarboxamide

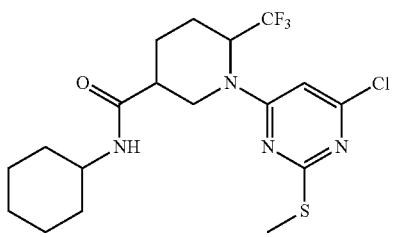 [SMILES: CSc1nc(Cl)cc(N2CC(C(=O)NC3CCCCC3)CCC2C(F)(F)F)n1]

To cis-N-cyclohexyl-6-(trifluoromethyl)-3-piperidinecarboxamide (1.0 g, 3.2 mmol) in THF (15 mL) was added 1M LiHMDS in THF (11 mL, 11.00 mmol) at room temperature. After 5 minutes, 4,6-dichloro-2-(methylthio)pyrimidine (0.620 g, 3.18 mmol) was added. After 10 minutes, LCMS analysis of the reaction mixture indicated the presence of ~85% desired product+13% of dichloropyrimidine SM. The reaction mixture was poured onto saturated NH$_4$Cl and EtOAc. The organic layer was separated, washed with brine, dried (MgSO$_4$), filtered and concentrated. A solid cartridge was prepared by adding EtOAc (~200 mL) to the crude and SiO$_2$ (3 g). The mixture was concentrated. Flash chromatography (100% Hexanes to 50% EtOAc in Hexanes, then 100% EtOAc) afforded the title compound (690 mg) as an off-white solid. LC-MS (ES) m/z=437, 439 [M+H]$^+$.

Intermediate 62

Cis-1-[6-Chloro-2-(methylsulfonyl)-4-pyrimidinyl]-N-cyclohexyl-6-(trifluoromethyl)-3-piperidinecarboxamide

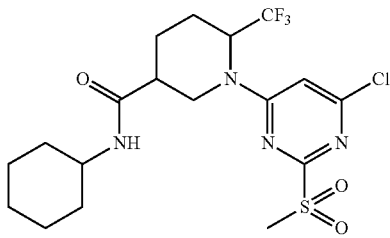 [SMILES: CS(=O)(=O)c1nc(Cl)cc(N2CC(C(=O)NC3CCCCC3)CCC2C(F)(F)F)n1]

To cis-1-[6-chloro-2-(methylthio)-4-pyrimidinyl]-N-cyclohexyl-6-(trifluoromethyl)-3-piperidinecarboxamide (590 mg, 1.350 mmol) in CH$_2$Cl$_2$ (12 mL) was added mCPBA (757 mg, 3.38 mmol), and the reaction mixture was stirred for 1 hour at room temperature. A saturated solution of Na$_2$SO$_3$ was added, and the resulting mixture was stirred for 30 minutes. The mixture was poured onto saturated aqueous NaHCO$_3$ and EtOAc. The organic layer was separated, washed with brine, dried (MgSO$_4$), filtered and concentrated to afford the title compound (640 mg) as a white solid. LC-MS (ES) m/z=469, 471 [M+H]$^+$.

Intermediate 63 cis1-[2-({[2,4-Bis(methyloxy)phenyl]methyl}amino)-6-chloro-4-pyrimidinyl]-N-cyclohexyl-6-(trifluoromethyl)-3-piperidinecarboxamide

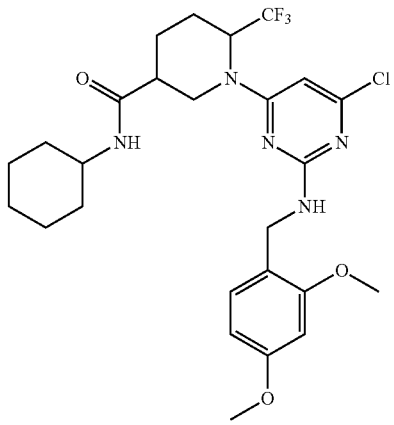 [SMILES: COc1ccc(CNc2nc(Cl)cc(N3CC(C(=O)NC4CCCCC4)CCC3C(F)(F)F)n2)c(OC)c1]

To cis-1-[6-chloro-2-(methylsulfonyl)-4-pyrimidinyl]-N-cyclohexyl-6-(trifluoromethyl)-3-piperidinecarboxamide (300 mg, 0.640 mmol) in 1,4-dioxane (8 mL) was added Hunig's base (0.22 mL, 1.28 mmol) followed by {[2,4-bis(methyloxy)phenyl]methyl}amine (0.19 mL, 1.28 mmol), and the reaction mixture was stirred overnight at 60° C. into a sealed tube. This reaction mixture was combined with another similar reaction mixture (~⅓ the scale) before work up. The combined reaction mixtures were poured onto water and EtOAc. The layers were separated, and the aqueous layer was further extracted with EtOAc. The combined organic layers were washed with brine, dried (MgSO$_4$), filtered and concentrated. Flash chromatography on SiO$_2$ (gradient: 100% Hexanes to 50% EtOAc in Hexanes) afforded the title compound (322 mg) as a white foam. LC-MS (ES) m/z=556 [M+H]$^+$.

Intermediate 64

Cis-1-[2-({[2,4-Bis(methyloxy)phenyl]methyl}amino)-6-(4-cyano-3-fluorophenyl)-4-pyrimidinyl]-N-cyclohexyl-6-(trifluoromethyl)-3-piperidinecarboxamide

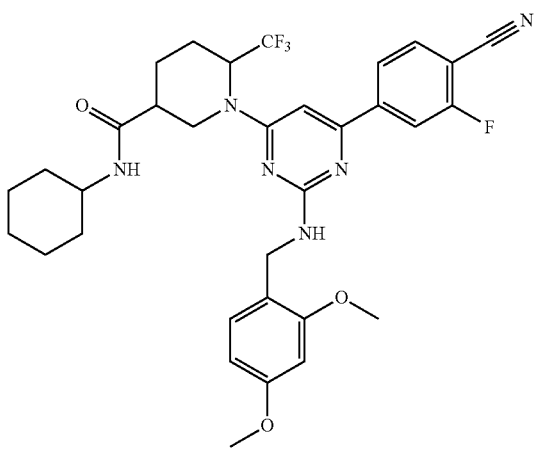 [SMILES: COc1ccc(CNc2nc(-c3ccc(C#N)c(F)c3)cc(N3CC(C(=O)NC4CCCCC4)CCC3C(F)(F)F)n2)c(OC)c1]

To cis-1-[2-({[2,4-bis(methyloxy)phenyl]methyl}amino)-6-chloro-4-pyrimidinyl]-N-cyclohexyl-6-(trifluoromethyl)-3-piperidinecarboxamide (322 mg, 0.58 mmol) and (4-cyano-3-fluorophenyl)boronic acid (124 mg, 0.75 mmol) were added 1,4-dioxane (6 mL) and saturated aqueous NaHCO$_3$ (3 mL), and the resulting mixture was purged ("degassed") with N$_2$ into a sealable tube for 5 minutes. Pd(Ph$_3$P)$_4$ (33.5 mg, 0.029 mmol) was added, and N$_2$ gas was bubbled through the mixture for an additional 5 minutes. The tube was sealed, and the reaction mixture was stirred overnight at 100° C. The reaction mixture was poured onto water and EtOAc. The organic layer was separated, washed with brine, dried (MgSO$_4$), filtered and concentrated. Flash chromatography on SiO$_2$ (gradient: 100% Hexanes to 50% EtOAc/Hexanes) afforded the title compound (305 mg) as a yellow foam. LC-MS (ES) m/z=641 [M+H]$^+$.

Intermediate 65

Cis-1-[6-(3-Amino-1H-indazol-6-yl)-2-({[2,4-bis(methyloxy)phenyl]methyl}amino)-4-pyrimidinyl]-N-cyclohexyl-6-(trifluoromethyl)-3-piperidinecarboxamide

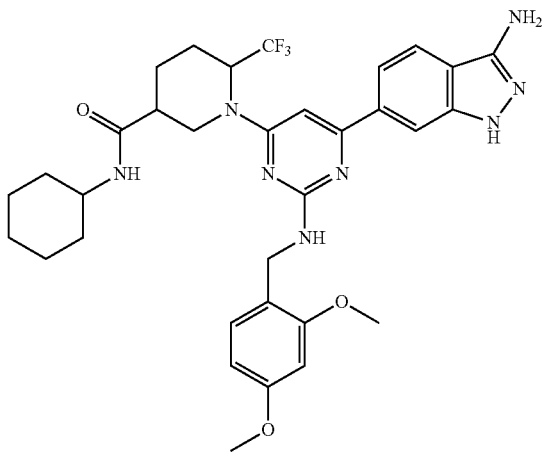 [SMILES: COc1ccc(CNc2nc(-c3ccc4c(N)n[nH]c4c3)cc(N3CC(C(=O)NC4CCCCC4)CCC3C(F)(F)F)n2)c(OC)c1]

To cis-1-[2-({[2,4-bis(methyloxy)phenyl]methyl}amino)-6-(4-cyano-3-fluorophenyl)-4-pyrimidinyl]-N-cyclohexyl-6-(trifluoromethyl)-3-piperidinecarboxamide (304 mg, 0.48 mmol) in ethanol (6 mL) was added hydrazine monohydrate (0.47 mL, 9.5 mmol), and the reaction mixture was stirred overnight at 100° C. into a sealed tube. The reaction was allowed to cool to room temperature and poured onto water (~200 mL). A white precipitate was formed. The mixture was filtered, and the solid was air dried for 2 hours to afford the title compound (270 mg) as a white solid. LC-MS (ES) m/z=653 [M+H]$^+$.

Example 48

Cis-1-[2-Amino-6-(3-amino-1H-indazol-6-yl)-4-pyrimidinyl]-N-cyclohexyl-6-(trifluoromethyl)-3-piperidinecarboxamide

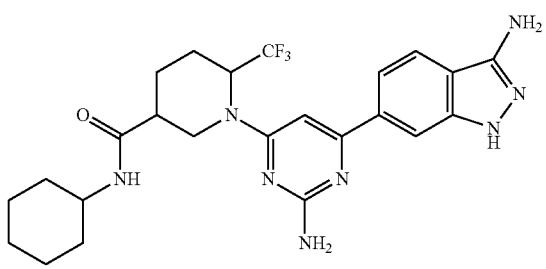 [SMILES: Nc1nc(-c2ccc3c(N)n[nH]c3c2)cc(N2CC(C(=O)NC3CCCCC3)CCC2C(F)(F)F)n1]

To cis-1-[6-(3-amino-1H-indazol-6-yl)-2-({[2,4-bis(methyloxy)phenyl]methyl}amino)-4-pyrimidinyl]-N-cyclohexyl-6-(trifluoromethyl)-3-piperidinecarboxamide (250 mg, 0.38 mmol) was added trifluoroacetic acid (TFA) (6 mL). After 3 hours, LCMS analysis indicated the reaction to be completed. The reaction mixture was concentrated under vacuum, and the resulting residue was co-evaporated from toluene (2×50 mL), then from CH$_3$CN (50 mL). To the resulting pink solid was added a saturated aqueous NaHCO$_3$ solution and EtOAc. The organic layer was separated, and the aqueous layer was further extracted with EtOAc. The combined organic layers were washed with brine, dried (MgSO$_4$), filtered and concentrated. This material was purified by flash chromatography (gradient: 100% CH$_2$Cl$_2$ to 90:10:1 CH$_2$Cl$_2$:CH$_3$OH:NH$_4$OH). The cleaner fractions were combined and concentrated under vacuum to afford a yellow solid. This material was dissolved in EtOAc (~2 mL), and the resulting solution was transfered to a microwave vial. The vial was capped, and heated to 70 C. Hexane was added dropwise until the solution became cloudy, then the mixture was allowed to cool to room temperature. A spatula was used to scrap the solid, and the mixture was filtered. The collected pink solid was washed with hexanes and a white solid precipitate from the filtrate. This white solid was collected by filtration to afford the desired product (35 mg). LC-MS (ES) m/z=503 [M+H]$^+$. $^1$H NMR (400 MHz, DMSO-d$_6$): δ 1.05-1.34 (m, 5H), 1.56 (m, 1H), 1.63-1.85 (m, 7H), 2.07 (m, 1H), 2.33, (m, 1H), 3.06 (bs, 1H), 3.53 (m, 1H), 5.39 (s, 2H), 6.29 (s, 2H), 6.78 (s, 1H), 7.63 (dd, J=8.5, 1.1 Hz, 1H), 7.72 (d, J=8.4 Hz, 1H), 7.84 (d, J=7.9 Hz, 1H), 7.99 (s, 1H), 11.54 (s, 1H).

Intermediate 66

Cis-1-[6-Chloro-2-(methylamino)-4-pyrimidinyl]-N-cyclohexyl-6-(trifluoromethyl)-3-piperidinecarboxamide

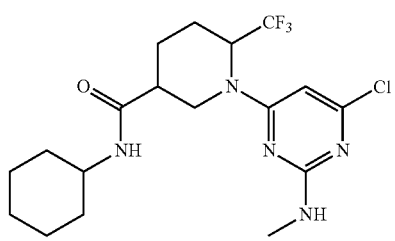 [SMILES: CNc1nc(Cl)cc(N2CC(C(=O)NC3CCCCC3)CCC2C(F)(F)F)n1]

To cis-1-[6-chloro-2-(methylsulfonyl)-4-pyrimidinyl]-N-cyclohexyl-6-(trifluoromethyl)-3-piperidinecarboxamide (390 mg, 0.832 mmol) in 1,4-dioxane (8 mL) was added Hunig's base (0.29 mL, 1.66 mmol) followed by 2M methylamine in THF (1 mL, 2 mmol), and the reaction mixture was stirred overnight at 60° C. into a sealed tube. The mixture was poured onto water and EtOAc. The organic layer was separated, washed with brine, dried (MgSO$_4$), filtered and concentrated. Flash chromatography on SiO$_2$ (gradient: 100% Hexanes to 50% EtOAc in Hexanes) afforded the title compound (204 mg) as a white foam. LC-MS (ES) m/z=420, 422 [M+H]$^+$.

Intermediate 67

Cis-1-[6-(4-Cyano-3-fluorophenyl)-2-(methylamino)-4-pyrimidinyl]-N-cyclohexyl-6-(trifluoromethyl)-3-piperidinecarboxamide

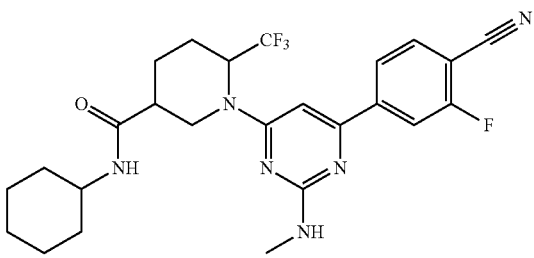 [SMILES: CNc1nc(-c2ccc(C#N)c(F)c2)cc(N2CC(C(=O)NC3CCCCC3)CCC2C(F)(F)F)n1]

To cis-1-[6-chloro-2-(methylamino)-4-pyrimidinyl]-N-cyclohexyl-6-(trifluoromethyl)-3-piperidinecarboxamide (204 mg, 0.486 mmol) and (4-cyano-3-fluorophenyl)boronic acid (104 mg, 0.632 mmol) were added 1,4-dioxane (6 mL) and saturated aqueous $NaHCO_3$ (3 mL), and the resulting mixture was purged ("degassed") with $N_2$ into a sealable tube for 5 minutes. $Pd(Ph_3P)_4$ (28 mg, 0.024 mmol) was added, and $N_2$ gas was bubbled through the mixture for an additional 5 minutes. The tube was sealed, and the reaction mixture was stirred overnight at 100° C. The reaction mixture was poured onto water. The precipitate formed was filtered. EtOAc was added to the solid in the filter, and the mixture was stirred gently with a spatula until the solid dissolved. The resulting solution was filtered, and the filtrate was dried ($MgSO_4$), filtered and concentrated. Flash chromatography on $SiO_2$ (gradient: 100% Hexanes to 50% EtOAc/Hexanes) afforded the title compound (152 mg) as a yellow foam. LC-MS (ES) m/z=505 [M+H]$^+$.

Example 49

Cis-1-[6-(3-Amino-1H-indazol-6-yl)-2-(methylamino)-4-pyrimidinyl]-N-cyclohexyl-6-(trifluoromethyl)-3-piperidinecarboxamide

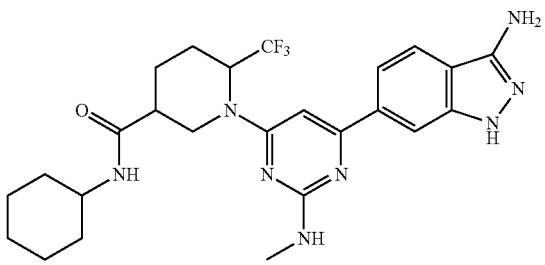 [SMILES: CNc1nc(-c2ccc3c(N)n[nH]c3c2)cc(N2CC(C(=O)NC3CCCCC3)CCC2C(F)(F)F)n1]

To cis-1-[6-(4-cyano-3-fluorophenyl)-2-(methylamino)-4-pyrimidinyl]-N-cyclohexyl-6-(trifluoromethyl)-3-piperidinecarboxamide (152 mg, 0.301 mmol) in ethanol (6 mL) was added hydrazine monohydrate (0.4 mL, 8.16 mmol), and the reaction mixture was stirred overnight at 100° C. into a sealed tube. The reaction was allowed to cool to room temperature and poured onto water and EtOAc. The organic layer was separated, and the aqueous layer was further extracted with EtOAc. The combined organic layers were washed with brine, dried ($MgSO_4$), filtered and concentrated. Flash chromatography on $SiO_2$ (gradient: 100% $CH_2Cl_2$ to 90:10:1 $CH_2Cl_2$:$CH_3OH$:$NH_4OH$) afforded the title compound (116 mg) as an off-white solid. LC-MS (ES) m/z=517 [M+H]$^+$. $^1$H NMR (400 MHz, DMSO-d$_6$): δ 1.05-1.34 (m, 5H), 1.56 (m, 1H), 1.62-1.85 (m, 7H), 2.08. (m, 1H), 2.34 (m, 1H), 2.84 (s, 3H), 3.07 (bs, 1H), 3.53 (m, 1H), 5.39 (s, 2H), 6.73 (bs, 1H), 6.78 (s, 1H), 7.63-7.69 (m, 1H), 7.70-7.75 (m, 1H), 7.84 (d, J=7.8 Hz, 1H), 8.02 (bs, 1H), 11.52 (s, 1H).

Intermediate 68

2-Fluoro-4-(4,4,5,5-tetramethyl-1,3,2-dioxaborolan-2-yl)benzonitrile

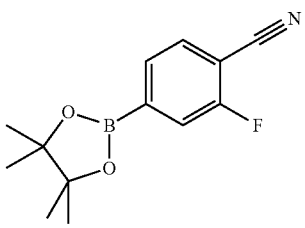 [SMILES: CC1(C)OB(c2ccc(C#N)c(F)c2)OC1(C)C]

A mixture of 4-bromo-2-fluorobenzonitrile (30 g, 150 mmol), bis(pinacolato)diboron (49.5 g, 195 mmol), potassium acetate (29.4 g, 300 mmol), and $Pd(dppf)Cl_2 \cdot CH_2Cl_2$ (12.2 g, 15.0 mmol) in DMSO and 1,4-dioxane (65 mL) was heated overnight at 110° C. under nitrogen. The reaction mixture was cooled to room temperature, filtered through Kieselguhr, and concentrated. The resilting residue was purified by $SiO_2$ chromatography (100:1 petroleum ether:EtOAc) to afford the title compound (35 g) as a white solid. LC-MS (ES) m/z=247 [M+H]$^+$.

Intermediate 69

6-Chloro-N$^4$-[(2-chlorophenyl)methyl]-2,4-pyrimidinediamine

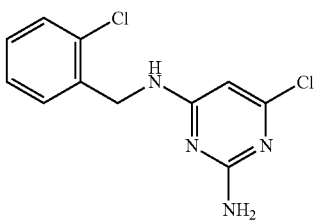 [SMILES: Nc1nc(Cl)cc(NCc2ccccc2Cl)n1]

A mixture of 4,6-dichloro-2-pyrimidinamine (1 g, 6.1 mmol), [(2-chlorophenyl)methyl]amine (2.23 g, 15.8 mmol) and triethylamine (1.86 g, 18.4 mmol) in $CH_3OH$ (40 mL) was stirred for 4 hours at 50° C. The reaction mixture was evaporated to provide a yellow residue, which was purified by $SiO_2$ chromatography (1:1 petroleum ether:EtOAc) to afford the title compound (1.2 g) as off-white solid. LC-MS (ES) m/z=328 [M+H]$^+$.

119

Intermediate 70

4-(2-Amino-6-{[(2-chlorophenyl)methyl]amino}-4-pyrimidinyl)-2-fluorobenzonitrile

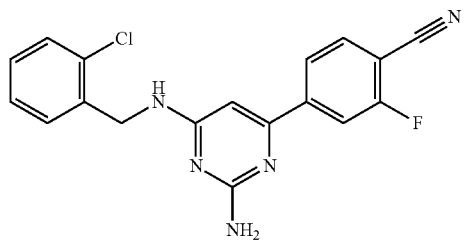 [SMILES: N#Cc1ccc(-c2cc(NCc3ccccc3Cl)nc(N)n2)cc1F]

A mixture of 6-chloro-N$^4$-[(2-chlorophenyl)methyl]-2,4-pyrimidinediamine (1.2 g, 4.46 mmol) and 2-fluoro-4-(4,4,5,5-tetramethyl-1,3,2-dioxaborolan-2-yl)benzonitrile (1.32 g, 5.35 mmol) in 1,4-dioxane (14.6 mL) and a solution of NaHCO$_3$ (3.12 mmol) in water (20 mL) was protected with N$_2$. Pd(Ph$_3$P)$_4$ (100 mg, 0.087 mmol) was added, and the reaction mixture was heated at 100° C. for 16 hours. The mixture was decanted to remove the solids, and the resulting solution was concentrated to dryness. The crude material was purified by SiO$_2$ chromatography (1:2 THF:petroleum ether) to afford the title compound (800 mg) as a yellow solid. LC-MS (ES) m/z=354 [M+H]$^+$.

Example 50

6-(3-Amino-1H-indazol-6-yl)-N$^4$-[(2-chlorophenyl)methyl]-2,4-pyrimidinediamine

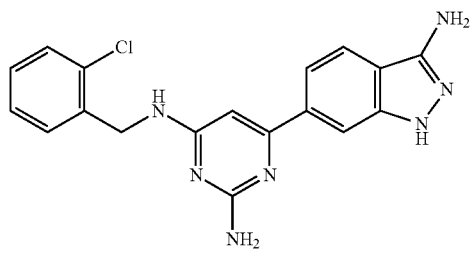 [SMILES: Nc1nc(NCc2ccccc2Cl)cc(-c2ccc3c(N)n[nH]c3c2)n1]

To 4-(2-amino-6-{[(2-chlorophenyl)methyl]amino}-4-pyrimidinyl)-2-fluorobenzonitrile (800 mg, 2.27 mmol) in ethanol (2 mL) was added hydrazine monohydrate (3 mL, 74 mmol), and the reaction mixture was heated to 100° C. for 1 hour in a BiotageInitiator® microwave synthesizer. Upon cooling, the reaction mixture was concentrated in vacuum and purified by RPHPLC (BiotageSP1) (gradient: 30% CH$_3$CN/H$_2$O to 60% CH$_3$CN/H$_2$O) to afford the title compound (151 mg) as an off-white solid. LC-MS (ES) m/z=366 [M+H]$^+$. $^1$H NMR (400 MHz, DMSO-d$_6$): δ 4.61 (d, J=5.6 Hz, 2H), 5.37 (s, 2H), 6.07 (s, 2H), 6.40 (s, 1H), 7.34-7.27 (m, 2H), 7.46-7.41 (m, 4H), 7.70 (d, J=8.8 Hz, 1H), 7.84 (s, 1H), 11.52 (s, 1H).

120

Example 51

6-(3-Amino-1H-indazol-6-yl)-N$^4$-cyclopropyl-2,4-pyrimidinediamine

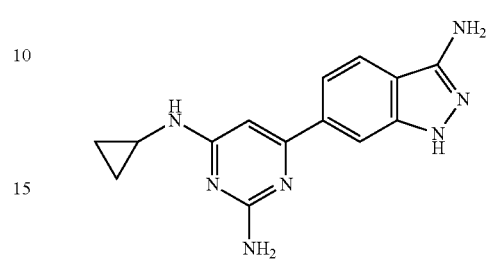

A mixture of 6-[2-amino-6-(methylsulfonyl)-4-pyrimidinyl]-1H-indazol-3-amine (650 mg, 2.14 mmol), cyclopropylamine (650 mg, 11.4 mmol), and Hunig's base (2 mL, 11.4 mmol) in 1,4-dioxane (5 mL) was heated for 2 hours at 120° C. in a BiotageInitiator® microwave synthesizer. Upon cooling, the mixture was decanted to remove the solids, and the resulting solution was concentrated to dryness. The crude material was purified by RPHPLC (gradient: 15% CH$_3$CN/H$_2$O to 45% CH$_3$CN/H$_2$O) to afford the title compound (32 mg) as a yellow solid. LC-MS (ES) m/z=282 [M+H]$^+$. $^1$H NMR (400 MHz, DMSO-d$_6$): δ 0.46-0.49 (m, 2H), 0.73 (t, J=6.8 Hz, 2H), 2.62-2.67 (m, 1H), 5.37 (s, 2H), 6.0 (s, 2H), 6.38 (s, 1H), 7.02 (s, 1H), 7.45 (d, J=8.8 Hz, 1H), 7.70 (d, J=8.0 Hz, 1H), 7.86 (s, 1H), 11.50 (s, 1H).

Example 52

6-(3-Amino-1H-indazol-6-yl)-N$^4$-(3-phenylpropyl)-2,4-pyrimidinediamine

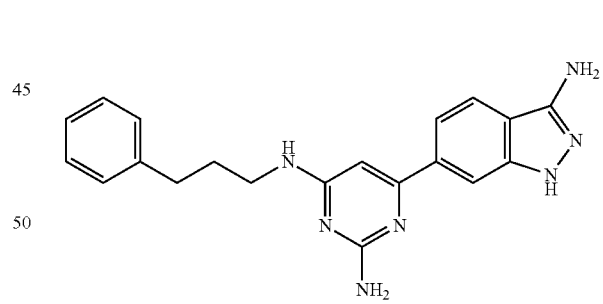

A mixture of 6-[2-amino-6-(methylsulfonyl)-4-pyrimidinyl]-1H-indazol-3-amine (500 mg, 1.64 mmol), (3-phenylpropyl)amine (500 mg, 3.70 mmol), and Hunig's base (2 mL) in 1-1-methyl-2-pyrrolidinone (NMP) (3 mL) was heated for 4 hours at 140° C. in a BiotageInitiator® microwave synthesizer. Upon cooling, the mixture was decanted to remove the solids, and the resulting solution was concentrated to dryness. The crude material was purified by RPHPLC (gradient: 10% CH$_3$CN/H$_2$O to 30% CH$_3$CN/H$_2$O) to afford the title compound (90 mg) as a yellow solid. LC-MS (ES) m/z=360 [M+H]$^+$. $^1$H NMR (400 MHz, DMSO-d$_6$): δ 1.80-1.87 (m, 2H), 2.64-2.68 (m, 2H), 3.28-3.30 (m, 2H), 5.37 (s, 2H), 5.97

(s, 2H), 6.27 (s, 1H), 6.93 (s, 1H), 7.17-7.31 (m, 5H), 7.40 (d, J=8.4 Hz, 1H), 7.70 (d, J=8.0 Hz, 1H), 7.84 (s, 1H), 11.51 (s, 1H).

Example 53

6-(3-Amino-1H-indazol-6-yl)-$N^4$-[2-(2-fluorophenyl)ethyl]-2,4-pyrimidinediamine

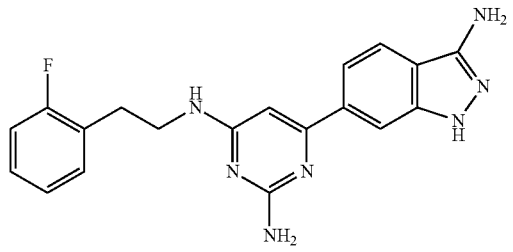 [SMILES: Nc1nc(NCCc2ccccc2F)cc(-c2ccc3c(N)n[nH]c3c2)n1]

A mixture of 6-[2-amino-6-(methylsulfonyl)-4-pyrimidinyl]-1H-indazol-3-amine (500 mg, 1.64 mmol), 2-(2-fluorophenyl)ethanamine (500 mg, 2.19 mmol), and Hunig's base (2 mL) in NMP (3 mL) was heated for 4 hours at 140° C. in a BiotageInitiator® microwave synthesizer. Upon cooling, the mixture was decanted to remove the solids, and the resulting solution was concentrated to dryness. The crude material was purified by RPHPLC (gradient: 20% $CH_3CN/H_2O$ to 40% $CH_3CN/H_2O$) to afford the title compound (166 mg) as a yellow solid. LC-MS (ES) m/z=364 $[M+H]^+$. $^1$H NMR (400 MHz, DMSO-$d_6$): δ 2.86-2.90 (m, 2H), 3.49-3.51 (m, 2H), 5.35 (s, 2H), 5.98 (s, 2H), 6.25 (s, 1H), 6.97 (s, 1H), 7.12-7.17 (m, 2H), 7.23-7.29 (m, 1H), 7.33-7.41 (m, 2H), 7.68 (d, J=8.4 Hz, 1H), 7.82 (s, 1H), 11.50 (s, 1H).

Example 54

6-(3-Amino-1H-indazol-6-yl)-$N^4$-{2-[2-(methyloxy)phenyl]ethyl}-2,4-pyrimidinediamine

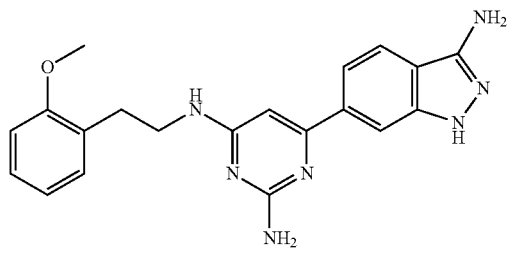 [SMILES: COc1ccccc1CCNc1cc(-c2ccc3c(N)n[nH]c3c2)nc(N)n1]

A mixture of 6-[2-amino-6-(methylsulfonyl)-4-pyrimidinyl]-1H-indazol-3-amine (500 mg, 1.64 mmol), 2-[2-(methyloxy)phenyl]ethanamine (500 mg, 3.31 mmol), and Hunig's base (2 mL) in NMP (3 mL) was heated for 4 hours at 140° C. in a BiotageInitiator® microwave synthesizer. Upon cooling, the mixture was decanted to remove the solids, and the resulting solution was concentrated to dryness. The crude material was purified by RPHPLC (gradient: 10% $CH_3CN/H_2O$ to 30% $CH_3CN/H_2O$) to afford the title compound (100 mg) as a yellow solid. LC-MS (ES) m/z=376 $[M+H]^+$. $^1$H NMR (400 MHz, DMSO-$d_6$): δ 2.81-2.84 (m, 2H), 3.52 (m, 2H), 3.74 (s, 3H), 5.37 (s, 2H), 6.01 (s, 2H), 6.28 (s, 1H), 6.76-6.86 (m, 4H), 7.22 (t, J=8.4 Hz, 1H), 7.41 (d, J=7.6 Hz, 1H), 7.69 (d, J=8.8 Hz, 1H), 7.84 (s, 1H), 11.51 (s, 1H).

Example 55

6-(3-Amino-1H-indazol-6-yl)-$N^4$-[2-(3-chlorophenyl)ethyl]-2,4-pyrimidinediamine

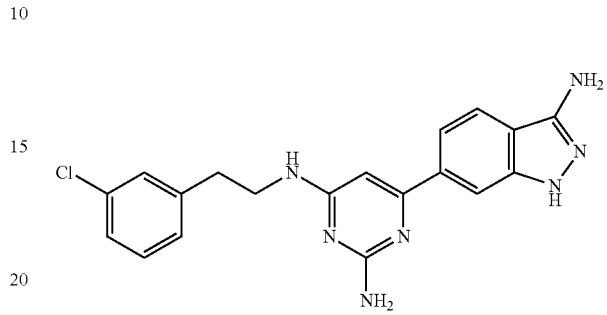

A mixture of 6-[2-amino-6-(methylsulfonyl)-4-pyrimidinyl]-1H-indazol-3-amine (300 mg, 0.99 mmol), 2-(2-chlorophenyl)ethanamine (300 mg, 1.94 mmol), and Hunig's base (2 mL) in NMP (3 mL) was heated for 2 hours at 160° C. in a BiotageInitiator® microwave synthesizer. Upon cooling, the mixture was decanted to remove the solids, and the resulting solution was concentrated to dryness. The crude material was purified by RPHPLC to afford the title compound (120 mg) as a yellow solid. $^1$H NMR (400 MHz, DMSO-$d_6$): δ 2.87 (t, J=7.2 Hz, 2H), 3.52-3.54 (m, 2H), 5.39 (s, 2H),), 6.05 (s, 2H), 6.29 (s, 1H), 6.97 (s, 1H), 7.25-7.44 (m, 5H), 7.71 (d, J=8.4 Hz, 1H), 7.86 (s, 1H), 11.54 (s, 1H).

Example 56

6-(3-Amino-1H-indazol-6-yl)-$N^4$-methyl-$N^4$-(2-phenylethyl)-2,4-pyrimidinediamine

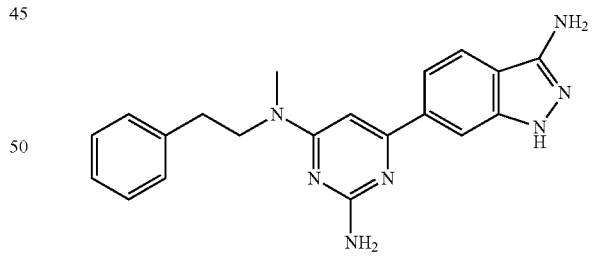

A mixture of 6-[2-amino-6-(methylsulfonyl)-4-pyrimidinyl]-1H-indazol-3-amine (300 mg, 0.99 mmol), N-methyl-2-phenylethanamine (300 mg, 2.22 mmol), and Hunig's base (2 mL) in NMP (3 mL) was heated for 2 hours at 160° C. for in a BiotageInitiator® microwave synthesizer. Upon cooling, the mixture was decanted to remove the solids, and the resulting solution was concentrated to dryness. The crude material was purified by RPHPLC to afford the title compound (50 mg) as a yellow solid. LC-MS (ES) m/z=360 $[M+H]^+$. $^1$H NMR (400 MHz, DMSO-$d_6$): δ 2.85 (t, J=7.6 Hz, 2H), 3.0 (s, 3H), 3.76 (t, J=7.6 Hz, 2H), 5.37 (s, 2H), 6.04 (s, 2H), 6.39 (s, 1H), 7.19-7.23 (m, 1H), 7.30-7.32 (m, 4H), 7.53 (d, J=8.4 Hz, 1H), 7.71 (d, J=8.8 Hz, 1H), 7.91 (s, 1H), 11.50 (s, 1H).

Example 57

6-(3-Amino-1H-indazol-6-yl)-$N^4$-[2-(3-fluorophenyl)ethyl]-2,4-pyrimidinediamine

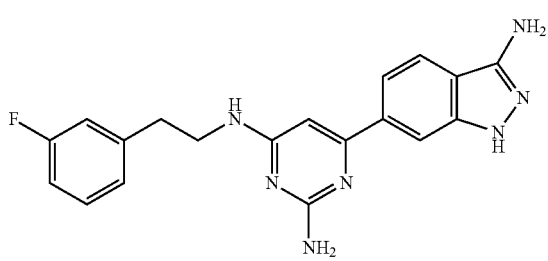 [SMILES: Nc1nc(NCCc2cccc(F)c2)cc(-c2ccc3c(N)n[nH]c3c2)n1]

A mixture of 6-[2-amino-6-(methylsulfonyl)-4-pyrimidinyl]-1H-indazol-3-amine (300 mg, 0.99 mmol), 2-(3-fluorophenyl)ethanamine (300 mg, 2.16 mmol), and Hunig's base (2 mL) in NMP (3 mL) was heated for 2 hours at 160° C. for in a BiotageInitiator® microwave synthesizer. Upon cooling, the mixture was decanted to remove the solids, and the resulting solution was concentrated to dryness. The crude material was purified by RPHPLC to afford the title compound (160 mg) as a yellow solid. LC-MS (ES) m/z=364 [M+H]$^+$. $^1$H NMR (400 MHz, DMSO-d$_6$): δ 2.86-2.90 (m, 2H), 3.51-3.56 (m, 2H), 5.39 (s, 2H), 6.04 (s, 2H), 6.29 (s, 1H), 6.97-7.43 (m, 6H), 7.70 (d, J=8.4 Hz, 1H), 7.85 (s, 1H), 11.53 (s, 1H).

Example 58

6-(3-Amino-1H-indazol-6-yl)-$N^4$-[2-(2-chlorophenyl)ethyl]-2,4-pyrimidinediamine

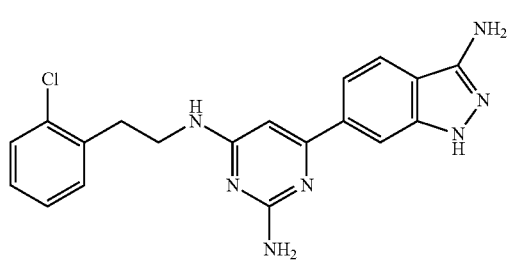

A mixture of 6-[2-amino-6-(methylsulfonyl)-4-pyrimidinyl]-1H-indazol-3-amine (300 mg, 0.99 mmol), 2-(2-chlorophenyl)ethanamine (300 mg, 1.94 mmol), and Hunig's base (2 mL) in NMP (3 mL) was heated for 2 hours at 160° C. in a BiotageInitiator® microwave synthesizer. Upon cooling, the mixture was decanted to remove the solids, and the resulting solution was concentrated to dryness. The crude material was purified by RPHPLC to afford the title compound (150 mg) as a yellow solid. $^1$H NMR (400 MHz, DMSO-d$_6$): δ 2.99 (t, J=8 Hz, 2H), 3.52-3.53 (m, 2H), 5.39 (s, 2H), 6.03 (s, 2H), 6.29 (s, 1H), 7.03 (s, 1H), 7.24-7.46 (m, 5H), 7.71 (d, J=8.0 Hz, 1H), 7.85 (s, 1H), 11.53 (s, 1H).

Example 59

6-(3-Amino-1H-indazol-6-yl)-$N^4$-[2-(2-methylphenyl)ethyl]-2,4-pyrimidinediamine

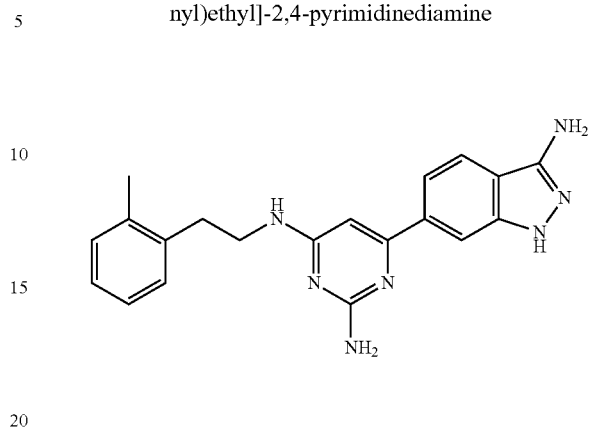

A mixture of 6-[2-amino-6-(methylsulfonyl)-4-pyrimidinyl]-1H-indazol-3-amine (300 mg, 0.99 mmol), 2-(2-methylphenyl)ethanamine (300 mg, 2.22 mmol), and Hunig's base (2 mL) in NMP (3 mL) was heated for 2 hours at 160° C. in a BiotageInitiator® microwave synthesizer. Upon cooling, the mixture was decanted to remove the solids, and the resulting solution was concentrated to dryness. The crude material was purified by RPHPLC to afford the title compound (150 mg) as a yellow solid. $^1$H NMR (400 MHz, DMSO-d$_6$): δ 2.33 (s, 3H), 2.82-2.86 (m, 2H), 3.50-3.45 (m, 2H), 5.36 (s, 2H), 5.98 (s, 2H), 6.29 (s, 1H), 6.97 (s, 1H), 7.09-7.22 (m, 4H), 7.43 (d, J=8.0 Hz, 1H), 7.85 (s, 1H), 11.51 (s, 1H).

Example 60

6-(3-Amino-1H-indazol-6-yl)-$N^4$-[2-(3-methylphenyl)ethyl]-2,4-pyrimidinediamine

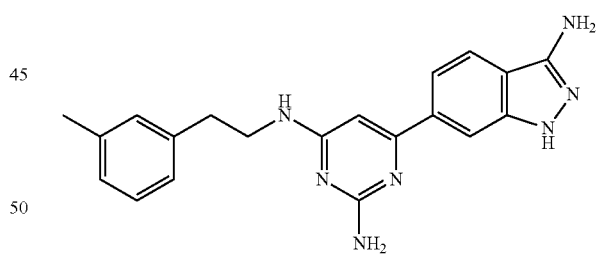

A mixture of 6-[2-amino-6-(methylsulfonyl)-4-pyrimidinyl]-1H-indazol-3-amine (300 mg, 0.99 mmol), 2-(3-methylphenyl)ethanamine (300 mg, 2.22 mmol), and Hunig's base (2 mL) in NMP (3 mL) was heated for 2 hours at 160° C. in a BiotageInitiator® microwave synthesizer. Upon cooling, the mixture was decanted to remove the solids, and the resulting solution was concentrated to dryness. The crude material was purified by RPHPLC to afford the title compound (125 mg) as a yellow solid. $^1$H NMR (400 MHz, DMSO-d$_6$): δ 2.03 (s, 3H), 2.79-2.82 (m, 2H), 3.49-3.51 (m, 2H), 5.35 (s, 2H), 5.99 (s, 2H), 6.28 (s, 1H), 6.92-7.10 (m, 4H), 7.41 (d, J=7.6 Hz, 1H), 7.69 (d, J=8.8 Hz, 1H), 7.84 (s, 1H), 11.49 (s, 1H).

Intermediate 71

1-(Phenylmethyl)cyclopropanamine

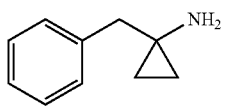

To a solution of phenylacetonitrile (3 g, 25.6 mmol) and tetraisopropylorthotitanate (8 mL, 27.2 mmol) in Et$_2$O/THF (1/1, 100 mL) was added ethylmagnesiumbromide (7.85 g, 58.9 mmol) dropwise at room temperature. The exothermic mixture was stirred at room temperature for 1 hour. Then BF$_3$.Et$_2$O (7.27 g, 51.2 mmol) was added dropwise and the mixture was stirred at room temperature for 1 hour. The mixture was poured into a cold aqueous solution of sodium hydroxide (10%) and diluted with EtOAc. The mixture was filtered, and the organic layer was washed with water and brine, dried (MgSO$_4$), filtered and concentrated in vacuum. The resulting solids were purified by reverse phase chromatography using CH$_3$CN in water (0.08% ammonium hydrogen carbonate) (gradient: from 37% to 47% in 7 min; flowrate: 40 mL/min). The pH of the solution was adjusted to 2 with concentrated HCl and concentrated in vacuum to afford the HCl salt of the title compound (700 mg) as a white solid. LC-MS (ES) m/z=148 [M+H]$^+$.

Intermediate 72

6-Chloro-N$^4$-[1-(phenylmethyl)cyclopropyl]-2,4-pyrimidinediamine

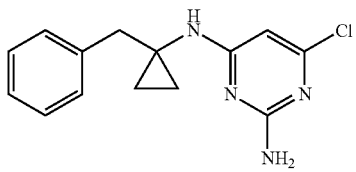 [SMILES: Nc1nc(Cl)cc(NC2(Cc3ccccc3)CC2)n1]

A mixture of 1-(phenylmethyl)cyclopropanamine_hydrochloride (530 mg, 2.88 mmol), 4,6-dichloro-2-pyrimidinamine (295 mg, 1.80 mmol), Et$_3$N (911 mg, 9 mmol) and K$_2$CO$_3$ (249 mg, 1.80 mmol) in ethanol (6 mL) was stirred and heated at 140° C. for 4 hours in a Biotage Initiator microwave synthesizer. The mixture was cooled to room temperature and concentrated to dryness. The resulting solids were partitioned between EtOAc and water. The organic layer was separated, dried (Na$_2$SO$_4$), concentrated to dryness and purified by reverse phase chromatography using CH$_3$CN in water from 32% to 42% (0.05% trifluoroacetic acid in water) in 8 min to afford the title compound (204 mg) as a white solid. LC-MS (ES) m/z=275 [M+H]$^+$.

Intermediate 73

4-(2-Amino-6-{[1-(phenylmethyl)cyclopropyl]amino}-4-pyrimidinyl)-2-fluorobenzonitrile

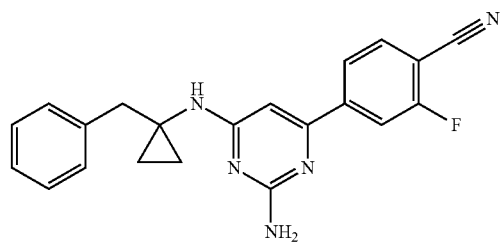 [SMILES: N#Cc1ccc(-c2cc(NC3(Cc4ccccc4)CC3)nc(N)n2)cc1F]

A mixture of 6-chloro-N$^4$-[1-(phenylmethyl)cyclopropyl]-2,4-pyrimidinediamine (185 mg, 0.67 mmol), 2-fluoro-4-(4,4,5,5-tetramethyl-1,3,2-dioxaborolan-2-yl)benzonitrile (247 mg, 1 mmol), Pd(PPh$_3$)$_4$ (81 mg, 0.07 mmol) and Na$_2$CO$_3$ (178 mg, 1.68 mmol) in 1,4-dioxane (30 mL) and water (10 mL) was stirred and heated at 110° C. for 3.5 hours under nitrogen. Then the mixture was cooled to room temperature and concentrated. The resulting residue was portioned between EtOAc and water. The aqueous was extracted with EtOAc (2×50 mL), and the organics were dried (MgSO$_4$), filtered, concentrated to dryness, and purified by SGC using a petroleum ether to 4:1 petroleum ether/EtOAc to 1:1 petroleum ether/EtOAc as eluent to afford the title compound (124 mg) as a brown oil solid. LC-MS (ES) m/z=360 [M+H]$^+$.

Example 61

6-(3-Amino-1H-indazol-6-yl)-N$^4$-[1-(phenylmethyl)cyclopropyl]-2,4-pyrimidinediamine

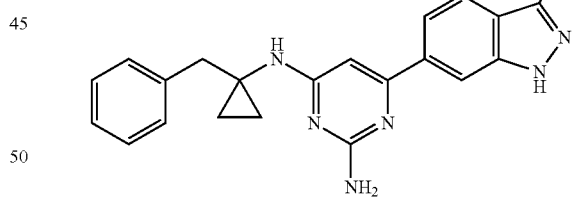

A mixture of 4-(2-amino-6-{[1-(phenylmethyl)cyclopropyl]amino}-4-pyrimidinyl)-2-fluorobenzonitrile (124 mg, 0.34 mmol) and hydrazine hydrate (99%, 2 mL) in ethanol (10 mL) was stirred and heated at 120° C. for 1 hour in a Biotage Initiator microwave synthesizer. The mixture was cooled to room temperature, filtered and concentrated in vacuo. The resulting solids were purified by reverse phase chromatography with CH$_3$CN in water (0.08% ammonium hydrogen carbonate) (gradient: 35% to 45% in 6 min: flowrate: 30 mL/min), to afford the title compound (30 mg) as a white solid. LC-MS (ES) m/z=372 [M+H]$^+$. $^1$H NMR (400 MHz, DMSO-d$_6$): δ 0.78 (d, 4H), 2.93 (s, 2H), 5.37 (s, 2H), 5.97 (s, 2H), 6.32 (s, 1H), 6.90 (s, 1H), 7.18 (d, 3H), 7.27 (t, 2H), 7.40 (s, 1H), 7.69 (d, 1H), 7.81 (s, 1H), 11.50 (s, 1H).

Intermediate 74

2,2-Dimethyl-3-phenylpropanoic acid

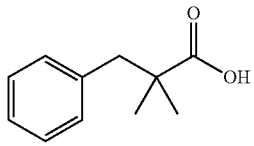

To a solution of diisopropylamine (48.91 g, 483 mmol) in THF (100 mL) under nitrogen at 0° C. was added a solution of 2.5M n-butyllithium in hexane (179 mL, 447.5 mmols.) followed by the dropwise addition of isobutyric acid (15.77 grams, 179 mmols). The reaction mixture was stirred at room temperature for 1.5 hours, then cooled to −15° C. Benzyl chloride (22.66 g, 179 mmol) was added dropwise while maintaining the temperature below −5° C., and the resulting mixture was stirred at room temperature overnight. The reaction mixture was partitioned between $Et_2O$ and water. The aqueous layer was acidified by the addition of concentrated HCl (36%, 50 mL), and extracted with $Et_2O$ (4×150 mL), The organic layer was dried over $MgSO_4$ and concentrated to afford the title compound (21.36 g) as a colorless liquid. LC-MS (ES) m/z=177 [M−H]⁻.

Intermediate 75

2-Methyl-1-phenyl-2-propanamine

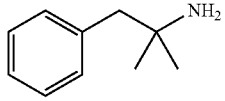

DPPA (16.87 g, 61.31 mmol) was added with external cooling to a stirred solution of 2,2-dimethyl-3-phenylpropanoic acid (10.21 g, 57.30 mmol) and triethylamine (6.20 g, 61.3 mmol) in dry toluene (100 mL). A slightly exothermic reaction commenced and was completed after about 1 hour. The reaction mixture was stirred for an additional 1 hour at room temperature, followed by refluxing for 3 hours. The solution was cooled and washed with water (3×100 mL), and the toluene phase was separated, dried over $Na_2SO_4$, and evaporated in vacuum. A mixture of 15% hydrochloric acid (20 mL) and acetic acid (20 mL) was added, and the resulting mixture was stirred at room temperature overnight. The mixture was partitioned between EtOAc and water. The aqueous layer was extracted with EtOAc (4×50 mL), and the aqueous was concentrated in vacuum to afford the HCl salt of the title compound (5.21 g) as a white solid. LC-MS (ES) m/z=150 [M+H]⁺.

Intermediate 76

6-Chloro-$N^4$-(1,1-dimethyl-2-phenylethyl)-2,4-pyrimidinediamine

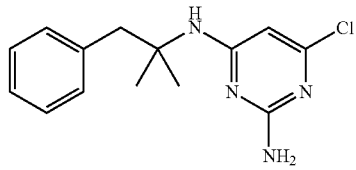 [SMILES: CC(C)(Cc1ccccc1)Nc1cc(Cl)nc(N)n1]

A mixture of 2-methyl-1-phenyl-2-propanamine hydrochloride (742 mg, 4 mmol), 4,6-dichloro-2-pyrimidinamine (438 mg, 2.67 mmol) and Hunig's base (1.55 g, 12 mmol) in $CH_3CN$ (8 mL) was stirred and heated for 6 hours at 160° C. in a Biotage Initiator microwave synthesizer. The mixture was cooled to room temperature and concentrated to dryness. The resulting solids were partitioned between EtOAc and water, and the organic layer was dried over $Na_2SO_4$, filtered and concentrated to dryness. Purification by reverse phase chromatography using $CH_3CN$ in water from 45% to 65% (0.08% ammonium hydrogen carbonate) in 18 min, afforded the title compound (373 mg) as a white solid. LC-MS (ES) m/z=277.0 [M+H]⁺.

Intermediate 77

4-{2-Amino-6-[(1,1-dimethyl-2-phenylethyl)amino]-4-pyrimidinyl}-2-fluorobenzonitrile

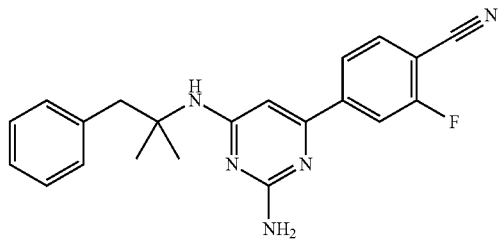 [SMILES: CC(C)(Cc1ccccc1)Nc1cc(-c2ccc(C#N)c(F)c2)nc(N)n1]

A mixture of 6-chloro-$N^4$-(1,1-dimethyl-2-phenylethyl)-2,4-pyrimidinediamine (338 mg, 1.22 mmol), 2-fluoro-4-(4,4,5,5-tetramethyl-1,3,2-dioxaborolan-2-yl)benzonitrile (452 mg, 1.83 mmol), $Pd(PPh_3)_4$ (139 mg, 0.12 mmol) and $Na_2CO_3$ (323 mg, 3.05 mmol) in 1,4-dioxane (6 mL) and water (2 mL) was stirred and heated at 140° C. for 30 min in a Biotage Initiator microwave synthesizer. The reaction mixture was cooled to room temperature and concentrated to dryness, and the resulting residue was partitioned between EtOAc and water. The aqueous layer was extracted by EtOAc (3×50 mL), and the combined organic layers were dried over $Na_2SO_4$, filtered and concentrated to dryness. Purification by RPHPLC with $CH_3CN$ in water (0.01% ammonium hydrogen carbonate) (gradient: from 70% to 80% in 7.5 min, flow rate: 30 mL/min), afforded the title compound (210 mg) as a white solid. LC-MS (ES) m/z=362 [M+H]⁺.

Example 62

6-(3-Amino-1H-indazol-6-yl)-N[4]-(1,1-dimethyl-2-phenylethyl)-2,4-pyrimidinediamine

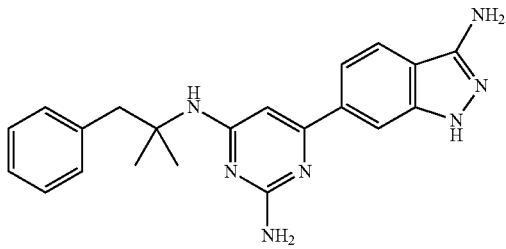 [SMILES: CC(C)(Cc1ccccc1)Nc1cc(-c2ccc3c(N)n[nH]c3c2)nc(N)n1]

A mixture of 4-{2-amino-6-[(1,1-dimethyl-2-phenylethyl)amino]-4-pyrimidinyl}-2-fluorobenzonitrile (210 mg, 0.58 mmol) and hydrazine hydrate (99%, 2 mL) in ethanol (3 mL) was stirred and heated at 120° C. for 1 h in a Biotage Initiator microwave synthesizer. The mixture was cooled to room temperature and concentrated in vacuo. Water (100 mL) was added, and the resulting mixture was filtered. The solids were dried under vacuum to afford the title compound (90 mg) as a yellow solid. LC-MS (ES) m/z=374 [M+H]$^+$. $^1$H NMR (400 MHz, DMSO-$d_6$): δ 1.34 (s, 6H), 3.26 (s, 2H), 5.37 (s, 2H), 6.05 (s, 2H), 6.34 (s, 1H), 6.40 (s, 1H), 7.10-7.25 (m, 5H), 7.39 (d, 1H), 7.70 (d, 1H), 7.84 (s, 1H).

Intermediate 78

1,1-Dimethylethyl 3-[(phenylamino)carbonyl]-1-pyrrolidinecarboxylate

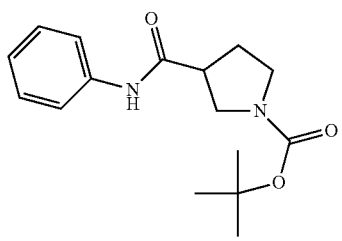 [SMILES: CC(C)(C)OC(=O)N1CCC(C(=O)Nc2ccccc2)C1]

A mixture of 1-{[(1,1-dimethylethyl)oxy]carbonyl}-3-pyrrolidinecarboxylic acid (1.0 g, 4.7 mmol), CDI (1.3 g, 7.0 mmol) and HOBT (0.5 g) in CH$_2$Cl$_2$ (20 mL) and Hunig's base (2.0 mL) was cooled to 0° C. and stirred for 15 minutes. Then aniline (520 mg, 5.6 mmol) was added and the reaction mixture was stirred at room temperature for 6 hours. The mixture was concentrated and purified by SiO$_2$ chromatography (eluent: 1:1 EtOAc:petroleum ether) to afford the title compound (1.3 g) as an oil. $^1$H NMR (400 MHz, CDCl$_3$): δ 1.40 (s, 9H), 2.10 (m, 2H), 3.0 (m, 1H), 3.7-4 (m, 4H), 4.2 (m, 1H), 7.21 (m, 1H), 7.40 (m, 2H), 7.51 (m, 1H).

Intermediate 79

N-Phenyl-3-pyrrolidinecarboxamide

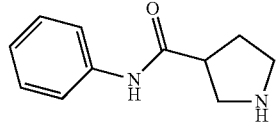 [SMILES: O=C(Nc1ccccc1)C1CCNC1]

A mixture of 1,1-dimethylethyl 3-[(phenylamino)carbonyl]-1-pyrrolidinecarboxylate (1.3 g, 4.5 mmol) in 3M HCl/EtOAc (30 mL) was stirred at room temperature for 2 hours. The mixture was concentrated and washed with Et$_2$O to afford the HCl salt of the title compound (900 mg) as a white solid.

Example 63

1-[2-Amino-6-(3-amino-1H-indazol-6-yl)-4-pyrimidinyl]-N-phenyl-3-pyrrolidinecarboxamide

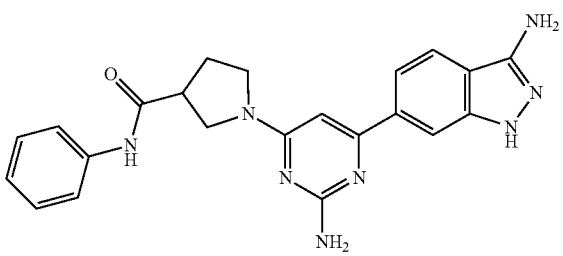 [SMILES: Nc1nc(-c2ccc3c(N)n[nH]c3c2)cc(N2CCC(C(=O)Nc3ccccc3)C2)n1]

A mixture of N-phenyl-3-pyrrolidinecarboxamide hydrochloride (500 mg, 2.21 mmol), 6-[2-amino-6-(methylsulfonyl)-4-pyrimidinyl]-1H-indazol-3-amine (500 mg, 1.6 mmol) in NMP (3 mL) and Hunig's base (1.5 mL) was heated at 160° C. for 1 hour under microwave conditions. The reaction mixture was concentrated and purified by SiO$_2$ chromatography (eluent: 4.5:4.5:1 EtOAc:THF:NH$_4$OH) to afford the title compound (50 mg) as a solid. $^1$H NMR (400 MHz, DMSO-$d_6$): δ 2.05 (m, 2H), 3.30 (m, 1H), 3.4-3.7 (m, 4H), 5.36 (s, 2H), 6.03 (s, 2H), 6.31 (s, 1H), 7.03 (m, 1H), 7.31 (m, 2H), 7.57-7.74 (m, 4H), 7.94 (s, 1H), 10.10 (s, 1H), 11.49 (s, 1H).

Intermediate 80

1,1-Dimethylethyl[(1R)-1-methyl-2-phenylethyl]carbamate

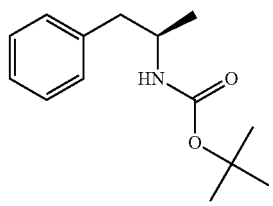 [SMILES: C[C@H](Cc1ccccc1)NC(=O)OC(C)(C)C]

To a stirred solution of (2R)-1-phenyl-2-propanamine D-(−)-tartaric acid (1.8 g, 6.31 mmol) in CH$_2$Cl$_2$ (150 mL) were added triethylamine (1.4 g, 1.9 mL, 13.9 mmol) and

Intermediate 81

(2R)—N-methyl-1-phenyl-2-propanamine

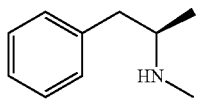

To a stirred suspension LiAlH₄ (0.77 g, 20.4 mmol) in THF (120 mL) was added a solution of 1,1-dimethylethyl[(1R)-1-methyl-2-phenylethyl]carbamate (2.4 g, 10.2 mmol) in THF (30.0 ml) dropwise at 0° C., and then the reaction mixture was heated at reflux for 2 hours. The mixture was cooled to 0° C., and quenched by addition of ice (1.0 g), then 15% aqueous sodium hydroxide (1.0 mL) followed by water (0.5 mL). The lithium salts were collected by filtration and washed with Et₂O (200 mL). The filtrate was dried (Na₂SO₄), filtered and concentrated. The resulting residue was distilled at reduced pressure to afford the title compound (1.6 g) as a light yellow oil. LC-MS (ES) m/z=150 [M+H]⁺.

Intermediate 82

6-Chloro-N⁴-methyl-N⁴-[(1R)-1-methyl-2-phenylethyl]-2,4-pyrimidinediamine

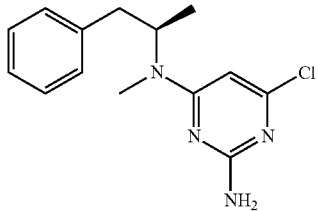 [SMILES: C[C@H](Cc1ccccc1)N(C)c1cc(Cl)nc(N)n1]

To a suspension of 4,6-dichloro-2-pyrimidinamine (1.0 g, 6.10 mmol) and K₂CO₃ (1.69 g, 12.2 mmol) in CH₃CN (6.0 mL) was added (2R)—N-methyl-1-phenyl-2-propanamine (1.09 g, 7.32 mmol), and the reaction mixture was heated at 140° C. under microwave conditions with stirring for 2 hours. The mixture was filtered and washed by EtOAc (50 mL). The solution was concentrated, and the resulting residue was purified by reversed phase chromatography using CH₃CN in water from 45% to 55% (0.5% ammonium hydrogen carbonate in water) to afford the title compound (910 mg) as a white solid. LC-MS (ES) m/z=277 [M+H]⁺.

Intermediate 83

4-(2-Amino-6-{methyl[(1R)-1-methyl-2-phenylethyl]amino}-4-pyrimidinyl)-2-fluorobenzonitrile

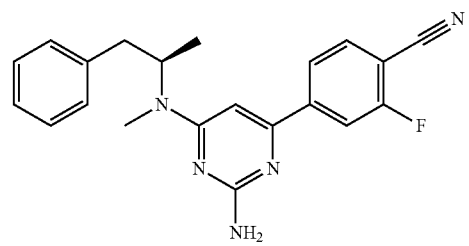 [SMILES: C[C@H](Cc1ccccc1)N(C)c1cc(-c2ccc(C#N)c(F)c2)nc(N)n1]

To a mixture of 6-chloro-N⁴-methyl-N⁴-[(1R)-1-methyl-2-phenylethyl]-2,4-pyrimidinediamine (0.4 g, 1.45 mmol), 2-fluoro-4-(4,4,5,5-tetramethyl-1,3,2-dioxaborolan-2-yl)benzonitrile (0.46 g, 1.88 mmol) and Na₂CO₃ (0.38 g, 3.63 mmol) in 1,4-dioxane (6 mL) and water (3 mL) was added Pd(PPh₃)₄ (16 mg, 0.015 mmol), the reaction mixture was heated at 140° C. under microwave conditions with stirring for 40 minutes. The mixture was filtered and concentrated, and the resulting residue was purified by reverse phase chromatography using CH₃CN in water from 45% to 55% (0.5% ammonium hydrogen carbonate in water) to afford the title compound (0.42 g) as a yellow solid. LC-MS (ES) m/z=362 [M+H]⁺.

Example 64

6-(3-Amino-1H-indazol-6-yl)-N⁴-methyl-N⁴-[(1R)-1-methyl-2-phenylethyl]-2,4-pyrimidinediamine

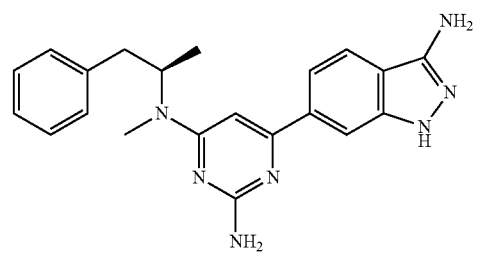 [SMILES: C[C@H](Cc1ccccc1)N(C)c1cc(-c2ccc3c(N)n[nH]c3c2)nc(N)n1]

To a suspension of 4-(2-amino-6-{methyl[(1R)-1-methyl-2-phenylethyl]amino}-4-pyrimidinyl)-2-fluorobenzonitrile (200 mg, 0.55 mmol) in ethanol (2 mL) was added hydrazine hydrate (2.0 mL, 99%), and the reaction mixture was heated at 120° C. under microwave conditions with stirring for 1 hour. The mixture was cooled to room temperature and concentrated. The resulting residue was washed with Et₂O (30 mL) and dried in vacuo to afford the title compound (156 mg) as a yellow solid. LC-MS (ES) m/z=374 [M+H]⁺. ¹H NMR (400 MHz, DMSO-d₆): δ 1.12 (d, J=6.0 Hz, 3H), 2.77-2.89 (m, 6H), 5.36 (s, 2H), 5.99 (s, 2H), 6.35 (s, 1H), 7.12-7.16 (m, 1H), 7.23-7.27 (m, 4H), 7.49-7.52 (m, 1H), 7.68-7.70 (m, 1H), 7.88 (s, 1H), 11.50 (s, 1H).

Intermediate 84

6-Chloro-$N^4$-(2,3-dihydro-1H-inden-1-yl)-2,4-pyrimidinediamine

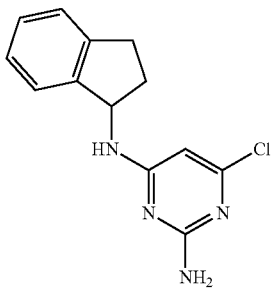 [SMILES: Nc1nc(Cl)cc(NC2CCc3ccccc32)n1]

A mixture of 4,6-dichloro-2-pyrimidinamine (500 mg, 3.09 mmol), 2,3-dihydro-1H-inden-1-amine (500 mg, 3.78 mmol) and triethylamine (2 mL) in NMP (3 mL) was heated to 160° C. for 2 hours in a BiotageInitiator® microwave synthesizer. The reaction mixture was evaporated and purified by $SiO_2$ chromatography eluting with 1:3 petroleum ether/THF to afford the title compound (700 mg) as a yellow solid. LC-MS (ES) m/z=261 $[M+H]^+$.

Intermediate 85

4-[2-Amino-6-(2,3-dihydro-1H-inden-1-ylamino)-4-pyrimidinyl]-2-fluorobenzonitrile

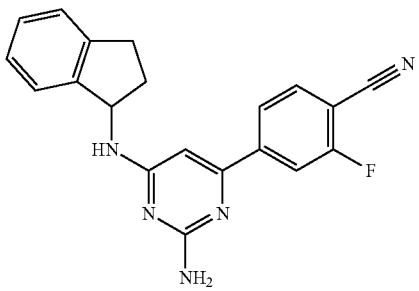 [SMILES: N#Cc1ccc(-c2cc(NC3CCc4ccccc43)nc(N)n2)cc1F]

A mixture of 6-chloro-$N^4$-(2,3-dihydro-1H-inden-1-yl)-2,4-pyrimidinediamine (700 mg, 2.69 mmol) and 2-fluoro-4-(4,4,5,5-tetramethyl-1,3,2-dioxaborolan-2-yl)benzonitrile (797 mg, 3.23 mmol) in 1,4-dioxane (150 mL) and a solution of $NaHCO_3$ (903 mg, 10.76 mmol) in water (50 mL) was protected with nitrogen. $Pd(Ph_3P)_4$ (31 mg, 0.0269 mmol) was added, and the reaction mixture was heated at 120° C. for 16 hours. The mixture was decanted to remove the solids, and the solution was concentrated to dryness. The crude material was purified by $SiO_2$ chromatography eluting with 1:1 THF: petroleum ether to afford the title compound (500 mg) as a yellow solid. LC-MS (ES) m/z=246 $[M+H]^+$.

Example 65

6-(3-Amino-1H-indazol-6-yl)-$N^4$-(2,3-dihydro-1H-inden-1-yl)-2,4-pyrimidinediamine

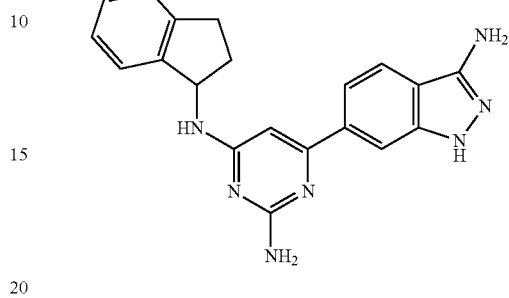

To 4-[2-amino-6-(2,3-dihydro-1H-inden-1-ylamino)-4-pyrimidinyl]-2-fluorobenzonitrile (500 mg, 1.45 mmol) in ethanol (2 mL) was added hydrazine monohydrate (3 mL, 74.0 mmol), and the reaction mixture was heated to 100° C. for 1 hour in a BiotageInitiator® microwave synthesizer. Upon cooling, the reaction mixture was concentrated in vacuum and purified by HPLC to afford the title compound (100 mg) as a brown solid. LC-MS (ES) m/z=358 $[M+H]^+$. $^1$H NMR (400 MHz, DMSO-$d_6$): δ 1.81 (s, 1H), 1.90-1.92 (m, 1H), 2.84-3.051 (m, 2H), 5.43 (s, 2H), 5.71 (s, 1H), 6.12 (s, 2H), 6.40 (s, 1H), 7.23-7.48 (m, 6H), 7.75 (d, J=8.4 Hz, 1H), 7.90 (s, 1H), 11.58 (s, 1H).

Intermediate 86

4-[2-Amino-6-(4-cyano-3-fluorophenyl)-4-pyrimidinyl]benzamide

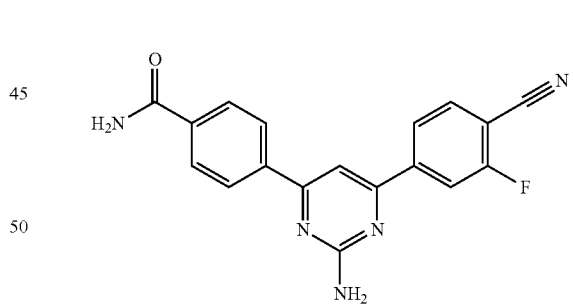

A mixture of 4-(2-amino-6-chloro-4-pyrimidinyl)-2-fluorobenzonitrile (400 mg, 1.61 mmol), 4-(4,4,5,5-tetramethyl-1,3,2-dioxaborolan-2-yl)benzamide (397.0 mg, 2.41 mmol), $Pd(PPh_3)_4$ (185 mg, 0.16 mmol), and $Na_2CO_3$ (427 mg, 4.02 mmol) in 1,4-dioxane (60 mL) and water (20.0 mL) was stirred and heated at 110° C. for 1 hour under nitrogen. The mixture was cooled to room temperature and concentrated, and the resulting residue was portioned between EtOAc (100 mL) and water (100 mL). The aqueous phase was extracted with EtOAc (2×50 mL), and the combined organic layers were dried $Na_2CO_3$, filtered and concentrated to dryness. Purification by $SiO_2$ chromatography using 4:1 petroleum ether/THF as eluent afforded the title compound (190 mg) as a white solid. LC-MS (ES) m/z=334 [M+H]+.

Example 66

4-[2-Amino-6-(3-amino-1H-indazol-6-yl)-4-pyrimidinyl]benzamide

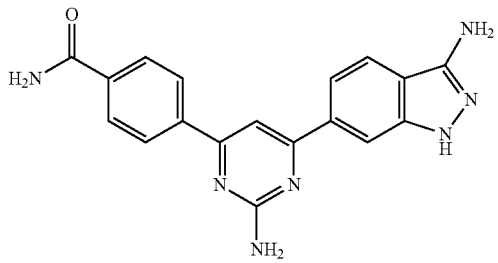 [SMILES: NC(=O)c1ccc(-c2cc(-c3ccc4c(N)n[nH]c4c3)nc(N)n2)cc1]

To a suspension of 4-[2-amino-6-(4-cyano-3-fluorophenyl)-4-pyrimidinyl]benzamide (200 mg, 0.6 mmol) in ethanol (2.0 mL) was added hydrazine hydrate (2.0 mL, 99%), and the reaction mixture was heated at 120° C. under microwave conditions with stirring for 40 minutes. The mixture was cooled to room temperature, filtered, washed by EtOAc (100 mL), and concentrated. The resulting residue was purified by $SiO_2$ chromatography using a 1:3 petroleum ether/THF as eluent to afford the title compound (25 mg) as a yellow solid. LC-MS (ES) m/z=346.0 [M+H]+. $^1$H NMR (400 MHz, DMSO-$d_6$): δ 5.45 (s, 2H), 6.81 (s, 2H), 7.48 (s, 1H), 7.79-7.82 (m, 3H), 8.01-8.03 (m, 2H), 8.11 (s, 1H), 8.14 (s, 1H), 8.30-8.31 (m, 2H), 11.66 (s, 1H).

Intermediate 87

[(2S,5R)-5-Methyl-4-(phenylmethyl)-2-morpholinyl]methanol

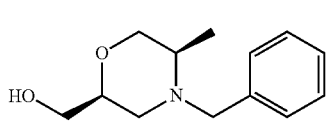 [SMILES: C[C@@H]1CO[C@H](CO)CN1Cc1ccccc1]

Prepared according to similar compounds reported by Breuning et al, *Eur. J. Org. Chem.* 2007, 2100-2106

To a stirred solution of (2R)-2-[(phenylmethyl)amino]-1-propanol (1.65 g, 9.99 mmol) in toluene (50 mL) was added (R)-(–)-epichlorohydrin (1.02 mL, 12.98 mmol) followed by lithium perchlorate (1.062 g, 9.99 mmol) under nitrogen. After stirring 2 days, TLC (5% methanol-dichloromethane) showed there was only a trace of starting material and a major product. A solution of sodium methoxide (25 wt % in $CH_3OH$) (5.71 mL, 24.96 mmol) was then added and the mixture was stirred for 3 days. Saturated aq. $NH_4Cl$ (75 ml) was added, and the product was extracted with EtOAc (3×75 mL). The combined organics were washed with brine, dried ($MgSO_4$) filtered and evaporated to give the crude product, which was purified by chromatography (Analogix RS-120 silica cartridge) eluting with 20-50% EtOAc-hexanes to afford the title compound (1.11 g) as a colorless oil. LC-MS (ES) m/z=222 [M+H]+. $[α]_D$=–5.2 (c=1.55, $CH_3OH$, 23.5° C.)

Intermediate 88

[(2S,5R)-5-Methyl-2-morpholinyl]methanol

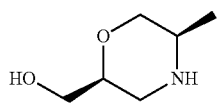

To a stirred solution of [(2S,5R)-5-methyl-4-(phenylmethyl)-2-morpholinyl]methanol (1.05 g, 4.74 mmol) in ethanol (15 mL) was added hydrochloric acid (concentrated, 12M) (0.435 mL, 5.22 mmol). The mixture was purged with nitrogen to degas, then 10% palladium on carbon (Degussa Type E101 NE/W, 50% wet) (150 mg, 0.070 mmol) was added and the mixture was purged with hydrogen and then stirred under the balloon. After stirring 4 hrs, TLC (50% EtOAc-hexanes) showed no starting material, and baseline product. The mixture was degassed with nitrogen, filtered through Celite, and evaporated to dryness to afford the title compound (880 mg) as the hydrochloride salt. $^1$H NMR (400 MHz, $D_2O$): δ 3.72-3.92 (m, 3H), 3.48-3.69 (m, 3H), 3.13-3.24 (m, 1H), 3.04-3.13 (m, 1H), 1.34 (d, J=7.1 Hz, 3H).

Intermediate 89

[(2S,5R)-4-(2-Amino-6-chloro-4-pyrimidinyl)-5-methyl-2-morpholinyl]methanol

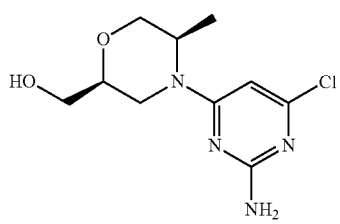 [SMILES: C[C@@H]1CO[C@H](CO)CN1c1cc(Cl)nc(N)n1]

In a 2-5 mL microwave vessel Hunig's base (0.59 mL, 3.35 mmol) was added to [(2S,5R)-5-methyl-2-morpholinyl]methanol hydrochloride (208 mg, 1.12 mmol) in $CH_3CN$ (3 mL), and then 2-amino-4,6-dichloropyrimidine (174 mg, 1.06 mmol) was added. The mixture was heated with stirring in a microwave reactor at 160° C. for 1 hour. HPLC indicated complete conversion. The mixture was filtered through a 0.45 um filter disc, evaporated, and the product was purified further by chomatography (Analogix SF25-40 g silica column) eluting with 2-5% $CH_3OH$—$CHCl_3$ to afford the title compound (258 mg) as a white foam. LC-MS (ES) m/z=260 [M+H]+.

Intermediate 90

4-{2-Amino-6-[(2S,5R)-2-(hydroxymethyl)-5-methyl-4-morpholinyl]-4-pyrimidinyl}-2-fluorobenzonitrile

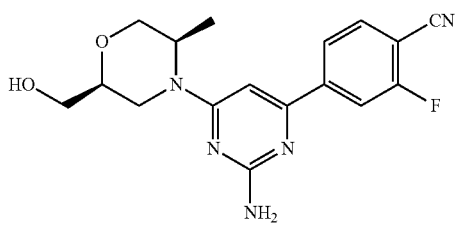 [SMILES: C[C@@H]1CO[C@H](CO)CN1c1cc(-c2ccc(C#N)c(F)c2)nc(N)n1]

In a 10-20 mL sealable vessel was added (4-cyano-3-fluorophenyl)boronic acid (163 mg, 0.986 mmol), [(2S,5R)-4-(2-amino-6-chloro-4-pyrimidinyl)-5-methyl-2-morpholinyl]methanol (232 mg, 0.897 mmol) and 1,4-dioxane (5 mL) and saturated aqueous NaHCO$_3$ (2.5 mL). The mixture was purged with nitrogen to degas, then Pd(PPh$_3$)$_4$ (104 mg, 0.090 mmol) was added, and the vessel was sealed and heated at 100° C. overnight. HPLC and LCMS indicated product formed with some starting material pyrimidine remaining. An additional 50 mg of boronic acid was added and the reaction was microwaved at 120° C. for 30 minutes. There was still 10% remaining starting material but the reaction was worked up by diluting with toluene and water. The aqueous layer was extracted with toluene (2×5 mL) and the combined organics were washed with water, brine, dried (MgSO$_4$) filtered, evaporated. The product was purified by silica gel chromatography (Analogix SF25-40 g) eluting with 2-10% CH$_3$OH—CHCl$_3$. The title compound (193 mg) was obtained as an off-white foam. LC-MS (ES) m/z=344 [M+H]$^+$.

Intermediate 91

(2S,5R)-4-[2-Amino-6-(4-cyano-3-fluorophenyl)-4-pyrimidinyl]-5-methyl-2-mornholinecarboxylic acid

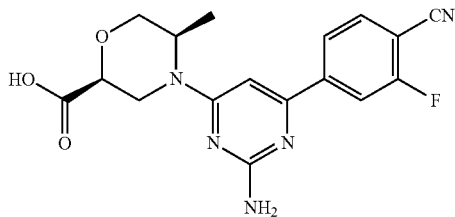 [SMILES: C[C@@H]1CO[C@H](C(=O)O)CN1c1cc(-c2ccc(C#N)c(F)c2)nc(N)n1]

A stock solution of oxidant was prepared according to Zhao et. al. (*Tetrahedron Letters* 1998, 39, 5323) by dissolving H$_5$IO$_6$ (11.4 g, 50 mmol) and CrO$_3$ (23 mg, 1.15 mol %) in wet CH$_3$CN (0.75% water) to a volume of 114 mL (takes about 2 hrs to dissolve). This stock solution is 0.439M in H$_5$IO$_6$ and 0.00202M in CrO$_3$.

In a 100 mL RB was placed 4-{2-amino-6-[(2S,5R)-2-(hydroxymethyl)-5-methyl-4-morpholinyl]-4-pyrimidinyl}-2-fluorobenzonitrile (188 mg, 0.548 mmol) and wet CH$_3$CN (0.75% water, 4.5 mL), the stirred solution was cooled in an ice bath, and 4.37 mL of the above stock solution was added very slowly dropwise (over 10 minutes). After 2 hours, there was a small amount of starting material observed by TLC (NaHCO$_3$ added to an aliquot, 5% CH$_3$OH—CHCl$_3$) so the reaction was placed in the refrigerator overnight. At this time there was no starting by TLC. The reaction was quenched by adding Na$_2$HPO$_4$ (0.5 g) in 5 mL of water. After stirring a few minutes the mixture was cloudy and the pH=5. The product was extracted with EtOAc (5×10 mL), and the combined organics were washed with 5% NaHSO$_3$, brine, dried (MgSO$_4$), filtered and evaporated to afford the crude title compound (102 mg) as an off-white. LC-MS (ES) m/z=358 [M+H]$^+$.

Intermediate 92

(2S,5R)-4-[2-Amino-6-(4-cyano-3-fluorophenyl)-4-pyrimidinyl]-5-methyl-N-phenyl-2-morpholinecarboxamide

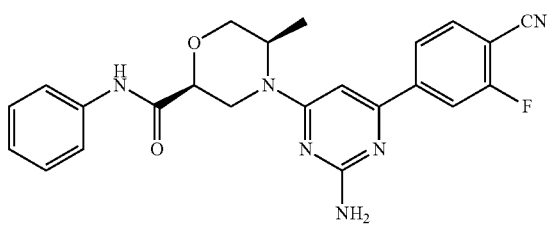 [SMILES: C[C@@H]1CO[C@H](C(=O)Nc2ccccc2)CN1c1cc(-c2ccc(C#N)c(F)c2)nc(N)n1]

A 5 mL vial was charged with (2S,5R)-4-[2-amino-6-(4-cyano-3-fluorophenyl)-4-pyrimidinyl]-5-methyl-2-morpholinecarboxylic acid (72 mg, 0.201 mmol), HOBT (29.9 mg, 0.222 mmol) and DMF (1 mL) under nitrogen. The mixture was stirred and cooled in an ice bath and then EDC (42.5 mg, 0.222 mmol) was added. After stirring 10 minutes, aniline (0.020 mL, 0.222 mmol) was added and the mixture was allowed to warm to room temperature and stir. At 2 and 4 hours, there was no change in progress. The mixture was diluted with EtOAc and washed with water, saturated NaHCO$_3$, brine, and dried (MgSO$_4$). After filtering, the filtrate was concentrated and the product was purified by silica gel chromatography (Analogix SF-4-g) eluting with 20-50% EtOAc—CHCl$_3$ to afford the title compound (59 mg) as a light orange oil. LC-MS (ES) m/z=433 [M+H]$^+$.

Example 67

(2S,5R)-4-[2-Amino-6-(3-amino-1H-indazol-6-yl)-4-pyrimidinyl]-5-methyl-N-phenyl-2-morpholinecarboxamide

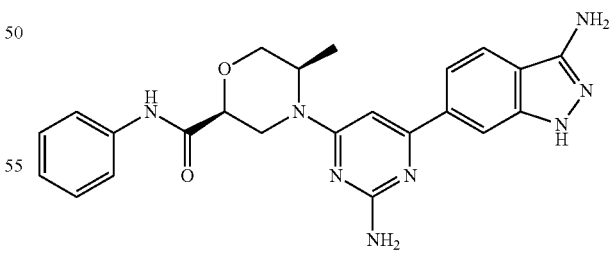

(2S,5R)-4-[2-amino-6-(4-cyano-3-fluorophenyl)-4-pyrimidinyl]-5-methyl-N-phenyl-2-morpholinecarboxamide (57 mg, 0.132 mmol) was dissolved in ethanol (3 mL) with stirring in a 5 mL microwave vessel. Hydrazine monohydrate (150 μL, 3.09 mmol) was added, and the mixture was capped and heated at 100° C. in an oil bath for 24 hours. The mixture was partitioned between EtOAc and water, and the aqueous layer was extracted with EtOAc. The combined organics were washed with brine, dried (MgSO$_4$) filtered and evaporated. Purification by silica gel chromatograpy (Analogix RS-4 g) eluting with 90:10:1 CHCl3:CH3OH:conc. aq. NH$_4$OH afforded the title compound (19 mg, 0.041 mmol, 30.8% yield) as a colorless film/foam. NMR showed a residual solvent peak with singlets at 1.9 and 3.36, so the material was azeotroped with CH$_3$CN and then triturated to give a white powder. $^1$H NMR (400 MHz, DMSO-d$_6$): δ 1.24 (d, J=6.3 Hz, 3H), 3.04 (bs, 1H), 3.82 (d, J=9.8 Hz, 1H), 3.93 (d, J=11.1 Hz, 1H), 4.07-4.23 (m, 1H), 4.53 (bs, 2H), 5.39 (bs, 2H), 6.22 (bs, 2H), 6.61 (s, 1H), 7.10 (t, J=7.1 Hz, 1H), 7.34 (t, J=7.7 Hz, 2H), 7.60 (d, J=8.3 Hz, 1H), 7.69-7.78 (m, 3H), 7.96 (s, 1H), 9.87 (bs, 1H), 11.52 (s, 1H).

Intermediate 93

1,1-Dimethylethyl[1-(2-amino-6-chloro-4-pyrimidinyl)-3-piperidinyl]carbamate

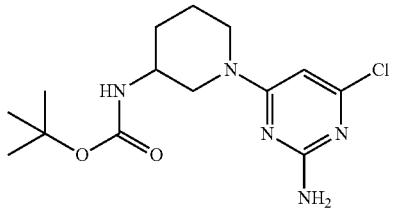 [SMILES: CC(C)(C)OC(=O)NC1CCCN(c2cc(Cl)nc(N)n2)C1]

2-Amino-4,6-dichloropyrimidine (3.33 g, 20.30 mmol) was added to a stirring mixture of 3-N-Boc-aminopiperidine (4.28 g, 21.4 mmol) and K$_2$CO$_3$ (2.95 g, 21.4 mmol) in ethanol (50 mL). The reaction was refluxed for 1 hour. HPLC indicated complete conversion. Water (50 mL) was slowly added to the hot mixture, which was then allowed to cool to room temperature with stirring. The precipitated product was collected by filtration and washed with 1:1 ethanol:water (50 mL) and dried to afford the title compound (5.98 g) as a white powder. LC-MS (ES) m/z=328 [M+H]$^+$.

Intermediate 94

1,1-Dimethylethyl{1-[2-amino-6-(4-cyano-3-fluorophenyl)-4-pyrimidinyl]-3-piperidinyl}carbamate

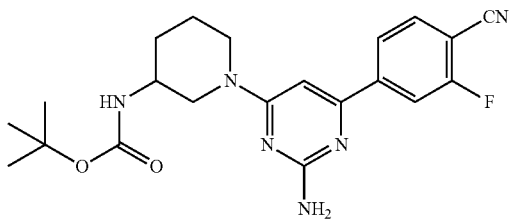 [SMILES: CC(C)(C)OC(=O)NC1CCCN(c2cc(-c3ccc(C#N)c(F)c3)nc(N)n2)C1]

Potassium carbonate (0.843 g, 6.10 mmol) and water (5 mL) were added to a stirring mixture of 1,1-dimethylethyl[1-(2-amino-6-chloro-4-pyrimidinyl)-3-piperidinyl]carbamate (1 g, 3.05 mmol) and (4-cyano-3-fluorophenyl)boronic acid (0.654 g, 3.97 mmol) in 1,4-dioxane (10 mL). After degassing, Pd(PPh$_3$)$_4$ (0.176 g, 0.153 mmol) was added, and the vessel was sealed and heated at 100° C. in an oil bath overnight. HPLC showed complete conversion. The cooled mixture was poured into water (50 mL) and extracted with EtOAc (3×25 mL). The combined organics were washed with brine, dried (MgSO$_4$) filtered and evaporated to give the crude residue, which was purified by silica gel chromatography (Analogix SF25-40 g) eluting with 15-50% EtOAc—CHCl$_3$ to afford the title compound (1.22 g) as a yellow foam. LC-MS (ES) m/z=413 [M+H]$^+$.

Example 68

1,1-Dimethylethyl{1-[2-amino-6-(3-amino-1H-indazol-6-yl)-4-pyrimidinyl]-3-piperidinyl}carbamate

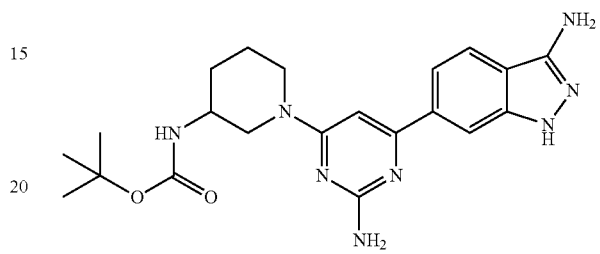

1,1-Dimethylethyl{1-[2-amino-6-(4-cyano-3-fluorophenyl)-4-pyrimidinyl]-3-piperidinyl}carbamate (1.2 g, 2.91 mmol), 1,4-dioxane (5 mL) and ethanol (5 mL) was added to a 10-20 mL microwave vessel, and hydrazine monohydrate (1.41 mL, 29.1 mmol) was added. The vessel was capped and heated in a microwave reactor for 45 minutes at 120° C. HPLC showed ~25% starting material remaining, so an additional 5 equivalents of hydrazine (0.71 mL) was added, and microwave heating was continued for 45 minutes. HPLC indicated complete conversion. The mixture was filtered through a 0.45 um nylon disc, washing with minimal ethanol. The filtrate was heated with stirring, and water was added dropwise until the hot solution remained slightly cloudy (~25 mL of water). After allowing to cool to room temperature with stirring, the solid was collected by filtration, washed with 2:1 water:ethanol, and air dried to afford the title compound (875 mg) as an off-white solid. LC-MS (ES) m/z=425 [M+H]$^+$. $^1$H NMR (400 MHz, DMSO-d$_6$): δ 1.38 (s, 9H), 1.43 (bs, 2H), 1.74 (bs, 1H), 1.86 (bs, 1H), 2.86 (bs, 1H), 3.02 (bs, 1H), 3.35 (s, 1H), 4.11 (d, J=12.6 Hz, 1H), 4.26 (bs, 1H), 5.38 (s, 2H), 6.08 (s, 2H), 6.57 (s, 1H), 6.93 (d, J=7.3 Hz, 1H), 7.55 (d, J=8.6 Hz, 1H), 7.70 (d, J=8.3 Hz, 1H), 7.93 (s, 1H), 11.51 (s, 1H).

Intermediate 95

6-[2-Amino-6-(3-amino-1-piperidinyl)-4-pyrimidinyl]-1H-indazol-3-amine

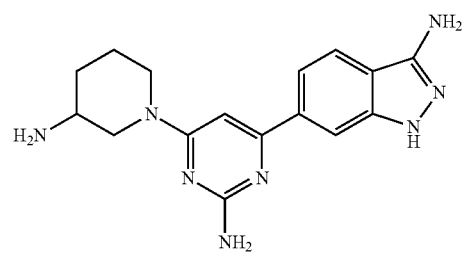 [SMILES: Nc1nc(-c2ccc3c(N)n[nH]c3c2)cc(N2CCCC(N)C2)n1]

1,1-Dimethylethyl{1-[2-amino-6-(3-amino-1H-indazol-6-yl)-4-pyrimidinyl]-3-piperidinyl}carbamate (865 mg, 2.04 mmol) was added portionwise to ice-cooled hydrochloric acid (concentrated aqueous) (8 mL, 96 mmol) with stirring. A solid yellow mass formed. The ice bath was removed and the reaction was allowed to warm to room temperature with stirring. HPLC indicated complete conversion. The mixture was diluted with ice-water (20 mL) and the solution was concentrated under reduced pressure. The residue was dissolve in ethanol (15 mL) and evaporated, followed by suspending in $CH_3CN$ (15 mL) and evaporating. The residue was then triturated with isopropanol (10 mL) and filtered, washed with isopropanol, followed by hexanes and dried under vacuum to afford an HCl salt of the title compound (761 mg) as a yellow powder. A 140 mg portion was suspended in $CH_3OH$ (2 mL) and water (1 mL) and was neutralized to pH 10 with 1 N NaOH. The solution was filtered and purified by Gilson automated reverse phase HPLC (Gemini Phenomenex C18 5u, 100×300 mm), eluting with 5-90% $CH_3CN$-water+0.1% $NH_4OH$). Pure fractions were combined, evaporated and dried to afford the title compound (72 mg) as a white solid. LC-MS (ES) m/z=325 [M+H]$^+$. $^1$H NMR (400 MHz, DMSO-$d_6$): δ 1.15-1.29 (m, 1H), 1.31-1.46 (m, 1H), 1.51 (bs, 2H), 1.62-1.75 (m, 1H), 1.87 (d, J=10.6 Hz, 1H), 2.53-2.68 (m, 2H), 2.83 (t, J=12.1 Hz, 1H), 4.30 (m, 2H), 5.38 (s, 2H), 6.03 (bs, 2H), 6.58 (s, 1H), 7.56 (d, J=8.6 Hz, 1H), 7.70 (d, J=8.3 Hz, 1H), 7.94 (s, 1H), 11.52 (s, 1H).

Example 69

N-{1-[2-Amino-6-(3-amino-1H-indazol-6-yl)-4-pyrimidinyl]-3-piperidinyl}benzamide

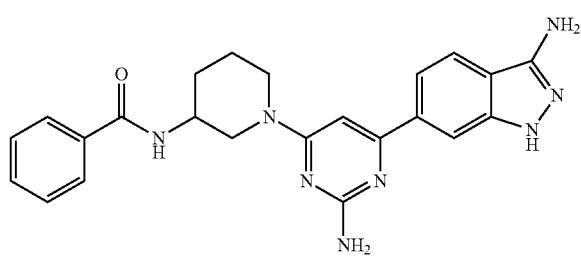 [SMILES: Nc1nc(-c2ccc3c(N)n[nH]c3c2)cc(N2CCCC(NC(=O)c3ccccc3)C2)n1]

Sodium bicarbonate (145 mg, 1.73 mmol) was added to a solution of 6-[2-amino-6-(3-amino-1-piperidinyl)-4-pyrimidinyl]-1H-indazol-3-amine trihydrochloride (150 mg, 0.346 mmol) in water (1.5 mL) with stirring. Tetrahydrofuran (THF) (1.5 mL) was added, the mixture was cooled in an ice bath, and benzoyl chloride (0.044 mL, 0.380 mmol) was added dropwise with stirring. The mixture was then warmed to room temperature and stirred for 2 hours. LCMS showed starting material remaining, product, and bis-benzoylation. An additional 40 uL of benzoyl chloride and 145 mg of $NaHCO_3$ were added, and the mixture was stirred for 1 hour. HPLC showed complete conversion to multi-benzoylated product. The reaction was diluted with EtOAc, washed with water, dried ($Na_2SO_4$), filtered and evaporated. The crude was suspended in $CH_3OH$ (8 mL), 1 mL of concentrated aqueous HCL was added, and the mixture was stirred 3 days at 65° C. HPLC showed conversion to the desired product. The mixture was concentrated to ~2 mL, then diluted with $CH_3CN$ (~8 mL) and heated. Additional $CH_3CN$ was added to the hot solution until turbid. The mixture was allowed to cool slowly to room temperature with strring over 2 hours. The precipitate was collected by filtration, washed with $CH_3CN$, then $Et_2O$ and finally hexanes. Drying afforded the title compound (156 mg) dihydrochloride as an off-white solid. A 100 mg portion was purified further by Gilson automated reverse phase HPLC (Gemini Phenomenex C18 5u, 100×300 mm), eluting with 5-90% $CH_3CN$-water+0.1% $NH_4OH$) to give the title compound (55 mg) as a white solid. LC-MS (ES) m/z=429 [M+H]$^+$. $^1$H NMR (400 MHz, DMSO-$d_6$): δ 1.43-1.60 (m, 1H), 1.60-1.74 (m, 1H), 1.76-1.86 (m, 1H), 1.92-2.03 (m, 1H), 2.87-3.00 (m, 2H), 3.83-3.95 (m, 1H), 4.27-4.39 (m, 1H), 4.49 (bs, 1H), 5.38 (s, 2H), 6.12 (s, 2H), 6.64 (s, 1H), 7.46 (t, J=7.3 Hz, 2H), 7.50-7.54 (m, 1H), 7.54-7.61 (m, 1H), 7.71 (d, J=8.6 Hz, 1H), 7.87 (d, J=7.1 Hz, 2H), 7.94 (s, 1H), 8.39 (d, J=7.6 Hz, 1H), 11.52 (s, 1H).

Intermediate 96

4-Chloro-6-[2-(trifluoromethyl)-1-pyrrolidinyl]-2-pyrimidinamine

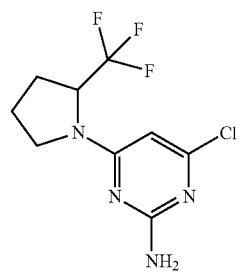 [SMILES: Nc1nc(Cl)cc(N2CCCC2C(F)(F)F)n1]

2-Amino-4,6-dichloropyrimidine (143 mg, 0.870 mmol) was added to a stirring mixture of 2-trifluoromethylpyrrolidine (121 mg, 0.870 mmol) and Hunig's base (0.23 mL, 1.31 mmol) in $CH_3CN$ (2.5 mL) in a microwave vessel. The reaction was capped and heated in a microwave reactor for 1 hour. Silica gel chromatography (Analogix RS-12 g cartridge) eluting with 5-10% EtOAc—$CHCl_3$ gave the title compound (85 mg) as a white solid. $^1$H NMR (400 MHz, $CDCl_3$, * denotes minor rotamer): δ 1.96-2.15 (m, 2H), 2.15-2.32 (m, 2H), 3.37-3.52 (m, 1H), 3.54-3.65 (m, 1H), 4.82, 5.60* (bs, 1H), 5.00 (bs, 2H), 5.94, 6.72* (s, 1H).

Intermediate 97

4-{2-Amino-6-[2-(trifluoromethyl)-1-pyrrolidinyl]-4-pyrimidinyl}-2-fluorobenzonitrile

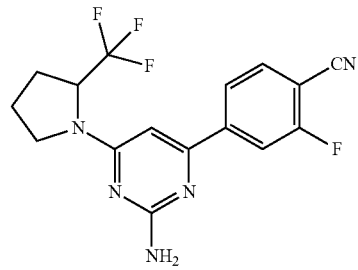 [SMILES: N#Cc1ccc(-c2cc(N3CCCC3C(F)(F)F)nc(N)n2)cc1F]

Potassium carbonate (129 mg, 0.934 mmol) and water (1.5 mL) were added to a stirring mixture of 4-chloro-6-[2-(trifluoromethyl)-1-pyrrolidinyl]-2-pyrimidinamine (83 mg, 0.311 mmol) and (4-cyano-3-fluorophenyl)boronic acid (61.6 mg, 0.374 mmol) in 1,4-dioxane (3 mL). After degassing, Pd(PPh$_3$)$_4$ (29 mg, 0.025 mmol) was added, and the vessel was seal and heated at 100° C. in an oil bath overnight. LCMS showed complete conversion. The mixture was diluted with EtOAc, and washed with water. The aqueous layer was back-extracted with EtOAc. The combined organics were washed with brine, dried (Na$_2$SO$_4$) filtered and evaporated. Purification by silica gel chromatography (Analogix RS-4 g) eluting with 5-20% EtOAc—CHCl$_3$ afforded the title compound (65 mg) as a white foam. The sample contained some PH$_3$P/Ph$_3$PO by NMR, but was suitable for subsequent reactions. LC-MS (ES) m/z=352 [M+H]$^+$.

Example 70

6-{2-Amino-6-[2-(trifluoromethyl)-1-pyrrolidinyl]-4-pyrimidinyl}-1H-indazol-3-amine

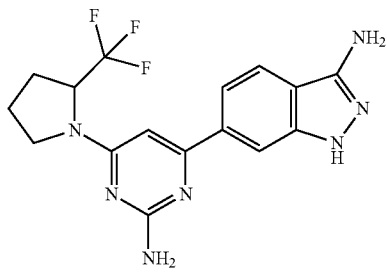 [SMILES: Nc1nc(-c2ccc3c(N)n[nH]c3c2)cc(N2CCCC2C(F)(F)F)n1]

4-{2-Amino-6-[2-(trifluoromethyl)-1-pyrrolidinyl]-4-pyrimidinyl}-2-fluorobenzonitrile (60 mg, 0.17 mmol) was disolved in ethanol (1.5 mL) with stirring in a 5 mL microwave vessel. Hydrazine monohydrate (0.207 mL, 4.27 mmol) was added, and the mixture was capped and heated at 100° C. in an oil bath overnight. HPLC showed complete conversion. The hot mixture was filtered through a 0.2 um filter disc, rinsing with ethanol (1 mL). Water (~3 mL) was added to the filtrate with stirring, and the mixture was heated to evaporate most of the ethanol to a volume of ~4 mL. The mixture was allowed to cool with stirring to room temperature, at which time some product had precipitated as a gum. Stirring was continued for approximately one hour and the precipitate became a free flowing white solid, which was filtered, washed with water and dried to afford the title compound (42 mg) as an off-white solid. LC-MS (ES) m/z=364 [M+H]$^+$. $^1$H NMR (400 MHz, DMSO-d$_6$): δ 1.98-2.08 (m, 2H), 2.08-2.23 (m, 2H), 3.49-3.60 (m, 1H), 3.60-3.72 (m, 1H), 5.06-5.17 (m, 1H), 5.39 (s, 2H), 6.22 (s, 2H), 6.52 (s, 1H), 7.57 (d, J=8.6 Hz, 1H), 7.73 (d, J=8.6 Hz, 1H), 7.94 (s, 1H), 11.54 (s, 1H).

Intermediate 98

(5R)-5-Ethyl-3-morpholinone

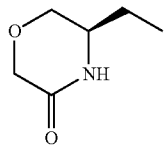

NaH (1.51 g, 37.9 mmol) in dry toluene (10 mL) was cooled to 0° C. under nitrogen, and (2R)-2-amino-1-butanol (1.5 g, 16.8 mmol) in toluene (5 mL) was added dropwise. The mixture was stirred for 20 minutes warming up to room temperature, and chloroacetyl chloride (1.5 mL, 18.9 mmol) in toluene (5 mL) was added dropwise. An exotherm was observed so the mixture was cooled in an ice bath during the addition. After the addition was completed, the reaction mixture was heated to 110° C. overnight. The mixture was cooled to room temperature and 5 g of ammonium chloride were added portionwise. The mixture was stirred for 20 minutes and filtered. The filter cake was washed with toluene and discarded. The filtrate was concentrated to give an orange oil that was dissolved in CH$_2$Cl$_2$ and purified by SiO$_2$ chromatography (gradient: 100% CH$_2$Cl$_2$ to 90:10:1 CH$_2$Cl$_2$/CH$_3$OH/NH$_4$OH) to afford the title compound (1.2 g) as a yellow solid. $^1$H NMR (400 MHz, CDCl$_3$): δ 0.96 (t, J=7.6 Hz, 3H), 1.52-1.63 (m, 2H), 3.40-3.51 (m, 2H), 3.85-3.94 (m, 1H), 4.07-4.20 (m, 2H), 7.55 (bs, 1H).

Intermediate 99

(3R)-3-Ethylmorpholine

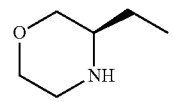

A solution of 1M LiAlH$_4$ in THF (7.7 mL, 7.7 mmol) was cooled in an ice-bath under nitrogen. A solution of (5R)-5-ethyl-3-morpholinone (500 mg, 3.87 mmol) in THF (10 mL) was added dropwise and the solution was heated to 70° C. for 16 hours. After aproximately 2 hours, a thick white precipitate had formed. The reaction mixture was cooled down to room temperature and carefully quenched with water (1 mL), 2M NaOH (1 mL) and water (4 mL). The resulting slurry was stirred at room temperature for 1 hour and then filtered through celite. The filter cake was washed with EtOAc and discarded. The filtrate was washed with brine, dried (MgSO$_4$), and filtered. HCl in ether (3.87 mL, 3.87 mmol) was added producing a cloudy solution and the solvent was evaporated to afford the HCL salt of the title compound (251 mg) as an orange solid. $^1$H NMR (400 MHz, DMSO-d$_6$): δ 0.88-0.97 (m, 3H), 1.46-1.72 (m, 2H), 2.91-3.18 (m, 3H), 3.46 (dd, J=12.3, 10.2 Hz, 1H), 3.71 (td, J=11.8, 2.7 Hz, 1H), 3.82-3.97 (m, 2H), 9.68 (bs, 2H).

Intermediate 100

4-Chloro-6-[(3R)-3-ethyl-4-morpholinyl]-2-pyrimidinamine

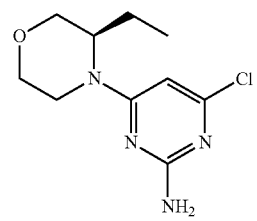

To 4,6-dichloro-2-pyrimidinamine (240 mg, 1.46 mmol) in CH$_3$CN (8 mL) were added (3R)-3-ethylmorpholine (244 mg, 1.61 mmol) and Hunig's base (1.02 mL, 5.85 mmol), and the reaction mixture was heated in a microwave at 150° C. for a total of 3 hours, checking the progression of the reaction at regular intervals. The mixture was evaporated under vacuum, and the resulting residue was partitioned between EtOAc and water. The aqueous layer was extracted with EtOAc (2×) and CH$_2$Cl$_2$ (2×). The organics were washed with water and brine, dried (MgSO$_4$), filtered and evaporated. The resulting material was triturated with Et$_2$O and dried in vacuo to afford the title compound (307 mg). LC-MS (ES) m/z=243, 245 [M+H]$^+$.

Example 71

6-{2-Amino-6-[(3R)-3-ethyl-4-morpholinyl]-4-pyrimidinyl}-1H-indazol-3-amine

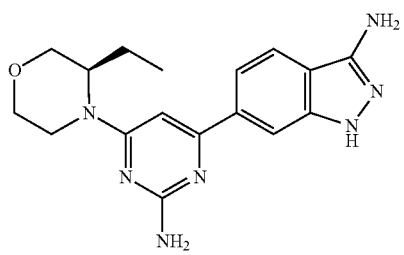 [SMILES: CC[C@@H]1COCCN1c1cc(-c2ccc3c(N)n[nH]c3c2)nc(N)n1]

Into a 25 mL sealable tube under nitrogen were combined 4-chloro-6-[(3R)-3-ethyl-4-morpholinyl]-2-pyrimidinamine (140 mg, 0.58 mmol) and (4-cyano-3-fluorophenyl)boronic acid (0.114 g, 0.69 mmol) in 1,4-dioxane (9 mL). Saturated aqueous NaHCO$_3$ (3 mL) was added, and the resulting mixture was degassed with nitrogen for 10 minutes. Pd(Ph$_3$P)$_4$ (0.76 g, 0.066 mmol) was added, the vessel was sealed, and the reaction mixture was stirred at 100° C. for 3 hours. The reaction was cooled to room temperature, the solids and other insoluble impurities formed during the reaction were filtered and the filtrate was concentrated. The resulting solid was partitioned between EtOAc and water, and extracted with EtOAc (2×) and CH$_2$Cl$_2$ (2×). The combined organic layers were washed with water and brine, dried (MgSO$_4$), filtered and concentrated. Flash chromatography on SiO$_2$ (gradient: 100% CHCl$_3$ to 90/10/1 CHCl$_3$/CH$_3$OH/NH$_4$OH) afforded a mixture of the desired Suzuki product with triphenylphosphine oxide. LC-MS (ES) m/z=328 [M+H]$^+$. In a 25 mL sealable tube under nitrogen were combined the crude containing the Suzuki product 4-{2-amino-6-[(3R)-3-ethyl-4-morpholinyl]-4-pyrimidinyl}-2-fluorobenzonitrile and hydrazine monohydrate (0.42 mL) in EtOH (6 mL). The vial was sealed, and the reaction mixture was stirred at 100° C. for 2 days. The reaction was filtered to remove some impurities and the filtrate was concentrated. The resulting solid was dissolved in a mixture of CH$_3$CN/H$_2$O/DMSO and purified on a Gilson RPHPLC (CH$_3$CN/H$_2$O w/0.1% TFA). The CH$_3$CN was evaporated, and saturated aqueous NaHCO$_3$ was added to the remaining water where a precipitate crashed out. The precipitate was filtered, triturated in Et$_2$O and dried in vacuo to afford the title compound (47 mg) as a tan solid. LC-MS (ES) m/z=340 [M+H]$^+$. $^1$H NMR (400 MHz, DMSO-d$_6$): δ 0.88 (t, J=7.5 Hz, 3H), 1.63-1.80 (m, 2H), 3.09 (td, J=12.8, 3.2 Hz, 1H), 3.37-3.46 (m, 2H), 3.51 (dd, J=11.4, 2.8 Hz, 1H), 3.80-3.91 (m, 2H), 4.30 (bs, 1H), 5.38 (s, 2H), 6.09 (bs, 2H), 6.56 (s, 1H), 7.56 (dd, J=8.6, 1.0 Hz, 1H), 7.71 (d, J=8.3 Hz, 1H), 7.94 (s, 1H), 11.52 (s, 1H).

Intermediate 101

6-Chloro-N$^4$-(1,1-dimethylethyl)-2,4-pyrimidinediamine

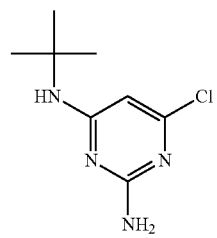

To 4,6-dichloro-2-pyrimidinamine (400 mg, 2.44 mmol) in CH$_3$CN (5 mL) were added (1,1-dimethylethyl)amine (0.34 mL, 3.17 mmol) and triethylamine (1.36 mL, 9.76 mmol), and the reaction mixture was heated in a microwave at 170° C. for a total of 2.25 hours, checking the progression of the reaction at regular intervals. The mixture was cooled down and evaporated. The resulting residue was partitioned between EtOAc and water, and extracted with EtOAc (2×) and CH$_2$Cl$_2$ (2×). The organics were washed with water and brine, dried (MgSO$_4$), filtered and evaporated. The resulting solid was triturated with Et$_2$O and dried in vacuo to afford the title compound (440 mg). LC-MS (ES) m/z=201, 203 [M+H]$^+$.

Intermediate 102

4-{2-Amino-6-[(1,1-dimethylethyl)amino]-4-pyrimidinyl}-2-fluorobenzonitrile

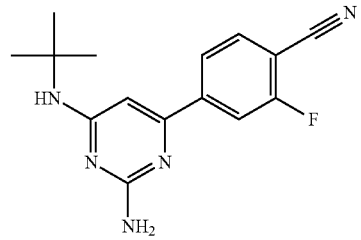 [SMILES: CC(C)(C)Nc1cc(-c2ccc(C#N)c(F)c2)nc(N)n1]

Into a 25 mL sealable tube under nitrogen were combined 6-chloro-N$^4$-(1,1-dimethylethyl)-2,4-pyrimidinediamine (440 mg, 2.19 mmol) and (4-cyano-3-fluorophenyl)boronic acid (0.416 g, 2.52 mmol) in 1,4-dioxane (8 mL). Saturated aqueous NaHCO$_3$ (4 mL) was added, and the resulting mixture was degassed with nitrogen for 10 minutes. Pd(Ph$_3$P)$_4$ (0.127 g, 0.11 mmol) was added, the vessel was sealed, and the reaction mixture was stirred at 95° C. overnight. The reaction was cooled to room temperature, solids and other insoluble impurities formed during the reaction were filtered, and the orange filtrate was concentrated. The resulting solid was partitioned between EtOAc and water, and extracted with EtOAc (2×) and CH$_2$Cl$_2$ (2×). The combined organic layers were washed with water and brine, dried (MgSO$_4$), filtered and concentrated. The resulting solid was dissolved in DMSO and purified on a Gilson RPHPLC (CH₃CN/H₂O w/0.1% TFA). Fractions were evaporated and solids were triturated in Et₂O and filtered to afford the title compound (553 mg). LC-MS (ES) m/z=286 [M+H]⁺.

Example 72

6-(3-Amino-1H-indazol-6-yl)-N⁴-(1,1-dimethylethyl)-2,4-pyrimidinediamine

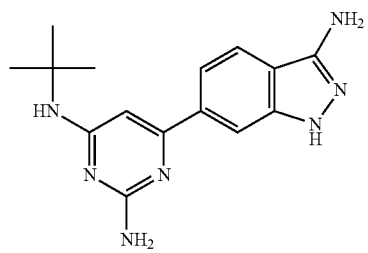 [SMILES: CC(C)(C)Nc1cc(-c2ccc3c(N)n[nH]c3c2)nc(N)n1]

Into a 25 mL sealable tube under nitrogen were combined 4-{2-amino-6-[(1,1-dimethylethyl)amino]-4-pyrimidinyl}-2-fluorobenzonitrile (500 mg, 1.25 mmol) and hydrazine monohydrate (1.22 mL) in EtOH (8 mL). The vial was sealed, and the reaction mixture was stirred at 95° C. for 22 hours. The solution was concentrated, partitioned between EtOAc and water, and extracted with EtOAC (×2) and CH₂Cl₂. The organic layer was separated, washed with NaHCO₃ and brine, dried (MgSO₄), filtered and concentrated. The resulting solid was dissolved in a mixture of CH₃CN/water/CH₃OH/DMSO and purified on a Gilson RPHPLC (CH₃CN/H₂O w/0.1% TFA). Fractions were evaporated, aqueous potassium carbonate was added to the residue and the solution was stirred at room temperature for 2 hrs. The aqueous mixture was extracted with EtOAc (×2) and DCM (×2). The organic layer was separated, washed with brine, dried (MgSO₄), filtered, concentrated and azeotroped with CH₃CN to give a brown solid. Minimum amount of acetonitrile was added to the solids, and the resulting mixture was sonicated. A white precipitate crashed out which was filtered and washed with hexanes and Et₂O to afford the title compound (102 mg) as a white solid. LC-MS (ES) m/z=298 [M+H]⁺. ¹H NMR (400 MHz, DMSO-d₆): δ 1.42 (s, 9H), 5.36 (s, 2H), 5.90 (s, 2H), 6.31 (s, 1H), 6.53 (s, 1H), 7.36 (dd, J=8.6, 1.3 Hz, 1H), 7.68 (d, J=8.3 Hz, 1H), 7.80 (s, 1H), 11.50 (s, 1H).

Example 73

6-(3-Amino-1H-indazol-6-yl)-N⁴-(2-methylpropyl)-2,4-pyrimidinediamine

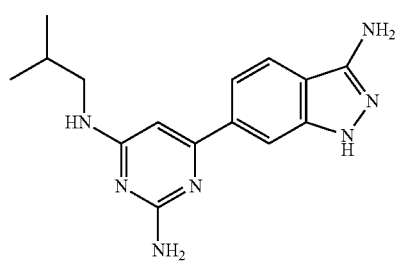 [SMILES: CC(C)CNc1cc(-c2ccc3c(N)n[nH]c3c2)nc(N)n1]

To 6-[2-amino-6-(methylsulfonyl)-4-pyrimidinyl]-1H-indazol-3-amine (300 mg, 0.56 mmol) in 1,4-dioxane (10 mL) was added triethylamine (0.39 mL, 2.82 mmol), and the resulting mixture was degassed with nitrogen for 5 minutes. (2-Methylpropyl)amine (57.7 mg, 0.79 mmol) was added and the resulting solution was heated to 95° C. overnight. An additional 0.5 eq of (2-methylpropyl)amine and 0.5 eq of triethylamine were added and the reaction mixture was heated to 95° C. overnight. The brown solution was cooled down and concentrated. The resulting solid was dissolved in a mixture of CH₃CN/H₂O/0.1% TFA and purified on a Gilson RPHPLC (CH₃CN/H₂O w/0.1% TFA). Fractions were evaporated and the resulting material was triturated with Et₂O, filtered and dried in vacuo to afford a TFA salt of the title compound (19 mg). LC-MS (ES) m/z=298 [M+H]⁺. ¹H NMR (400 MHz, CD₃OD): δ 1.01 (d, J=6.8 Hz, 6H), 1.99 (m, 1H), 3.36-3.40 (m, 2H), 6.41 (s, 1H), 7.36 (dd, J=8.6, 1.5 Hz, 1H), 7.73 (s, 1H), 7.95-7.99 (m, 1H).

Example 74

6-(3-Amino-1H-indazol-6-yl)-N⁴-propyl-2,4-pyrimidinediamine

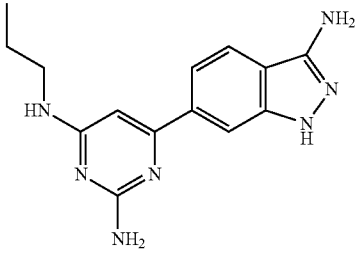 [SMILES: CCCNc1cc(-c2ccc3c(N)n[nH]c3c2)nc(N)n1]

To 6-[2-amino-6-(methylsulfonyl)-4-pyrimidinyl]-1H-indazol-3-amine (300 mg, 0.56 mmol) in 1,4-dioxane (5 mL) was added triethylamine (0.39 mL, 2.82 mmol), and the resulting mixture was degassed with nitrogen for 5 minutes. Propylamine (50 mg, 0.84 mmol) was added, and the resulting solution was heated in a microwave at 160° C. for 2 hours, and at 180° C. for 1 hour. The brown solution was cooled down and concentrated. The resulting solid was dissolved in a mixture of CH₃CN/H₂O/0.1% TFA and purified on a Gilson RPHPLC (CH₃CN/H₂O w/0.1% TFA). Fractions were evaporated and the resulting material was triturated with Et₂O, filtered and dried in vacuo to afford a TFA salt of the title compound (40 mg) as a shiny light brown solid. LC-MS (ES) m/z=284 [M+H]⁺. ¹H NMR (400 MHz, CD₃OD): δ 1.02 (t, J=7.3 Hz, 3H), 1.65-1.75 (m, 2H), 3.5 (m, 2H), 6.39 (s, 1H), 7.39 (dd, J=8.6, 1.5 Hz, 1H), 7.76 (s, 1H), 8.00 (d, J=8.6 Hz, 1H).

Intermediate 103

(2R)-2-[(Phenylmethyl)amino]-1-propanol

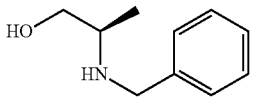

To (2R)-2-amino-1-propanol (4.5 g, 60 mmol) in toluene (120 mL) was added benzaldehyde (636 mL). A Dean-Stark trap was placed on the flask, and the reaction mixture was heated to reflux until no further water evolved. The reaction was cooled down to room temperature and concentrated. The resulting residue was dissolved in ethanol (120 mL), and treated with NaBH$_4$ (5.67 g, 150 mmol) at 0° C. followed by sufficient 4N HCl in dioxane to adjust the pH to 2. The reaction mixture was stirred overnight at room temperature, and then concentrated in vacuo. The resulting residue was dissolved in 1N aq. HCl (200 mL) and washed with CH$_2$Cl$_2$ (2×100 mL). The aqueous phase was then adjusted to pH>13 with 6N aqueous NaOH and extracted with CH$_2$Cl$_2$ (2×150 mL). The combined organic phase was dried over anhydrous Na$_2$SO$_4$, filtered, and concentrated to afford the title compound (9.44 g, 95%) as a colorless oil which solidified under high vacuum. LC-MS (ES) m/z=166.2 [M+H]$^+$ Intermediate 104

(5R)-5-Methyl-4-(phenylmethyl)-3-morpholinone

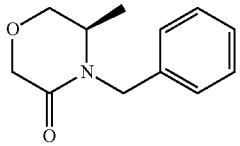

To (2R)-2-[(phenylmethyl)amino]-1-propanol (8.43 g, 51 mmol) in THF (50 mL) was added a solution of K$_2$CO$_3$ (21.15 g, 153 mmol) in water (50 mL). To the resulting mixture at 0° C. was added slowly via syringe chloroacetyl chloride (5.7 mL, 71.4 mmol) with vigorous stirring, and the reaction mixture was stirred for 1 hour at 0° C. A 50% aqueous NaOH solution was added to adjust the pH>13, and the resulting mixture was warmed up overnight to room temperature. The solution was extracted with CH$_2$Cl$_2$ (2×200 mL), and the organic layer was dried (Na$_2$SO$_4$), filtered and concentrated to afford the title compound (100% crude yield) as a colorless oil. LC-MS (ES) m/z=206 [M+H]$^+$ Intermediate 105

(3R)-3-Methyl-4-(phenylmethyl)morpholine

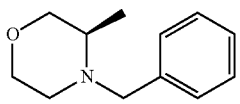

To a solution of (5R)-5-methyl-4-(phenylmethyl)-3-morpholinone (11.7 g, 57 mmol) in toluene (140 mL) at 0° C. was added sodium bis(2-methoxyethoxy)aluminumhydride (Red-Al) (35 mL, 3 mL/g of morpholinone) slowly via addition funnel, and the reaction mixture was stirred overnight at 60° C. The reaction was cooled down to 0° C. and quenched by dropwise addition of 1N aqueous NaOH (15 mL). The resulting mixture was partitioned between Et$_2$O (100 mL) and of 1N aqueous NaOH (100 mL). The organic layer was separated, and the aqueous layer was further extracted with Et$_2$O (50 mL). The combined organic layers were dried (Na$_2$SO$_4$), filtered and concentrated. The resulting residue was azeotroped with CH$_3$OH (50 mL) to afford the title compound (10.69 g) as a colorless oil. LC-MS (ES) m/z=192 [M+H]$^+$ Intermediate 106

(3R)-3-Methylmorpholine

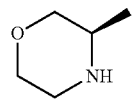

To (3R)-3-methyl-4-(phenylmethyl)morpholine (10.7 g, 56 mmol) in CH$_3$OH (110 mL) were added 6N aqueous HCl (9.3 mL) and Pd/C (1.07 g, 10 wt %), and the reaction mixture was stirred overnight at room temperature under a H$_2$ atmosphere (balloon setup). The mixture was filtered through a glass fiber filter, and the filter cake was washed with CH$_3$OH. The combined filtrate was concentrated and azeotroped with CH$_3$OH (4×100 mL) to afford the HCl salt of the title compound as a yellow oil that solidified under high vacuum (7.91 g). $^1$H NMR (400 MHz, CD$_3$OD): δ 3.95-4.05 (m, 2H), 3.77 (m, 1H), 3.47-3.54 (m, 1H), 3.38-3.47 (m, 1H), 3.30-3.34 (m, 1H), 3.18-3.28 (m, 1H), 1.29 (d, J=6.3 Hz, 3H).

Intermediate 107

4-Chloro-6-[(3R)-3-methyl-4-morpholinyl]-2-pyrimidinamine

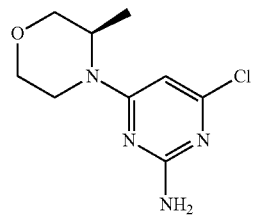

To 4,6-dichloro-2-pyrimidinamine (500 mg, 3.05 mmol) in CH$_3$OH (10 mL) were added (3R)-3-methylmorpholine hydrochloride (441 mg, 3.2 mmol) and triethylamine (1.28 mL, 9.2 mmol), and the reaction mixture was heated in a microwave at 120° C. for 35 minutes. Side-product started to form. An additional 0.5 eq of (3R)-3-methylmorpholine hydrochloride and 0.2 mL of triethylamine were added, and the mixture was heated in an oil bath at 50° C. for 3 days and in a microwave at 100° C. for 3 hours. The mixture was cooled down, evaporated under vacuum, and the resulting residue was partitioned between EtOAc and water, and extracted with EtOAc (2×) and CH$_2$Cl$_2$ (2×). The combined organics were washed with water and brine, dried (MgSO$_4$), filtered, and evaporated. The resulting material was triturated with Et$_2$O and dried in vacuo to afford the title compound (524 mg). LC-MS (ES) m/z=229, 231 [M+H]$^+$.

Intermediate 108

4-{2-Amino-6-[(3R)-3-methyl-4-morpholinyl]-4-pyrimidinyl}-2-fluorobenzonitrile

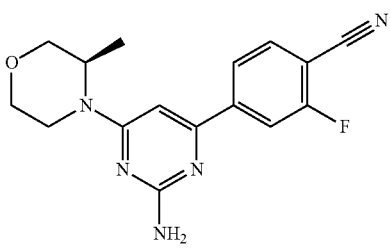 [SMILES: C[C@@H]1COCCN1c1cc(-c2ccc(C#N)c(F)c2)nc(N)n1]

Into a 25 mL sealable tube under nitrogen were combined 4-chloro-6-[(3R)-3-methyl-4-morpholinyl]-2-pyrimidinamine (500 mg, 2.19 mmol) and (4-cyano-3-fluorophenyl)boronic acid (0.397 g, 2.4 mmol) in 1,4-dioxane (10 mL). Saturated aqueous NaHCO$_3$ (5 mL) was added, and the resulting mixture was degassed with nitrogen for 10 minutes. Pd(Ph$_3$P)$_4$ (0.126 g, 0.11 mmol) was added, the vessel was sealed, and the reaction mixture was stirred at 95° C. overnight. The reaction was cooled to room temperature, solids and other insoluble impurities formed during the reaction were filtered, and the orange filtrate was concentrated. The resulting solid was partitioned between EtOAc and water, and extracted with EtOAc (2×) and CH$_2$Cl$_2$ (2×). The organic layer was separated, washed with water and brine, dried (MgSO$_4$), filtered and concentrated. The resulting solid was dissolved in CH$_2$Cl$_2$ and purified by flash chromatography on SiO$_2$ (gradient: 100% CH$_2$Cl$_2$ to 15% of 90/10/1 CH$_2$Cl$_2$/CH$_3$OH/NH$_4$OH). Fractions were evaporated, and the solids were triturated with Et$_2$O and filtered to afford the title compound (403 mg) as a yellow solid. LC-MS (ES) m/z=314 [M+H]$^+$.

Example 75

6-{2-Amino-6-[(3R)-3-methyl-4-morpholinyl]-4-pyrimidinyl}-1H-indazol-3-amine

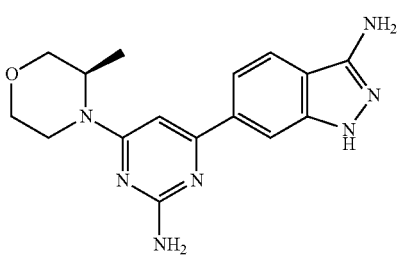 [SMILES: C[C@@H]1COCCN1c1cc(-c2ccc3c(N)n[nH]c3c2)nc(N)n1]

To a solution of 4-{2-amino-6-[(3R)-3-methyl-4-morpholinyl]-4-pyrimidinyl}-2-fluorobenzonitrile (400 mg, 1.28 mmol) in EtOH (12 mL) was added hydrazine monohydrate (1.25 mL, 25.5 mmol), and the resulting suspension was stirred at 95° C. for 18 hours. The reaction mixture was concentrated, and the resulting residue was partitioned between EtOAc and water and extracted with EtOAc (2×) and CH$_2$Cl$_2$ (1×). The combined organics were washed with saturated aqueous NaHCO$_3$ and brine, dried (MgSO$_4$) filtered and evaporated. The resulting residue was dissolved in a mixture of CH$_3$CN/water/DMSO and purified by RPHPLC (CH$_3$CN/H$_2$O w/0.1% TFA) to afford a TFA salt of the title compound as a pale yellow solid. A portion of this material (180 mg) was treated with potassium carbonate in water. The aqueous mixture was stirred at room temperature for 2 hours, and extracted with EtOAc (2×). The combined organics were washed with brine, dried (MgSO$_4$), filtered and evaporated to afford the title compound (69 mg) as a white solid. LC-MS (ES) m/z=326 [M+H]$^+$. $^1$H NMR (400 MHz, DMSO-d$_6$): δ 1.19 (d, J=6.8 Hz, 3H), 3.11 (m, 1H), 3.44 (m, 1H), 3.56-3.63 (m, 1H), 3.68-3.74 (m, 1H), 3.92 (dd, J=11.1, 3.0 Hz, 1H), 4.05-4.14 (m, 1H), 4.49 (bs, 1H), 5.38 (s, 2H), 6.11 (s, 2H), 6.55 (s, 1H), 7.57 (dd, J=8.6, 1.3 Hz, 1H), 7.71 (d, J=8.6 Hz, 1H), 7.95 (s, 1H), 11.52 (s, 1H).

Intermediate 109

N-Phenyl-2-morpholinecarboxamide

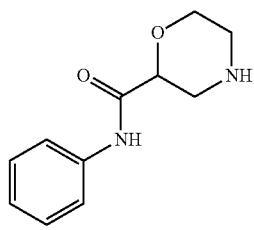 [SMILES: O=C(Nc1ccccc1)C1CNCCO1]

To a stirred solution of 4-{[(1,1-dimethylethyl)oxy]carbonyl}-2-morpholinecarboxylic acid (500 mg, 2.16 mmol) in dry DMF (2 mL) at 0° C. were added EDCI (456 mg, 2.38 mmol), HOBT (331 mg, 2.16 mmol) and aniline (0.22 mL, 2.38 mmol). The solution was stirred at room temperature overnight. The solvent was evaporated and the resulting residue was poured onto water and extracted with EtOAc (2×) and CH$_2$Cl$_2$ (2×). The combined organics were washed with brine and dried (MgSO$_4$), filtered and evaporated. To this crude material dissolved in CH$_2$Cl$_2$/CH$_3$OH (3 mL/0.3 mL) was added TFA (1.5 mL), and the reaction mixture was stirred at room temperature for 3 hours. The mixture was concentrated and dried in vacuo to afford a light brown oil. Et$_2$O and hexanes were added and a precipitate crashed out. The mixture was sonicated and filtered to afford the title compound (604 mg). LC-MS (ES) m/z=207 [M+H]$^+$.

Intermediate 110

4-(2-Amino-6-chloro-4-pyrimidinyl)-N-phenyl-2-morpholinecarboxamide

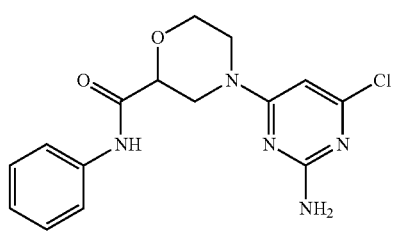 [SMILES: Nc1nc(Cl)cc(N2CCOC(C(=O)Nc3ccccc3)C2)n1]

To 4,6-dichloro-2-pyrimidinamine (160 mg, 0.98 mmol) in CH$_3$CN (5 mL) were added N-phenyl-2-m or pholinecarboxamide (400 mg, 1.25 mmol) and triethylamine (0.68 mL, 4.88 mmol), and the reaction mixture was heated in a microwave at 140° C. for 25 minutes. The reaction was cooled down and a precipitate crashed out. The mixture was filtered, and

Example 76

4-[2-Amino-6-(3-amino-1H-indazol-6-yl)-4-pyrimidinyl]-N-phenyl-2-morpholinecarboxamide

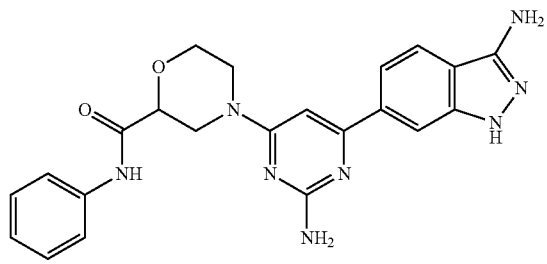

Into a 25 mL sealable tube under nitrogen were combined 4-(2-amino-6-chloro-4-pyrimidinyl)-N-phenyl-2-morpholinecarboxamide (290 mg, 0.87 mmol) and (4-cyano-3-fluorophenyl)boronic acid (0.172 g, 1.04 mmol) in 1,4-dioxane (8 mL). Saturated aqueous $NaHCO_3$ (4 mL) was added, and the resulting mixture was degassed with nitrogen for 10 minutes. $Pd(Ph_3P)_4$ (0.050 g, 0.043 mmol) was added, the vessel was sealed, and the reaction mixture was stirred at 95° C. overnight. The reaction was cooled to room temperature, solids and other insoluble impurities formed during the reaction were filtered, and the filtrate was concentrated. The resulting solid was partitioned between EtOAc and water, and extracted with EtOAc (2×) and $CH_2Cl_2$ (2×). The combined organic layers were washed with water and brine, dried ($MgSO_4$), filtered and concentrated. The resulting crude Suzuki product contained triphenylphosphine oxide. LC-MS (ES) m/z=419 [M+H]$^+$. Into a 25 mL sealable tube under nitrogen were combined the crude Suzuki product 4-[2-amino-6-(4-cyano-3-fluorophenyl)-4-pyrimidinyl]-N-phenyl-2-morpholinecarboxamide and hydrazine monohydrate (0.64 mL) in EtOH (8 mL). The vial was sealed, and the reaction mixture was stirred at 80° C. for 14 hrs and at 90° C. for 8 hrs. The green precipitate that formed during the reaction and containing impurities was filtered and the filtrate was concentrated. Trituration in EtOAc/Hexane and then EtOH/$Et_2O$ gave a grey solid containing impurities that was filtered, and the filtrate was evaporated. $CH_3OH$ was added and a white precipitate crashed out. Some hexanes and water were added and the mixture was sonicated. The solids were filtered and dried in vacuo overnight to afford the title compound (85 mg, 21%) as a white solid. LC-MS (ES) m/z=431 [M+H]$^+$. $^1$H NMR (400 MHz, DMSO-$d_6$): δ 2.99-3.16 (m, 2H), 3.70 (td, J=11.4, 2.5 Hz, 1H), 4.09 (d, J=11.4 Hz, 1H), 4.15-4.29 (m, 2H), 4.65 (bs, 1H), 5.38 (s, 2H), 6.23 (bs, 2H), 6.68 (s, 1H), 7.09 (t, J=7.45 Hz, 1H), 7.33 (t, J=8.0 Hz, 2H), 7.60 (dd, J=8.6, 1.3 Hz, 1H), 7.69-7.74 (m, 3H), 7.97 (s, 1H), 9.84 (s, 1H), 11.53 (s, 1H).

Intermediate 111

Cis-3-Methyl1-(phenylmethyl)-6-methyl-1,3-piperidinedicarboxylate

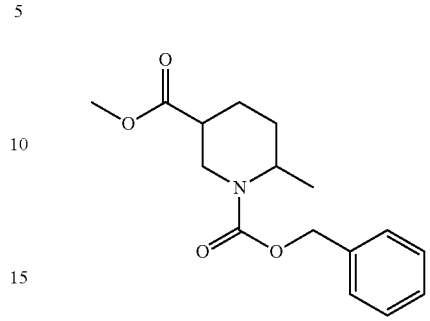

A solution of methyl 6-methylnicotinate (50 g, 331 mmol, 1 equiv.) in $CH_3OH$ (400 mL) and conc. HCl (26 mL) was added to a slurry of platinum (IV) oxide (2.0 g) in 50 mL of $CH_3OH$/water (4/1) in a Parr Bottle. The mixture was hydrogenated at room temperature under 60 psi of hydrogen gas for 4.5 hours. The mixture was then filtered through celite. The filtrate was concentrated in vacuo, after chasing with 500 mL of toluene, to about 77 g of syrup. This residue was dissolved in $CH_2Cl_2$ (500 mL) and chilled in an ice bath. To this stirred solution was added DMAP (0.4 g, 3.31 mmol), followed by TEA (101 mL, 728 mmol, 2.2 equiv.) portionwise. A suspension formed when TEA was added. This mixture was chilled to 15° C. To the resulting suspension was added benzylchloroformate (52 mL, 364 mmol, 1.1 equiv) dropwise over a 25 minutes period such that the temp of the mixture was kept at 15-20° C. After completion of benzylchloroformate addition, the mixture was stirred chilled with an ice bath for another 30 minutes, and then at ambient temperature for 1 hour. This mixture was washed with 300 mL of cold 1N HCl. The organic was concentrated in vacuo. The residue was partitioned between toluene (400 mL), MTBE (200 mL), and water (250 mL). The organic was washed with brine, dried over $MgSO_4$, filtered, and concentrated in vacuo to give an oil (97 g) as the crude. Silica gel column chromatography using gradient elution of EtOAc in hexane gave 64.4 g (65% yield) of the title compound. LC-MS (ES) m/z=292 [M+H]$^+$.

Resolution of Intermediate 111:

Intermediate 111 can be resolved by chiral stationary phase HPLC, SFC or by crystallization of a tartrate salt. The following conditions were used for the HPLC analysis and preparative resolution:

Separation Method:

HPLC was used for the analytical and SFC was preparative chiral separation.

Analytical Separation Method:
Instrument: Shimadzu 20-AB analytical HPLC
Column: ChiralPak AD-3, 150×4.6 mm I.D.
Mobile phase: A for Hex (0.1% DEA) and B for Ethanol
Gradient: B 15%
Flow rate: 1 ml/min
Wavelength: 220 nm
Preparative Separation Method
Instrument: Berger SFCIII preparative SFC
Column: ChiralPak IC-H, 250×30 mml·D.
Mobile phase: A for SFC $CO_2$ and B for 2-Propanol
Gradient: A:B 75:25
Flow rate: 90 mL/min
Sample preparation: dissolved in 2-Propanol, 200 mg/mL
Injection: 1 mL per injection.

Resolution by crystallization of the tartrate salt is described in the example below to produce intermediate 113.

Intermediate 112

Cis-methyl-6-methyl-3-piperidinecarboxylate

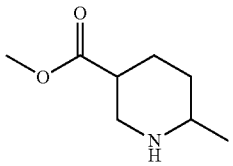

A solution of cis-3-methyl 1-(phenylmethyl)-6-methyl-1,3-piperidinedicarboxylate (69 g, 237 mol) in EtOH (50 mL) and EtOAc (300 mL) was added to a slurry of 10% Pd/C (3.7 g) in EtOAc (30 mL) and EtOH (10 mL) EtOH under nitrogen in a Parr Shaker bottle. The mixture was hydrogenated under 65 psi at room temperature for 4 hours. The mixture was filtered through celite, and washed with EtOAc. The filtrate was concentrated in vacuo to give 37 g of the title compound as a liquid. LC-MS (ES) m/z=158 [M+H]$^+$.

Intermediate 113

Methyl(3S,6R)-6-methyl-3-piperidinecarboxylate
L-(+)-tartaric acid salt

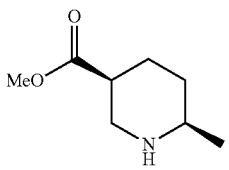

L-(+)-Tartaric acid salt

A suspension of L-(+)-tartaric acid (39 g, 260 mmol, 1.05 equiv) in IPA (200 mL) and water (13 mL) water was heated in a water bath at 60° C. until all dissolved. To this hot stirred solution was added neat racemic methyl(3S,6R)-6-methyl-3-piperidinecarboxylate (39 g, 248 mmol), followed by addition of 25 mL of IPA rinse. The resulting mixture was heated to 60° C., resulting in a clear solution, and then cooled to room temperature, while the hot water bath was removed. This hot solution was seeded with a sample of methyl (3S,6R)-6-methyl-3-piperidinecarboxylate L-(+)-tartaric acid salt that had a chiral purity of 98% ee, and aged at ambient temperature (with the water bath removed) for 20 minutes. The mixture turned into an oily texture with seeds still present. To the mixture was added 5 mL of water, and heated in the warm water bath at 43° C. The mixture became clear with the seeds still present. The heating was stopped, and the mixture was stirred in the warm water bath. After 20 minutes, the mixture gradually turned into a paste. After another 10 min, the water bath was removed, and the mixture was stirred at ambient temperature for another 1 hour. The resulting paste was filtered. The cake was washed with 50 mL of IPA, giving 62 g of wet solids. This cake was taken up in 150 mL of IPA and 8 mL of water, and stirred as a slurry while being heated in a water bath to 60° C. (internal temp 55° C.) for 5 minutes. The heating was turned off while the mixture was still stirred in the warm water bath. After 30 min, the mixture was filtered. The cake was washed with 100 mL of IPA. Drying under house vacuum at room temperature for 48 hours gave 46.7 g of solids. An analytical sample was derivatised to the corresponding N-Cbz derivative (as in the preparation of intermediate 111), which was determined by chiral HPLC (methods used to analyze the resolution of intermediate 111 above) to have 85% ee. This material was taken up in IPA (420 mL) and water (38 mL) as a suspension. The mixture was heated in a water bath to 65° C., at which time the mixture became a clear solution. The heating bath was removed. The mixture was seeded and aged at ambient temp for 20 hours. The solids formed were filtered, and washed with 100 mL of IPA. The solids collected were dried under house vacuum at room temperature for 24 h, and then under vacuum at room temperature for another 24 hours to give 28.5 g of the title compound. An analytical sample was converted to the N-Cbz derivative. The ee was determined to be 97.7%. LC-MS (ES) m/z=158 [M+H]$^+$.

Intermediate 114

4,6-Dichloro-N-methyl-2-pyrimidinamine

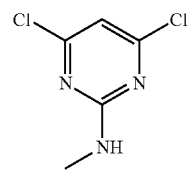

Methylamine (2M solution, 113 mL, 217 mmol, 2.05 equiv) was charged to a 1 L 3-neck flask fitted with a magnetic stirrer and a thermometer. The mixture was chilled in an ice bath. To this stirred solution was added via addition funnel a solution of 4,6-dichloro-2-(methylsulfonyl)pyrimidine (25 g, 110 mmol) in EtOAc (250 mL) portionwise over a 25 minutes period. The temp was between 5-10° C. After completion of addition, the ice bath was removed, and the mixture was stirred for 1 hour at ambient temperature. LCMS showed conversion complete. The suspension was filtered, and washed with EtOAc. The filtrate was concentrated in vacuo. The residue was partitioned between water (100 mL) and EtOAc (450 mL). The organic was washed with brine, dried over MgSO$_4$, filtered and concentrated in vacuo to give white solids, which were triturated in 150 mL of CH$_2$Cl$_2$. These solids were collected by filtration and washing with cold CH$_2$Cl$_2$ (50 mL). Drying under house vacuum at room temperature for 20 hours, and then high vacuum at room temperature for 3 hours gave 9.31 g of the title compound as a solid. LC-MS (ES) m/z=179 [M+H]$^+$.

Intermediate 115

(3S,6R)-1-[6-Chloro-2-(methylamino)-4-pyrimidinyl]-6-methyl-3-piperidinecarboxylic acid

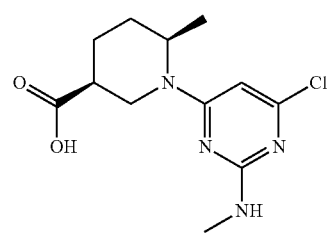 [SMILES: CNc1nc(Cl)cc(N2C[C@@H](C(=O)O)CC[C@H]2C)n1]

Methyl(3S,6R)-6-methyl-3-piperidinecarboxylate L-tartaric acid salt (4.0 g, 13.02 mmol) was dissolved in water (25 mL), to which was added LiOH.H$_2$O (1.80 g, 43.0 mmol, 3.3 equiv). The mixture was stirred at room temperature for 20 hours. LCMS showed ester hydrolysis complete. To this mixture was added NaHCO$_3$ (4.81 mg, 57.3 mmol, 4.4 equiv), 4,6-dichloro-N-methyl-2-pyrimidinamine (2.32 g, 13.02 mmol, 1 equiv) and 1,4-dioxane (25 mL). The reaction mixture was heated under reflux at 100° C. for 24 hours. The mixture was concentrated in vacuo. The resulting residue was suspended in 40 mL of water, to which was added cold 2N HCl until pH=3. The resulting mixture was filtered, and the solids were washed with water, dried under house vacuum at room temperature for 18 hours, and then under vacuum over P$_2$O$_5$ at room temperature for 24 hours to give the title compound (3.23 g) as a solid. LC-MS (ES) m/z=285 [M+H]$^+$.

Intermediate 116

(3S,6R)-1-[6-Chloro-2-(methylamino)-4-pyrimidinyl]-6-methyl-N-phenyl-3-piperidinecarboxamide

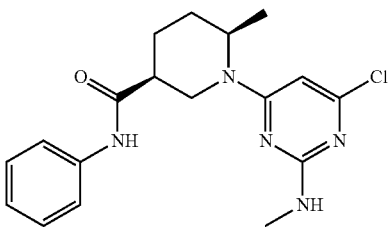 [SMILES: CNc1nc(Cl)cc(N2C[C@@H](C(=O)Nc3ccccc3)CC[C@H]2C)n1]

To (3S,6R)-1-[6-chloro-2-(methylamino)-4-pyrimidinyl]-6-methyl-3-piperidinecarboxylic acid (880 mg, 3.09 mmol) in CH$_2$Cl$_2$ (15 mL) at room temperature was added Hunig's base (1.62 mL, 9.27 mmol, 3 equiv) and aniline (0.56 mL, 6.18 mmol, 2 equiv), and the resulting mixture was chilled in an ice bath. To this stirred solution was added HATU (1.29 g, 3.40 mmol, 1.1 equiv) in one portion. The resulting suspension was stirred in the ice bath for 45 minutes. LCMS showed conversion complete. The mixture was filtered, and the filtrate was concentrated in vacuo. Silica gel column chromatography with gradient elution of 1% EtOAc in CHCl$_3$ to 35% EtOAc in CHCl$_3$ gave 700 mg of the title compound. LC-MS (ES) m/z=360 [M+H]$^+$.

Intermediate 117

1,1-Dimethylethyl 3-(bis{[(1,1-dimethylethyl)oxy]carbonyl}amino)-6-bromo-1H-indazole-1-carboxylate

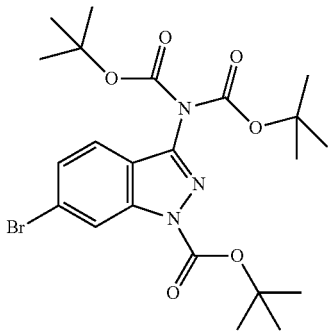 [SMILES: CC(C)(C)OC(=O)N(C(=O)OC(C)(C)C)c1nn(C(=O)OC(C)(C)C)c2cc(Br)ccc12]

To a stirred suspension of 6-bromo-1H-indazol-3-amine (25 g, 118 mmol) and DMAP (0.72 g, 5 mole %) in CH$_3$CN (400 mL) was added (Boc)$_2$O (129 g, 589 mmol, 5 equiv) in one portion, followed by heating to 80° C. for 1 hour, and then cooling to 45° C. To the mixture was added another 30 g of (Boc)$_2$O. The mixture was stirred at ambient temperature for 20 minutes and concentrated in vacuo. The resulting residue was partitioned between CH$_2$Cl$_2$ (500 mL) and water (250 mL). The organic was washed with brine, dried (Na$_2$SO$_4$), filtered and concentrated in vacuo to give an oil (95 g), which upon aging at rt for 48 hours became a suspension. To this mixture was added some hexane, and chilled in the refrigerator. The solids formed were collected by filtration, and washed with cold hexane (100 mL). Drying under vacuum at room temperature gave 37.58 g of the title compound as a beige solid. LC-MS (ES) m/z=512, 514 [M+H]$^+$.

Intermediate 118

1,1-Dimethylethyl 3-(bis{[(1,1-dimethylethyl)oxy]carbonyl}amino)-6-(4,4,5,5-tetramethyl-1,3,2-dioxaborolan-2-yl)-1H-indazole-1-carboxylate

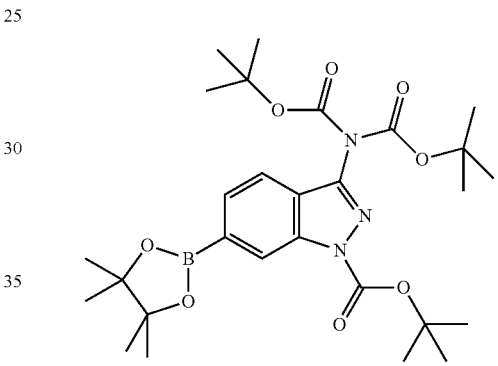

A mixture of 1,1-dimethylethyl 3-(bis{[(1,1-dimethylethyl)oxy]carbonyl}amino)-6-bromo-1H-indazole-1-carboxylate (17.64 g, 34.4 mmol), bis(pinacolato)diboron (10.49 g, 41.3 mmol, 1.2 equiv), KOAc (8.45 g, 86 mmol, 2.5 equiv) and PdCl$_2$(dppf).CH$_2$Cl$_2$ adduct (1.97 g, 2.41 mmol, 0.07 equiv) in 1,4-dioxane (270 mL) was degassed 4× with nitrogen, and heated to 100° C. for 18 hours. The mixture was cooled to room temperature, filtered and washed with EtOAc (200 mL). The filtrate was concentrated in vacuo to a give a dark brownish foam. This residue was taken up between EtOAc (500 mL) and water (200 mL). The mixture was filtered through celite, and the filtrate was partitioned. The organic was washed with brine, dried (Na$_2$SO$_4$), filtered, and concentrated in vacuo. The dark brownish foamy residue was dissolved in EtOAc (25 mL). To this solution was added 800 mL of hexane to precipitate out brownish solids. The cloudy solution was filtered. Again, particles developed in the filtrate, which was filtered again. The resulting dark orange filtrate was treated with Darco and filtered through celite. The filtrate became a light yellow solution, and was concentrated in vacuo to give a foam. Drying under vacuum at room temperature overnight afforded the title compound (17.2 g) as a beige solid. LC-MS (ES) m/z=560 [M+H]$^+$.

Intermediate 119

Potassium(3-(bis{[(1,1-dimethylethyl)oxy]carbonyl}amino)-1-{[(1,1-dimethylethyl)oxy]carbonyl}-1H-indazol-6-yl)(trifluoro)borate(1-)

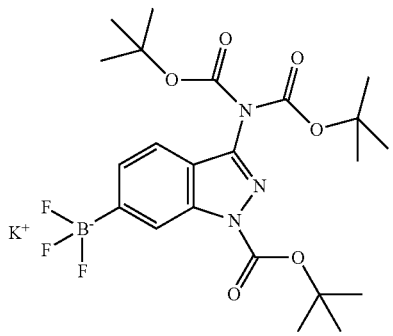 [SMILES: [K+] ; CC(C)(C)OC(=O)N(C(=O)OC(C)(C)C)c1nn(C(=O)OC(C)(C)C)c2cc([B-](F)(F)F)ccc12]

A saturated solution of aqueous $KHF_2$ was prepared by taking up $KHF_2$ (3.69 g, 14.3 mmol, 3.3 equiv) in water (12 mL) and sonicating for 10 min, resulting in just a slightly cloudy solution. Most solids went into solution. To a solution of the 1,1-dimethylethyl 3-(bis{[(1,1-dimethylethyl)oxy]carbonyl}amino)-6-(4,4,5,5-tetramethyl-1,3,2-dioxaborolan-2-yl)-1H-indazole-1-carboxylate (8 g, 3.69 mmol) in $CH_3OH$ (30 mL) was added the $KHF_2$ aqueous solution. The resulting mixture was concentrated in vacuo, and chased with $CH_3OH$ (3×80 mL). The resulting residue was dried under vacuum at room temperature for 18 hours. This material was taken up in acetone (100 mL), and the resulting suspension was sonicated and filtered. The filtrate was concentrated in vacuo, and the residue was taken up in MTBE (200 mL). The resulting suspension was sonicated, filtered, and the solids were dried under vacuum at room temperature for 5 hours to afford the title compound (5.70 g). LC-MS showed the mass of the corresponding boronic acid. LC-MS (ES) m/z=478 [M+H]$^+$

Intermediate 120

1,1-Dimethylethyl[6-(2-(methylamino)-6-{(2R,5S)-2-methyl-5-[(phenylamino)carbonyl]-1-piperidinyl}-4-pyrimidinyl)-1H-indazol-3-yl]carbamate

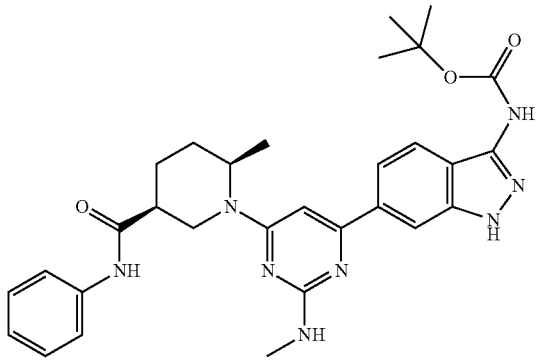 [SMILES: CNc1nc(-c2ccc3c(NC(=O)OC(C)(C)C)n[nH]c3c2)cc(N2C[C@@H](C(=O)Nc3ccccc3)CC[C@H]2C)n1]

(3S,6R)-1-[6-chloro-2-(methylamino)-4-pyrimidinyl]-6-methyl-N-phenyl-3-piperidinecarboxamide (570 mg, 1.58 mmol), potassium (3-(bis{[(1,1-dimethylethyl)oxy]carbonyl}amino)-1-{[(1,1-dimethylethyl)oxy]carbonyl}-1H-indazol-6-yl)(trifluoro)borate(1-) (1.45 g, 2.69 mmol, 1.7 equiv), $Pd_2(dba)_3$ (109 mg, 0.12 mmol, 0.075 equiv), tricyclohexylphosphine (67 mg, 0.24 mmol, 0.15 equiv), and $K_3PO_4$ (572 mg, 2.69 mmol, 1.7 equiv) were charged to a 20 mL microwave vial, followed by addition of 1,4-dioxane (12 mL) and water (4 mL). The resulting mixture was bubbled with argon at room temperature for 10 minutes, followed by heating at 100° C. for 18 hours. After cooling to room temperature, the upper organic layer was pipetted out and filtered through celite. The filtrate was concentrated in vacuo. Purification of the resulting residue by silica gel column chromatography using gradient elution 1% A in $CHCl_3$ to 100% A (A was a mixture of 200/800/3 $CH_3OH/CHCl_3/7N$ $NH_3$ in $CH_3OH$) afforded the title compound (567 mg). LC-MS (ES) m/z=557 [M+H]$^+$.

Example 77

(3S,6R)-1-[6-(3-amino-1H-indazol-6-yl)-2-(methylamino)-4-pyrimidinyl]-6-methyl-N-phenyl-3-piperidinecarboxamide

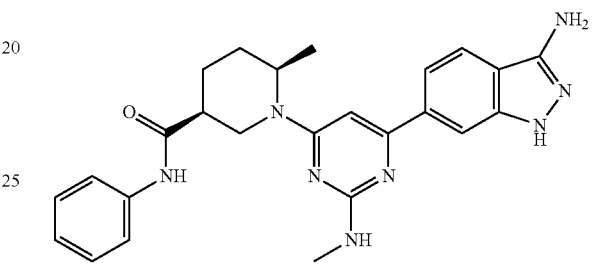

A mixture of 1,1-dimethylethyl[6-(2-(methylamino)-6-{(2R,5S)-2-methyl-5-[(phenylamino)carbonyl]-1-piperidinyl}-4-pyrimidinyl)-1H-indazol-3-yl]carbamate (530 mg, 0.95 mmol) in $CH_3OH$ (15 mL) and conc. HCl (0.5 mL) was heated at 50° C. for a total of 6 hours. The residue was taken up in 5 mL of water, to which was added 5 mL of sat. $NaHCO_3$. The resulting suspension was sonicated, and filtered. The yellow solids collected underwent purification by silica gel column chromatography using elution of gradient 1% A in $CHCl_3$ to 60% A in $CHCl_3$ (A was 200/800/20 $CH_3OH/CHCl_3/NH_4OH$). Trituration of the residue obtained from the chromatography in MTBE (6 mL), followed by drying under vacuum at 50° C. for 20 hours afforded the title compound (221 mg) as a yellow solid. LC-MS (ES) m/z=457 [M+H]$^+$. $^1H$ NMR (400 MHz, $CD_3OD$): δ 1.33 (d, J=6.8 Hz, 3H), 1.82-1.97 (m, 3H), 2.06-2.16 (m, 1H), 2.57-2.65 (m, 1H), 2.98 (s, 3H), 3.15-3.25 (m, 1H), 6.51 (s, 1H), 7.12 (t, J=7.5 Hz, 1H), 7.34 (t, J=8.1 Hz, 2H), 7.54 (dd, J=8.5, 1.1 Hz, 1H), 7.60 (dd, J=8.6, 1.3 Hz, 2H), 7.76 (d, J=8.3 Hz, 1H), 7.87 (s, 1H).

Intermediate 121

(3S,6R)-1-[6-Chloro-2-(methylamino)-4-pyrimidinyl]-N-cyclohexyl-6-methyl-3-piperidinecarboxamide

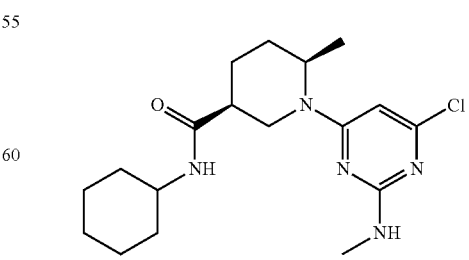

To a suspension of (3S,6R)-1-[6-chloro-2-(methylamino)-4-pyrimidinyl]-6-methyl-3-piperidinecarboxylic acid (3.05 g, 10.71 mmol) in $CH_2Cl_2$ (50 mL) at room temperature was added Hunig's base (2.70 mL, 15.43 mmol, 1.3 equiv) and cyclohexylamine (1.60 mL, 14.2 mmol, 1.2 equiv), and the resulting mixture was chilled in an ice bath. To this stirred solution was added HATU (4.96 g, 13.1 mmol, 1.1 equiv) in one portion, and the resulting suspension was stirred in the ice bath for 30 minutes. LCMS showed conversion complete. The mixture was diluted with $CH_2Cl_2$ (50 mL) and filtered through celite. The filtrate was washed water (2×25 mL) and then brine. The organic was dried over $Na_2SO_4$, filtered, and concentrated in vacuo. Silica gel column chromatography using gradient elution of 1% EtOAc in $CHCl_3$ to 50% EtOAc in $CHCl_3$ afforded the title compound (4.26 g) as a foam. LC-MS (ES) m/z=366 [M+H]$^+$.

Intermediate 122

(3S,6R)-1-[6-(4-Cyano-3-fluorophenyl)-2-(methylamino)-4-pyrimidinyl]-N-cyclohexyl-6-methyl-3-piperidinecarboxamide

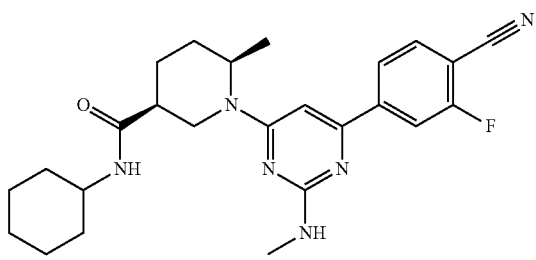 [SMILES: CNc1nc(-c2ccc(C#N)c(F)c2)cc(N2C[C@@H](C(=O)NC3CCCCC3)CC[C@H]2C)n1]

(3S,6R)-1-[6-Chloro-2-(methylamino)-4-pyrimidinyl]-N-cyclohexyl-6-methyl-3-piperidinecarboxamide (300 mg, 0.82 mmol), (4-cyano-3-fluorophenyl)boronic acid (176 mg, 1.07 mmol, 1.3 equiv), $Pd_2(dba)_3$ (56 mg, 0.061 mmol, 0.075 equiv), tricyclohexylphosphine (34.5 mg, 0.123 mmol, 0.15 equiv) and $K_3PO_4$ (296 mg, 1.39 mmol, 1.7 equiv) were charged to a 30 mL microwave vial, followed by addition of 1,4-dioxane (6 mL) and water (2 mL). The mixture was bubbled with argon for 10 minutes, and heated at 100° C. for 20 hours. The mixture was filtered through celite, and the filtrate was concentrated in vacuo. The residue was partitioned between EtOAc (75 mL) and brine (20 mL). The organic was dried ($Na_2SO_4$), filtered and concentrated in vacuo to give a residue. This crude material was purified by silica gel column chromatography using gradient elution of 1% EtOAc in $CHCl_3$ to 100% EtOAc to afford the title compound (258 mg). LC-MS (ES) m/z=451 [M+H]$^+$.

Example 78

(3S,6R)-1-[6-(3-Amino-1H-indazol-6-yl)-2-(methylamino)-4-pyrimidinyl]-N-cyclohexyl-6-methyl-3-piperidinecarboxamide

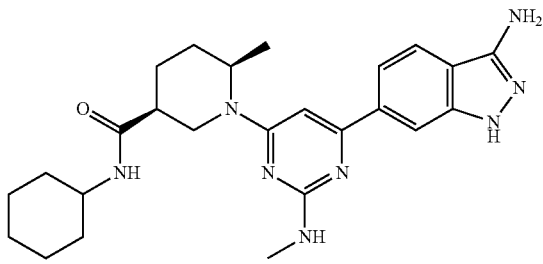

To (3S,6R)-1-[6-(4-cyano-3-fluorophenyl)-2-(methylamino)-4-pyrimidinyl]-N-cyclohexyl-6-methyl-3-piperidinecarboxamide (260 mg, 0.58 mmol) in EtOH (10 mL) as a suspension at room temperature in a microwave vial was added hydrazine monohydrate (807 uL, 16.7 mmol, 30 equiv) in one portion. The mixture was capped and heated at 100° C. for 48 hours. A duplicate run was performed. The crude reactions from both runs were combined, and concentrated in vacuo. The residue was taken up in 10 mL of water. The resulting suspension was sonicated briefly, and filtered. The solids collected were dried under vacuum at room temperature over $P_2O_5$ for 18 hours, and then at 65° C. under vacuum for another 18 hours to afford the title compound (410 mg) as a cream-colored solid. LC-MS (ES) m/z=463 [M+H]$^+$. $^1$H NMR (400 MHz, $CD_3OD$): δ 1.16-1.32 (m, 3H), 1.29 (d, J=6.8 Hz, 3H), 1.34-1.45 (m, 2H), 1.65-1.68 (m, 1H), 1.76-1.81 (m, 5H), 1.85-1.92 (m, 2H), 1.97-2.05 (m, 1H), 2.35-2.42 (m, 1H), 2.97 (s, 3H), 3.11-3.15 (m, 1H), 3.64-3.70 (m, 1H), 4.45-4.65 (bs, 1H), 4.72-4.92 (bs, 1H), 6.45 (s, 1H), 7.52 (dd, J=8.5, 1.14 Hz, 1H), 7.75 (d, J=8.3 Hz, 1H), 7.85 (s, 1H).

Example 79

(3S,6R)—N-Cyclohexyl-1-[6-(1H-indazol-6-yl)-2-(methylamino)-4-pyrimidinyl]-6-methyl-3-piperidinecarboxamide

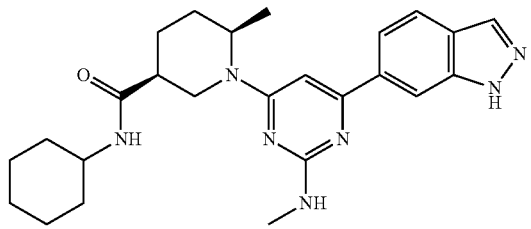 [SMILES: CNc1nc(-c2ccc3cn[nH]c3c2)cc(N2C[C@@H](C(=O)NC3CCCCC3)CC[C@H]2C)n1]

(3S,6R)-1-[6-Chloro-2-(methylamino)-4-pyrimidinyl]-N-cyclohexyl-6-methyl-3-piperidinecarboxamide (700 mg, 1.91 mmol), 6-(4,4,5,5-tetramethyl-1,3,2-dioxaborolan-2-yl)-1H-indazole (607 mg, 2.50 mmol, 1.3 equiv), $Pd_2(dba)_3$ (131 mg, 0.14 mmol, 0.075 equiv), tricyclohexylphosphine (80 mg, 0.287 mmol, 0.15 equiv), and $K_3PO_4$ (690 mg, 3.25 mmol, 1.7 equiv) were charged to a 30 mL microwave vial, followed by addition of 1,4-dioxane (12 mL) and water (4 mL). The mixture was bubbled with argon for 10 minutes, and heated at 100° C. for 20 hours. After cooling to room temperature, the mixture was filtered through celite, and the filtrate was concentrated in vacuo. The resulting residue was partitioned between EtOAc (50 mL) and brine (15 mL). The organic was dried over $Na_2SO_4$, filtered, and concentrated in vacuo. Purification was performed by silica gel column chromatography using a gradient elution of 1% A in $CHCl_3$ to 75% A in $CHCl_3$ (A was a mixture of 200/80/800 $CH_3OH$/$NH_4OH$/$CHCl_3$). Trituration of the residue obtained from the chromatography in a mixture of MTBE (3 mL) and hexane (3 mL), followed by drying under vacuum at 65° C. for 24 hours afforded the title compound (496 mg) as solids. LC-MS (ES) m/z=448 [M+H]$^+$. $^1$H NMR (400 MHz, $CD_3OD$): δ 1.20-1.30 (m, 3H), 1.30 (d, J=6.8 Hz, 3H), 1.35-1.48 (m, 2H), 1.64-1.74 (m, 1H), 1.75-1.84 (m, 5H), 1.86-1.94 (m, 2H), 1.96-2.08 (m, 1H), 2.34-2.45 (m, 1H), 2.98 (s, 3H), 3.08-3.18 (m, 1H), 3.64-3.71 (m, 1H), 4.50-4.70 (bs, 1H), 4.75-4.95 (bs, 1H), 6.50 (s, 1H), 7.69 (dd, J=8.5, 1.1 Hz, 1H), 7.85 (d, J=8.6 Hz, 1H), 8.09 (s, 1H), 8.11 (s, 1H).

Intermediate 123

(3S,6R)-1-[6-Chloro-2-(methylamino)-4-pyrimidinyl]-6-methyl-N-(phenylmethyl)-3-piperidinecarboxamide

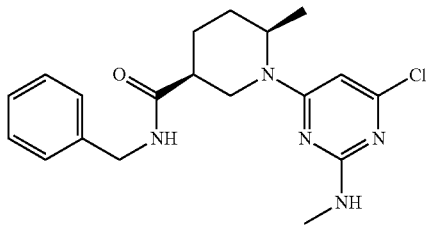 [SMILES: CNc1nc(Cl)cc(N2C[C@@H](C(=O)NCc3ccccc3)CC[C@H]2C)n1]

To a suspension of (3S,6R)-1-[6-chloro-2-(methylamino)-4-pyrimidinyl]-6-methyl-3-piperidinecarboxylic acid (2.2 g, 7.73 mmol) in $CH_2Cl_2$ (30 mL) at room temperature was added Hunig's base (1.75 mL, 10.04 mmol, 1.3 equiv) and benzylamine (1.01 mL, 9.27 mmol, 1.2 equiv), and the resulting mixture was chilled in an ice bath. To this stirred solution was added HATU (3.23 g, 8.50 mmol, 1.1 equiv) in one portion, and the resulting suspension was stirred in the ice bath for 30 minutes. LCMS showed conversion complete. The mixture was filtered through celite, and the filtrate was concentrated in vacuo. Silica gel column chromatography using a gradient elution of 1% EtOAc in $CHCl_3$ to 40% EtOAc in $CHCl_3$ afforded the title compound (3.05 g) as a gum. LC-MS (ES) m/z=374 [M+H]$^+$.

Intermediate 124

(3S,6R)-1-[6-(4-Cyano-3-fluorophenyl)-2-(methylamino)-4-pyrimidinyl]-6-methyl-N-(phenylmethyl)-3-piperidinecarboxamide

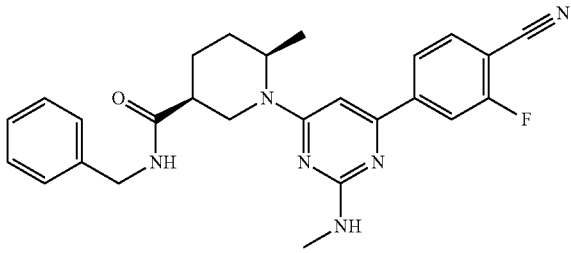 [SMILES: CNc1nc(-c2ccc(C#N)c(F)c2)cc(N2C[C@@H](C(=O)NCc3ccccc3)CC[C@H]2C)n1]

(3S,6R)-1-[6-Chloro-2-(methylamino)-4-pyrimidinyl]-6-methyl-N-(phenylmethyl)-3-piperidinecarboxamide (300 mg, 0.80 mmol), (4-cyano-3-fluorophenyl)boronic acid (176 mg, 1.07 mmol, 1.3 equiv), $Pd_2(dba)_3$ (56 mg, 0.061 mmol, 0.075 equiv), tricyclohexylphosphine (34.5 mg, 0.123 mmol, 0.15 equiv), and $K_3PO_4$ (296 mg, 1.39 mmol, 1.7 equiv) were charged to a 30 mL microwave vial, followed by addition of 1,4-dioxane (6 mL) and water (2 mL). The mixture was bubbled with argon for 10 minutes, and heated at 100° C. for 20 hours. A duplicate run was performed. The crude mixture of both runs were combined and filtered through celite, and the filtrate was concentrated in vacuo. The residue was partitioned between EtOAc (50 mL) and brine (15 mL). The organic was dried over $Na_2SO_4$, filtered and conc in vacuo. Purification by silica gel column chromatography using gradient elution of 1% EtOAc in $CHCl_3$ to 100% EtOAc gave the title compound (636 mg) as a foam. LC-MS (ES) m/z=459 [M+H]$^+$.

Example 80

(3S,6R)-1-[6-(3-Amino-1H-indazol-6-yl)-2-(methylamino)-4-pyrimidinyl]-6-methyl-N-(phenylmethyl)-3-piperidinecarboxamide

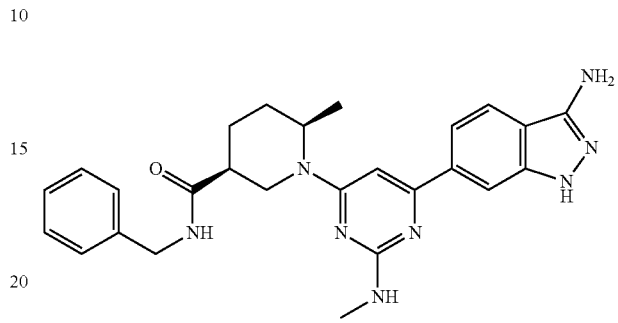

(3S,6R)-1-[6-(4-Cyano-3-fluorophenyl)-2-(methylamino)-4-pyrimidinyl]-6-methyl-N-(phenylmethyl)-3-piperidinecarboxamide (630 mg, 1.37 mmol) was chased with EtOH to remove traces of EtOAc, and the residue was taken up as a suspension in 25 mL of EtOH. To the mixture was added hydrazine monohydrate (2.0 mL) at room temperature in one portion, and the reaction mixture was heated at 100° C. under a gentle reflux for 20 hours. After cooling to room temperature, the mixture was filtered through celite, and the filtrate was concentrated in vacuo. The residue was suspended in water (10 mL) and filtered. The residue was purified by silica gel column chromatography using gradient elution of 1% A to 70% A in $CHCl_3$ (A was a mixture of 200/80/800 $CH_3OH/NH_4OH/CHCl_3$). The residue collected from the chromatography was triturated in a mixture of $CHCl_3$ (1 mL), MTBE (3 mL) and hexane (4 mL). Washing with hexane and drying under vacuum at 65° C. for 20 hours afforded the title compound (457 mg) as a pale yellow solid. LC-MS (ES) m/z=471 [M+H]$^+$. $^1$H NMR (400 MHz, $CD_3OD$): δ 1.30 (d, J=6.8 Hz, 3H), 1.77-1.88 (m, 3H), 2.00-2.09 (m, 1H), 2.44-2.52 (m, 1H), 2.96 (s, 3H), 3.14-3.19 (m, 1H), 4.42 (s, 2H), 4.56-4.73 (bs, 1H), 4.76-4.93 (bs, 1H), 6.46 (s, 1H), 7.24-7.38 (m, 5H), 7.51 (dd, J=8.6, 1.3 Hz, 1H), 7.75 (d, J=8.3 Hz, 1H), 7.85 (s, 1H).

Example 81

(3S,6R)-1-[6-(1H-Indazol-6-yl)-2-(methylamino)-4-pyrimidinyl]-6-methyl-N-(phenylmethyl)-3-piperidinecarboxamide

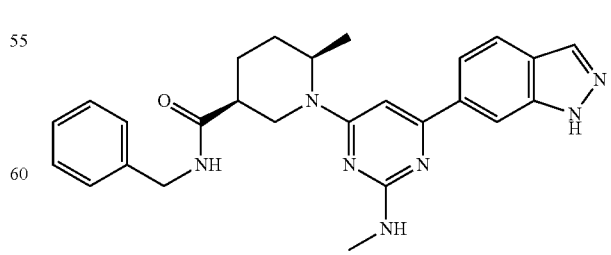

(3S,6R)-1-[6-Chloro-2-(methylamino)-4-pyrimidinyl]-6-methyl-N-(phenylmethyl)-3-piperidinecarboxamide (600 mg, 1.61 mmol), 6-(4,4,5,5-tetramethyl-1,3,2-dioxaborolan- 2-yl)-1H-indazole (509 mg, 2.09 mmol, 1.3 equiv), Pd$_2$(dba)$_3$ (110 mg, 0.12 mmol, 0.075 equiv), tricyclohexylphosphine (68 mg, 0.24 mmol, 0.15 equiv), and K$_3$PO$_4$ (579 mg, 2.73 mmol, 1.7 equiv) were charged to a 30 mL microwave vial, followed by addition of 1,4-dioxane (12 mL) and water (4 mL). The mixture was bubbled with argon for 10 minutes, and heated at 100° C. for 20 hours. After cooling to room temperature, the mixture was filtered through celite, and the filtrate was concentrated in vacuo. The residue was partitioned between EtOAc (50 mL) and brine (15 mL). The organic was dried over Na$_2$SO$_4$, filtered, and concentrated in vacuo. Purification was performed by silica gel column chromatography using gradient elution of 1% A to 70% A in CHCl$_3$ (A was a mixture of 200/80/800 CH$_3$OH/NH$_4$OH/CHCl$_3$). Trituration of the residue collected from the chromatography in a mixture of CHCl$_3$ (2 mL), MTBE (3 mL) hexane (6 mL), followed by drying under vacuum at 65° C. for 20 hours gave the title compound (526 mg) as a pale yellowish solid. LC-MS (ES) m/z=456 [M+H]$^+$. $^1$H NMR (400 MHz, CD$_3$OD): δ 1.31 (d, J=7.1 Hz, 3H), 1.75-1.90 (m, 3H), 1.99-2.10 (m, 1H), 2.45-2.55 (m, 1H), 2.97 (s, 3H), 3.10-3.19 (m, 1H), 4.42 (s, 2H), 4.50-4.60 (bs, 1H), 4.75-4.85 (bs, 1H), 6.50 (s, 1H), 7.24-7.38 (m, 5H), 7.69 (dd, J=8.5, 1.1 Hz, 1H), 7.84 (d, J=8.6 Hz, 1H), 8.09 (s, 1H), 8.10 (s, 1H).

Intermediate 125

6-Bromo-3-methyl-1H-indazole

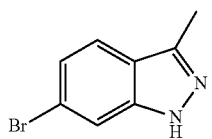

A suspension of 1-(4-bromo-2-fluorophenyl)ethanone (8.33 g, 38.4 mmol) in 15 mL of hydrazine monohydrate (309 mmol, 8 equiv) was heated to 120° C. under a reflux condenser for 23 hours. The resulting suspension (after cooling to room temperature) was filtered. The white solids were washed with water (2×15 mL), sucked under house vacuum at room temperature for 24 hours, and then dried under vacuum at room temperature over P$_2$O$_5$ for 24 hours to afford the title compound (7.59 g) as a yellow solid. LC-MS (ES) m/z=211, 213 [M+H]$^+$.

Intermediate 126

3-Methyl-6-(4,4,5,5-tetramethyl-1,3,2-dioxaborolan-2-yl)-1H-indazole

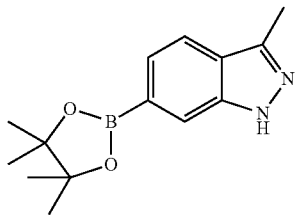 [SMILES: Cc1n[nH]c2cc(B3OC(C)(C)C(C)(C)O3)ccc12]

A mixture of 6-bromo-3-methyl-1H-indazole (8.32 g, 39.4 mmol), bis(pinacolato)diboron (11.01 g, 43.4 mmol, 1.1 equiv), potassium acetate (11.61 g, 118 mmol, 3 equiv) and PdCl$_2$(dppf).CH$_2$Cl$_2$ adduct (1.61 g, 1.97 mmol, 0.05 equiv) in 1,4-dioxane (80 mL) was degassed and back flushed with argon. This action was repeated five times. The mixture was heated at 100° C. for 20 hours. After cooling to room temperature, the mixture was filtered through celite, and rinsed with EtOAc (200 mL). The filtrate was concentrated in vacuo, and the resulting residue was taken up in EtOAc (200 mL) and brine (50 mL), followed by filtration through celite. The filtrate was partitioned between phases, and the organic phase was treated with Darco and Na$_2$SO$_4$, filtered, and concentrated in vacuo. The residue was triturated in 30 mL of hexane, the resulting suspension was filtered, and the cake was washed with hexane (2×10 mL). Drying under vacuum at room temperature for 20 hours afforded the title compound (9.91 g) as a light pinkish solid. LC-MS (ES) m/z=259 [M+H]$^+$.

Example 82

(3S,6R)-6-Methyl-1-[2-(methylamino)-6-(3-methyl-1H-indazol-6-yl)-4-pyrimidinyl]-N-phenyl-3-piperidinecarboxamide

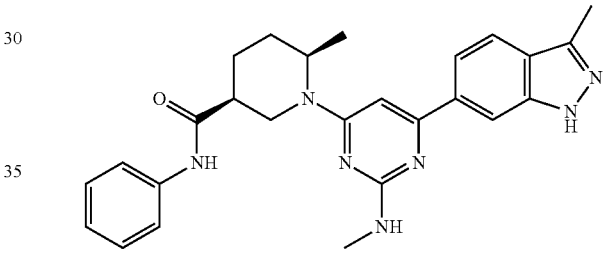

(3S,6R)-1-[6-Chloro-2-(methylamino)-4-pyrimidinyl]-6-methyl-N-phenyl-3-piperidinecarboxamide (420 mg, 1.17 mmol), 3-methyl-6-(4,4,5,5-tetramethyl-1,3,2-dioxaborolan-2-yl)-1H-indazole (452 mg, 1.75 mmol, 1.5 equiv), tricyclohexylphosphine (49 mg, 0.175 mmol, 0.15 equiv), Pd$_2$(dba)$_3$ (80 mg, 0.088 mmol, 0.075 equiv) and K$_3$PO$_4$ (412 mg, 1.98 mmol, 1.7 equiv) were charged to a 30 mL microwave vial, followed by addition of 1,4-dioxane (6 mL) and water (2 mL). The mixture was bubbled with argon for 10 minutes, followed by heating at 100° C. for 20 hours. After cooling to room temperature, the mixture was filtered through celite and rinsed with EtOAc (30 mL). The filtrate was concentrated in vacuo, and the resulting residue was partitioned between EtOAc (30 mL) and brine (10 mL). The organic was dried over Na$_2$SO$_4$, filtered, and concentrated in vacuo. The residue was purified by silica gel column chromatography using gradient elution of 1% A in CHCl$_3$ to 70% A in CHCl$_3$ (A was a mixture of 800/80/3200 CH$_3$OH/NH$_4$OH/CHCl$_3$). Trituration of the purified material in a mixture of CHCl$_3$ (1 mL), MTBE (2 mL) and hexane (6 mL), and drying under vacuum at 65° C. for 20 hours afforded the title compound (208 mg) as a tan solid. LC-MS (ES) m/z=456 [M+H]$^+$. $^1$H NMR (400 MHz, CD$_3$OD): δ 1.33 (d, J=6.8 Hz, 3H), 1.78-1.96 (m, 3H), 2.05-2.16 (m, 1H), 2.58-2.16 (m, 1H), 2.59 (s, 3H), 2.99 (s, 3H), 3.18-3.27 (m, 1H), 6.53 (s, 1H), 7.12 (t, J=7.3 Hz, 1H), 7.34 (t, J=8.0 Hz, 2H), 7.60 (d, J=7.3 Hz, 2H), 7.68 (d, J=8.0 Hz, 1H), 7.78 (d, J=8.0 Hz, 1H), 8.04 (s, 1H).

Example 83

(3S,6R)—N-Cyclohexyl-6-methyl-1-[2-(methylamino)-6-(3-methyl-1H-indazol-6-yl)-4-pyrimidinyl]-3-piperidinecarboxamide

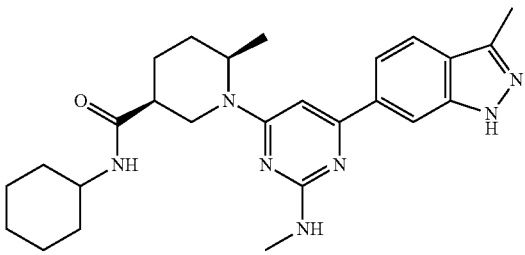 [SMILES: CNc1nc(-c2ccc3c(C)n[nH]c3c2)cc(N2C[C@@H](C(=O)NC3CCCCC3)CC[C@H]2C)n1]

(3S,6R)-1-[6-Chloro-2-(methylamino)-4-pyrimidinyl]-N-cyclohexyl-6-methyl-3-piperidinecarboxamide (440 mg, 1.20 mmol), 3-methyl-6-(4,4,5,5-tetramethyl-1,3,2-dioxaborolan-2-yl)-1H-indazole (466 mg, 1.80 mmol, 1.5 equiv), tricyclohexylphosphine (50 mg, 0.18 mmol, 0.15 equiv), Pd$_2$(dba)$_3$ (83 mg, 0.09 mmol, 0.075 equiv) and K$_3$PO$_4$ (434 mg, 2.04 mmol, 1.7 equiv) were charged to a 30 mL microwave vial, followed by addition of 1,4-dioxane (4.5 mL) and water (1.5 mL). The mixture was bubbled with argon for 10 minutes, followed by capping and heating at 100° C. for 20 hours. The mixture was filtered through celite, and rinsed with EtOAc (50 mL). The filtrate was concentrated in vacuo, and the residue was partitioned between EtOAc (50 mL) and brine (20 mL). The organic was dried over Na$_2$SO$_4$, filtered and concentrated in vacuo. The residue was purified by silica gel column chromatography using a gradient elution with 1% EtOAc in CHCl$_3$ to 100% EtOAc. This purified material was combined with purified product from a duplicate run. The combined residue was triturated in a mixture of CHCl$_3$ (1 mL) and hexane (6 mL). Drying under vacuum at 65° C. for 20 hours afforded the title compound (194 mg) as a beige solid. LC-MS (ES) m/z=462 [M+H]$^+$. $^1$H NMR (400 MHz, CD$_3$OD): δ 1.20-1.34 (m, 3H), 1.30 (d, J=6.8 Hz, 3H), 1.35-1.45 (m, 2H), 1.64-1.71 (m, 1H), 1.73-1.83 (m, 5H), 1.85-1.95 (m, 2H), 1.95-2.07 (m, 1H), 2.35-2.45 (m, 1H), 2.59 (s, 3H), 2.98 (s, 3H), 3.07-3.17 (m, 1H), 3.63-3.73 (m, 1H), 4.45-4.65 (bs, 1H), 6.48 (s, 1H), 7.66 (dd, J=8.5, 1.1 Hz, 1H), 7.78 (d, J=8.6 Hz, 1H), 8.02 (s, 1H).

Example 84

(3S,6R)-6-Methyl-1-[2-(methylamino)-6-(3-methyl-1H-indazol-6-yl)-4-pyrimidinyl]-N-(phenylmethyl)-3-piperidinecarboxamide

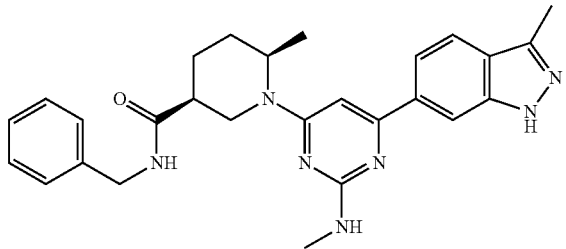 [SMILES: CNc1nc(-c2ccc3c(C)n[nH]c3c2)cc(N2C[C@@H](C(=O)NCc3ccccc3)CC[C@H]2C)n1]

(3S,6R)-1-[6-Chloro-2-(methylamino)-4-pyrimidinyl]-6-methyl-N-(phenylmethyl)-3-piperidinecarboxamide (370 mg, 0.99 mmol), 3-methyl-6-(4,4,5,5-tetramethyl-1,3,2-dioxaborolan-2-yl)-1H-indazole (383 mg, 1.48 mmol, 1.5 equiv), tricyclohexylphosphine (42 mg, 0.5 mmol, 0.15 equiv), Pd$_2$(dba)$_3$ (68 mg, 0.07 mmol, 0.075 equiv) and K$_3$PO$_4$ (357 mg, 1.68 mmol, 1.7 equiv) were charged to a 30 mL microwave vial, followed by addition of 1,4-dioxane (4 mL) and water (1.33 mL). The mixture was bubbled with argon for 10 minutes, followed by capping and heating at 100° C. for 20 hours. This mixture was combined with another run starting with 200 mg of (3S,6R)-1-[6-chloro-2-(methylamino)-4-pyrimidinyl]-6-methyl-N-(phenylmethyl)-3-piperidinecarboxamide. The combined mixture was filtered through celite, and rinsed with EtOAc (50 mL). The filtrate was concentrated in vacuo, and the resulting residue was partitioned between EtOAc (75 mL) and brine (20 mL). The organic was dried over Na$_2$SO$_4$, filtered and concentrated in vacuo. The residue was purified by silica gel column chromatography using gradient elution of 1% A in CHCl$_3$ to 50% A in CHCl$_3$ (where A was a mixture of 800/80/3200 CH$_3$OH/NH$_4$OH/CHCl$_3$). Trituration of the purified material in a mixture of CHCl$_3$ (1 mL) and hexane (6 mL), and drying under vacuum at 65° C. afforded the title compound (312 mg) as a tan solid. LC-MS (ES) m/z=470 [M+H]$^+$. $^1$H NMR (400 MHz, CD$_3$OD): δ 1.30 (d, J=6.8 Hz, 3H), 1.75-1.90 (m, 3H), 1.97-2.10 (m, 1H), 2.42-2.54 (m, 1H), 2.59 (s, 3H), 2.97 (s, 3H), 3.10-3.20 (m, 1H), 4.42 (s, 2H), 4.60-4.70 (bs, 1H), 4.75-4.85 (bs, 1H), 6.49 (s, 1H), 7.25-7.37 (m, 5H), 7.65 (d, J=8.0 Hz, 1H), 7.78 (d, J=8.3 Hz, 1H), 8.02 (s, 1H).

Intermediate 127

4-Bromo-2,6-difluorobenzoic acid

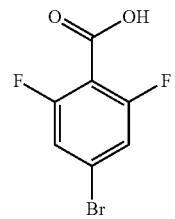

n-BuLi (220 mL, 550 mmol, 2.5 M) was added dropwise to a solution of diisopropylamine (61 g) in THF (500 mL) with stirring at −50° C. under N$_2$. After the addition, the reaction mixture was stirred at −50° C. for 15 minutes, and then warmed to 0° C. for 1 hour. The reaction was cooled to −50° C. and then a solution of 3,5-difluorobromobenzene (96 g, 0.5 mole) in THF (500 mL) was added dropwise. After the addition, the reaction mixture was stirred at −50° C. for 2 hours and then dry ice (about 200 g) was added portion-wise. The resulting mixture was warmed gradually to room temperature and stirred overnight. The mixture was concentrated under reduced pressure, and the resulting residue was partitioned between CH$_2$Cl$_2$ (1 L) and water (1 L). An aqueous NaOH solution was added to adjust the pH of the mixture to 10. The organic layer was discarded and the water phase was adjust the pH to 2 with HCl solution. The mixture was extracted with CH$_2$Cl$_2$ (3×400 mL), and the extracts were combined, dried over MgSO$_4$, filtered and evaporated under vacuum to provide the title compound (45 g) as a white solid.

$^1$H NMR (300 MHz, DMSO-d$_6$): δ 7.61 (m, 2H), 14.1 (bs, 1H).

Intermediate 128

4-Bromo-2,6-difluorobenzamide

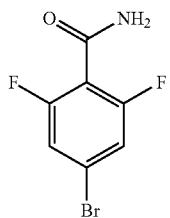

To a mixture of 4-bromo-2,6-difluorobenzoic acid (110 g) and triethylamine (65 g) in THF (1.5 L) at −50° C. was added ethylchloroformate (60 g) dropwise. After the addition, the reaction mixture was warmed to 0° C. and stirred at this temperature for 1 hour. Ammonia (2 L, 0.5 M in 1,4-dioxane) was added dropwise, and the reaction mixture was stirred overnight at room temperature. The mixture was concentrated, and the resulting residue was partitioned between 1N HCl aqueous solution (2 L) and $CH_2Cl_2$ (1 L). The resulting solid was filtered and washed with $CH_2Cl_2$ to afford the title compound (60 g). The organic layer of the filtrate was separated, dried over $MgSO_4$, filtered and evaporated under vacuum to afford another portion of the title compound (50 g). $^1$H NMR (300 MHz, DMSO-$d_6$): δ 7.56 (m, 2H), 7.91 (s, 1H), 8.15 (s, 1H).

Intermediate 129

4-Bromo-2,6-difluorobenzonitrile

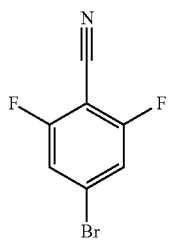

To a stirred solution of 4-bromo-2,6-difluorobenzamide (9 5 g) in DMF (1 L) at 0° C. was added cyanuric chloride (82 g) slowly, and the reaction mixture was stirred at 0° C. for 4 hours. Water (5 L) was added slowly to the reaction, and it was extracted with EtOAc (2 L). The organic layer was separated, dried over $MgSO_4$, filtered and evaporated under vacuum to afford the crude product, which was purified by chromatography ($SiO_2$, 300-400 mesh, petroleum ether:EtOAc=200:1) to provide 47 g of pure title compound and 17 g of impure title compound. $^1$H NMR (300 MHz, DMSO-$d_6$): δ 7.90 (m, 2H).

Intermediate 130

2,6-Difluoro-4-(4,4,5,5-tetramethyl-1,3,2-dioxaborolan-2-yl)benzonitrile

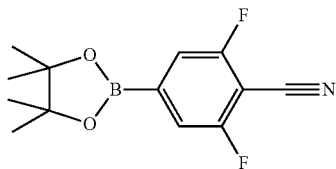

A mixture of 4-bromo-2,6-difluorobenzonitrile (40 g), potassium acetate (36 g), bis[(pinacolato)]diboron (51 g, 1.1 eq) and Pd(dppf)Cl$_2$ (3.0 g, 0.02 eq) in 1,4-dioxane (500 mL) and DMSO (10 mL) was degassed and then re-charged with nitrogen for 3 times, and then the mixture was heated at 100° C. overnight under N$_2$. The reaction mixture was evaporated under vacuum, and the resulting residue was cooled with ice. 2N sodium hydroxide (1 L) solution was added at 0° C., and the resulting mixture was stirred at this temperature for 20 minutes. The mixture was filtered, and the filtrate was washed with diethyl ether (1 L). The aqueous layer was adjusted to pH 5 with 5 N hydrochloric acid at 0° C., and the resulting solid was collected and dissolved in EtOAc (1 L). The resulting organic solution was dried over $MgSO_4$, filtered and evaporated under vacuum to provide 35 g of crude product. The filtrate was extracted with EtOAc, and the EtOAc layer was dried over $MgSO_4$, filtered and evaporated under vacuum to provide another 3 g of crude product. The combined 38 g of crude product was further purified by distillation under reduced pressure (130° C./2 mmHg)) to afford the title compound (25 g) as a white solid.
$^1$H NMR (400 MHz, DMSO-$d_6$): δ 1.31 (s, 12H), 7.49 (m, 2H).

Intermediate 131

(4-Cyano-3,5-difluorophenyl)boronic acid

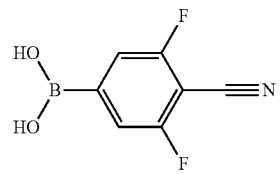 [SMILES: N#Cc1c(F)cc(B(O)O)cc1F]

2,6-Difluoro-4-(4,4,5,5-tetramethyl-1,3,2-dioxaborolan-2-yl)benzonitrile (55 g) was dissolved in acetone (1 L) and water (1 L). T this stirred mixture was added NaIO$_4$ (160 g) and NH$_4$OAc (50 g). The reaction mixture was stirred at room temperature overnight and then filtered. The filtrate was evaporated under vacuum at 40° C. until most of acetone was removed. The residue was cooled to 0° C. and 2N NaOH (1 L) solution was added with stirring over 30 minutes. The mixture was filtered, and the filtrate was washed with $CH_2Cl_2$ (1 L). To the aqueous layer was added 5N hydrochloric acid at 0° C. until pH=2. The resulting solid was filtered and then dissolved in EtOAc (1.5 L), dried over Na$_2$SO$_4$, filtered and evaporated under vacuum to provide 30 g of the title compound as a white solid.

Intermediate 132

(3S,6R)-1-[6-(4-Cyano-3,5-difluorophenyl)-2-(methylamino)-4-pyrimidinyl]-N-cyclohexyl-6-methyl-3-piperidinecarboxamide

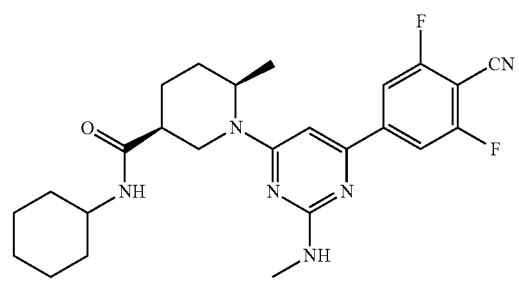 [SMILES: CNc1nc(-c2cc(F)c(C#N)c(F)c2)cc(N2C[C@@H](C(=O)NC3CCCCC3)CC[C@H]2C)n1]

(3S,6R)-1-[6-Chloro-2-(methylamino)-4-pyrimidinyl]-N-cyclohexyl-6-methyl-3-piperidinecarboxamide (600 mg, 1.64 mmol) and (4-cyano-3,5-difluorophenyl)boronic acid (390 mg, 2.13 mmol, 1.3 equiv), Pd$_2$(dba)$_3$ (113 mg, 0.12 mmol, 0.075 equiv), tricyclohexylphosphine (69 mg, 0.246 mmol, 0.15 equiv), and K$_3$PO$_4$ (592 mg, 2.79 mmol, 1.7 equiv) were charged to a seal tube, followed by addition of 1,4-dioxane (12 mL) and water (4 mL). The mixture was bubbled with argon for 10 minutes, capped and heated at 100°

C. for 20 hours. The mixture was filtered through celite, and the filtrate was concentrated in vacuo. The resulting residue was partitioned between EtOAc (50 mL) and brine (15 mL), and the organic layer was dried over Na$_2$SO$_4$, filtered, and concentrated in vacuo. Purification by silica gel column chromatography using gradient elution of 1% EtOAc in CHCl$_3$ to 100% EtOAc afforded the title compound (490 mg). LC-MS (ES) m/z=469 [M+H]$^+$.

Example 85

(3S,6R)-1-[6-(3-Amino-4-fluoro-1H-indazol-6-yl)-2-(methylamino)-4-pyrimidinyl]-N-cyclohexyl-6-methyl-3-piperidinecarboxamide

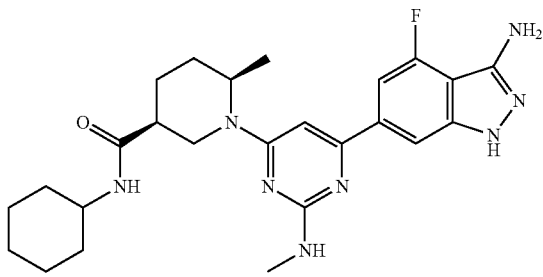 [SMILES: CNc1nc(-c2cc(F)c3c(N)n[nH]c3c2)cc(N2C[C@@H](C(=O)NC3CCCCC3)CC[C@H]2C)n1]

(3S,6R)-1-[6-(4-Cyano-3,5-difluorophenyl)-2-(methylamino)-4-pyrimidinyl]-N-cyclohexyl-6-methyl-3-piperidinecarboxamide (480 mg, 1.02 mmol) was chased with EtOH to remove traces of EtOAc, and taken up as a suspension in 25 mL of EtOH. To the mixture was added hydrazine monohydrate (1.5 mL) at room temperature in one portion, and the reaction mixture was heated at 100° C. for 20 hours. After cooling to room temperature, the mixture was filtered through celite, and the filtrate was concentrated in vacuo. The resulting residue was suspended in water (10 mL) and filtered. The solids were dried under vacuum at room temperature for 24 hours, followed by washing with hexane. Drying under vacuum at 65° C. for 20 hours afforded the title compound (438 mg) as a cream-colored powder. LC-MS (ES) m/z=481 [M+H]$^+$. $^1$H NMR (400 MHz, CD$_3$OD): δ 1.16-1.34 (m, 3H), 1.29 (d, J=6.8 Hz, 3H), 1.34-1.50 (m, 2H), 1.62-1.71 (m, 2H), 1.72-1.84 (m, 5H), 1.84-1.95 (m, 2H), 1.96-2.06 (m, 1H), 2.32-3.43 (m, 1H), 2.96 (s, 3H), 3.05-3.17 (m, 1H), 3.60-3.72 (m, 1H), 4.47-4.65 (bs, 1H), 4.75-4.90 (bs, 1H), 6.45 (s, 1H), 7.20 (d, J=11.9 Hz, 1H), 7.67 (s, 1H).

Intermediate 133

(3S,6R)-1-[6-(4-Cyano-3,5-difluorophenyl)-2-(methylamino)-4-pyrimidinyl]-6-methyl-N-(phenylmethyl)-3-piperidinecarboxamide

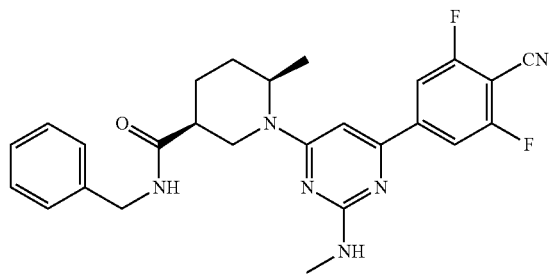 [SMILES: CNc1nc(-c2cc(F)c(C#N)c(F)c2)cc(N2C[C@@H](C(=O)NCc3ccccc3)CC[C@H]2C)n1]

(3S,6R)-1-[6-Chloro-2-(methylamino)-4-pyrimidinyl]-6-methyl-N-(phenylmethyl)-3-piperidinecarboxamide (500 mg, 1.34 mmol) and (4-cyano-3,5-difluorophenyl)boronic acid (318 mg, 1.74 mmol, 1.3 equiv), Pd$_2$(dba)$_3$ (92 mg, 0.10 mmol, 0.075 equiv), tricyclohexylphosphine (56 mg, 0.20 mmol, 0.15 equiv), and K$_3$PO$_4$ (483 mg, 2.27 mmol, 1.7 equiv) were charged to a 30 mL microwave vial, followed by addition of 1,4-dioxane (10 mL) and water (3.3 mL). The mixture was bubbled with argon for 10 minutes, and heated at 100° C. for 20 hours. After cooling to room temperature, the mixture was filtered through celite, and the filtrate was concentrated in vacuo. The resulting residue was partitioned between EtOAc (50 mL) and brine (15 mL), and the organic layer was dried over Na$_2$SO$_4$, filtered, and concentrated in vacuo. Purification by silica gel column chromatography using gradient elution of 1% EtOAc in CHCl$_3$ to 100% EtOAc afforded the title compound (470 mg) as a yellow/greenish gum. LC-MS (ES) m/z=477 [M+H]$^+$.

Example 86

(3S,6R)-1-[6-(3-Amino-4-fluoro-1H-indazol-6-yl)-2-(methylamino)-4-pyrimidinyl]-6-methyl-N-(phenylmethyl)-3-piperidinecarboxamide

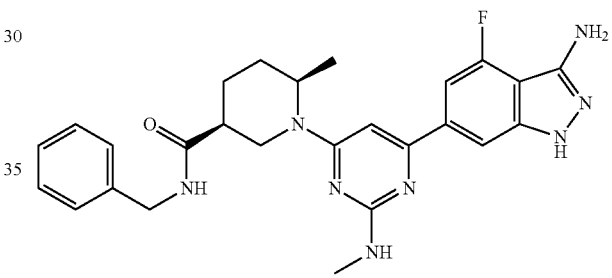

(3S,6R)-1-[6-(4-Cyano-3,5-difluorophenyl)-2-(methylamino)-4-pyrimidinyl]-6-methyl-N-(phenylmethyl)-3-piperidinecarboxamide (460 mg, 0.97 mmol) was chased with EtOH to remove traces of EtOAc, and the resulting residue was taken up as a suspension in 20 mL of EtOH. To the mixture was added hydrazine monohydrate (2.0 mL) at room temperature in one portion, and the reaction mixture was heated at 100° C. under a gentle reflux for 20 hours. After cooling to room temperature, the mixture was filtered, and the filtrate was concentrated in vacuo. The resulting residue was suspended in water (10 mL) and filtered. Purification by silica gel column chromatography using gradient of 1% A in CHCl$_3$ to 70% A in CHCl$_3$ (where A was a mixture of 200/80/800 CH$_3$OH/NH$_4$OH/CHCl$_3$), and trituration of the residue collected from the chromatography in a mixture of CHCl$_3$ (2 mL), MTBE (2 mL) and hexane (4 mL) afforded the title compound (318 mg) as a pale yellow solid. LC-MS (ES) m/z=489 [M+H]$^+$. $^1$H NMR (400 MHz, CD$_3$OD): δ 1.30 (d, J=6.8 Hz, 3H), 1.74-1.88 (m, 3H), 1.98-2.10 (m, 1H), 2.42-2.52 (m, 1H), 2.96 (s, 3H), 3.10-3.19 (m, 1H), 4.42 (s, 2H), 4.55-4.70 (bs, 1H), 4.75-4.90 (bs, 1H), 6.46 (s, 1H), 7.18-7.37 (m, 6H), 7.67 (s, 1H).

Intermediate 134

1-(1,1-dimethylethyl) 3-ethyl 2-chloro-5-methyl-1H-pyrrole-1,3-dicarboxylate

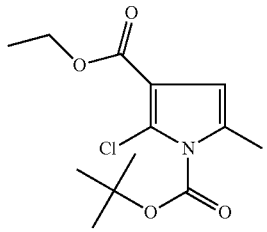 [SMILES: CCOC(=O)c1cc(C)n(C(=O)OC(C)(C)C)c1Cl]

To a stirred solution of ethyl 2-chloro-5-methyl-1H-pyrrole-3-carboxylate (11 g, 58.6 mmol) and DMAP (358 mg, 2.93 mmol, 0.05 equiv) in $CH_3CN$ (77 mL) at room temperature was added $(Boc)_2O$ (14.07 g, 64.5 mmol) in one portion. The mixture gradually turned from a suspension to a clear pinkish solution. The mixture was stirred at room temperature for 1 hour. LCMS showed conversion complete. The mixture was concentrated in vacuo to give an oil. This material was combined with the crude from another run starting with 1 g of ethyl 2-chloro-5-methyl-1H-pyrrole-3-carboxylate. The combined mixture was concentrated in vacuo, and the resulting residue was partitioned between $CH_2Cl_2$ (150 mL) and water (30 mL). The organic was dried over $MgSO_4$, filtered and concentrated in vacuo to give an oil (20 g). This crude was passed through a silica gel column, eluting with 10% EtOAc, to afford, after concentration in vacuo, 18 g of the title compound as a clear oil. LC-MS (ES) m/z=288 $[M+H]^+$.

Intermediate 135

1-(1,1-Dimethylethyl) 3-ethyl 5-methyl-1,3-pyrrolidinedicarboxylate

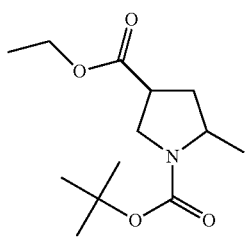 [SMILES: CCOC(=O)C1CC(C)N(C(=O)OC(C)(C)C)C1]

1-(1,1-Dimethylethyl) 3-ethyl 2-chloro-5-methyl-1H-pyrrole-1,3-dicarboxylate (3 g, 10.4 mmol) in 30 mL of EtOH was added to a slurry of 5% Pt/C (Degussa type, 0.5 g) in 10 mL of EtOH under nitrogen in a small Parr Bottle. The mixture was hydrogenated under a hydrogen pressure of 60 psi at room temperature. LCMS samples were taken at 1.5 h and 5.5 h. It was not complete. Hydrogenation at room temperature under 60 psi was continued for another 18 h. LCMS showed there was still 21% starting material left, and the product was mostly the dechloro-analog at M+H+ at 254 (the pyrrole ring was untouched). The mixture was flushed with $N_2$ 3× and filtered through microdisc filters. The filtrate was treated with 1 g of Darco and stirred in a warm water bath (60° C.) for a few minutes, and was filtered. The filtrate was combined with the material below for another hydrogneation run.

1-(1,1-Dimethylethyl) 3-ethyl 2-chloro-5-methyl-1H-pyrrole-1,3-dicarboxylate (15 g) was dissolved in 100 mL of EtOH, treated with 3 g of Darco and warmed in a water bath (60° C.) for 5 min. The mixture was filtered. The filtrate was combined with the material above and conc in vacuo to about 100 mL. This mixture was added to a slurry of 4.5 g of 5% Pt/C in 10 mL of EtOH in a Parr Bottle under $N_2$. The mixture was hydrogenated under 60 psi at rt for 18 h. LCMS showed still presence of the dechloro derivative. The mixture was filtered through celite. The filtrate was treated with 4 g of Darco and filtered again. The filtrate was conc on vacuo to give a clear oil (17 g). NMR confirmed the presence of the dechloro product as 2 aromatic signals were detected. The ratio of the desired fully reduced product vs dechloro was 4/1 by NMR. The oil took on a pale yellowish color upon standing at room temperature for 30 min. This material was taken up in 200 mL of EtOH and subjected to hydrogenation again in the presence of 5 g of 5% Pt/C under 60 psi at room temperature for another 24 h. The hydrogen gas was removed and the mixture was stored over nitrogen at rt for 2 days.

LCMS showed no dechloropyrrole left. The mixture was filtered through celite and conc in vacuo to give the product (15.4 g). NMR showed there were some impurities, while LCMS could not tell. TLC showed 2 spots (silica gel, hexane/EtOAc (4/1)). A 1.5 g sample was chomatographed on silica. The more polar spot was the desired material (a mixture of cis and trans isomers, 0.75 g). Two 9 g chromatography runs were carried out using gradient elution from 1% EtOAc in hexane to 30% EtOAc in hexane to give 9.54 g of the title compound as an oil. Result from a previous small scale run suggested this was a 3:1 mixture of cis/trans isomers. LC-MS (ES) m/z=280 $[M+Na]^+$.

Intermediate 136

1-{[(1,1-Dimethylethyl)oxy]carbonyl}-5-methyl-3-pyrrolidinecarboxylic acid

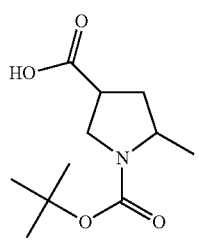 [SMILES: CC1CC(C(=O)O)CN1C(=O)OC(C)(C)C]

1-(1,1-Dimethylethyl) 3-ethyl 5-methyl-1,3-pyrrolidinedicarboxylate (1.0 g, 3.89 mmol, an estimated 3:1 mixture of cis/trans isomers) and $LiOH \cdot H_2O$ (228 mg, 5.44 mmol, 1.4 equiv) was stirred in THF (5 mL) and water (2 mL) as a two-phase mixture at room temperature for 18 hours. The mixture was concentrated in vacuo, and the resulting residue was taken up in 15 mL of water, acidified with cold 2N HCl, and extracted with 2×50 mL of EtOAc. The organic were dried over $Na_2SO_4$, filtered and concentrated in vacuo to afford the title compound (1.03 g) as an oil. LC-MS (ES) m/z=230 $[M+H]^+$.

Intermediate 137

1,1-Dimethylethyl 2-methyl-4-{[(phenylmethyl)amino]carbonyl}-1-pyrrolidinecarboxylate

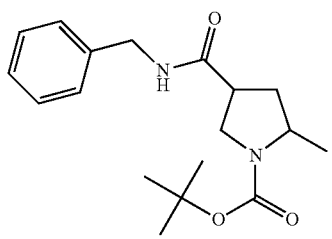 [SMILES: CC1CC(C(=O)NCc2ccccc2)CN1C(=O)OC(C)(C)C]

To a solution of 1-{[(1,1-dimethylethyl)oxy]carbonyl}-5-methyl-3-pyrrolidinecarboxylic acid (0.9 g, 3.93 mmol) in CH$_2$Cl$_2$ (15 mL) at room temperature was added Hunig's base (0.89 mL, 5.10 mmol, 1.3 equiv) and benzylamine (0.56 mL, 5.10 mmol, 1.3 equiv) in one portion. The resulting mixture was chilled in an ice bath, followed by addition of HATU (1.64 g, 4.32 mmol, 1.1 equiv) in one portion, and the reaction mixture was stirred in the ice bath for 30 minutes. The mixture was filtered through celite, and rinsed with CH$_2$Cl$_2$. The filtrate was washed with water and dried over Na$_2$SO$_4$, followed by filtration and concentration in vacuo. The resulting residue was purified by silica gel column chromatography resulting in 1.70 g of the title compound as an oil. The ratio of cis/trans isomers could not be determined. LC-MS (ES) m/z=319 [M+H]$^+$.

Intermediate 138

Cis-1-[6-chloro-2-(methylamino)-4-pyrimidinyl]-5-methyl-N-(phenylmethyl)-3-pyrrolidinecarboxamide

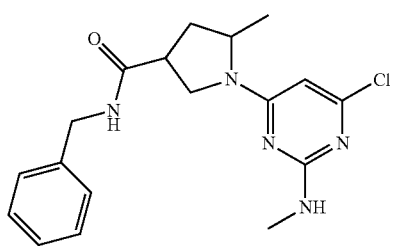 [SMILES: CNc1nc(Cl)cc(N2CC(C(=O)NCc3ccccc3)CC2C)n1]

To a stirred solution of 1,1-dimethylethyl 2-methyl-4-{[(phenylmethyl)amino]carbonyl}-1-pyrrolidinecarboxylate (3.93 mmol, theoretical, 1.70 g from above) in CH$_2$Cl$_2$ (6 mL) at room temperature was added TFA (2 mL, 26 mmol, 6.6 equiv) in one portion, and the resulting mixture was stirred at room temperature for 1 hour. LCMS showed Boc cleavage complete. The mixture was concentrated in vacuo to give an oil as the TFA salt. To this oil, dissolved in 1,4-dioxane (10 mL), was added water (8 mL), followed by NaHCO$_3$ (1.65 g, 19.65 mmol, 5 equiv). After foaming subsided, 4,6-dichloro-N-methyl-2-pyrimidinamine (0.80 g, 4.49 mmol, 1.14 equiv) was added in one portion, and the resulting mixture was heated in an oil bath at 100° C. under a gentle reflux for 20 hours. LCMS showed only a small amount of product formed. Checking of pH showed it was only 3 (using pH paper). To the mixture was added 5 mL of aqueous saturated NaHCO$_3$, and the mixture was heated at 100° C. for another 20 hours, resulting in a suspension. After cooling to room temperature, the suspension was filtered. The collected solids were washed with EtOAc, and dried under vacuum to give 644 mg of the title compound as the pure cis isomer. LC-MS (ES) m/z=360 [M+H]$^+$.

Intermediate 139

Cis-1-[6-(4-cyano-3-fluorophenyl)-2-(methylamino)-4-pyrimidinyl]-5-methyl-N-(phenylmethyl)-3-pyrrolidinecarboxamide

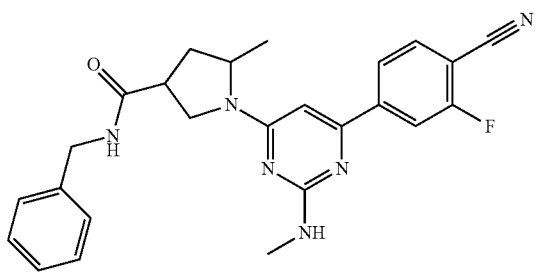 [SMILES: CNc1nc(-c2ccc(C#N)c(F)c2)cc(N2CC(C(=O)NCc3ccccc3)CC2C)n1]

Racemic (3S,5R)-1-[6-chloro-2-(methylamino)-4-pyrimidinyl]-5-methyl-N-(phenylmethyl)-3-pyrrolidinecarboxamide (100 mg, 0.28 mmol), (4-cyano-3-fluorophenyl)boronic acid (60 mg, 0.36 mmol, 1.3 equiv), tricyclohexylphosphine (12 mg, 0.043 mmol, 0.15 equiv), Pd$_2$(dba)$_3$ (20 mg, 0.022 mmol, 0.075 equiv) and K$_3$PO$_4$ (101 mg, 0.48 mmol, 1.7 equiv) were charged to a 20 mL microwave vial, followed by addition of 1,4-dioxane (3 mL) and water (1 mL). The mixture was bubbled with argon for 15 minutes, followed by capping and heating to 100° C. for 21 hours. This crude mixture was combined with another run starting with 300 mg of racemic (3S,5R)-1-[6-chloro-2-(methylamino)-4-pyrimidinyl]-5-methyl-N-(phenylmethyl)-3-pyrrolidinecarboxamide. The combined mixture was filtered through celite, and the cake was rinsed with EtOAc (100 mL). The filtrate was concentrated in vacuo, and the resulting residue was taken up in 25 mL of water, sonicated briefly, and filtered. The dark colored solids were washed with water, and dried under house vacuum for 1 hour. Attempt was made to dissolve these solids in CHCl$_3$, EtOAc, and CH$_3$OH, but there was always some residue left. The residue was checked by LCMS be the pure desired product. This dark colored residue was collected by filtration, and dissolved in CHCl$_3$ with a small amount of MeOH (2% by volume, total solvent used about 100 mL) to give a dark solution, which was filterd through celite. The filtrate was concentrated in vacuo, and the resulting yellowish residue was dried under vacuum to give 142 mg of the title compound. The above organic filtrate (combined CHCl$_3$, EtOAc and CH$_3$OH wash) was concentrated in vacuo. Trituration in EtOAc (6 mL) and drying under vacuum gave another 220 mg of the title compound.

The filtrate from the trituration underwent silica gel column chromatography using gradient elution of 1% A in CHCl$_3$ to 50% A in CHCl$_3$ (A was a mixture of 800/80/3200 CH$_3$OH/NH$_4$OH/CHCl$_3$), resulting in another 192 mg of the title compound as a light yellow residue. LC-MS (ES) m/z=445 [M+H]$^+$.

Example 87 cis-1-[6-(3-amino-1H-indazol-6-yl)-2-(methylamino)-4-pyrimidinyl]-5-methyl-N-(phenylmethyl)-3-pyrrolidinecarboxamide

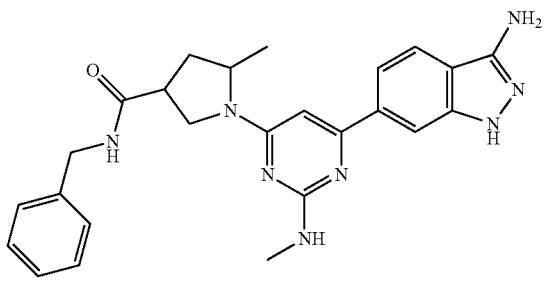 [SMILES: CNc1nc(-c2ccc3c(N)n[nH]c3c2)cc(N2CC(C(=O)NCc3ccccc3)CC2C)n1]

To a suspension of racemic (3S,5R)-1-[6-(4-cyano-3-fluorophenyl)-2-(methylamino)-4-pyrimidinyl]-5-methyl-N-(phenylmethyl)-3-pyrrolidinecarboxamide (360 mg total, 0.81 mmol) in EtOH (50 mL) at room temperature was added hydrazine monohydrate (2 mL) in one portion. The suspension was heated in an oil bath to 100° C. for 20 hours. LCMS showed there was still 40% starting material remaining. To the mixture was added 2 mL of hydrazine monohydrate, followed by heating to 100° C. for another 24 h. LCMS showed conversion complete. The mixture was cooled to room temperature, and filtered through celite. The filtrate was concentrated in vacuo, and the resulting residue was taken up in 8 mL of water to form a suspension, which was briefly sonicated. The mixture was filtered. The solids collected were combined with another run starting with 190 mg of racemic (3S,5R)-1-[6-(4-cyano-3-fluorophenyl)-2-(methylamino)-4-pyrimidinyl]-5-methyl-N-(phenylmethyl)-3-pyrrolidinecarboxamide. The combined crude products were purified by silica gel column chromatography using gradient elution of 1% A in CHCl$_3$ to 75% A in CHCl$_3$. A was a mixture of 800/80/3200 CH$_3$OH/NH$_4$OH/CHCl$_3$. Trituration of the purified material in a mixture of CHCl$_3$ (2 mL) and hexane (8 mL), followed by drying under vacuum at 65° C. for 14 hours afforded the title compound (228 mg) as a beige powder. LC-MS (ES) m/z=457 [M+H]$^+$. $^1$H NMR (400 MHz, CD$_3$OD): δ 1.42 (d, J=6.1 Hz, 3H), 2.00-2.06 (m, 1H), 2.52-2.58 (m, 1H), 2.99 (s, 3H), 3.00-3.10 (m, 1H), 3.68-3.73 (m, 1H), 3.95-4.10 (bs, 1H), 4.21-4.33 (bs, 1H), 4.39-4.47 (m, 2H), 6.23 (s, 1H), 7.25-7.37 (m, 5H), 7.52 (dd, J=8.5, 1.1 Hz, 1H), 7.75 (d, J=8.6 Hz, 1H), 7.85 (s, 1H).

Intermediate 140

3-Morpholinecarboxamide

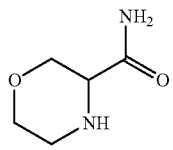

A mixture of 4-{[(1,1-dimethylethyl)oxy]carbonyl}-3-morpholinecarboxylic acid (2.86 g, 12.4 mmol), EDC (2.83 g, 14.7 mmol), and HOBt (1.25 g, 7.36 mmol) in DMF (50 mL) was stirred for about 5 minutes. Ammonium chloride (2.09 g, 39.1 mmol) and triethylamine (8.5 mL, 61.0 mmol) were then added, and the reaction was stirred at room temperature under nitrogen for 18 hours. The mixture was then poured into water (100 mL) and extracted with Et$_2$O (3×50 mL). The extracts were washed with brine (50 mL), dried (Na$_2$SO$_4$), filtered, and concentrated in vacuo. The combined aqueous layers were further extracted with CH$_2$Cl$_2$ (3×75 mL), and the extracts were dried (Na$_2$SO$_4$), filtered, combined with the Et$_2$O extracts, and concentrated in vacuo. The residue was stirred in CH$_2$Cl$_2$ (50 mL) and TFA (10 mL) at room temperature for one hour, then concentrated in vacuo. Et$_2$O was added and the mixture was stirred vigorously for 3 days. The precipitate was collected by vacuum filtration to give a TFA salt of the title compound (2.31 g, ca. 90% pure) as a white solid. LC-MS (ES) m/z=131 [M+H]$^+$.

Intermediate 141

4-(2-Amino-6-chloro-4-pyrimidinyl)-3-morpholinecarboxamide

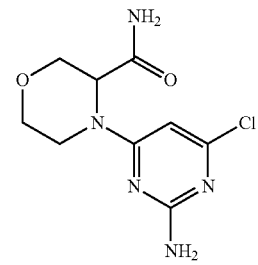 [SMILES: NC(=O)C1COCCN1c1cc(Cl)nc(N)n1]

A mixture of 3-morpholinecarboxamide (830 mg, 3.40 mmol), 2-amino-4,6-dichloropyrimidine (502 mg, 3.06 mmol), and Hunig's base (1.6 mL, 9.16 mmol) in CH$_3$CN (12 mL) was stirred at 100° C. in a sealed tube for 40 hours. The mixture was diluted with EtOAc (100 mL), and washed with saturated aqueous NaHCO$_3$ (2×50 mL) and brine (50 mL). The combined aqueous phases were further extracted with CH$_2$Cl$_2$ (3×50 mL) and EtOAc (3×50 mL). All of the organic phases were combined, dried (Na$_2$SO$_4$), filtered, and concentrated in vacuo. The residue was purified by silica gel chromatography (34 g SiO$_2$, CH$_2$Cl$_2$ to 90/10/1 CH$_2$Cl$_2$/CH$_3$OH/NH$_4$OH gradient) to give the title compound (394 mg) as a white solid. LC-MS (ES) m/z=258, 260 [M+H]$^+$.

Intermediate 142

4-[2-Amino-6-(4-cyano-3-fluorophenyl)-4-pyrimidinyl]-3-morpholinecarboxamide

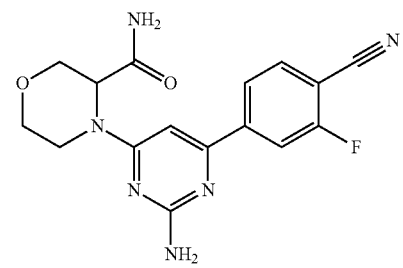 [SMILES: N#Cc1ccc(-c2cc(N3CCOCC3C(N)=O)nc(N)n2)cc1F]

A mixture of 4-(2-amino-6-chloro-4-pyrimidinyl)-3-morpholinecarboxamide (390 mg, 1.51 mmol), Pd(PPh$_3$)$_4$ (91 mg, 0.08 mmol), and (4-cyano-3-fluorophenyl)boronic acid (285 mg, 1.73 mmol) in 1,4-dioxane (6 mL) and saturated aqueous NaHCO$_3$ (2 mL) was stirred at 95° C. under argon in a sealed tube for 18 hours. The mixture was cooled, quenched with saturated aqueous NaHCO$_3$ (25 mL) and extracted with EtOAc (3×25 mL). The extracts were washed with brine (50 mL), dried (Na$_2$SO$_4$), filtered, and concentrated in vacuo. The residue was purified by silica gel chromatography (34 g, SiO$_2$, CH$_2$Cl$_2$ to 90/10/1 CH$_2$Cl$_2$/CH$_3$OH/NH$_4$OH gradient) to give the title compound (360 mg) as a white solid. LC-MS (ES) m/z=343 [M+H]$^+$.

Example 88

4-[2-Amino-6-(3-amino-1H-indazol-6-yl)-4-pyrimidinyl]-3-morpholinecarboxamide

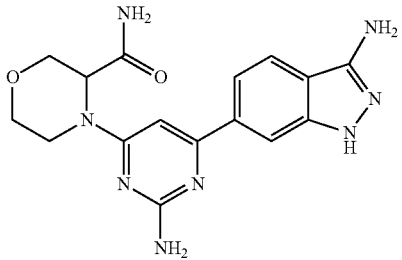 [SMILES: NC(=O)C1COCCN1c1cc(-c2ccc3c(N)n[nH]c3c2)nc(N)n1]

A mixture of 4-[2-amino-6-(4-cyano-3-fluorophenyl)-4-pyrimidinyl]-3-morpholinecarboxamide (360 mg, 1.05 mmol) and hydrazine monohydrate (2.58 mL, 52.6 mmol) in ethanol (10 mL) was stirred at 90° C. in a sealed tube for 16 hours. The mixture was cooled and diluted with water. Attempts to extract the product from the water using 90/10 CH$_2$Cl$_2$/IPA were unsuccessful, so the aqueous phase was combined with the residue from the concentrated CH$_2$Cl$_2$/IPA extractions and the mixture was concentrated in vacuo. The residue was purified by silica gel chromatography (68 g SiO$_2$, CHCl$_3$ to 80/20/2 CHCl$_3$/CH$_3$OH/NH$_4$OH gradient with a 10 minute hold at 90/10/1 CHCl$_3$/CH$_3$OH/NH$_4$OH) to give the title compound (40 mg) as an off-white solid. LC-MS (ES) m/z=355 [M+H]$^+$. $^1$H NMR (400 MHz, DMSO-d$_6$): δ 3.29-3.41 (m, 1H), 3.41-3.50 (m, 1H), 3.61 (dd, J=11.6, 3.5 Hz, 1H), 3.85-3.93 (m, 1H), 3.99-4.18 (bs, 1H), 4.35 (d, J=11.6 Hz, 1H), 4.82-5.08 (bs, 1H), 5.39 (s, 2H), 6.12 (s, 2H), 6.55 (s, 1H), 7.19 (s, 1H), 7.35 (s, 1H), 7.57 (d, J=8.3 Hz, 1H), 7.72 (d, J=8.6 Hz, 1H), 7.95 (s, 1H), 11.54 (s, 1H).

Intermediate 143

[(2S,5R)-4-(2-Amino-6-chloro-4-pyrimidinyl)-5-methyl-2-morpholinyl]methyl methanesulfonate

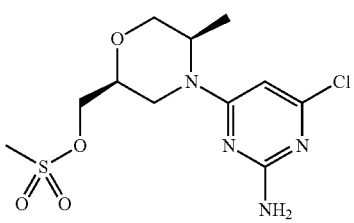 [SMILES: C[C@@H]1CO[C@H](COS(C)(=O)=O)CN1c1cc(Cl)nc(N)n1]

Triethylamine (0.65 mL, 4.69 mmol) and methanesulfonyl chloride (0.34 mL, 4.36 mmol) were added dropwise to a solution of [(2S,5R)-4-(2-amino-6-chloro-4-pyrimidinyl)-5-methyl-2-morpholinyl]methanol (1.00 g, 3.88 mmol) in CH$_2$Cl$_2$ (35 mL), and the mixture was stirred at room temperature under nitrogen. After 75 minutes another portion each of triethylamine (0.16 mL, 1.16 mmol) and methanesulfonyl chloride (0.076 mL, 0.97 mmol) were added dropwise and stirring continued for an additional 30 minutes. The reaction mixture was then poured into saturated aqueous NaHCO$_3$ (100 mL) and extracted with CH$_2$Cl$_2$ (3×75 mL). The extracts were dried (Na$_2$SO$_4$), filtered, and concentrated in vacuo to give the title compound (1.53 g, about 85% purity) as a white foam. LC-MS (ES) m/z=337, 339 [M+H]$^+$.

Intermediate 144

4-[(2S,5R)-2-(Azidomethyl)-5-methyl-4-morpholinyl]-6-chloro-2-pyrimidinamine


A mixture of crude [(2S,5R)-4-(2-amino-6-chloro-4-pyrimidinyl)-5-methyl-2-morpholinyl]methyl methanesulfonate (1.53 g, about 85% pure, 3.88 mmol) and sodium azide (0.382 g, 5.88 mmol) in DMF (75 mL) was stirred at 80° C. under nitrogen for 20.5 hours. Another portion of sodium azide (0.094 g, 1.45 mmol) was then added and stirring continued at 80° C. for an additional 6.5 hours. The mixture was then cooled, diluted with EtOAc (200 mL), washed with water (2×150 mL) and brine (1×150 mL), dried (Na$_2$SO$_4$), filtered, and concentrated in vacuo. The residue was purified by flash chromatography (60 g SiO$_2$, 1:1 hexanes/CH$_2$Cl$_2$ to 45:45:10 hexanes/CH$_2$Cl$_2$/CH$_3$CN gradient) to give the title compound (890 mg) as a thick colorless oil. LC-MS (ES) m/z=284, 286 [M+H]$^+$.

Intermediate 145

4-[(2R,5R)-2-(Aminomethyl)-5-methyl-4-morpholinyl]-6-chloro-2-pyrimidinamine


A suspension of 4-[(2S,5R)-2-(azidomethyl)-5-methyl-4-morpholinyl]-6-chloro-2-pyrimidinamine (890 mg, 3.14 mmol) and 10% Pd/C (95 mg, 0.09 mmol) in ethanol (35 mL) was stirred under an atmosphere of hydrogen for 1.5 hours,

Intermediate 146

4-{2-Amino-6-[(2R,5R)-2-(aminomethyl)-5-methyl-4-morpholinyl]-4-pyrimidinyl}-2-fluorobenzonitrile

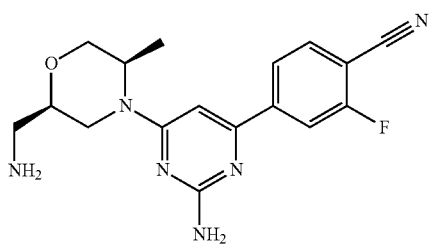 [SMILES: C[C@@H]1CO[C@H](CN)CN1c1cc(-c2ccc(C#N)c(F)c2)nc(N)n1]

A mixture of 4-[(2R,5R)-2-(aminomethyl)-5-methyl-4-morpholinyl]-6-chloro-2-pyrimidinamine (0.809 g, 3.14 mmol) and (4-cyano-3-fluorophenyl)boronic acid (1.038 g, 6.29 mmol) in 1,4-dioxane (30 mL) and saturated aqueous NaHCO$_3$ (10 mL) was degassed with nitrogen for 10 minutes. Pd(PPh$_3$)$_4$ (0.185 g, 0.16 mmol) was then added and the mixture was stirred at reflux under nitrogen for 16 hours. The mixture was then cooled and slowly quenched with 1 M HCl (75 mL), then washed with EtOAc (2×75 mL). The aqueous phase was then neutralized with saturated aqueous NaHCO$_3$, brought to about pH 10 with saturated aqueous Na$_2$CO$_3$, and then extracted with 90/10 CH$_2$Cl$_2$/IPA (3×100 mL). The extracts were dried (Na$_2$SO$_4$), filtered, and concentrated in vacuo. The residue was purified by flash chromatography (40 g SiO$_2$, CH$_2$Cl$_2$ to 90/10/1 CH$_2$Cl$_2$/CH$_3$OH/NH$_4$OH gradient). The product fractions were concentrated and azeotroped a few times with CH$_3$CN to give the title compound (642 mg) as a yellow solid. LC-MS (ES) m/z=343 [M+H]$^+$.

Intermediate 147

N-({(2R,5R)-4-[2-Amino-6-(4-cyano-3-fluorophenyl)-4-pyrimidinyl]-5-methyl-2-morpholinyl}methyl)benzamide

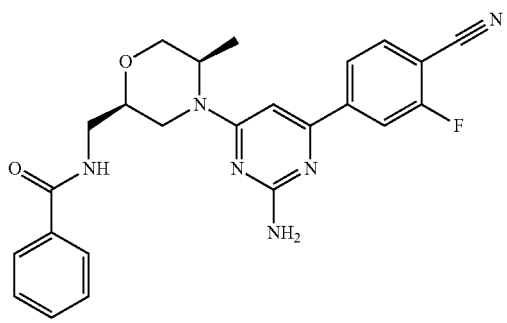 [SMILES: C[C@@H]1CO[C@H](CNC(=O)c2ccccc2)CN1c1cc(-c2ccc(C#N)c(F)c2)nc(N)n1]

Triethylamine (48 µL, 0.34 mmol) and benzoyl chloride (31 µL, 0.27 mmol) were added to a solution of 4-{2-amino-6-[(2R,5R)-2-(aminomethyl)-5-methyl-4-morpholinyl]-4-pyrimidinyl}-2-fluorobenzonitrile (77 mg, 0.23 mmol) in THF (5 mL), and the mixture was stirred at room temperature under nitrogen for 30 minutes. The mixture was quenched with saturated aqueous NaHCO$_3$ (15 mL) and extracted with EtOAc (2×10 mL). The extracts were washed with brine (10 mL), dried (Na$_2$SO$_4$), filtered, and concentrated in vacuo to give the title compound (115 mg) as a yellow glass. LC-MS (ES) m/z=447 [M+H]$^+$.

Example 89

N-({(2R,5R)-4-[2-Amino-6-(3-amino-1H-indazol-6-yl)-4-pyrimidinyl]-5-methyl-2-morpholinyl}methyl)benzamide

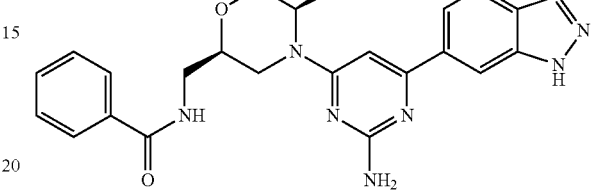

A mixture of crude N-({(2R,5R)-4-[2-amino-6-(4-cyano-3-fluorophenyl)-4-pyrimidinyl]-5-methyl-2-morpholinyl}methyl)benzamide (0.23 mmol theoretical) and hydrazine monohydrate (0.25 mL, 5.14 mmol) in ethanol (3 mL) was stirred at 100° C. in a sealed tube for 15 hours. The mixture was cooled, poured into saturated aqueous NaHCO$_3$ (15 mL), and extracted with EtOAc (2×10 mL). The extracts were washed with brine (10 mL), dried (Na$_2$SO$_4$), filtered, and concentrated in vacuo. The residue was purified on a Gilson reverse phase HPLC (CH$_3$CN/water with 0.1% TFA). The product fractions were concentrated in vacuo, taken up in a small amount of CH$_3$OH, and added to saturated aqueous NaHCO$_3$ (25 mL). That mixture was extracted with 90/10 CH$_2$Cl$_2$/IPA (3×25 mL), and the extracts were dried (Na$_2$SO$_4$), filtered, and concentrated in vacuo to afford the title compound (47 mg) as a pale yellow solid. LC-MS (ES) m/z=459 [M+H]$^+$. $^1$H NMR (400 MHz, DMSO-d$_6$): δ 1.19 (d, J=6.8 Hz, 3H), 2.73-2.91 (m, 1H), 3.39-3.55 (m, 2H), 3.57-3.71 (m, 2H), 3.73-3.83 (m, 1H), 4.08-4.74 (bs, 2H), 5.39 (s, 2H), 6.14 (s, 2H), 6.57 (s, 1H), 7.45-7.51 (m, 2H), 7.51-7.60 (m, 2H), 7.72 (d, J=8.6 Hz, 1H), 7.90 (d, J=7.6 Hz, 2H), 7.95 (s, 1H), 8.68 (t, J=5.5 Hz, 1H), 11.53 (s, 1H).

Intermediate 148

N-({(2S,5R)-4-[2-Amino-6-(4-cyano-3-fluorophenyl)-4-pyrimidinyl]-5-methyl-2-morpholinyl}methyl)benzenesulfonamide

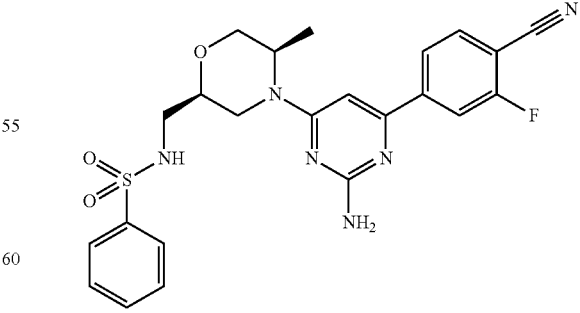

Triethylamine (0.05 mL, 0.36 mmol) and benzenesulfonyl chloride (0.04 mL, 0.31 mmol) were added to a solution of 4-{2-amino-6-[(2R,5R)-2-(aminomethyl)-5-methyl-4-morpholinyl]-4-pyrimidinyl}-2-fluorobenzonitrile (99 mg, 0.29 mmol) in THF (3 mL), and the mixture was stirred at room Example 90

N-({(2S,5R)-4-[2-Amino-6-(3-amino-1H-indazol-6-yl)-4-pyrimidinyl]-5-methyl-2-morpholinyl}methyl)benzenesulfonamide

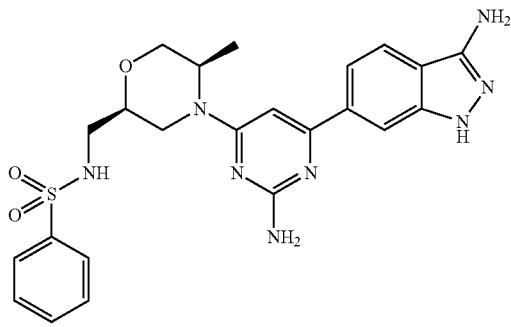 [SMILES: C[C@@H]1CO[C@H](CNS(=O)(=O)c2ccccc2)CN1c1cc(-c2ccc3c(N)n[nH]c3c2)nc(N)n1]

A mixture of crude N-({(2S,5R)-4-[2-amino-6-(4-cyano-3-fluorophenyl)-4-pyrimidinyl]-5-methyl-2-morpholinyl}methyl)benzenesulfonamide (0.29 mmol theoretical) and hydrazine monohydrate (0.28 mL, 5.78 mmol) in ethanol (3 mL) was stirred at 100° C. in a sealed tube for 17 hours. The mixture was concentrated in vacuo and the residue was purified on a Gilson reverse phase HPLC (CH$_3$CN/water with 0.1% TFA). The product fractions were combined and concentrated in vacuo, taken up in EtOAc (15 mL) and a little CH$_3$OH, washed with saturated aqueous NaHCO$_3$ (2×10 mL) and brine (10 mL), then dried (Na$_2$SO$_4$), filtered, and concentrated in vacuo to afford the title compound (59 mg) as a pale yellow solid. LC-MS (ES) m/z=495 [M+H]$^+$. $^1$H NMR (400 MHz, DMSO-d$_6$): δ 1.12 (d, J=6.3 Hz, 3H), 2.65-2.80 (m, 1H), 2.86-3.04 (m, 2H), 3.34-3.43 (m, 1H), 3.47-3.59 (m, 1H), 3.65-3.75 (m, 1H), 3.85-4.75 (bs, 2H), 5.39 (s, 2H), 6.13 (s, 2H), 6.52 (s, 1H), 7.56 (dd, J=8.6, 1.0 Hz, 1H), 7.58-7.68 (m, 3H), 7.69-7.74 (m, 1H), 7.85 (dd, J=7.6, 1.7 Hz, 2H), 7.88-7.97 (m, 2H), 11.53 (s, 1H).

Intermediate 149

N-({(2R,5R)-4-[2-Amino-6-(4-cyano-3-fluorophenyl)-4-pyrimidinyl]-5-methyl-2-morpholinyl}methyl)-2,2-dimethylpropanamide

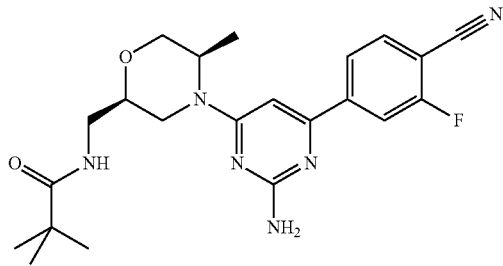 [SMILES: C[C@@H]1CO[C@H](CNC(=O)C(C)(C)C)CN1c1cc(-c2ccc(C#N)c(F)c2)nc(N)n1]

Triethylamine (0.05 mL, 0.36 mmol) and pivaloyl chloride (0.04 mL, 0.33 mmol) were added to a solution of 4-{2-amino-6-[(2R,5R)-2-(aminomethyl)-5-methyl-4-morpholinyl]-4-pyrimidinyl}-2-fluorobenzonitrile (99 mg, 0.29 mmol) in THF (5 mL), and the mixture was stirred at room temperature under nitrogen for 45 minutes. The mixture was quenched with saturated aqueous NaHCO$_3$ (10 mL) and extracted with EtOAc (2×10 mL). The extracts were washed with brine (15 mL), dried (Na$_2$SO$_4$), filtered, and concentrated in vacuo to give the title compound as a yellow oil. LC-MS (ES) m/z=483 [M+H]$^+$.

Example 91

N-({(2R,5R)-4-[2-Amino-6-(3-amino-1H-indazol-6-yl)-4-pyrimidinyl]-5-methyl-2-morpholinyl}methyl)-2,2-dimethylpropanamide

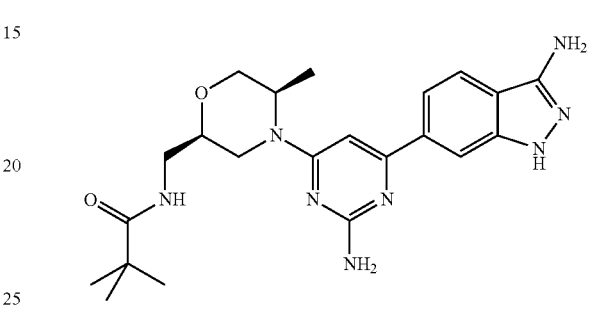

A mixture of crude N-({(2R,5R)-4-[2-amino-6-(4-cyano-3-fluorophenyl)-4-pyrimidinyl]-5-methyl-2-morpholinyl}methyl)-2,2-dimethylpropanamide (0.29 mmol theoretical) and hydrazine monohydrate (0.28 mL, 5.78 mmol) in ethanol (3 mL) was stirred at 100° C. in a sealed tube for 17 hours. The mixture was concentrated in vacuo and the residue was purified on a Gilson reverse phase HPLC (CH$_3$CN/water with 0.1% TFA). The product fractions were combined and concentrated in vacuo, taken up in EtOAc (15 mL), washed with saturated aqueous NaHCO$_3$ (2×10 mL) and brine (10 mL), then dried (Na$_2$SO$_4$), filtered, and concentrated in vacuo to afford the title compound (81 mg) as a pale yellow solid. LC-MS (ES) m/z=439 [M+H]$^+$. $^1$H NMR (400 MHz, DMSO-d$_6$): δ 1.13 (s, 9H), 1.17 (d, J=6.6 Hz, 3H), 2.64-2.84 (m, 1H), 3.20-3.30 (m, 2H), 3.42-3.52 (m, 1H), 3.63 (dd, J=11.4, 2.5 Hz, 1H), 3.77 (d, J=11.1 Hz, 1H), 3.98-4.79 (bs, 2H), 5.39 (s, 2H), 6.12 (s, 2H), 6.50 (s, 1H), 7.53 (d, J=8.3 Hz, 1H), 7.63 (t, J=5.7 Hz, 1H), 7.71 (d, J=8.3 Hz, 1H), 7.93 (s, 1H), 11.53 (s, 1H).

Example 92

Methyl({(2R,5R)-4-[2-amino-6-(3-amino-1H-indazol-6-yl)-4-pyrimidinyl]-5-methyl-2-morpholinyl}methyl)carbamate

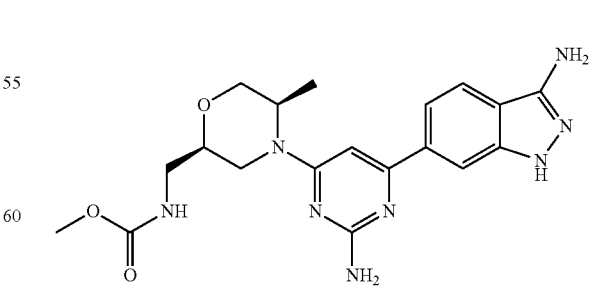

Methyl chloroformate (16 µL, 0.21 mmol) was added dropwise to a mixture of 4-{2-amino-6-[(2R,5R)-2-(aminomethyl)-5-methyl-4-morpholinyl]-4-pyrimidinyl}-2-fluorobenzonitrile (65 mg, 0.19 mmol) and triethylamine (40 µL, 0.29 mmol) in THF (2 mL), and the mixture was stirred at room temperature under nitrogen. After 1.5 hours another portion of methyl chloroformate (10 µL, 0.13 mmol) was added dropwise and stirring continued for 30 more minutes. The mixture was then quenched with saturated aqueous NaHCO₃ (10 mL) and extracted with EtOAc (2×10 mL). The extracts were washed with brine (15 mL), dried (Na₂SO₄), filtered, and concentrated in vacuo to give the methyl carbamate. The crude carbamate was dissolved in CH₃OH (2 mL), hydrazine monohydrate (185 µL, 3.81 mmol) was added, and the mixture was stirred at 80° C. in a sealed tube for 16 hours. The mixture was concentrated in vacuo and the residue was purified on a Gilson reverse phase HPLC (CH₃CN/water with 0.1% TFA). The product fractions were combined and concentrated in vacuo, taken up in EtOAc (15 mL), washed with saturated aqueous NaHCO₃ (2×10 mL) and brine (10 mL), then dried (Na₂SO₄), filtered, and concentrated in vacuo to afford the title compound (35 mg) as a pale yellow solid. LC-MS (ES) m/z=413 [M+H]⁺. ¹H NMR (400 MHz, DMSO-d₆): δ 1.16 (d, J=6.6 Hz, 3H), 2.65-2.83 (m, 1H), 3.13-3.24 (m, 2H), 3.39-3.48 (m, 1H), 3.55 (s, 3H), 3.58-3.68 (m, 1H), 3.76 (d, J=11.1 Hz, 1H), 4.01-4.71 (bs, 2H), 5.39 (s, 2H), 6.14 (s, 2H), 6.56 (s, 1H), 7.34 (t, J=5.7 Hz, 1H), 7.57 (dd, J=8.4, 1.1 Hz, 1H), 7.72 (d, J=8.6 Hz, 1H), 7.95 (s, 1H), 11.53 (s, 1H).

Intermediate 150

N-({(2S,5R)-4-[2-Amino-6-(4-cyano-3-fluorophenyl)-4-pyrimidinyl]-5-methyl-2-morpholinyl}methyl)methanesulfonamide

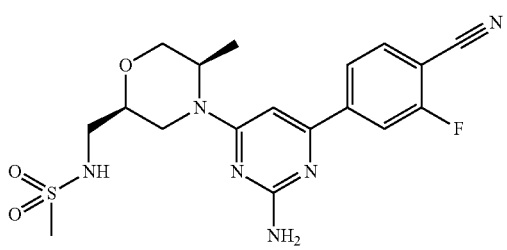 [SMILES: C[C@@H]1CO[C@H](CNS(C)(=O)=O)CN1c1cc(-c2ccc(C#N)c(F)c2)nc(N)n1]

Triethylamine (41 µL, 0.30 mmol) and methanesulfonyl chloride (21 µL, 0.27 mmol) were added to a solution of 4-{2-amino-6-[(2R,5R)-2-(aminomethyl)-5-methyl-4-morpholinyl]-4-pyrimidinyl}-2-fluorobenzonitrile (85 mg, 0.25 mmol) in THF (3 mL), and the mixture was stirred at room temperature under nitrogen for 30 minutes. The mixture was quenched with saturated aqueous NaHCO₃ (10 mL) and extracted with EtOAc (2×10 mL). The extracts were washed with brine (15 mL), dried (Na₂SO₄), filtered, and concentrated in vacuo to give the title compound (108 mg, about 90% pure) as a yellow solid. LC-MS (ES) m/z=421 [M+H]⁺.

Example 93

N-({(2S,5R)-4-[2-Amino-6-(3-amino-1H-indazol-6-yl)-4-pyrimidinyl]-5-methyl-2-morpholinyl}methyl)methanesulfonamide

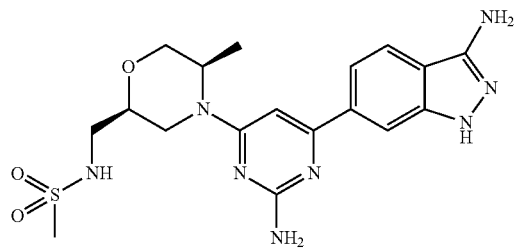 [SMILES: C[C@@H]1CO[C@H](CNS(C)(=O)=O)CN1c1cc(-c2ccc3c(N)n[nH]c3c2)nc(N)n1]

A mixture of crude N-({(2S,5R)-4-[2-amino-6-(4-cyano-3-fluorophenyl)-4-pyrimidinyl]-5-methyl-2-morpholinyl}methyl)methanesulfonamide (0.25 mmol theoretical) and hydrazine monohydrate (0.24 mL, 4.95 mmol) in 1,4-dioxane (3 mL) was stirred at 100° C. in a sealed tube for 17 hours. The mixture was concentrated in vacuo and the residue was purified on a Gilson reverse phase HPLC (CH₃CN/water with 0.1% TFA). The product fractions were concentrated in vacuo, taken up in EtOAc (25 mL), washed with saturated aqueous NaHCO₃ (2×15 mL) and brine (15 mL), then dried (Na₂SO₄), filtered, and concentrated in vacuo to afford the title compound (29 mg) as a pale yellow solid. LC-MS (ES) m/z=433 [M+H]⁺. ¹H NMR (400 MHz, DMSO-d₆): δ 1.18 (d, J=6.6 Hz, 3H), 2.72-2.88 (m, 1H), 2.96 (s, 3H), 3.09-3.22 (m, 2H), 3.45-3.55 (m, 1H), 3.67 (dd, J=11.4, 2.5 Hz, 1H), 3.79 (d, J=11.1 Hz, 1H), 4.04-4.75 (bs, 2H), 5.39 (s, 2H), 6.14 (s, 2H), 6.56 (s, 1H), 7.23 (t, J=6.1 Hz, 1H), 7.57 (dd, J=8.6, 1.0 Hz, 1H), 7.72 (d, J=8.6 Hz, 1H), 7.94 (s, 1H), 11.53 (s, 1H).

Intermediate 151

N-({(2S,5R)-4-[2-Amino-6-(4-cyano-3-fluorophenyl)-4-pyrimidinyl]-5-methyl-2-morpholinyl}methyl)cyclohexanesulfonamide

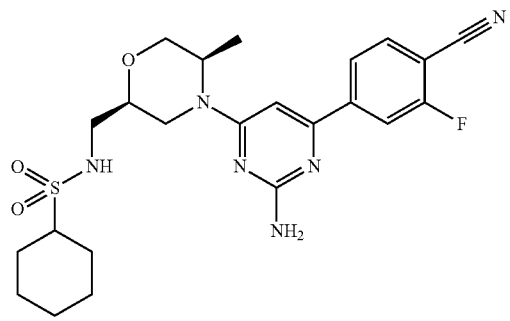 [SMILES: C[C@@H]1CO[C@H](CNS(=O)(=O)C2CCCCC2)CN1c1cc(-c2ccc(C#N)c(F)c2)nc(N)n1]

Triethylamine (41 µL, 0.30 mmol) and cylcohexanesulfonyl chloride (44 µL, 0.27 mmol) were added to a solution of 4-{2-amino-6-[(2R,5R)-2-(aminomethyl)-5-methyl-4-morpholinyl]-4-pyrimidinyl}-2-fluorobenzonitrile (85 mg, 0.25 mmol) in THF (3 mL), and the mixture was stirred at room temperature under nitrogen for 22 hours. LC-MS indicated only about 25% conversion, so more triethylamine (0.15 mL, 1.08 mmol) and cyclohexanesulfonyl chloride (0.15 mL, 1.03 mmol) were added, and stirring continued at room temperature for another 26 hours. The mixture was then quenched with saturated aqueous NaHCO$_3$ (25 mL) and extracted with EtOAc (3×15 mL). The extracts were washed with brine (15 mL), dried (Na$_2$SO$_4$), filtered, and concentrated in vacuo to give the crude title compound (180 mg, about 45% pure according to LC-MS) as a yellow foam. LC-MS (ES) m/z=489 [M+H]$^+$.

Example 94

N-({(2S,5R)-4-[2-Amino-6-(3-amino-1H-indazol-6-yl)-4-pyrimidinyl]-5-methyl-2-morpholinyl}methyl)cyclohexanesulfonamide

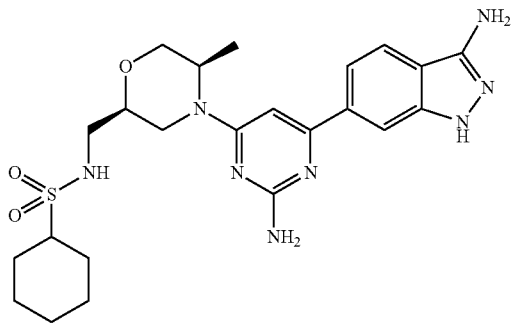 [SMILES: C[C@@H]1CO[C@H](CNS(=O)(=O)C2CCCCC2)CN1c1cc(-c2ccc3c(N)n[nH]c3c2)nc(N)n1]

A mixture of crude N-({(2S,5R)-4-[2-amino-6-(4-cyano-3-fluorophenyl)-4-pyrimidinyl]-5-methyl-2-morpholinyl}methyl)cyclohexanesulfonamide (0.2 mmol theoretical) and hydrazine monohydrate (0.30 mL, 6.20 mmol) in 1,4-dioxane (3 mL) was stirred at 120° C. in the microwave for 2 hours. The mixture was concentrated in vacuo and the residue was purified on an Agilent reverse phase HPLC (CH$_3$CN/water with 0.1% TFA) to give a TFA salt of the title compound (17 mg) as a pale yellow solid. LC-MS (ES) m/z=501 [M+H]$^+$. $^1$H NMR (400 MHz, DMSO-d$_6$, several milligrams of Na$_2$CO$_3$ added to form the free base): δ 1.06-1.43 (m, 5H), 1.17 (d, J=6.6 Hz, 3H), 1.58-1.69 (m, 1H), 1.73-1.85 (m, 2H), 2.00-2.12 (m, 2H), 2.72-2.88 (m, 1H), 2.94-3.05 (m, 1H), 3.07-3.22 (m, 2H), 3.40-3.51 (m, 1H), 3.65 (dd, J=11.2, 2.4 Hz, 1H), 3.79 (d, J=11.1 Hz, 1H), 3.98-4.73 (bs, 2H), 5.39 (s, 2H), 6.13 (s, 2H), 6.55 (s, 1H), 7.19-7.31 (m, 1H), 7.56 (dd, J=8.4, 0.9 Hz, 1H), 7.72 (d, J=8.3 Hz, 1H), 7.94 (s, 1H), 11.53 (s, 1H).

Intermediate 152

4-(Phenylmethyl)-2-morpholinecarbonitrile

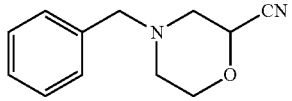 [SMILES: N#CC1CN(Cc2ccccc2)CCO1]

A 500 mL reactor under nitrogen was successively loaded with toluene (50 mL) and 2-chloro-2-propenenitrile (14.26 mL, 179 mmol) at 25° C., and then 2-[(phenylmethyl)amino]ethanol (25.4 mL, 179 mmol) was added over 15 minutes. The reaction mixture was post-agitated at 25° C. for 16 hours. The mixture was diluted with toluene (100 mL), cooled to −5° C., and potassium tert-butoxide (20.04 g, 179 mmol) in THF (90 mL) was slowly added over 30 minutes, maintaining the temperature at −5° C. to 0° C. The mixture was post-agitated at about −5° C. to 0° C. for 1 hour, then quenched by the addition of water (150 mL), and the mixture was allowed to warm to 25° C. The aqueous was extracted with EtOAc (4×150 mL), dried (Na$_2$SO$_4$), filtered, and concentrated to afford the title compound (36 g) as a brown solid. LC-MS (ES) m/z=203 [M+H]$^+$.

Intermediate 153

4-(Phenylmethyl)-2-morpholinecarboxylic acid

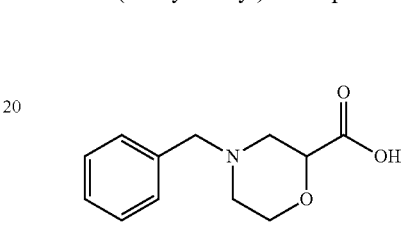

4-(Phenylmethyl)-2-morpholinecarbonitrile (36 g, 178 mmol) was dissolved in toluene (150 mL) and extracted with a 18% solution of hydrochloric acid (240 mL, 1424 mmol). The aqueous phase was heated at reflux for 1.5 hours, then the mixture was allowed to stir at 25° C. for 4 hours. The mixture was filtered, and the solid was rinsed with 6 N hydrochloric acid (60 mL) and dried in vacuo to afford an HCl salt of the title compound (29 g) as a gray solid. LC-MS (ES) m/z=222 [M+H]$^+$.

Intermediate 154

N-[2-(4-Chlorophenyl)-2-oxoethyl]-4-(phenylmethyl)-2-morpholinecarboxamide

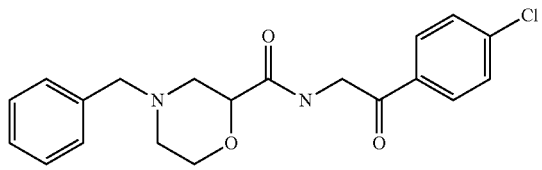 [SMILES: O=C(CNC(=O)C1CN(Cc2ccccc2)CCO1)c1ccc(Cl)cc1]

To a mixture of 4-(phenylmethyl)-2-morpholinecarboxylic acid (1.61 g, 7.28 mmol) and DMF (0.1 mL) in CH$_2$Cl$_2$ (70 mL) was added oxalyl chloride (0.956 mL, 10.92 mmol) at 25° C. The mixture was stirred at this temperature for 1 hour and the mixture turned clear. The solvent and excess of oxalyl chloride were removed in vacuo, and the resulting residue was dissolved in CH$_2$Cl$_2$ (70 mL). 2-Amino-1-(4-chlorophenyl)ethanone (1.5 g, 7.28 mmol) and triethylamine (4.06 mL, 29.1 mmol) were added, and the resulting mixture was stirred overnight. Water (80 mL) was added to quench the reaction. The organic layer was separated and the aqueous layer was extracted with CH$_2$Cl$_2$ (2×80 mL). The combined organics were washed with sat. NaHCO$_3$ aq. (80 mL), then brine (2×80 mL), dried (MgSO$_4$), and evaporated to get 3.4 g yellow residue, which was chromatographed (EtOAc-petroleum ether, 1:1) to afford the title compound (2.5 g). LC-MS (ES) m/z=373 [M+H]+.

Intermediate 155

2-[4-(4-Chlorophenyl)-1H-imidazol-2-yl]-4-(phenylmethyl)morpholine

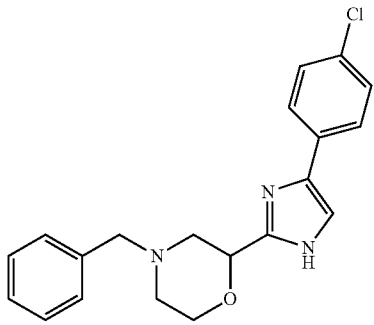 [SMILES: Clc1ccc(-c2c[nH]c(C3CN(Cc4ccccc4)CCO3)n2)cc1]

A mixture of N-[2-(4-chlorophenyl)-2-oxoethyl]-4-(phenylmethyl)-2-morpholinecarboxamide (3.3 g, 8.85 mmol) and ammonium trifluoroacetate (5.27 g, 44.3 mmol) was heated at 150° C. for 20 minutes. After cooling, to the resulting mixture was added water (50 mL) and CH$_2$Cl$_2$ (50 mL). The organic layer was separated and washed with brine, dried (MgSO$_4$), and concentrated to afford the crude title compound (2.8 g). LC-MS (ES) m/z=354 [M+H]+.

Intermediate 156

2-[4-(4-Chlorophenyl)-1H-imidazol-2-yl]morpholine

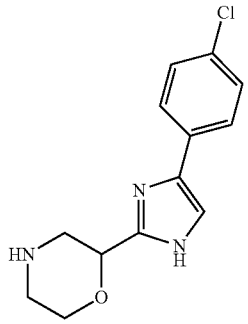 [SMILES: Clc1ccc(-c2c[nH]c(C3CNCCO3)n2)cc1]

2-[4-(4-Chlorophenyl)-1H-imidazol-2-yl]-4-(phenylmethyl)morpholine (2.8 g, 7.91 mmol) was hydrogenated in ethanol (30 mL) over of Pd/C (10 wt %, 0.842 g, 0.791 mmol). To the mixture 0.2 mL of concentrated hydrochloric acid was added. After stirred at room temperature overnight, the catalyst was filtered off. The filtrate was concentrated to get 2.9 g of residue, which was purified by preparative HPLC to afford the title compound (200 mg) as a pale solid. LC-MS (ES) m/z=264 [M+H]+.

Intermediate 157

4-Chloro-6-{2-[4-(4-chlorophenyl)-1H-imidazol-2-yl]-4-morpholinyl}-2-pyrimidinamine

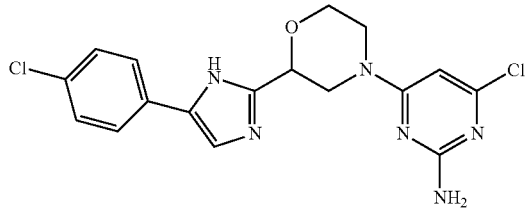 [SMILES: Nc1nc(Cl)cc(N2CCOC(c3ncc(-c4ccc(Cl)cc4)[nH]3)C2)n1]

A solution of 2-[4-(4-chlorophenyl)-1H-imidazol-2-yl]morpholine (322 mg, 1.22 mmol), 4,6-dichloro-2-pyrimidinamine (200 mg, 1.220 mmol) and Hunig's base (531 μL, 3.05 mmol) in ethanol (6.1 mL) was heated at 85° C. overnight. The mixture was evaporated and chromatographed (PE-EtOAc, 2:3) to afford the title compound (220 mg). LC-MS (ES) m/z=391 [M+H]+.

Intermediate 158

4-(2-Amino-6-{2-[4-(4-chlorophenyl)-1H-imidazol-2-yl]-4-morpholinyl}-4-pyrimidinyl)-2-fluorobenzonitrile

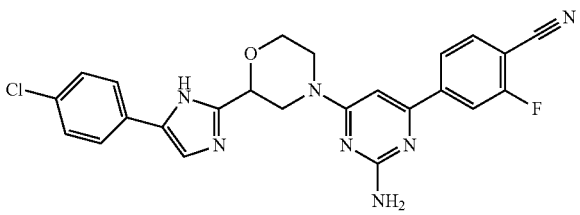 [SMILES: N#Cc1ccc(-c2cc(N3CCOC(c4ncc(-c5ccc(Cl)cc5)[nH]4)C3)nc(N)n2)cc1F]

A mixture of 4-chloro-6-{2-[4-(4-chlorophenyl)-1H-imidazol-2-yl]-4-morpholinyl}-2-pyrimidinamine (300 mg, 0.767 mmol), 2-fluoro-4-(4,4,5,5-tetramethyl-1,3,2-dioxaborolan-2-yl)benzonitrile (246 mg, 0.997 mmol), Na$_2$CO$_3$ (203 mg, 1.917 mmol) and Pd(PPh$_3$)$_4$ (89 mg, 0.077 mmol) in 1,4-dioxane (6 mL) and water (2 mL) was heated at 140° C. under microwave condition with stirring for 1 hour. The mixture was filtered, washed with EtOAc (150 mL), evaporated, and then chromatographed to afford the title compound (305 mg). LC-MS (ES) m/z=476 [M+H]+.

Example 95

6-(2-Amino-6-{2-[4-(4-chlorophenyl)-1H-imidazol-2-yl]-4-morpholinyl}-4-pyrimidinyl)-1H-indazol-3-amine

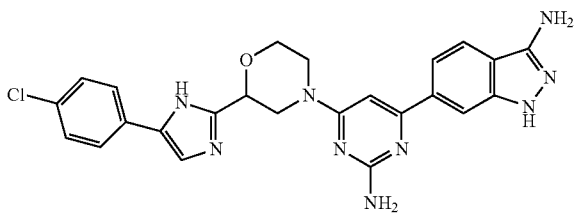 [SMILES: Nc1nc(-c2ccc3c(N)n[nH]c3c2)cc(N2CCOC(c3ncc(-c4ccc(Cl)cc4)[nH]3)C2)n1]

A mixture of 4-(2-amino-6-{2-[4-(4-chlorophenyl)-1H-imidazol-2-yl]-4-morpholinyl}-4-pyrimidinyl)-2-fluorobenzonitrile (155 mg, 0.326 mmol) and hydrazine (1.033 mL, 32.6 mmol) in ethanol (4 mL) was heated at 120° C. under microwave conditions with stirring for 1 hour. The solvent was evaporated to get 200 mg of residue, which was purified by preparative HPLC to afford the title compound (19 mg) as a yellow powder. LC-MS (ES) m/z=488 [M+H]$^+$. $^1$H NMR (400 MHz, DMSO-d$_6$): δ 3.32-3.08 (m, 2H), 3.72 (t, J=11.2 Hz, 1H), 4.06-4.01 (m, 1H), 4.31-4.34 (m, 1H), 4.61 (d, J=14.0 Hz, 1H), 4.72 (bs, 1H), 5.38 (s, 2H), 6.20 (s, 2H), 6.75 (s, 1H), 7.39 (d, J=8.8 Hz, 2H), 7.76-7.46 (m, 3H), 7.81 (d, J=8.4 Hz 2H), 7.99 (s, 1H), 11.53 (s, 1H), 12.41 (s, 1H).

Intermediate 159

N-[(1R,2R)-2-Hydroxycyclohexyl]-4-(phenylmethyl)-2-morpholinecarboxamide

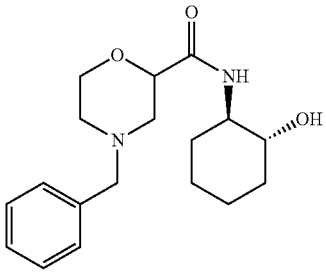 [SMILES: O=C(N[C@@H]1CCCC[C@H]1O)C1CN(Cc2ccccc2)CCO1]

To a mixture of 4-(phenylmethyl)-2-morpholinecarboxylic acid (5 g, 22.60 mmol) and DMF (0.1 mL) in CH$_2$Cl$_2$ (113 mL) was added oxalyl chloride (2.97 mL, 33.9 mmol) at 25° C. The mixture was stirred at this temperature for 1 hour and the mixture turned clear. The solvent and excess of oxalyl chloride were removed in vacuo, and the resulting residue was dissolved in CH$_2$Cl$_2$ (113 mL). (1R,2R)-2-Aminocyclohexanol (2.60 g, 22.60 mmol) and triethylamine (12.60 mL, 90 mmol) were added, and the resulting mixture was stirred overnight. Water (80 mL) was added to quench the reaction. the organic layer was separated and the aqueous layer was extracted with CH$_2$Cl$_2$ (2×80 mL). The combined organics were washed with sat. NaHCO$_{3(aq)}$ (80 mL), then brine (2×80 mL), dried (MgSO$_4$), and evaporated to afford the title compound (5.3 g). LC-MS (ES) m/z=319 [M+H]$^+$.

Intermediate 160

N-[(1R)-2-Oxocyclohexyl]-4-(phenylmethyl)-2-morpholinecarboxamide

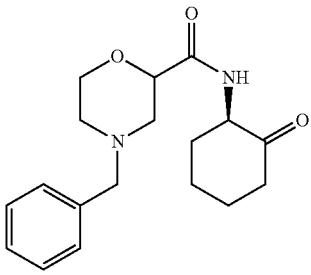 [SMILES: O=C(N[C@@H]1CCCCC1=O)C1CN(Cc2ccccc2)CCO1]

A suspension of N-[(1R,2R)-2-hydroxycyclohexyl]-4-(phenylmethyl)-2-morpholinecarboxamide (5.0 g, 15.7 mmol) and pyridinium chlorochromate (PCC) (4.06 g, 18.84 mmol) in CH$_2$Cl$_2$ (79 mL) was stirred at room temperature for 18 hours. The reaction mixture was filtered through a pad of silica gel and washed with EtOAc to get crude product (4.0 g). Purification was carried out on column chromatography (EtOAc—PE, from 2:1 to 2:0) to afford the title compound (0.7 g). LC-MS (ES) m/z=317 [M+H]$^+$.

Intermediate 161

2-[4-(Phenylmethyl)-2-morpholinyl]-4,5,6,7-tetrahydro-1H-benzimidazole

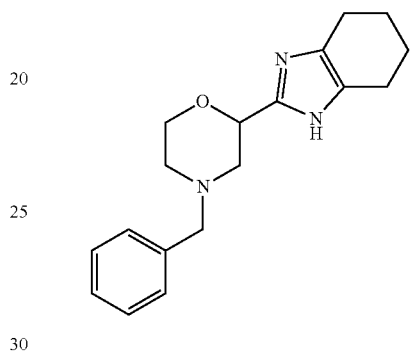

A mixture of N-[(1R)-2-oxocyclohexyl]-4-(phenylmethyl)-2-morpholinecarboxamide (1.1 g, 3.48 mmol) and ammonium trifluoroacetate (2.069 g, 17.38 mmol) was heated at 150° C. for 20 minutes. After cooling, to the mixture was added water (30 mL) and CH$_2$Cl$_2$ (50 mL). The organic layer was separated and washed with brine, dried (MgSO$_4$), and concentrated to afford the crude title compound (0.78 g). LC-MS (ES) m/z=298 [M+H]$^+$.

Intermediate 162

2-(2-Morpholinyl)-4,5,6,7-tetrahydro-1H-benzimidazole

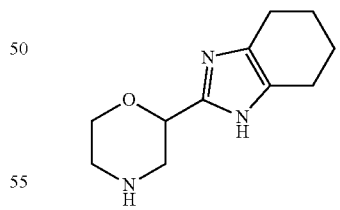

2-[4-(Phenylmethyl)-2-morpholinyl]-4,5,6,7-tetrahydro-1H-benzimidazole (0.78 g, 2.62 mmol) was hydrogenated in ethanol (30 mL) in the presence of Pd/C (10 wt %, 0.279 g, 0.262 mmol). To the reaction mixture was added 0.2 mL of concentrated hydrochloric acid. After stirring at room temperature overnight, the catalyst was filtered off. The filtrate was concentrated to afford the title compound (0.8 g) as a yellow oil. LC-MS (ES) m/z=208 [M+H]$^+$.

Intermediate 163

4-Chloro-6-[2-(4,5,6,7-tetrahydro-1H-benzimidazol-2-yl)-4-morpholinyl]-2-pyrimidinamine

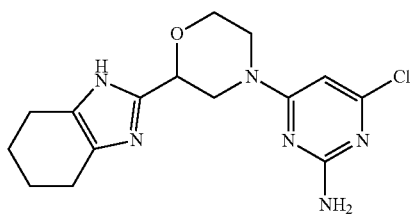 [SMILES: Nc1nc(Cl)cc(N2CCOC(c3nc4c([nH]3)CCCC4)C2)n1]

A solution of 2-(2-morpholinyl)-4,5,6,7-tetrahydro-1H-benzimidazole (0.8 g, 3.86 mmol), 4,6-dichloro-2-pyrimidinamine (0.633 g, 3.86 mmol) and Hunig's base (1.681 mL, 9.65 mmol) in ethanol (19.3 mL) was heated at 85° C. overnight. The mixture was concentrated and chromatographed (eluent EtOAc+NH$_4$OH) to afford the title compound (200 mg). LC-MS (ES) m/z=335 [M+H]$^+$.

Intermediate 164

4-{2-Amino-6-[2-(4,5,6,7-tetrahydro-1H-benzimidazol-2-yl)-4-morpholinyl]-4-pyrimidinyl}-2-fluorobenzonitrile

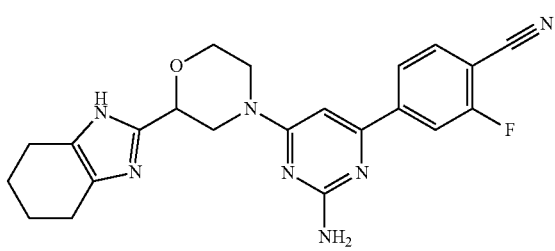 [SMILES: N#Cc1ccc(-c2cc(N3CCOC(c4nc5c([nH]4)CCCC5)C3)nc(N)n2)cc1F]

A mixture of 4-chloro-6-[2-(4,5,6,7-tetrahydro-1H-benzimidazol-2-yl)-4-morpholinyl]-2-pyrimidinamine (208 mg, 0.623 mmol), 2-fluoro-4-(4,4,5,5-tetramethyl-1,3,2-dioxaborolan-2-yl)benzonitrile (200 mg, 0.809 mmol), Na$_2$CO$_3$ (165 mg, 1.557 mmol) and Pd(PPh$_3$)$_4$ (72 mg, 0.062 mmol) in 1,4-dioxane (6 mL) and water (2 mL) was heated at 140° C. under microwave condition with stirring for 1 hour. The mixture was filtered, washed by EtOAc (150 mL), evaporated, and chromatographed (PE-EtOAc, 3:1) to afford the title compound (150 mg) as a yellow solid. LC-MS (ES) m/z=420 [M+H]$^+$.

Example 96

6-{2-Amino-6-[2-(4,5,6,7-tetrahydro-1H-benzimidazol-2-yl)-4-morpholinyl]-4-pyrimidinyl}-1H-indazol-3-amine

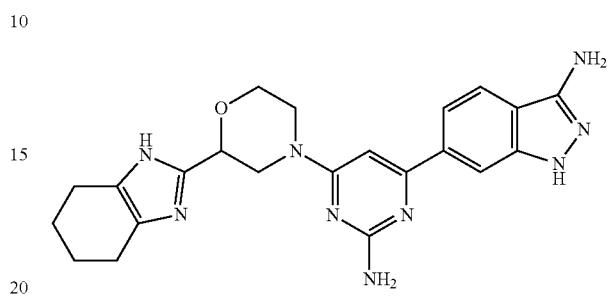

A mixture of 4-{2-amino-6-[2-(4,5,6,7-tetrahydro-1H-benzimidazol-2-yl)-4-morpholinyl]-4-pyrimidinyl}-2-fluorobenzonitrile (150 mg, 0.358 mmol) and hydrazine (1.13 mL, 35.8 mmol) in ethanol (4 mL) was heated at 120° C. under microwave conditions with stirring for 1 hour. The solvent was evaporated to get 200 mg of residue, which was purified by preparative HPLC to afford the title compound (42 mg) as a yellow powder. LC-MS (ES) m/z=432 [M+H]$^+$. $^1$H NMR (400 MHz, DMSO-d$_6$): δ 1.71 (s, 4H), 2.42 (s, 2H), 3.12-2.99 (m, 2H), 3.66 (dt, J=11.6 Hz, 2.4 Hz, 1H), 4.00 (dd, J=11.6 Hz, 2.0 Hz, 1H), 4.33-4.30 (m, 1H), 4.44 (dd, J=10.8 Hz, 2.4 Hz, 1H), 4.62 (bs, 1H), 5.28 (s, 2H), 6.18 (s, 2H), 6.66 (s, 1H), 7.61 (dd, J=8.4 Hz, 0.8 Hz, 1H), 7.71 (d, J=8.4 Hz, 1H), 7.97 (s, 1H), 11.51 (s, 1H), 11.68 (s, 1H).

Intermediate 165

1-(2-Oxo-2-phenylethyl)-3,5,7-triaza-1-azoniatricyclo[3.3.1.1$^{3,7}$]decane bromide

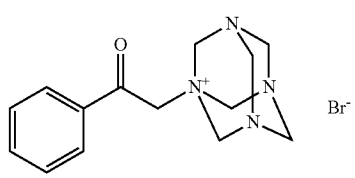 [SMILES: O=C(C[N+]12CN3CN(CN(C3)C1)C2)c1ccccc1 ; [Br-]]

2-Bromo-1-phenylethanone (2.0 g, 10.05 mmol) was added to a solution of hexamethylenetetramine (1.409 g, 10.05 mmol) in CHCl$_3$ (60 mL), and the resulting mixture was heated at 50° C. for 1 hour. The mixture was cooled to room temperature and the white precipitate was collected by filtration, washed with CHCl$_3$, and dried under vacuo to afford the title compound (3.3 g) as a white solid. LC-MS (ES) m/z=259 [M+H]$^+$.

Intermediate 166

2-Amino-1-phenylethanone

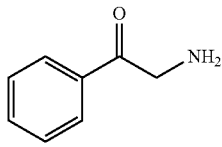

1-(2-oxo-2-phenylethyl)-3,5,7-triaza-1-azoniatricyclo[3.3.1.1³,⁷]decane bromide (3.3 g, 9.73 mmol) was suspended in a mixture of ethanol (50 mL) and hydrochloric acid (4.93 mL, 58.4 mmol) and heated at reflux in ethanol (50 mL) for 1.5 hours. The mixture was cooled to 0° C., filtered, and washed by ethanol (30 mL). The organic phase was evaporated to afford an HCl salt of the title compound (1.7 g) as a pale yellow solid. LC-MS (ES) m/z=136 [M+H]⁺.

Intermediate 167

N-(2-oxo-2-phenylethyl)-4-(phenylmethyl)-2-morpholinecarboxamide

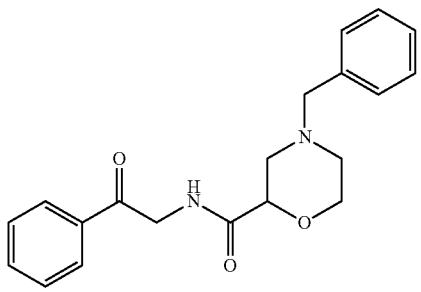 [SMILES: O=C(CNC(=O)C1CN(Cc2ccccc2)CCO1)c1ccccc1]

Oxalyl chloride (1.187 mL, 13.56 mmol) was added to a suspension of 4-(phenylmethyl)-2-morpholinecarboxylic acid (2.0 g, 9.04 mmol) in CH₂Cl₂ (70 mL) at 0° C. in 10 minutes, and the resulting mixture was stirred at 25° C. for 2 hours. The mixture was concentrated, and the resulting residue was treated with CH₂Cl₂ (70 mL), triethylamine (2.77 mL, 19.89 mmol) and 2-amino-1-phenylethanone (1.551 g, 9.04 mmol) at 0° C. The reaction mixture was stirred at 25° C. for 3 hours. Water (150 mL) was added, and the resulting aqueous mixture was extracted with EtOAc (3×80 mL). The combined organic layers were dried (Na₂SO₄), filtered, and concentrated. The resulting residue was purified by silica gel chromatography to afford the title compound (1.0 g) as a brown solid. LC-MS (ES) m/z=339 [M+H]⁺.

Intermediate 168

2-(4-Phenyl-1H-imidazol-2-yl)-4-(phenylmethyl)morpholine

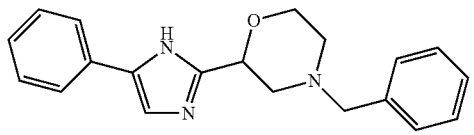 [SMILES: c1ccc(CN2CCOC(c3ncc(-c4ccccc4)[nH]3)C2)cc1]

A mixture of N-(2-oxo-2-phenylethyl)-4-(phenylmethyl)-2-morpholinecarboxamide (850 mg, 2.51 mmol) and ammonium trifluoroacetate (1317 mg, 10.05 mmol) was heated at 150° C. under microwave condition with stirring for 1 hour. Water (150 mL) was added to the residue, and extracted with EtOAc (200 mL). The organic layer was dried (Na₂SO₄), filtered, and concentrated to afford the crude title compound (1.3 g) as a brown oil. This material was combined with another batch of crude title compound (250 mg) and purified by silica gel chromatography using as eluent EtOAc (1600 mL) in hexanes (400 mL) to afford the title compound (900 mg, 2.82 mmol) as a brown solid. LC-MS (ES) m/z=320 [M+H]⁺.

Intermediate 169

2-(4-Phenyl-1H-imidazol-2-yl)morpholine

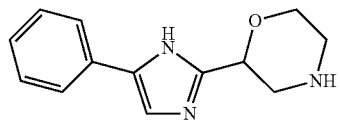 [SMILES: c1ccc(-c2cnc(C3CNCCO3)[nH]2)cc1]

Palladium on carbon (10 wt %, 300 mg, 0.282 mmol) was added to a solution of 2-(4-phenyl-1H-imidazol-2-yl)-4-(phenylmethyl)morpholine (900 mg, 2.82 mmol) and 36% aqueous HCl (0.713 mL, 8.45 mmol) in CH₃OH (50 mL) under nitrogen, and the reaction mixture was stirred under hydrogen at 25° C. for 1.5 hours. The mixture was filtered, washed by methanol (150 mL), and concentrated to afford an HCl salt of the title compound (600 mg) as a brown solid. LC-MS (ES) m/z=230 [M+H]⁺.

Intermediate 170

4-Chloro-6-[2-(4-phenyl-1H-imidazol-2-yl)-4-morpholinyl]-2-pyrimidinamine

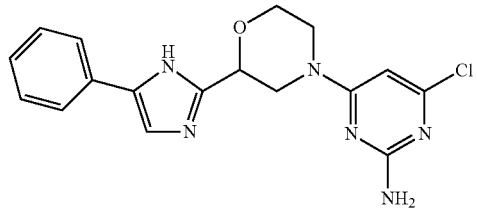 [SMILES: Nc1nc(Cl)cc(N2CCOC(c3ncc(-c4ccccc4)[nH]3)C2)n1]

A solution of 2-(4-phenyl-1H-imidazol-2-yl)morpholine (550 mg, 2.07 mmol), 4,6-dichloro-2-pyrimidinamine (339 mg, 2.07 mmol) and Hunig's base (0.901 mL, 5.17 mmol) in ethanol (80 mL) was heated at 85° C. for 5 hours. The mixture was concentrated to afford the crude title compound (850 mg) as a brown oil. LC-MS (ES) m/z=357 [M+H]⁺.

Intermediate 171

4-{2-Amino-6-[2-(4-phenyl-1H-imidazol-2-yl)-4-morpholinyl]-4-pyrimidinyl}-2-fluorobenzonitrile

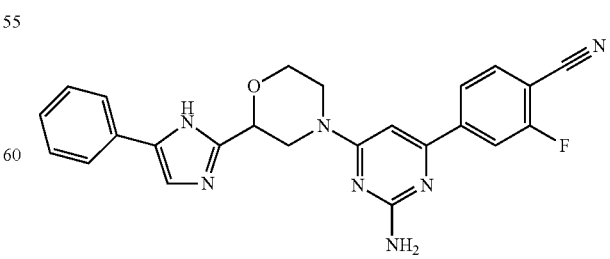

A mixture of crude 4-chloro-6-[2-(4-phenyl-1H-imidazol-2-yl)-4-morpholinyl]-2-pyrimidinamine, 2-fluoro-4-(4,4,5, 5-tetramethyl-1,3,2-dioxaborolan-2-yl)benzonitrile (765 mg, 3.10 mmol), Na$_2$CO$_3$ (631 mg, 5.96 mmol) and Pd(PPh$_3$)$_4$ (275 mg, 0.238 mmol) in 1,4-dioxane (6 mL) and water (2 mL) was heated at 140° C. under microwave conditions with stirring for 1.0 hour. The mixture was filtered, washed by EtOAc (150 mL), and concentrated to afford the crude title compound (1.3 g) as a yellow solid. This material was combined with another batch of crude title compound (100 mg). The combined material was washed by EtOAc (150 mL), and concentrated. The resulting residue was purified by silica gel chromatography using EtOAc in petroleum ether from 50% to 70% to afford the title compound (400 mg) as a light yellow solid. LC-MS (ES) m/z=442 [M+H]$^+$.

Example 97

6-{2-Amino-6-[2-(4-phenyl-1H-imidazol-2-yl)-4-morpholinyl]-4-pyrimidinyl}-1H-indazol-3-amine

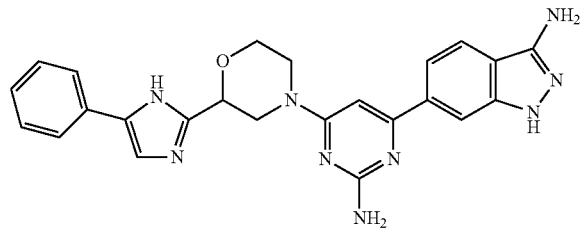 [SMILES: Nc1nc(-c2ccc3c(N)n[nH]c3c2)cc(N2CCOC(c3ncc(-c4ccccc4)[nH]3)C2)n1]

A mixture of 4-{2-amino-6-[2-(4-phenyl-1H-imidazol-2-yl)-4-morpholinyl]-4-pyrimidinyl}-2-fluorobenzonitrile (310 mg, 0.702 mmol) and hydrazine (2.5 mL, 79 mmol) in ethanol (4 mL) was heated under microwave conditions with stirring for 1 hour. The mixture was concentrated to afford the crude title compound (400 mg) as a yellow solid. This material was combined with another batch of crude title compound (100 mg). The combined material was washed with CH$_2$Cl$_2$ (2×8 mL) and dried in vacuo. The resulting residue was purified by Prep-HPLC using CH$_3$CN in water (0.5% ammonium hydrogen carbonate in water) from 25% to 30% to afford the title compound (220 mg) as a yellow solid. LC-MS (ES) m/z=454 [M+H]$^+$. $^1$H NMR (400 MHz, DMSO-d$_6$): δ 3.08-3.14 (m, 1H), 3.18-3.24 (m, 1H), 3.72 (m, 1H), 4.04-4.07 (m, 1H), 4.30-4.34 (m, 1H), 4.59-4.64 (m, 1H), 4.73-4.75 (m, 1H), 5.39 (s, 2H), 6.21 (s, 2H), 6.71 (s, 1H), 7.16-7.20 (m, 1H), 7.31-7.36 (m, 2H), 7.61-7.63 (m, 2H), 7.71 (d, J=8.4 Hz, 1H), 7.78 (d, J=7.2 Hz, 2H), 7.99 (s, 1H), 11.53 (s, 1H), 12.33-12.62 (m, 1H).

Intermediate 172

2-Amino-1-(3-chlorophenyl)ethanone

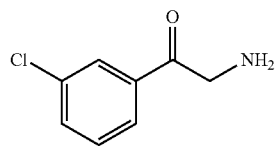 [SMILES: NCC(=O)c1cccc(Cl)c1]

2-Bromo-1-(3-chlorophenyl)ethanone (2.0 g, 8.57 mmol) was added to a solution of hexamethylenetetramine (1.201 g, 8.57 mmol) in CHCl$_3$ (60 mL), and the resulting mixture was heated at 55° C. for 1 hour. The mixture was cooled to room temperature, and the white precipitate was collected by filtration, washed with CHCl$_3$, and dried in vacuo to afford 3.1 g. This white solid was suspended in a mixture of ethanol (50 mL) and hydrochloric acid (0.25 mL, 8.30 mmol) and heated at 105° C. for 1.5 hours. The mixture was cooled to 0° C., filtered and washed by ethanol (30 mL). The organic phase was concentrated to afford an HCl salt of the title compound (1.74 g) as a pale yellow solid. LC-MS (ES) m/z=170 [M+H]$^+$.

Intermediate 173

N-[2-(3-Chlorophenyl)-2-oxoethyl]-4-(phenylmethyl)-2-morpholinecarboxamide

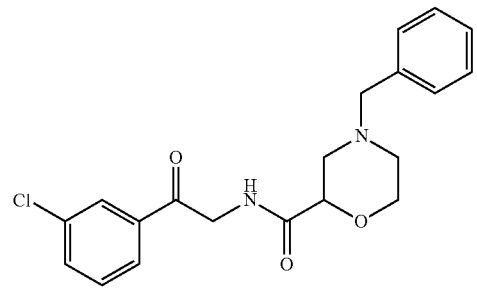 [SMILES: O=C(CNC(=O)C1CN(Cc2ccccc2)CCO1)c1cccc(Cl)c1]

Oxalyl chloride (1.32 mL, 15.03 mmol) was added to the suspension of 4-(phenylmethyl)-2-morpholinecarboxylic acid (2.218 g, 10.02 mmol) and DMF (0.155 mL, 2.005 mmol) in CH$_2$Cl$_2$ (100 mL) at 0° C. in 10 minutes, and the resulting mixture was stirred at 25° C. for 2 hours. The mixture was concentrated, and the resulting residue was dissolved in CH$_2$Cl$_2$ (100 mL) and triethylamine (3.07 mL, 22.05 mmol). 2-Amino-1-(3-chlorophenyl)ethanone (1.7 g, 10.02 mmol) was added to the brown solution at 0° C., and the reaction mixture was stirred at 25° C. for 3 hours. Water (150 mL) was added to the reaction mixture, and the aqueous mixture was extracted with EtOAc (3×100 mL). The combined organic layers were dried (Na$_2$SO$_4$), filtered, and evaporated. The resulting residue was purified by silica gel chromatography using as eluent 50% EtOAc in petroleum ether to afford the title compound (800 mg) as a pale yellow solid. LC-MS (ES) m/z=373 [M+H]$^+$.

Intermediate 174

2-[4-(3-Chlorophenyl)-1H-imidazol-2-yl]-4-(phenylmethyl)morpholine

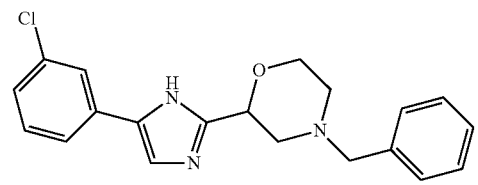 [SMILES: Clc1cccc(-c2cnc(C3CN(Cc4ccccc4)CCO3)[nH]2)c1]

A mixture of N-[2-(3-chlorophenyl)-2-oxoethyl]-4-(phenylmethyl)-2-morpholinecarboxamide (350 mg, 0.939 mmol) and ammonium trifluoroacetate (615 mg, 4.69 mmol) was stirred for 2.5 hours at 150° C. Water (150 mL) was added to the residue, and the aqueous mixture was extracted with EtOAc (200 mL). The organic phase was dried (Na$_2$SO$_4$), Intermediate 175

2-[4-(3-Chlorophenyl)-1H-imidazol-2-yl]morpholine

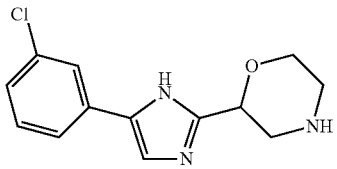 [SMILES: Clc1cccc(-c2cnc(C3CNCCO3)[nH]2)c1]

Palladium on carbon (10 wt %, 208 mg, 0.195 mmol) was added to a solution of 2-[4-(3-chlorophenyl)-1H-imidazol-2-yl]-4-(phenylmethyl)morpholine (690 mg, 1.950 mmol) and hydrochloric acid (0.823 mL, 9.75 mmol) in CH$_3$OH (50 mL) under nitrogen, and the reaction mixture was stirred under hydrogen at 25° C. for 1.5 hours. The mixture was filtered washing with CH$_3$OH (150 mL), and concentrated to afford the crude HCl salt of title compound (600 mg) as a brown solid. LC-MS (ES) m/z=264 [M+H]$^+$.

Intermediate 176

4-Chloro-6-{2-[4-(3-chlorophenyl)-1H-imidazol-2-yl]-4-morpholinyl}-2-primidinamine

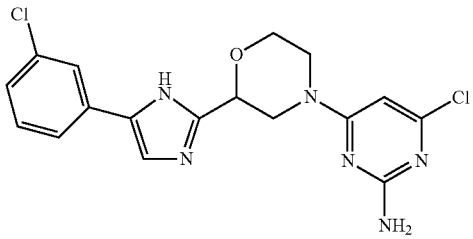 [SMILES: Nc1nc(Cl)cc(N2CCOC(c3ncc(-c4cccc(Cl)c4)[nH]3)C2)n1]

A solution of 2-[4-(3-chlorophenyl)-1H-imidazol-2-yl]morpholine (600 mg, 2.0 mmol), 4,6-dichloro-2-pyrimidinamine (328 mg, 2.0 mmol) and Hunig's base (0.870 mL, 5.00 mmol) in ethanol (80 mL) was heated overnight at 85° C. The reaction mixture was filtered and concentrated to afford the crude title compound (1.1 g) as a brown oil. LC-MS (ES) m/z=391 [M+H]$^+$.

Intermediate 177

4-(2-Amino-6-{2-[4-(3-chlorophenyl)-1H-imidazol-2-yl]-4-morpholinyl}-4-pyrimidinyl)-2-fluorobenzonitrile

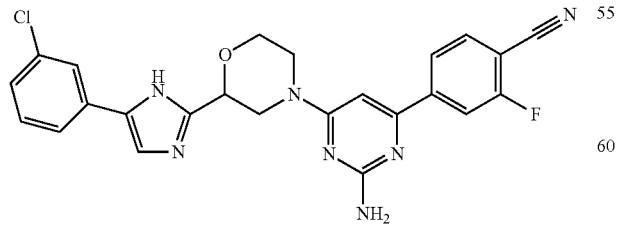

A mixture of 4-chloro-6-{2-[4-(3-chlorophenyl)-1H-imidazol-2-yl]-4-morpholinyl}-2-pyrimidinamine (1.1 g, 2.81 mmol), 2-fluoro-4-(4,4,5,5-tetramethyl-1,3,2-dioxaborolan-2-yl)benzonitrile (0.903 g, 3.65 mmol), Na$_2$CO$_3$ (0.745 g, 7.03 mmol) and Pd(PPh$_3$)$_4$ (0.325 g, 0.281 mmol) in 1,4-dioxane (4 mL) and water (1 mL) was heated at 140° C. under microwave condition with stirring for 1 hour. The reaction mixture was filtered, washed by ethyl acetate (100 mL) and concentrated to afford the crude title compound (310 mg) as a yellow solid. LC-MS (ES) m/z=476 [M+H]$^+$.

Example 98

6-(2-Amino-6-{2-[4-(3-chlorophenyl)-1H-imidazol-2-yl]-4-morpholinyl}-4-pyrimidinyl)-1H-indazol-3-amine

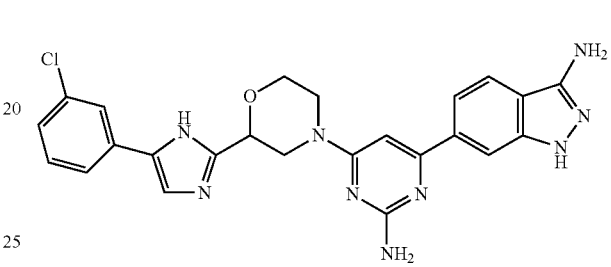

A mixture of 4-(2-amino-6-{2-[4-(3-chlorophenyl)-1H-imidazol-2-yl]-4-morpholinyl}-4-pyrimidinyl)-2-fluorobenzonitrile (310 mg, 0.651 mmol) and hydrazine (1.03 mL, 32.6 mmol) in ethanol (4 mL) was heated under microwave conditions with stirring for 1 hour. The mixture was concentrated, and the resulting residue was purified by Prep-HPLC using CH$_3$CN in water (10 mmol ammonium hydrogen carbonate in water) from 40% to 60% in 9 minutes to afford the title compound (96 mg) as a yellow solid. LC-MS (ES) m/z=488 [M+H]$^+$. $^1$H NMR (400 MHz, DMSO-d$_6$): δ 3.07-3.15 (m, 1H), 3.17-3.23 (m, 1H), 3.69-3.75 (m, 1H), 4.04-4.06 (m, 1H), 4.30-4.34 (m, 1H), 4.60-4.64 (m, 1H), 4.72-4.75 (m, 1H), 5.38 (s, 2H), 6.20 (s, 2H), 6.71 (s, 1H), 7.21-7.30 (m, 1H), 7.34-7.47 (m, 1H), 7.60-7.63 (m, 1H), 7.69-7.72 (m, 1H), 7.74-7.76 (m, 2H), 7.83-7.85 (m, 1H), 7.99 (s, 1H), 11.52 (s, 1H), 12.43-12.70 (m, 1H).

Intermediate 178

2-Azido-1-[4-(methyloxy)phenyl]ethanone

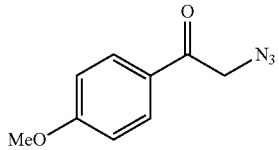 [SMILES: COc1ccc(C(=O)CN=[N+]=[N-])cc1]

A mixture of 2-bromo-1-[4-(methyloxy)phenyl]ethanone (3.5 g, 15.28 mmol) and sodium azide (1.490 g, 22.92 mmol) in THF (40 mL) and water (13.33 mL) was stirred at 25° C. for 2 hours. The mixture was diluted with water (150 mL), and extracted with Et$_2$O (3×100 mL), dried (Na$_2$SO$_4$), filtered, concentrated to afford the title compound (3.0 g) as a pink solid. $^1$H NMR (400 MHz, DMSO-d$_6$): δ 3.87 (s, 3H), 4.83 (s, 2H), 7.07 (d, 2H), 7.93 (d, 2H).

Intermediate 179

2-Amino-1-[4-(methyloxy)phenyl]ethanone

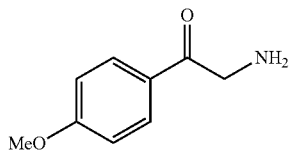

Palladium on carbon (10 wt %, 1.67 g, 1.57 mmol) was added to a solution of 2-azido-1-[4-(methyloxy)phenyl]ethanone (3.0 g, 15.69 mmol) and hydrochloric acid (6.62 mL, 78 mmol) in $CH_3OH$ (90 mL) under nitrogen, and the reaction mixture was stirred under hydrogen overnight at 25° C. The mixture was filtered, washed by EtOAc (150 mL), and concentrated to afford an HCl salt of the title compound (3.0 g) as a yellow solid. LC-MS (ES) m/z=166 $[M+H]^+$.

Intermediate 180

N-{2-[4-(Methyloxy)phenyl]-2-oxoethyl}-4-(phenylmethyl)-2-morpholinecarboxamide

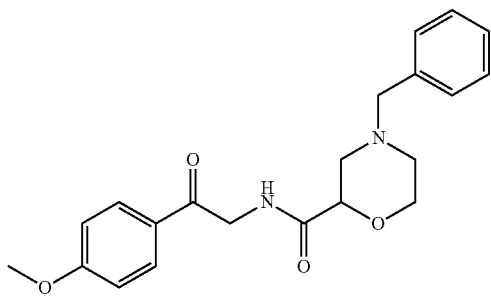 [SMILES: COc1ccc(C(=O)CNC(=O)C2CN(Cc3ccccc3)CCO2)cc1]

Oxalyl chloride (2.385 mL, 27.2 mmol) was added to a suspension of 4-(phenylmethyl)-2-morpholinecarboxylic acid (4.02 g, 18.16 mmol) and DMF (0.703 mL, 9.08 mmol) in $CH_2Cl_2$ (100 mL) at 0° C. in 10 minutes, and the reaction mixture was stirred at 25° C. for 2 hours. The mixture was concentrated, and the resulting residue was dissolved in $CH_2Cl_2$ (100 mL) and triethylamine (5.57 mL, 40.0 mmol). 2-Amino-1-[4-(methyloxy)phenyl]ethanone (3.0 g, 18.16 mmol) was added to the brown solution at 0° C., and the reaction mixture was stirred at 25° C. for 3 hours. Water (150 mL) was added to the reaction mixture, and the aqueous mixture was extracted with EtOAc (3×100 mL). The combined organic layers were dried ($Na_2SO_4$), filtered, and evaporated to afford the title compound (3.4 g) as a brown solid. LC-MS (ES) m/z=369 $[M+H]^+$.

Intermediate 181

2-{4-[4-(Methyloxy)phenyl]-1H-imidazol-2-yl}-4-(phenylmethyl)morpholine

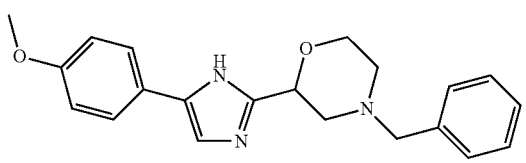 [SMILES: COc1ccc(-c2cnc(C3CN(Cc4ccccc4)CCO3)[nH]2)cc1]

A mixture of N-{2-[4-(methyloxy)phenyl]-2-oxoethyl}-4-(phenylmethyl)-2-morpholinecarboxamide (2.5 g, 6.79 mmol) and ammonium trifluoroacetate (4.45 g, 33.9 mmol) was stirred for 2.5 hours at 150° C. Water (150 mL) was added to the residue, and the aqueous mixture was extracted with EtOAc (3×80 mL). The combined organic phases were dried ($Na_2SO_4$), filtered, and concentrated to afford the title compound (2.3 g) as a brown solid. LC-MS (ES) m/z=350 $[M+H]^+$.

Intermediate 182

2-{4-[4-(Methyloxy)phenyl]-1H-imidazol-2-yl}morpholine

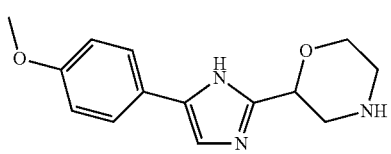 [SMILES: COc1ccc(-c2cnc(C3CNCCO3)[nH]2)cc1]

Palladium on carbon (10 wt %, 0.700 g, 0.658 mmol) was added to a solution of 2-{4-[4-(methyloxy)phenyl]-1H-imidazol-2-yl}-4-(phenylmethyl)morpholine (2.3 g, 6.58 mmol) and hydrochloric acid (2.78 mL, 32.9 mmol) in $CH_3OH$ (80 mL) under nitrogen, and the reaction mixture was stirred under hydrogen at 25° C. for 1.5 hours. The reaction mixture was filtered, washed by $CH_3OH$ (150 mL) and concentrated to afford an HCl salt of the title compound (1.9 g) as a brown solid. LC-MS (ES) m/z=260 $[M+H]^+$.

Intermediate 183

4-Chloro-6-(2-{4-[4-(methyloxy)phenyl]-1H-imidazol-2-yl}-4-morpholinyl)-2-pyrimidinamine

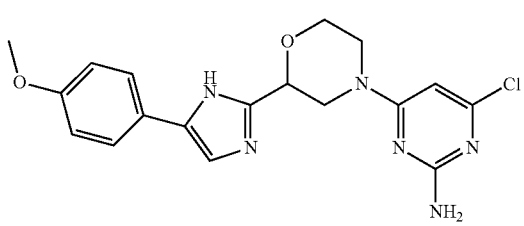 [SMILES: COc1ccc(-c2cnc(C3CN(c4cc(Cl)nc(N)n4)CCO3)[nH]2)cc1]

A solution of 2-{4-[4-(methyloxy)phenyl]-1H-imidazol-2-yl}morpholine (1.9 g, 6.42 mmol), 4,6-dichloro-2-pyrimidinamine (1.053 g, 6.42 mmol) and Hunig's base (2.8 mL, 16.1 mmol) in ethanol (80 mL) was heated overnight at 85° C.

The reaction mixture was concentrated, and the resulting residue was purified by silica gel chromatography using as eluent 40% EtOAc in CH$_2$Cl$_2$ to afford the title compound (1.8 g) as a white solid. LC-MS (ES) m/z=387 [M+H]$^+$.

Intermediate 184

4-[2-Amino-6-(2-{4-[4-(methyloxy)phenyl]-1H-imidazol-2-yl}-4-morpholinyl)-4-pyrimidinyl]-2-fluorobenzonitrile

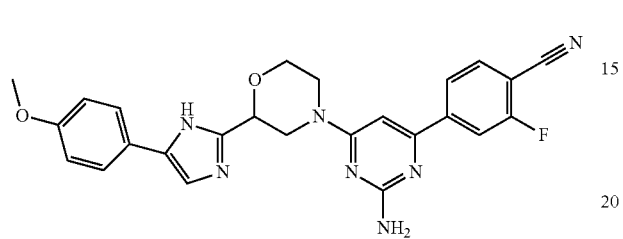

A mixture of 4-chloro-6-(2-{4-[4-(methyloxy)phenyl]-1H-imidazol-2-yl}-4-morpholinyl)-2-pyrimidinamine (1.0 g, 2.59 mmol), 2-fluoro-4-(4,4,5,5-tetramethyl-1,3,2-dioxaborolan-2-yl)benzonitrile (0.83 g, 3.36 mmol), Na$_2$CO$_3$ (0.685 g, 6.46 mmol) and Pd(PPh$_3$)$_4$ (0.30 g, 0.26 mmol) in 1,4-dioxane (8 mL) and water (2 mL) was heated at 140° C. under microwave conditions with stirring for 1 hour. The reaction mixture was filtered, washed by ethyl acetate (100 mL), and concentrated. The resulting residue was purified by silica gel chromatography using EtOAc/petroleum ether (3:1) to afford the title compound (675 mg) as a yellow solid. LC-MS (ES) m/z=472 [M+H]$^+$.

Example 99

6-[2-Amino-6-(2-{4-[4-(methyloxy)phenyl]-1H-imidazol-2-yl}-4-morpholinyl)-4-pyrimidinyl]-1H-indazol-3-amine

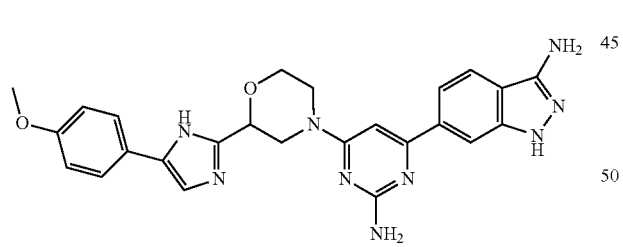

A mixture of 4-[2-amino-6-(2-{4-[4-(methyloxy)phenyl]-1H-imidazol-2-yl}-4-morpholinyl)-4-pyrimidinyl]-2-fluorobenzonitrile (350 mg, 0.742 mmol) and hydrazine (1.18 mL, 37.1 mmol) in ethanol (4 mL) was heated under microwave conditions with stirring for 1 hour. The mixture was concentrated. Ethanol (15 mL) was added to the resulting residue, and the resulting mixture was heated to 85° C. for 20 minutes, and then filtered while hot and dried in vacuo to afford the title compound (115 mg) as a pale yellow solid. LC-MS (ES) m/z=484 [M+H]$^+$. $^1$H NMR (400 MHz, DMSO-d$_6$): δ 3.09-3.15 (m, 1H), 3.19-3.25 (m, 1H), 3.69-3.77 (m, 4H), 4.02-4.05 (m, 1H), 4.29-4.36 (m, 1H), 4.56-4.62 (m, 1H), 4.72 (s, 1H), 5.39 (s, 2H), 6.21 (s, 2H), 6.71 (s, 1H), 6.89-6.98 (m, 2H), 7.21-7.68 (m, 1H), 7.60-7.65 (m, 1H), 7.68-7.72 (m, 3H), 7.99 (s, 1H), 11.52 (s, 1H), 12.22-12.48 (m, 1H).

Intermediate 185

6-Bromo-4-fluoro-1H-indazol-3-amine

Five batches of the below reaction were run in sequence in a microwave reactor: To a 5-mL microwave vial was added 4-bromo-2,6-difluorobenzonitrile (3 g, 13.76 mmol), hydrazine (0.864 mL, 27.5 mmol), Hunig's base (4.81 mL, 27.5 mmol) and ethanol (10 mL). The vial was capped and stirred for 10 minutes at 150° C. in a microwave reactor. The reaction mixture was cooled (ice-water bath) and a yellow precipitate formed. The yellow precipitates were collected, combined and the solids were washed with cold ethanol to yield pale yellow rods of the title compound (13.0 g). LC-MS (ES) m/z=230 and 232 (1:1 intensity) [M+H]$^+$.

Intermediate 186

N-Acetyl-N-(1-acetyl-6-bromo-4-fluoro-1H-indazol-3-yl)acetamide

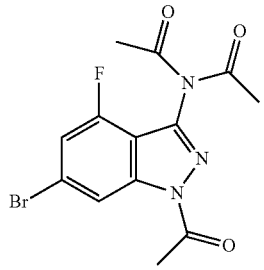 [SMILES: CC(=O)N(C(C)=O)c1nn(C(C)=O)c2cc(Br)cc(F)c12]

To a 100-mL RBF was added 6-bromo-1H-indazol-3-amine (8 g, 34.8 mmol) and acetic anhydride (49.2 mL, 522 mmol), and the reaction mixture was heated at 120° C. over the weekend. LCMS analysis after this time indicated an estimated 2:1 mixture of tris-acylated to bis-acylated products. The acetic anhydride was removed in vacuo, and the residue was dissolved in acetone and dry-loaded onto silica. The residue was purified by flash chromatography (0-40% EtOAc/hexanes, 80 g column) to yield the title compound (8.7 g) as an off-white solid. LC-MS (ES) m/z=356 and 358 (1:1 intensity) [M+H]$^+$.

Intermediate 187

N-Acetyl-N-[1-acetyl-4-fluoro-6-(4,4,5,5-tetramethyl-1,3,2-dioxaborolan-2-yl)-1H-indazol-3-yl]acetamide

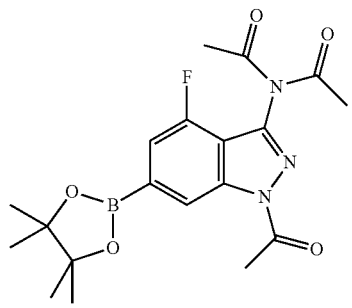 [SMILES: CC(=O)N(C(C)=O)c1nn(C(C)=O)c2cc(B3OC(C)(C)C(C)(C)O3)cc(F)c12]

A 500-mL RBF was charged with N-acetyl-N-(1-acetyl-6-bromo-4-fluoro-1H-indazol-3-yl)acetamide (10.7 g, 30.0 mmol), bis(pinacolato)diboron (7.63 g, 30.0 mmol), potassium acetate (7.37 g, 75 mmol), PdCl$_2$(dppf).CH$_2$Cl$_2$ adduct (2.453 g, 3.00 mmol) and 1,4-dioxane (100 mL), and placed under nitrogen. The reaction was stirred at 100° C. on a stirrer hotplate overnight. The dioxane was removed in vacuo, and the residue was partitioned between CH$_2$Cl$_2$ (300 mL) and water (100 mL). The aqueous was extracted with CH$_2$Cl$_2$ (2×100 mL) and the combined organics dried over Na$_2$SO$_4$. The dried organics were filtered through celite and concentrated. The residue was dissolved in CH$_2$Cl$_2$ (50 mL), then hexanes (250 mL) was added to cause precipitation, and the precipitate filtered. Additional hexanes was added (500 mL), and the mixture allowed to stand. A crystalline precipitate formed over ca. 1 hour, which was collected as product. The filtrate was concentrated, redissolved in CH$_2$Cl$_2$, and precipitated with hexanes. This procedure was repeated 3 times. The combined crystalline residues were collected to provide the title compound (8.7 g) as a brown solid. $^1$H NMR (400 MHz, DMSO-d$_6$): δ 1.34 (s, 12H), 2.35 (s, 6H), 2.73 (s, 3H), 7.36 (d, J=10.1 Hz, 1H), 8.51 (s, 1H).

Intermediate 188

(3S)-1-{[(1,1-Dimethylethyl)oxy]carbonyl}-3-piperidinecarboxylic acid

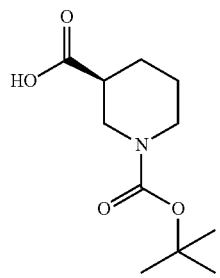 [SMILES: CC(C)(C)OC(=O)N1CCC[C@H](C(=O)O)C1]

Into a premixed solvent sustem of CH$_2$Cl$_2$ (20 mL) and DMF (2 mL) were added (3S)-3-piperidinecarboxylic acid (2 g, 15.49 mmol) and (Boc)$_2$O (4.31 mL, 18.58 mmol). The solids were not very soluble but the reaction was allowed to stir overnight at room temperature. The reaction was concentrated to afford the crude title compound. LC-MS (ES) m/z=230 [M+H]$^+$.

Intermediate 189

(3S)—N-Phenyl-3-piperidinecarboxamide

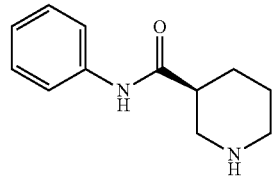 [SMILES: O=C(Nc1ccccc1)[C@H]1CCCNC1]

To a mixture of (3S)-1-{[(1,1-dimethylethyl)oxy]carbonyl}-3-piperidinecarboxylic acid (500 mg, 2.181 mmol), HOBT (668 mg, 4.36 mmol) and EDC (502 mg, 2.62 mmol) in DMF (5 mL) was added N-methylmorpholine (1.20 mL, 10.90 mmol), and the solution was stirred for 10 minutes. Aniline (223 mg, 2.399 mmol) was added, and the reaction mixture was stirred overnight at room temperature. The reaction was diluted with EtOAc (50 mL), then washed with water and brine. The organic was then dried (Na$_2$SO$_4$), filtered, and concentrated to give a light yellow oil. The oil was purified on Biotage SP1 25 m column with a gradient of 0 to 40% EtOAc in hexane over 14 column volumes. Then 5 mL of a premixed 2:1 CH$_2$Cl$_2$:TFA solution was added, and the resulting mixture was stirred for 15 minutes, then concentrated to isolate the crude TFA salt of the title compound. LC-MS (ES) m/z=205 [M+H]$^+$.

Intermediate 190

(3S)-1-(2-Amino-6-chloro-4-pyrimidinyl)-N-phenyl-3-piperidinecarboxamide

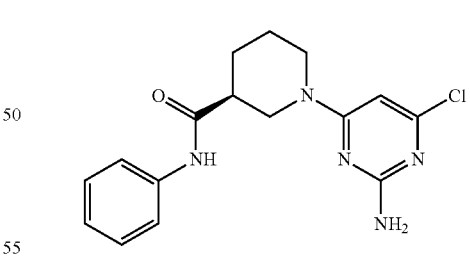

To (3S)—N-phenyl-3-piperidinecarboxamide (327 mg, 1.6 mmol) in CH$_3$CN (10 mL) was added 4,6-dichloro-2-pyrimidinamine (289 mg, 1.760 mmol) and triethylamine (0.446 mL, 3.20 mmol), and the solution was allowed to stir overnight at 50° C. The reaction was then quenched with water (2 mL), and extracted 3× with EtOAc. The organics were combined, dried (Na$_2$SO$_4$), filtered and concentrated to afford the crude title compound (350 mg) as a solid. LC-MS (ES) m/z=332 [M+H]$^+$.

Example 100

(3S)-1-[2-Amino-6-(3-amino-4-fluoro-1H-indazol-6-yl)-4-pyrimidinyl]-N-phenyl-3-piperidinecarboxamide

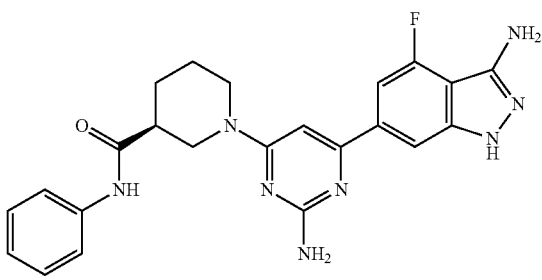 [SMILES: Nc1nc(-c2cc(F)c3c(N)n[nH]c3c2)cc(N2CCC[C@H](C(=O)Nc3ccccc3)C2)n1]

To a 20-mL microwave vial was added (3S)-1-(2-amino-6-chloro-4-pyrimidinyl)-N-phenyl-3-piperidinecarboxamide (82 mg, 0.248 mmol), N-acetyl-N-[1-acetyl-4-fluoro-6-(4,4,5,5-tetramethyl-1,3,2-dioxaborolan-2-yl)-1H-indazol-3-yl]acetamide (200 mg, 0.496 mmol), $K_2CO_3$ (0.372 mL, 0.744 mmol), $PdCl_2(dppf).CH_2Cl_2$ adduct (10.13 mg, 0.012 mmol) and 1,4-dioxane (3 mL). The vial was capped and stirred for 10 minutes at 150° C. in a microwave reactor, then the reaction mixture was poured into $CH_2Cl_2$ (50 mL), and partitioned with water (10 mL). The aqueous was extracted with $CH_2Cl_2$ (2×50 mL) and the organic layer concentrated. The residue was dissolved in $CH_3OH$, treated with 0.1 mL HCl (6 N), and heated to reflux overnight. The $CH_3OH$ was removed in vacuo, and the residue dissolved in DMSO and purified by RPHPLC to afford a TFA salt of the title compound (26.3 mg). LC-MS (ES) m/z=447 [M+H]$^+$. $^1$H NMR (400 MHz, DMSO-$d_6$): δ 1.38-1.62 (m, 1H), 1.67-1.95 (m, 2H), 1.97-2.17 (m, 1H), 2.54-2.69 (m, 1H), 4.33-4.63 (m, 2H), 4.65-4.86 (m, 1H), 4.89-5.11 (m, 1H), 6.89-7.13 (m, 3H), 7.15-7.39 (m, 3H), 7.51-7.72 (m, 3H), 10.08 (s, 1H), 11.99-12.24 (m, 1H), 12.22-12.45 (m, 1H).

Intermediate 191

(3S)—N-Cyclohexyl-3-piperidinecarboxamide

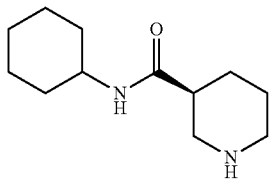 [SMILES: O=C(NC1CCCCC1)[C@H]1CCCNC1]

A mixture of (3S)-1-{[(1,1-dimethylethyl)oxy]carbonyl}-3-piperidinecarboxylic acid (500 mg, 2.181 mmol), HOBT (668 mg, 4.36 mmol), EDC (502 mg, 2.62 mmol), and N-methylmorpholine (1.199 mL, 10.90 mmol) in DMF (5 mL) was stirred for 5 minutes. Then cyclohexanamine (260 mg, 2.62 mmol) was added, and the reaction mixture was stirred overnight at room temperature. The reaction was quenched with 30 mL of water and extracted with EtOAc (3×30 mL). The combined organics were dried over $Na_2SO_4$, filtered and concentrated, and then loaded onto a plug of silica gel (4 grams) and eluted with EtOAc:Hexane (1:1, 150 mL). The organic was concentrated and recrystallized with hot Hexane. The solid was then added to a premixed solution of TFA (1 mL, 12.98 mmol) and $CH_2Cl_2$ (2 mL), and the resulting mixture was stirred for 0.5 hours, then concentrated to afford the crude TFA salt of the title compound. LC-MS (ES) m/z=211 [M+H]$^+$.

Intermediate 192

(3S)-1-(2-Amino-6-chloro-4-pyrimidinyl)-N-cyclohexyl-3-piperidinecarboxamide

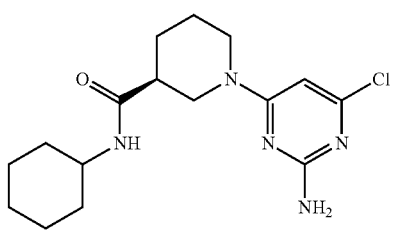 [SMILES: Nc1nc(Cl)cc(N2CCC[C@H](C(=O)NC3CCCCC3)C2)n1]

To (3S)—N-cyclohexyl-3-piperidinecarboxamide (446 mg, 2.12 mmol) in $CH_3CN$ (10 mL) was added 4,6-dichloro-2-pyrimidinamine (382 mg, 2.332 mmol) and triethylamine (0.591 mL, 4.24 mmol), and the reaction mixture was stirred overnight at 50° C. LCMS show no starting material after 3 hours. The reaction was concentrated, and 3 mL of EtOAc was added until solid dissolved. Then 15 mL of hexane was added and solid crashed out of the solution. The solid was isolated by filtration to afford the title compound (430 mg) as a white solid. LC-MS (ES) m/z=338 [M+H]$^+$.

Example 101

(3S)-1-[2-Amino-6-(3-amino-4-fluoro-1H-indazol-6-yl)-4-pyrimidinyl]-N-cyclohexyl-3-piperidinecarboxamide

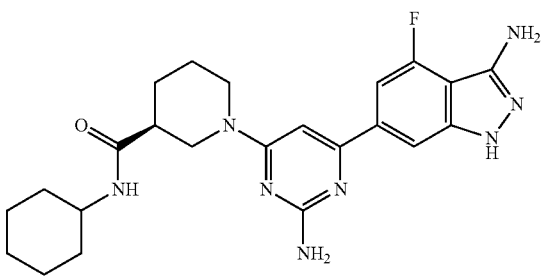 [SMILES: Nc1nc(-c2cc(F)c3c(N)n[nH]c3c2)cc(N2CCC[C@H](C(=O)NC3CCCCC3)C2)n1]

To a 20-mL microwave vial was added (3S)-1-(2-amino-6-chloro-4-pyrimidinyl)-N-cyclohexyl-3-piperidinecarboxamide (84 mg, 0.248 mmol), N-acetyl-N-[1-acetyl-4-fluoro-6-(4,4,5,5-tetramethyl-1,3,2-dioxaborolan-2-yl)-1H-indazol-3-yl]acetamide (200 mg, 0.496 mmol), $K_2CO_3$ (0.372 mL, 0.744 mmol), $PdCl_2(dppf).CH_2Cl_2$ adduct (10.13 mg, 0.012 mmol) and 1,4-dioxane (3 mL). The vial was capped and stirred for 10 minutes at 150° C. in a microwave reactor. The reaction mixture was poured into $CH_2Cl_2$ (50 mL), and partitioned with water (10 mL). The aqueous was extracted with $CH_2Cl_2$ (2×50 mL) and the organic layer was concentrated. The residue was dissolved in $CH_3OH$, treated with 0.1 mL HCl (6 N), and heated to reflux overnight. The CH$_3$OH was removed in vacuo, and the residue dissolved in DMSO and purified by RP-HPLC (15-30% CH$_3$CN in H$_2$O; 0.1% TFA) to afford a TFA salt of the title compound (42.6 mg). LC-MS (ES) m/z=453 [M+H]$^+$. $^1$H NMR (400 MHz, DMSO-d$_6$): δ 0.93-1.98 (m, 12H), 2.21-2.43 (m, 2H), 3.03-3.28 (m, 2H), 4.23-4.47 (m, 2H), 4.52-4.69 (m, 1H), 4.76-4.92 (m, 1H), 6.89-7.03 (m, 1H), 7.13-7.29 (m, 1H), 7.55-7.64 (m, 1H), 7.71-7.94 (m, 1H), 11.94-12.18 (m, 1H), 12.22-12.51 (m, 1H).

Intermediate 193

6-Chloro-N$^4$-methyl-N$^4$-phenyl-2,4-pyrimidinediamine

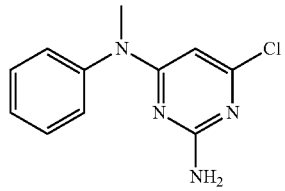 [SMILES: CN(c1ccccc1)c1cc(Cl)nc(N)n1]

A 20-mL screw-cap vial was charged with N-methylaniline (0.653 g, 6.1 mmol), 4,6-dichloro-2-pyrimidinamine (1 g, 6.1 mmol), 1,4-dioxane (5 mL), and HCl (0.152 mL, 0.61 mmol, 4M in 1,4-dioxane). The vial was capped and stirred at reflux overnight. At this time, LCMS analysis indicated good conversion to the desired product, so the reaction mixture was poured into 1:1 NaHCO$_3$ (sat) and water (20 mL) and extracted with EtOAc (3×50 mL). The combined organics were dried (Na$_2$SO$_4$) and concentrated. The solid residue was triturated with CH$_2$Cl$_2$, to yield the title compound (644 mg) as an off-white solid. LC-MS (ES) m/z=235 [M+H]$^+$.

Example 102

6-(3-Amino-1H-indazol-6-yl)-N$^4$-methyl-N$^4$-phenyl-2,4-pyrimidinediamine

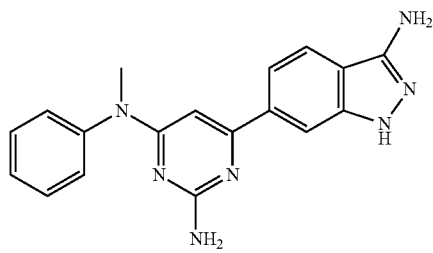 [SMILES: CN(c1ccccc1)c1cc(-c2ccc3c(N)n[nH]c3c2)nc(N)n1]

To a 5-mL microwave vial was added 6-chloro-N$^4$-methyl-N$^4$-phenyl-2,4-pyrimidinediamine (61 mg, 0.260 mmol), 1,1-dimethylethyl 3-(bis{[(1,1-dimethylethyl)oxy]carbonyl}amino)-6-(4,4,5,5-tetramethyl-1,3,2-dioxaborolan-2-yl)-1H-indazole-1-carboxylate (218 mg, 0.390 mmol), K$_2$CO$_3$ (0.130 mL, 0.260 mmol), PdCl$_2$(dppf).CH$_2$Cl$_2$ adduct (212 mg, 0.260 mmol) and 1,4-dioxane (3 mL). The vial was capped and stirred for 10 minutes at 150° C. in a microwave reactor. The reaction mixture was concentrated in vacuo, and the residue was dissolved in EtOAc (50 mL) and water (20 mL). The aqueous layer was extracted with EtOAc (2×50 mL) and the combined organics were dried with Na$_2$SO$_4$, then filtered. The filtrate was concentrated, and dissolved in dioxane (10 mL) and CH$_3$OH (1 mL), and HCl (0.5 mL, 2 mmol) in dioxane was added. The reaction was stirred overnight at 40° C. At this time, LCMS analysis indicated complete conversion to the desired product. The reaction mixture was concentrated, and the residue was dissolved in DMSO and purified by RP-HPLC (15-35% CH$_3$CN in H$_2$O; 0.1% TFA). The fractions containing the product were combined, concentrated to remove the CH$_3$CN, basified (NaHCO$_3$, pH paper) and extracted into EtOAc. The organic layer was dried and concentrated to afford the title compound as a yellow solid (19 mg). LC-MS (ES) m/z=332 [M+H]$^+$. $^1$H NMR (400 MHz, DMSO-d$_6$): δ 3.46 (s, 3H), 5.38-5.52 (m, 2H), 5.94-6.15 (m, 1H), 6.25-7.00 (bs, 1H), 7.12-7.27 (m, 1H), 7.34-7.46 (m, 4H), 7.47-7.57 (m, 2H), 7.58-7.66 (m, 1H), 7.67-7.78 (m, 1H), 11.40-11.77 (m, 1H).

Intermediate 194

2-[4-(Phenylmethyl)-2-morpholinyl]-1H-imidazo[4,5-c]pyridine

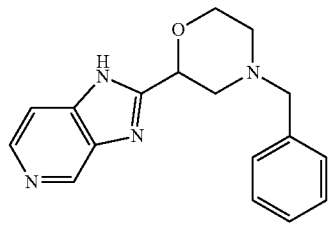 [SMILES: c1ccc(CN2CCOC(c3nc4cnccc4[nH]3)C2)cc1]

A mixture of 3,4-pyridinediamine (1.7 g, 15.58 mmol), 4-benzylmorpholine-2-carboxylic acid hydrochloride (4.82 g, 18.69 mmol) and polyphosphoric acid (40 mL, 15.58 mmol) was refluxed for 12 hours. Then water (70 mL) and NH$_4$OH were added thereto, and the resulting mixture was extracted with CH$_2$Cl$_2$ (10% CH$_3$OH) (3×80 mL). The combined organic solution was washed with brine (2×100 mL), dried, and evaporated in vacuo to afford the title compound (1.0 g). LC-MS (ES) m/z=295 [M+H]$^+$.

Intermediate 195

2-(2-Morpholinyl)-1H-imidazo[4,5-c]pyridine

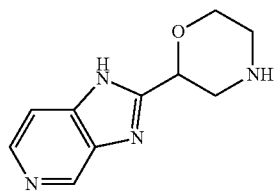 [SMILES: c1cc2[nH]c(C3CNCCO3)nc2cn1]

2-[4-(Phenylmethyl)-2-morpholinyl]-1H-imidazo[4,5-c]pyridine (1.0 g, 3.40 mmol) was hydrogenated in ethanol (30 mL) in the presence of Pd/C (10 wt %, 0.362 g, 0.340 mmol) and 0.2 mL of concentrated hydrochloric acid. After stirring

Intermediate 196

4-Chloro-6-[2-(1H-imidazo[4,5-c]pyridin-2-yl)-4-morpholinyl]-2-pyrimidinamine

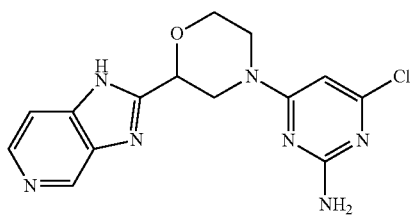 [SMILES: Nc1nc(Cl)cc(N2CCOC(c3nc4cnccc4[nH]3)C2)n1]

a solution of 2-(2-morpholinyl)-1H-imidazo[4,5-c]pyridine (0.996 g, 4.88 mmol), 4,6-dichloro-2-pyrimidinamine (0.8 g, 4.88 mmol) and Hunig's base (2.12 mL, 12.2 mmol) in ethanol (24.39 mL) was heated at 85° C. overnight. The mixture was concentrated and chromatographed (PE-EtOAc, 1:5) to afford the title compound (0.9 g). LC-MS (ES) m/z=332 [M+H]+.

Intermediate 197

4-{2-Amino-6-[2-(1H-imidazo[4,5-c]pyridin-2-yl)-4-morpholinyl]-4-pyrimidinyl}-2-fluorobenzonitrile

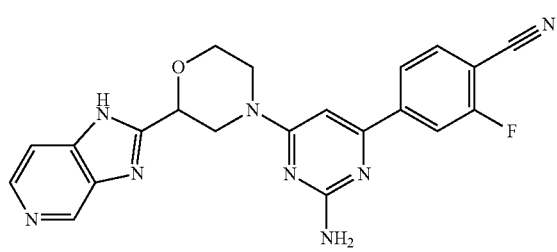 [SMILES: N#Cc1ccc(-c2cc(N3CCOC(c4nc5cnccc5[nH]4)C3)nc(N)n2)cc1F]

A mixture of 4-chloro-6-[2-(1H-imidazo[4,5-c]pyridin-2-yl)-4-morpholinyl]-2-pyrimidinamine (403 mg, 1.21 mmol), 2-fluoro-4-(4,4,5,5-tetramethyl-1,3,2-dioxaborolan-2-yl)benzonitrile (390 mg, 1.58 mmol), Na$_2$CO$_3$ (322 mg, 3.04 mmol) and Pd(PPh$_3$)$_4$ (140 mg, 0.121 mmol) in 1,4-dioxane (6 mL) and water (2 mL) was heated at 140° C. under microwave conditions with stirring for 1 hour. The mixture was filtered, washed by EtOAc (150 mL), and evaporated to give a yellow solid which was chromatographed to afford the title compound (430 mg) as a yellow solid. LC-MS (ES) m/z=417 [M+H]+.

At room temperature overnight, the catalyst was filtered off. The filtrate was concentrated to afford an HCl salt of the title compound (0.8 g) as a yellow oil. LC-MS (ES) m/z=205 [M+H]+.

Example 103

6-{2-Amino-6-[2-(1H-imidazo[4,5-d]pyridin-2-yl)-4-morpholinyl]-4-pyrimidinyl}-1H-indazol-3-amine

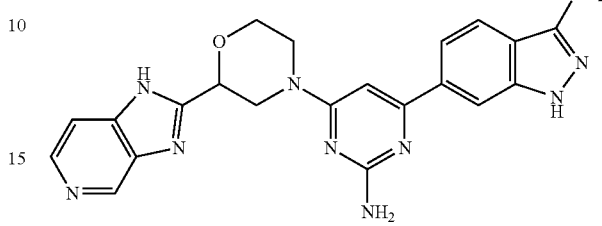

A mixture of 4-{2-amino-6-[2-(1H-imidazo[4,5-c]pyridin-2-yl)-4-morpholinyl]-4-pyrimidinyl}-2-fluorobenzonitrile (380 mg, 0.913 mmol) and hydrazine (1.432 mL, 45.6 mmol) in ethanol (3 mL) was heated under microwave conditions with stirring for 1 hour. The mixture was concentrated. Water (20 mL) was added, and the resulting mixture was filtered to afford the crude title compound (135 mg) as a brown solid. This material was combined with another sample of the title compound (25 mg), and the combined material was purified by preparative HPLC using CH$_3$CN in water (10 mmol ammonium hydrogen carbonate in water) from 40% to 60% in 9 min to afford the title compound (21 mg) as an off-white solid. LC-MS (ES) m/z=429 [M+H]+. $^1$H NMR (400 MHz, DMSO-d$_6$): δ 3.13-3.22 (m, 2H), 3.81-3.91 (m, 1H), 4.14 (d, J=11.2 Hz, 1H), 4.34 (d, J=11.6 Hz, 1H), 4.91 (dd, J=10.0 Hz, 2H), 5.39 (s, 2H), 6.25 (s, 2H), 6.72 (s, 1H), 7.54 (s, 1H), 7.62 (m, 1H), 7.72 (d, J=8.8 Hz, 1H), 7.97 (s, 1H), 8.31 (d, J=5.6 Hz, 1H), 8.91 (s, 1H), 11.54 (s, 1H), 13.01 (s, 1H).

Intermediate 198

2-Azido-1-[3-(methyloxy)phenyl]ethanone

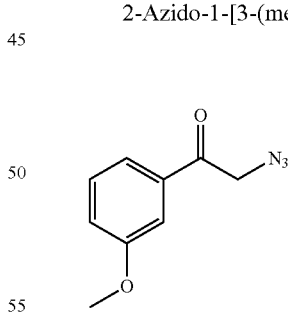

To a solution of 2-bromo-1-[3-(methyloxy)phenyl]ethanone (2.4 g, 10.5 mmol) in THF (80 mL) and water (20 mL) was added sodium azide (1.703 g, 26.2 mmol), and the reaction mixture was stirred at room temperature for 60 hours. Water (40 mL) was added, and the aqueous mixture was extracted with EtOAc (3×80 mL). The organics were dried (Na$_2$SO$_4$), filtered, and concentrated under reduced pressure to afford the title compound (1.87 g) as a brown oil. $^1$H NMR (400 MHz, CDCl$_3$): δ 3.87 (s, 3H), 4.55 (s, 2H), 7.15-7.18 (m, 1H), 7.38-7.42 (m, 1H), 7.44-7.47 (m, 2H).

Intermediate 199

2-Amino-1-[3-(methyloxy)phenyl]ethanone

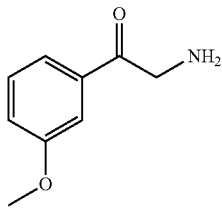

Palladium on carbon (10 wt %, 10.41 g, 9.78 mmol) was added to a solution of 2-azido-1-[3-(methyloxy)phenyl]ethanone (1.87 g, 9.78 mmol) and hydrochloric acid (8.14 mL, 98 mmol) in $CH_3OH$ (50 mL) under nitrogen, and the reaction mixture was stirred under hydrogen overnight at 25° C. The mixture was filtered, washing with $CH_2Cl_2$ (50 mL) and $CH_3OH$ (100 mL), and then concentrated. Water (150 mL) was added, and the mixture was lyophilized to afford an HCl salt of the title compound (2.0 g) as a brown solid. LC-MS (ES) m/z=166 $[M+H]^+$.

Intermediate 200

N-{2-[3-(Methyloxy)phenyl]-2-oxoethyl}-4-(phenylmethyl)-2-morpholinecarboxamide

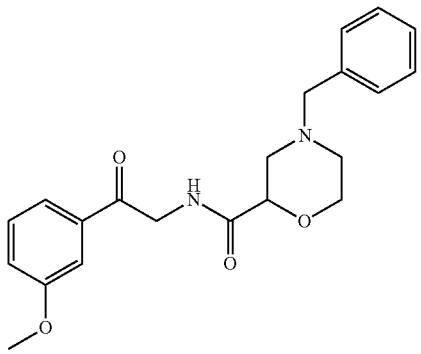 [SMILES: COc1cccc(C(=O)CNC(=O)C2CN(Cc3ccccc3)CCO2)c1]

Oxalyl chloride (1.139 mL, 13.02 mmol) was added to a suspension of 4-(phenylmethyl)-2-morpholinecarboxylic acid (2.237 g, 8.68 mmol) and DMF (0.034 mL, 0.434 mmol) in $CH_2Cl_2$ (80 mL) at 0° C., and the resulting mixture was stirred at 25° C. for 2 hours. The mixture was concentrated, and the resulting residue was dissolved in $CH_2Cl_2$ (80 mL). The resulting brown solution was added to a suspension of triethylamine (3.63 mL, 26.0 mmol) and 2-amino-1-[3-(methyloxy)phenyl]ethanone (1.75 g, 8.68 mmol) in $CH_2Cl_2$ at 0° C., and the reaction mixture was stirred at 25° C. for 3 hours. Water (150 mL) was added to the reaction mixture, and the resulting mixture was extracted with $CH_2Cl_2$ (3×100 mL). The combined organic layers were dried ($Na_2SO_4$), filtered, and concentrated. Purification by silica gel chromatography eluting with EtOAc in PE from 0% to 50% afforded the title compound (1.6 g) as an orange oil. LC-MS (ES) m/z=369 $[M+H]^+$.

Intermediate 201

2-{4-[3-(Methyloxy)phenyl]-1H-imidazol-2-yl}-4-(phenylmethyl)morpholine

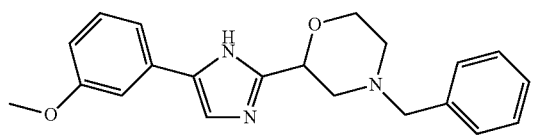 [SMILES: COc1cccc(-c2cnc(C3CN(Cc4ccccc4)CCO3)[nH]2)c1]

A mixture of N-{2-[3-(methyloxy)phenyl]-2-oxoethyl}-4-(phenylmethyl)-2-morpholinecarboxamide (1.6 g, 4.34 mmol) and ammonium trifluoroacetate (2.85 g, 21.71 mmol) was stirred for 0.75 hours at 150° C. The LCMS indicated that the starting material was consumed. The desired product was contained in the residue. Water (50 mL) was added to the residue, and the resulting mixture was extracted with EtOAc (3×50 mL). The organics were dried ($Na_2SO_4$), filtered, and concentrated to afford the title compound (1.56 g) as a brown oil. LC-MS (ES) m/z=350 $[M+H]^+$.

Intermediate 202

2-{4-[3-(Methyloxy)phenyl]-1H-imidazol-2-yl}morpholine

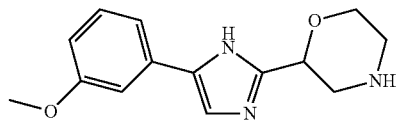 [SMILES: COc1cccc(-c2cnc(C3CNCCO3)[nH]2)c1]

Palladium on carbon (10 wt %, 0.609 g, 0.572 mmol) was added to a solution of 2-{-4-[3-(methyloxy)phenyl]-1H-imidazol-2-yl}-4-(phenylmethyl)morpholine (2.0 g, 5.72 mmol) and hydrochloric acid (4.76 mL, 57.2 mmol) in $CH_3OH$ (80 mL) under nitrogen, and the resulting mixture was stirred under hydrogen overnight at room temperature. The mixture was filtered, washing with $CH_2Cl_2$ (50 mL) and $CH_3OH$ (3×50 mL), and then concentrated. Water (80 mL) was added, and the resulting mixture was lyophilized to afford an HCL salt of the title compound (2.5 g) as a brown oil. LC-MS (ES) m/z=260 $[M+H]^+$.

Intermediate 203

4-Chloro-6-(2-{4-[3-(methyloxy)phenyl]-1H-imidazol-2-yl}-4-morpholinyl)-2-pyrimidinamine

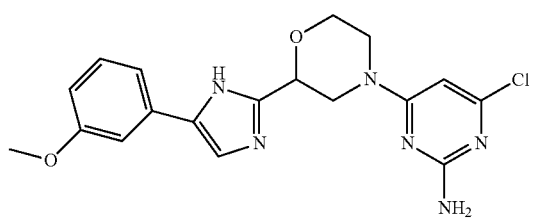 [SMILES: COc1cccc(-c2cnc(C3CN(c4cc(Cl)nc(N)n4)CCO3)[nH]2)c1]

To a stirred solution of 2-{4-[3-(methyloxy)phenyl]-1H-imidazol-2-yl}morpholine (1.5 g, 5.07 mmol) and 4,6-dichloro-2-pyrimidinamine (0.832 g, 5.07 mmol) in ethanol (100 mL) was added Hunig's base (4.5 mL, 25.4 mmol), and the reaction mixture was stirred overnight at reflux. Water (150 mL) was added, and the resulting mixture was extracted with EtOAc (3×100 mL). The organic was dried (Na₂SO₄), filtered, and concentrated. Purification by silica gel chromatography, eluting with EtOAc in PE from 50% to 80% afforded the title compound (830 mg) as a brown solid. LC-MS (ES) m/z=387 [M+H]⁺.

Intermediate 204

4-[2-Amino-6-(2-{4-[3-(methyloxy)phenyl]-1H-imidazol-2-yl}-4-morpholinyl)-4-pyrimidinyl]-2-fluorobenzonitrile

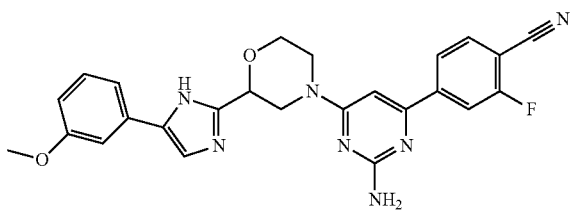 [SMILES: COc1cccc(-c2cnc(C3CN(c4cc(-c5ccc(C#N)c(F)c5)nc(N)n4)CCO3)[nH]2)c1]

A mixture of 4-chloro-6-(2-{4-[3-(methyloxy)phenyl]-1H-imidazol-2-yl}-4-morpholinyl)-2-pyrimidinamine (770 mg, 1.991 mmol), 2-fluoro-4-(4,4,5,5-tetramethyl-1,3,2-dioxaborolan-2-yl)benzonitrile (590 mg, 2.389 mmol), Na₂CO₃ (464 mg, 4.38 mmol) and Pd(PPh₃)₄ (138 mg, 0.119 mmol) in 1,4-dioxane (8 mL) and water (2 mL) was heated at 140° C. under microwave condition with stirring for 1 hour. The mixture was filtered, washing with EtOAc (100 mL), and concentrated to afford the crude title compounde (1.0 g) as a grey oil. This material was combined with another sample of the title compound (100 mg). The combined material was purified by silica gel chromatography, eluting with EtOAc in PE from 50% to 80% to afford the title compound (760 mg) as a brown solid. LC-MS (ES) m/z=472 [M+H]⁺.

Example 104

6-[2-Amino-6-(2-{4-[3-(methyloxy)phenyl]-1H-imidazol-2-yl}-4-morpholinyl)-4-pyrimidinyl]-1H-indazol-3-amine

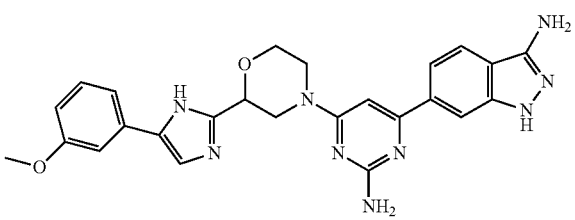 [SMILES: COc1cccc(-c2cnc(C3CN(c4cc(-c5ccc6c(N)n[nH]c6c5)nc(N)n4)CCO3)[nH]2)c1]

A mixture of 4-[2-amino-6-(2-{4-[3-(methyloxy)phenyl]-1H-imidazol-2-yl}-4-morpholinyl)-4-pyrimidinyl]-2-fluorobenzonitrile (700 mg, 1.485 mmol) and hydrazine (2.35 mL, 74.2 mmol) in ethanol (8.0 mL) was heated under microwave conditions with stirring for 1 hour. The mixture was concentrated, and water (20 mL) was added. The resulting mixture was filtered to afford the crude title compound (725 mg) as a yellow solid. This material was combined with another sample of the title compound (25 mg). The combined material was washed with CH₂Cl₂ (2×25 mL) and EtOAc (2×20 mL), and dried under high vacuum to afford the title compound (216 mg) as a yellow solid. LC-MS (ES) m/z=484 [M+H]⁺. ¹H NMR (400 MHz, DMSO-d₆): δ 3.08-3.15 (m, 1H), 3.23 (d, J=8.8 Hz, 1H), 3.69-3.76 (m, 1H), 3.79 (s, 3H), 4.05 (d, J=11.2 Hz, 1H), 4.33 (d, J=9.6 Hz, 1H), 4.62 (dd, J=10.0 Hz, 2.4 Hz, 1H), 4.73 (s, 1H), 5.38 (s, 2H), 6.21 (s, 2H), 6.71 (s, 1H), 6.76 (d, J=8.2 Hz, 1H), 7.25 (t, J=8.0 Hz, 1H), 7.35-7.37 (m, 2H), 7.54-7.63 (m, 2H), 7.71 (d, J=8.4 Hz, 1H), 7.97 (s, 1H), 11.52 (s, 1H), 12.34 (s, 1H).

Intermediate 205

5-(Methyloxy)-2-[4-(phenylmethyl)-2-morpholinyl]-1H-benzimidazole

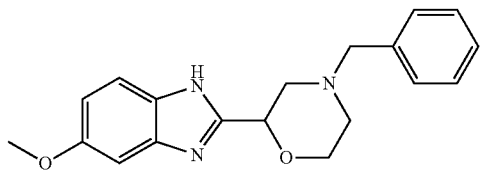 [SMILES: COc1ccc2[nH]c(C3CN(Cc4ccccc4)CCO3)nc2c1]

A solution of 4-methoxybenzene-1,2-diamine (0.5 g, 2.369 mmol) and 4-(phenylmethyl)-2-morpholinecarboxylic acid (1.221 g, 4.74 mmol) in 6N HCl (10 mL) was stirred at 105° C. overnight. The reaction mixture was neutralized with aqueous NaOH and partitioned between EtOAc (50 mL) and water (50 mL). The organic phase was washed with water (50 mL), dried (MgSO₄), and evaporated in vacuo to give the crude product as a black oil. The crude product was added to a silica gel column and was eluted with 90:10 CH₂Cl₂/CH₃OH to afford the title compound (0.6 g). LC-MS (ES) m/z=324 [M+H]⁺.

Intermediate 206

5-(Methyloxy)-2-(2-morpholinyl)-1H-benzimidazole

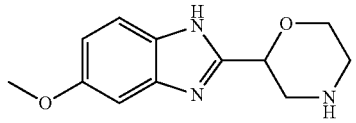 [SMILES: COc1ccc2[nH]c(C3CNCCO3)nc2c1]

To a solution of 5-(methyloxy)-2-[4-(phenylmethyl)-2-morpholinyl]-1H-benzimidazole (2.0 g, 6.18 mmol), and hydrogen chloride (0.451 g, 12.37 mmol) in CH₃OH (50 mL) stirred under nitrogen at room temperature was added palladium on carbon (0.066 g, 0.618 mmol). The reaction mixture was stirred under hydrogen at 25° C. for 3 hours. CH₂Cl₂ was added and the mixture was filtered. The filtrate was concentrated in vacuo. The crude product was added to a silica gel column and was eluted with 90:10 CH₂Cl₂/CH₃OH to afford the title compound (500 mg). LC-MS (ES) m/z=234 [M+H]⁺.

Intermediate 207

4-Chloro-6-{2-[5-(methyloxy)-1H-benzimidazol-2-yl]-4-morpholinyl}-2-pyrimidinamine

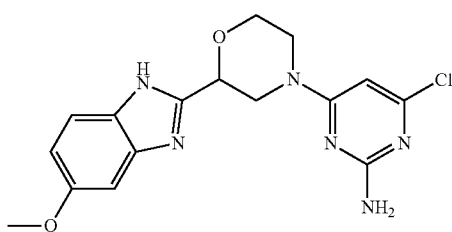 [SMILES: COc1ccc2[nH]c(C3CN(c4cc(Cl)nc(N)n4)CCO3)nc2c1]

To a suspension of 5-(methyloxy)-2-(2-morpholinyl)-1H-benzimidazole (500 mg, 2.143 mmol) and DIPEA (693 mg, 5.36 mmol) in ethanol (10 mL) stirred at room temperature was added solid 4,6-dichloro-2-pyrimidinamine (352 mg, 2.143 mmol). The reaction mixture was stirred at 85° C. overnight. The reaction mixture was cooled to room temperature and partitioned between EtOAc (25 mL) and water (25 mL). The solvent was evaporated in vacuo to give the crude product. The crude product was added to a silica gel column and was eluted with $CH_2Cl_2/CH_3OH$ to afford the title compound (300 mg). LC-MS (ES) m/z=361 [M+H]$^+$.

Intermediate 208

4-(2-Amino-6-{2-[5-(methyloxy)-1H-benzimidazol-2-yl]-4-morpholinyl}-4-pyrimidinyl)-2-fluorobenzonitrile

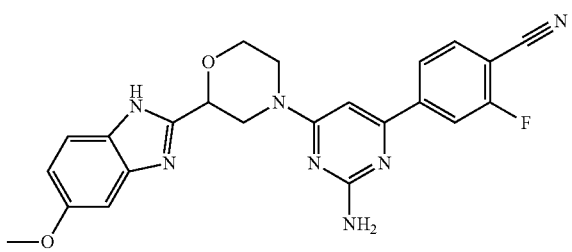 [SMILES: COc1ccc2[nH]c(C3CN(c4cc(-c5ccc(C#N)c(F)c5)nc(N)n4)CCO3)nc2c1]

To a solution of 4-chloro-6-{2-[5-(methyloxy)-1H-benzimidazol-2-yl]-4-morpholinyl}-2-pyrimidinamine (150 mg, 0.416 mmol), 2-fluoro-4-(4,4,5,5-tetramethyl-1,3,2-dioxaborolan-2-yl)benzonitrile (134 mg, 0.540 mmol) and $Na_2CO_3$ (110 mg, 1.039 mmol) in 1,4-dioxane (1.8 mL) and water (0.6 mL) stirred under nitrogen at room temperature was added solid Pd(PPh$_3$)$_4$ (48.0 mg, 0.042 mmol) in one charge. The reaction vessel was sealed and heated in Biotage Initiator using initial high to 140° C. for 1 hour. The reaction mixture was partitioned between EtOAc/THF 25/25 mL and water 50 mL. The organic phase was washed with water (50 mL), dried (Na$_2$SO$_4$) and concentrated in vacuo. The crude product was added to a silica gel column and was eluted with Hexanes/EtOAc to afford the title compound (180 mg). LC-MS (ES) m/z=446 [M+H]$^+$.

Example 105

6-(2-Amino-6-{2-[5-(methyloxy)-1H-benzimidazol-2-yl]-4-morpholinyl}-4-pyrimidinyl)-1H-indazol-3-amine

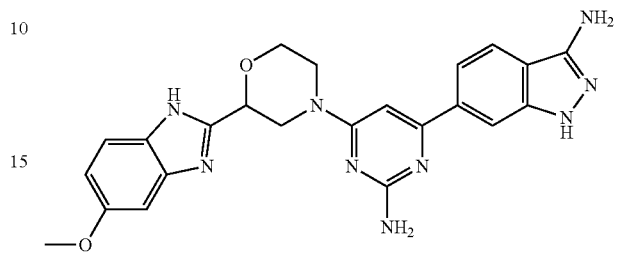

To a suspension of 4-(2-amino-6-{2-[5-(methyloxy)-1H-benzimidazol-2-yl]-4-morpholinyl}-4-pyrimidinyl)-2-fluorobenzonitrile (340 mg, 0.763 mmol) in ethanol (8 mL) at room temperature was added hydrazine hydrate (764 mg, 15.27 mmol). The reaction vessel was sealed and heated in CEM Discover using initial high to 120° C. for 1 hour. After cooling, the reaction was poured into water. The resulting precipitate was filtered and dried under vacuum to afford the title compound (148 mg). LC-MS (ES) m/z=458 [M+H]$^+$. $^1$H NMR (400 MHz, DMSO-d$_6$): δ 3.21-3.10 (m, 2H), 3.82-3.78 (m, 4H), 4.11 (d, 1H), 4.34 (d, 1H), 4.86-4.77 (m, 2H), 5.39 (bs, 2H), 6.23 (bs, 2H), 6.71 (s, 1H), 6.85-6.78 (m, 1H), 7.14-6.95 (m, 1H), 7.50-7.34 (m, 1H), 7.61 (d, 1H), 7.71 (d, 1H), 7.99 (s, 1H), 11.53 (s, 1H), 12.43 (s, 1H).

Intermediate 209

[(2S,5R)-4-(2-Amino-6-chloro-4-pyrimidinyl)-5-methyl-2-morpholinyl]methyl phenylcarbamate

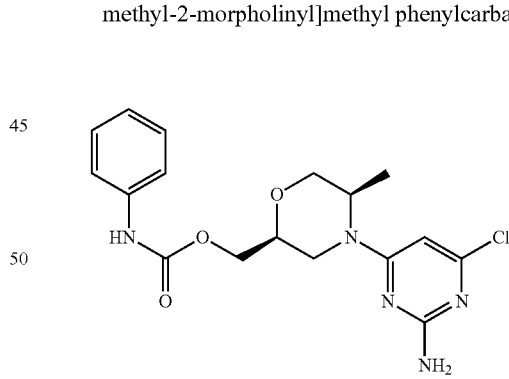

To a 20-mL screw-cap vial was added [(2S,5R)-4-(2-amino-6-chloro-4-pyrimidinyl)-5-methyl-2-morpholinyl] methanol (100 mg, 0.387 mmol), Hunig's base (0.135 mL, 0.773 mmol) and CHCl$_3$ (10 mL). The reaction was cooled to 0° C., then phenyl isocyanate (0.046 mL, 0.425 mmol) in CHCl$_3$ (2 mL) was added dropwise via syringe. The solution was allowed to warm to room temperature and then stirred overnight. An additional portion of Hunig's base (0.135 mL, 0.773 mmol) and phenyl isocyanate (0.046 mL, 0.425 mmol) was added, and the reaction stirred at 60° C. overnight. The solvents were removed in vacuo, and the residue was purified Intermediate 210

{(2S,5R)-4-[2-Amino-6-(4-cyano-3-fluorophenyl)-4-pyrimidinyl]-5-methyl-2-morpholinyl}methyl phenylcarbamate

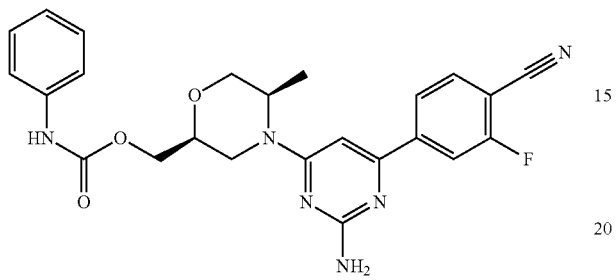

A biphasic suspension of [(2S,5R)-4-(2-amino-6-chloro-4-pyrimidinyl)-5-methyl-2-morpholinyl]methyl phenylcarbamate (123 mg, 0.326 mmol), (4-cyano-3-fluorophenyl)boronic acid (107 mg, 0.651 mmol), PdCl$_2$(dppf).CH$_2$Cl$_2$ adduct (13.3 mg, 0.016 mmol), 2N aqueous K$_2$CO$_3$ (0.488 mL, 0.977 mmol), and 1,4-dioxane (3 mL) was heated in a microwave reactor for 10 minutes at 140° C. The reaction was poured into 0.1 N HCl (30 mL) and CH$_2$Cl$_2$ (50 mL) and the aqueous was extracted with CH$_2$Cl$_2$ (2×50 mL). The combined organics were dried over Na$_2$SO$_4$, and concentrated to yield the title compound (151 mg) as a dark brown oil. LC-MS (ES) m/z=463 [M+H]$^+$.

Example 106

{(2S,5R)-4-[2-Amino-6-(3-amino-1H-indazol-6-yl)-4-pyrimidinyl]-5-methyl-2-morpholinyl}methyl phenylcarbamate

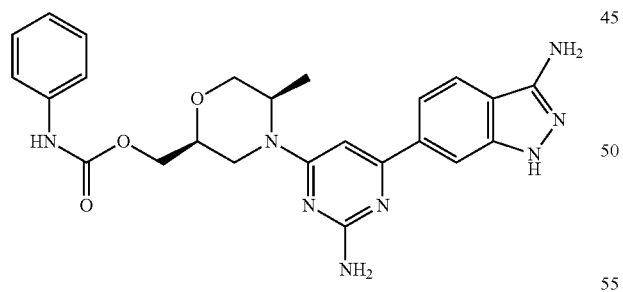

To a solution of {(2S,5R)-4-[2-amino-6-(4-cyano-3-fluorophenyl)-4-pyrimidinyl]-5-methyl-2-morpholinyl}methyl phenylcarbamate (151 mg, 0.326 mmol) in ethanol (3 mL) was added Hunig's base (0.455 mL, 2.61 mmol) and hydrazine (0.041 mL, 1.304 mmol). The resulting solution was heated at 150° C. in a microwave reactor for 30 minutes. LCMS analysis indicated partial conversion, so the reaction was heated for an additional 30 minutes at 150° C. in the microwave reactor. LCMS analysis indicated better conversion. The reaction mixture was concentrated, and the residue purified by RPHPLC (Gilson, 30 mm column, 25-55% CH$_3$CN in water, 0.1% TFA) to yield a TFA salt of the title compound (40 mg) as a brown solid. $^1$H NMR (400 MHz, DMSO-d$_6$): δ 1.28-1.36 (m, 3H) 3.03-3.17 (m, 0.5H), 3.25-3.39 (m, 0.5H), 3.65-3.90 (m, 3H), 4.13-4.38 (m, 2.5H), 4.50-4.62 (m, 0.5H), 4.63-4.75 (m, 0.5H), 4.88-5.00 (m, 0.5H), 5.10-6.20 (bs, 3H), 6.85-6.95 (m, 1H), 6.96-7.06 (m, 1H), 7.25-7.35 (m, 2H), 7.37-7.43 (m, 1H), 7.45-7.55 (m, 2H), 7.72-7.77 (m, 1H), 7.90-7.95 (m, 1H), 9.58-10.04 (m, 1H), 11.63-12.67 (m, 2H). Note: apparent doubling of some peaks in this sample likely due to rotamers. LC-MS (ES) m/z=475 [M+H]$^+$.

Intermediate 211

2-Bromo-1-phenyl-1-propanone

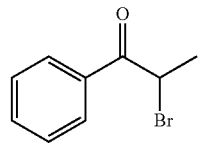

To a CH$_2$Cl$_2$ solution (5 mL) of propiophenone (4.93 g, 36.82 mmol), a CH$_2$Cl$_2$ solution (5 mL) of bromine (6.49 g, 40 mmol) was gradually added at 15° C., followed by 1 hour of stirring. To the resulting solution, 30 mL of saturated NaHCO$_3$ solution and 40 mL of EtOAc were added to conduct extraction. The organic layer was washed with 20 mL of a 20 wt % sodium thiosulfate aqueous solution and then with 20 mL of saturated brine, dried (MgSO$_4$), and subjected to distillation under reduced pressure to remove the solvent. The title compound (7.7 g) was obtained as a yellow oil. LC-MS (ES) m/z=214 [M+H]$^+$.

Intermediate 212

2-Azido-1-phenyl-1-propanone

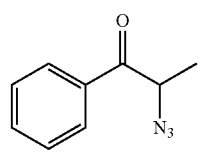

To a solution of 2-bromo-1-phenyl-1-propanone (2.29 g, 10.75 mmol) in THF (80 mL) and water (20 mL) was added sodium azide (1.75 g, 26.9 mmol). The reaction mixture was stirred at room temperature for 3 hours. TLC showed the reaction was complete. Water (40 mL) was added, and the resulting mixture was extracted with EtOAc (3×80 mL). the organics were dried over Na$_2$SO$_4$, filtered, and concentrated under reduced pressure to yield the title compound (1.76) as a brown oil. $^1$H NMR: (400 MHz, CDCl$_3$) δ 7.94-7.96 (m, 2H), 7.60-7.64 (m, 1H), 7.49-7.52 (m, 2H), 4.71 (q, J=6.8 Hz, 1H), 1.58 (d, J=6.8 Hz, 3H).

Intermediate 213

2-Amino-1-phenyl-1-propanone

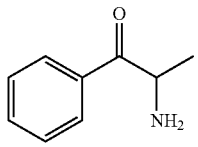

Palladium on carbon (1.069 g, 1.005 mmol) was added to the solution of 2-azido-1-phenyl-1-propanone (1.76 g, 10.05 mmol) and hydrochloric acid (6.69 mL, 80 mmol) in CH$_3$OH (50 mL) under nitrogen, and the reaction mixture was stirred under hydrogen overnight at 25° C. The mixture was filtered, washing with CH$_2$Cl$_2$ (50 mL) and CH$_3$OH (100 mL), and concentrated. Water (100 mL) was added, and the resulting mixture was lyophilized to yield an HCl salt of the title compound (1.9 g) as a brown solid. LC-MS (ES) m/z=150 [M+H]$^+$.

Intermediate 214

N-(1-Methyl-2-oxo-2-phenylethyl)-4-(phenylmethyl)-2-morpholinecarboxamide

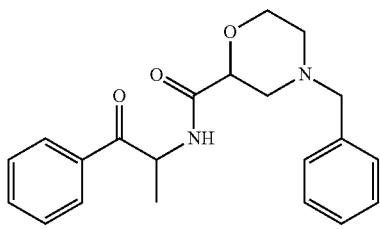 [SMILES: CC(NC(=O)C1CN(Cc2ccccc2)CCO1)C(=O)c1ccccc1]

Oxalyl chloride (1.17 mL, 13.3 mmol) was added to the suspension of 4-(phenylmethyl)-2-morpholinecarboxylic acid (2.290 g, 8.89 mmol) and DMF (0.034 mL, 0.444 mmol) in CH$_2$Cl$_2$ (60 mL) at 0° C., and the resulting mixture was stirred at 25° C. for 2 hours, and then evaporated. CH$_2$Cl$_2$ (60 mL) was added to the resulting residue, and the resulting brown solution was added to a suspension of triethylamine (4.34 mL, 31.1 mmol) and 2-amino-1-phenyl-1-propanone (1.65 g, 8.89 mmol) in CH$_2$Cl$_2$ (60 mL) at 0° C. The reaction mixture was stirred at 25° C. overnight. Water (150 mL) was added, and the resulting mixture was extracted with EtOAc (3×80 mL). The organics were dried (Na$_2$SO$_4$), filtered, and evaporated. The resulting residue was purified by silica gel chromatography, eluting with EtOAc in PE from 20% to 50% to afford the title compound (1.3 g) as a yellow oil. LC-MS (ES) m/z=353 [M+H]$^+$.

Intermediate 215

2-(4-Methyl-5-phenyl-1H-imidazol-2-yl)-4-(phenylmethyl)morpholine

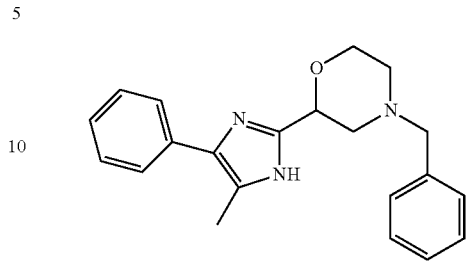

A mixture of N-(1-methyl-2-oxo-2-phenylethyl)-4-(phenylmethyl)-2-morpholinecarboxamide (1.3 g, 3.69 mmol) and ammonium trifluoroacetate (2.417 g, 18.44 mmol) was stirred for 0.75 hours at 150° C. The LCMS indicated that the starting material was consumed. The desired product was contained in the residue. Water (150 mL) was added to the residue, and the resulting mixture was extracted with EtOAc (3×100 mL). The organics were dried (Na$_2$SO$_4$), filtered, and evaporated to afford the title compound (1.2 g) as a brown oil. LC-MS (ES) m/z=334 [M+H]$^+$.

Intermediate 216

2-(4-Methyl-5-phenyl-1H-imidazol-2-yl)morpholine

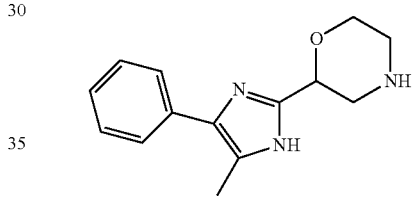

Palladium on carbon (0.527 g, 0.495 mmol) was added to a solution of 2-(4-methyl-5-phenyl-1H-imidazol-2-yl)-4-(phenylmethyl)morpholine (1.65 g, 4.95 mmol) and hydrochloric acid (4.12 mL, 49.5 mmol) in CH$_3$OH (80 mL) under nitrogen, and the reaction mixture was stirred under hydrogen for 2 hours at 25° C. TLC indicated that the starting material was consumed. The mixture was filtered, washing with EtOAc (50 mL) and CH$_3$OH (50 mL), and concentrated. Water (80 mL) was added, and the resulting mixture was lyophilized to afford the title compound (980 mg) as a brown solid. LC-MS (ES) m/z=244 [M+H]$^+$.

Intermediate 217

4-Chloro-6-[2-(4-methyl-5-phenyl-1H-imidazol-2-yl)-4-morpholinyl]-2-pyrimidinamine

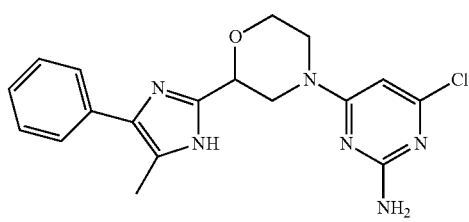 [SMILES: Cc1[nH]c(C2CN(c3cc(Cl)nc(N)n3)CCO2)nc1-c1ccccc1]

A suspension of DIPEA (2.39 g, 18.50 mmol), 2-(4-methyl-5-phenyl-1H-imidazol-2-yl)morpholine (1.5 g, 6.17 mmol) and 4,6-dichloro-2-pyrimidinamine (1.011 g, 6.17 mmol) in ethanol (200 mL) was stirred at 100° C. overnight. The solvent was removed under reduced pressure, and the crude product was purified by silica gel chromatography, eluting with $CH_2Cl_2$/EtOAc (10:1) to afford the title compound (1.2 g) as a white solid. LC-MS (ES) m/z=371, 373 $[M+H]^+$.

Intermediate 218

4-{2-Amino-6-[2-(4-methyl-5-phenyl-1H-imidazol-2-yl)-4-morpholinyl]-4-pyrimidinyl}-2-fluorobenzonitrile

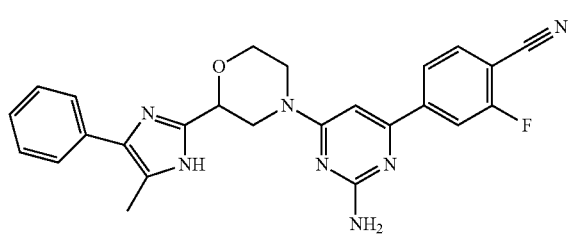 [SMILES: Cc1[nH]c(C2CN(c3cc(-c4ccc(C#N)c(F)c4)nc(N)n3)CCO2)nc1-c1ccccc1]

A mixture of 4-chloro-6-[2-(4-methyl-5-phenyl-1H-imidazol-2-yl)-4-morpholinyl]-2-pyrimidinamine (1.2 g, 3.24 mmol), 2-fluoro-4-(4,4,5,5-tetramethyl-1,3,2-dioxaborolan-2-yl)benzonitrile (1.199 g, 4.85 mmol), $Na_2CO_3$ (0.857 g, 8.09 mmol) and $Pd(PPh_3)_4$ (0.374 g, 0.324 mmol) was placed into a microwave vial and heated in Biotage Initiator using initial 150 W to 140° C. for 1 hour. After cooling the reaction, the solvent was removed under reduced pressure, and the crude product was added to a silica gel column and eluted with Hex/EtOAc (1:3) to afford the title compound (1.2 g) as a yellow solid. LC-MS (ES) m/z=456 $[M+H]^+$.

Example 107

6-{2-Amino-6-[2-(4-methyl-5-phenyl-1H-imidazol-2-yl)-4-morpholinyl]-4-pyrimidinyl}-1H-indazol-3-amine

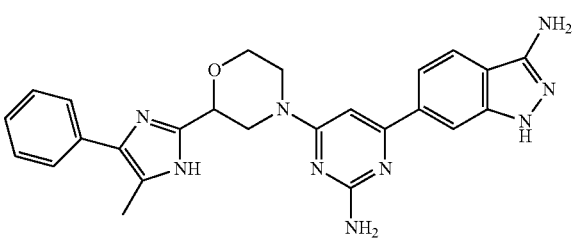 [SMILES: Cc1[nH]c(C2CN(c3cc(-c4ccc5c(N)n[nH]c5c4)nc(N)n3)CCO2)nc1-c1ccccc1]

A mixture of 4-{2-amino-6-[2-(4-methyl-5-phenyl-1H-imidazol-2-yl)-4-morpholinyl]-4-pyrimidinyl}-2-fluorobenzonitrile (100 mg, 0.220 mmol) and hydrazine (0.348 mL, 10.98 mmol) in ethanol (2 mL) was heated under microwave conditions with stirring for 1 hour. The mixture was concentrated, and the crude product was purified by RPHPLC to afford the title compound (90 mg) as a pale yellow solid. LC-MS (ES) m/z=468 $[M+H]^+$. $^1H$ NMR (400 MHz, DMSO-$d_6$): δ 2.35 (s, 3H), 3.04-3.22 (m, 2H), 3.66-3.75 (m, 1H), 4.04 (d, J=11.2 Hz, 1H), 4.32 (d, J=12.8 Hz, 1H), 4.52-4.58 (m, 1H), 4.70 (s, 1H), 5.38 (s, 2H), 6.20 (s, 2H), 6.70 (s, 1H), 7.17-7.28 (m, 1H), 7.34-7.46 (m, 2H), 7.52-7.66 (m, 3H), 7.71 (d, J=8.4 Hz, 1H), 7.96 (s, 1H), 11.52 (s, 1H), 12.20 (s, 1H).

Intermediate 219

5-Chloro-2-[4-(phenylmethyl)-2-morpholinyl]-1H-benzimidazole

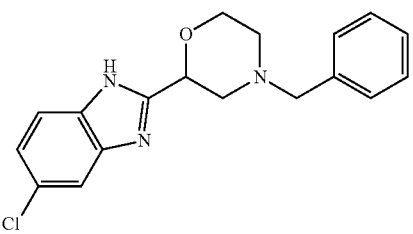 [SMILES: Clc1ccc2[nH]c(C3CN(Cc4ccccc4)CCO3)nc2c1]

A mixture of 4-chlorobenzene-1,2-diamine (2.0 g, 14.03 mmol) and 4-benzylmorpholine-2-carboxylic acid (4.66 g, 21.04 mmol) in polyphosphoric acid (20 mL) was stirred at 140° C. overnight. The reaction mixture was cooled to room temperature and treated with 100 mL of water. The aqueous phase was adjusted to weakly basic with 2 N aqueous sodium hydroxide and extracted with EtOAc. The organic phase was dried over $MgSO_4$ and concentrated in vacuo to give the crude product as a off-white solid. The residue was triturated with hex/EtOAc (1×25 mL). The resulting solid was filtered, rinsed with n-hexane, and collected. The solvent was evaporated in vacuo to afford the title compound (2.1 g). LC-MS (ES) m/z=328 $[M+H]^+$.

Intermediate 220

5-Chloro-2-(2-morpholinyl)-1H-benzimidazole

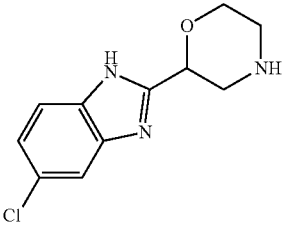 [SMILES: Clc1ccc2[nH]c(C3CNCCO3)nc2c1]

To a solution of 4-benzyl-2-(5-chloro-1H-benzo[d]imidazol-2-yl)morpholine (2.1 g, 6.41 mmol), and hydrogen chloride (0.234 g, 6.41 mmol) in $CH_3OH$ (50 mL) stirred under nitrogen at room temperature was added palladium on carbon (0.068 g, 0.641 mmol). The reaction mixture was stirred under hydrogen at 25° C. for 3 hours. $CH_2Cl_2$ was added and the mixture was filtered. The filtrate was evaporated in vacuo and the residue was dissolved in water (10 mL). The crude product was purified via reverse phase chromatography, eluting with 5~50% of $CH_3OH$ in water, to afford the title compound (400 mg) as a white solid. LC-MS (ES) m/z=238 $[M+H]^+$.

Intermediate 221

4-Chloro-6-[2-(5-chloro-1H-benzimidazol-2-yl)-4-morpholinyl]-2-pyrimidinamine

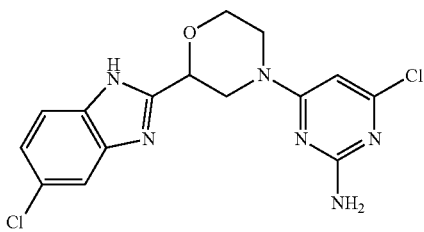 [SMILES: Nc1nc(Cl)cc(N2CCOC(c3nc4cc(Cl)ccc4[nH]3)C2)n1]

To a solution of 5-chloro-2-(2-morpholinyl)-1H-benzimidazole (200 mg, 0.841 mmol) and Hunig's base (109 mg, 0.841 mmol) in ethanol (10 mL) stirred at room temperature was added 4,6-dichloro-2-pyrimidinamine (138 mg, 0.841 mmol), and the reaction mixture was stirred overnight at 85° C. The reaction mixture was cooled to room temperature and partitioned between EtOAc (25 mL) and water (25 mL). The solvent was evaporated in vacuo to give the crude product. The residue was triturated with EtOAc (1×5 mL). The resulting solid was filtered, and collected to afford the title compound (300 mg). LC-MS (ES) m/z=365, 367 [M+H]$^+$.

Intermediate 222

4-{2-Amino-6-[2-(5-chloro-1H-benzimidazol-2-yl)-4-morpholinyl]-4-pyrimidinyl}-2-fluorobenzonitrile

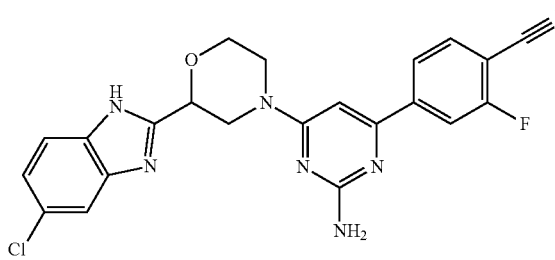

To a suspension of 4-chloro-6-(2-(5-chloro-1H-benzo[d]imidazol-2-yl)morpholino)pyrimidin-2-amine (200 mg, 0.548 mmol), 2-fluoro-4-(4,4,5,5-tetramethyl-1,3,2-dioxaborolan-2-yl)benzonitrile (176 mg, 0.712 mmol) and Na$_2$CO$_3$ (145 mg, 1.369 mmol) in 1,4-dioxane (2.4 mL) and water (0.8 mL) under nitrogen was added Pd(PPh$_3$)$_4$ (63.3 mg, 0.055 mmol). The reaction vessel was sealed and heated in Biotage Initiator using initial high to 140° C. for 1 hour. The reaction mixture was partitioned between EtOAc/THF (25/25 mL) and water (50 mL). The organic phase was washed with water (50 m, dried (Na$_2$SO$_4$) and evaporated in vacuo. The residue was triturated with EtOAc (1×10 mL). The resulting solid was filtered through a coarse fritted glass funnel and collected to afford the title compound (140 mg). LC-MS (ES) m/z=450 [M+H]$^+$.

Example 108

6-{2-Amino-6-[2-(5-chloro-1H-benzimidazol-2-yl)-4-morpholinyl]-4-pyrimidinyl}-1H-indazol-3-amine

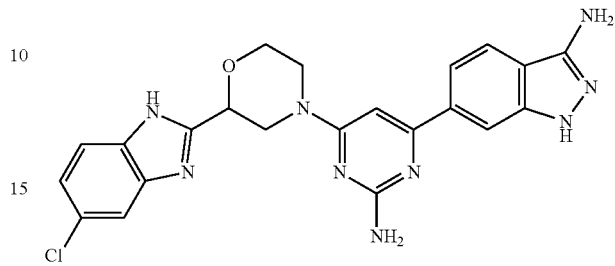

To a solution of 4-{2-amino-6-[2-(5-chloro-1H-benzimidazol-2-yl)-4-morpholinyl]-4-pyrimidinyl}-2-fluorobenzonitrile (140 mg, 0.311 mmol) in ethanol (5 mL) stirred at room temperature was added hydrazine hydrate (156 mg, 3.11 mmol), and the reaction mixture was stirred overnight at 85° C. The solvent was evaporated in vacuo to give the crude product. The crude product was added to a silica gel column and was eluted with CH$_2$Cl$_2$/MeOH to afford the title compound (41 mg) as a yellow solid. LC-MS (ES) m/z=462 [M+H]$^+$. $^1$H NMR (400 MHz, DMSO-d$_6$): δ 3.13-3.17 (m, 2H), 3.81 (t, J=13.2 Hz, 1H), 4.12 (d, J=9.6 Hz, 1H), 4.35 (d, J=9.6 Hz, 1H), 4.84-4.89 (m, 2H), 5.40 (s, 2H), 6.30 (s, 2H), 6.72 (s, 1H), 7.22 (t, J=9.6 Hz, 1H), 7.48-7.50 (m, 1H), 7.60-7.73 (m, 3H), 7.97 (s, 1H), 11.55 (s, 1H), 12.80 (m, 1H).

Intermediate 223

5-Fluoro-2-[4-(phenylmethyl)-2-morpholinyl]-1H-benzimidazole

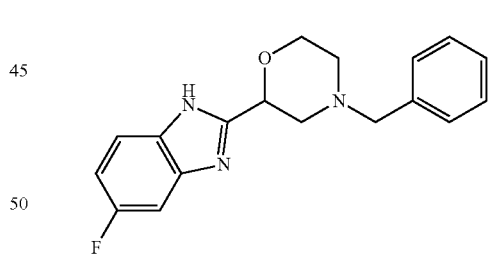

A mixture of 4-fluorobenzene-1,2-diamine (2.0 g, 15.86 mmol) and 4-benzylmorpholine-2-carboxylic acid (5.26 g, 23.78 mmol) in polyphosphoric acid (20 mL) was stirred at 140° C. overnight. The reaction mixture was cooled to room temperature and treated with 100 mL of water. The aqueous phase was adjusted to weakly basic with 2 N aqueous sodium hydroxide and extracted with EtOAc. The organic phase was dried over MgSO$_4$ and evaporated in vacuo to give the crude product as a red solid. The residue was triturated with Hexanes/EtOAc (1×25 mL). The resulting solid was filtered, rinsed with n-hexane, and collected. The solvent was evaporated in vacuo to afford the title compound (3.0 g). LC-MS (ES) m/z=312 [M+H]$^+$.

Intermediate 224

5-Fluoro-2-(2-morpholinyl)-1H-benzimidazole

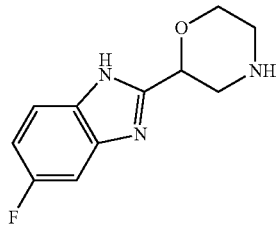 [SMILES: Fc1ccc2[nH]c(C3CNCCO3)nc2c1]

To a solution of 5-fluoro-2-[4-(phenylmethyl)-2-morpholinyl]-1H-benzimidazole (3.0 g, 9.64 mmol), and hydrogen chloride (0.703 g, 19.27 mmol) in CH$_3$OH (50 mL) stirred under nitrogen at room temperature was added palladium on carbon (0.103 g, 0.964 mmol), and the reaction mixture was stirred under hydrogen at 25° C. overnight. CH$_2$Cl$_2$ was added and the mixture was filtered. The filtrate was concentrated in vacuo and the residue was triturated with EtOAc, filtered and dried to afford a hydrochloride salt of the title compound as a off-white solid (2.0 g). LC-MS (ES) m/z=222 [M+H]$^+$.

Intermediate 225

4-Chloro-6-[2-(5-fluoro-1H-benzimidazol-2-yl)-4-morpholinyl]-2-pyrimidinamine

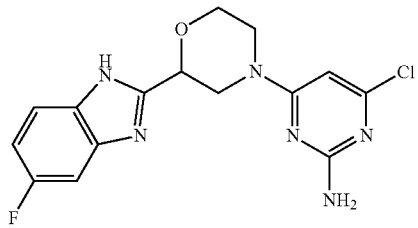 [SMILES: Nc1nc(Cl)cc(N2CCOC(c3nc4cc(F)ccc4[nH]3)C2)n1]

To a suspension of 5-fluoro-2-(2-morpholinyl)-1H-benzimidazole (200 mg, 0.904 mmol) and Hunig's base (409 mg, 3.16 mmol) in ethanol (10 mL) stirred at room temperature was added 4,6-dichloro-2-pyrimidinamine (148 mg, 0.904 mmol), and the reaction mixture was stirred overnight at 85° C. The reaction mixture was cooled to room temperature and partitioned between EtOAc (25 mL) and water (25 mL). The organic solvent was evaporated in vacuo to give the crude product. The residue was triturated with EtOAc (1×5 mL). The resulting solid was filtered and collected to afford the title compound (250 mg). LC-MS (ES) m/z=349 [M+H]$^+$.

Intermediate 226

4-{2-Amino-6-[2-(5-fluoro-1H-benzimidazol-2-yl)-4-morpholinyl]-4-pyrimidinyl}-2-fluorobenzonitrile

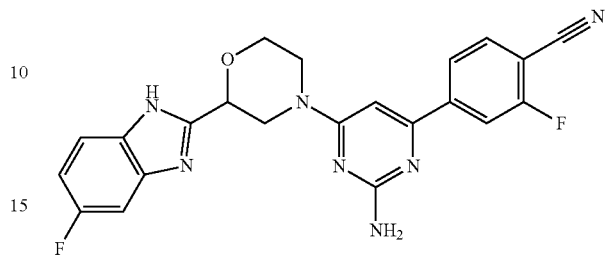

To a suspension of 4-fluoro-6-(2-(5-chloro-1H-benzo[d]imidazol-2-yl)morpholino)pyrimidin-2-amine (250 mg, 0.717 mmol), 2-fluoro-4-(4,4,5,5-tetramethyl-1,3,2-dioxaborolan-2-yl)benzonitrile (230 mg, 0.932 mmol) and Na$_2$CO$_3$ (190 mg, 1.792 mmol) in 1,4-dioxane (3 mL) and water (1.0 mL) under nitrogen was added Pd(PPh$_3$)$_4$ (83 mg, 0.072 mmol). The reaction vessel was sealed and heated in Biotage Initiator using initial high to 140° C. for 1 hour. The reaction mixture was partitioned between EtOAc/THF (25/25 mL) and water (50 mL). The organic phase was washed with water (50 mL), dried over Na$_2$SO$_4$ and evaporated in vacuo. The residue was triturated with EtOAc (1×10 mL). The resulting solid was filtered through a coarse fritted glass funnel and collected to afford the title compound (130 mg). LC-MS (ES) m/z=434 [M+H]$^+$.

Example 109

6-{2-Amino-6-[2-(5-fluoro-1H-benzimidazol-2-yl)-4-morpholinyl]-4-pyrimidinyl}-1H-indazol-3-amine

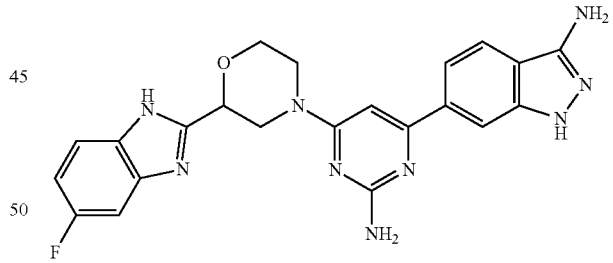

To a solution of 4-{2-amino-6-[2-(5-fluoro-1H-benzimidazol-2-yl)-4-morpholinyl]-4-pyrimidinyl}-2-fluorobenzonitrile (120 mg, 0.277 mmol) in ethanol (3.0 mL) at room temperature was added hydrazine hydrate (139 mg, 2.77 mmol). The reaction vessel was sealed and heated in Biotage Initiator using initial high to 120° C. for 1 hour. After cooling the reaction, the solvent was evaporated in vacuo to give the crude product which was triturated with EtOAc (1×5 mL). The resulting solid was filtered through a medium fritted glass funnel, and collected to afford the title compound (37 mg). LC-MS (ES) m/z=446 [M+H]$^+$. $^1$H NMR (400 MHz, DMSO-d$_6$): δ 3.10-3.17 (m, 2H), 3.81 (t, J=9.6 Hz, 1H), 4.12 (d, J=10.4 Hz, 1H), 4.34 (d, J=12.0 Hz, 1H), 4.82-4.84 (m, 2H), 5.39 (s, 2H), 6.23 (s, 2H), 6.71 (s, 1H), 7.02-7.09 (m, 1H), 7.25 (d, J=8.8 Hz, 0.5H), 7.41-7.49 (m, 1H), 7.61 (d, J=9.6 Hz, 1.5H), 7.71 (d, J=8.0 Hz, 1H), 7.98 (s, 1H), 11.53 (s, 1H), 12.7 (bs, 1H).

Intermediate 227

(3S,6R)-6-Methyl-1-{[(Phenylmethyl)oxy]carbonyl}-3-piperidinecarboxylic acid

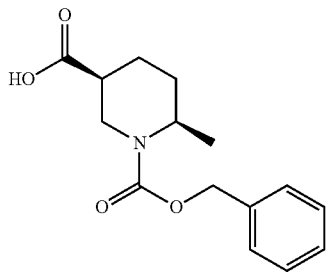 [SMILES: C[C@@H]1CC[C@H](C(=O)O)CN1C(=O)OCc1ccccc1]

To a solution of 3-methyl 1-(phenylmethyl) (3S,6R)-6-methyl-1,3-piperidinedicarboxylate (15 g, 51.5 mmol) in THF/water/CH$_3$OH (10/5/1, 480 mL) was added LiOH.H$_2$O (2.59 g, 61.8 mmol), and the reaction mixture was stirred at room temperature for about 1 hour. The mixture was acidified with 1N HCl until the pH was ~5, and then concentrated in vacuo. The resulting residue was extracted with EtOAc (2×300 mL) and CHCl$_3$ (2×300 mL), and the combined organic layers were dried (MgSO$_4$), filtered and concentrated in vacuo to afford the crude title compound (17 g). LC-MS (ES) m/z=278 [M+H]$^+$.

Intermediate 228

Phenylmethyl(2R,5S)-2-methyl-5-[(phenylamino)carbonyl]-1-piperidinecarboxylate

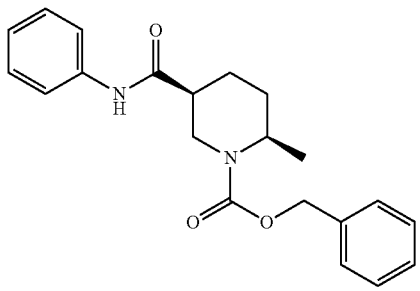 [SMILES: C[C@@H]1CC[C@H](C(=O)Nc2ccccc2)CN1C(=O)OCc1ccccc1]

To a solution of (3S,6R)-6-methyl-1-{[(phenylmethyl)oxy]carbonyl}-3-piperidinecarboxylic acid (17 g, 61.3 mmol) in DMF (400 mL) was added aniline (8.56 g, 92 mmol), Hunig's base (32.1 mL, 184 mmol), HOBt (14.08 g, 92 mmol) and EDC (17.63 g, 92 mmol) at room temperature. The reaction mixture was stirred overnight at room temperature, then diluted with H$_2$O (~100 mL), and extracted with EtOAc (3×250 mL). The combined organic layers were washed with 1N HCl (100 mL), H$_2$O (3×100 mL), brine (100 mL), dried (MgSO$_4$), filtered and concentrated in vacuo to afford the crude title compound (21 g). LC-MS (ES) m/z=353 [M+H]$^+$.

Intermediate 229

(3S,6R)-6-Methyl-N-phenyl-3-piperidinecarboxamide

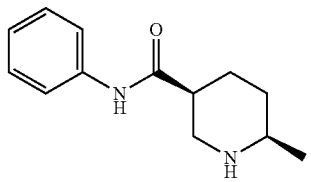 [SMILES: C[C@@H]1CC[C@H](C(=O)Nc2ccccc2)CN1]

A solution of phenylmethyl(2R,5S)-2-methyl-5-[(phenylamino)carbonyl]-1-piperidinecarboxylate (21 g, 59.6 mmol) in EtOAc (250 mL) and EtOH (250 mL) was degassed. Pd/C (10%, 6.34 g, 5.96 mmol) was added and then H$_2$ was bubbled through the mixture. The reaction mixture was stirred at room temperature under H$_2$ balloon overnight. The mixture was filtered through a pad of celite, and concentrated in vacuo to afford the crude title compound (12 g). LC-MS (ES) m/z=219 [M+H]$^+$.

Intermediate 230

(3S,6R)-1-(2-Amino-6-chloro-4-pyrimidinyl)-6-methyl-N-phenyl-3-piperidinecarboxamide

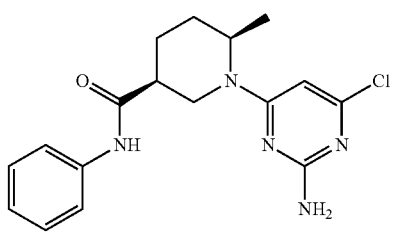 [SMILES: C[C@@H]1CC[C@H](C(=O)Nc2ccccc2)CN1c1cc(Cl)nc(N)n1]

To a solution of (3S,6R)-6-methyl-N-phenyl-3-piperidinecarboxamide (12 g, 55 mmol) in 1,4-dioxane (250 mL) was added 4,6-dichloro-2-pyrimidinamine (8.11 g, 49.5 mmol) and sat. aqueous NaHCO$_3$ (125 mL), and the reaction mixture was then refluxed overnight. The reaction was not completed. The reaction mixture was cooled, added 4,6-dichloro-2-pyrimidinamine (0.9 g, 5.5 mmol), and refluxed overnight. When the reaction was completed, the mixture was cooled down. To the mixture was added about 500 mL of H$_2$O to form a precipitate, and then filtered to obtain a gummy solid. The gummy solid was then dissolved in EtOAc (~800 mL). The organic solution was washed with water (2×200 mL), brine (200 mL), dried (Na$_2$SO$_4$), filtered, and concentrated in vacuo to afford the crude title compound (20 g). LC-MS (ES) m/z=346 [M+H]$^+$.

Intermediate 231

(3S,6R)-1-[2-Amino-6-(4-cyano-3-fluorophenyl)-4-pyrimidinyl]-6-methyl-N-phenyl-3-piperidinecarboxamide

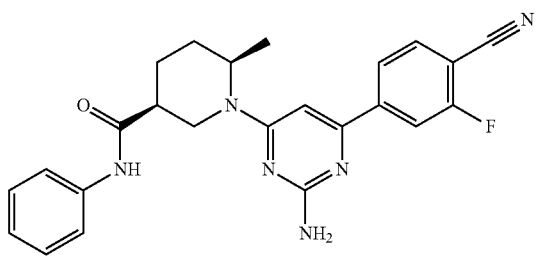 [SMILES: C[C@@H]1CC[C@H](C(=O)Nc2ccccc2)CN1c1cc(-c2ccc(C#N)c(F)c2)nc(N)n1]

To a solution of (3S,6R)-1-(2-amino-6-chloro-4-pyrimidinyl)-6-methyl-N-phenyl-3-piperidinecarboxamide (8 g, 23.1 mmol) in 1,4-dioxane (250 mL) was added (4-cyano-3-fluorophenyl)boronic acid (5.72 g, 34.7 mmol), Pd(PPh$_3$)$_4$ (2.67 g, 2.3 mmol), and sat. aqueous NaHCO$_3$ (125 mL). The resulting mixture was refluxed overnight, cooled, and diluted with H$_2$O (~400 mL) to form precipitate. The mixture was filtered, and the gummy solid was dissolved in EtOAc (~800 mL) and concentrated in vacuo to about 50 mL solvent left. The crude solution was purified by silica gel chromatography (400 g column) eluting with 20% EtOAc/hexanes to 70% EtOAc/hexanes. The fractions that contained the desired product were combined and concentrated in vacuo to afford the title compound (10 g). LC-MS (ES) m/z=431 [M+H]$^+$.

Example 110

(3S,6R)-1-[2-Amino-6-(3-amino-1H-indazol-6-yl)-4-pyrimidinyl]-6-methyl-N-phenyl-3-piperidinecarboxamide

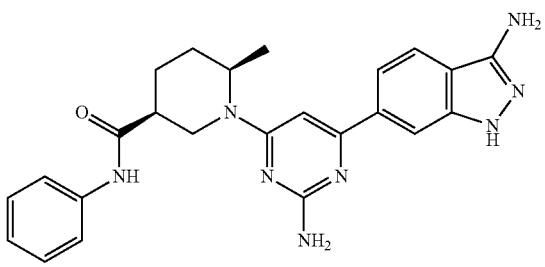 [SMILES: C[C@@H]1CC[C@H](C(=O)Nc2ccccc2)CN1c1cc(-c2ccc3c(N)n[nH]c3c2)nc(N)n1]

To a solution of (3S,6R)-1-[2-amino-6-(4-cyano-3-fluorophenyl)-4-pyrimidinyl]-6-methyl-N-phenyl-3-piperidinecarboxamide (10 g, 23.2 mmol) in EtOH (400 mL) was added hydrazine (22.8 mL, 465 mmol). The resulting mixture was heated in seal tube at 100° C. overnight, cooled down, and concentrated in vacuo. The crude solution was purified by the silica gel chromatography (200 g column) eluting from 100% CHCl$_3$ to CHCl$_3$/CH$_3$OH/NH$_4$OH (9:1:0.1). The pure fractions that contained the desired product were combined and concentrated in vacuo to afford the title compound (3 g). LC-MS (ES) m/z=443 [M+H]$^+$. $^1$H NMR (400 MHz, DMSO-d$_6$): δ 1.18 (d, J=6.8 Hz, 3H), 1.75 (s, 2H), 1.83 (m, 1H), 1.92 (m, 1H), 5.37 (s, 2H), 6.10 (s, 2H), 6.64 (s, 1H), 7.03 (s, 1H), 7.32 (s, 2H), 7.29-7.34 (m, 2H), 7.64 (d, J=7.3 Hz, 4H), 7.96 (s, 1H), 8.32 (s, 1H), 10.06 (s, 1H), 11.49 (s, 1H). The rest of fractions that contained the desired product and a small amount of impurities were combined, concentrated in vacuo and crystallized from CH$_3$OH (~10 mL). The crystalline material was obtained (3.6 g).

Intermediate 232

Cis-phenylmethyl-5-({[(1,1-dimethylethyl)oxy]carbonyl}amino)-2-methyl-1-piperidinecarboxylate

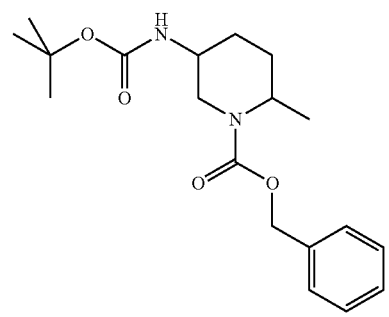 [SMILES: CC1CCC(NC(=O)OC(C)(C)C)CN1C(=O)OCc1ccccc1]

cis-6-methyl-1-{[(phenylmethyl)oxy]carbonyl}-3-piperidinecarboxylic acid (2.62 g, 9.45 mmol) was dissolved in t-butyl alcohol (20 mL, 212 mmol) (anhydrous) in a 40 mL vial. Triethylamine (1.975 mL, 14.17 mmol) was added, followed by the slow addition of diphenyl azidophosphate (dppa) (1.87 mL, 8.65 mmol) at room temperature. The reaction was stirred at room temperature for 30 minutes, and then heated at 100° C. overnight. The reaction mixture was concentrated, and then redissolved with 150 mL of EtOAc. The resulting organic mixture was washed with water (50 mL), brine, dried (Na$_2$SO$_4$), filtered, and concentrated. The resulting clear oil was purified in 50 g Biotage SNAP column with gradient of 0 to 50% of EtOAc in Hexane over 40 minutes to afford the title compound (1.06 g) as a clear oil. LC-MS (ES) m/z=349 [M+H]$^+$.

Intermediate 233

Cis-1,1-dimethylethyl[(6-methyl-3-piperidinyl)]carbamate

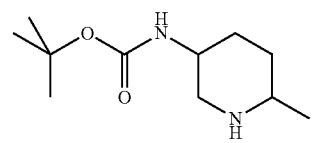

Into a 50 mL RB flask was added the Pd/C Degussa Type (1.240 g, 0.583 mmol) followed by cis-phenylmethyl-5-({[(1,1-dimethylethyl)oxy]carbonyl}amino)-2-methyl-1-piperidinecarboxylate (2.03 g, 5.83 mmol) in ethanol (3 mL). The mixture was evacuated then recharged with hydrogen (0.012 g, 5.83 mmol) in balloon, and the reaction mixture was stirred at room temperature for 3 hours. The reaction was filtered thought a syringe filter, washed with ethanol, and concentrated to afford the title compound (1.21 g) as a clear oil. LC-MS (ES) m/z=215 [M+H]⁺.

Intermediate 234

Cis-1,1-dimethylethyl[(1-(2-amino-6-chloro-4-pyrimidinyl)-6-methyl-3-piperidinyl]carbamate

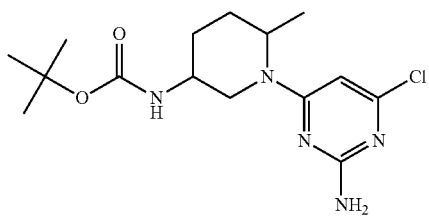 [SMILES: CC1CCC(NC(=O)OC(C)(C)C)CN1c1cc(Cl)nc(N)n1]

A mixture of cis-1,1-dimethylethyl[6-methyl-3-piperidinyl]carbamate (1.21 g, 5.65 mmol) and 4,6-dichloro-2-pyrimidinamine (1.852 g, 11.29 mmol) was dissolved in ethanol (10 mL) in a 5 mL microwave vial. Triethylamine was added (1.57 mL, 11.3 mmol), and the solution was heated at 100° C. overnight. The reaction was concentrated and purified on Biotage SNAP 10 g column gradient of 0 to 50% EtOAc in Hexane. Two spots were isolated. The spot eluded out later was the title compound (1.70 g) as a clear oil. LC-MS (ES) m/z=341 [M+H]⁺.

Intermediate 235

Cis-1,1-dimethylethyl{(1-[2-amino-6-(4-cyano-3-fluorophenyl)-4-pyrimidinyl]-6-methyl-3-piperidinyl}carbamate

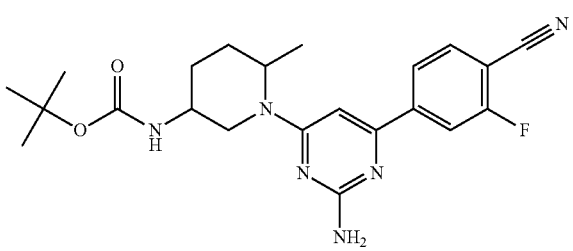 [SMILES: CC1CCC(NC(=O)OC(C)(C)C)CN1c1cc(-c2ccc(C#N)c(F)c2)nc(N)n1]

Into a 20 mL sealable vial were added cis-1,1-dimethylethyl[1-(2-amino-6-chloro-4-pyrimidinyl)-6-methyl-3-piperidinyl]carbamate (1.07 g, 3.13 mmol), (4-cyano-3-fluorophenyl)boronic acid (0.774 g, 4.70 mmol), 1,4-dioxane (10 mL), and sat. aqueous NaHCO₃ (5 mL), and N₂ gas was bubbled through the resulting mixture for 10 minutes. Pd(Ph₃P)₄ (0.543 g, 0.470 mmol) was added, and N₂ gas was bubbled through the mixture for an additional 5 minutes. The vial was capped and heated at 100° C. overnight. LCMS shows about 30% done. Additional 200 mg of the boronic acid and 150 mg of catalyst were added, and the reaction mixture was stirred overnight at 110° C. The reaction was diluted with 100 mL of EtOAc and washed with 30 mL of water and brine. The organic was then dried over MgSO₄, filtered and concentrated. Purification on 40 g Biotage SNAP column with gradient of 0 to 60% EtOAc in Hexane over 40 minutes afforded the title compound (984 mg) as a clear oil. LC-MS (ES) m/z=427 [M+H]⁺.

Example 111

Cis-1,1-dimethylethyl{(1-[2-amino-6-(3-amino-1H-indazol-6-yl)-4-pyrimidinyl]-6-methyl-3-piperidinyl}carbamate

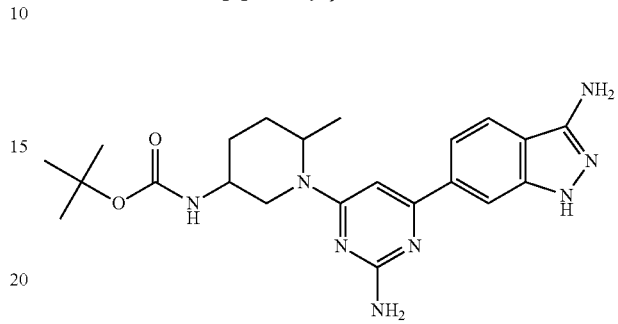

cis-1,1-dimethylethyl{(1-[2-amino-6-(4-cyano-3-fluorophenyl)-4-pyrimidinyl]-6-methyl-3-piperidinyl}carbamate (77 mg, 0.181 mmol) was dissolved in ethanol (3 mL) into a 5 mL sealable vial. Hydrazine monohydrate (0.266 mL, 5.42 mmol) was added, the vial was sealed, and the reaction mixture was heated overnight at 100° C. The reaction was then concentrated, re-dissolved in 2 mL of DMSO, and purified on HPLC (HPLC condition: open-access Gilson using Unipoint software with a Varian Polaris 5u C18(2) 100A, 50×30.00 mm 5 micron. 10-minute run (30 ml/min, 20% CH₃CN/H₂O, 0.1% TFA to 45% CH₃CN/H₂O, 0.1% TFA) with UV detection at 254 nm). The fractions with the desired product were combined, and the volume was reduced until most of the CH₃CN was removed. To the resulting aqueous mixture was added a saturated aqueous NaHCO₃ solution and then it was extracted with EtOAc (3×50 mL). The combined organic layers were washed with brine, dried over MgSO₄, filtered and concentrated to afford the title compound. LC-MS (ES) m/z=439 [M+H]⁺. ¹H NMR (400 MHz, DMSO-d₆): δ 1.11 (d, J=6.8 Hz, 3H), 1.24 (d, J=1.0 Hz, 1H), 1.42 (s, 9H), 1.65 (m, 4H), 2.56-2.68 (m, 1H), 4.41 (d, J=5.6 Hz, 1H), 4.69 (bs, 1H), 5.38 (s, 2H), 6.09 (bs, 2H), 6.56 (s, 1H), 6.94 (d, J=8.1 Hz, 1H), 7.55 (d, J=8.3 Hz, 1H), 7.70 (d, J=8.3 Hz, 1H), 7.93 (s, 1H), 11.50 (s, 1H).

Intermediate 236

4-{2-Amino-6-[(2R,5S)-5-amino-2-methyl-1-piperidinyl]-4-pyrimidinyl}-2-fluorobenzonitrile

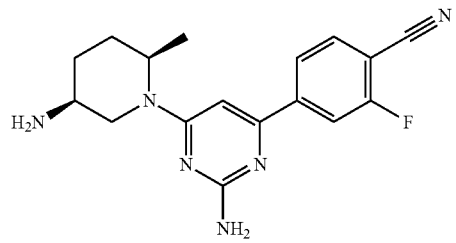 [SMILES: C[C@@H]1CC[C@H](N)CN1c1cc(-c2ccc(C#N)c(F)c2)nc(N)n1]

To a solution of 1,1-dimethylethyl{(3S,6R)-1-[2-amino-6-(4-cyano-3-fluorophenyl)-4-pyrimidinyl]-6-methyl-3- piperidinyl}carbamate (985 mg, 2.310 mmol) in 1,4-dioxane (5 mL) was added 4M HCl in 1,4-dioxane (10 mL, 40.0 mmol) into a 40 mL vial. A solid formed, and the mixture was stirred at room temperature for 30 minutes, then concentrated to afford an HCl salt of the title compound (1.15 g) as a white solid. LC-MS (ES) m/z=327 [M+H]⁺.

Intermediate 237

Phenylmethyl{(3S,6R)-1-[2-amino-6-(4-cyano-3-fluorophenyl)-4-pyrimidinyl]-6-methyl-3-piperidinyl}carbamate

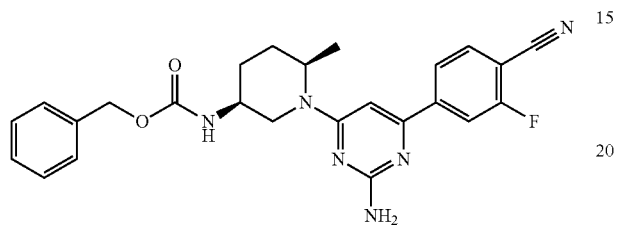

To a solution of 4-{2-amino-6-[(2R,5S)-5-amino-2-methyl-1-piperidinyl]-4-pyrimidinyl}-2-fluorobenzonitrile (170 mg, 0.426 mmol) in THF (4 mL) was added saturated aqueous NaHCO₃ (2 mL) followed by phenylmethyl chloridocarbonate (0.07 mL, 0.47 mmol), and the reaction mixture was stirred at room temperature for 4 hours. The mixture was diluted with 3 mL of water and then extracted with EtOAc (3×30 mL). The organic was then washed with brine, dried over MgSO₄, filtered and concentrated. The resulting yellow oil was purified on a Biotage SNAP 10 g column with gradient of 0 to 50% EtOAc in hexane over 30 minutes to afford the title compound (57 mg) as a yellow oil. LC-MS (ES) m/z=327 [M+H]⁺.

Example 112

Phenylmethyl{(3S,6R)-1-[2-amino-6-(3-amino-1H-indazol-6-yl)-4-pyrimidinyl]-6-methyl-3-piperidinyl}carbamate

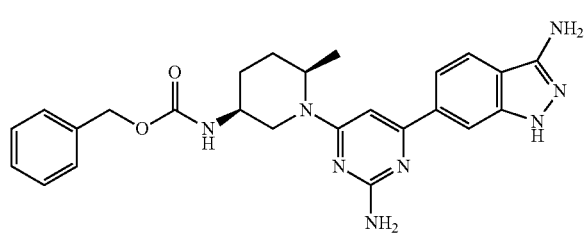 [SMILES: C[C@@H]1CC[C@H](NC(=O)OCc2ccccc2)CN1c1cc(-c2ccc3c(N)n[nH]c3c2)nc(N)n1]

To phenylmethyl{(3S,6R)-1-[2-amino-6-(4-cyano-3-fluorophenyl)-4-pyrimidinyl]-6-methyl-3-piperidinyl}carbamate (57 mg, 0.124 mmol) in ethanol (3 mL) was added hydrazine (0.182 mL, 3.71 mmol) into a 5 mL sealable vial. The solution was then capped and heated at 100° C. overnight. The reaction was then concentrated, re-dissolved in 2 mL of DMSO, and purified on HPLC (HPLC condition: open-access Gilson using Unipoint software with a Varian Polaris 5u C18(2) 100A, 50×30.00 mm 5 micron. 10-minute run (30 ml/min, 33% CH₃CN/H₂O, 0.1% TFA to 58% CH₃CN/H₂O, 0.1% TFA) with UV detection at 254 nm). Product fractions were combined, and the volume was reduced to remove the CH₃CN. To the resulting aqueous mixture was added 5 mL of saturated aqueous NaHCO₃, and then extracted 3× with EtOAc. The organics were then combined, washed with brine, dried over MgSO₄, filtered and concentrated to afford the title compound (37 mg) as a light yellow solid. LC-MS (ES) m/z=473 [M+H]⁺. ¹H NMR (400 MHz, DMSO-d₆): δ 1.12 (d, J=6.8 Hz, 3H), 1.66 (m, 4H), 2.67 (dt, J=3.7, 1.8 Hz, 1H), 3.38 (bs, 1H), 4.50 (bs, 1H), 4.73 (bs, 1H), 5.06 (d, J=5.3 Hz, 2H), 5.39 (s, 2H), 6.04-6.20 (bs, 2H), 6.58 (bs, 1H), 7.30-7.46 (m, 6H), 7.55 (d, J=8.3 Hz, 1H), 7.71 (d, J=8.3 Hz, 1H), 7.93 (s, 1H), 11.52 (bs, 1H).

Intermediate 238

N-{(3S,6R)-1-[2-Amino-6-(4-cyano-3-fluorophenyl)-4-pyrimidinyl]-6-methyl-3-piperidinyl}benzamide

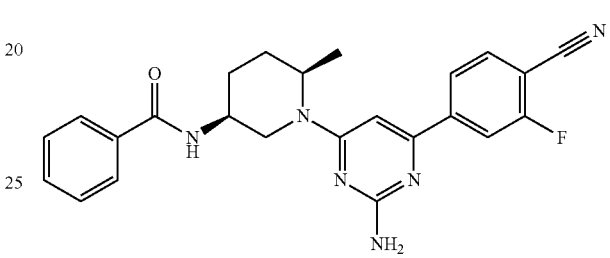

To 1,1-dimethylethyl{(3S,6R)-1-[2-amino-6-(4-cyano-3-fluorophenyl)-4-pyrimidinyl]-6-methyl-3-piperidinyl}carbamate (100 mg, 0.234 mmol) in a 20 mL vial was added 2 mL of 4M HCl in 1,4-dioxane, and the solution was stirred at room temperature for 30 minutes. The reaction was then concentrated. To the resulting whitish solid was added a premixed solution of benzoic acid (34.4 mg, 0.281 mmol), EDC (67.4 mg, 0.352 mmol), HOBT (71.8 mg, 0.469 mmol), and N-methylmorpholine (0.129 mL, 1.172 mmol) in DMF (2 mL), and the resulting solution was stirred at room temperature overnight. The reaction was diluted with water (10 mL), then extracted with EtOAc (3×10 mL). The organics were combined, washed with brine, then dried over MgSO₄, filtered and concentrated to afford the crude title compound (30 mg) as a yellow oil. LC-MS (ES) m/z=431 [M+H]⁺.

Example 113

N-{(3S,6R)-1-[2-Amino-6-(3-amino-1H-indazol-6-yl)-4-pyrimidinyl]-6-methyl-3-piperidinyl}benzamide

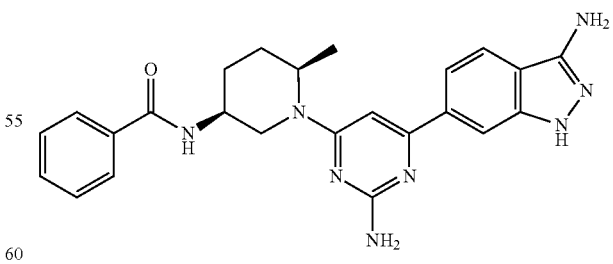

To N-{(3S,6R)-1-[2-amino-6-(4-cyano-3-fluorophenyl)-4-pyrimidinyl]-6-methyl-3-piperidinyl}benzamide (101 mg, 0.234 mmol) in ethanol (2 mL) into a 5 mL sealable vial was added hydrazine monohydrate (0.22 mL, 7.02 mmol), and the reaction was capped and heat overnight at 100° C. The reaction was concentrated, re dissolved in 1 mL of DMSO, and purified on HPLC (HPLC condition: open-access Gilson using Unipoint software with a Varian Polaris 5u C18(2) 100A, 50×30.00 mm 5 micron. 10-minute run (30 ml/min, 15% CH$_3$CN/H$_2$O, 0.1% TFA to 40% CH$_3$CN/H$_2$O, 0.1% TFA) with UV detection at 254 nm). Product fractions were combined and the volume was reduced to remove most of the CH$_3$CN. To the resulting aqueous mixture was added sat. aqueous NaHCO$_3$, and then it was extracted with EtOAc (3×15 mL). The organic was washed with brine, dried over MgSO$_4$, filtered and concentrated to afford the title compound (20 mg) as a light yellow solid. LC-MS (ES) m/z=443 [M+H]$^+$. $^1$H NMR (400 MHz, DMSO-d$_6$): δ 1.19 (d, J=6.8 Hz, 3H), 1.24 (s, 1H), 1.66-1.93 (m, 5H), 2.54 (s, 1H), 3.89 (d, J=4.0 Hz, 1H), 5.39 (s, 2H), 6.13 (bs, 1H), 6.62 (s, 1H), 7.47-7.59 (m, 5H), 7.71 (d, J=8.6 Hz, 1H), 7.90 (d, J=7.1 Hz, 2H), 7.94 (s, 1H), 8.43 (d, J=8.1 Hz, 1H), 11.51 (bs, 1H).

Intermediate 239

N-{(3S,6R)-1-[2-Amino-6-(4-cyano-3-fluorophenyl)-4-pyrimidinyl]-6-methyl-3-piperidinyl}-2-phenylacetamide

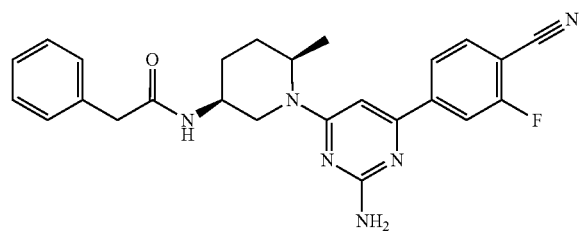 [SMILES: C[C@@H]1CC[C@H](NC(=O)Cc2ccccc2)CN1c1cc(-c2ccc(C#N)c(F)c2)nc(N)n1]

A premixed solution of phenylacetic acid (45.0 mg, 0.331 mmol), EDC (79 mg, 0.413 mmol), HOBT (84 mg, 0.551 mmol), and N-methylmorpholine (0.152 mL, 1.378 mmol) in DMF (2 mL) was added to 4-{2-amino-6-[(2R,5S)-5-amino-2-methyl-1-piperidinyl]-4-pyrimidinyl}-2-fluorobenzonitrile (100 mg, 0.276 mmol) in DMF (2 mL). The solution was stirred at room temperature overnight. The reaction was diluted with water (10 mL), and then extracted with EtOAc (3×10 mL). The organics were combined, washed brine, dried over MgSO$_4$, filtered and concentrated. The resulting oil was purified with a 10 g Biotage SNAP column with gradient of 0 to 85% EtOAc in Hexane for 25 minutes to afford the title compound (105 mg) as a yellow oil. LC-MS (ES) m/z=445 [M+H]$^+$.

Example 114

N-{(3S,6R)-1-[2-Amino-6-(3-amino-1H-indazol-6-yl)-4-pyrimidinyl]-6-methyl-3-piperidinyl}-2-phenylacetamide

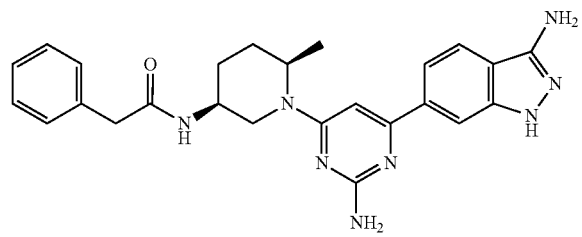 [SMILES: C[C@@H]1CC[C@H](NC(=O)Cc2ccccc2)CN1c1cc(-c2ccc3c(N)n[nH]c3c2)nc(N)n1]

To N-{(3S,6R)-1-[2-amino-6-(4-cyano-3-fluorophenyl)-4-pyrimidinyl]-6-methyl-3-piperidinyl}-2-phenylacetamide (105 mg, 0.236 mmol) in ethanol (2 mL) into a 5 mL sealable vial was added hydrazine (0.22 mL, 7.1 mmol), and the reaction was then capped and heated on a hot plate at 100° C. overnight. The reaction was concentrated, then redissolved in 1 mL of DMSO and purified on HPLC (HPLC condition: open-access Gilson using Unipoint software with a Varian Polaris 5u C18(2) 100A, 50×30.00 mm 5 micron. 10-minute run (30 ml/min, 15% CH$_3$CN/H$_2$O, 0.1% TFA to 45% CH$_3$CN/H$_2$O, 0.1% TFA) with UV detection at 254 nm). Product fractions were combined and the volume was reduced to remove most of the CH$_3$CN. To the resulting aqueous mixture was added sat. aqueous NaHCO$_3$, and then it was extracted with EtOAc (3×15 mL). The organic was washed with brine, dried over MgSO$_4$, filtered, concentrated, and transferred to a haystack vial. Water (1 mL) was added, and the resulting mixture was freeze dried to afford the title compound (44 mg) as a light yellow solid. LC-MS (ES) m/z=457 [M+H]$^+$. $^1$H NMR (400 MHz, DMSO-d$_6$): δ 1.15 (d, J=6.8 Hz, 3H), 1.61-1.76 (m, 4H), 2.57-2.68 (m, 1H), 3.44 (s, 2H), 3.59 (dd, J=7.7, 3.4 Hz, 1H), 4.38-4.84 (m, 2H), 5.38 (s, 2H), 6.11 (bs, 2H), 6.56 (s, 1H), 7.21-7.36 (m, 5H), 7.54 (dd, J=8.6, 1.0 Hz, 1H), 7.71 (d, J=8.3 Hz, 1H), 7.92 (s, 1H), 8.16 (d, J=8.1 Hz, 1H), 11.51 (s, 1H).

Intermediate 240

Cis-Methyl 6-(trifluoromethyl)-3-piperidinecarboxylate

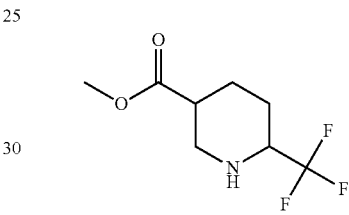

To a solution of methyl 6-(trifluoromethyl)-3-pyridinecarboxylate (10 g, 48.7 mmol) in CH$_3$OH (100 mL) was added platinum(IV) oxide (0.332 g, 1.462 mmol) followed by concentrated HCl (4.47 mL, 53.6 mmol) into a Parr Shaker. The mixture was degassed (3×) with nitrogen, and the reaction mixture was stirred overnight under a 55 psi H$_2$ atmosphere (during the first hour ~3 refills with H$_2$ gas were necessary to re-establish the 55 psi pressure). The reaction mixture was degassed (3×) with nitrogen, filtered, treated with 1 mL of 12N HCl and concentrated. The resulting residue was co-evaporated from toluene (100 mL) followed by CH$_3$CN (100 mL) and dried under vacuum to afford the HCl salt of the title compound (10.8 g) as a white solid which was 90% cis isomer. $^1$H NMR (400 MHz, CD$_3$OD): δ 1.84 (m, 1H), 2.00 (m, 1H), 2.15 (dq, J=14.2, 3.5 Hz, 1H), 2.30-2.39 (m, 1H), 3.09-3.16 (m, 1H), 3.42 (dd, J=13.4, 4.3, 1H), 3.80 (s, 3H), 4.17-4.35 (m, 1H).

Intermediate 241

Cis-6-(Trifluoromethyl)-3-piperidinecarboxylic acid

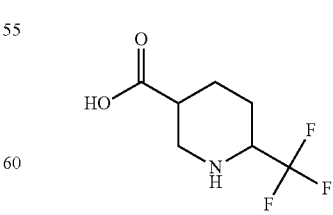

Into a sealable tube was added cis-methyl 6-(trifluoromethyl)-3-piperidinecarboxylate (7.8 g, 31.5 mmol) followed by 1,4-dioxane (30 mL) and concentrated HCl (30 mL). The tube was sealed, and the resulting mixture was stirred for 6 hours at 100° C. The reaction was allowed to cool to room temperature, and diluted with toluene (~100 mL). The mixture was concentrated, and the resulting residue was azeotroped with more toluene (~100 mL), followed by evaporation from CH₃CN (~50 mL). The resulting solid was triturated with CH₃CN and filtered to afford the HCl salt of the desired product (5.9 g) as a white solid. ¹H NMR (400 MHz, CD₃OD): δ 1.78-1.92 (m, 1H), 2.00 (m, 1H), 2.16 (m, 1H), 2.33 (m, 1H), 3.07 (m, 1H), 3.37 (dd, J=13.4, 4.3 Hz, 1H), 3.79 (d, J=13.1 Hz, 1H), 4.25 (m, 1H).

Intermediate 242

Cis-1-[6-Chloro-2-(methylthio)-4-pyrimidinyl]-6-(trifluoromethyl)-3-piperidinecarboxylic acid

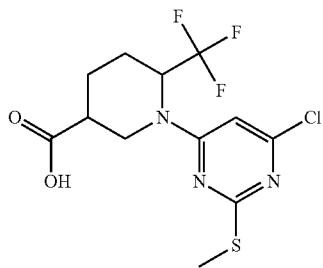 [SMILES: CSc1nc(Cl)cc(N2CC(C(=O)O)CCC2C(F)(F)F)n1]

To cis-6-(trifluoromethyl)-3-piperidinecarboxylic acid (3.393 g, 14.52 mmol) in THF (1.5 mL) were added molecular sieves, and the resulting mixture was stirred for 5 minutes into a 250 mL RB flask. The mixture was cooled in an ice bath, and then LiHMDS (43.6 mL, 43.6 mmol) was added slowly. After the addition was completed, 4,6-dichloro-2-(methylthio)pyrimidine (3.40 g, 17.43 mmol) was added. After 0.5 hours, the reaction was quenched with 30 mL of water and by the dropwise addition of 6N HCl until pH was acidic. The resulting mixture was extracted with EtOAc (3×30 mL). The organics were combined, washed with brine, dried (MgSO₄), filtered and concentrated to afford the crude title compound as an oil. LC-MS (ES) m/z=356 [M+H]⁺.

Intermediate 243

Cis-1-[6-Chloro-2-(methylsulfonyl)-4-pyrimidinyl]-6-(trifluoromethyl)-3-piperidinecarboxylic acid

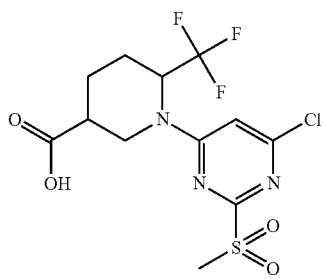 [SMILES: CS(=O)(=O)c1nc(Cl)cc(N2CC(C(=O)O)CCC2C(F)(F)F)n1]

A suspension of cis-1-[6-chloro-2-(methylthio)-4-pyrimidinyl]-6-(trifluoromethyl)-3-piperidinecarboxylic acid (180 mg, 0.506 mmol) in CH₃OH (8 mL) and water (2.5 mL) was cooled in an ice bath and treated slowly with a premixed solution of oxone (778 mg, 1.27 mmol) in water (3 mL). The reaction was stirred at room temperature overnight. The pH was adjusted pH to acidic with 1N HCl and then 5 mL of water was added. The resulting mixture was filtered over fritted funnel to isolate the title compound (79 mg) as a white solid. LC-MS (ES) m/z=388, 390 [M+H]⁺.

Intermediate 244

Cis-1-[6-Chloro-2-(methylamino)-4-pyrimidinyl]-N-cyclopentyl-6-(trifluoromethyl)-3-piperidinecarboxamide

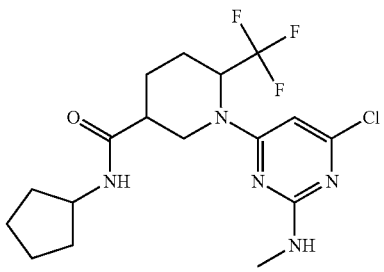 [SMILES: CNc1nc(Cl)cc(N2CC(C(=O)NC3CCCC3)CCC2C(F)(F)F)n1]

Into a 20 mL vial, cis-1-[6-chloro-2-(methylsulfonyl)-4-pyrimidinyl]-6-(trifluoromethyl)-3-piperidinecarboxylic acid (77 mg, 0.199 mmol) was dissolved in 1,4-dioxane (1 mL), and Hunig's base was added (0.14 mL, 0.794 mmol) followed by methylamine (0.199 mL, 0.397 mmol). The reaction mixture was stirred at room temperature overnight. Additional 100 uL of 2M methylamine in THF were added, and the reaction mixture was stirred at room temperature until LCMS analysis indicates>95% completion. The reaction was concentrated, then re-dissolved with DMF (2 mL), and added HOBT (60.8 mg, 0.397 mmol), EDC (57.1 mg, 0.298 mmol), N-methylmorpholine (0.109 mL, 0.993 mmol) and cyclopentylamine (0.029 mL, 0.298 mmol). The reaction was stirred at room temperature overnight. Water (15 mL) was added, and the resulting mixture was extracted with EtOAc (3×10 mL). The organics were combined, washed with brine, dried (MgSO₄), filtered, and concentrated. The resulting material was dissolved in 1 mL DMSO and purified on HPLC (HPLC condition: open-access Gilson using Unipoint software with a Varian Polaris 5u C18(2) 100A, 50×30.00 mm 5 micron. 10-minute run (30 ml/min, 40% CH₃CN/H₂O, 0.1% TFA to 60% CH₃CN/H₂O, 0.1% TFA) with UV detection at 254 nm). Product fractions were pooled and concentrated and freeze-dried to afford the title compound (40 mg) as a white solid. LC-MS (ES) m/z=406 [M+H]⁺.

Intermediate 245

Cis-1-[6-(4-Cyano-3-fluorophenyl)-2-(methylamino)-4-pyrimidinyl]-N-cyclopentyl-6-(trifluoromethyl)-3-piperidinecarboxamide

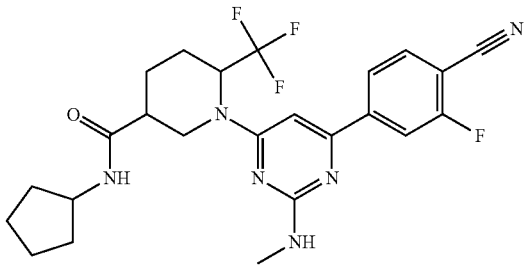 [SMILES: CNc1nc(-c2ccc(C#N)c(F)c2)cc(N2CC(C(=O)NC3CCCC3)CCC2C(F)(F)F)n1]

To a mixture of cis-1-[6-chloro-2-(methylamino)-4-pyrimidinyl]-N-cyclopentyl-6-(trifluoromethyl)-3-piperidinecarboxamide (46 mg, 0.113 mmol) and (4-cyano-3-fluorophenyl)boronic acid (28.0 mg, 0.170 mmol) in 1,4-dioxane (1 mL) was added saturated aqueous NaHCO$_3$ (0.5 mL), and N$_2$ gas was bubbled through the resulting mixture for 10 minutes into a 5 mL sealable vial. Pd(Ph$_3$P)$_4$ (19.7 mg, 0.017 mmol) was added, and N$_2$ was bubbled for an additional 5 minute. The vial was capped, and the reaction mixture was heated at 100° C. overnight. The reaction was diluted with water (5 mL) and then extracted with EtOAc (3×10 mL). The organics were dried over MgSO$_4$, filtered and concentrated. The resulting yellow oil was then purified on Biotage SNAP column 10 g with gradient of 0 to 40% EtOAc in Hexane to afford the title compound (37 mg) as a yellow oil. LC-MS (ES) m/z=491 [M+H]$^+$.

Example 115 cis-1-[6-(3-amino-1H-indazol-6-yl)-2-(methylamino)-4-pyrimidinyl]-N-cyclopentyl-6-(trifluoromethyl)-3-piperidinecarboxamide

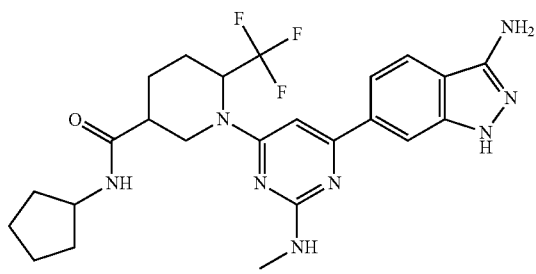 [SMILES: CNc1nc(-c2ccc3c(N)n[nH]c3c2)cc(N2CC(C(=O)NC3CCCC3)CCC2C(F)(F)F)n1]

To cis-1-[6-(4-cyano-3-fluorophenyl)-2-(methylamino)-4-pyrimidinyl]-N-cyclopentyl-6-(trifluoromethyl)-3-piperidinecarboxamide (37 mg, 0.075 mmol) in ethanol (2 mL) was added hydrazine monohydrate (0.11 mL, 2.26 mmol) into a 5 mL sealable vial, and the reaction was capped and heated overnight at 100° C. The reaction was concentrated, then redissolved in 1 mL of DMSO and purified on HPLC (HPLC condition: open-access Gilson using Unipoint software with a Varian Polaris 5u C18(2) 100A, 50×30.00 mm 5 micron. 10-minute run (35 ml/min, 25% CH$_3$CN/H$_2$O, 0.1% TFA to 50% CH$_3$CN/H$_2$O, 0.1% TFA) with UV detection at 254 nm). Product fractions were combined, and the volume was reduced by reduce pressure until most of the CH$_3$CN was removed. To the resulting aqueous mixture was added saturated aqueous NaHCO$_3$ (10 mL) solution. The mixture was then extracted with EtOAc (3×10 mL). The organics were combined, washed with brine, dried over MgSO$_4$, filtered, and concentrated. The resulting material was transferred to a vial and water was added to freeze dried overnight and afford the title compound (20 mg) as a light yellow solid. LC-MS (ES) m/z=503 [M+H]$^+$. $^1$H NMR (400 MHz, DMSO-d$_6$): δ 1.30-1.45 (m, 3H), 1.47-1.58 (m, 2H), 1.64 (dd, J=8.3, 4.3 Hz, 2H), 1.73-1.87 (m, 5H), 2.08 (bs, 1H), 2.33 (d, J=1.8 Hz, 1H), 2.84 (bs, 3H), 3.94-4.07 (m, 1H), 5.39 (s, 2H), 6.78 (bs, 2H), 7.62-7.74 (m, 2H), 7.94 (d, J=7.1 Hz, 1H), 8.02 (bs, 1H), 11.52 (s, 1H).

Intermediate 246

Cis-1-[6-chloro-2-(methylthio)-4-pyrimidinyl]-N-(phenylmethyl)-6-(trifluoromethyl)-3-piperidinecarboxamide

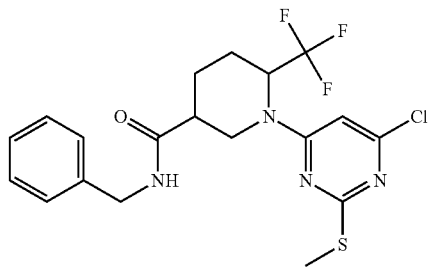 [SMILES: CSc1nc(Cl)cc(N2CC(C(=O)NCc3ccccc3)CCC2C(F)(F)F)n1]

To cis-6-(trifluoromethyl)-3-piperidinecarboxylic acid (50 mg, 0.254 mmol) in THF (1.5 mL) into a 5 mL sealable vial were added molecular sieves, and the resulting mixture was stirred for 5 minutes. LiHMDS (0.888 mL, 0.888 mmol) was added dropwise, and the resulting mixture was stirred at room temperature for 2 minutes, then added 4,6-dichloro-2-(methylthio)pyrimidine (59.4 mg, 0.304 mmol). The reaction was check by LCMS after 5 minutes and observed a very clean conversion. The reaction was then stirred at room temperature for an additional 0.5 hours. Water (5 mL) was added followed by the dropwise addition of 1N HCl until the mixture became slightly acidic. The mixture was then extracted with EtOAc (3×10 mL), and the organics were combined, washed with brine, dried over MgSO$_4$, filtered and concentrated. The crude oil was dissolved in DMF (1.5 mL), and then HOBT (78 mg, 0.507 mmol), EDC (58.3 mg, 0.304 mmol), and N-methylmorpholine (0.139 mL, 1.268 mmol) were added. The resulting mixture was stirred for 10 minutes. Benzylamine (0.033 mL, 0.304 mmol) was added, and the reaction mixture was stirred overnight at room temperature. LCMS of the reaction indicated clean conversion. To the reaction was added water (10 mL), and the resulting mixture was extracted with EtOAc (3×10 mL). The organics were then combined, washed with brine, dried over MgSO$_4$, filtered and concentrated. The yellow oil was then purified on Biotage SNAP 10 g column gradient of 0 to 35% EtOAc in Hexanes over 30 minutes to afford the title compound (49 mg) as a clear oil. LC-MS (ES) m/z=445 [M+H]$^+$.

Intermediate 247

1-[6-Chloro-2-(methylsulfonyl)-4-pyrimidinyl]-N-(phenylmethyl)-6-(trifluoromethyl)-3-piperidinecarboxamide

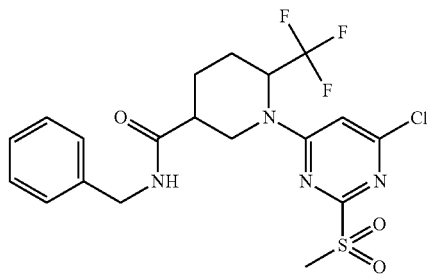 [SMILES: CS(=O)(=O)c1nc(Cl)cc(N2CC(C(=O)NCc3ccccc3)CCC2C(F)(F)F)n1]

A suspension of cis-1-[6-chloro-2-(methylthio)-4-pyrimidinyl]-N-(phenylmethyl)-6-(trifluoromethyl)-3-piperidinecarboxamide (550 mg, 1.236 mmol) in CH$_3$OH (5 mL) and water (1.5 mL) was cooled in an ice bath and treated slowly with a premixed solution of oxone (2280 mg, 3.71 mmol) in water (0.5 mL). The reaction was stirred at room temperature over the weekend. Water (10 mL) was added and the resulting mixture was filtered. The solid was dried in vacuum oven at 35° C. overnight to afford the crude title compound (834 mg) as an off-white solid. LC-MS (ES) m/z=477 [M+H]+.

Intermediate 248 cis 1-[6-Chloro-2-(methylamino)-4-pyrimidinyl]-N-(phenylmethyl)-6-(trifluoromethyl)-3-piperidinecarboxamide

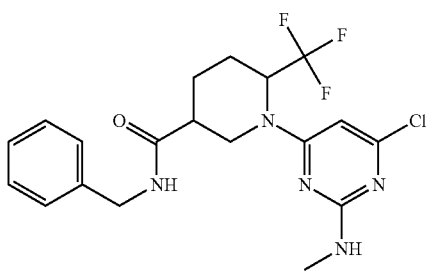 [SMILES: CNc1nc(Cl)cc(N2CC(C(=O)NCc3ccccc3)CCC2C(F)(F)F)n1]

Into a 100 mL RB flask was dissolved cis-1-[6-chloro-2-(methylsulfonyl)-4-pyrimidinyl]-N-(phenylmethyl)-6-(trifluoromethyl)-3-piperidinecarboxamide (400 mg, 0.839 mmol) in 1,4-dioxane (5 mL), then added Hunig's base (0.730 mL, 4.19 mmol), and the resulting mixture was stirred for 5 minutes. Methylamine (1.677 mL, 3.35 mmol, 2M in THF) was added, and the reaction mixture was stirred overnight at room temperature. The reaction was concentrated, and then CH3OH (15 mL) was added. An insoluble solid was observed and the mixture was filtered. The filtrate was concentrated to afford the title compound (301 mg) as a clear oil. LC-MS (ES) m/z=428 [M+H]+.

Intermediate 249

Cis-1-[6-(4-Cyano-3-fluorophenyl)-2-(methylamino)-4-pyrimidinyl]-N-(phenylmethyl)-6-(trifluoromethyl)-3-piperidinecarboxamide

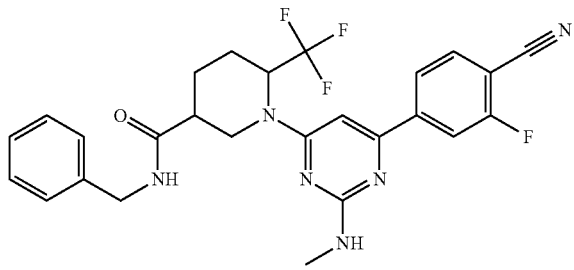 [SMILES: CNc1nc(-c2ccc(C#N)c(F)c2)cc(N2CC(C(=O)NCc3ccccc3)CCC2C(F)(F)F)n1]

To a mixture of cis-1-[6-chloro-2-(methylamino)-4-pyrimidinyl]-N-(phenylmethyl)-6-(trifluoromethyl)-3-piperidinecarboxamide (100 mg, 0.234 mmol) and (4-cyano-3-fluorophenyl)boronic acid (57.8 mg, 0.351 mmol) in 1,4-dioxane (2 mL) was added saturated aqueous NaHCO3, and N2 gas was bubbled through the mixture for 10 minutes into a 5 mL microwave vial. Pd(Ph3P)4 (40.5 mg, 0.035 mmol) was added, and N2 gas was bubbled through the mixture for an additional 5 minutes. The vial was capped, and the reaction mixture was heated overnight over a hot plate at 100° C. The reaction was diluted with water (5 mL), and the resulting mixture was extracted with EtOAc (3×10 mL). The combined organic layers were dried over MgSO4, filtered and concentrated. The resulting yellow oil was purified on Biotage SNAP 10 g column with gradient of 0 to 40% EtOAc in Hexane over 30 minutes to afford the title compound (66 mg) as a yellow oil. LC-MS (ES) m/z=513 [M+H]+.

Example 116

Cis-1-[6-(3-amino-1H-indazol-6-yl)-2-(methylamino)-4-pyrimidinyl]-N-(phenylmethyl)-6-(trifluoromethyl)-3-piperidinecarboxamide

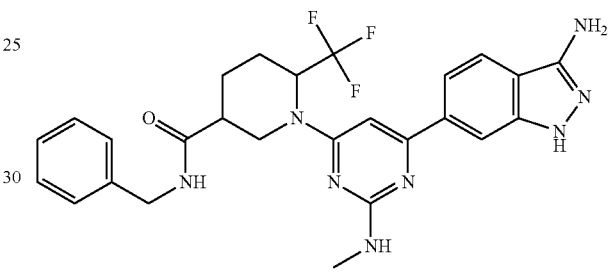

To a solution of 1-[6-(4-cyano-3-fluorophenyl)-2-(methylamino)-4-pyrimidinyl]-N-(phenylmethyl)-6-(trifluoromethyl)-3-piperidinecarboxamide (66 mg, 0.129 mmol) in ethanol (2 mL) into a 5 mL microwave vial was added hydrazine monohydrate (0.121 mL, 3.86 mmol). The reaction was capped and heated overnight. Since the reaction was not completed, additional 50 uL of hydrazine monohydrate was added and heated overnight. The reaction was concentrated then re-dissolved in 1 mL of DMSO and purified on HPLC (HPLC condition: open-access Gilson using Unipoint software with a Varian Polaris 5u C18(2) 100A, 50×30.00 mm 5 micron. 10-minute run (35 mL/min, 25% CH3CN/H2O, 0.1% TFA to 50% CH3CN/H2O, 0.1% TFA) with UV detection at 254 nm). Product fractions were combined and the volume was reduced under vacuum until most of the CH3CN was removed. Saturated aqueous NaHCO3 (10 mL) was added, and the resulting mixture was extracted with EtOAc (3×10 mL). The organics were combined, washed with brine, dried over MgSO4, filtered, and concentrated. The resulting material was transferred into a vial and water was added and freeze dried overnight to afford the title compound (27 mg) as a light yellow solid. LC-MS (ES) m/z=525 [M+H]+. 1H NMR (400 MHz, DMSO-d6): δ 1.81-1.88 (m, 3H), 2.06-2.14 (m, 1H), 2.43-2.49 (m, 1H), 2.84 (bs, 3H), 3.14 (bs, 1H), 4.20-4.43 (m, 2H), 5.40 (s, 2H), 6.80 (bs, 1H), 7.22-7.31 (m, 3H), 7.31-7.38 (m, 2H), 7.62-7.69 (m, 1H), 7.71-7.75 (m, 1H), 8.02 (bs, 1H), 8.54 (t, J=5.9 Hz, 1H), 11.53 (s, 1H).

Example 117

(3S)-1-[2-Amino-6-(3-amino-1H-indazol-6-yl)-4-pyrimidinyl]-N-cyclohexyl-3-piperidinecarboxamide

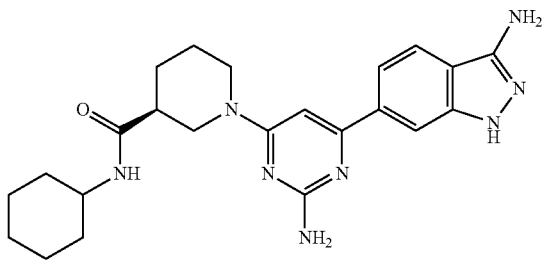 [SMILES: Nc1nc(-c2ccc3c(N)n[nH]c3c2)cc(N2CCC[C@H](C(=O)NC3CCCCC3)C2)n1]

A 5 mL microwave vial was charged with (3S)-1-(2-amino-6-chloro-4-pyrimidinyl)-N-cyclohexyl-3-piperidinecarboxamide (50 mg, 0.148 mmol), N-acetyl-N-[1-acetyl-6-(4,4,5,5-tetramethyl-1,3,2-dioxaborolan-2-yl)-1H-indazol-3-yl]acetamide (68.4 mg, 0.178 mmol), and PdCl$_2$(dppf).CH$_2$Cl$_2$ adduct (121 mg, 0.148 mmol). 1,4-Dioxane (1.5 mL) and 2M K$_2$CO$_3$ (0.75 mL) were added, the vial was sealed, and the reaction mixture was heated in microwave for 10 minutes at 150° C. The top organic layer was separated and concentrated. The resulting material was dissolved in 1 mL of DMSO, then purified in HPLC (HPLC condition: open-access Gilson using Trilution software with a phenomenex Luna 5u C18(2) 100A, AXIA. 50×30.00 mm 5 micron. 7.3-minute run (47 mL/min, 10% CH$_3$CN/H$_2$O, 0.1% TFA to 40% CH$_3$CN/H$_2$O, 0.1% TFA) with UV detection at 254 nm). Product fractions were combined, concentrated and freeze-dried to isolate 19 mg of the Suzuki product intermediate as a TFA salt. The solid was then dissolved in CH$_3$OH (4 mL) and 6N HCl(aq) (100 µL, 0.600 mmol), and the resulting mixture was heated at 95° C. for 2 hour. The reaction was then concentrated and redissolved in 2 mL of water and 1 mL of CH$_3$CN. The resulting mixture was freeze-dried to afford an HCl salt of the title compound (30 mg) as a light yellow solid. LC-MS (ES) m/z=435 [M+H]$^+$. NMR spectrum observed a large water peak. $^1$H NMR (400 MHz, DMSO-d$_6$): δ 1.08-1.30 (m, 4H), 1.36-1.59 (m, 2H), 1.59-1.77 (m, 4H), 1.91 (d, J=3.3 Hz, 1H), 3.09 (d, J=11.9 Hz, 1H), 3.20 (d, J=11.4 Hz, 1H), 4.38 (bs, 1H), 4.57-4.91 (m, 1H), 6.99 (d, J=14.2 Hz, 1H), 7.57 (dd, J=8.0, 4.7 Hz, 1H), 7.85 (d, J=7.3 Hz, 1H), 7.94-8.01 (m, 2H), 12.62 (d, J=1.0 Hz, 1H).

Intermediate 250

(3S)-1-[2-Amino-6-(4-cyano-3-fluorophenyl)-4-pyrimidinyl]-N-phenyl-3-piperidinecarboxamide

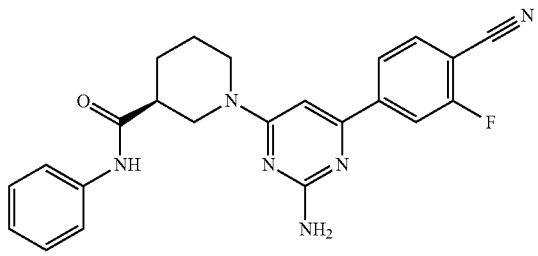 [SMILES: N#Cc1ccc(-c2cc(N3CCC[C@H](C(=O)Nc4ccccc4)C3)nc(N)n2)cc1F]

A 5 mL microwave vial was charged with (3S)-1-(2-amino-6-chloro-4-pyrimidinyl)-N-phenyl-3-piperidinecarboxamide (100 mg, 0.301 mmol), (4-cyano-3-fluorophenyl)boronic acid (59.6 mg, 0.362 mmol), and PdCl$_2$(dppf).CH$_2$Cl$_2$ adduct (24.61 mg, 0.030 mmol). 1,4-Dioxane (4 mL) and 2M K$_2$CO$_3$ (2 mL) were added, and the vial was sealed and heated in microwave for 10 minutes at 150° C. The top organic layer was separated and concentrated. The resulting oil was dissolved in 1 mL of DMSO and purified on HPLC (HPLC condition: open-access Gilson using Trilution software with a phenomenex Luna 5u C18(2) 100A, AXIA. 50×30.00 mm 5 micron. 7.3-minute run (47 mL/min, 23% CH$_3$CN/H$_2$O, 0.1% TFA to 53% CH$_3$CN/H$_2$O, 0.1% TFA) with UV detection at 254 nm). Product fractions were combined, concentrated and freeze-dried to afford a TFA salt of the title compound (59 mg) as a light yellow solid. LC-MS (ES) m/z=417 [M+H]$^+$.

Example 118

(3S)-1-[2-Amino-6-(3-amino-1H-indazol-6-yl)-4-pyrimidinyl]-N-phenyl-3-piperidinecarboxamide

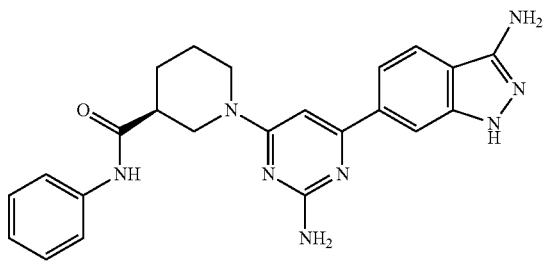 [SMILES: Nc1nc(-c2ccc3c(N)n[nH]c3c2)cc(N2CCC[C@H](C(=O)Nc3ccccc3)C2)n1]

To a solution of (3S)-1-[2-amino-6-(4-cyano-3-fluorophenyl)-4-pyrimidinyl]-N-phenyl-3-piperidinecarboxamide (55 mg, 0.132 mmol) in ethanol (3 mL) into a 5 mL sealable vial was added hydrazine monohydrate (0.149 mL, 3.04 mmol). The vial was capped and heated at 100° C. overnight. HPLC showed 70% complete clean. Additional 100 uL of hydrazine monohydrate were added and heating continued. The reaction was concentrated, and the resulting material was dissolved in 1 mL of DMSO and purified on HPLC (HPLC condition: open-access Gilson using Trilution software with a phenomenex Luna 5u C18(2) 100A, AXIA. 50×30.00 mm 5 micron. 7.3-minute run (47 mL/min, 10% CH$_3$CN/H$_2$O, 0.1% TFA to 40% CH$_3$CN/H$_2$O, 0.1% TFA) with UV detection at 254 nm). Product fractions were combined, concentrated and freeze-dried to afford a TFA salt of the title compound (42 mg) as a light yellow. LC-MS (ES) m/z=429 [M+H]$^+$. $^1$H NMR (400 MHz, DMSO-d$_6$): δ 1.43-1.59 (m, 1H), 1.75-1.94 (m, 2H), 2.03-2.16 (m, 1H), 2.57-2.69 (m, 1H), 3.12-3.31 (m, 2H), 3.43-3.54 (m, 2H), 4.40-4.58 (m, 1H), 4.72-5.07 (m, 1H), 6.94-7.11 (m, 2H), 7.30 (m, 2H), 7.37-7.43 (m, 1H), 7.61 (d, J=8.1 Hz, 2H), 7.75 (bs, 1H), 7.90 (d, 1H), 10.08 (d, J=12.9 Hz, 1H), 12.10 (bs, 2H).

Intermediate 251

(3R)—N-Phenyl-3-piperidinecarboxamide

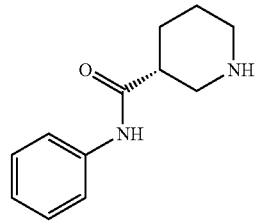 [SMILES: O=C(Nc1ccccc1)[C@@H]1CCCNC1]

A solution of (3R)-1-{[(1,1-dimethylethyl)oxy]carbonyl}-3-piperidinecarboxylic acid (1 g, 4.36 mmol), HOBT (1.336 g, 8.72 mmol), EDC (1.003 g, 5.23 mmol), and N-methylmorpholine (2.40 mL, 21.81 mmol) in DMF (5 mL) was stirred for 5 minutes. Then aniline (0.48 mL, 5.23 mmol) was added, and the reaction mixture was stirred at room temperature over 72 hours. The reaction was then quenched with 30 mL of water and extracted with EtOAc (3×30 mL). The organics were combined, dried over Na$_2$SO$_4$, filtered and concentrated. The resulting oil was purified by silica gel column with gradient of 0 to 35% EtOAc in hexane to isolate 1.01 g of the N-Boc protected product as a solid. To the solid was then added a premixed solution of TFA (2 mL, 13 mmol) and CH$_2$Cl$_2$ (4 mL). The resulting mixture was stirred over 0.5 hours, and then concentrated to obtain a TFA salt of the crude title compound as a yellow oil. LC-MS (ES) m/z=205 [M+H]$^+$.

Intermediate 252

(3R)-1-(2-Amino-6-chloro-4-pyrimidinyl)-N-phenyl-3-piperidinecarboxamide

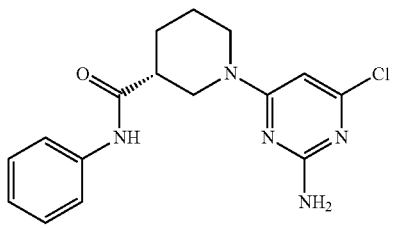 [SMILES: Nc1nc(Cl)cc(N2CCC[C@@H](C(=O)Nc3ccccc3)C2)n1]

To a solution of (3R)—N-phenyl-3-piperidinecarboxamide (339 mg, 1.66 mmol) in CH$_3$CN (3 mL) in a 5 mL microwave vial, was added Hunig's base (0.87 mL, 4.98 mmol) and 4,6-dichloro-2-pyrimidinamine (299 mg, 1.83 mmol), and the reaction mixture was heated at 160° C. under microwave conditions for 0.5 hours. A solid formed upon cooling of the reaction mixture. The solid was then isolated by filtration, washing with CH$_3$CN to afford the crude title compound (239 mg) as a light brown solid. LC-MS (ES) m/z=332 [M+H]$^+$.

Intermediate 253

(3R)-1-[2-Amino-6-(4-cyano-3-fluorophenyl)-4-pyrimidinyl]-N-phenyl-3-piperidinecarboxamide

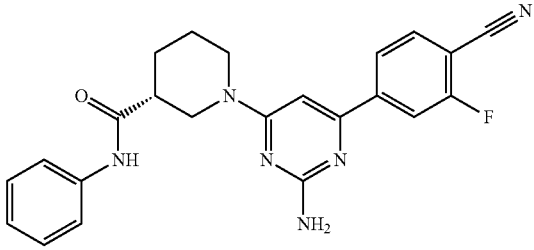 [SMILES: N#Cc1ccc(-c2cc(N3CCC[C@@H](C(=O)Nc4ccccc4)C3)nc(N)n2)cc1F]

A 5 mL microwave vial was charged with (3R)-1-(2-amino-6-chloro-4-pyrimidinyl)-N-phenyl-3-piperidinecarboxamide (100 mg, 0.301 mmol), (4-cyano-3-fluorophenyl)boronic acid (59.6 mg, 0.362 mmol), and PdCl$_2$(dppf).CH$_2$Cl$_2$ adduct (24.6 mg, 0.030 mmol). 1,4-Dioxane (4 mL) and 2M K$_2$CO$_3$ (2 mL) were added, and the vial was sealed and heated at 150° C. under microwave conditions 10 minutes. The top organic layer was separated and concentrated. The resulting oil was dissolved in 1 mL of DMSO and purified on HPLC (HPLC condition: open-access Gilson using Trilution software with a phenomenex Luna 5u C18(2) 100A, AXIA. 50×30.00 mm 5 micron. 7.3-minute run (47 mL/min, 23% CH$_3$CN/H$_2$O, 0.1% TFA to 53% CH$_3$CN/H$_2$O, 0.1% TFA) with UV detection at 254 nm). Product fractions were combined, concentrated and freeze-dried to afford a TFA salt of the title compound (93 mg) as a light yellow solid. LC-MS (ES) m/z=417 [M+H]$^+$.

Example 119

(3R)-1-[2-Amino-6-(3-amino-1H-indazol-6-yl)-4-pyrimidinyl]-N-phenyl-3-piperidinecarboxamide

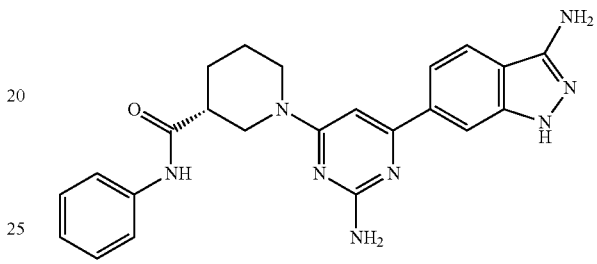

To a solution (3R)-1-[2-amino-6-(4-cyano-3-fluorophenyl)-4-pyrimidinyl]-N-phenyl-3-piperidinecarboxamide (90 mg, 0.216 mmol) in Ethanol (4 mL) into a 5 mL microwave vial was added hydrazine monohydrate (0.24 mL, 4.97 mmol). The vial was capped and heated overnight at 100° C. The reaction was only 50% done by HPLC. Additional hydrazine monohydrate (0.244 mL, 4.97 mmol) was added and the reaction mixture was continued to heat overnight. Reaction was concentrated, and the resulting material was dissolved in 1 mL of DMSO and purified on HPLC (HPLC condition: open-access Gilson using Trilution software with a phenomenex Luna 5u C18(2) 100A, AXIA. 50×30.00 mm 5 micron. 7.3-minute run (47 mL/min, 12% CH$_3$CN/H$_2$O, 0.1% TFA to 42% CH$_3$CN/H$_2$O, 0.1% TFA) with UV detection at 254 nm). Product fractions were combined, concentrated and freeze-dried to afford a TFA salt of the title compound (66 mg) as a light yellow solid. LC-MS (ES) m/z=429 [M+H]$^+$. $^1$H NMR (400 MHz, DMSO-d$_6$): δ 1.43-1.62 (m, 1H), 1.75-1.94 (m, 2H), 2.02-2.14 (m, 1H), 2.55-2.69 (m, 1H), 3.11-3.31 (m, 2H), 3.43-3.53 (m, 1H), 4.41-4.58 (m, 1H), 4.72-5.06 (m, 1H), 6.96-7.10 (m, 2H), 7.31 (m, 2H), 7.37-7.43 (m, 1H), 7.61 (d, J=8.1 Hz, 2H), 7.75 (bs, 1H), 7.89 (d, J=8.8 Hz, 1H), 10.08 (d, J=12.9 Hz, 1H), 12.10 (bs, 2H).

Intermediate 254

Cis-phenylmethyl 5-{[(cyclopentyloxy)carbonyl]amino}-2-methyl-1-piperidinecarboxylate

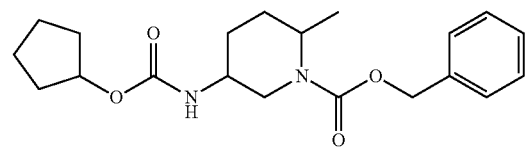 [SMILES: CC1CCC(NC(=O)OC2CCCC2)CN1C(=O)OCc1ccccc1]

To a mixture of cis-6-methyl-1-{[(phenylmethyl)oxy]carbonyl}-3-piperidinecarboxylic acid (200 mg, 0.721 mmol), cyclopentyl alcohol (1.5 mL, 16.51 mmol), and triethylamine (0.151 mL, 1.082 mmol) was added slowly diphenyl azidophosphate (dppa) (0.171 mL, 0.793 mmol), and the reaction mixture was stirred at room temperature for 15 minutes, and then at 125° C. After 4 hr, the reaction was diluted with EtOAc (40 mL) and washed with water. The organic was then dried over MgSO₄, filtered, concentrated and purified with Biotage SNAP 10 g column with gradient of 0 to 50% EtOAc in hexane over 35 minutes to afford the title compound (160 mg) as a clear oil. LC-MS (ES) m/z=361 [M+H]⁺.

Intermediate 255

Cis-cyclopentyl[6-methyl-3-piperidinyl]carbamate

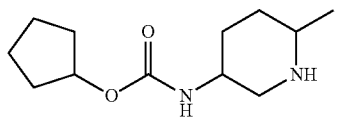 [SMILES: CC1CCC(NC(=O)OC2CCCC2)CN1]

cis-phenylmethyl 5-{[(cyclopentyloxy)carbonyl]amino}-2-methyl-1-piperidinecarboxylate (160 mg, 0.444 mmol) was dissolved in ethanol (3 mL) into a 25 mL RB flask. Pd/C (94 mg, 0.044 mmol) degussa type was added, and the resulting mixture was degassed with vacuum and charged with H₂ in balloon. The reaction was stirred for 4 hours, and then filter through syringe filter. The filtrate was concentrated to afford the crude title compound (107 mg) as a clear oil. LC-MS (ES) m/z=227 [M+H]⁺.

Intermediate 256

Cis-Cyclopentyl[1-(2-amino-6-chloro-4-pyrimidinyl)-6-methyl-3-piperidinyl]carbamate

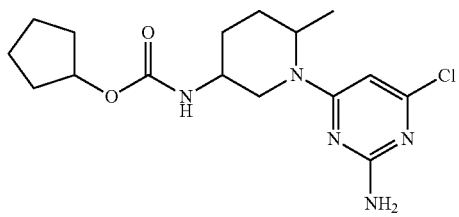 [SMILES: CC1CCC(NC(=O)OC2CCCC2)CN1c1cc(Cl)nc(N)n1]

To a solution of cis-cyclopentyl[6-methyl-3-piperidinyl]carbamate (107 mg, 0.473 mmol) in ethanol (3 mL) were added 4,6-dichloro-2-pyrimidinamine (116 mg, 0.709 mmol) and K₂CO₃ (98 mg, 0.709 mmol) in a 5 mL sealable vial. The solution was capped and heated at 100° C. overnight. The reaction was then check with LCMS and was not complete. Additional 4,6-dichloro-2-pyrimidinamine (30 mg) and K₂CO₃ (50 mg) were added and the resulting mixture was heated overnight. The reaction was concentrated, then 5 mL of DMF were added. Some solids were not soluble. Water (10 mL) was added, and the resulting mixture was extracted 3× with EtOAc. The organics were combined, washed with brine, dried over MgSO₄, filtered and concentrated. The clear oil was then purified on Biotage SNAP 10 g column with gradient of 0 to 50% EtOAc in hexane over 30 minutes to afford the title compound (135 mg) as a clear oil. LC-MS (ES) m/z=354 [M+H]⁺.

Intermediate 257

Cis-cyclopentyl{1-[2-amino-6-(4-cyano-3-fluorophenyl)-4-pyrimidinyl]-6-methyl-3-piperidinyl}carbamate

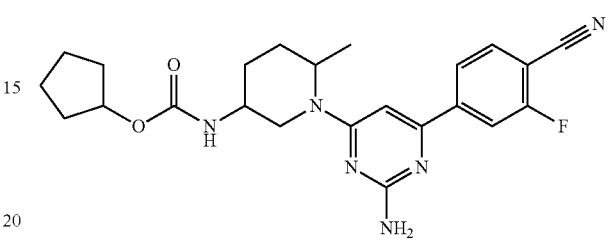

cis-cyclopentyl[1-(2-amino-6-chloro-4-pyrimidinyl)-6-methyl-3-piperidinyl]carbamate (135 mg, 0.382 mmol) and (4-cyano-3-fluorophenyl)boronic acid (94 mg, 0.572 mmol) were dissolved 1,4-dioxane (3 mL) into a 20 mL sealable vial. Saturated aqueous NaHCO₃ (1.5 mL) was added, and the resulting mixture was bubbled with N₂ gas for 10 minutes. Pd(Ph₃P)₄ (66 mg, 0.057 mmol) was added, and N₂ gas was bubbled through the mixture for an additional 5 minutes. The vial was capped and heated overnight at 100° C. The reaction was filtered thought syringe filter and washed with 1,4-dioxane. The filtrate was concentrated, then redissolved in 2 mL of DMSO and purified on HPLC (HPLC condition: open-access Gilson using Unipoint software with a Varian Polaris 5u C18 (2) 100A, 50×30.00 mm 5 micron. 10-minute run (30 mL/min, 33% CH₃CN/H₂O, 0.1% TFA to 58% CH₃CN/H₂O, 0.1% TFA) with UV detection at 254 nm). Product fractions were combined and freeze-dried to afford a TFA salt of the title compound (98 mg) as a light yellow solid. LC-MS (ES) m/z=439 [M+H]⁺.

Example 120

Cis-cyclopentyl{1-[2-amino-6-(3-amino-1H-indazol-6-yl)-4-pyrimidinyl]-6-methyl-3-piperidinyl}carbamate

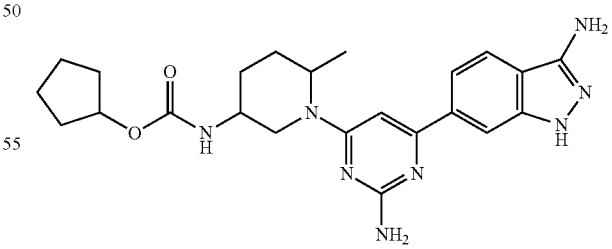

cis-Cyclopentyl{1-[2-amino-6-(4-cyano-3-fluorophenyl)-4-pyrimidinyl]-6-methyl-3-piperidinyl}carbamate (98 mg, 0.223 mmol) was dissolved in ethanol (3 mL) into a 5 mL sealable vial. Hydrazine monohydrate (0.329 mL, 6.70 mmol) was added, the vial was capped, and the reaction mixture was heated overnight at 100° C. The reaction was then concentrated, redissolved in 2 mL of DMSO, and purified on HPLC (HPLC condition: open-access Gilson using Unipoint software with a Varian Polaris 5u C18(2) 100A, 50×30.00 mm 5 micron. 10-minute run (30 mL/min, 20% CH$_3$CN/H$_2$O, 0.1% TFA to 45% CH$_3$CN/H$_2$O, 0.1% TFA) with UV detection at 254 nm). Product fractions were combined, concentrated and freeze-dried to obtain a TFA salt of the title compound (57 mg) as a light yellow solid. LC-MS (ES) m/z=450 [M+H]$^+$. $^1$H NMR (400 MHz, DMSO-d$_6$): δ 1.21 (d, J=6.3 Hz, 3H), 1.52-1.74 (m, 8H), 1.76-1.85 (m, 2H), 2.66-3.08 (m, 1H), 3.40 (bs, 2H), 4.18-4.76 (m, 1H), 4.85-5.35 (m, 1H), 4.99 (bs, 1H), 6.83-6.95 (m, 1H), 7.24 (d, J=8.3 Hz, 1H), 7.38 (d, J=8.34 Hz, 1H), 7.70-7.77 (m, 1H), 7.91 (d, J=8.3 Hz, 1H), 11.93-12.27 (m, 2H).

Intermediate 258

(3S,6R)-6-Methyl-3-piperidinecarboxylic acid

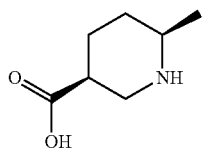

Into a 75 mL sealable tube, were added 3-methyl 1-(phenylmethyl) (3S,6R)-6-methyl-1,3-piperidinedicarboxylate (10 g, 34.3 mmol), 1,4-dioxane (20 mL) and concentrated HCl (20 mL), and the mixture was stirred at 100° C. for 3 hours. The mixture was then cooled to room temperature. HPLC showed no starting material and NMR showed major was the desired product. The solution was transfered to a 500 mL round bottom flask, and concentrated to dryness. Trituration with Et$_2$O and CH$_3$CN afforded the HCl salt of the title compound (6.17 g) as a colorless oil that turned into a white solid after standing overnight. $^1$H NMR (400 MHz, CD$_3$OD): δ 6.51 (s, 1H), 7.04 (m, 1H), 7.32 (m, 2H), 7.46 (dd, J=8.6, 1.3 Hz, 1H), 7.66 (m, 2H), 7.75 (dd, J=8.3, 0.8 Hz, 1H), 7.81 (s, 1H).

Intermediate 259

(3S,6R)-1-[2-Amino-6-(4-cyano-3-fluorophenyl)-4-pyrimidinyl]-6-methyl-3-piperidinecarboxylic acid

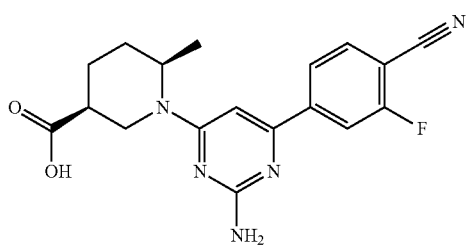 [SMILES: C[C@@H]1CC[C@H](C(=O)O)CN1c1cc(-c2ccc(C#N)c(F)c2)nc(N)n1]

A mixture of 4,6-dichloro-2-pyrimidinamine (3 g, 18.3 mmol), (3S,6R)-6-methyl-3-piperidinecarboxylic acid (3.98 g, 20.12 mmol), and NaHCO$_3$ (7.68 g, 91 mmol) in 1,4-dioxane (100 mL) and water (50 mL) was stirred overnight at 117° C. into a sealed tube. The reaction was allowed to cool to room temperature. LCMS showed that most of the starting material 4,6-dichloro-2-pyrimidinamine had been consumed. Then 4-cyano-3-fluorobenzeneboronic acid (3.32 g, 20.12 mmol) and Pd(Ph$_3$P)$_4$ (0.423 g, 0.366 mmol) were added, and the reaction mixture was stirred for 24 hours at 117° C. The mixture was poured into water (300 mL) and EtOAc (200 mL). At this moment the pH of the solution was 9. The compound stayed in the water layer. The water layer was separated from the organic layer. There was some black colored and yellow colored suspension in the water layer, which was filtered out. (They were not product). To the aqueous layer, 6N HCl was added dropwise to make the pH=4. A precipitate was formed. The precipitate was filtered, washed with water, and dried to afford the title compound (3.6 g) as a light yellow solid. LC-MS (ES) m/z=356 [M+H]$^+$.

Intermediate 260

(3S,6R)-1-[2-Amino-6-(4-cyano-3-fluorophenyl)-4-pyrimidinyl]-N-cyclohexyl-6-methyl-3-piperidinecarboxamide

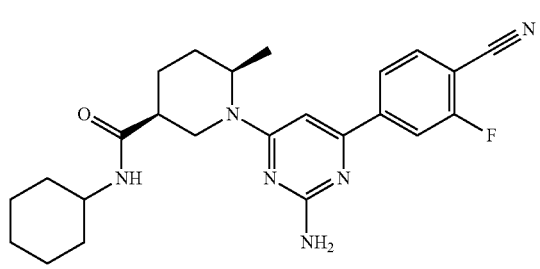 [SMILES: C[C@@H]1CC[C@H](C(=O)NC2CCCCC2)CN1c1cc(-c2ccc(C#N)c(F)c2)nc(N)n1]

To a solution of (3S,6R)-1-[2-amino-6-(4-cyano-3-fluorophenyl)-4-pyrimidinyl]-6-methyl-3-piperidinecarboxylic acid (415 mg, 1.128 mmol) and HATU (533 mg, 1.401 mmol) in DMF (3 mL) into a 10 mL round-bottomed flask was added Hunig's base (0.408 mL, 2.34 mmol), and the resulting mixture was stirred at room temperature for 15 minutes. Cyclohexylamine (0.16 mL, 1.401 mmol) was added, and the reaction mixture was stirred at room temperature for 0.5 hours. LCMS showed reaction was completed. The reaction was poured into water, and EtOAc was added to extract the product. The product stayed in the EtOAc layer. The organic layer solution was concentrated, and the formed solid was recrystallized in CH$_3$CN to afford the title compound (245 mg) as a light yellow solid. LC-MS (ES) m/z=437 [M+H]$^+$.

Example 121

(3S,6R)-1-[2-Amino-6-(3-amino-1H-indazol-6-yl)-4-pyrimidinyl]-N-cyclohexyl-6-methyl-3-piperidinecarboxamide

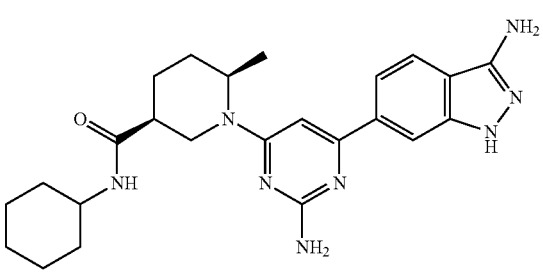 [SMILES: C[C@@H]1CC[C@H](C(=O)NC2CCCCC2)CN1c1cc(-c2ccc3c(N)n[nH]c3c2)nc(N)n1]

Into a microwave tube, (3S,6R)-1-[2-amino-6-(4-cyano-3-fluorophenyl)-4-pyrimidinyl]-N-cyclohexyl-6-methyl-3-piperidinecarboxamide (235 mg, 0.538 mmol), 5 ml of EtOH, Hunig's base (0.376 ml, 2.153 mmol), and hydrazine anhydrous (0.101 mL, 3.23 mmol) were added, and the yellow suspension mixture was heated overnight at 110° C. in an oil bath. When the temperature of the reaction reached 100° C. while heating, the solid in the mixture was all dissolved. After overnight, there were yellow suspension as well as some black colored solid formed. LCMS showed mainly product. The black solid and the yellow solid were carefully separated due to the black solid being heavier than yellow solid in the CH$_3$OH solvent. The yellow solid in CH$_3$OH was filtered and washed with CH$_3$OH to remove the color and afford the title compound (157 mg) as a white solid. LC-MS (ES) m/z=449 [M+H]$^+$. $^1$H NMR (400 MHz, DMSO-d$_6$): δ 1.05-1.35 (m, 8H), 1.50-1.88 (m, 9H), 2.24 (s, 1H), 2.90 (s, 1H), 3.46-3.60 (m, 1H), 5.38 (s, 2H), 6.07 (s, 2H), 6.57 (s, 1H), 7.57 (d, J=8.3 Hz, 1H), 7.70 (d, J=8.3 Hz, 1H), 7.79 (d, J=7.6 Hz, 1H), 7.94 (s, 1H), 11.49 (s, 1H).

Intermediate 261

(3S)-1-(2-amino-6-chloro-4-pyrimidinyl)-3-piperidinecarboxylic acid

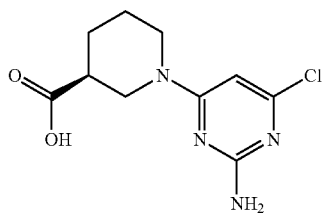 [SMILES: Nc1nc(Cl)cc(N2CCC[C@H](C(=O)O)C2)n1]

A mixture of 4,6-dichloro-2-pyrimidinamine (1.397 g, 8.52 mmol), (3S)-3-piperidinecarboxylic acid (1 g, 7.74 mmol) and Hunig's base (2.70 ml, 15.49 mmol) in NMP (10 mL) was heated in the microwave at 140° C. for 90 minutes. LCMS showed mainly desired product. The reaction was cooled down to room temperature, and poured onto water (160 mL). The formed solid was filtered, and the filtered solid was identified as the SM 4,6-dichloro-2-pyrimidinamine. The product stayed in the aqueous solution. 1N HCl was added to adjust the pH=7. Then the aqueous solution was extracted 3× with a mixture of CHCl$_3$ and isopropanol (200:10 mL). The organic layers were combined and evaporated to afford the title compound (1.99 g) as a yellow solid. LC-MS (ES) m/z=257 [M+H]$^+$.

Intermediate 262

(3S)-1-[2-Amino-6-(4-cyano-3-fluorophenyl)-4-pyrimidinyl]-3-piperidinecarboxylic acid

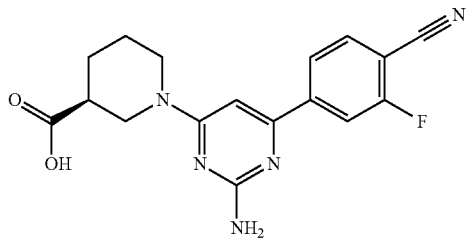 [SMILES: N#Cc1ccc(-c2cc(N3CCC[C@H](C(=O)O)C3)nc(N)n2)cc1F]

A mixture of (3S)-1-(2-amino-6-chloro-4-pyrimidinyl)-3-piperidinecarboxylic acid (1.9 g, 7.40 mmol), (4-cyano-3-fluorophenyl)boronic acid (1.465 g, 8.88 mmol) and NaHCO$_3$ (0.622 g, 7.40 mmol) in 1,4-dioxane (10 mL) and water (2.5 mL) was stirred for 10 minutes under nitrogen. Pd(Ph$_3$P)$_4$ (0.171 g, 0.148 mmol) was added, and the microwave tube was heated at 140° C. for 50 minutes in microwave. LCMS showed 50% desired product. The reaction was then heated at 100° C. overnight. The yellow mixture was filtered and dried. The solid was washed with Et$_2$O (3×), and dried. The filtrate was poured into water. The formed solid was filtered and dried. The solids were combined to afford the title compound (1.8 g) as a yellow solid. LC-MS (ES) m/z=342 [M+H]$^+$.

Intermediate 263

(3S)-1-[2-Amino-6-(4-cyano-3-fluorophenyl)-4-pyrimidinyl]-N-(4-fluorophenyl)-3-piperidinecarboxamide

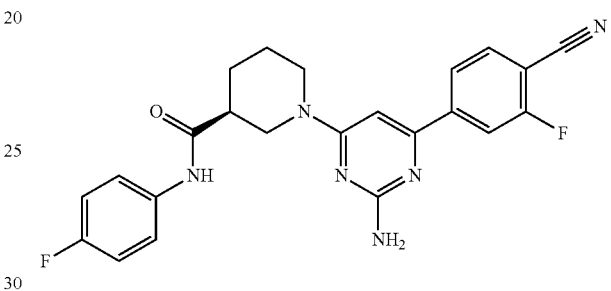

To a solution of (3S)-1-[2-amino-6-(4-cyano-3-fluorophenyl)-4-pyrimidinyl]-3-piperidinecarboxylic acid (150 mg, 0.439 mmol), EDC (118 mg, 0.615 mmol), and HOBT (83 mg, 0.615 mmol) in DMF (8 mL) was added 4-fluoroaniline (68.4 mg, 0.615 mmol), and the reaction mixture was stirred at room temperature for 4 hours. LCMS showed reaction was completed. The reaction was poured into water, and EtOAc was added to extract the product. The product stayed in the EtOAc layer. The organic solution was concentrated to dryness to give the title compound (90 mg) as a yellow solid. LC-MS (ES) m/z=435 [M+H]$^+$.

Example 122

(3S)-1-[2-Amino-6-(3-amino-1H-indazol-6-yl)-4-pyrimidinyl]-N-(4-fluorophenyl)-3-piperidinecarboxamide

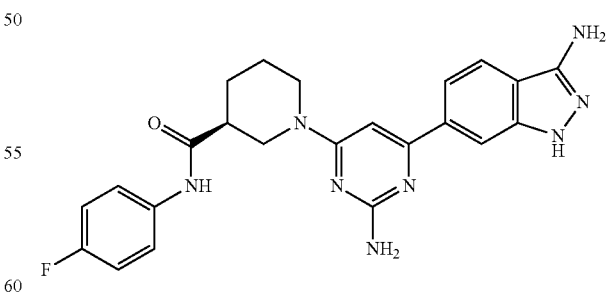

Into a microwave tube, (3S)-1-[2-amino-6-(4-cyano-3-fluorophenyl)-4-pyrimidinyl]-N-(4-fluorophenyl)-3-piperidinecarboxamide (90 mg, 0.207 mmol), 3 mL of EtOH, Hunig's base (0.11 mL, 0.621 mmol) and hydrazine anhydrous (0.026 mL, 0.829 mmol) were added, and the yellow mixture was heated at 150° C. for 150 minutes in microwave. The solution turned black. LCMS showed mainly product with 10% of remaining starting material. The black solids were filtered, and the yellow filtrate was evaporated. The resulting yellow residue was dissolved in CH₃OH, and purified by HPLC (CH₃CN/H₂O w/0.1% HCO₂H) to afford a formic acid salt of the title compound (20 mg) as a light yellow solid. LC-MS (ES) m/z=447 [M+H]⁺. ¹H NMR (400 MHz, DMSO-d₆): δ 1.50 (m, 1H), 1.85 (m, 2H), 2.07 (m, 1H), 3.17 (m, 2H), 4.52 (m, 1H), 4.74 (m, 1H), 4.98 (m, 1H), 6.94-7.08 (m, 1H), 7.16 (m, 2H), 7.39 (s, 1H), 7.56-7.69 (m, 2H), 7.73 (s, 1H), 7.82-8.04 (m, 1H), 10.13 (m, 1H), 11.86-12.16 (m, 2H).

Intermediate 264

(3S)-1-[2-Amino-6-(4-cyano-3-fluorophenyl)-4-pyrimidinyl]-N-(3-methylphenyl)-3-piperidinecarboxamide

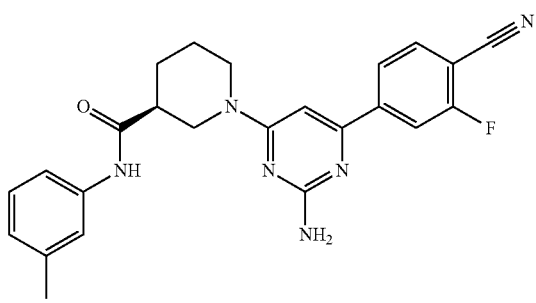 [SMILES: Cc1cccc(NC(=O)[C@H]2CCCN(c3cc(-c4ccc(C#N)c(F)c4)nc(N)n3)C2)c1]

To solution of (3S)-1-[2-amino-6-(4-cyano-3-fluorophenyl)-4-pyrimidinyl]-3-piperidinecarboxylic acid (146 mg, 0.428 mmol), EDC (115, 0.599 mmol), and HOBT (81 mg, 0.599 mmol) in DMF (8 mL) into a 100 mL round-bottomed flask, was added m-toluidine (45.8 mg, 0.428 mmol), and the reaction mixture was stirred at room temperature for 4 hours. LCMS showed reaction was completed. The reaction was poured into water, and EtOAc was added to extract the product. The product stayed in the EtOAc layer. The organic solution was concentrated to dryness to give the title compound (90 mg) as a yellow solid. LC-MS (ES) m/z=431 [M+H]⁺.

Example 123

(3S)-1-[2-Amino-6-(3-amino-1H-indazol-6-yl)-4-pyrimidinyl]-N-(3-methylphenyl)-3-piperidinecarboxamide

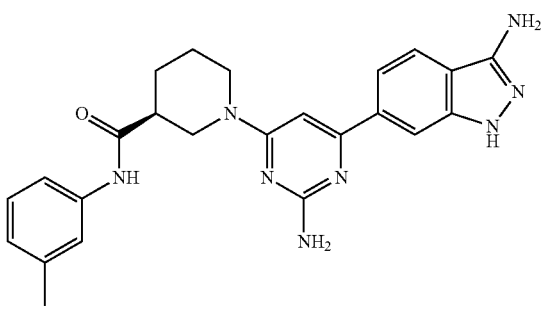 [SMILES: Cc1cccc(NC(=O)[C@H]2CCCN(c3cc(-c4ccc5c(N)n[nH]c5c4)nc(N)n3)C2)c1]

Into a microwave tube, (3S)-1-[2-amino-6-(4-cyano-3-fluorophenyl)-4-pyrimidinyl]-N-(3-methylphenyl)-3-piperidinecarboxamide (90 mg, 0.209 mmol), 3 mL of EtOH, Hunig's base (0.11 ml, 0.627 mmol), and hydrazine anhydrous (0.026 ml, 0.836 mmol) were added, and the yellow mixture was heated at 150° C. for 150 minutes in microwave. The solution turned black. LCMS showed mainly product with 10% of remaining starting material. The black solids were filtered and the yellow filtrate was evaporated. The resulting yellow residue was dissolved in CH₃OH, and purified by HPLC (CH₃CN/H₂O w/0.1% HCO₂H) to afford a formic acid salt of the title compound (77 mg) as a light yellow solid. LC-MS (ES) m/z=443 [M+H]⁺. ¹H NMR (400 MHz, DMSO-d₆): δ 1.52 (m, 1H), 1.84 (m, 2H), 2.07 (m, 1H), 2.27 (s, 3H), 3.50 (m, 1H), 4.48 (m, 2H), 4.75 (m, 1H), 4.90-5.13 (m, 1H), 6.87 (s, 1H), 6.94-7.08 (m, 1H), 7.13-7.26 (m, 1H), 7.41 (m, 6H), 7.75 (s, 1H), 7.83-8.00 (m, 1H), 10.00 (s, 1H), 12.07 (s, 2H).

Intermediate 265

(3S)-1-[2-Amino-6-(4-cyano-3-fluorophenyl)-4-pyrimidinyl]-N-(3,4-difluorophenyl)-3-piperidinecarboxamide

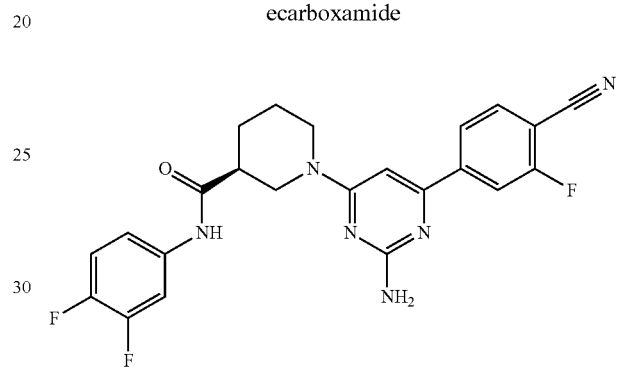

To a solution of (3S)-1-[2-amino-6-(4-cyano-3-fluorophenyl)-4-pyrimidinyl]-3-piperidinecarboxylic acid (146 mg, 0.428 mmol), EDC (115 mg, 0.599 mmol), and HOBT (81 mg, 0.599 mmol) in DMF (8 mL was added 3,4-difluoroaniline (77 mg, 0.599 mmol), and the reaction mixture was stirred at room temperature for 4 hours. LCMS showed reaction was completed. The reaction was poured onto water, and EtOAc was added to extract the product. The product stayed in the EtOAc layer. The organic solution was concentrated to dryness to give the title compound (95 mg) as a yellow solid. LC-MS (ES) m/z=453 [M+H]⁺.

Example 124

(3S)-1-[2-Amino-6-(3-amino-1H-indazol-6-yl)-4-pyrimidinyl]-N-(3,4-difluorophenyl)-3-piperidinecarboxamide

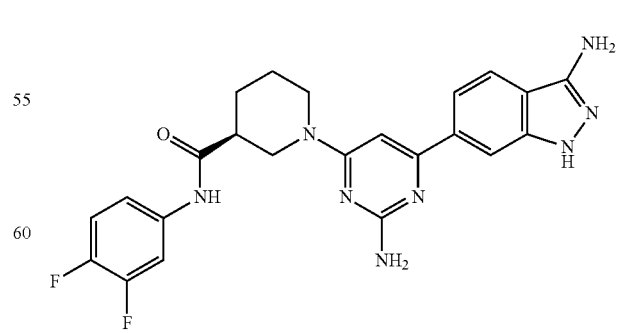

Into a microwave tube, (3S)-1-[2-amino-6-(4-cyano-3-fluorophenyl)-4-pyrimidinyl]-N-(3,4-difluorophenyl)-3-piperidinecarboxamide (90 mg, 0.199 mmol), 3 mL of EtOH, hunig's base (0.104 ml, 0.597 mmol), and hydrazine anhydrous (0.025 ml, 0.796 mmol) weres added, and the yellow mixture was heated at 150° C. for 150 minutes under microwave conditions. The solution turned black. LCMS showed mainly product. The black solids were filtered and the yellow filtrate was evaporated. The resulting yellow residue was dissolved in CH$_3$OH, and purified by HPLC (CH$_3$CN/H$_2$O w/0.1% HCO$_2$H) to afford the title compound (65 mg) as a light yellow solid. LC-MS (ES) m/z=465 [M+H]$^+$. $^1$H NMR (400 MHz, DMSO-d$_6$): δ 1.50 (m, 1H), 1.69-1.96 (m, 2H), 2.06 (m, 1H), 3.19 (m, 1H), 3.40-3.55 (m, 1H), 4.36-4.56 (m, 2H), 4.73-4.97 (m, 1H), 6.91-7.09 (m, 1H), 7.25-7.52 (m, 4H), 7.66-8.03 (m, 4H), 10.25-10.42 (m, 1H), 10.33 (d, J=8.8 Hz, 1H), 12.09 (s, 2H).

Intermediate 266

(3S)-1-[2-Amino-6-(4-cyano-3-fluorophenyl)-4-pyrimidinyl]-N-(4-methylphenyl)-3-piperidinecarboxamide

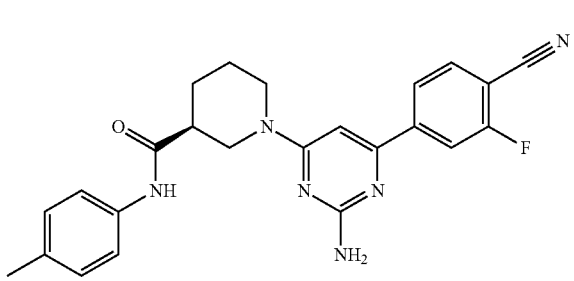 [SMILES: Cc1ccc(NC(=O)[C@H]2CCCN(c3cc(-c4ccc(C#N)c(F)c4)nc(N)n3)C2)cc1]

To a solution of (3S)-1-[2-amino-6-(4-cyano-3-fluorophenyl)-4-pyrimidinyl]-3-piperidinecarboxylic acid (146 mg, 0.428 mmol), EDC (115 mg, 0.599 mmol), and HOBT (81 mg, 0.599 mmol) in DMF (8 mL) was added p-toluidine (46 mg, 0.43 mmol), and the reaction mixture was stirred at room temperature for 4 hours. LCMS showed reaction was completed. The reaction was poured onto water, and EtOAc was added to extract the product. The product stayed in the EtOAc layer. The organic solution was concentrated to dryness to give the title compound (94 mg) as a yellow solid. LC-MS (ES) m/z=431 [M+H]$^+$.

Example 125

(3S)-1-[2-Amino-6-(3-amino-1H-indazol-6-yl)-4-pyrimidinyl]-N-(4-methylphenyl)-3-piperidinecarboxamide

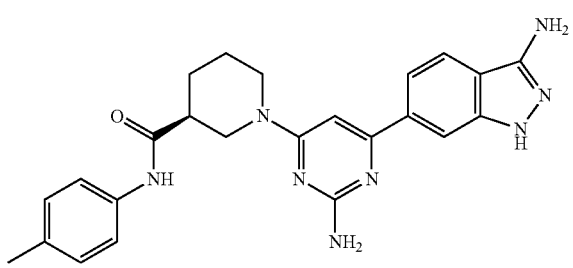 [SMILES: Cc1ccc(NC(=O)[C@H]2CCCN(c3cc(-c4ccc5c(N)n[nH]c5c4)nc(N)n3)C2)cc1]

Into a microwave tube, (3S)-1-[2-amino-6-(4-cyano-3-fluorophenyl)-4-pyrimidinyl]-N-(4-methylphenyl)-3-piperidinecarboxamide (90 mg, 0.209 mmol), 3 mL of EtOH, Hunig's base (0.11 mL, 0.627 mmol), and hydrazine anhydrous (0.026 mL, 0.836 mmol) were added, and the resulting yellow mixture was heated at 150° C. for 150 minutes under microwave conditions. The solution turned black. LCMS showed mainly product with 10% of remaining starting material. The black solids were filtered, and the yellow filtrate was evaporated. The resulting yellow residue was dissolved in CH$_3$OH, and purified by HPLC (CH$_3$CN/H$_2$O w/0.1% HCO$_2$H) to afford a formic acid salt of the title compound (31 mg) as a light yellow solid. LC-MS (ES) m/z=443 [M+H]$^+$. $^1$H NMR (400 MHz, DMSO-d$_6$): δ 1.49 (m, 1H), 1.70-1.95 (m, 2H), 1.98-2.12 (m, 1H), 2.25 (s, 3H), 3.16 (m, 1H), 3.48 (m, 1H), 4.49 (m, 2H), 4.74-4.99 (m, 1H), 7.11 (t, J=8.3 Hz, 2H), 7.39 (d, J=7.8 Hz, 1H), 7.49 (d, J=8.3 Hz, 2H), 7.74 (d, J=3.0 Hz, 1H), 7.89 (d, J=10.1 Hz, 1H), 9.97 (d, J=12.4 Hz, 1H), 12.03 (m, 2H).

Intermediate 267

(3S)-1-[2-Amino-6-(4-cyano-3-fluorophenyl)-4-pyrimidinyl]-N-(2-fluorophenyl)-3-piperidinecarboxamide

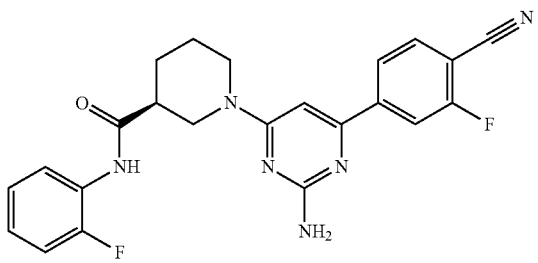 [SMILES: N#Cc1ccc(-c2cc(N3CCC[C@H](C(=O)Nc4ccccc4F)C3)nc(N)n2)cc1F]

To a solution of (3S)-1-[2-amino-6-(4-cyano-3-fluorophenyl)-4-pyrimidinyl]-3-piperidinecarboxylic acid (150 mg, 0.439 mmol), EDC (118 mg, 0.615 mmol), and HOBT (83 mg, 0.615 mmol) in DMF (8 mL) was added 2-fluoroaniline (68.4 mg, 0.615 mmol), and the reaction mixture was stirred at room temperature for 4 hours. LCMS showed reaction was completed. The reaction was poured onto water, and EtOAc was added to extract the product. The product stayed in the EtOAc layer. The organic solution was concentrated to dryness to give the title compound (191 mg) as a yellow solid. LC-MS (ES) m/z=435 [M+H]$^+$.

Example 126

(3S)-1-[2-Amino-6-(3-amino-1H-indazol-6-yl)-4-pyrimidinyl]-N-(2-fluorophenyl)-3-piperidinecarboxamide

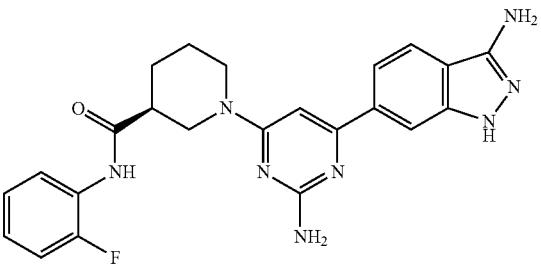 [SMILES: Nc1nc(-c2ccc3c(N)n[nH]c3c2)cc(N2CCC[C@H](C(=O)Nc3ccccc3F)C2)n1]

Into a microwave tube, (3S)-1-[2-amino-6-(4-cyano-3-fluorophenyl)-4-pyrimidinyl]-N-(2-fluorophenyl)-3-piperidinecarboxamide (191 mg, 0.440 mmol), 3 mL of EtOH, Hunig's base (0.077 mL, 0.440 mmol), and hydrazine anhydrous (0.055 mL, 1.759 mmol) were added, and the resulting yellow mixture was heated at 150° C. for 150 minutes under microwave conditions. The solution turned black. LCMS showed mainly product. The black solids were filtered and the yellow filtrate was evaporated. The yellow residue was dissolved in CH$_3$OH, and purified by HPLC (CH$_3$CN/H$_2$O w/0.1% HCO$_2$H) to afford a formic acid salt of the title compound (20 mg) as a light yellow solid. LC-MS (ES) m/z=447 [M+H]$^+$. $^1$H NMR (400 MHz, DMSO-d$_6$): δ 1.51 (m, 1H), 1.84 (m, 2H), 2.01-2.20 (m, 1H), 3.21-3.24 (m, 2H), 3.44-3.61 (m, 1H), 4.36-4.53 (m, 1H), 4.61-5.09 (m, 1H), 6.97 (m, 1H), 7.17 (m, 3H), 7.39 (s, 1H), 7.67-8.01 (m, 3H), 9.84 (m, 1H), 11.87-12.17 (m, 2H).

Intermediate 268

(3S)-1-[2-Amino-6-(4-cyano-3-fluorophenyl)-4-pyrimidinyl]-N-(3-fluorophenyl)-3-piperidinecarboxamide

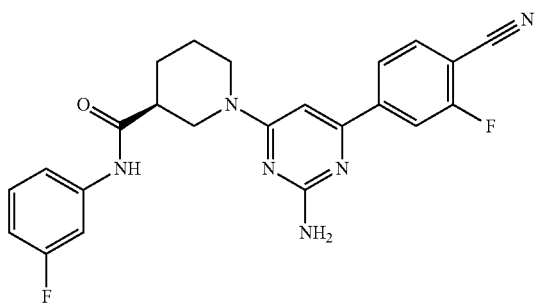

To a solution of (3S)-1-[2-amino-6-(4-cyano-3-fluorophenyl)-4-pyrimidinyl]-3-piperidinecarboxylic acid (150 mg, 0.439 mmol), EDC (118 mg, 0.615 mmol), and HOBT (83 mg, 0.615 mmol) in DMF (8 mL) was added 3-fluoroaniline (68.4 mg, 0.615 mmol), and the reaction mixture was stirred at room temperature for 4 hours. LCMS showed reaction was completed. The reaction was poured onto water, and EtOAc was added to extract the product. The product stayed in the EtOAc layer. The organic solution was concentrated to dryness to give the title compound (97 mg) as a yellow solid. LC-MS (ES) m/z=434 [M+H]$^+$.

Example 127

(3S)-1-[2-Amino-6-(3-amino-1H-indazol-6-yl)-4-pyrimidinyl]-N-(3-fluorophenyl)-3-piperidinecarboxamide

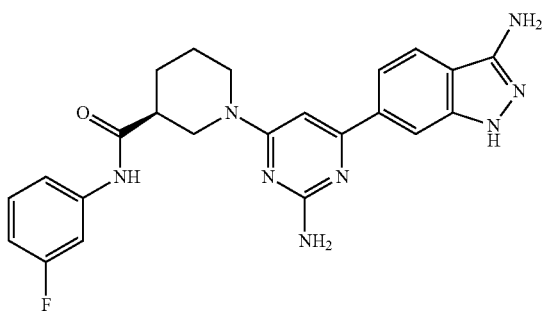 [SMILES: Nc1nc(-c2ccc3c(N)n[nH]c3c2)cc(N2CCC[C@H](C(=O)Nc3cccc(F)c3)C2)n1]

Into a microwave tube, (3S)-1-[2-amino-6-(4-cyano-3-fluorophenyl)-4-pyrimidinyl]-N-(3-fluorophenyl)-3-piperidinecarboxamide (90 mg, 0.207 mmol), 3 mL of EtOH, Hunig's base (0.109 mL, 0.621 mmol), and hydrazine anhydrous (0.026 mL, 0.829 mmol) were added, and the yellow mixture was heated at 150° C. for 150 minutes under microwave conditions. The solution turned into black. LCMS showed mainly product. The black solids were filtered and the yellow filtrate was evaporated. The resulting yellow residue was dissolved in CH$_3$OH, and purified by HPLC (CH$_3$CN/H$_2$O w/0.1% HCO$_2$H) to afford a formic acid salt of the title compound (65 mg) as a light yellow solid. LC-MS (ES) m/z=447 [M+H]$^+$. $^1$H NMR (400 MHz, CD$_3$OD): δ 1.35-1.44 (m, 1H), 1.69 (m, 1H), 1.91-2.11 (m, 2H), 2.12-2.27 (m, 1H), 2.61-2.78 (m, 1H), 3.39-3.80 (m, 1H), 4.24-4.41 (m, 1H), 4.68-5.17 (m, 1H), 6.85 (m, 2H), 7.22-7.47 (m, 3H), 7.51-7.60 (m, 1H), 7.79 (m, 1H), 7.89-8.01 (m, 1H).

Intermediate 269

(3S)-1-[2-Amino-6-(4-cyano-3-fluorophenyl)-4-pyrimidinyl]-N-(2-methylphenyl)-3-piperidinecarboxamide

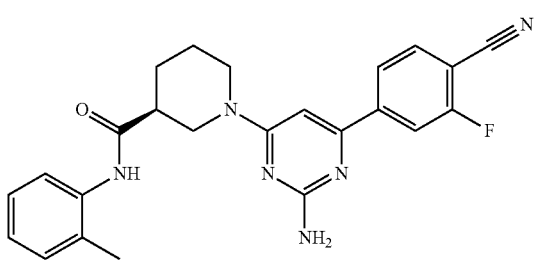 [SMILES: Cc1ccccc1NC(=O)[C@H]1CCCN(c2cc(-c3ccc(C#N)c(F)c3)nc(N)n2)C1]

To a solution of (3S)-1-[2-amino-6-(4-cyano-3-fluorophenyl)-4-pyrimidinyl]-3-piperidinecarboxylic acid (146 mg, 0.428 mmol), EDC (115, 0.599 mmol), and HOBT (81 mg, 0.599 mmol) in DMF (8 mL) was added o-toluidine (64 mg, 0.60 mmol), and the reaction mixture was stirred at room temperature for 4 hours. LCMS showed reaction was completed. The reaction was poured onto water, and EtOAc was added to extract the product. The product stayed in the EtOAc layer. The organic solution was concentrated to dryness to give the title compound (92 mg) as a yellow solid. LC-MS (ES) m/z=431 [M+H]$^+$.

Example 128

(3S)-1-[2-Amino-6-(3-amino-1H-indazol-6-yl)-4-pyrimidinyl]-N-(2-methylphenyl)-3-piperidinecarboxamide

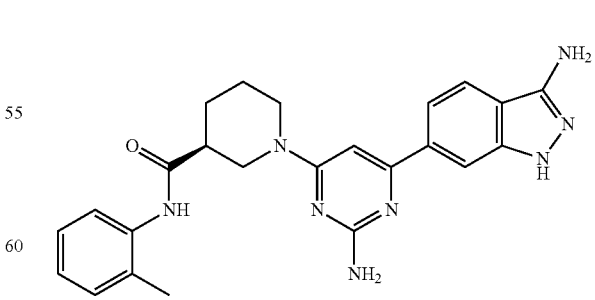

Into a microwave tube, (3S)-1-[2-amino-6-(4-cyano-3-fluorophenyl)-4-pyrimidinyl]-N-(2-methylphenyl)-3-piperidinecarboxamide (90 mg, 0.209 mmol), 3 mL of EtOH, Hunig's base (0.11 mL, 0.627 mmol), and hydrazine anhydrous (0.026 mL, 0.836 mmol) were added, and the yellow mixture was heated at 150° C. for 150 minutes under microwave conditions. The solution turned black. LCMS showed mainly product with 10% of remaining starting material. The black solids were filtered and the yellow filtrate was evaporated. The resulting yellow residue was dissolved in CH$_3$OH, and purified by HPLC (CH$_3$CN/H$_2$O w/0.1% HCO$_2$H) to afford a formic acid salt of the title compound (50 mg) as a light yellow solid. LC-MS (ES) m/z=443 [M+H]$^+$. $^1$H NMR (400 MHz, CD$_3$OD): δ 1.73 (m, 1H), 1.91-2.15 (m, 2H), 2.26 (m, 4H), 2.70-2.92 (m, 1H), 3.44 (m, 1H), 3.50-3.84 (m, 1H), 4.30 (d, J=12.6 Hz, 1H), 4.67-5.11 (m, 1H), 6.79-6.95 (m, 1H), 7.09-7.33 (m, 4H), 7.47 (d, J=7.8 Hz, 1H), 7.83 (s, 1H) 7.99 (m, 1H).

Intermediate 270

(3S)-1-[2-Amino-6-(4-cyano-3-fluorophenyl)-4-pyrimidinyl]-N-(4-chlorophenyl)-3-piperidinecarboxamide

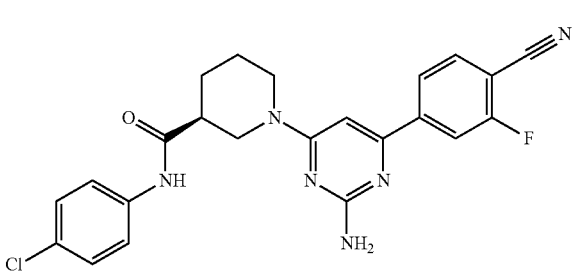 [SMILES: N#Cc1ccc(-c2cc(N3CCC[C@H](C(=O)Nc4ccc(Cl)cc4)C3)nc(N)n2)cc1F]

To a solution of (3S)-1-[2-amino-6-(4-cyano-3-fluorophenyl)-4-pyrimidinyl]-3-piperidinecarboxylic acid (150 mg, 0.439 mmol), EDC (118 mg, 0.615 mmol), and HOBT (83 mg, 0.615 mmol) in DMF (3 mL) was added 4-chloroaniline (56 mg, 0.44 mmol), and the reaction mixture was stirred at room temperature for 4 hours. LCMS showed reaction was completed. The reaction was poured onto water, and EtOAc was added to extract the product. The product stayed in the EtOAc layer. The organic solution was concentrated to dryness to give the title compound as a yellow solid. LC-MS (ES) m/z=451 [M+H]$^+$.

Example 129

(3S)-1-[2-Amino-6-(3-amino-1H-indazol-6-yl)-4-pyrimidinyl]-N-(4-chlorophenyl)-3-piperidinecarboxamide

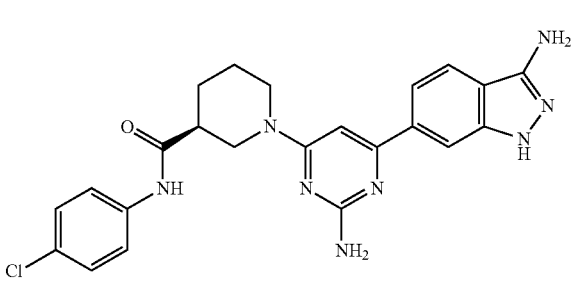 [SMILES: Nc1nc(-c2ccc3c(N)n[nH]c3c2)cc(N2CCC[C@H](C(=O)Nc3ccc(Cl)cc3)C2)n1]

Into a microwave tube, (3S)-1-[2-amino-6-(4-cyano-3-fluorophenyl)-4-pyrimidinyl]-N-(4-chlorophenyl)-3-piperidinecarboxamide (190 mg, 0.421 mmol), 3 mL of EtOH, Hunig's base (0.22 mL, 1.26 mmol), and hydrazine anhydrous (0.053 mL, 1.69 mmol) were added, and the yellow mixture was heated at 150° C. for 180 minutes under microwave conditions. The solution turned black. LCMS showed mainly product. The black solids were filtered and the yellow filtrate was evaporated. The resulting yellow residue was dissolved in CH$_3$OH at 50° C., EtOAc was used to triturate. When the solution turned slightly cloudy, it was cooled down to room temperature to get pure crystallized light yellow title compound (59 mg). LC-MS (ES) m/z=463 [M+H]$^+$. $^1$H NMR (400 MHz, DMSO-d$_6$): δ 1.45 (m, 1H), 1.64-1.85 (m, 2H), 1.99 (m, 1H), 2.55 (m, 1H), 2.78-3.07 (m, 2H), 4.38-4.82 (m, 2H), 5.37 (s, 2H), 6.10 (s, 2H), 6.64-6.74 (m, 1H), 7.31-7.40 (m, 2H), 7.53-7.76 (m, 4H), 7.97 (s, 1H), 10.18 (s, 1H), 11.50 (s, 1H).

Intermediate 271

(3S)-1-[2-Amino-6-(4-cyano-3-fluorophenyl)-4-pyrimidinyl]-N-[4-(methyloxy)phenyl]-3-piperidinecarboxamide

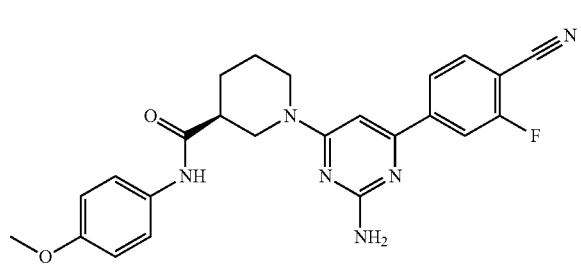 [SMILES: COc1ccc(NC(=O)[C@H]2CCCN(c3cc(-c4ccc(C#N)c(F)c4)nc(N)n3)C2)cc1]

To a solution of (3S)-1-[2-amino-6-(4-cyano-3-fluorophenyl)-4-pyrimidinyl]-3-piperidinecarboxylic acid (150 mg, 0.439 mmol), EDC (118 mg, 0.615 mmol), and HOBT (83 mg, 0.615 mmol) in DMF (3 mL) was added p-anisidine (54 mg, 0.44 mmol), and the reaction mixture was stirred at room temperature for 4 hours. LCMS showed reaction was completed. The reaction was poured onto water, and EtOAc was added to extract the product. The product stayed in the EtOAc layer. The organic solution was concentrated to dryness to give the title compound (191 mg) as a yellow solid. LC-MS (ES) m/z=447 [M+H]$^+$.

Example 130

(3S)-1-[2-Amino-6-(3-amino-1H-indazol-6-yl)-4-pyrimidinyl]-N-[4-(methyloxy)phenyl]-3-piperidinecarboxamide

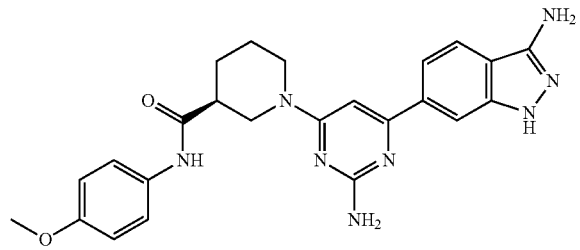 [SMILES: COc1ccc(NC(=O)[C@H]2CCCN(c3cc(-c4ccc5c(N)n[nH]c5c4)nc(N)n3)C2)cc1]

Into a microwave tube, (3S)-1-[2-amino-6-(4-cyano-3-fluorophenyl)-4-pyrimidinyl]-N-[4-(methyloxy)phenyl]-3-piperidinecarboxamide (190 mg, 0.426 mmol), 3 mL of EtOH, Hunig's base (0.223 mL, 1.28 mmol), and hydrazine anhydrous (0.053 ml, 1.702 mmol) were added, and the yellow mixture was heated to 150° C. for 180 minutes in microwave. The solution turned black. LCMS showed mainly product. The black solids were filtered and the yellow filtrate was evaporated. The resulting yellow residue was dissolved in CH₃OH at 50° C., and EtOAc was used to triturate. When the solution turned slightly cloudy, it was cooled to room temperature to get pure crystallized light yellow title compound (22 mg). LC-MS (ES) m/z=459 [M+H]⁺. ¹H NMR (400 MHz, DMSO-d₆): δ 1.46 (m, 1H), 1.65-1.84 (m, 2H), 1.98 (m, 1H), 2.79-3.06 (m, 2H), 3.72 (s, 3H), 4.49 (m, 1H), 4.68 (m, 1H), 5.37 (s, 2H), 6.10 (s, 2H), 6.68 (s, 1H), 6.88 (d, J=9.1 Hz, 2H), 7.53 (d, J=9.1 Hz, 2H), 7.58-7.65 (m, 1H), 7.66-7.78 (m, 1H), 7.97 (s, 1H), 9.87 (s, 1H), 11.49 (s, 1H).

Intermediate 272

(3S)-1-[2-Amino-6-(4-cyano-3-fluorophenyl)-4-pyrimidinyl]-N-[3-(methyloxy)phenyl]-3-piperidinecarboxamide

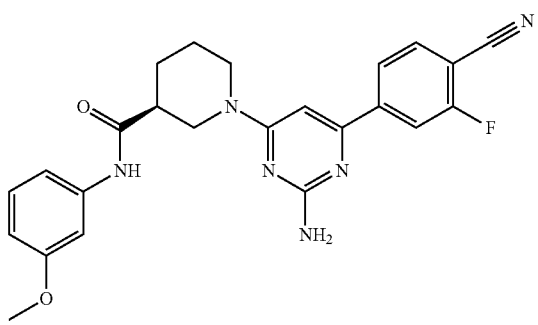 [SMILES: COc1cccc(NC(=O)[C@H]2CCCN(c3cc(-c4ccc(C#N)c(F)c4)nc(N)n3)C2)c1]

To a solution of (3S)-1-[2-amino-6-(4-cyano-3-fluorophenyl)-4-pyrimidinyl]-3-piperidinecarboxylic acid (150 mg, 0.439 mmol), EDC (118 mg, 0.615 mmol), and HOBT (83 mg, 0.615 mmol) in DMF (3 mL) was added m-anisidine (54 mg, 0.44 mmol), and the mixture was stirred at room temperature for 4 hours. LCMS showed reaction was completed. The reaction was poured onto water, and EtOAc was added to extract the product. The product stayed in the EtOAc layer. The organic solution was concentrated to dryness to give the title compound (194 mg) as a yellow solid. LC-MS (ES) m/z=447 [M+H]⁺.

Example 131

(3S)-1-[2-Amino-6-(3-amino-1H-indazol-6-yl)-4-pyrimidinyl]-N-[3-(methyloxy)phenyl]-3-piperidinecarboxamide

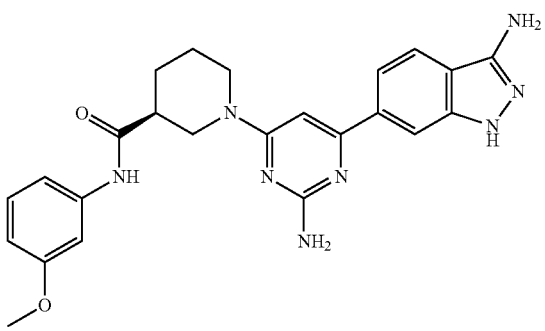 [SMILES: COc1cccc(NC(=O)[C@H]2CCCN(c3cc(-c4ccc5c(N)n[nH]c5c4)nc(N)n3)C2)c1]

Into a microwave tube, (3S)-1-[2-amino-6-(4-cyano-3-fluorophenyl)-4-pyrimidinyl]-N-[3-(methyloxy)phenyl]-3-piperidinecarboxamide (190 mg, 0.426 mmol), 3 mL of EtOH, Hunig's base (0.223 l, 1.277 mmol), and hydrazine anhydrous (0.053 ml, 1.702 mmol) were added, and the yellow mixture was heated at 150° C. for 180 minutes under microwave conditions. The solution turned black. LCMS showed mainly product. The black solids were filtered off and the yellow filtrate was evaporated. To the resulting brown liquid was added EtOAc (1 mL), and the mixture was warmed to 50° C. Two layers formed. The top layer is EtOAc solution, and it was pipeted to a different vial. The bottom layer is the comparatively pure product. This compound was treated with water at 50° C., and a solid was formed. This material was filtered and dried to give the title compound (90 mg) as a light yellow solid. LC-MS (ES) m/z=459 [M+H]⁺. ¹H NMR (400 MHz, DMSO-d₆): δ 1.45 (m, 1H), 1.61-1.85 (m, 2H), 2.01 (m, 1H), 2.79-3.06 (m, 2H), 3.74 (s, 3H), 4.36-4.79 (m, 2H), 5.37 (s, 2H), 6.02-6.15 (s, 2H), 6.55-6.74 (m, 2H), 7.09-7.26 (m, 2H), 7.32-7.41 (m, 1H), 7.51-7.78 (m, 2H), 7.91-8.00 (m, 1H), 10.01 (s, 1H), 11.50 (s, 1H).

Intermediate 273

(3S)-1-[2-Amino-6-(4-cyano-3-fluorophenyl)-4-pyrimidinyl]-N-(3-chlorophenyl)-3-piperidinecarboxamide

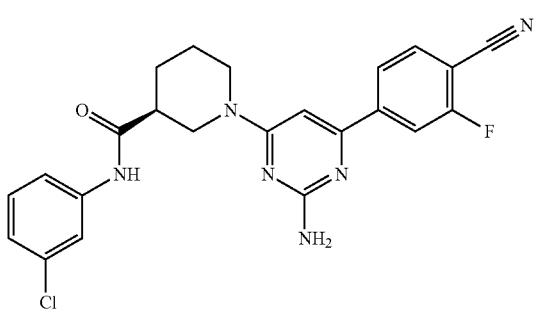 [SMILES: N#Cc1ccc(-c2cc(N3CCC[C@H](C(=O)Nc4cccc(Cl)c4)C3)nc(N)n2)cc1F]

To a solution of (3S)-1-[2-amino-6-(4-cyano-3-fluorophenyl)-4-pyrimidinyl]-3-piperidinecarboxylic acid (150 mg, 0.439 mmol), EDC (118 mg, 0.615 mmol), and HOBT (83 mg, 0.615 mmol) in DMF (3 mL) was added 3-chloroaniline (56 mg, 0.44 mmol), and the mixture was stirred at room temperature for 4 hours. LCMS showed reaction was completed. The reaction was poured onto water, and EtOAc was added to extract the product. The product stayed in the EtOAc layer. The organic solution was concentrated to dryness to give the title compound (193 mg) as a yellow solid. LC-MS (ES) m/z=451 [M+H]⁺.

Example 132

(3S)-1-[2-Amino-6-(3-amino-1H-indazol-6-yl)-4-pyrimidinyl]-N-(3-chlorophenyl)-3-piperidinecarboxamide

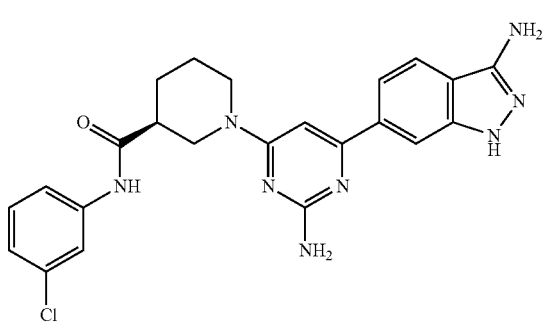 [SMILES: Nc1nc(-c2ccc3c(N)n[nH]c3c2)cc(N2CCC[C@H](C(=O)Nc3cccc(Cl)c3)C2)n1]

Into a microwave tube, (3S)-1-[2-amino-6-(4-cyano-3-fluorophenyl)-4-pyrimidinyl]-N-(3-chlorophenyl)-3-piperidinecarboxamide (190 mg, 0.421 mmol), 3 mL of EtOH, Hunig's base (0.22 mL, 1.26 mmol), and hydrazine anhydrous (0.053 mL, 1.69 mmol) were added, and the yellow mixture was heated at 150° C. for 180 minutes under microwave conditions. The solution turned black. LCMS showed mainly product. The black solids were filtered off and the yellow filtrate was evaporated. To the resulting brown liquid was added EtOAc (1 mL), and the mixture was warmed to 50° C. Two layers formed. The top layer is EtOAc solution, and it was pipeted to a different vial. The bottom layer is the comparatively pure product. This compound was treated with water at 50° C., and a solid was formed. This material was filtered and dried to give the title compound as a light yellow solid (150 mg). LC-MS (ES) m/z=463 [M+H]+. $^1$H NMR (400 MHz, DMSO-d$_6$): δ 1.45 (m, 1H), 1.63-1.85 (m, 2H), 2.01 (m, 1H), 2.79-3.06 (m, 2H), 4.62-4.76 (m, 1H), 5.37 (s, 2H), 6.11 (s, 2H), 6.69 (s, 1H), 7.10 (m, 1H), 7.28 (m, 1H), 7.52 (m, 1H), 7.55 (m, 1H), 7.79 (m, 1H), 7.82 (s, 1H), 8.03 (s, 1H), 10.22 (s, 1H), 11.45-11.57 (s, 1H).

Intermediate 274

(3S)-1-[2-Amino-6-(4-cyano-3-fluorophenyl)-4-pyrimidinyl]-N-(phenylmethyl)-3-piperidinecarboxamide

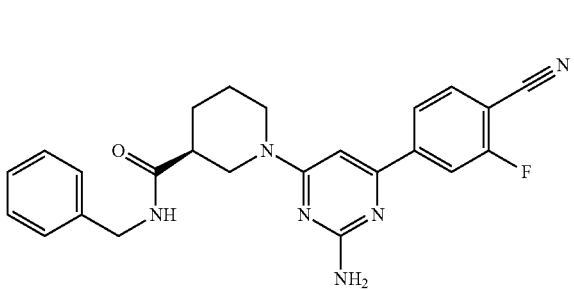 [SMILES: N#Cc1ccc(-c2cc(N3CCC[C@H](C(=O)NCc4ccccc4)C3)nc(N)n2)cc1F]

To a solution of (3S)-1-[2-amino-6-(4-cyano-3-fluorophenyl)-4-pyrimidinyl]-3-piperidinecarboxylic acid (150 mg, 0.439 mmol), EDC (118 mg, 0.615 mmol), and HOBT (83 mg, 0.615 mmol) in DMF (3 mL) was added 1-phenylmethanamine (47 mg, 0.44 mmol), and the mixture was stirred at room temperature for 4 hours. LCMS showed reaction was completed. The reaction was poured onto water, and EtOAc was added to extract the product. The product stayed in the EtOAc layer. The organic solution was concentrated to dryness to give the title compound (190 mg) as a yellow solid. LC-MS (ES) m/z=431 [M+H]+.

Example 133

(3S)-1-[2-Amino-6-(3-amino-1H-indazol-6-yl)-4-pyrimidinyl]-N-(phenylmethyl)-3-piperidinecarboxamide

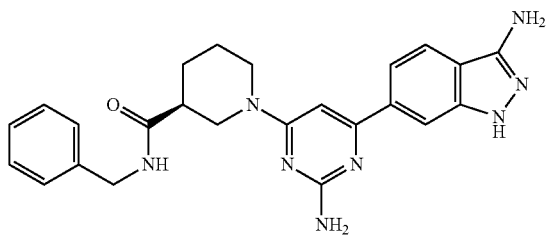 [SMILES: Nc1nc(-c2ccc3c(N)n[nH]c3c2)cc(N2CCC[C@H](C(=O)NCc3ccccc3)C2)n1]

Into a microwave tube, (3S)-1-[2-amino-6-(4-cyano-3-fluorophenyl)-4-pyrimidinyl]-N-(phenylmethyl)-3-piperidi-necarboxamide (190 mg, 0.441 mmol), 3 mL of EtOH, Hunig's base (0.308 ml, 1.761 mmol), and hydrazine anhydrous (0.083 ml, 2.64 mmol) were added, and the yellow mixture was heated at 150° C. for 180 minutes under microwave conditions. The solution turned black. LCMS showed mainly product. The black solids were filtered and the yellow filtrate was evaporated. The resulting yellow residue was dissolved in CH$_3$OH, and EtOAc was used to triturate, affording the title compound (29 mg) as a light yellow solid. LC-MS (ES) m/z=443 [M+H]+. $^1$H NMR (400 MHz, DMSO-d$_6$): δ 1.31-1.52 (m, 1H), 1.61-1.81 (m, 2H), 1.86-2.04 (m, 1H), 2.29-2.45 (m, 1H), 2.77-3.05 (m, 2H), 4.17-4.25 (m, 1H), 4.31-4.69 (m, 3H), 5.38 (s, 2H), 6.09 (s, 2H), 6.58-6.70 (m, 1H), 7.17-7.39 (m, 5H), 7.58 (dd, J=8.6, 1.3 Hz, 1H), 7.70 (d, J=8.6 Hz, 1H), 7.96 (s, 1H), 8.46 (t, J=5.9 Hz, 1H), 11.50 (s, 1H).

Intermediate 275

(3S)-1-[2-Amino-6-(4-cyano-3-fluorophenyl)-4-pyrimidinyl]-N-(4-pyridinylmethyl)-3-piperidinecarboxamide

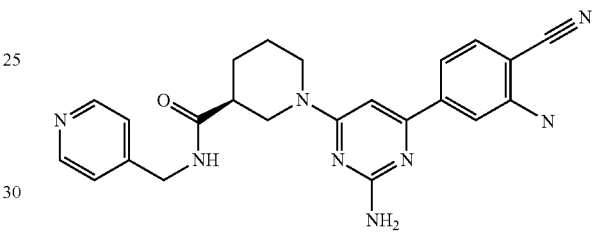

To a solution of (3S)-1-[2-amino-6-(4-cyano-3-fluorophenyl)-4-pyrimidinyl]-3-piperidinecarboxylic acid (150 mg, 0.439 mmol), EDC (118 mg, 0.615 mmol), and HOBT (83 mg, 0.615 mmol) in DMF (3 mL) was added 4-(aminomethyl)pyridine (47.5 mg, 0.439 mmol), and the mixture was stirred at room temperature for 4 hours. LCMS showed reaction was completed. The reaction was poured onto water, and EtOAc was added to extract the product. The product stayed in the EtOAc layer. The organic solution was concentrated to dryness to give the title compound (190 mg) as a yellow solid. LC-MS (ES) m/z=432 [M+H]+.

Example 134

(3S)-1-[2-Amino-6-(3-amino-1H-indazol-6-yl)-4-pyrimidinyl]-N-(4-pyridinylmethyl)-3-piperidinecarboxamide

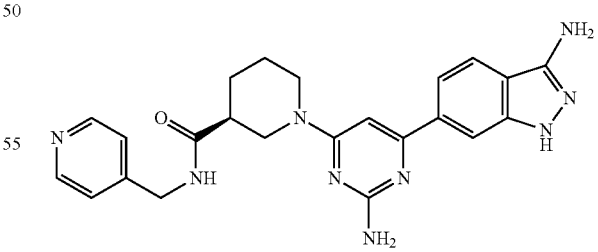

Into a microwave tube, (3S)-1-[2-amino-6-(4-cyano-3-fluorophenyl)-4-pyrimidinyl]-N-(phenylmethyl)-3-piperidi-necarboxamide (190 mg, 0.440 mmol), 3 mL of EtOH, Hunig's base (0.31 mL, 1.76 mmol), and hydrazine anhydrous (0.083 mL, 2.64 mmol) were added, and the yellow mixture was heated at 150° C. for 180 minutes under microwave conditions. The solution turned black. LCMS showed mainly product. The black solids were filtered and the yellow filtrate was evaporated. The yellow residue was sonicated in EtOAc at 50° C., and the solid was filtered. This material was then sonicated in water at 50° C., and the solid was filtered and washed with water to afford the title compound (92 mg) as a light yellow solid. LC-MS (ES) m/z=444 [M+H]+. 1H NMR (400 MHz, DMSO-d6): δ 1.37-1.55 (m, 1H), 1.62-1.80 (m, 2H), 1.96 (m, 1H), 2.35-2.45 (m, 1H), 2.81-3.05 (m, 2H), 4.18-4.46 (m, 3H), 4.56 (m, 1H), 5.38 (s, 2H), 6.10 (s, 2H), 6.65 (s, 1H), 7.25 (d, J=5.8 Hz, 2H), 7.59 (dd, J=8.6, 1.3 Hz, 1H), 7.67-7.78 (m, 1H), 7.96 (s, 1H), 8.45-8.65 (m, 3H), 11.51 (s, 1H).

Intermediate 276

(3S)-1-[2-Amino-6-(4-cyano-3-fluorophenyl)-4-pyrimidinyl]-N-(4-methylcyclohexyl)-3-piperidinecarboxamide

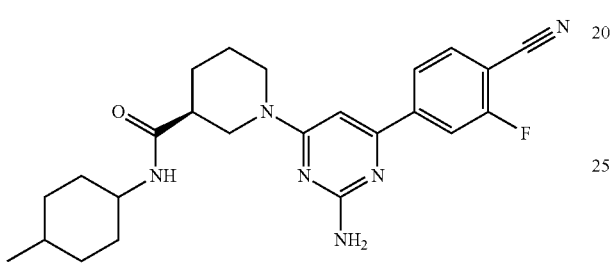

To a solution of (3S)-1-[2-amino-6-(4-cyano-3-fluorophenyl)-4-pyrimidinyl]-3-piperidinecarboxylic acid (150 mg, 0.439 mmol), EDC (118 mg, 0.615 mmol), and HOBT (83 mg, 0.615 mmol) in DMF (3 mL) into a 100 mL round-bottomed flask was added 4-methylcyclohexanamine (50 mg, 0.44 mmol), and The mixture was stirred at room temperature for 4 hours. LCMS showed the reaction was completed. The reaction was poured into water, and EtOAc was added to extract the product. The product stayed in the EtOAc layer. The organic solution was concentrated to dryness to give the title compound (190 mg) as a yellow solid. LC-MS (ES) m/z=437 [M+H]+.

Example 135

(3S)-1-[2-Amino-6-(3-amino-1H-indazol-6-yl)-4-pyrimidinyl]-N-(4-methylcyclohexyl)-3-piperidinecarboxamide

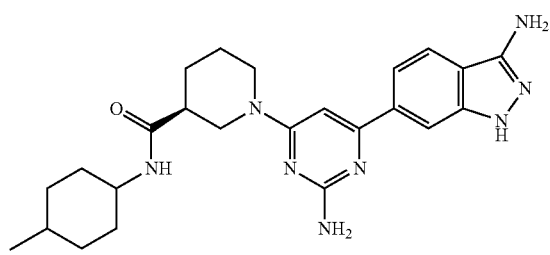 [SMILES: CC1CCC(NC(=O)[C@H]2CCCN(c3cc(-c4ccc5c(N)n[nH]c5c4)nc(N)n3)C2)CC1]

Into a microwave tube, (3S)-1-[2-amino-6-(4-cyano-3-fluorophenyl)-4-pyrimidinyl]-N-(4-methylcyclohexyl)-3-piperidinecarboxamide (190 mg, 0.435 mmol), 3 mL of EtOH, Hunig's base (0.30 mL, 1.74 mmol), and hydrazine anhydrous (0.082 mL, 2.61 mmol) were added, and the yellow mixture was heated at 150° C. for 180 minutes under microwave conditions. The solution turned black. LCMS showed mainly product. The black solids were filtered and the yellow filtrate was evaporated. The yellow residue was sonicated in EtOAc at 50° C., and the solid was filtered. This material was then sonicated in water at 50° C., and the solid was filtered and washed with water to afford the title compound (125 mg) as a light yellow solid. LC-MS (ES) m/z=449 [M+H]+. 1H NMR (400 MHz, DMSO-d6): δ 0.87 (m, 3H), 0.89-1.94 (m, 13H), 2.18-2.44 (m, 1H), 2.78-3.05 (m, 2H), 3.76 (m, 1H), 4.39 (m, 2H), 5.38 (s, 2H), 6.12 (s, 2H), 6.62 (s, 1H), 7.54-7.79 (m, 3H), 7.90-7.99 (m, 1H), 11.51 (s, 1H).

Intermediate 277

(3S)-1-[2-Amino-6-(4-cyano-3-fluorophenyl)-4-pyrimidinyl]-N-(1-methyl-1H-pyrazol-5-yl)-3-piperidinecarboxamide

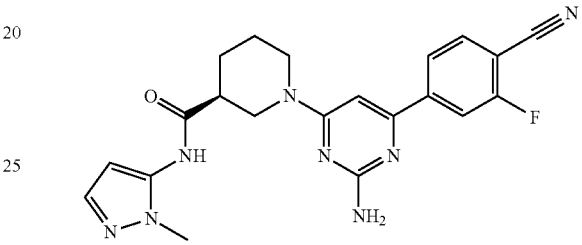

To a solution of (3S)-1-[2-amino-6-(4-cyano-3-fluorophenyl)-4-pyrimidinyl]-3-piperidinecarboxylic acid (150 mg, 0.439 mmol) and HATU (201 mg, 0.527 mmol) in DMF (3 mL) was added Hunig's base (0.15 mL, 0.88 mmol), and the mixture was stirred at room temperature for 15 minutes. 1-Methyl-1H-pyrazol-5-amine (51 mg, 0.53 mmol) was added, and the reaction mixture was stirred at room temperature for 0.5 hours. LCMS showed the reaction was completed. The reaction was poured onto water, and EtOAc was added to extract the product. The product stayed in the EtOAc layer. The organic solution was concentrated to dryness to give the title compound (180 mg) as a yellow solid. LC-MS (ES) m/z=421 [M+H]+.

Example 136

(3S)-1-[2-Amino-6-(3-amino-1H-indazol-6-yl)-4-pyrimidinyl]-N-(1-methyl-1H-pyrazol-5-yl)-3-piperidinecarboxamide

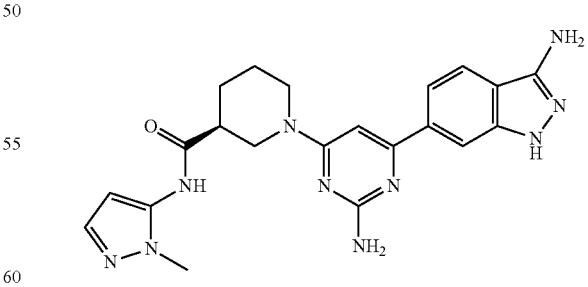

Into a microwave tube, (3S)-1-[2-amino-6-(4-cyano-3-fluorophenyl)-4-pyrimidinyl]-N-(1-methyl-1H-pyrazol-5-yl)-3-piperidinecarboxamide (180 mg, 0.428 mmol), 3 mL of EtOH, Hunig's base (0.30 mL, 1.71 mmol), and hydrazine anhydrous (0.081 mL, 2.57 mmol) were added, and the yellow mixture was heated overnight at 110° C. in an oil bath.

The solution turned black. LCMS showed mainly product. The black solids were filtered and the yellow filtrate was evaporated. The resulting yellow residue was treated with EtOAc (3 mL) at 50° C. with stirring, and the clear layer of EtOAc solution was poured out. The solid layer was then treated with water (3 mL) at 50° C. with stirring, and the suspension was filtered. The light yellow colored solid was washed by water, and dried to give the title compound (82 mg) as a light yellow solid. LC-MS (ES) m/z=433 [M+H]$^+$. $^1$H NMR (400 MHz, DMSO-d$_6$): δ 1.39-1.57 (m, 1H), 1.62-1.84 (m, 2H), 2.04 (m, 1H), 2.55-2.71 (m, 1H), 2.81-2.94 (m, 1H), 2.97-3.11 (m, 1H), 3.67 (s, 3H), 4.39-4.73 (m, 2H), 5.38 (s, 2H), 6.11 (s, 2H), 6.21 (s, 1H), 6.69 (s, 1H), 7.33 (s, 1H), 7.56-7.77 (m, 2H), 7.97 (s, 1H), 10.00 (s, 1H), 11.50 (s, 1H).

Intermediate 278

(3S)-1-[2-Amino-6-(4-cyano-3-fluorophenyl)-4-pyrimidinyl]-N-(1,3-dimethyl-1H-pyrazol-5-yl)-3-piperidinecarboxamide

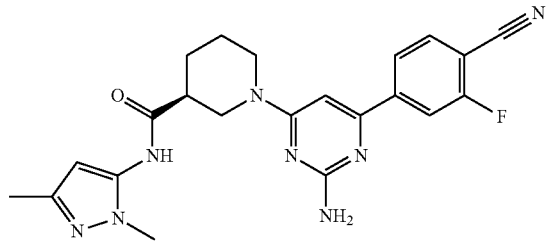 [SMILES: Cc1cc(NC(=O)[C@H]2CCCN(c3cc(-c4ccc(C#N)c(F)c4)nc(N)n3)C2)n(C)n1]

In a 100 mL round-bottomed flask, To a solution of (3S)-1-[2-amino-6-(4-cyano-3-fluorophenyl)-4-pyrimidinyl]-3-piperidinecarboxylic acid (150 mg, 0.439 mmol) and HATU (201 mg, 0.527 mmol) in DMF (3 mL) was added Hunig's base (0.15 mL, 0.88 mmol), and the mixture was stirred at room temperature for 15 minutes. 1,3-Dimethyl-1H-pyrazol-5-amine (59 mg, 0.53 mmol) was added, and the reaction mixture was stirred at room temperature for 0.5 hours. LCMS showed the reaction was completed. The reaction was poured onto water, and EtOAc was added to extract the product. The product stayed in the EtOAc layer. The organic solution was concentrated to dryness to give the title compound (190 mg) as a yellow solid. LC-MS (ES) m/z=435 [M+H]$^+$.

Example 137

(3S)-1-[2-Amino-6-(3-amino-1H-indazol-6-yl)-4-pyrimidinyl]-N-(1,3-dimethyl-1H-pyrazol-5-yl)-3-piperidinecarboxamide

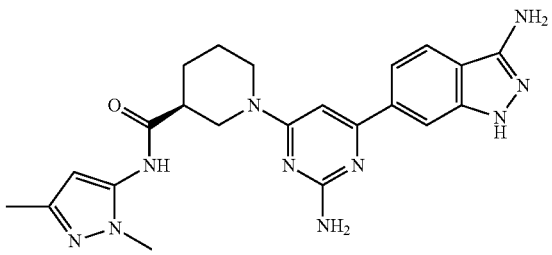 [SMILES: Cc1cc(NC(=O)[C@H]2CCCN(c3cc(-c4ccc5c(N)n[nH]c5c4)nc(N)n3)C2)n(C)n1]

Into a microwave tube, (3S)-1-[2-amino-6-(4-cyano-3-fluorophenyl)-4-pyrimidinyl]-N-(1-methyl-1H-pyrazol-5-yl)-3-piperidinecarboxamide (190 mg, 0.437 mmol), 3 mL of EtOH, Hunig's base (0.31 mL, 1.75 mmol), and hydrazine anhydrous (0.082 mL, 2.62 mmol) were added, and the yellow mixture was heated overnight at 110° C. in an oil bath. The solution turned black. LCMS showed mainly product. The black solids were filtered off and the yellow filtrate was evaporated. The resulting yellow residue was treated with EtOAc (3 mL) at 50° C. with stirring, and the clear layer of EtOAc solution was poured out. The solid layer was then treated with water (3 mL) water at 50° C. with stirring, and the suspension was filtered. The light yellow colored solid was washed by water, and dried to give the title compound (3.3 mg) as a yellow solid. LC-MS (ES) m/z=447 [M+H]$^+$. $^1$H NMR (400 MHz, DMSO-d$_6$): δ 1.47 (s, 1H), 1.74 (s, 2H), 2.08 (s, 4H), 2.33 (m, 1H), 2.67 (m, 1H), 2.82-3.09 (m, 2H), 3.57 (s, 3H), 5.38 (s, 2H), 6.00 (s, 1H), 6.07-6.27 (m, 2H), 6.69 (s, 1H), 7.61 (s, 1H), 7.71 (d, J=8.6 Hz, 1H), 7.96 (s, 1H), 9.92 (s, 1H), 11.51 (s, 1H).

The filtrate was dried, and in MeOH, and purified by HPLC. 30 mL/min. starting with 14% CH3CN/Water, with 0.1% of HCO$_2$H, ending with 17% of CH3CN/Water, with 0.1% of HCO2H. 10 minutes run. The product is light yellow colored solid, as its formic acid salt. LC-MS (ES) m/z=447 [M+H]$^+$.

Intermediate 279

(3S,6R)-1-[6-(4-Acetyl-3-fluorophenyl)-2-amino-4-pyrimidinyl]-6-methyl-3-piperidinecarboxylic acid

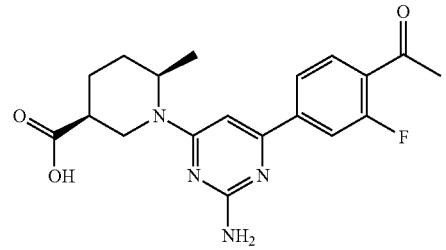 [SMILES: CC(=O)c1ccc(-c2cc(N3C[C@@H](C(=O)O)CC[C@H]3C)nc(N)n2)cc1F]

A mixture of 4,6-dichloro-2-pyrimidinamine (1.69 g, 10.31 mmol), (3S,6R)-6-methyl-3-piperidinecarboxylic acid (2.037 g, 10.31 mmol) and NaHCO$_3$ (3.90 g, 46.4 mmol) in 1,4-dioxane (100 mL) and water (50 mL) was stirred overnight at 117° C. into a sealed tube. The reaction was allowed to cool to room temperature. LCMS showed that most of the starting material 4,6-dichloro-2-pyrimidinamine had been consumed. Then (4-acetyl-3-fluorophenyl)boronic acid (2.81 g, 15.5 mmol) and Pd(Ph$_3$P)$_4$ (0.238 g, 0.206 mmol) were added, and the reaction mixture was stirred for 24 hours at 117° C. The mixture was poured into water (300 mL) and EtOAc (200 mL). At this moment the pH of the solution was 9. The compound stayed in the water layer. The water layer was separated from the organic layer. There was some black colored and yellow colored suspension in the warer layer, which was filtered out. (They were not product). To the aqueous layer, 6N HCl was added dropwise until the pH=4. A precipitate was formed. The precipitate was filtered, washed with water, and dried to afford the title compound (1.87 g) as a light yellow solid. LC-MS (ES) m/z=373 [M+H]$^+$.

Intermediate 280

(3S,6R)-1-[6-(4-Acetyl-3-fluorophenyl)-2-amino-4-pyrimidinyl]-6-methyl-N-(phenylmethyl)-3-piperidinecarboxamide

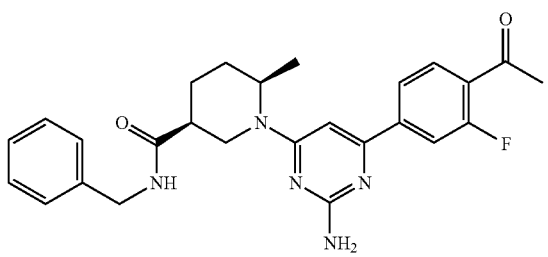 [SMILES: CC(=O)c1ccc(-c2cc(N3C[C@@H](C(=O)NCc4ccccc4)CC[C@H]3C)nc(N)n2)cc1F]

To a solution of (3S,6R)-1-[6-(4-acetyl-3-fluorophenyl)-2-amino-4-pyrimidinyl]-6-methyl-3-piperidinecarboxylic acid (308 mg, 0.827 mmol) and HATU (377 mg, 0.992 mmol) in DMF (3 mL) was added Hunig's base (0.289 ml, 1.654 mmol), and the mixture was stirred at room temperature for 15 minutes. Then benzylamine (0.11 mL, 0.99 mmol) was added, and the reaction mixture was stirred at room temperature for 0.5 hours. LCMS showed reaction was completed. The reaction was poured onto water, and EtOAc was added to extract the product. The product stayed in the EtOAc layer. The organic solution was concentrated to dryness to give the title compound (339 mg) as a yellow solid. LC-MS (ES) m/z=462 [M+H]$^+$.

Example 138

(3S,6R)-1-[2-Amino-6-(3-methyl-1H-indazol-6-yl)-4-pyrimidinyl]-6-methyl-N-(phenylmethyl)-3-piperidinecarboxamide

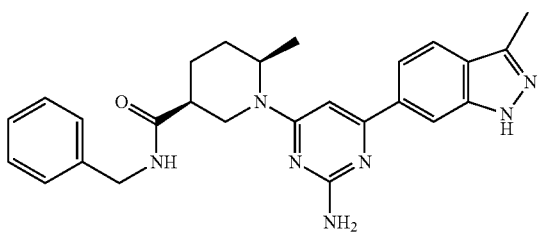 [SMILES: Cc1n[nH]c2cc(-c3cc(N4C[C@@H](C(=O)NCc5ccccc5)CC[C@H]4C)nc(N)n3)ccc12]

Into a sealed tube, (3S,6R)-1-[6-(4-acetyl-3-fluorophenyl)-2-amino-4-pyrimidinyl]-6-methyl-N-(phenylmethyl)-3-piperidinecarboxamide (90 mg, 0.195 mmol), O-methylhydroxylamine hydrochloride (16.3 mg, 0.20 mmol), and K$_2$CO$_3$ (32.3 mg, 0.234 mmol) were stirred together in DME (3 mL) for 4 hours at 57° C. The reaction mixture was filtered, and the filtrate containing the oxime intermediate was concentrated in vacuo to 2 mL. Then EtOH (3 mL), Hunig's base (0.05 mL, 0.27 mmol), and hydrazine anhydrous (0.013 mL, 0.410 mmol) were added, and the resulting yellow mixture was heated overnight at 120° C. in an oil bath. The solution turned black. LCMS showed mainly product. The black solid was filtered and the yellow filtrate was evaporated. The resulting yellow residue was dissolved in CH$_3$OH, and purified by HPLC (CH$_3$CN/H$_2$O w/0.1% HCO$_2$H) to afford a formic acid salt of the title compound (9 mg) as a light yellow solid. LC-MS (ES) m/z=456 [M+H]$^+$. $^1$H NMR (400 MHz, CD$_3$OD): δ 1.32 (m, 4H), 1.75-1.91 (m, 3H), 1.97-2.12 (m, 1H), 2.41-2.53 (m, 1H), 2.60 (s, 3H), 3.11-3.27 (m, 1H), 4.33-4.50 (m, 2H), 4.56-4.74 (m, 1H), 6.59 (s, 1H), 7.23-7.41 (m, 5H), 7.54-7.63 (m, 1H), 7.96 (m, 1H), 7.94 (s, 1H).

Intermediate 281

(3S,6R)-1-[2-Amino-6-(1H-indazol-6-yl)-4-pyrimidinyl]-6-methyl-3-piperidinecarboxylic acid

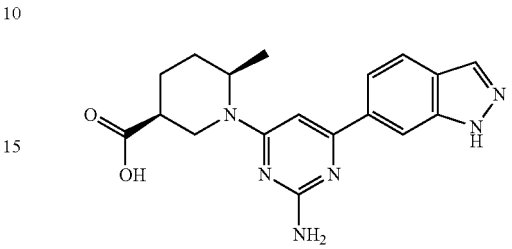

A mixture of 4,6-dichloro-2-pyrimidinamine (0.2 g, 1.22 mmol), (3S,6R)-6-methyl-3-piperidinecarboxylic acid (0.265 g, 1.342 mmol) and NaHCO$_3$ (V, 6.10 mmol) in 1,4-dioxane (10 mL) and water (5 mL) was stirred overnight at 117° C. into a sealed tube. The reaction was allowed to cool to room temperature. LCMS showed that most of the starting material 4,6-dichloro-2-pyrimidinamine had been consumed. Then 1H-indazole-6-boronic acid pinacol ester (0.327 g, 1.342 mmol) and Pd(Ph$_3$P)$_4$ (0.028 g, 0.024 mmol) were added, and the reaction mixture was stirred for 24 hours at 117° C. The mixture was poured into water (200 mL). The formed solid was filtered. To the aqueous layer, 6N HCl was added dropwise until the pH=4. A precipitate was formed and the solution looked cloudy. A solution of 10% isopropanol in EtOAc (200 mL) was used to extract the compound, but most of the compound stayed in water. This organic layer was discarded. Then a solution of 10% isopropanol in CH$_2$Cl$_2$ (100 mL) was used for the extraction. The mixture turned cloudy after sitting for 30 minutes, and a significant amount of solid was formed. The white solid was filtered, washed with water, and dried to afford the title compound (95 mg) as a white solid. LC-MS (ES) m/z=353 [M+H]$^+$.

Example 139

(3S,6R)-1-[2-Amino-6-(1H-indazol-6-yl)-4-pyrimidinyl]-N-cyclohexyl-6-methyl-3-piperidinecarboxamide

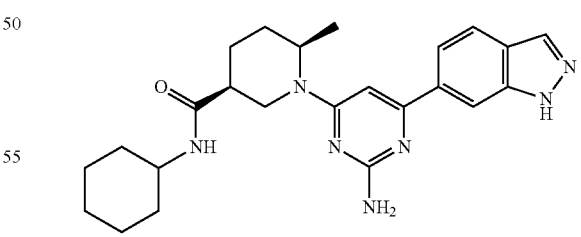

To a solution of (3S,6R)-1-[2-amino-6-(1H-indazol-6-yl)-4-pyrimidinyl]-6-methyl-3-piperidinecarboxylic acid (95 mg, 0.270 mmol) and HATU (123 mg, 0.324 mmol) in DMF (3 mL) was added Hunig's base (0.094 mL, 0.54 mmol), and the mixture was stirred at room temperature for 15 minutes. Then cyclohexylamine (0.037 mL, 0.324 mmol) was added, and the reaction mixture was stirred at room temperature for 0.5 hours. LCMS showed reaction was completed. The reaction was poured into water, and EtOAc was added to extract the product. The product stayed in the EtOAc layer. The organic layer was concentrated to dryness, and the resulting glass like solid was dissolved in $CH_3OH$. Water was poured into the solution, and a white solid was formed, which was filtered, washed by water, and dried under vacuum to give the title compound (100 mg) as a white solid. LC-MS (ES) m/z=434 [M+H]+. 1H NMR (400 MHz, $CD_3OD$): δ 1.29 (m, 9H), 1.62-2.09 (m, 9H), 2.32-2.45 (m, 1H), 3.06-3.18 (m, 1H), 3.61-3.73 (m, 1H), 4.44-4.84 (m, 1H), 6.53 (s, 1H), 7.65 (dd, J=8.5, 1.4 Hz, 1H), 7.85 (dd, J=8.5, 1.4 Hz, 1H), 8.06 (s, 1H), 8.09 (s, 1H).

Intermediate 282

(3S,6R)-1-[2-amino-6-(4-cyano-3-fluorophenyl)-4-pyrimidinyl]-N-(cyclohexylmethyl)-6-methyl-3-piperidinecarboxamide

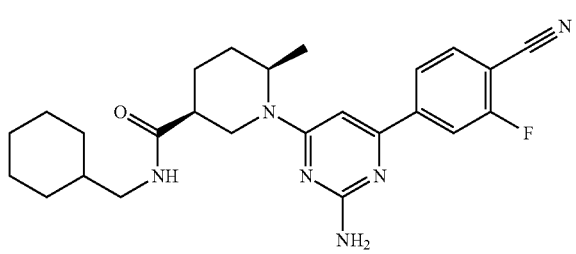 [SMILES: C[C@@H]1CC[C@H](C(=O)NCC2CCCCC2)CN1c1cc(-c2ccc(C#N)c(F)c2)nc(N)n1]

To a solution of (3S,6R)-1-[2-amino-6-(4-cyano-3-fluorophenyl)-4-pyrimidinyl]-6-methyl-3-piperidinecarboxylic acid (170 mg, 0.478 mmol) and HATU (218 mg, 0.574 mmol) in DMF (3 mL) was added Hunig's base (0.17 mL, 0.96 mmol), and the mixture was stirred at room temperature for 5 minutes. Then cyclohexylmethylamine (0.07 ml, 0.53 mmol) was added, and the reaction mixture was stirred at room temperature for 0.5 hours. LCMS showed reaction was completed. The reaction was poured into water, and the formed solid was filtered, washed by water, and dried to afford the title compound (187 mg) as a yellow solid. LC-MS (ES) m/z=451 [M+H]+.

Example 140

(3S,6R)-1-[2-amino-6-(3-amino-1H-indazol-6-yl)-4-pyrimidinyl]-N-(cyclohexylmethyl)-6-methyl-3-piperidinecarboxamide

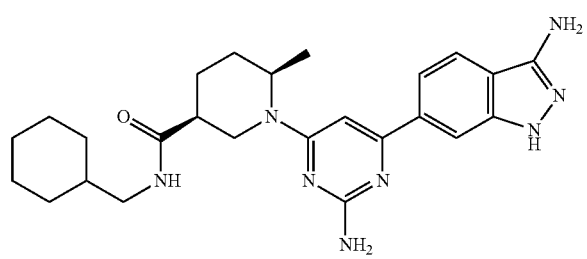 [SMILES: C[C@@H]1CC[C@H](C(=O)NCC2CCCCC2)CN1c1cc(-c2ccc3c(N)n[nH]c3c2)nc(N)n1]

Into a microwave tube, (3S,6R)-1-[2-amino-6-(4-cyano-3-fluorophenyl)-4-pyrimidinyl]-N-(cyclohexylmethyl)-6-methyl-3-piperidinecarboxamide (187 mg, 0.415 mmol), 5 mL of EtOH, Hunig's base (0.290 ml, 1.66 mmol), and hydrazine anhydrous (0.078 ml, 2.49 mmol) were added, and the yellow suspension mixture was heated overnight at 110° C. in an oil bath. LCMS showed mainly product. $CH_3OH$ (5 mL) was added to the solution. The black solid and the yellow solution were carefully separated due to the black solid being heavier than yellow solution. Water (20 mL) was added to the yellow solution, and a solid formed. The solid was filtered and washed by water, dried in vacuum, and then treated with EtOAc and $CH_3OH$. The solid in the solvent was filtered, washed by EtOAc, and dried in vacuum to afford the title compound (115 mg) as a light yellow solid. LC-MS (ES) m/z=463 [M+H]+. 1H NMR (400 MHz, DMSO-$d_6$): δ 0.88 (m, 2H), 1.05-1.26 (m, 6H), 1.32-1.46 (m, 1H), 1.54-1.74 (m, 8H), 1.75-1.88 (m, 1H), 2.21-2.38 (m, 1H), 2.76-3.08 (m, 3H), 5.38 (s, 2H), 6.07 (s, 2H), 6.57 (s, 1H), 7.54-7.59 (m, 1H), 7.66-7.72 (m, 1H), 7.87-7.92 (m, 1H), 7.94 (s, 1H), 11.50 (s, 1H).

Intermediate 283

(3S,6R)-1-[2-amino-6-(4-cyano-3-fluorophenyl)-4-pyrimidinyl]-6-methyl-N-{[4-(methyloxy)phenyl]methyl}-3-piperidinecarboxamide

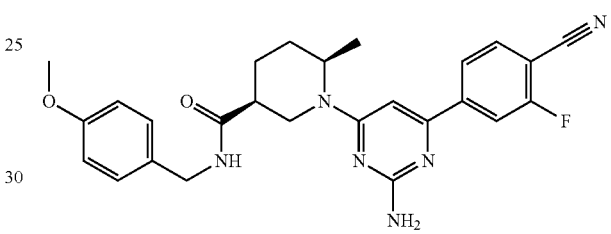

To a solution of (3S,6R)-1-[2-amino-6-(4-cyano-3-fluorophenyl)-4-pyrimidinyl]-6-methyl-3-piperidinecarboxylic acid (170 mg, 0.478 mmol) and HATU (218 mg, 0.574 mmol) in DMF (3 mL) was added Hunig's base (0.167 mL, 0.957 mmol), and the mixture was stirred at room temperature for 5 minutes. Then 1-[4-(methyloxy)phenyl]methanamine (65.6 mg, 0.478 mmol) was added, and the reaction mixture was stirred at room temperature for 0.5 hours. LCMS showed reaction was completed. The reaction was poured onto water, and the formed solid was filtered, washed by water and dried to give the title compound (203 mg) as a yellow solid. LC-MS (ES) m/z=475 [M+H]+.

Example 141

(3S,6R)-1-[2-amino-6-(3-amino-1H-indazol-6-yl)-4-pyrimidinyl]-6-methyl-N-{[4-(methyloxy)phenyl]methyl}-3-piperidinecarboxamide

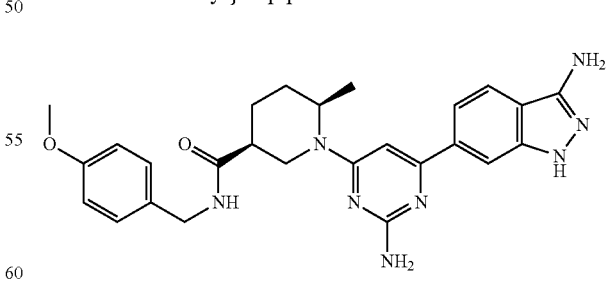

Into a microwave tube, (3S,6R)-1-[2-amino-6-(4-cyano-3-fluorophenyl)-4-pyrimidinyl]-6-methyl-N-{[4-(methyloxy)phenyl]methyl}-3-piperidinecarboxamide (203 mg, 0.43 mmol), 5 mL of EtOH, Hunig's base (0.30 mL, 1.71 mmol), and hydrazine anhydrous (0.080 mL, 2.56 mmol) were added, and the yellow suspension mixture was heated overnight at 110° C. in an oil bath. LCMS showed mainly product.

CH₃OH (5 mL) was added to the solution. The black solid and the yellow solution were carefully separated due to the black solid is heavier than yellow solution. Water (20 mL) was added to the yellow solution, and a solid formed. The solid was filtered and washed by water, dried in vacuum, and then treated with EtOAc and CH₃OH. The solid in the solvent was filtered, washed by EtOAc, and dried in vacuum to afford the title compound (101 mg) as a light yellow solid. LC-MS (ES) m/z=487 [M+H]⁺. ¹H NMR (400 MHz, DMSO-d₆): δ 1.07-1.22 (m, 3H), 1.56-1.94 (m, 4H), 2.33 (m, 1H), 2.94 (m, 1H), 3.74 (s, 3H), 4.10-4.22 (m, 1H), 4.23-4.37 (m, 1H), 5.38 (s, 2H), 6.08 (s, 2H), 6.58 (s, 1H), 6.83-6.97 (m, 2H), 7.20 (d, J=8.6 Hz, 2H), 7.57 (dd, J=8.6, 1.26 Hz, 1H), 7.70 (d, J=8.3 Hz, 1H), 7.98 (s, 1H) 8.36-8.48 (m, 1H), 11.50 (s, 1H).

Intermediate 284

(3S,6R)-1-[2-amino-6-(4-cyano-3-fluorophenyl)-4-pyrimidinyl]-N-cyclopentyl-6-methyl-3-piperidinecarboxamide

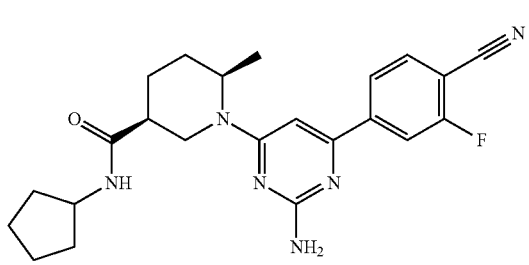 [SMILES: C[C@@H]1CC[C@H](C(=O)NC2CCCC2)CN1c1cc(-c2ccc(C#N)c(F)c2)nc(N)n1]

To a solution of (3S,6R)-1-[2-amino-6-(4-cyano-3-fluorophenyl)-4-pyrimidinyl]-6-methyl-3-piperidinecarboxylic acid (170 mg, 0.478 mmol) and HATU (218 mg, 0.574 mmol) in DMF (3 mL) was added Hunig's base (0.167 mL, 0.957 mmol), and the mixture was stirred at room temperature for 5 minutes. Then, cyclopentylamine (44.8 mg, 0.526 mmol) was added, and the reaction mixture was stirred at room temperature for 0.5 hours. LCMS showed reaction was completed. The reaction was poured into water, and the formed solid was filtered, washed by water and dried to afford the title compound (174 mg) as a yellow solid. LC-MS (ES) m/z=423 [M+H]⁺.

Example 142

(3S,6R)-1-[2-amino-6-(3-amino-1H-indazol-6-yl)-4-pyrimidinyl]-N-cyclopentyl-6-methyl-3-piperidinecarboxamide

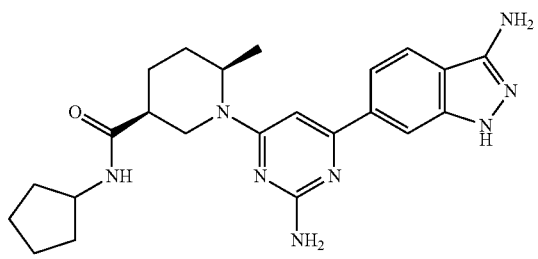 [SMILES: C[C@@H]1CC[C@H](C(=O)NC2CCCC2)CN1c1cc(-c2ccc3c(N)n[nH]c3c2)nc(N)n1]

Into a microwave tube, (3S,6R)-1-[2-amino-6-(4-cyano-3-fluorophenyl)-4-pyrimidinyl]-N-cyclopentyl-6-methyl-3-piperidinecarboxamide (174 mg, 0.412 mmol), 5 mL of EtOH, Hunig's base (0.288 mL, 1.647 mmol), and hydrazine anhydrous (0.078 mL, 2.471 mmol) were added, and the yellow suspension mixture was heated overnight at 110° C. in an oil bath. LCMS showed mainly product. CH₃OH (5 mL) was added to the solution. The black solid and the yellow solution were carefully separated due to the black solid is heavier than yellow solution. Water (20 mL) was added to the yellow solution, and a solid formed. The solid was filtered and washed by water, dried in vacuum, and then treated with EtOAc and CH₃OH. The solid in the solvent was filtered, washed by EtOAc, and dried in vacuum to afford the title compound (82 mg) as a light yellow solid. LC-MS (ES) m/z=435 [M+H]⁺. ¹H NMR (400 MHz, DMSO-d₆): δ 1.14 (m, 3H), 1.65 (m, 12H), 2.14-2.33 (m, 1H), 2.76-3.08 (m, 1H), 3.93-4.12 (m, 1H), 5.38 (s, 2H), 6.07 (s, 2H), 6.57 (s, 1H), 7.57 (m, 1H), 7.69 (m, 1H), 7.87 (m, 1H), 7.94 (s, 1H), 11.49 (s, 1H).

Intermediate 285

(3S,6R)-1-[2-Amino-6-(4-cyano-3-fluorophenyl)-4-pyrimidinyl]-N-[(1R)-1-cyclohexylethyl]-6-methyl-3-piperidinecarboxamide

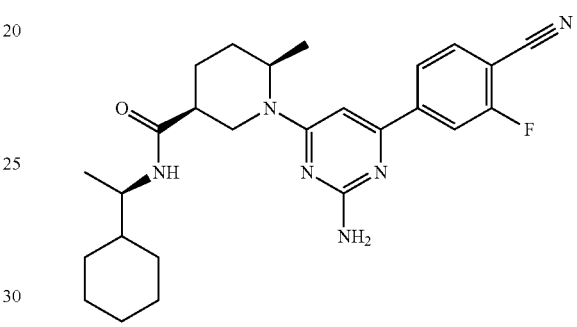

To a solution of (3S,6R)-1-[2-amino-6-(4-cyano-3-fluorophenyl)-4-pyrimidinyl]-6-methyl-3-piperidinecarboxylic acid (170 mg, 0.478 mmol) and HATU (218 mg, 0.574 mmol) in DMF (3 mL) was added Hunig's base (0.167 mL, 0.957 mmol), and the mixture was stirred at room temperature for 5 minutes. Then (1R)-1-cyclohexylethanamine (60.9 mg, 0.478 mmol) was added, and the reaction mixture was stirred at room temperature for 0.5 hours. LCMS showed reaction was completed. The reaction was poured onto water, and the formed solid was filtered, washed by water and dried to give the title compound (196 mg) as a yellow solid. LC-MS (ES) m/z=465 [M+H]⁺.

Example 143

(3S,6R)-1-[2-Amino-6-(3-amino-1H-indazol-6-yl)-4-pyrimidinyl]-N-[(1R)-1-cyclohexylethyl]-6-methyl-3-piperidinecarboxamide

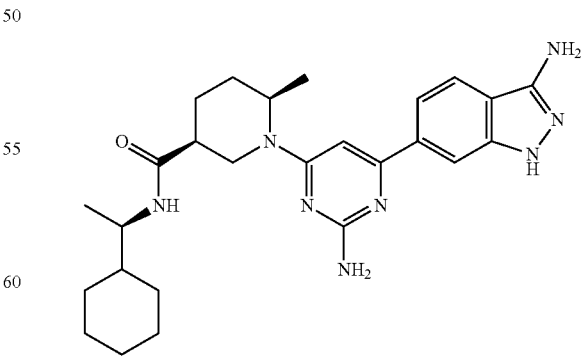

Into a microwave tube, (3S,6R)-1-[2-amino-6-(4-cyano-3-fluorophenyl)-4-pyrimidinyl]-N-[(1R)-1-cyclohexylethyl]-6-methyl-3-piperidinecarboxamide (195.6 mg, 0.421 mmol), 5 mL of EtOH, Hunig's base (0.294 mL, 1.684 mmol), and hydrazine anhydrous (0.079 mL, 2.53 mmol) were added, and the yellow suspension mixture was heated overnight at 110° C. in an oil bath. LCMS showed mainly product. CH$_3$OH (5 mL) was added to the solution. The black solid and the yellow solution were carefully separated due to the black solid is heavier than yellow solution. Water (20 mL) was added to the yellow solution, and a solid formed. The solid was filtered, washed by water and dried in vacuum. The solid was recrystallized using CH$_3$CN, and the solid in the solvent was filtered, washed by EtOAc and CH$_3$CN, and dried in vacuum to afford the title compound (102 mg) as a light yellow solid. LC-MS (ES) m/z=477 [M+H]$^+$. $^1$H NMR (400 MHz, DMSO-d$_6$): δ 0.83-1.36 (m, 12H), 1.55-1.85 (m, 9H), 2.20-2.37 (m, 1H), 2.92 (m, 1H), 3.56-3.71 (m, 1H), 5.38 (s, 2H), 6.07 (s, 2H), 6.57 (s, 1H), 7.54-7.61 (m, 1H), 7.66-7.78 (m, 2H), 7.94 (s, 1H), 11.50 (s, 1H).

C. in an oil bath. LCMS showed mainly product. CH$_3$OH (5 mL) was added to the solution. The black solid and the yellow solution were carefully separated due to the black solid is heavier than yellow solution. Water (20 mL) was added to the yellow solution, and a solid formed. The solid was filtered, washed by water, and dried in vacuum. The solid was recrystallized using CH$_3$CN, and the solid in the solvent was filtered, washed by EtOAc and CH$_3$CN, and dried in vacuum to afford the title compound (94 mg) as a light yellow solid. LC-MS (ES) m/z=475 [M+H]$^+$. $^1$H NMR (400 MHz, DMSO-d$_6$): δ 1.16 (m, 3H), 1.60-1.92 (m, 4H), 2.29-2.44 (m, 1H), 2.84-3.07 (m, 1H), 4.20-4.45 (m, 2H), 5.36 (s, 2H), 6.08 (s, 2H), 6.60 (s, 1H), 7.10 (m, 3H), 7.32-7.50 (m, 1H), 7.54-7.63 (m, 1H), 7.70 (s, 1H), 7.95 (s, 1H), 8.49-8.59 (m, 1H), 11.50 (s, 1H).

Intermediate 286

(3S,6R)-1-[2-Amino-6-(4-cyano-3-fluorophenyl)-4-pyrimidinyl]-N-[(3-fluorophenyl)methyl]-6-methyl-3-piperidinecarboxamide Intermediate 287

(3S,6R)-1-[2-Amino-6-(4-cyano-3-fluorophenyl)-4-pyrimidinyl]-6-methyl-N-(phenylmethyl)-3-piperidinecarboxamide

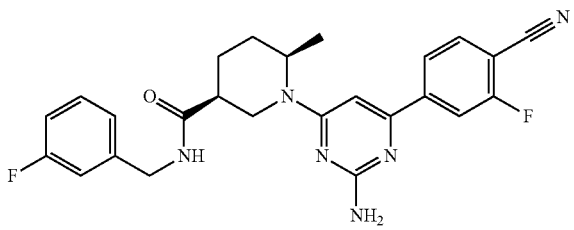 [SMILES: C[C@@H]1CC[C@H](C(=O)NCc2cccc(F)c2)CN1c1cc(-c2ccc(C#N)c(F)c2)nc(N)n1]

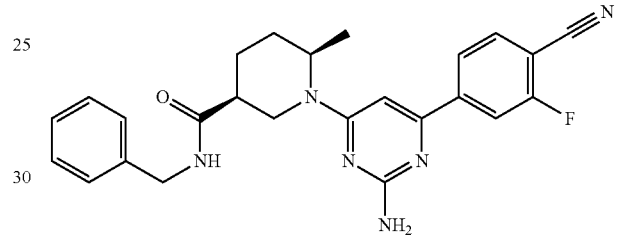

To a solution of (3S,6R)-1-[2-amino-6-(4-cyano-3-fluorophenyl)-4-pyrimidinyl]-6-methyl-3-piperidinecarboxylic acid (170 mg, 0.478 mmol) and HATU (218 mg, 0.574 mmol) in DMF (3 mL) was added Hunig's base (0.167 mL, 0.957 mmol), and the mixture was stirred at room temperature for 5 minutes. Then 1-(3-fluorophenyl)methanamine (60 mg, 0.48 mmol) was added, and the reaction mixture was stirred at room temperature for 0.5 hours. LCMS showed reaction was completed. The reaction was poured onto water, and the formed solid was filtered, washed by water and dried to give the title compound (201 mg) as a yellow solid. LC-MS (ES) m/z=463 [M+H]$^+$.

To a solution of (3S,6R)-1-[2-amino-6-(4-cyano-3-fluorophenyl)-4-pyrimidinyl]-6-methyl-3-piperidinecarboxylic acid (170 mg, 0.478 mmol) and HATU (218 mg, 0.574 mmol) in DMF (3 mL) was added Hunig's base (0.167 mL, 0.957 mmol), and the mixture was stirred at room temperature for 5 minutes. Then benzylamine (56.4 mg, 0.526 mmol) was added, and the reaction mixture was stirred at room temperature for 0.5 hours. LCMS showed reaction was completed. The reaction was poured onto water, and the formed solid was filtered, washed by water, and dried to afford the title compound (210 mg) as a yellow solid. LC-MS (ES) m/z=445 [M+H]$^+$.

Example 144

(3S,6R)-1-[2-Amino-6-(3-amino-1H-indazol-6-yl)-4-pyrimidinyl]-N-[(3-fluorophenyl)methyl]-6-methyl-3-piperidinecarboxamide Example 145

(3S,6R)-1-[2-Amino-6-(3-amino-1H-indazol-6-yl)-4-pyrimidinyl]-6-methyl-N-(phenylmethyl)-3-piperidinecarboxamide

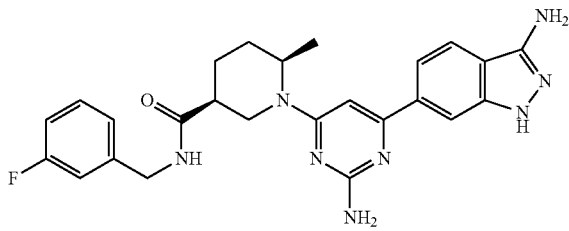 [SMILES: C[C@@H]1CC[C@H](C(=O)NCc2cccc(F)c2)CN1c1cc(-c2ccc3c(N)n[nH]c3c2)nc(N)n1]

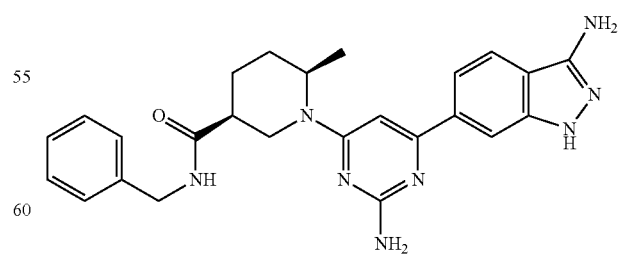

Into a microwave tube, (3S,6R)-1-[2-amino-6-(4-cyano-3-fluorophenyl)-4-pyrimidinyl]-N-[(3-fluorophenyl)methyl]-6-methyl-3-piperidinecarboxamide (201 mg, 0.435 mmol), 5 mL of EtOH, Hunig's base (0.304 mL, 1.738 mmol), and hydrazine anhydrous (0.082 mL, 2.61 mmol) were added, and the yellow suspension mixture was heated overnight at 110°

Into a microwave tube, (3S,6R)-1-[2-amino-6-(4-cyano-3-fluorophenyl)-4-pyrimidinyl]-6-methyl-N-(phenylmethyl)-3-piperidinecarboxamide (201 mg, 0.472 mmol), 5 mL of EtOH, Hunig's base (0.330 ml, 1.890 mmol), and hydrazine anhydrous (0.089 mL, 2.83 mmol) were added, and the yellow suspension mixture was heated overnight at 110° C. in an oil bath. LCMS showed mainly product. CH₃OH (5 mL) was added to the solution. The black solid and the yellow solution were carefully separated due to the black solid is heavier than yellow solution. Water (20 mL) was added to the yellow solution, and a solid formed. The solid was filtered, washed by water, and dried in vacuum. The solid was recrystallized using CH₃CN, and the solid in the solvent was filtered, washed by EtOAc and CH₃CN, and dried in vacuum to afford the title compound (81 mg) as a light yellow solid. LC-MS (ES) m/z=457 [M+H]⁺. ¹H NMR (400 MHz, DMSO-d₆): δ 1.12-1.21 (m, 3H), 1.59-1.92 (m, 5H), 2.27-2.44 (m, 1H), 2.96 (m, 1H), 4.16-4.45 (m, 2H), 5.38 (s, 2H), 6.00-6.16 (m, 2H), 6.59 (s, 1H), 7.18-7.42 (m, 5H), 7.58 (dd, J=8.6, 1.3 Hz, 1H), 7.71 (d, J=8.6 Hz, 1H), 7.90-8.00 (m, 1H), 8.43-8.55 (m, 1H), 11.50 (s, 1H).

Intermediate 288

(3S,6R)-1-[2-Amino-6-(4-cyano-3-fluorophenyl)-4-pyrimidinyl]-6-methyl-N-[(4-methylphenyl)methyl]-3-piperidinecarboxamide

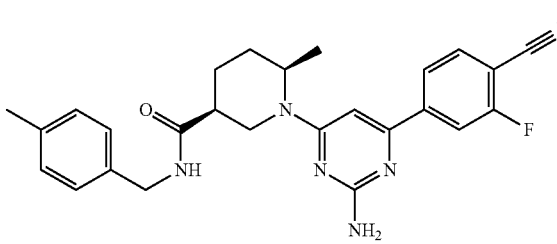

To a solution of (3S,6R)-1-[2-amino-6-(4-cyano-3-fluorophenyl)-4-pyrimidinyl]-6-methyl-3-piperidinecarboxylic acid (170 mg, 0.478 mmol) and HATU (218 mg, 0.574 mmol) in DMF (3 mL) was added Hunig's base (0.167 mL, 0.957 mmol), and the mixture was stirred at room temperature for 5 minutes. Then 1-(4-methylphenyl)methanamine (63.8 mg, 0.526 mmol) was added, and the reaction mixture was stirred at room temperature for 0.5 hours. LCMS showed reaction was completed. The reaction was poured onto water, and the formed solid was filtered, washed by water, and dried to give the yellow title compound (190 mg) as a yellow solid. LC-MS (ES) m/z=459 [M+H]⁺.

Example 146

(3S,6R)-1-[2-Amino-6-(3-amino-1H-indazol-6-yl)-4-pyrimidinyl]-6-methyl-N-[(4-methylphenyl)methyl]-3-piperidinecarboxamide

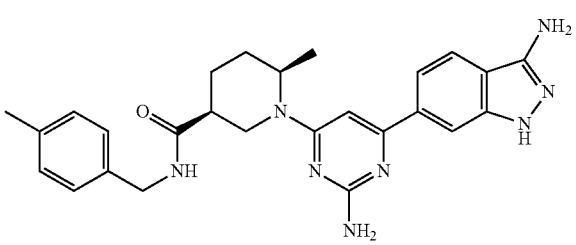 [SMILES: Cc1ccc(CNC(=O)[C@H]2CC[C@@H](C)N(c3cc(-c4ccc5c(N)n[nH]c5c4)nc(N)n3)C2)cc1]

Into a microwave tube, (3S,6R)-1-[2-amino-6-(4-cyano-3-fluorophenyl)-4-pyrimidinyl]-6-methyl-N-[(4-methylphenyl)methyl]-3-piperidinecarboxamide (189.5 mg, 0.413 mmol), 5 mL of EtOH, Hunig's base (0.289 mL, 1.653 mmol), and hydrazine anhydrous (0.078 mL, 2.480 mmol) were added, and the yellow suspension mixture was heated overnight at 110° C. in an oil bath. LCMS showed mainly product. CH₃OH (5 mL) was added to the solution. The black solid and the yellow solution were carefully separated due to the black solid is heavier than yellow solution. Water (20 mL) was added to the yellow solution, and a solid formed. The solid was filtered, washed by water, and dried in vacuum. The solid was recrystallized using CH₃CN, and the solid in the solvent was filtered, washed by EtOAc and CH₃CN, and dried in vacuum to afford the light yellow title compound (82 mg). LC-MS (ES) m/z=471 [M+H]⁺. ¹H NMR (400 MHz, DMSO-d₆): δ 1.15 (d, J=6.6 Hz, 3H), 1.57-1.94 (m, 5H), 2.23-2.42 (m, 5H), 2.94 (m, 1H), 4.13-4.43 (m, 2H), 5.38 (s, 2H), 6.08 (s, 2H), 6.58 (s, 1H), 7.16 (m, 4H), 7.50-7.62 (m, 1H), 7.63-7.77 (m, 1H), 7.94 (s, 1H), 8.33-8.53 (m, 1H), 11.50 (s, 1H).

Intermediate 289

(3S,6R)-1-[2-Amino-6-(4-cyano-3-fluorophenyl)-4-pyrimidinyl]-N-[(4-fluorophenyl)methyl]-6-methyl-3-piperidinecarboxamide

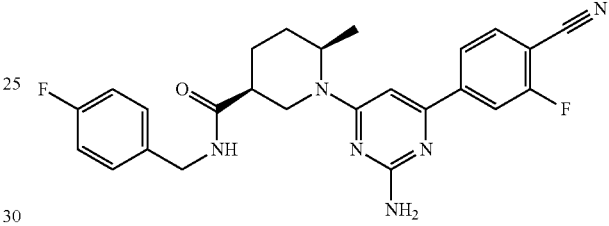

To a solution of (3S,6R)-1-[2-amino-6-(4-cyano-3-fluorophenyl)-4-pyrimidinyl]-6-methyl-3-piperidinecarboxylic acid (170 mg, 0.478 mmol) and HATU (218 mg, 0.574 mmol) in DMF (3 mL) was added Hunig's base (0.167 mL, 0.957 mmol), and the mixture was stirred at room temperature for 5 minutes. Then 1-(4-fluorophenyl)methanamine (60 mg, 0.48 mmol) was added, and the reaction mixture was stirred at room temperature for 0.5 hours. LCMS showed reaction was completed. The reaction was poured onto water, and the formed solid was filtered, washed by water, and dried to give the yellow title compound (193 mg) as a yellow solid. LC-MS (ES) m/z=463 [M+H]⁺.

Example 147

(3S,6R)-1-[2-Amino-6-(3-amino-1H-indazol-6-yl)-4-pyrimidinyl]-N-[(4-fluorophenyl)methyl]-6-methyl-3-piperidinecarboxamide

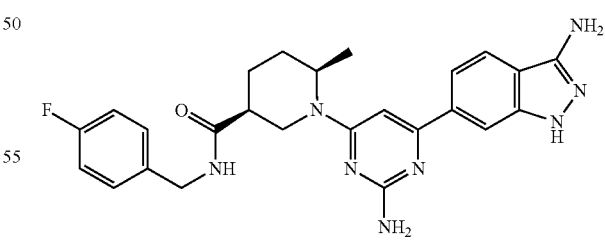

In a microwave tube, (3S,6R)-1-[2-amino-6-(4-cyano-3-fluorophenyl)-4-pyrimidinyl]-N-[(4-fluorophenyl)methyl]-6-methyl-3-piperidinecarboxamide (192.5 mg, 0.416 mmol), 5 mL of EtOH, Hunig's base (0.291 ml, 1.665 mmol), and hydrazine anhydrous (0.078 mL, 2.497 mmol) were added, and the yellow suspension mixture was heated overnight at 110° C. in an oil bath. LCMS showed mainly product. CH₃OH (5 mL) was added to the solution. The black solid and the yellow solution were carefully separated due to the black solid is heavier than yellow solution. Water (20 mL) was added to the yellow solution, and a solid formed. The solid was filtered, washed by water, and dried in vacuum. The solid was recrystallized using CH$_3$CN, and the solid in the solvent was filtered, washed by EtOAc and CH$_3$CN, and dried in vacuum to afford the light yellow title compound (84 mg). LC-MS (ES) m/z=475 [M+H]$^+$. $^1$H NMR (400 MHz, DMSO-d$_6$): δ 1.08-1.24 (m, 3H), 1.58-2.01 (m, 4H), 2.22-2.42 (m, 1H), 2.94 (m, 1H), 4.16-4.42 (m, 2H), 5.38 (s, 2H), 6.08 (s, 2H), 6.55-6.65 (m, 1H), 7.12-7.24 (m, 2H), 7.27-7.39 (m, 2H), 7.58 (dd, J=8.5, 1.1 Hz, 1H), 7.70 (d, J=8.6 Hz, 1H), 7.95 (s, 1H), 8.50 (m, 1H), 11.50 (s, 1H).

Intermediate 290

(3S,6R)-1-[2-Amino-6-(4-cyano-3-fluorophenyl)-4-pyrimidinyl]-6-methyl-N-(3-methylcyclohexyl)-3-piperidinecarboxamide

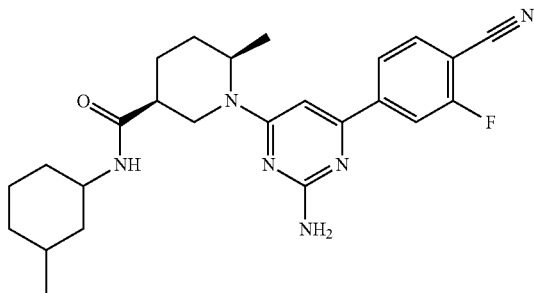 [SMILES: CC1CCCC(NC(=O)[C@H]2CC[C@@H](C)N(c3cc(-c4ccc(C#N)c(F)c4)nc(N)n3)C2)C1]

To a solution of (3S,6R)-1-[2-amino-6-(4-cyano-3-fluorophenyl)-4-pyrimidinyl]-6-methyl-3-piperidinecarboxylic acid (170 mg, 0.478 mmol) and HATU (218 mg, 0.574 mmol) in DMF (3 mL) was added Hunig's base (0.167 mL, 0.957 mmol), and the mixture was stirred at room temperature for 5 minutes. Then 3-methylcyclohexanamine (54.2 mg, 0.478 mmol) was added, and the reaction mixture was stirred at room temperature for 0.5 hours. LCMS showed reaction was completed. The reaction was poured onto water, and the formed solid was filtered, washed by water, and dried to give the yellow title compound (186 mg). LC-MS (ES) m/z=451 [M+H]$^+$.

Example 148

(3S,6R)-1-[2-Amino-6-(3-amino-1H-indazol-6-yl)-4-pyrimidinyl]-6-methyl-N-(3-methylcyclohexyl)-3-piperidinecarboxamide

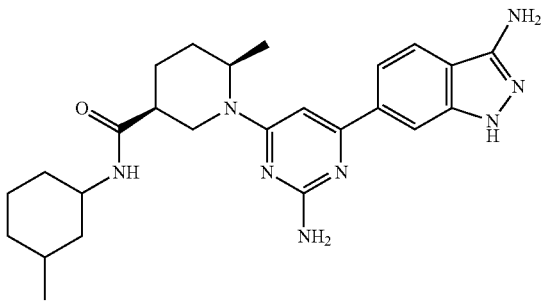 [SMILES: CC1CCCC(NC(=O)[C@H]2CC[C@@H](C)N(c3cc(-c4ccc5c(N)n[nH]c5c4)nc(N)n3)C2)C1]

Into a microwave tube, (3S,6R)-1-[2-amino-6-(4-cyano-3-fluorophenyl)-4-pyrimidinyl]-6-methyl-N-(3-methylcyclohexyl)-3-piperidinecarboxamide (186.2 mg, 0.413 mmol), 5 mL of EtOH, Hunig's base (0.289 ml, 1.653 mmol), and hydrazine anhydrous (0.078 mL, 2.480 mmol) were added, and the yellow suspension mixture was heated overnight at 110° C. in an oil bath. LCMS showed mainly product. CH$_3$OH (5 mL) was added to the solution. The black solid and the yellow solution were carefully separated due to the black solid is heavier than yellow solution. Water (20 mL) was added to the yellow solution, and a solid formed. The solid was filtered, washed by water, and dried in vacuum. The solid was recrystallized using CH$_3$CN, and the solid in the solvent was filtered, washed by EtOAc and CH$_3$CN, and dried in vacuum to afford the light yellow title compound (34 mg). LC-MS (ES) m/z=463 [M+H]$^+$. $^1$H NMR (400 MHz, DMSO-d$_6$): δ 0.67-0.94 (m, 6H), 0.97-1.33 (m, 6H), 1.36-1.87 (m, 7H), 2.13-2.42 (m, 1H), 2.90 (m, 1H), 3.45-3.63 (m, 1H), 4.67 (m, 2H), 5.38 (s, 2H), 6.07 (s, 2H), 6.57 (s, 1H), 7.57 (dd, J=8.6, 1.0 Hz, 1H), 7.70 (m, 2H), 7.94 (s, 1H), 11.49 (s, 1H).

Intermediate 291

(3S,6R)-1-[2-Amino-6-(4-cyano-3-fluorophenyl)-4-pyrimidinyl]-6-methyl-N-(2-phenylethyl)-3-piperidinecarboxamide

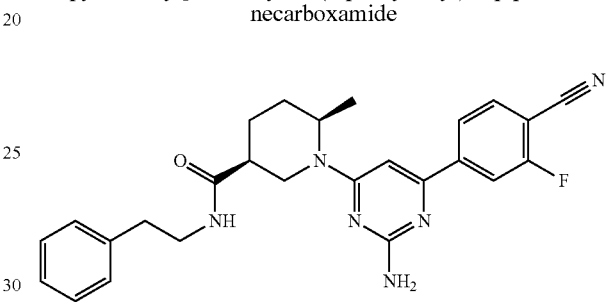

To a solution of (3S,6R)-1-[2-amino-6-(4-cyano-3-fluorophenyl)-4-pyrimidinyl]-6-methyl-3-piperidinecarboxylic acid (170 mg, 0.478 mmol) and HATU (218 mg, 0.574 mmol) in DMF (3 mL) was added Hunig's base (0.167 mL, 0.957 mmol), and the mixture was stirred at room temperature for 5 minutes. Then 2-phenylethanamine (58.0 mg, 0.478 mmol) was added, and the reaction mixture was stirred at room temperature for 0.5 hours. LCMS showed reaction was completed. The reaction was poured onto water, and the formed solid was filtered, washed by water, and dried to give the yellow title compound (198 mg). LC-MS (ES) m/z=459 [M+H]$^+$.

Example 149

(3S,6R)-1-[2-Amino-6-(3-amino-1H-indazol-6-yl)-4-pyrimidinyl]-6-methyl-N-(2-phenylethyl)-3-piperidinecarboxamide

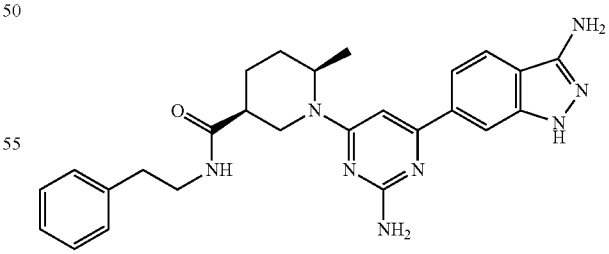

Into a microwave tube, (3S,6R)-1-[2-amino-6-(4-cyano-3-fluorophenyl)-4-pyrimidinyl]-6-methyl-N-(2-phenylethyl)-3-piperidinecarboxamide (197.7 mg, 0.431 mmol), 5 mL of EtOH, Hunig's base (0.289 mL, 1.653 mmol), and hydrazine anhydrous (0.078 mL, 2.480 mmol) were added, and the yellow suspension mixture was heated overnight at 110° C. in an oil bath. When the temperature of the reaction reached to 100° C., the solid in the mixture was all dissolved. After overnight, there was a yellow suspension as well as some black colored solid formed. LCMS showed mainly product. CH₃OH (5 mL) was added to the solution. The black solid and the yellow solution were carefully separated due to the black solid being heavier than the yellow solution. Water (20 mL) was added to the yellow solution, and a solid formed. The solid was filtered, washed by water, and dried in vacuum. The solid was recrystallized using CH₃CN, and the solid in the solvent was filtered, washed by EtOAc and CH₃CN, and dried in vacuum. The yellow residue was dissolved in CH₃OH, and purified by HPLC to afford the light yellow title compound (31 mg). LC-MS (ES) m/z=517 [M+H]$^+$. $^1$H NMR (400 MHz, DMSO-d$_6$): δ 1.08-1.18 (m, 4H), 1.56-1.70 (m, 4H), 1.71-1.86 (m, 1H), 2.17-2.31 (m, 1H), 2.68-2.78 (m, 3H), 2.82-2.99 (m, 1H), 5.24-5.57 (m, 2H), 6.03-6.13 (m, 2H), 6.50-6.58 (m, 1H), 7.16-7.37 (m, 5H), 7.50-7.61 (m, 1H), 7.66-7.76 (m, 1H), 7.90-7.97 (m, 1H), 8.01-8.12 (m, 1H), 8.19 (s, 1H).

Intermediate 292

(3S,6R)-1-[2-Amino-6-(4-cyano-3-fluorophenyl)-4-pyrimidinyl]-6-methyl-N-(4-methylcyclohexyl)-3-piperidinecarboxamide

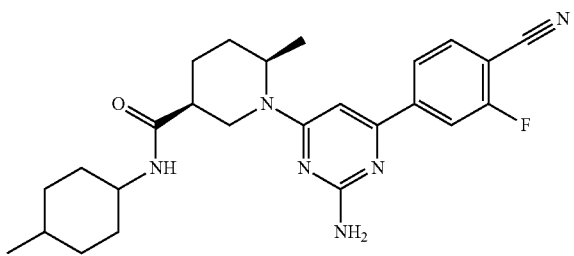 [SMILES: CC1CCC(NC(=O)[C@H]2CC[C@@H](C)N(c3cc(-c4ccc(C#N)c(F)c4)nc(N)n3)C2)CC1]

To a solution of (3S,6R)-1-[2-amino-6-(4-cyano-3-fluorophenyl)-4-pyrimidinyl]-6-methyl-3-piperidinecarboxylic acid (170 mg, 0.478 mmol) and HATU (218 mg, 0.574 mmol) in DMF (3 mL) was added Hunig's base (0.167 mL, 0.957 mmol), and the mixture was stirred at room temperature for 5 minutes. Then 4-methylcyclohexanamine (54.2 mg, 0.478 mmol) was added, and the mixture was stirred at room temperature for 0.5 hours. LCMS showed reaction was completed. The reaction was poured onto water, and the formed solid was filtered, washed by water, and dried to give the yellow title compound (192 mg). LC-MS (ES) m/z=451 [M+H]$^+$.

Example 150

(3S,6R)-1-[2-Amino-6-(3-amino-1H-indazol-6-yl)-4-pyrimidinyl]-6-methyl-N-(4-methylcyclohexyl)-3-piperidinecarboxamide

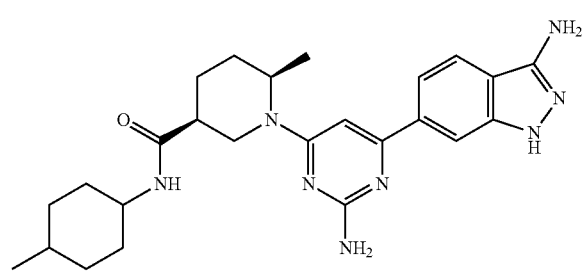 [SMILES: CC1CCC(NC(=O)[C@H]2CC[C@@H](C)N(c3cc(-c4ccc5c(N)n[nH]c5c4)nc(N)n3)C2)CC1]

Into a microwave tube, (3S,6R)-1-[2-amino-6-(4-cyano-3-fluorophenyl)-4-pyrimidinyl]-6-methyl-N-(4-methylcyclohexyl)-3-piperidinecarboxamide (192.2 mg, 0.427 mmol), 5 mL of EtOH, Hunig's base (0.298 mL, 1.706 mmol), and hydrazine anhydrous (0.080 mL, 2.56 mmol) were added, and the yellow suspension mixture was heated overnight at 110° C. in an oil bath. When the temperature of the reaction reached 100° C., the solid in the mixture was all dissolved. After overnight, there was a yellow suspension as well as some black colored solid formed. LCMS showed mainly product. CH₃OH (5 mL) was added to the solution. The black solid and the yellow solution were carefully separated due to the black solid being heavier than the yellow solution. Water (20 mL) was added to the yellow solution, and a solid formed. The solid was filtered, washed by water, and dried in vacuum. The solid was recrystallized using CH₃CN, and the solid in the solvent was filtered, washed by EtOAc and CH₃CN, and dried in vacuum. The yellow residue was dissolved in CH₃OH, and purified by HPLC to afford the light yellow title compound (95 mg). LC-MS (ES) m/z=509 [M+H]$^+$. $^1$H NMR (400 MHz, DMSO-d$_6$): δ 0.81-1.04 (m, 4H), 1.08-1.37 (m, 6H), 1.40-1.86 (m, 10H), 2.16-2.44 (m, 1H), 2.92 (m, 1H), 3.78 (m, 1H), 5.38 (s, 2H), 6.08 (s, 2H), 6.56 (s, 1H), 7.57 (d, J=8.6 Hz, 1H), 7.67-7.82 (m, 2H), 7.88-7.99 (m, 1H), 8.16 (s, 1H).

Intermediate 293

(5R)-5-(1-Methylethyl)-3-morpholinone

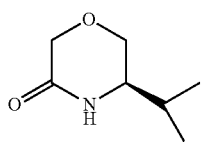

NaH (6.24 g, 60% wt in mineral oil, 156 mmol, 2.3 equiv) was charged into a 1 L RB flask, followed by addition of 100 mL of toluene. The suspension was stirred in an ice bath. (2R)-2-Amino-3-methyl-1-butanol (7.0 g, 67.9 mmol) in 50 mL of toluene was added portion-wise. Addition took 10 minutes, followed with removal of the cooling bath. The mixture was stirred at ambient temperature for 15 minutes, and cooled in an ice bath. To the cooled mixture was added portion-wise a solution of chloroacetyl chloride (6.25 mL, 78 mmol, 1.15 equiv) in 50 mL of toluene. The mixture began to foam. When the addition neared completion, foaming subsided. The resulting mixture was heated under a reflux condenser to 90° C. (oil bath temp) for 20 hours. The mixture was cooled to room temperature, followed by addition of 22 g of NH₄Cl and then water (50 mL). The phases were separated. The aqueous phase was extracted with EtOAc (2×150 mL). The combined organic was dried over Na₂SO₄, filtered and concentrated in vacuo. The residue was triturated in 30 mL of hexane. The solids formed were collected by filtration, washing with hexane (2×10 mL). Drying under vacuum at room temperature for 5 hours gave the title compound (6.53 g) as a cream-colored solid. LC-MS (ES) m/z=144

Intermediate 294

(3R)-3-(1-Methylethyl)morpholine hydrochloride salt

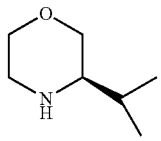

A solution of (5R)-5-(1-methylethyl)-3-morpholinone (6.38 g, 44.6 mmol) in THF (80 mL) was added at room temperature via addition funnel into a stirred solution of LiAlH₄ (85 mL, 85 mmol, 1.9 equiv) in a 1 L 3-neck flask under nitrogen dropwise over a 15 minutes period. The resulting mixture was heated in an oil bath to 70° C. (under a gentle reflux) for 4 hours. LCMS showed conversion complete. The mixture was cooled to room temperature and then in an ice bath. To the mixture was added 3.2 mL of water in THF (20 mL) dropwise, followed by 3.2 mL of a 15% aq NaOH solution, and 9.6 mL of water. The resulting mixture was stirred at room temperature for 30 minutes, followed by filtration through celite, washing with EtOAc (250 mL). To the filtrate was added 50 mL of 2N HCl/Et$_2$O solution, resulting in a suspension. The solids were collected by filtration. Washing with EtOAc (10 mL), and drying under vacuum at room temperature for 18 hours afforded the title compound (4.33 g) as a white solid. The filtrate was concentrated in vacuo, and azeotroped with ethanol (3×70 mL). The resulting brownish residue was dried under vacuum at room temperature for 18 hours to give another batch (2.51 g) of the title compound. LC-MS (ES) m/z=130 [M+H]$^+$.

Intermediate 295

4-Chloro-N-methyl-6-[(3R)-3-(1-methylethyl)-4-morpholinyl]-2-pyrimidinamine

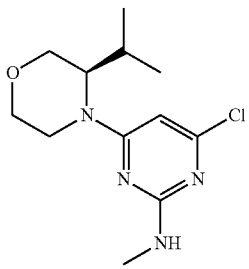 [SMILES: CNc1nc(Cl)cc(N2CCOC[C@H]2C(C)C)n1]

(3R)-3-(1-Methylethyl)morpholine hydrochloride salt (3.0 g, 18.11 mmol) and 4,6-dichloro-N-methyl-2-pyrimidinamine (3.22 g, 18.11 mmol, 1 equiv) were charged into a 60 mL sealable tube, followed with addition of propionitrile (25 mL) and Hunig's base (9.49 mL, 54.3 mmol, 3 equiv). The vessel was sealed and heated at 110° C. in an oil bath for 96 hours. The mixture was concentrated in vacuo. The residue was partitioned between cold 2N HCl (100 mL) and EtOAc (2×100 mL). The organic was dried over Na$_2$SO$_4$, filtered and concentrated in vacuo. The acidic aqueous phase was basified with 6N NaOH to pH=10, followed by extraction with EtOAc (2×100 mL). The organic was dried over Na$_2$SO$_4$, filtered, and concentrated in vacuo to give a dark brownish oil. Both samples were purified by silica gel column chromatography using gradient elution of 1% EtOAc in CHCl$_3$ to 40% EtOAc in CHCl$_3$. The combined fractions were concentrated in vacuo. The residue was dried under vacuum at room temperature for 7 hours to give the title compound (2.17 g). LC-MS (ES) m/z=271 [M+H]$^+$.

Intermediate 296

2,6-Difluoro-4-{2-(methylamino)-6-[(3R)-3-(1-methylethyl)-4-morpholinyl]-4-pyrimidinyl}benzonitrile

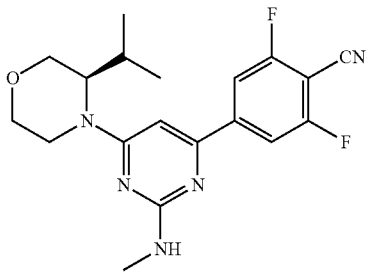 [SMILES: CNc1nc(-c2cc(F)c(C#N)c(F)c2)cc(N2CCOC[C@H]2C(C)C)n1]

4-Chloro-N-methyl-6-[(3R)-3-(1-methylethyl)-4-morpholinyl]-2-pyrimidinamine (1.70 g, 6.28 mmol), (4-cyano-3,5-difluorophenyl)boronic acid (1.72 g, 9.42 mmol, 1.5 equiv), tricyclohexylphosphine (0.264 g, 0.94 mmol, 0.15 equiv), Pd$_2$(dba)$_3$ (0.431 g, 0.47 mmol, 0.075 equiv), and K$_3$PO$_4$ (2.27 g, 10.67 mmol, 1.7 equiv) were charged into a 250 mL RB flask, followed by addition of 1,4-dioxane (30 mL) and water (10 mL). The mixture was degassed and back flushed with argon (5×). The mixture was heated in an oil bath at 100° C. for 20 hours. LCMS showed complete conversion. The mixture was filtered through celite and rinsed with EtOAc (150 mL). The filtrate was concentrated in vacuo. The residue was partitioned between EtOAc (150 mL) and brine (40 mL). The organic was dried over Na$_2$SO$_4$, filtered, and concentrated in vacuo. The residue was purified by silica gel column chromatography using gradient elution of 1% EtOAc in CHCl$_3$ to 100% EtOAc, to afford the title compound (1.64 g) as a yellow foam. LC-MS (ES) m/z=374 [M+H]$^+$.

Intermediate 297

2-Fluoro-4-{2-(methylamino)-6-[(3R)-3-(1-methylethyl)-4-morpholinyl]-4-pyrimidinyl}-6-(methyloxy)benzonitrile

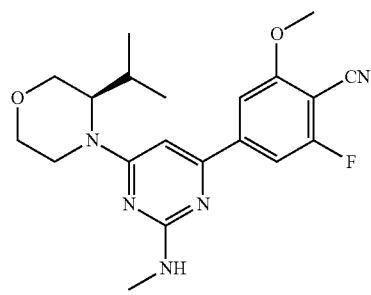

2,6-Difluoro-4-{2-(methylamino)-6-[(3R)-3-(1-methylethyl)-4-morpholinyl]-4-pyrimidinyl}benzonitrile (360 mg, 0.96 mmol) was azeotroped with toluene (2×12 mL). The resulting residue was taken up in 7.5 mL of CH$_3$OH as a suspension. NaH (260 mg, 60% wt in mineral oil, 6.5 mmol) was added to a chilled (ice bath) solution of CH$_3$OH (12.5 mL) under nitrogen portion-wise. After completion of addition, the ice bath was removed. The resulting mixture was stirred at ambient temperature for 10 minutes (concentration of CH$_3$ONa was assumed to be 0.52 mmol/mL). A 2.25 mL portion (1.17 mmol, 1.2 equiv) of this mixture was added to the above suspension at room temperature in one portion. The resulting suspension was stirred at room temperature for 2 hours. LCMS showed no conversion. After another 1 h, 5 mL of DMF was added to the mixture, which became milky. The mixture was stirred at room temperature for another 16 hours, upon which time, it became a clear solution. LCMS showed conversion complete. The mixture was concentrated in vacuo. The residue was taken up in water (20 mL) as a suspension, which was sonicated briefly, and then filtered. The solids collected were dried under house vacuum at room temperature for 1 hour. Purification by silica gel column chromatography using gradient elution of 1% EtOAc in CHCl$_3$ to 100% EtOAc gave the title compound (350 mg) as a foam. LC-MS (ES) m/z=386 [M+H]$^+$.

Example 151

6-{2-(Methylamino)-6-[(3R)-3-(1-methylethyl)-4-morpholinyl]-4-pyrimidinyl}-4-(methyloxy)-1H-indazol-3-amine

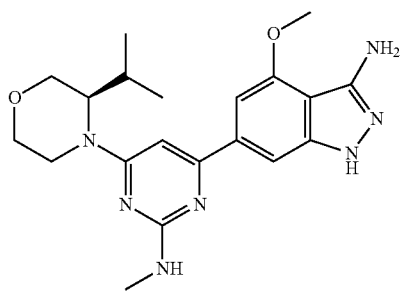 [SMILES: CNc1nc(-c2cc(OC)c3c(N)n[nH]c3c2)cc(N2CCOC[C@H]2C(C)C)n1]

To a solution of 2-fluoro-4-{2-(methylamino)-6-[(3R)-3-(1-methylethyl)-4-morpholinyl]-4-pyrimidinyl}-6-(methyloxy)benzonitrile (350 mg, 0.91 mmol) in ethanol (10 mL) was added hydrazine monohydrate (2.5 mL) in one portion. The mixture was heated at 100° C. for 20 hours, cooled to room temperature and concentrated in vacuo. The residue was taken up in water (10 mL) as a suspension. The solids were collected by filtration, washed with water (2×2 mL), and dried under vacuum at room temperature over $P_2O_5$ for 20 hours. The solids were washed with hexane (2×3 mL). Drying under vacuum at 65° C. for 20 hours afforded the title compound (302 mg) as a cream-colored solid. LC-MS (ES) m/z=398 [M+H]$^+$. $^1$H NMR (400 MHz, CD$_3$OD): δ 0.89 (d, J=6.8 Hz, 3H), 1.11 (d, J=6.6 Hz, 3H), 2.45-2.55 (m, 1H), 2.96 (s, 3H), 3.25-3.35 (m, 1H), 3.53-3.61 (m, 2H), 3.94 (dd, J=11.1, 3.5 Hz, 1H), 4.04 (s, 3H), 4.11 (d, J=11.9 Hz, 1H), 6.38 (s, 1H), 6.89 (s, 1H), 7.35 (s, 1H).

Intermediate 298

2-(Ethyloxy)-6-fluoro-4-{2-(methylamino)-6-[(3R)-3-(1-methylethyl)-4-morpholinyl]-4-pyrimidinyl}benzonitrile

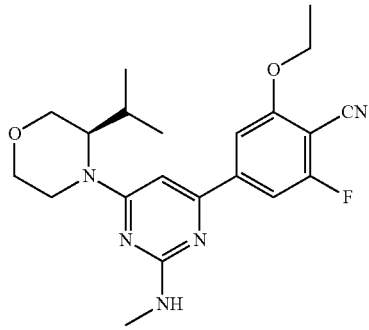 [SMILES: CCOc1cc(-c2cc(N3CCOC[C@H]3C(C)C)nc(NC)n2)cc(F)c1C#N]

2,6-Difluoro-4-{2-(methylamino)-6-[(3R)-3-(1-methylethyl)-4-morpholinyl]-4-pyrimidinyl}benzonitrile (377 mg, 1.01 mmol) was azeotroped with toluene (2×15 mL). The residue was dissolved in 5 mL of DMF as a clear yellow solution. NaH (260 mg, 60% wt in mineral oil, 6.5 mmol) was weighted into a 50 mL 3-neck RB, to which under nitrogen was added ethanol (7.5 mL) portion-wise. The resulting clear solution was stirred at ambient temperature for 10 minutes. A portion of this solution (1.40 mL, 1.21 mmol of NaOEt, 1.2 equiv) was added to the above yellowish solution via syringe at room temperature under nitrogen in one portion. The resulting orange clear solution was stirred at room temperature for 20 hours. LCMS showed complete conversion. The mixture was concentrated in vacuo, and then pumped under vacuum to give a residue, which was taken up in 20 mL of water as a suspension. This suspension was sonicated briefly and filtered. The collected solids were dissolved in EtOAc (50 mL), and the resulting organic solution was washed with brine, dried over Na$_2$SO$_4$, filtered, and concentrated in vacuo. Purification of the resulting residue by silica gel column chromatography using gradient elution of 1% EtOAc in CHCl$_3$ to 100% EtOAc gave the title compound (315 mg) as a yellowish residue. LC-MS (ES) m/z=400 [M+H]$^+$.

Example 152

4-(Ethyloxy)-6-{2-(methylamino)-6-[(3R)-3-(1-methylethyl)-4-morpholinyl]-4-pyrimidinyl}-1H-indazol-3-amine

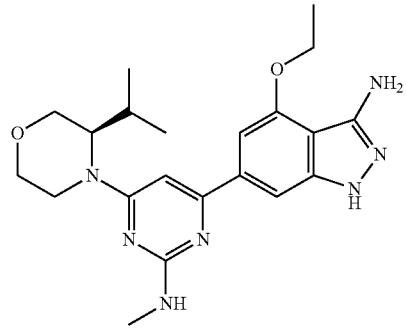 [SMILES: CCOc1cc(-c2cc(N3CCOC[C@H]3C(C)C)nc(NC)n2)cc2[nH]nc(N)c12]

To a solution of 2-(ethyloxy)-6-fluoro-4-{2-(methylamino)-6-[(3R)-3-(1-methylethyl)-4-morpholinyl]-4-pyrimidinyl}benzonitrile (315 mg, 0.79 mmol) in ethanol (10 mL) was added hydrazine monohydrate (2.5 mL) in one portion. The mixture was heated at 100° C. for 20 hours, cooled to room temperature and concentrated in vacuo. The residue was taken up in water (10 mL) as a suspension. The solids were collected by filtration and washed with water (3×2 mL). Further purification was carried out by silica gel column chromatography using gradient elution of 1% A in CHCl$_3$ to 75% A in CHCl$_3$ (where A was a mixture of 800/80/3200 CH$_3$OH/NH$_4$OH/CHCl$_3$). The fraction containing the desired product were combined and concentrated. The resulting residue was dissolved in a solution of 5% CH$_3$OH in CHCl$_3$ (15 mL) and filtered. The filtrate was concentrated in vacuo, and azeotroped with 10 mL of ethanol. The resulting residue was taken up in 10 mL of water, and sonicated. A suspension formed and was filtered. The solids collected were dried under vacuum at room temperature over P$_2$O$_5$ for 18 hours, and then washed with hexane (3×2 mL). Further drying under vacuum at 65° C. for 20 hours gave the title compound (231 mg) as a cream-colored solid. LC-MS (ES) m/z=412 [M+H]$^+$. $^1$H NMR (400 MHz, CD$_3$OD): δ 0.89 (d, J=6.8 Hz, 3H), 1.11 (d, J=6.6 Hz, 3H), 1.55 (t, J=7.0 Hz, 3H), 2.45-2.55 (m, 1H), 2.96 (s, 3H), 3.25-3.35 (m, 1H), 3.53-3.61 (m, 2H), 3.94 (dd, J=11.1, 3.5 Hz, 1H), 4.11 (d, J=11.6 Hz, 1H), 4.30 (q, J=7.0 Hz, 2H), 6.37 (s, 1H), 6.86 (s, 1H), 7.33 (s, 1H).

Intermediate 299

2-Fluoro-4-{2-(methylamino)-6-[(3R)-3-(1-methylethyl)-4-morpholinyl]-4-pyrimidinyl}-6-(methylthio)benzonitrile

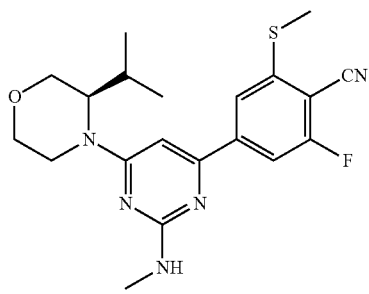

2,6-Difluoro-4-{2-(methylamino)-6-[(3R)-3-(1-methylethyl)-4-morpholinyl]-4-pyrimidinyl}benzonitrile (348 mg, 0.93 mmol) was azeotroped with toluene (2×10 mL). The residue was dissolved in DMF (5 mL), to which was added 479 mg of an aqueous NaSMe solution (15% wt, 479 mg, 1.03 mmol, 1.1 equiv) in one portion at room temperature (together with 1 mL of DMF rinse). The resulting brownish but clear mixture was stirred at room temperature for 18 hours. LCMS showed there was 22% starting material remaining. To the mixture was added another 100 mg of the aqueous NaSMe solution. The mixture was stirred at room temperature for another 20 hours. LCMS showed there was still 6% starting material present. To the mixture was added 40 mg of the aqueous NaSMe solution. The mixture was stirred at room temperature for another 6 hours. LCMS showed no starting material left. The mixture was concentrated in vacuo. The gum-like residue was taken up in 30 mL of water, sonicated briefly to give a suspension and filtered. The residue was purified by silica gel column chromatography using gradient elution of 1% EtOAc in CHCl$_3$ to 80% EtOAc in CHCl$_3$, to afford the title compound (350 mg) as a yellowish foam. LC-MS (ES) m/z=402 [M+H]$^+$.

Example 153

6-{2-(Methylamino)-6-[(3R)-3-(1-methylethyl)-4-morpholinyl]-4-pyrimidinyl}-4-(methylthio)-1H-indazol-3-amine

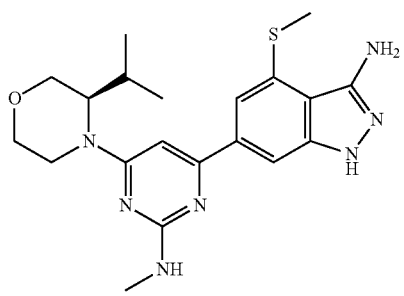 [SMILES: CNc1nc(-c2cc(SC)c3c(N)n[nH]c3c2)cc(N2CCOC[C@H]2C(C)C)n1]

To a suspension of 2-fluoro-4-{2-(methylamino)-6-[(3R)-3-(1-methylethyl)-4-morpholinyl]-4-pyrimidinyl}-6-(methylthio)benzonitrile (350 mg, 0.87 mmol) in ethanol (10 mL) was added hydrazine monohydrate (2.5 mL) in one portion. The resulting suspension was heated in an oil bath to 100° C. under a reflux condenser for 20 hours. LCMS showed complete conversion. The mixture was filtered through celite, and the filtrate was concentrated in vacuo. The residue was taken up in water (30 mL) and sonicated briefly. The resulting suspension was filtered. The collected solids underwent purification by silica gel column chromatography using gradient elution of 1% A in CHCl$_3$ to 100% A (where A was a mixture of 800/80/3200 CH$_3$OH/NH$_4$OH/CHCl$_3$). After removal of eluant solvents, the residue was redissolved in CHCl$_3$, filtered, and concentrated in vacuo. The residue was taken up in water (15 mL) as a suspension. The solids formed were collected by filtration and dryed under vacuum at room temperature over P$_2$O$_5$ for 20 hours. These solids were washed with hexane (3×3 mL). Further drying under vacuum at 65° C. for 20 hours gave the title compound (282 mg) as a cream-colored solid. LC-MS (ES) m/z=414 [M+H]$^+$. $^1$H NMR (400 MHz, CD$_3$OD): δ 0.89 (d, J=6.8 Hz, 3H), 1.11 (d, J=6.6 Hz, 3H), 2.45-2.55 (m, 1H), 2.65 (s, 3H), 2.96 (s, 3H), 3.25-3.35 (m, 1H), 3.53-3.61 (m, 2H), 3.94 (dd, J=11.2, 3.4 Hz, 1H), 4.11 (d, J=11.9 Hz, 1H), 6.40 (s, 1H), 7.40 (s, 1H), 7.62 (s, 1H).

Intermediate 300

(3R,6S)-6-Methyl-1-{[(phenylmethyl)oxy]carbonyl}-3-piperidinecarboxylic acid

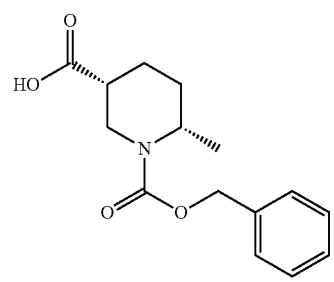 [SMILES: C[C@H]1CC[C@@H](C(=O)O)CN1C(=O)OCc1ccccc1]

To a stirred solution of 3-methyl 1-(phenylmethyl) (3R,6S)-6-methyl-1,3-piperidinedicarboxylate (58.9 g, 202 mmol) in THF (350 mL) at room temperature was added LiOH.H$_2$O (10.18 g, 243 mmol, 1.2 equiv), followed by water (175 mL) and CH$_3$OH (85 mL). The mixture was stirred at ambient temperature for 20 hours. LCMS showed complete hydrolysis. The mixture was concentrated in vacuo. The residue was taken up in EtOAc (500 mL), acidified with 120 mL of cold 2N HCl, and diluted with 200 mL of brine. The phases were separated. The aqueous phase was extracted with EtOAc (2×300 mL). The combined organic was dried over Na$_2$SO$_4$, filtered, and concentrated in vacuo to give the title compound (57 g) as an oil. LC-MS (ES) m/z=278 [M+H]$^+$.

Intermediate 301

Phenylmethyl(2S,5R)-5-({[(1,1-dimethylethyl)oxy]carbonyl}amino)-2-methyl-1-piperidinecarboxylate

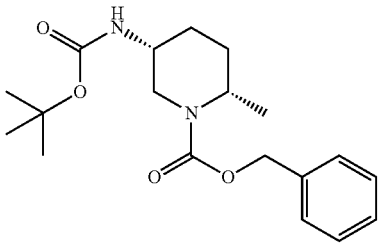 [SMILES: C[C@H]1CC[C@@H](NC(=O)OC(C)(C)C)CN1C(=O)OCc1ccccc1]

(3R,6S)-6-Methyl-1-{[(phenylmethyl)oxy]carbonyl}-3-piperidinecarboxylic acid (85 g, 307 mmol) in a 2 L RB flask was azeotroped with toluene (3×200 mL). The residue (an oil) was dissolved in 500 mL of t-butanol (anhydrous grade). To this solution was added triethylamine (64.1 mL, 460 mmol, 1.5 equiv) at room temperature in one portion. Diphenyl azidophosphate (110 g, 398 mmol, 1.3 equiv) was added via an addition funnel at room temperature portion-wise into this stirred mixture. Addition took 20 minutes. The resulting mixture (a light yellow clear solution) was stirred at room temperature for 30 minutes, followed by heating in an oil bath to 100° C. under reflux for 20 hours. LCMS showed conversion complete. The mixture was concentrated in vacuo to remove as much t-butanol as possible. The residue was diluted with EtOAc (1 L), which was washed with 200 mL of cold 2N HCl, followed by 200 mL of 2.5 N NaOH. The NaOH portion was salted with NaCl, and back extracted with EtOAc (400 mL). All the organic portions were combined, washed with brine, dried over $MgSO_4$, filtered, and concentrated in vacuo. The residue was taken up in hexane (500 mL) and EtOAc (20 mL). A waxy paste developed. The mixture was chilled in the refrigerator for 20 hours, resulting in a 2-phase mixture. The top layer was decanted off, and gave 42 g as an oil after concentration in vacuo, which would undergo further silica gel column purification. The waxy bottom component was taken up in $CHCl_3$ (300 mL) and EtOAc (30 mL). The mixture was stirred for 5 minutes, and filtered. The filtrate was concentrated in vacuo to give an oil (150 g), which would undergo further silica gel column purification. The waxy solids (30 g) collected were identified as $(PhO)_2POOH$, and were discarded. Silica gel column chromatography of the above two samples on multiple runs using gradient elution of 1% EtOAc in $CHCl_3$ to 50% EtOAc in $CHCl_3$ gave the title compound (88.28 g) as a thick clear syrup. LC-MS (ES) m/z=349 $[M+H]^+$.

Intermediate 302

1,1-Dimethylethyl[(3R,6S)-6-methyl-3-piperidinyl]carbamate

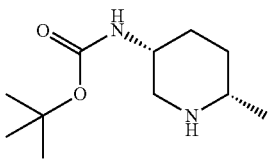

Pd/C (6.30 g) was added into a 2 L Parr Bottle, followed by addition of EtOAc (50 mL) under nitrogen. The mixture was stirred as a slurry, followed by addition of a solution of phenylmethyl(2S,5R)-5-({[(1,1-dimethylethyl)oxy]carbonyl}amino)-2-methyl-1-piperidinecarboxylate (58 g, 166 mmol) in EtOAc (330 mL). The mixture was hydrogenated under a 50 psi pressure at room temperature for 4 hours. LCMS showed complete conversion. The mixture was filtered through celite, and rinsed with EtOAc. The filtrate was concentrated in vacuo to give the title compound (35.47 g) as an oil. LC-MS (ES) m/z=215 $[M+H]^+$.

Intermediate 303

1,1-Dimethylethyl[(3R,6S)-1-(2-amino-6-chloro-4-pyrimidinyl)-6-methyl-3-piperidinyl]carbamate

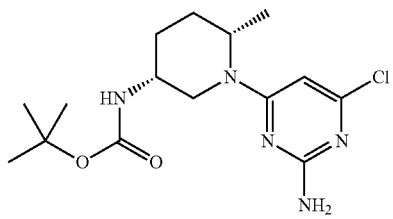 [SMILES: C[C@H]1CC[C@@H](NC(=O)OC(C)(C)C)CN1c1cc(Cl)nc(N)n1]

A mixture of 1,1-dimethylethyl[(3R,6S)-6-methyl-3-piperidinyl]carbamate (6.0 g, 28 mmol), 4,6-dichloro-2-pyrimidinamine (5.05 g, 30.8 mmol, 1.1 equiv) and Hunig's base (12.2 mL, 70.0 mmol, 2.5 equiv) in propionitrile (50 mL) was heated in an oil bath to 100° C. under reflux for 20 hours. LCMS showed complete conversion. The mixture was concentrated in vacuo. The residue was partitioned between EtOAc (100 mL) and brine (30 mL). The organic was dried over $Na_2SO_4$, filtered, and concentrated in vacuo to give a foam. This foam was triturated in $CHCl_3$ and EtOAc. The resulting suspension was filtered. The solids (0.93 g) recovered were identified as the starting 4,6-dichloro-2-pyrimidinamine. The filtrate was purified by silica gel column chromatography using gradient elution of 1% EtOAc in $CHCl_3$ to 100% EtOAc to give the title compound (8.20 g) as a white foam. LC-MS (ES) m/z=342 $[M+H]^+$.

Intermediate 304

1,1-Dimethylethyl{(3R,6S)-1-[2-amino-6-(4-cyano-3-fluorophenyl)-4-pyrimidinyl]-6-methyl-3-piperidinyl}carbamate

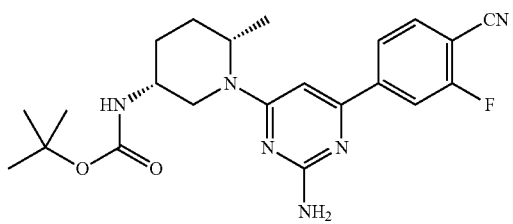 [SMILES: C[C@H]1CC[C@@H](NC(=O)OC(C)(C)C)CN1c1cc(-c2ccc(C#N)c(F)c2)nc(N)n1]

A mixture of 1,1-dimethylethyl[(3R,6S)-1-(2-amino-6-chloro-4-pyrimidinyl)-6-methyl-3-piperidinyl]carbamate (7.0 g, 24.0 mmol, this material was azeotroped with 2×40 mL of toluene prior to mixing), (4-cyano-3-fluorophenyl)boronic acid (5.14 g, 31.2 mmol, 1.3 equiv), tricyclohexylphosphine (1.0 g, 3.6 mmol, 0.15 equiv), $Pd_2(dba)_3$ (1.64 g, 1.80 mmol, 0.075 equiv) and $K_3PO_4$ (8.66 g, 40.8 mmol, 1.7 equiv) in 1,4-dioxane (100 mL) and water (33 mL) was degassed and back flushed with nitrogen (5×), and then heated in an oil bath at 100° C. under a reflux condenser for 20 hours. LCMS showed complete conversion. The mixture was filtered through celite. The filtrate was concentrated in vacuo. The residue was partitioned between EtOAc (350 mL) and brine (80 mL). The organic was dried over $Na_2SO_4$, filtered, and concentrated in vacuo. The residue was purified by silica gel column chromatography using gradient elution of 1% EtOAc in CHCl₃ to 100% EtOAc to give the title compound (9.24 g) as a pale yellow foam. LC-MS (ES) m/z=427 [M+H]⁺.

Example 154

1,1-Dimethylethyl{(3R,6S)-1-[2-amino-6-(3-amino-1H-indazol-6-yl)-4-pyrimidinyl]-6-methyl-3-piperidinyl}carbamate

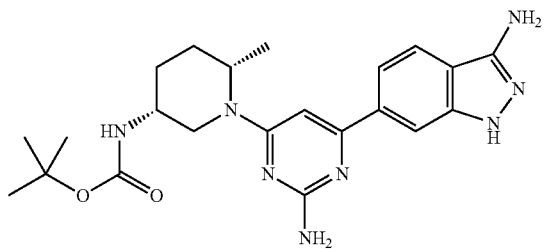 [SMILES: C[C@H]1CC[C@@H](NC(=O)OC(C)(C)C)CN1c1cc(-c2ccc3c(N)n[nH]c3c2)nc(N)n1]

1,1-Dimethylethyl{(3R,6S)-1-[2-amino-6-(4-cyano-3-fluorophenyl)-4-pyrimidinyl]-6-methyl-3-piperidinyl}carbamate (2.5 g, 5.86 mmol) was azeotroped with ethanol (2×25 mL). The residue was dissolved in ethanol (25 mL), to which was added 5 mL of hydrazine monohydrate in one portion at room temperature. The resulting mixture was heated to 100° C. in an oil bath under reflux for 4 hours. The mixture was cooled to room temperature. To this cooled mixture was added another 1.2 g of 1,1-dimethylethyl{(3R,6S)-1-[2-amino-6-(4-cyano-3-fluorophenyl)-4-pyrimidinyl]-6-methyl-3-piperidinyl}carbamate (2.81 mmol) in ethanol (12 mL). The resulting mixture was heated at 100° C. for 24 hours. LCMS showed complete conversion. The mixture was filtered through celite, and the filtrate was concentrated in vacuo. The residue was taken up in water (20 mL). The resulting suspension was sonicated briefly, and filtered. The solids were washed with water and dried under house vacuum at room temperature for 48 hours, and then under vacuum at room temperature over P₂O₅ for 20 hours to give the title compound (3.42 g) as a beige-colored solid. LC-MS (ES) m/z=439 [M+H]⁺. ¹H NMR (400 MHz, CD₃OD): δ 1.25 (d, J=7.1 Hz, 3H), 1.48 (s, 9H), 1.64-1.77 (m, 2H), 1.78-1.87 (m, 2H), 2.73 (t, J=12.1 Hz, 1H), 3.41-3.48 (m, 1H), 4.50-4.60 (bs, 1H), 4.75-4.85 (bs, 1H), 6.52 (s, 1H), 7.48 (d, J=8.3 Hz, 1H), 7.77 (d, J=8.3 Hz, 1H), 7.80 (s, 1H).

Intermediate 305

1,1-Dimethylethyl{(3R,6S)-1-[6-chloro-2-(methylamino)-4-pyrimidinyl]-6-methyl-3-piperidinyl}carbamate

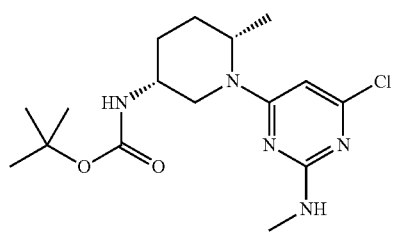 [SMILES: CNc1nc(Cl)cc(N2C[C@H](NC(=O)OC(C)(C)C)CC[C@@H]2C)n1]

A mixture of 1,1-dimethylethyl[(3R,6S)-6-methyl-3-piperidinyl]carbamate (13.7 g, 63.9 mmol), 4,6-dichloro-N-methyl-2-pyrimidinamine (12.52 g, 70.3 mmol, 1.1 equiv) and Hunig's base (24.5 mL, 141 mmol, 2.2 equiv) in propionitrile (100 mL) was heated in an oil bath to 100° C. under reflux for 20 hours. LCMS showed complete conversion. The mixture was concentrated in vacuo. The residue was partitioned between EtOAc (250 mL) and brine (50 mL). The organic was dried over Na₂SO₄, filtered, and concentrated in vacuo to give a suspension. This suspension (in ca. 35 mL of EtOAc) was diluted with CHCl₃. The resulting suspension was filtered. The solids collected were identified by LCMS to be the starting 4,6-dichloro-N-methyl-2-pyrimidinamine. The filtrate was purified by silica gel column chromatography using gradient elution of 1% EtOAc in CHCl₃ to 100% EtOAc to give the title compound (15.23 g) as a white glassy foam. LC-MS (ES) m/z=356 [M+H]⁺.

Intermediate 306

1,1-Dimethylethyl{(3R,6S)-1-[6-(4-cyano-3-fluorophenyl)-2-(methylamino)-4-pyrimidinyl]-6-methyl-3-piperidinyl}carbamate

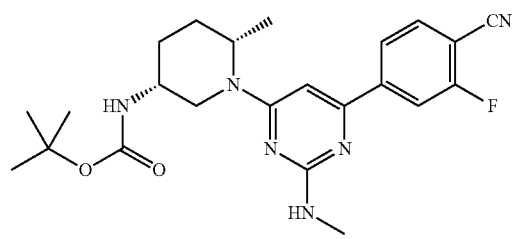 [SMILES: CNc1nc(-c2ccc(C#N)c(F)c2)cc(N2C[C@H](NC(=O)OC(C)(C)C)CC[C@@H]2C)n1]

A mixture of 1,1-dimethylethyl{(3R,6S)-1-[6-chloro-2-(methylamino)-4-pyrimidinyl]-6-methyl-3-piperidinyl}carbamate (8.0 g, 22.48 mmol, this material was azeotroped with 2×40 mL of toluene prior to mixing), (4-cyano-3-fluorophenyl)boronic acid (4.82 g, 29.2 mmol, 1.3 equiv), tricyclohexylphosphine (0.95 g, 3.37 mmol, 0.15 equiv), Pd₂(dba)₃ (1.54 g, 1.69 mmol, 0.075 equiv) and K₃PO₄ (8.11 g, 38.2 mmol, 1.7 equiv) in 1,4-dioxane (100 mL) and water (33 mL) was degassed with nitrogen and back flushed (5×), and then heated in an oil bath at 100° C. under a reflux condenser for 20 hours. LCMS showed complete conversion. The mixture was filtered through celite. The residue was partitioned between EtOAc (300 mL) and brine (80 mL). The organic was dried over Na₂SO₄, filtered, and concentrated in vacuo. The residue was purified by silica gel column chromatography using gradient elution of 1% EtOAc in CHCl₃ to 80% EtOAc to give the title compound (8.89 g) as a yellow foam. LC-MS (ES) m/z=441 [M+H]⁺.

Example 155

1,1-Dimethylethyl{(3R,6S)-1-[6-(3-amino-1H-indazol-6-yl)-2-(methylamino)-4-pyrimidinyl]-6-methyl-3-piperidinyl}carbamate

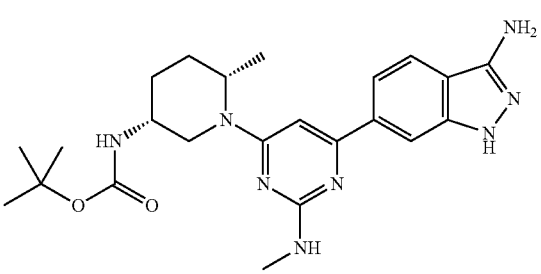 [SMILES: CNc1nc(-c2ccc3c(N)n[nH]c3c2)cc(N2C[C@H](NC(=O)OC(C)(C)C)CC[C@@H]2C)n1]

To a solution of 1,1-dimethylethyl{(3R,6S)-1-[6-(4-cyano-3-fluorophenyl)-2-(methylamino)-4-pyrimidinyl]-6-methyl-3-piperidinyl}carbamate (2.5 g, 5.68 mmol, this material was azeotroped with 2×30 mL of ethanol prior to mixing) in ethanol (25 mL) was added hydrazine monohydrate (5 mL) in one portion. The resulting mixture was heated in an oil bath to 100° C. for 24 hours. LCMS showed complete conversion. The mixture was concentrated in vacuo. The residue was taken up in water (25 mL). The resulting suspension was sonicated briefly, followed by filtration. The solids collected were washed with water. Drying under vacuum at room temperature over $P_2O_5$ for 20 hours gave the title compound (1.76 g) as a beige solid. LC-MS (ES) m/z=453 [M+H]$^+$. $^1$H NMR (400 MHz, CD$_3$OD): δ 1.25 (d, J=6.8 Hz, 3H), 1.49 (s, 9H), 1.63-1.79 (m, 2H), 1.80-1.93 (m, 2H), 2.74 (t, J=12.0 Hz, 1H), 2.98 (s, 3H), 3.40-3.54 (bs, 1H), 4.50-4.63 (bs, 1H), 4.80-4.90 (bs, 1H), 6.47 (s, 1H), 7.52 (d, J=8.1 Hz, 1H), 7.76 (d, J=8.6 Hz, 1H), 7.85 (s, 1H).

Example 156

6-{2-Amino-6-[(2R,5R)-2-(aminomethyl)-5-methyl-4-morpholinyl]-4-pyrimidinyl}-1H-indazol-3-amine

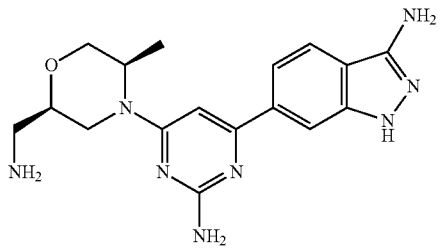 [SMILES: C[C@@H]1CO[C@H](CN)CN1c1cc(-c2ccc3c(N)n[nH]c3c2)nc(N)n1]

A mixture of 4-{2-amino-6-[(2R,5R)-2-(aminomethyl)-5-methyl-4-morpholinyl]-4-pyrimidinyl}-2-fluorobenzonitrile (55 mg, 0.16 mmol) and hydrazine monohydrate (0.16 mL, 3.29 mmol) in EtOH (2 mL) was stirred at 100° C. in a sealed tube for 20 hours. The mixture was then concentrated and the residue was purified on a Gilson reverse phase HPLC (CH$_3$CN/H$_2$O with 0.1% TFA). The product fractions were concentrated in vacuo, triturated with Et$_2$O, and dried in a vacuum oven overnight to give a TFA salt of the title compound (36 mg) as a yellow solid. LC-MS (ES) m/z=355 [M+H]$^+$. $^1$H NMR (400 MHz, CD$_3$OD, several milligrams of Na$_2$CO$_3$ added to form the free base, * denotes minor rotamer): δ 1.29 (d, J=6.6 Hz, 3H), 2.77-2.85 (m, 1H), 2.85-3.01 (m, 1H), 3.22-3.37 (m, 1H), 3.45-3.60 (m, 1H), 3.73-3.84 (m, 1H), 3.84-3.94 (m, 1H), 4.08-4.38 (bs, 1H), 4.38-4.73 (bs, 1H), 6.48* and 6.50 (s, 1H), 7.50 (dd, J=8.4, 1.4 Hz, 1H), 7.77 (d, J=8.4 Hz, 1H), 7.82 (s, 1H).

Example 157

6-[2-Amino-6-((2R,5R)-5-methyl-2-{[(phenylmethyl)amino]methyl}-4-morpholinyl)-4-pyrimidinyl]-1H-indazol-3-amine

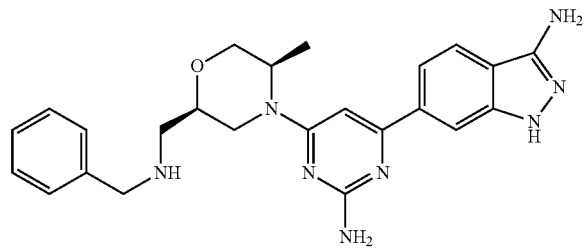 [SMILES: C[C@@H]1CO[C@H](CNCc2ccccc2)CN1c1cc(-c2ccc3c(N)n[nH]c3c2)nc(N)n1]

Sodium triacetoxyborohydride (62 mg, 0.29 mmol) was added to a mixture of 4-{2-amino-6-[(2R,5R)-2-(aminomethyl)-5-methyl-4-morpholinyl]-4-pyrimidinyl}-2-fluorobenzonitrile (80 mg, 0.23 mmol) and benzaldehyde (26 μL, 0.26 mmol) in THF (2.5 mL), and the mixture was stirred at room temperature for 16 hours. Another portion of sodium triacetoxyborohydride (62 mg, 0.29 mmol) was then added, and stirring continued for an additional 27 hours, after which another portion each of benzaldehyde (26 μL, 0.26 mmol) and sodium triacetoxyborohydride (62 mg, 0.29 mmol) were added. After 4 hours the mixture was quenched with saturated aqueous NaHCO$_3$ (15 mL) and extracted with EtOAc (2×15 mL). The extracts were washed with brine (15 mL), dried (Na$_2$SO$_4$), filtered, and concentrated in vacuo to give a mixture containing mono- and dibenzylated amine as a yellow oil (149 mg). That residue was dissolved in EtOH (3.5 mL), hydrazine monohydrate (0.50 mL, 10.29 mmol) was added, and the mixture was stirred at 100° C. in a sealed tube for 15 hours. The reaction mixture was then cooled and concentrated in vacuo, and the residue was purified on a Gilson reverse phase HPLC (CH$_3$CN/H$_2$O with 0.1% TFA) to give a TFA salt of the title compound (28 mg) as a pale yellow solid. LC-MS (ES) m/z=445 [M+H]$^+$. $^1$H NMR (400 MHz, DMSO-d$_6$, 3 mg of Na$_2$CO$_3$ added to form the free base, * denotes minor rotamer): δ 1.15 (d, J=6.6 Hz, 3H), 2.59-2.72 (m, 2H), 2.72-2.89 (m, 1H), 3.46-3.57 (m, 1H), 3.59-3.69 (m, 1H), 3.70-3.81 (m, 3H), 3.90-4.83 (bs, 2H), 5.38 (s, 2H), 6.11 (s, 2H), 6.51* and 6.55 (s, 1H), 6.60-6.77 (bs, 1H), 7.20-7.29 (m, 1H), 7.29-7.39 (m, 4H), 7.56 (d, J=8.6 Hz, 1H), 7.71 (d, J=8.3 Hz, 1H), 7.94 (s, 1H), 11.52 (s, 1H).

Intermediate 307

{(2S,5R)-4-[6-Chloro-2-(methylamino)-4-pyrimidinyl]-5-methyl-2-morpholinyl}methanol

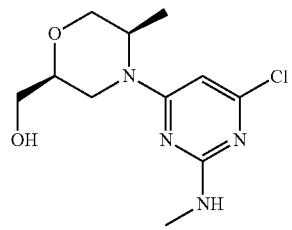 [SMILES: CNc1nc(Cl)cc(N2C[C@@H](CO)OC[C@H]2C)n1]

A mixture of [(2S,5R)-5-methyl-2-morpholinyl]methanol (11.50 g, 65.2 mmol), 4,6-dichloro-N-methyl-2-pyrimidinamine (11.38 g, 63.9 mmol), and K$_2$CO$_3$ (19.87 g, 144 mmol) in EtOH (250 mL) was stirred at reflux under nitrogen for 23 hours. The mixture was cooled, poured into water (500 mL), and extracted with CH$_2$Cl$_2$ (3×400 mL). The extracts were dried (Na$_2$SO$_4$), filtered, and concentrated in vacuo to give a cream solid. The residue was purified by flash chromatography (400 g SiO$_2$, 10-60% EtOAc in hexanes gradient). The product was collected and concentrated in vacuo to give a very sticky foam. The residue was taken up in Et$_2$O (250 mL) and HCl (4.0 M in 1,4-dioxane, 10 mL) was added dropwise while the mixture was swirled. The solid that formed was collected by vacuum filtration and dried in the vacuum oven overnight to give a hydrochloride salt of the title compound (9.75 g) as a white solid. LC-MS (ES) m/z=273, 275 [M+H]$^+$.

Intermediate 308

2-Fluoro-4-[6-[(2S,5R)-2-(hydroxymethyl)-5-methyl-4-morpholinyl]-2-(methylamino)-4-pyrimidinyl]benzonitrile

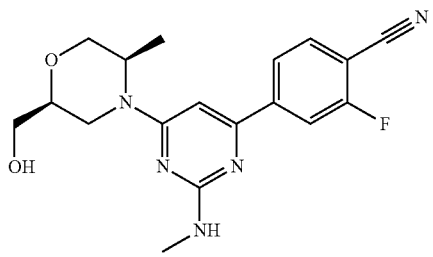 [SMILES: CNc1nc(-c2ccc(C#N)c(F)c2)cc(N2C[C@@H](CO)OC[C@H]2C)n1]

A mixture of {(2S,5R)-4-[6-chloro-2-(methylamino)-4-pyrimidinyl]-5-methyl-2-morpholinyl}methanol (2.24 g, 7.24 mmol), (4-cyano-3-fluorophenyl)boronic acid (2.64 g, 16.01 mmol), and Pd(PPh$_3$)$_4$ (0.43 g, 0.37 mmol) in 1,4-dioxane (50 mL) and saturated aqueous NaHCO$_3$ (25 mL) was degassed with nitrogen for 10 minutes. It was then stirred at 100° C. under nitrogen for 17 hours, cooled, diluted with water (25 mL) and saturated aqueous NaHCO$_3$ (100 mL), and extracted with EtOAc (3×100 mL). The extracts were washed with brine (150 mL), dried (Na$_2$SO$_4$), filtered, and concentrated in vacuo. The residue was purified by flash chromatography (90 g SiO$_2$, 20-100% EtOAc in hexanes gradient) to give the title compound (2.36 g) as a yellow solid. LC-MS (ES) m/z=358 [M+H]$^+$.

Example 158

{(2S,5R)-4-[6-(3-Amino-1H-indazol-6-yl)-2-(methylamino)-4-pyrimidinyl]-5-methyl-2-morpholinyl}methanol

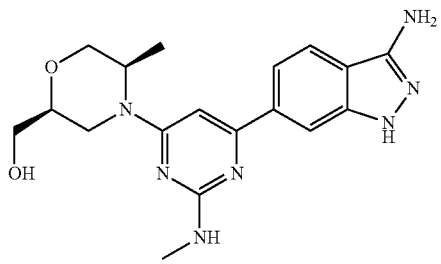 [SMILES: CNc1nc(-c2ccc3c(N)n[nH]c3c2)cc(N2C[C@@H](CO)OC[C@H]2C)n1]

A mixture of 2-fluoro-4-[6-[(2S,5R)-2-(hydroxymethyl)-5-methyl-4-morpholinyl]-2-(methylamino)-4-pyrimidinyl]benzonitrile (151 mg, 0.42 mmol) and hydrazine monohydrate (0.41 mL, 8.44 mmol) in EtOH (4 mL) was stirred at 100° C. in a sealed tube for 42 hours. It was then cooled, filtered, and concentrated in vacuo. The residue was purified by flash chromatography (24 g SiO$_2$, CH$_2$Cl$_2$ to 90/10/1 CH$_2$Cl$_2$/CH$_3$OH/NH$_4$OH gradient) to give the title compound (113 mg) as a white solid. LC-MS (ES) m/z=370 [M+H]$^+$. $^1$H NMR (400 MHz, DMSO-d$_6$): δ 1.17 (d, J=6.6 Hz, 3H), 2.72-2.93 (m, 4H), 3.37-3.59 (m, 3H), 3.66 (d, J=11.2 Hz, 1H), 3.77 (d, J=11.1 Hz, 1H), 3.94-4.74 (bs, 2H), 4.38 (t, J=5.7 Hz, 1H), 5.38 (s, 2H), 6.54 (m, 2H), 7.59 (d, J=8.3 Hz, 1H), 7.72 (d, J=8.6 Hz, 1H), 7.98 (s, 1H), 11.50 (s, 1H).

Intermediate 309

(2S,5R)-4-[6-(4-Cyano-3-fluorophenyl)-2-(methylamino)-4-pyrimidinyl]-5-methyl-2-morpholinecarboxylic acid

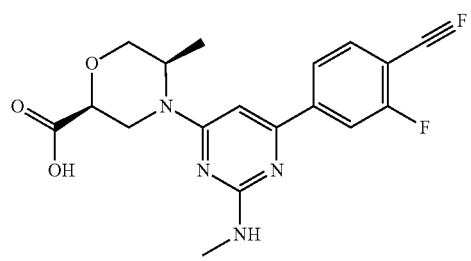

TEMPO (0.18 g, 1.17 mmol) and iodobenzene diacetate (3.88 g, 12.05 mmol) were added to a mixture of 2-fluoro-4-[6-[(2S,5R)-2-(hydroxymethyl)-5-methyl-4-morpholinyl]-2-(methylamino)-4-pyrimidinyl]benzonitrile (2.09 g, 5.85 mmol) in CH$_2$Cl$_2$ (20 mL) and water (10 mL) at 0° C., and the mixture was allowed to slowly warm to room temperature and it was vigorously stirred for 42 hours. The mixture was quenched with CH$_3$OH (10 mL), poured into saturated aqueous NaHCO$_3$ (100 mL), diluted with water (15 mL), and washed with CH$_2$Cl$_2$ (2×50 mL). The aqueous phase was then brought to pH 5 by very slow addition of solid citric acid (monohydrate, about 9.5 g). While acidifying the mixture a really bad emulsion formed. After trying several tricks that failed (salting, using chloroform, filtering, etc) the emulsion was finally mostly broken by diluting up to about 1.5 L of aqueous and about 1 L of CH$_2$Cl$_2$ and CHCl$_3$. The organic layer was collected and the aqueous phase was further extracted with 90/10 CH$_2$Cl$_2$/IPA (5×500 mL). The extracts were combined, dried (Na$_2$SO$_4$), filtered, and concentrated in vacuo to give the title compound (1.63 g, about 90% purity) as a yellow solid. LC-MS (ES) m/z=372 [M+H]$^+$.

Intermediate 310

(2S,5R)-4-[6-(4-Cyano-3-fluorophenyl)-2-(methylamino)-4-pyrimidinyl]-5-methyl-N-phenyl-2-morpholinecarboxamide

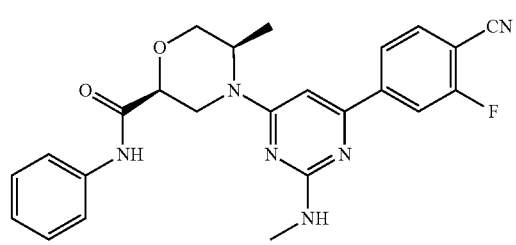 [SMILES: CNc1nc(-c2ccc(C#N)c(F)c2)cc(N2C[C@@H](C(=O)Nc3ccccc3)OC[C@H]2C)n1]

A mixture of (2S,5R)-4-[6-(4-cyano-3-fluorophenyl)-2-(methylamino)-4-pyrimidinyl]-5-methyl-2-morpholinecarboxylic acid (300 mg, 0.81 mmol), HATU (340 mg, 0.89 mmol), and Hünig's base (0.21 mL, 1.20 mmol) in DMF (5 mL) was stirred at room temperature for 10 minutes. Aniline (0.085 mL, 0.93 mmol) was then added, and stirring continued at room temperature for 17 hours. LC-MS indicated about 50% conversion, so another portion each of Hünig's base (0.21 mL, 1.20 mmol) and HATU (340 mg, 0.89 mmol) were added. After about 10 minutes more aniline (0.085 mL, 0.93

Example 159

(2S,5R)-4-[6-(3-amino-1H-indazol-6-yl)-2-(methylamino)-4-pyrimidinyl]-5-methyl-N-phenyl-2-morpholinecarboxamide

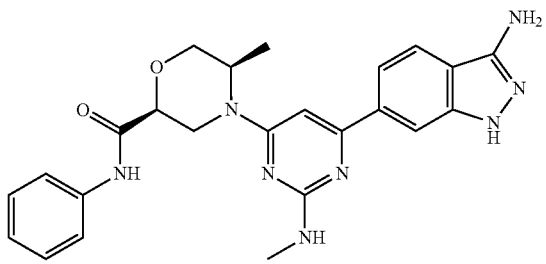

A mixture of (2S,5R)-4-[6-(4-cyano-3-fluorophenyl)-2-(methylamino)-4-pyrimidinyl]-5-methyl-N-phenyl-2-morpholinecarboxamide (340 mg, 0.61 mmol) and hydrazine monohydrate (0.39 mL, 12.54 mmol) in 1,4-dioxane (5 mL) was stirred at 100° C. in a sealed tube for 18 hours. The reaction mixture was cooled and concentrated in vacuo, and the residue was purified by flash chromatography (60 g SiO$_2$, CH$_2$Cl$_2$ to 90/10/1 CH$_2$Cl$_2$/CH$_3$OH/NH$_4$OH gradient) to give the title compound (243 mg) as a pale yellow solid. LC-MS (ES) m/z=459 [M+H]$^+$. $^1$H NMR (400 MHz, DMSO-d$_6$): δ 1.24 (d, J=6.6 Hz, 3H), 2.86 (d, J=4.0 Hz, 3H), 2.97-3.15 (m, 1H), 3.83 (d, J=11.1 Hz, 1H), 3.94 (d, J=11.1 Hz, 1H), 4.16 (dd, J=11.2, 2.9 Hz, 1H), 4.33-4.88 (bs, 2H), 5.39 (s, 2H), 6.56-6.73 (m, 2H), 7.10 (t, J=7.3 Hz, 1H), 7.34 (t, J=7.9 Hz, 2H), 7.63 (d, J=8.3 Hz, 1H), 7.73 (d, J=8.3 Hz, 3H), 8.01 (s, 1H), 9.88 (s, 1H), 11.51 (s, 1H).

Intermediate 311

(2S,5R)-4-[6-(4-Cyano-3-fluorophenyl)-2-(methylamino)-4-pyrimidinyl]-N-cyclohexyl-5-methyl-2-morpholinecarboxamide

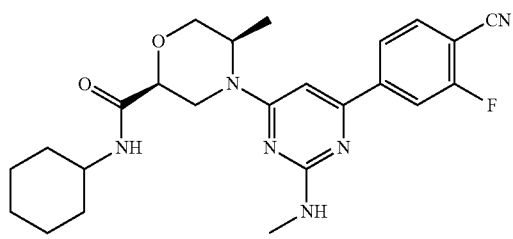 [SMILES: CNc1nc(-c2ccc(C#N)c(F)c2)cc(N2C[C@@H](C(=O)NC3CCCCC3)OC[C@H]2C)n1]

A mixture of (2S,5R)-4-[6-(4-cyano-3-fluorophenyl)-2-(methylamino)-4-pyrimidinyl]-5-methyl-2-morpholinecarboxylic acid (302 mg, 0.81 mmol), HATU (343 mg, 0.90 mmol), and Hünig's base (0.21 mL, 1.20 mmol) in DMF (5 mL) was stirred at room temperature for 10 minutes. Cyclohexylamine (0.105 mL, 0.92 mmol) was then added and stirring continued at room temperature for 17 hours. LC-MS indicated abot 50% conversion so another portion each of Hünig's base (0.21 mL, 1.20 mmol) and HATU (343 mg, 0.90 mmol) was added, and the mixture was stirred for an additional 1.5 hours. It was then diluted with EtOAc (25 mL) and washed successively with water, saturated aqueous NaHCO$_3$, and brine (25 mL each). The organic phase was then dried (Na$_2$SO$_4$), filtered, and concentrated in vacuo. The residue was purified by flash chromatography (40 g SiO$_2$, 10-35% EtOAc in hexanes gradient) to give the title compound (340 mg, about 80% purity) as a yellow oil. LC-MS (ES) m/z=447 [M+H]$^+$.

Example 160

(2S,5R)-4-[6-(3-amino-1H-indazol-6-yl)-2-(methylamino)-4-pyrimidinyl]-N-cyclohexyl-5-methyl-2-morpholinecarboxide

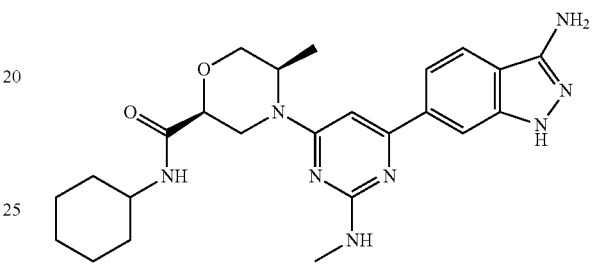

A mixture of (2S,5R)-4-[6-(4-cyano-3-fluorophenyl)-2-(methylamino)-4-pyrimidinyl]-N-cyclohexyl-5-methyl-2-morpholinecarboxamide (328 mg, 0.65 mmol) and hydrazine monohydrate (0.41 mL, 13.18 mmol) in 1,4-dioxane (5 mL) was stirred at 100° C. in a sealed tube for 18 hours. The mixture was cooled and concentrated in vacuo, and the residue was purified by flash chromatography (60 g SiO$_2$, CH$_2$Cl$_2$ to 90/10/1 CH$_2$Cl$_2$/CH$_3$OH/NH$_4$OH gradient) to give the title compound (244 mg) as a pale yellow solid. LC-MS (ES) m/z=465 [M+H]$^+$. $^1$H NMR (400 MHz, DMSO-d$_6$): δ 1.04-1.16 (m, 1H), 1.19 (d, J=6.6 Hz, 3H), 1.23-1.37 (m, 4H), 1.52-1.63 (m, 1H), 1.63-1.79 (m, 4H), 2.76-2.99 (m, 4H), 3.55-3.68 (m, 1H), 3.74 (dd, J=11.4, 2.8 Hz, 1H), 3.86 (d, J=11.1 Hz, 1H), 3.91 (dd, J=11.4, 2.8 Hz, 1H), 4.20-4.83 (bs, 2H), 5.39 (s, 2H), 6.50-6.71 (m, 2H), 7.56-7.69 (m, 2H), 7.72 (d, J=8.3 Hz, 1H), 7.99 (s, 1H), 11.50 (s, 1H).

Intermediate 312

(2S,5R)-4-[6-(4-cyano-3-fluorophenyl)-2-(methylamino)-4-pyrimidinyl]-5-methyl-N-(phenylmethyl)-2-morpholinecarboxamide

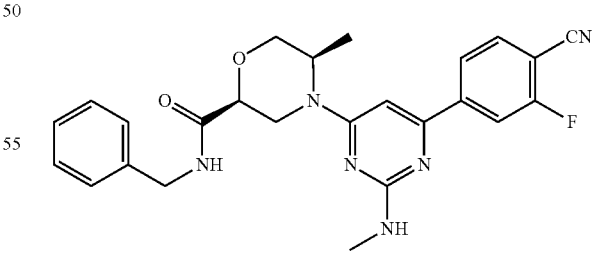

A mixture of (2S,5R)-4-[6-(4-cyano-3-fluorophenyl)-2-(methylamino)-4-pyrimidinyl]-5-methyl-2-morpholinecarboxylic acid (302 mg, 0.81 mmol), HATU (340 mg, 0.89 mmol), and Hünig's base (0.21 mL, 1.20 mmol) in DMF (5 mL) was stirred at room temperature for 10 minutes. Benzylamine (0.100 mL, 0.92 mmol) was then added and stirring continued at room temperature for 17 hours. LC-MS indicated about 50% conversion so another portion each of Hünig's base (0.21 mL, 1.20 mmol) and HATU (343 mg, 0.90 mmol) were added. After about 10 minutes more cyclohexylamine (0.105 mL, 0.92 mmol) was added, and the mixture was stirred for an additional 1.5 hours, then diluted with EtOAc (25 mL) and washed successively with water, saturated aqueous NaHCO$_3$, and brine (25 mL each). The organic phase was then dried (Na$_2$SO$_4$), filtered, and concentrated in vacuo. The residue was purified by flash chromatography (40 g SiO$_2$, 10-40% EtOAc in hexanes gradient) to give the title compound (328 mg) as a yellow oil. LC-MS (ES) m/z=453 [M+H]$^+$.

Hünig's base (0.21 mL, 1.20 mmol) and HATU (340 mg, 0.89 mmol) were added. After about 10 minutes more benzylamine (0.100 mL, 0.92 mmol) was added, and the mixture was stirred for an additional 1.5 hours, then diluted with EtOAc (25 mL) and washed successively with water, saturated aqueous NaHCO$_3$, and brine (25 mL each). The organic phase was then dried (Na$_2$SO$_4$), filtered, and concentrated in vacuo. The residue was purified by flash chromatography (40 g SiO$_2$, 15-50% EtOAc in hexanes gradient) to give the title compound (302 mg) as a yellow oil. LC-MS (ES) m/z=461 [M+H]$^+$.

Example 161

(2S,5R)-4-[6-(3-Amino-1H-indazol-6-yl)-2-(methylamino)-4-pyrimidinyl]-5-methyl-N-(phenylmethyl)-2-morpholinecarboxamide

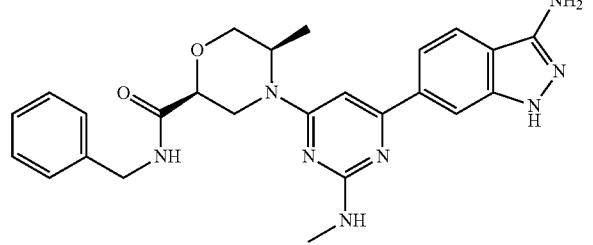

A mixture of (2S,5R)-4-[6-(4-cyano-3-fluorophenyl)-2-(methylamino)-4-pyrimidinyl]-5-methyl-N-(phenylmethyl)-2-morpholinecarboxamide (302 mg, 0.66 mmol) and hydrazine monohydrate (0.41 mL, 13.18 mmol) in 1,4-dioxane (5 mL) was stirred at 100° C. in a sealed tube for 18 hours. The reaction mixture was cooled and concentrated in vacuo, and the residue was purified by flash chromatography (60 g SiO$_2$, CH$_2$Cl$_2$ to 90/10/1 CH$_2$Cl$_2$/CH$_3$OH/NH$_4$OH gradient) to give the title compound (239 mg) as a light yellow solid. LC-MS (ES) m/z=473 [M+H]$^+$. $^1$H NMR (400 MHz, DMSO-d$_6$): δ 1.21 (d, J=6.6 Hz, 3H), 2.77-3.02 (m, 4H), 3.78 (d, J=11.2 Hz, 1H), 3.88 (d, J=11.1 Hz, 1H), 4.02 (dd, J=11.2, 2.9 Hz, 1H), 4.27-4.41 (m, 2H), 4.41-4.85 (bs, 2H), 5.39 (s, 2H), 6.51-6.72 (m, 2H), 7.19-7.38 (m, 5H), 7.62 (d, J=8.6 Hz, 1H), 7.72 (d, J=8.3 Hz, 1H), 7.99 (s, 1H), 8.54 (t, J=6.2 Hz, 1H), 11.50 (s, 1H).

Intermediate 313

{(2S,5R)-4-[6-Chloro-2-(methylamino)-4-pyrimidinyl]-5-methyl-2-morpholinyl}methyl methanesulfonate

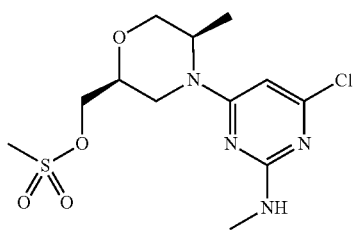 [SMILES: CNc1nc(Cl)cc(N2C[C@@H](COS(C)(=O)=O)OC[C@H]2C)n1]

Triethylamine (1.95 mL, 14.07 mmol) and methanesulfonyl chloride (0.52 mL, 6.67 mmol) were added dropwise to a solution of {(2S,5R)-4-[6-chloro-2-(methylamino)-4-pyrim idinyl]-5-methyl-2-morpholinyl}methanol (1.52 g, 5.57 mmol) in CH$_2$Cl$_2$ (50 mL) at 0° C., and the mixture was stirred at 0° C. under nitrogen for 45 minutes. It was then poured into saturated aqueous NaHCO$_3$ (100 mL) and extracted with CH$_2$Cl$_2$ (3×100 mL). The extracts were dried (Na$_2$SO$_4$), filtered, and concentrated in vacuo to give the title compound (1.88 g) as a foam that was crushed into an off-white solid. LC-MS (ES) m/z=351, 353 [M+H]$^+$.

Intermediate 314

4-Chloro-6-{(2R,5R)-2-[(dimethylamino)methyl]-5-methyl-4-morpholinyl}-N-methyl-2-pyrimidinamine

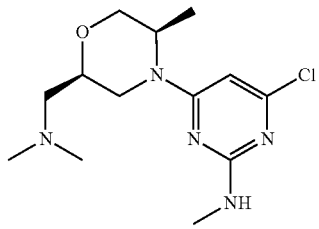 [SMILES: CNc1nc(Cl)cc(N2C[C@@H](CN(C)C)OC[C@H]2C)n1]

A mixture of {(2S,5R)-4-[6-chloro-2-(methylamino)-4-pyrimidinyl]-5-methyl-2-morpholinyl}methyl methanesulfonate (161 mg, 0.46 mmol) and dimethylamine (2.0 M in THF, 5.0 mL, 10.0 mmol) was stirred at 120° C. in a sealed tube for 32 hours. The mixture was cooled, poured into saturated aqueous NaHCO$_3$ (15 mL), diluted with water (5 mL), and extracted with EtOAc (3×15 mL). The extracts were washed with brine (15 mL), dried (Na$_2$SO$_4$), filtered, and concentrated in vacuo. The residue was purified by flash chromatography (24 g SiO$_2$, CH$_2$Cl$_2$ to 95/5/0.5 CH$_2$Cl$_2$/CH$_3$OH/NH$_4$OH gradient) to give the title compound (62 mg, about 85% purity) as an off-white foam. LC-MS (ES) m/z=300, 302 [M+H]$^+$.

Intermediate 315

4-[6-{(2R,5R)-2-[(Dimethylamino)methyl]-5-methyl-4-morpholinyl}-2-(methylamino)-4-pyrimidinyl]-2-fluorobenzonitrile

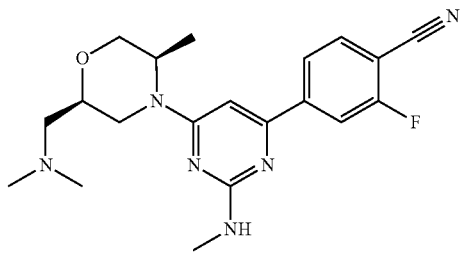 [SMILES: CNc1nc(-c2ccc(C#N)c(F)c2)cc(N2C[C@@H](CN(C)C)OC[C@H]2C)n1]

A mixture of 4-chloro-6-{(2R,5R)-2-[(dimethylamino)methyl]-5-methyl-4-morpholinyl}-N-methyl-2-pyrimidinamine (60 mg, 0.20 mmol), (4-cyano-3-fluorophenyl)boronic acid (73 mg, 0.44 mmol), and Pd(PPh$_3$)$_4$ (12 mg, 0.010 mmol) in 1,4-dioxane (2 mL) and saturated aqueous NaHCO$_3$ (1 mL) was degassed with nitrogen for 10 minutes. The vial was then capped and stirred at 100° C. for 15 hours. The mixture was cooled, diluted with saturated aqueous NaHCO$_3$ (5 mL) and water (5 mL), and extracted with EtOAc (2×10 mL). The extracts were washed with brine (10 mL), dried (Na₂SO₄), filtered, and concentrated in vacuo. The residue was purified by flash chromatography (10 g SiO₂, CH₂Cl₂ to 95/5/0.5 CH₂Cl₂/CH₃OH/NH₄OH gradient) to give the title compound (58 mg, about 85% purity) as a yellow oil. LC-MS (ES) m/z=385 [M+H]⁺.

Example 162

6-[6-{(2R,5R)-2-[(Dimethylamino)methyl]-5-methyl-4-morpholinyl}-2-(methylamino)-4-pyrimidinyl]-1H-indazol-3-amine

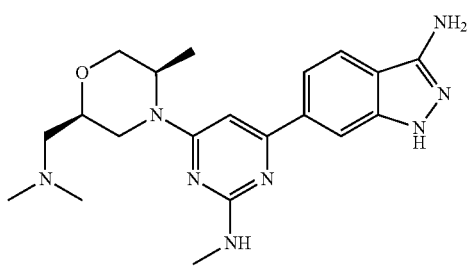 [SMILES: CNc1nc(-c2ccc3c(N)n[nH]c3c2)cc(N2C[C@@H](CN(C)C)OC[C@H]2C)n1]

A mixture of 4-[6-{(2R,5R)-2-[(dimethylamino)methyl]-5-methyl-4-morpholinyl}-2-(methylamino)-4-pyrimidinyl]-2-fluorobenzonitrile (58 mg, 0.15 mmol) and hydrazine monohydrate (0.10 mL, 3.21 mmol) in 1,4-dioxane (2 mL) was stirred in a sealed tube at 100° C. for 15 hours. The reaction mixture was then cooled and concentrated in vacuo, and the residue was purified by flash chromatography (24 g SiO₂, CH₂Cl₂ to 90/10/1 CH₂Cl₂/CH₃OH/NH₄OH gradient) to give the title compound (44 mg) as an off-white solid. LC-MS (ES) m/z=397 [M+H]⁺. ¹H NMR (400 MHz, DMSO-d₆): δ 1.17 (d, J=6.6 Hz, 3H), 2.22 (s, 6H), 2.35-2.45 (m, 2H), 2.66-2.80 (m, 1H), 2.84 (d, J=4.3 Hz, 3H), 3.49-3.60 (m, 1H), 3.66 (d, J=11.4 Hz, 1H), 3.75 (d, J=11.1 Hz, 1H), 4.02-4.79 (bs, 2H), 5.38 (s, 2H), 6.48-6.65 (m, 2H), 7.60 (d, J=8.6 Hz, 1H), 7.72 (d, J=8.3 Hz, 1H), 7.98 (s, 1H), 11.50 (s, 1H).

Intermediate 316

N-[2-(2-Chlorophenyl)-2-oxoethyl]-4-(phenylmethyl)-2-morpholinecarboxamide

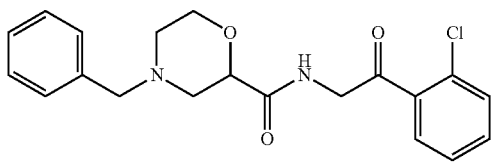 [SMILES: O=C(CNC(=O)C1CN(Cc2ccccc2)CCO1)c1ccccc1Cl]

Oxalyl chloride (0.765 mL, 8.73 mmol) was added to a suspension of 4-(phenylmethyl)-2-morpholinecarboxylic acid (1.288 g, 5.82 mmol) and DMF (0.090 mL, 1.165 mmol) in CH₂Cl₂ (80 mL) at 0° C. over 10 minutes. The reaction mixture was stirred at 25° C. for 2 h, and then concentrated. The residue was dissolved in CH₂Cl₂ (80 mL), then triethylamine (2.029 mL, 14.56 mmol) and 2-amino-1-(2-chlorophenyl)ethanone (1.2 g, 5.82 mmol) were added to the brown solution at 0° C. The mixture was stirred at 25° C. for 3 hours, and at this time, water (150 mL) was added. The mixture was extracted with EtOAc (3×100 mL), and the combined organics were dried with anhydrous Na₂SO₄, filtered, and concentrated. The resulting residue was purified by silica gel chromatography using 50% EtOAc in petroleum ether to afford the title compound (350 mg) as a pale yellow solid. LC-MS (ES) m/z=373 [M+H]⁺.

Intermediate 317

2-[4-(2-Chlorophenyl)-1H-imidazol-2-yl]-4-(phenylmethyl)morpholine

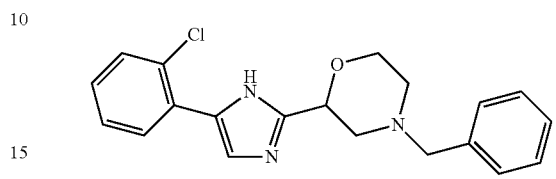

A mixture of N-[2-(2-chlorophenyl)-2-oxoethyl]-4-(phenylmethyl)-2-morpholinecarboxamide (350 mg, 0.939 mmol) and ammonium trifluoroacetate (615 mg, 4.69 mmol) was heated at 150° C. for 1.5 hours. Water (150 mL) was added to the residue, and the mixture was extracted with EtOAc (3×100 mL). The combined organics were dried with anhydrous Na₂SO₄, filtered and concentrated to afford the title compound (320 mg) as a brown solid. LC-MS (ES) m/z=354 [M+H]⁺.

Intermediate 318

2-[4-(2-Chlorophenyl)-1H-imidazol-2-yl]morpholine

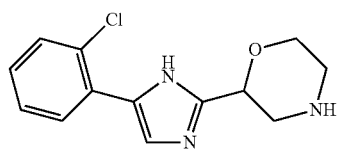 [SMILES: Clc1ccccc1-c1cnc(C2CNCCO2)[nH]1]

Palladium on carbon (10 wt %, 96 mg, 0.090 mmol) was added to a solution of 2-[4-(2-chlorophenyl)-1H-imidazol-2-yl]-4-(phenylmethyl)morpholine (320 mg, 0.904 mmol) and hydrochloric acid (36%, 0.382 mL, 4.52 mmol) in CH₃OH (80 mL) under nitrogen, and the mixture was stirred under hydrogen at 25° C. for 1.5 hours. The reaction mixture was filtered, washed by CH₃OH (150 mL), and concentrated to afford the title compound (250 mg) as a brown solid. LC-MS (ES) m/z=264 [M+H]⁺.

Intermediate 319

4-Chloro-6-{2-[4-(2-chlorophenyl)-1H-imidazol-2-yl]-4-morpholinyl}-2-pyrimidinamine

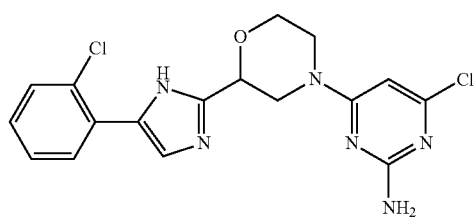 [SMILES: Nc1nc(Cl)cc(N2CCOC(c3ncc(-c4ccccc4Cl)[nH]3)C2)n1]

A solution of 2-[4-(2-chlorophenyl)-1H-imidazol-2-yl] morpholine (250 mg, 0.833 mmol), 4,6-dichloro-2-pyrimidinamine (137 mg, 0.833 mmol) and Hunig's base (0.36 mL, 2.08 mmol) in ethanol (80 mL) was heated at 85° C. for 3 hours. The reaction mixture was filtered, and the filtrate was concentrated. The resulting residue was purified by silica gel chromatography using 50% EtOAc in petroleum ether to afford the title compound (100 mg) as a white solid. LC-MS (ES) m/z=391, 393 [M+H]$^+$.

Intermediate 320

4-(2-Amino-6-{2-[4-(2-chlorophenyl)-1H-imidazol-2-yl]-4-morpholinyl}-4-pyrimidinyl)-2-fluorobenzonitrile

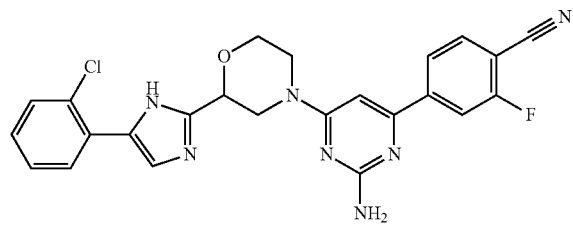 [SMILES: N#Cc1ccc(-c2cc(N3CCOC(c4ncc(-c5ccccc5Cl)[nH]4)C3)nc(N)n2)cc1F]

A mixture of 4-chloro-6-{2-[4-(2-chlorophenyl)-1H-imidazol-2-yl]-4-morpholinyl}-2-pyrimidinamine (100 mg, 0.256 mmol), 2-fluoro-4-(4,4,5,5-tetramethyl-1,3,2-dioxaborolan-2-yl)benzonitrile (82 mg, 0.332 mmol), Na$_2$CO$_3$ (67.7 mg, 0.639 mmol) and Pd(PPh$_3$)$_4$ (29.5 mg, 0.026 mmol) in 1,4-dioxane (4 mL) and water (1 mL) was heated at 140° C. under microwave conditions with stirring for 1 hour. The reaction mixture was filtered, washed by EtOAc (100 mL), and concentrated. The resulting residue was purified by prep-HPLC using CH$_3$CN in water (10 mmol NH$_4$HCO$_3$ in water) from 60% to 70% in 7 minutes to afford the title compound (50 mg) as a yellow solid. LC-MS (ES) m/z=476 [M+H]$^+$.

Example 163

6-(2-Amino-6-{2-[4-(2-chlorophenyl)-1H-imidazol-2-yl]-4-morpholinyl}-4-pyrimidinyl)-1H-indazol-3-amine

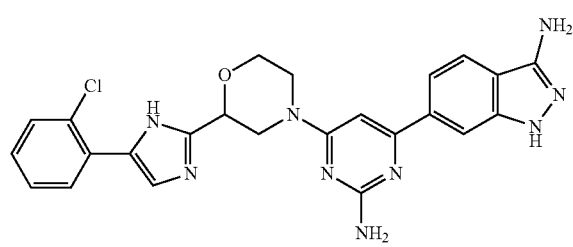 [SMILES: Nc1nc(-c2ccc3c(N)n[nH]c3c2)cc(N2CCOC(c3ncc(-c4ccccc4Cl)[nH]3)C2)n1]

A mixture of 4-(2-amino-6-{2-[4-(2-chlorophenyl)-1H-imidazol-2-yl]-4-morpholinyl}-4-pyrimidinyl)-2-fluorobenzonitrile (50 mg, 0.105 mmol) and hydrazine (0.167 mL, 5.25 mmol) in ethanol (2 mL) was heated at 120° C. under microwave conditions with stirring for 1 hour. The reaction mixture was filtered and concentrated, and the resulting residue dried in vacuo to afford the title compound (40 mg) as a yellow solid. LC-MS (ES) m/z=488 [M+H]$^+$. $^1$H NMR (400 MHz, DMSO-d$_6$): δ 3.10-3.16 (m, 1H), 3.22-3.28 (m, 1H), 3.71-3.76 (m, 1H), 4.04-4.07 (m, 1H), 4.30-4.34 (m, 1H), 4.65- 4.68 (m, 1H), 4.73 (m, 1H), 5.38 (s, 2H), 6.20 (s, 2H), 6.71 (s, 1H), 7.21-7.25 (m, 1H), 7.33-7.37 (m, 1H), 7.46-7.48 (m, 1H), 7.60-7.63 (m, 1H), 7.69-7.73 (m, 2H), 7.99 (s, 1H), 8.11-8.13 (m, 1H), 11.52 (s, 1H), 12.53 (s, 1H).

Intermediate 321

4-Chloro-N-methyl-6-[(3R)-3-methyl-4-morpholinyl]-2-pyrimidinamine

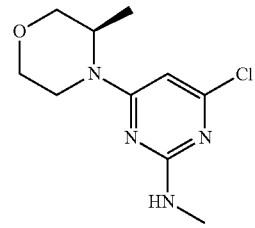 [SMILES: CNc1nc(Cl)cc(N2CCOC[C@H]2C)n1]

To a solution of 4,6-dichloro-N-methyl-2-pyrimidinamine (2 g, 11.23 mmol) in ethanol (50 mL) in a 200-mL RBF were added Hunig's base (5.89 mL, 33.7 mmol) and (3R)-3-methylmorpholine (1.546 g, 11.23 mmol). The reaction mixture was stirred at 100° C. in a sealed tube on a stirrer hotplate for 2 days. The reaction was concentrated in vacuo, and the residue was dissolved in EtOAc (200 mL) and washed with water (50 mL). The organic layer was dried over Na$_2$SO$_4$, filtered, then concentrated to afford the title compound (1.873 g) as a white solid. LC-MS (ES) m/z=243 [M+H]$^+$.

Intermediate 322

2,6-Difluoro-4-{2-(methylamino)-6-[(3R)-3-methyl-4-morpholinyl]-4-pyrimidinyl}benzonitrile

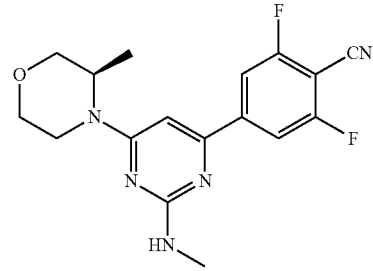 [SMILES: CNc1nc(-c2cc(F)c(C#N)c(F)c2)cc(N2CCOC[C@H]2C)n1]

To a 20-mL microwave vial was added 4-chloro-N-methyl-6-[(3R)-3-methyl-4-morpholinyl]-2-pyrimidinamine (500 mg, 2.060 mmol), (4-cyano-3,5-difluorophenyl)boronic acid (754 mg, 4.12 mmol), PdCl$_2$(dppf).CH$_2$Cl$_2$ adduct (84 mg, 0.103 mmol), K$_2$CO$_3$ (2 M, 3.09 mL, 6.18 mmol), and 1,4-dioxane (9 mL). The reaction mixture was heated at 140° C. for 10 mins in a microwave reactor. The 1,4-dioxane was removed, and the aqueous layer was extracted with EtOAc (2×10 mL). The combined organics were dried over Na$_2$SO$_4$ and concentrated. The resulting residue was purified by flash chromatography (0-50% EtOAc in hexanes, 12 g column) to afford the title compound (312 mg) as a yellow solid. LC-MS (ES) m/z=346 [M+H]$^+$.

Example 164

4-Fluoro-6-{2-(methylamino)-6-[(3R)-3-methyl-4-morpholinyl]-4-pyrimidinyl}-1H-indazol-3-amine

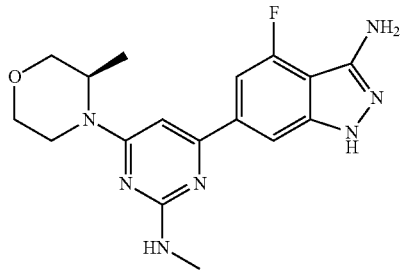 [SMILES: CNc1nc(-c2cc(F)c3c(N)n[nH]c3c2)cc(N2CCOC[C@H]2C)n1]

A 2-mL microwave vial was charged with 2,6-difluoro-4-{2-(methylamino)-6-[(3R)-3-methyl-4-morpholinyl]-4-pyrimidinyl}benzonitrile (75 mg, 0.217 mmol), hydrazine (0.027 mL, 0.869 mmol), Hunig's base (0.152 mL, 0.869 mmol) and ethanol (1 mL). The reaction mixture was heated at 150° C. for 15 minutes in a microwave reactor. The reaction mixture was allowed to cool, then was poured into EtOAc (50 mL) and water (25 mL). The aqueous layer was extracted with two further portion of EtOAc (2×50 mL), and the combined organics dried over $Na_2SO_4$. The dried solution was filtered and concentrated, and the resulting residue was purified by RP-HPLC (0-30% $CH_3CN$ in $H_2O$, 0.1% TFA) to afford the title compound (53.2 mg) as a yellow solid. LC-MS (ES) m/z=358 [M+H]$^+$. $^1$H NMR (400 MHz, DMSO-$d_6$): δ 1.19 (d, J=6.6 Hz, 3H), 2.83 (bs, 3H), 3.06-3.20 (m, 1H), 3.40-3.52 (m, 1H), 3.55-3.66 (m, 1H), 3.69-3.78 (m, 1H), 3.88-4.00 (m, 1H), 4.06-4.24 (m, 1H), 4.43-4.62 (m, 1H), 5.27 (bs, 2H), 6.45-6.71 (m, 2H), 7.26-7.49 (m, 1H), 7.76-7.96 (m, 1H), 11.71-12.13 (m, 1H).

Intermediate 323

2-Fluoro-4-{2-(methylamino)-6-[(3R)-3-methyl-4-morpholinyl]-4-pyrimidinyl}benzonitrile

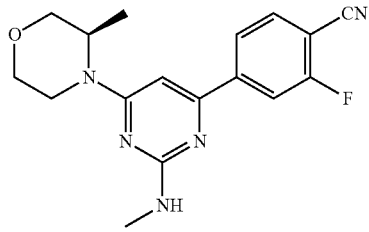 [SMILES: CNc1nc(-c2ccc(C#N)c(F)c2)cc(N2CCOC[C@H]2C)n1]

To a 5-mL microwave vial was added 4-chloro-N-methyl-6-[(3R)-3-methyl-4-morpholinyl]-2-pyrimidinamine (200 mg, 0.824 mmol), (4-cyano-3-fluorophenyl)boronic acid (177 mg, 1.071 mmol), $PdCl_2$(dppf).$CH_2Cl_2$ adduct (33.6 mg, 0.041 mmol), $K_2CO_3$ (1.236 mL, 2.472 mmol), and 1,4-dioxane (3 mL). The reaction mixture was heated at 140° C. for 10 minutes in a microwave reactor. The 1,4-dioxane was removed, and the aqueous layer was extracted with EtOAc (2×20 mL). The combined organics were dried over $Na_2SO_4$ and concentrated. The resulting residue was purified by flash chromatography (0-50% EtOAc in hexanes, 12 g column) to afford the title compound (294 mg) as a yellow oil. LC-MS (ES) m/z=328 [M+H]$^+$.

Example 165

6-{2-(Methylamino)-6-[(3R)-3-methyl-4-morpholinyl]-4-pyrimidinyl}-1H-indazol-3-amine

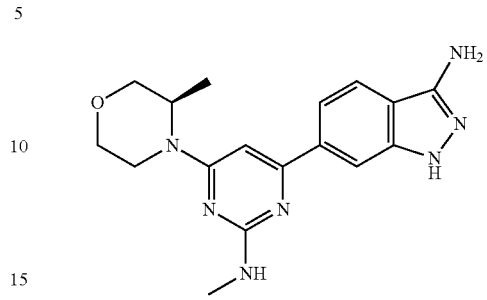

To a 5-mL microwave vial was added 2-fluoro-4-{2-(methylamino)-6-[(3R)-3-methyl-4-morpholinyl]-4-pyrimidinyl}benzonitrile (270 mg, 0.824 mmol), hydrazine (0.31 mL, 9.9 mmol), Hunig's base (0.576 mL, 3.30 mmol), and ethanol (3 mL). The reaction mixture was heated at 150° C. for 70 minutes in a microwave reactor. LCMS analysis indicated good conversion, so the reaction mixture was concentrated, dissolved in DMSO and purified by RP-HPLC (8-32% $CH_3CN$ in water, 0.1% TFA). The product fractions were pooled, then basified with $NaHCO_3$ and extracted with EtOAc. The organic layer was dried and concentrated to afford the title compound (117 mg). LC-MS (ES) m/z=340 [M+H]$^+$. $^1$H NMR (400 MHz, DMSO-$d_6$): δ 1.17-1.23 (m, 3H), 2.84 (d, J=4.0 Hz, 3H), 3.02-3.20 (m, 1H), 3.38-3.51 (m, 1H), 3.56-3.66 (m, 1H), 3.67-3.78 (m, 1H), 3.87-3.98 (m, 1H), 4.07-4.19 (m, 1H), 4.45-4.57 (m, 1H), 5.38 (s, 2H), 6.55 (bs, 2H), 7.61 (s, 1H), 7.71 (d, J=8.3 Hz, 1H), 7.98 (bs, 1H), 11.51 (s, 1H).

Example 166

6-{2-(Methylamino)-6-[(3R)-3-methyl-4-morpholinyl]-4-pyrimidinyl}-4-(methyloxy)-1H-indazol-3-amine

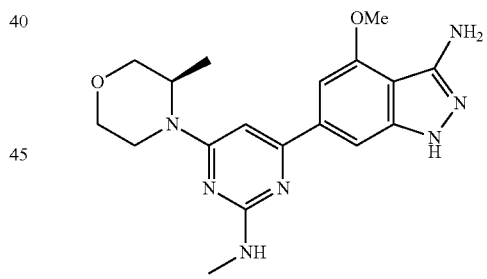

A 100 mL RBF was charged with sodium hydride (73.1 mg, 2.90 mmol), placed under a nitrogen atmosphere and cooled to 0° C. Then $CH_3OH$ (10 mL) was added dropwise via syringe, and the resulting mixture was stirred at this temperature for 10 minutes. Then the mixture was warmed to room temperature for 10 minutes to give a cloudy solution of sodium methoxide in $CH_3OH$. To a 4-mL vial was added 2,6-difluoro-4-{2-(methylamino)-6-[(3R)-3-methyl-4-morpholinyl]-4-pyrimidinyl}benzonitrile (100 mg, 0.290 mmol), DMF (1 mL), and 1.2 mL of the solution of sodium methoxide in $CH_3OH$ (1.2 equiv). The reaction was stirred for 2 hours at room temperature, then was poured into EtOAc (10 mL). The aqueous was extracted with EtOAc (2×10 mL) and the combined organics were dried over $Na_2SO_4$, and then concentrated. The residue was transferred to a 2-mL microwave vial, and ethanol (1.5 mL), Hunig's base (0.152 mL, 0.869 mmol) and hydrazine hydrate (0.101 mL, 1.74 mmol) were added. The resulting mixture was heated at 150° C. for 30 minutes in Intermediate 324

2-Fluoro-4-{2-(methylamino)-6-[(3R)-3-methyl-4-morpholinyl]-4-pyrimidinyl}-6-(methylthio)benzonitrile

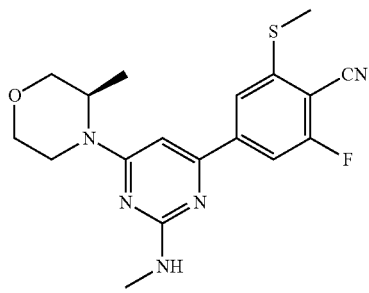 [SMILES: CNc1nc(-c2cc(F)c(C#N)c(SC)c2)cc(N2CCOC[C@H]2C)n1]

To a 4-mL vial was added 2,6-difluoro-4-{2-(methylamino)-6-[(3R)-3-methyl-4-morpholinyl]-4-pyrimidinyl}benzonitrile (100 mg, 0.290 mmol), DMF (1 mL), and 15% aqueous NaSMe (162 mg, 0.347 mmol), and the reaction mixture was stirred for 2 h at room temperature. The mixture was poured into EtOAc (10 mL). The aqueous was extracted with EtOAc (2×10 mL) and the combined organics were dried over $Na_2SO_4$, and then concentrated. The residue was purified by flash chromatography (0-40% EtOAc in hexanes, 12 g column) to afford the title compound (40 mg) as a yellow oil. LC-MS (ES) m/z=374 $[M+H]^+$.

Example 167

6-{2-(Methylamino)-6-[(3R)-3-methyl-4-morpholinyl]-4-pyrimidinyl}-4-(methylthio)-1H-indazol-3-amine

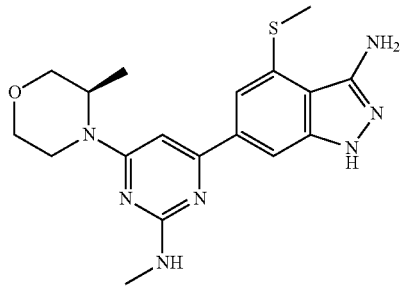 [SMILES: CNc1nc(-c2cc(SC)c3c(N)n[nH]c3c2)cc(N2CCOC[C@H]2C)n1]

A 2-mL microwave vial was charged with 2-fluoro-4-{2-(methylamino)-6-[(3R)-3-methyl-4-morpholinyl]-4-pyrimidinyl}-6-(methylthio)benzonitrile (40 mg, 0.107 mmol), hydrazine (0.037 mL, 0.643 mmol), Hunig's base (0.056 mL, 0.321 mmol) and ethanol (1.5 mL). The mixture was heated at 150° C. for 90 minutes in a microwave reactor. The reaction mixture was allowed to cool, and then concentrated. The resulting residue was dissolved in DMSO and purified by RP-HPLC (0-30% $CH_3CN$ in $H_2O$, 0.1% TFA). The product fractions were pooled, basified with $NaHCO_3$, then extracted into EtOAc. The organic layer was dried, then concentrated to afford the title compound (28 mg) as an off-white solid. LC-MS (ES) m/z=386 $[M+H]^+$. $^1$H NMR (400 MHz, DMSO-$d_6$): δ 1.19 (d, J=6.8 Hz, 3H), 2.61 (s, 3H), 2.83 (d, J=4.3 Hz, 3H), 3.04-3.22 (m, 1H), 3.40-3.52 (m, 1H), 3.55-3.66 (m, 1H), 3.67-3.79 (m, 1H), 3.85-3.99 (m, 1H), 4.05-4.23 (m, 1H), 4.44-4.59 (m, 1H), 5.10 (s, 2H), 6.38-6.71 (m, 2H), 7.26-7.49 (m, 1H), 7.66-7.88 (m, 1H), 11.62-11.92 (m, 1H).

Example 168

$N^4$-Methyl-6-{2-(methylamino)-6-[(3R)-3-methyl-4-morpholinyl]-4-pyrimidinyl}-1H-indazole-3,4-diamine

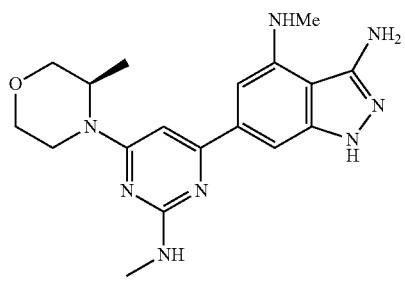 [SMILES: CNc1nc(-c2cc(NC)c3c(N)n[nH]c3c2)cc(N2CCOC[C@H]2C)n1]

To a 20-mL vial was added 2,6-difluoro-4-{2-(methylamino)-6-[(3R)-3-methyl-4-morpholinyl]-4-pyrimidinyl}benzonitrile (100 mg, 0.290 mmol), DMF (1 mL), and methylamine (2 M in THF, 0.174 mL, 0.347 mmol). The reaction was stirred overnight at room temperature. An additional 0.6 equiv of methylamine solution (2 M in THF) was added and the reaction stirred at room temperature for 3 days over the weekend. The reaction mixture was concentrated in vacuo, and the residue was dissolved in ethanol (1.5 mL), and hydrazine (0.101 mL, 1.737 mmol) and Hunig's base (0.152 mL, 0.869 mmol) were added. The reaction was heated at 150° C. for 60 minutes in a microwave reactor. The reaction mixture was concentrated, and the residue dissolved in DMSO and purified by RPHPLC. The product fractions were combined, basified with $NaHCO_3$ and extracted with EtOAc. The organics were combined, dried and concentrated to afford the title compound (40.5 mg) as a brown solid. LC-MS (ES) m/z=369 $[M+H]^+$. $^1$H NMR (400 MHz, DMSO-$d_6$): δ 1.18 (d, J=6.8 Hz, 3H), 2.73-2.91 (m, 6H), 3.03-3.15 (m, 1H), 3.39-3.52 (m, 1H), 3.62 (d, J=2.5 Hz, 1H), 3.67-3.78 (m, 1H), 3.87-3.98 (m, 1H), 4.01-4.15 (m, 1H), 4.41-4.55 (m, 1H), 5.07 (s, 2H), 5.59-5.74 (m, 1H), 6.26-6.62 (m, 3H), 7.14 (br. s., 1H), 11.35 (s, 1H).

Intermediate 325

4-Bromo-2-fluoro-6-[(phenylmethyl)oxy]benzonitrile

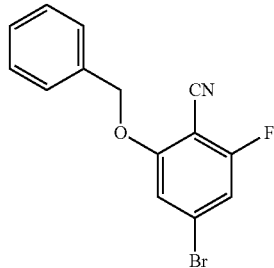 [SMILES: N#Cc1c(F)cc(Br)cc1OCc1ccccc1]

To a 500-mL RBF was added NaH (0.660 g, 27.5 mmol) and THF (100 mL). To this solution was added benzyl alcohol (2.385 mL, 22.94 mmol) in THF slowly via syringe, with external cooling (ice bath) when necessary. After the addition, the reaction mixture was stirred for 1 hour at room temperature. At this time, the mixture was transferred via syringe slowly to a solution of 4-bromo-2,6-difluorobenzonitrile (5 g, 22.94 mmol) in THF at 0° C. The solution was allowed to warm to room temperature and stirred over the weekend. The reaction was poured into water (50 mL), and extracted with EtOAc (3×100 mL). The organic layers were combined and dried over $Na_2SO_4$. The dried solution was filtered, and the filtrate was concentrated in vacuo to yield a pale yellow solid which was purified by flash chromatography (gradient elution 0-30% EtOAc in hexanes) to afford the title compound (3.911 g) as a white fluffy solid. $^1$H NMR (400 MHz, DMSO-$d_6$): δ 5.35 (s, 2H), 7.27-7.66 (m, 7H).

Intermediate 326

4-Bromo-2-fluoro-6-hydroxybenzonitrile

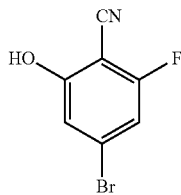

To a 500-mL RBF was added 4-bromo-2-fluoro-6-[(phenylmethyl)oxy]benzonitrile (5 g, 16.33 mmol) and $CH_2Cl_2$ (100 mL). The flask was cooled in an ice-water bath and $BBr_3$ (49.0 mL, 49.0 mmol) (solution in $CH_2Cl_2$) was added dropwise via syringe. The red solution was allowed to warm to room temperature over 1 hour. The solution was poured into water (200 mL) and extracted with EtOAc (3×200 mL). The combined organics were concentrated to a yellow residue. The residue was treated with $CH_2Cl_2$, and a precipitate formed which was collected to afford the title compound (2.830 g) as a fine yellow solid. $^1$H NMR (400 MHz, DMSO-$d_6$): δ 7.03 (t, J=1.4 Hz, 1H), 7.29 (dd, J=9.0, 1.6 Hz, 1H), 12.23 (s, 1H).

Intermediate 327

2-Fluoro-6-hydroxy-4-{2-(methylamino)-6-[(3R)-3-methyl-4-morpholinyl]-4-pyrimidinyl}benzonitrile

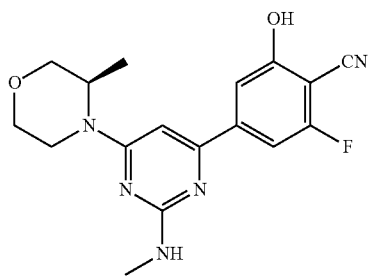 [SMILES: CNc1nc(-c2cc(O)c(C#N)c(F)c2)cc(N2CCOC[C@H]2C)n1]

To a 20-mL screw-cap vial was added 4-bromo-2-fluoro-6-hydroxybenzonitrile (500 mg, 2.315 mmol), bis-pinacolato diboron (705 mg, 2.78 mmol), potassium acetate (568 mg, 5.79 mmol), PdCl$_2$(dppf).CH$_2$Cl$_2$ adduct (95 mg, 0.116 mmol), and 1,4-dioxane (8 mL). The vial was capped and stirred for 4 h at 100° C. on a stirrer hot-plate. The reaction mixture was allowed to cool, then was diluted with ethyl acetate (50 mL) and washed with water (20 mL). The organic layer was dried over Na$_2$SO$_4$ and concentrated. The residue was added to a 20 mL microwave vial and 4-chloro-N-methyl-6-[(3R)-3-methyl-4-morpholinyl]-2-pyrimidinamine (0.279 g, 1.15 mmol), PdCl$_2$(dppf).CH$_2$Cl$_2$ adduct (0.047 g, 0.058 mmol), K$_2$CO$_3$ (2 M, 1.725 mL, 3.45 mmol), and 1,4-dioxane (6 mL) were added. The resulting mixture was heated at 140° C. for 10 minutes in a microwave reactor. The organic layer was separated and the aqueous was diluted with water (10 mL), neutralized with 0.1 N HCl (pH paper), then extracted with EtOAc (3×50 mL). The organics were combined, and then dried over Na2SO4. The dried solution was concentrated, then purified by flash chromatography 0-10% CH$_3$OH in CH$_2$Cl$_2$ (24 g column, dry-loaded) to afford the title compound (0.37 g) as a brown solid. LC-MS (ES) m/z=344 [M+H]$^+$.

Intermediate 328

2-Cyano-3-fluoro-5-{2-(methylamino)-6-[(3R)-3-methyl-4-morpholinyl]-4-pyrimidinyl}phenyl trifluoromethanesulfonate

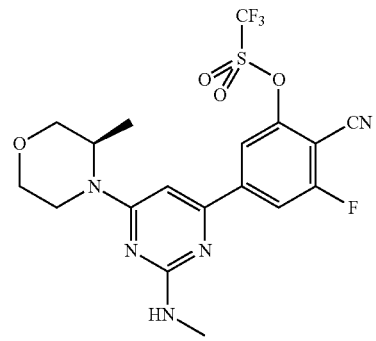 [SMILES: CNc1nc(-c2cc(F)c(C#N)c(OS(=O)(=O)C(F)(F)F)c2)cc(N2CCOC[C@H]2C)n1]

To a solution of 2-fluoro-6-hydroxy-4-{2-(methylamino)-6-[(3R)-3-methyl-4-morpholinyl]-4-pyrimidinyl}benzonitrile (270 mg, 0.786 mmol) and pyridine (0.382 mL, 4.72 mmol) in CH$_2$Cl$_2$ (9 mL) at 0° C. was added a solution of triflic anhydride (0.199 mL, 1.180 mmol) in CH$_2$Cl$_2$ (9 mL). The reaction was stirred overnight at room temperature then was poured into ammonium chloride (20 mL) and extracted with CH$_2$Cl$_2$ (3×50 mL). The combined organics were dried over Na$_2$SO$_4$ and concentrated to afford the crude title compound (374 mg). LC-MS (ES) m/z=476 [M+H]$^+$.

Intermediate 329

2-Fluoro-6-(2-furanyl)-4-{2-(methylamino)-6-[(3R)-3-methyl-4-morpholinyl]-4-pyrimidinyl}benzonitrile

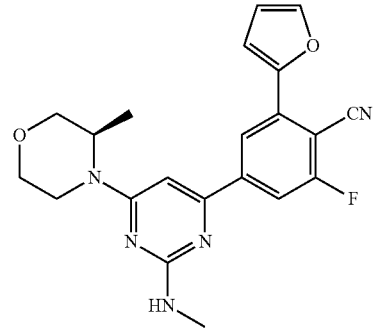 [SMILES: CNc1nc(-c2cc(F)c(C#N)c(-c3ccco3)c2)cc(N2CCOC[C@H]2C)n1]

A solution of 2-cyano-3-fluoro-5-{2-(methylamino)-6-[(3R)-3-methyl-4-morpholinyl]-4-pyrimidinyl}phenyl trifluoromethanesulfonate (374 mg, 0.786 mmol), 2-furanylboronic acid (176 mg, 1.572 mmol), PdCl$_2$(dppf).CH$_2$Cl$_2$ adduct (32.1 mg, 0.039 mmol), and K$_3$PO$_4$ (500 mg, 2.358 mmol) in 1,4-dioxane (10 mL) was heated overnight at 100° C. in a sealed tube. The reaction mixture was allowed to cool, then was partitioned between EtOAc (50 mL) and water (50 mL). The aqueous layer was neutralized with 0.1 M HCl (pH paper) and extracted with EtOAc (3×50 mL). The combined organics were dried over Na$_2$SO$_4$, and concentrated. The residue was purified by RP-HPLC (15-50% CH$_3$CN in water, 0.1% TFA). The product fractions were combined, basified with NaHCO$_3$, extracted with EtOAc, dried, and concentrated to afford the title compound (74 mg) as a brown solid LC-MS (ES) m/z=394 [M+H]$^+$.

Example 169

4-(2-Furanyl)-6-{2-(methylamino)-6-[(3R)-3-methyl-4-morpholinyl]-4-pyrimidinyl}-1H-indazol-3-amine

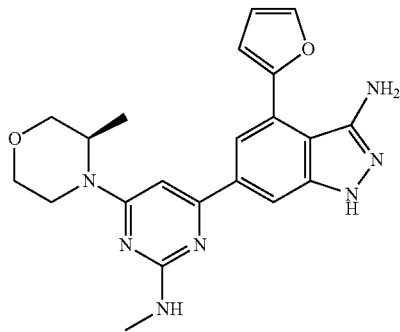 [SMILES: CNc1nc(-c2cc(-c3ccco3)c3c(N)n[nH]c3c2)cc(N2CCOC[C@H]2C)n1]

To a 2-mL microwave vial was added 2-fluoro-6-(2-furanyl)-4-{2-(methylamino)-6-[(3R)-3-methyl-4-morpholinyl]-4-pyrimidinyl}benzonitrile (50 mg, 0.127 mmol), hydrazine (0.044 mL, 0.763 mmol), Hunig's base (0.067 mL, 0.381 mmol) and ethanol (1 mL). The reaction was heated at 150° C. for 90 minutes in a microwave reactor. The reaction mixture was allowed to cool, then was concentrated in vacuo, and the residue was purified by flash chromatography (0-10% CH$_3$OH in CH$_2$Cl$_2$) to afford the title compound (35 mg, 0.086 mmol) as a yellow solid. LC-MS (ES) m/z=406 [M+H]$^+$. $^1$H NMR (400 MHz, DMSO-d$_6$): δ 1.20 (d, J=6.6 Hz, 3H), 2.75-2.94 (m, 3H), 3.05-3.21 (m, 1H), 3.41-3.52 (m, 1H), 3.57-3.67 (m, 1H), 3.68-3.80 (m, 1H), 3.87-4.00 (m, 1H), 4.06-4.21 (m, 1H), 4.45-4.62 (m, 1H), 5.11 (s, 2H), 6.46-6.68 (m, 2H), 6.68-6.74 (m, 1H), 6.97-7.16 (m, 1H), 7.74-7.82 (m, 1H), 7.89-7.95 (m, 1H), 7.97-8.07 (m, 1H), 11.95 (s, 1H).

Example 170

6-{2-Amino-6-[(3R)-3-methyl-4-morpholinyl]-4-pyrimidinyl}-4-(ethyloxy)-1H-indazol-3-amine

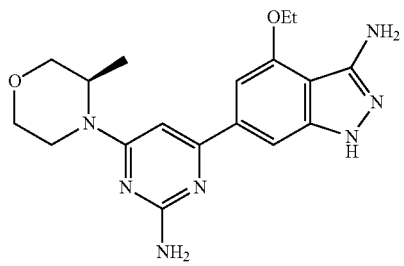 [SMILES: CCOc1cc(-c2cc(N3CCOC[C@H]3C)nc(N)n2)cc2[nH]nc(N)c12]

A stock solution of sodium ethoxide in ethanol was generated by the addition of ethanol (20 mL) to NaH (254 mg, 10.56 mmol), followed by stirring at room temperature for 30 minutes. To a 20-mL microwave vial was added 4-{2-amino-6-[(3R)-3-methyl-4-morpholinyl]-4-pyrimidinyl}-2,6-difluorobenzonitrile (700 mg, 2.11 mmol), DMF (2 mL), and ethanol (3 mL). The reaction was cooled to 0° C., and a solution of sodium ethoxide in ethanol (4.40 mL, 2.324 mmol) was added. The reaction was stirred overnight, and an additional portion of DMF was added, and the reaction was allowed to stir overnight at room temperature. An additional 0.25 equiv of sodium ethoxide in ethanol (1 mL) was added and the reaction was stirred for 8 hours. The reaction mixture was poured into NH$_4$Cl (sat.) and water (1:1, 30 mL) and extracted with EtOAc (3×100 mL). The combined organics were dried over Na$_2$SO$_4$ and concentrated. The residue was dissolved in ethanol (10 mL), and hydrazine hydrate (0.73 mL, 12.7 mmol) and Hunig's base (1.11 mL, 6.34 mmol) were added. The reaction was heated in a microwave reactor for 90 minutes at 150° C. The reaction was allowed to cool to room temperature, concentrated, and the resulting precipitate collected by filtration, washed with ethanol and dried in vacuo to afford the title compound (400 mg) as a white solid. LC-MS (ES) m/z=370 [M+H]$^+$. $^1$H NMR (400 MHz, DMSO-d$_6$): δ 1.18 (d, J=6.6 Hz, 3H), 1.45 (t, J=7.0 Hz, 3H), 3.05-3.15 (m, 1H), 3.38-3.49 (m, 1H), 3.54-3.65 (m, 1H), 3.66-3.78 (m, 1H), 3.88-3.96 (m, 1H), 4.08 (d, J=12.6 Hz, 1H), 4.21 (q, J=6.8 Hz, 2H), 4.50 (d, J=4.8 Hz, 1H), 5.00 (s, 2H), 6.10 (s, 2H), 6.49 (s, 1H), 6.91 (s, 1H), 7.49 (s, 1H), 11.53 (s, 1H).

Example 171

6-{2-Amino-6-[(3R)-3-methyl-4-morpholinyl]-4-pyrimidinyl}-4-[(1-methylethyl)oxy]-1H-indazol-3-amine

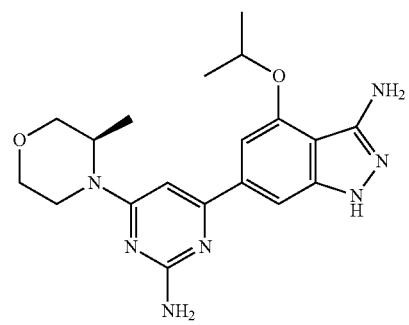 [SMILES: CC(C)Oc1cc(-c2cc(N3CCOC[C@H]3C)nc(N)n2)cc2[nH]nc(N)c12]

A stock solution of sodium isopropoxide in isopropanol was generated by the addition of isopropanol (40 mL) to NaH (254 mg, 10.56 mmol) at 0° C., followed by stirring at room temperature for 30 minutes, then at 40° C. for 30 minutes. The clear, colorless solution was allowed to cool to room temperature. To a 20-mL microwave vial was added 4-{2-amino-6-[(3R)-3-methyl-4-morpholinyl]-4-pyrimidinyl}-2,6-difluorobenzonitrile (700 mg, 2.11 mmol), DMF (2 mL) and isopropanol (3 mL). The reaction was cooled to 0° C., and a solution of sodium isopropoxide in isopropanol (8.80 mL, 2.324 mmol) was added dropwise. The reaction was stirred overnight. Then an additional portion of DMF (2 mL) was added, and the reaction was allowed to stir overnight at room temperature. At this time, an additional 0.4 equiv of sodium isopropoxide in isopropanol (3.2 mL) was added, and the reaction was stirred for 3 days over the weekend. The reaction mixture was concentrated, and the resulting residue was dissolved in ethanol (10 mL). Hydrazine hydrate (0.73 mL, 12.7 mmol) and Hunig's base (1.11 mL, 6.34 mmol) were added, and the reaction mixture was heated in a microwave reactor for 90 minutes at 150° C. The reaction was allowed to cool to room temperature, whereupon a precipitate formed. The precipitate was collected by filtration, washed with ethanol and dried in vacuo to afford the title compound (600 mg) as a white solid. LC-MS (ES) m/z=384 [M+H]$^+$. $^1$H NMR (400 MHz, DMSO-d$_6$): δ 1.18 (d, J=6.8 Hz, 3H), 1.38 (d, J=5.8, 3H), 1.37 (d, J=5.8, 3H), 3.03-3.19 (m, 1H), 3.40-3.50 (m, 1H), 3.53-3.65 (m, 1H), 3.66-3.79 (m, 1H), 3.92 (dd, J=11.1, 3.0 Hz, 1H), 4.08 (d, J=12.6 Hz, 1H), 4.45-4.55 (d, J=5.1 Hz, 1H), 4.78-4.94 (m, 1H), 4.99 (s, 2H), 6.09 (s, 2H), 6.47 (s, 1H), 6.94 (s, 1H), 7.45 (s, 1H), 11.50 (s, 1H).

Intermediate 330

(2R)-2-[(Phenylmethyl)amino]-1-butanol

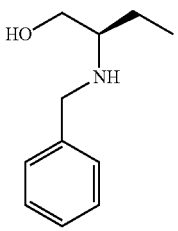

To (R)-(−)-2-amino-1-butanol (5 g, 56.1 mmol) in CH$_3$OH (120 mL) was added benzaldehyde (6.24 mL, 61.7 mmol), and the reaction mixture was stirred under nitrogen for 15 minutes. The mixture was then cooled in an ice bath and sodium borohydride (2.33 g, 61.7 mmol) was added portionwise. The mixture was stirred in the ice bath for 1.5 hours. NaOH (6 N, 25 mL) was added and the mixture was concentrated. The resulting residue was taken up in 100 mL H$_2$O and extracted with Et$_2$O (2×). The organics were combined, dried over Na$_2$SO$_4$ and concentrated to afford the title compound (10.92 g) as a fluffy white solid. LC-MS (ES) m/z=180 [M+H]$^+$.

Intermediate 331

[(2S,5R)-5-Ethyl-4-(phenylmethyl)-2-morpholinyl]methanol

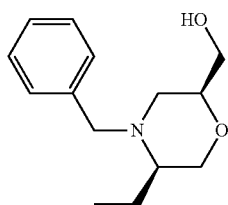 [SMILES: CC[C@@H]1CO[C@H](CO)CN1Cc1ccccc1]

To a solution of (2R)-2-[(phenylmethyl)amino]-1-butanol (10.06 g, 56.1 mmol) in 1,2-dichloroethane (DCE) (250 mL) was added (R)-(−)-epichlorohydrin (6.75 g, 72.9 mmol) followed by lithium perchlorate (5.97 g, 56.1 mmol) under nitrogen. The reaction was stirred for 2 days at room temperature, then sodium ethoxide (52.4 mL, 140 mmol) was added and the reaction continued to stir for 3 days. Saturated NH$_4$Cl was added, and the product was extracted with EtOAc. The organic layers were combined, dried over Na$_2$SO$_4$, and concentrated to afford the title compound (16.2 g) as a colorless oil. LC-MS (ES) m/z=236 [M+H]$^+$.

Intermediate 332

[(2S,5R)-5-Ethyl-2-morpholinyl]methanol

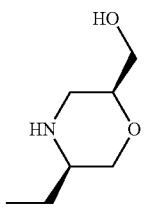

[(2S,5R)-5-Ethyl-4-(phenylmethyl)-2-morpholinyl]methanol (0.5 g, 2.125 mmol) was dissolved in CH$_3$OH (20 mL) and placed under a nitrogen atmosphere. Palladium on carbon (10 wt %, 0.023 g, 0.212 mmol) was added and the flask was flushed with nitrogen and evacuated (3×). Then the reaction was placed under an atmosphere of hydrogen (balloon), and stirred at room temperature overnight. The reaction mixture was filtered through celite and concentrated to afford the title compound (0.309 g) as a colorless oil. LC-MS (ES) m/z=146 [M+H]$^+$.

Intermediate 333

1,1-Dimethylethyl(2S,5R)-5-ethyl-2-(hydroxymethyl)-4-morpholinecarboxylate

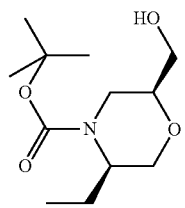 [SMILES: CC[C@@H]1CO[C@H](CO)CN1C(=O)OC(C)(C)C]

To [(2S,5R)-5-ethyl-2-morpholinyl]methanol (0.309 g, 2.125 mmol) in THF (10 mL) were added Boc$_2$O (0.493 mL, 2.125 mmol) and Hunig's base (0.371 mL, 2.125 mmol), and the reaction mixture was heated to 40° C. and stirred overnight. The reaction was then cooled to room temperature and concentrated to afford the title compound (0.488 g). LC-MS (ES) m/z=246 [M+H]$^+$.

Intermediate 334

(2S,5R)-4-{[(1,1-Dimethylethyl)oxy]carbonyl}-5-ethyl-2-morpholinecarboxylic acid

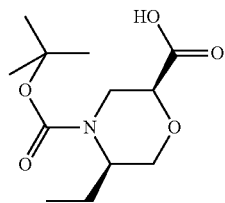 [SMILES: CC[C@@H]1CO[C@H](C(=O)O)CN1C(=O)OC(C)(C)C]

To a vigorously stirred solution of 1,1-dimethylethyl(2S,5R)-5-ethyl-2-(hydroxymethyl)-4-morpholinecarboxylate (2.52 g, 10.27 mmol) in CH₂Cl₂ (50 mL) that was cooled to 0° C. were added TEMPO (0.321 g, 2.054 mmol) and (diacetoxyiodo)benzene (7.28 g, 22.60 mmol). The ice bath was removed, and the reaction was allowed to warm to room temperature and stirred overnight. The reaction was quenched with CH₃OH and then concentrated to afford the title compound (0.711 g) as a yellow oil. LC-MS (ES) m/z=260 [M+H]⁺.

Intermediate 335

1,1-Dimethylethyl(2S,5R)-5-ethyl-2-[(phenylamino)carbonyl]-4-morpholinecarboxylate

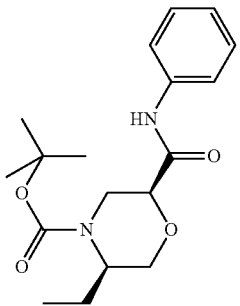 [SMILES: CC[C@@H]1CO[C@H](C(=O)Nc2ccccc2)CN1C(=O)OC(C)(C)C]

To (2S,5R)-4-{[(1,1-dimethylethyl)oxy]carbonyl}-5-ethyl-2-morpholinecarboxylic acid (0.250 g, 0.964 mmol) in CH₂Cl₂ (10 mL) were added aniline (0.088 mL, 0.964 mmol), HOAt (0.131 g, 0.964 mmol) and EDC (0.222 g, 1.157 mmol), and the reaction mixture was stirred at room temperature overnight. The reaction mixture was washed with water (2×), and the organics were dried over Na₂SO₄ and concentrated to afford the title compound (0.247 g) as a brown oil. LC-MS (ES) m/z=240 [M+H]⁺.

Intermediate 336

(2S,5R)-5-Ethyl-N-phenyl-2-morpholinecarboxamide

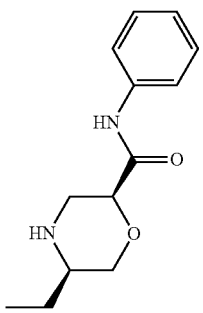 [SMILES: CC[C@@H]1CO[C@H](C(=O)Nc2ccccc2)CN1]

1,1-Dimethylethyl(2S,5R)-5-ethyl-2-[(phenylamino)carbonyl]-4-morpholinecarboxylate (0.269 g, 0.804 mmol) was taken up in HCl in 1,4-dioxane (4 M, 0.024 mL, 0.804 mmol) and stirred at room temperature overnight. The reaction was concentrated to yield a HCl salt of the title compound (0.198 g) as a brown oil. LC-MS (ES) m/z=235 [M+H]⁺.

Intermediate 337

(2S,5R)-4-(2-Amino-6-chloro-4-pyrimidinyl)-5-ethyl-N-phenyl-2-morpholinecarboxamide

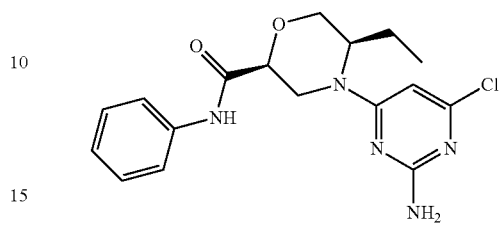

(2S,5R)-5-Ethyl-N-phenyl-2-morpholinecarboxamide (0.3118 g, 1.331 mmol) and 2,6-dichloropyrimidine (0.218 g, 1.331 mmol) were added to a 20 mL microwave vessel and dissolved in CH₃CN (5 mL). Hunig's base (1.162 mL, 6.65 mmol) was added, and the reaction was capped and irradiated at 150° C. for 2 hours. The reaction mixture was then diluted with H₂O and extracted with EtOAc. The organic layers were combined and dried to afford the title compound (0.419 g). LC-MS (ES) m/z=362 [M+H]⁺.

Example 172

(2S,5R)-4-[2-Amino-6-(3-amino-1H-indazol-6-yl)-4-pyrimidinyl]-5-ethyl-N-phenyl-2-morpholinecarboxamide

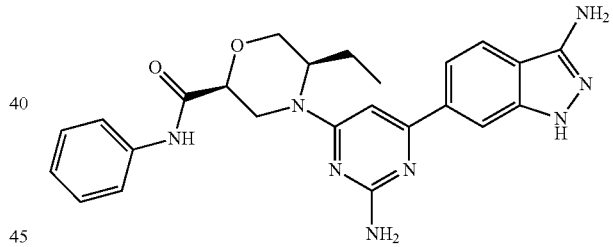

(2S,5R)-4-(2-Amino-6-chloro-4-pyrimidinyl)-5-ethyl-N-phenyl-2-morpholinecarboxamide (0.4185 g, 1.157 mmol), (4-cyano-3-fluorophenyl)boronic acid (0.572 g, 3.47 mmol) and Pd(PPh₃)₄ (0.067 g, 0.058 mmol) were added to a 20 mL microwave vessel followed by 1,4-dioxane (5 mL) and saturated aqueous NaHCO₃ (2.5 mL). The reaction was irradiated at 130° C. for 30 minutes. SiliaBond® Thiol (4.45 g, 5.78 mmol) was added and the reaction stirred at room temperature for 3 h. The reaction was then filtered and the filtrate was diluted with H₂O and washed with EtOAc (2×). The organics were dried over Na₂SO₄ and concentrated to afford a brown oil which was taken up in CH₃CN (5 mL) in a 20 mL microwave vessel. Hydrazine (0.17 mL, 5.5 mmol) and Hunig's base (1.92 mL, 11.0 mmol) were added, and the reaction was irradiated at 150° C. for 10 minutes. The reaction mixture was concentrated and then purified by reverse phase HPLC (25-55% CH₃CN/H₂O, 0.1% TFA). Product fractions were combined and concentrated to afford a yellow solid that was taken up in 1 mL H₂O and lyophilized to afford a TFA salt of the title compound (12.7 mg) as a yellow solid. LC-MS (ES) m/z=459 [M+H]⁺.

Intermediate 338

1,1-Dimethylethyl(2S,5R)-2-[(cyclohexylamino)carbonyl]-5-ethyl-4-morpholinecarboxylate

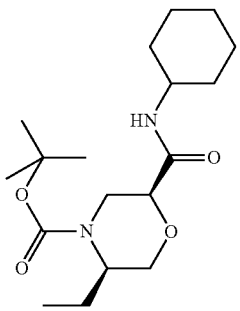 [SMILES: CC[C@@H]1CO[C@H](C(=O)NC2CCCCC2)CN1C(=O)OC(C)(C)C]

To (2S,5R)-4-{[(1,1-dimethylethyl)oxy]carbonyl}-5-ethyl-2-morpholinecarboxylic acid (0.250 g, 0.964 mmol) in CH$_2$Cl$_2$ (10 mL) were added cyclohexylamine (0.096 g, 0.964 mmol), HOAt (0.131 g, 0.964 mmol) and EDC (0.222 g, 1.157 mmol), and the reaction was stirred at room temperature overnight. The reaction mixture was washed with H$_2$O (2×) and the organics were dried over Na$_2$SO$_4$ and concentrated to afford the title compound (0.296 g) as a brown oil. LC-MS (ES) m/z=241 [M+H-Boc]$^+$.

Intermediate 339

(2S,5R)—N-Cyclohexyl-5-ethyl-2-morpholinecarboxamide

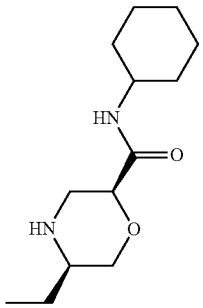 [SMILES: CC[C@@H]1CO[C@H](C(=O)NC2CCCCC2)CN1]

1,1-Dimethylethyl(2S,5R)-2-[(cyclohexylamino)carbonyl]-5-ethyl-4-morpholinecarboxylate (0.2963 g, 0.870 mmol) was taken up in HCl in 1,4-dioxane (4 M, 5 ml, 165 mmol) and stirred at room temperature overnight. The reaction was concentrated to afford a HCl salt of the title compound (0.256 g). LC-MS (ES) m/z=241 [M+H]$^+$.

Intermediate 340

(2S,5R)-4-[2-Amino-6-(4-cyano-3-fluorophenyl)-4-pyrimidinyl]-N-cyclohexyl-5-ethyl-2-morpholinecarboxamide

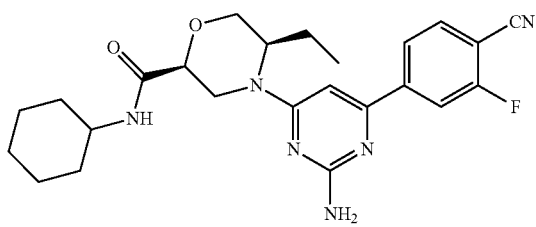 [SMILES: CC[C@@H]1CO[C@H](C(=O)NC2CCCCC2)CN1c1cc(-c2ccc(C#N)c(F)c2)nc(N)n1]

(2S,5R)—N-Cyclohexyl-5-ethyl-2-morpholinecarboxamide (0.256 g, 1.07 mmol) was taken up in CH$_3$CN (5 mL) in a 20 mL microwave vessel, followed by the addition of Hunig's base (0.93 mL, 5.33 mmol) and 2,6-dichloropyrimidine (0.175 g, 1.07 mmol). The reaction was irradiated at 150° C. for 2 hours. The reaction mixture was then diluted with H$_2$O and extracted with EtOAc (2×). The organics were dried and concentrated to afford a brown oil which was added to a 20 mL microwave vessel with Pd(PPh$_3$)$_4$ (0.054 g, 0.047 mmol) followed by 1,4-dioxane (5 mL) and saturated aqueous NaHCO$_3$ (2.5 mL). The reaction was irradiated at 130° C. for 30 minutes. SiliaBond® Thiol (4.45 g, 5.78 mmol) was added to the reaction mixture and stirred at room temperature for 3 hours. The reaction was then filtered and the filtrate was diluted with H$_2$O and washed with EtOAc (2×). The organics were dried over Na$_2$SO$_4$ and concentrated to afford the crude title compound (0.583 g) as a brown oil. LC-MS (ES) m/z=453 [M+H]$^+$.

Example 173

(2S,5R)-4-[2-Amino-6-(3-amino-1H-indazol-6-yl)-4-pyrimidinyl]-N-cyclohexyl-5-ethyl-2-morpholinecarboxamide

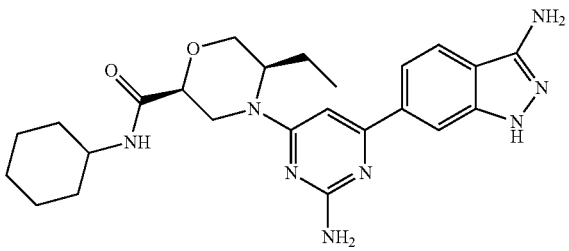 [SMILES: CC[C@@H]1CO[C@H](C(=O)NC2CCCCC2)CN1c1cc(-c2ccc3c(N)n[nH]c3c2)nc(N)n1]

(2S,5R)-4-[2-Amino-6-(4-cyano-3-fluorophenyl)-4-pyrimidinyl]-N-cyclohexyl-5-ethyl-2-morpholinecarboxamide (0.583 g, 1.288 mmol) was taken up in CH$_3$CN (5 mL) followed by the addition of hydrazine (0.162 mL, 5.15 mmol) and Hunig's base (1.800 mL, 10.31 mmol) in a 20 mL microwave vessel. The reaction was irradiated at 150° C. for 10 minutes. The reaction mixture was purified by reverse phase HPLC (25-55% CH$_3$CN/H$_2$O, 0.1% TFA). Product fractions were combined and concentrated to afford a TFA salt of the title compound (29 mg) as a yellow solid. LC-MS (ES) m/z=465 [M+H]$^+$.

Intermediate 341

(2S,5R)-4-[6-Chloro-2-(methylamino)-4-pyrimidinyl]-5-ethyl-N-phenyl-2-morpholinecarboxamide

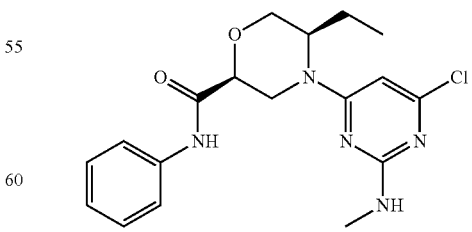

4,6-Dichloro-N-methyl-2-pyrimidinamine (0.150 g, 0.845 mmol) was added to a 20 mL microwave vial followed by the addition of (2S,5R)-5-ethyl-N-phenyl-2-morpholinecarboxamide (0.198 g, 0.845 mmol) in CH$_3$CN (5 mL) and Hunig's base (0.738 mL, 4.23 mmol). The reaction was irradiated at 150° C. for 10 minutes. The reaction was left in the 20 mL sealed microwave vessel and heated to 100° C. over the weekend. The reaction mixture was diluted with water and extracted with EtOAc (2×). The organic layers were combined and dried to afford the crude title compound (0.410 g). LC-MS (ES) m/z=376 [M+H]$^+$.

Intermediate 342

(2S,5R)-4-[6-(4-Cyano-3-fluorophenyl)-2-(methylamino)-4-pyrimidinyl]-5-ethyl-N-phenyl-2-morpholinecarboxamide

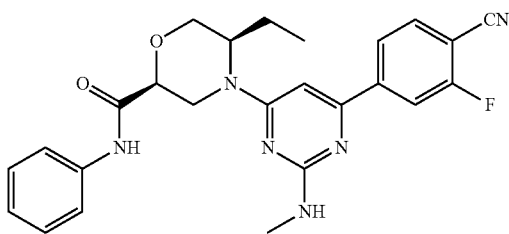 [SMILES: CC[C@@H]1CO[C@H](C(=O)Nc2ccccc2)CN1c1cc(-c2ccc(C#N)c(F)c2)nc(NC)n1]

4-Cyano-3-fluorophenyl)boronic acid (0.279 g, 1.690 mmol) was added to a 20 mL microwave vessel followed by the addition of Pd(PPh$_3$)$_4$ (0.049 g, 0.042 mmol) and (2S,5R)-4-[6-chloro-2-(methylamino)-4-pyrimidinyl]-5-ethyl-N-phenyl-2-morpholinecarboxamide (0.318 g, 0.845 mmol) dissolved in 1,4-dioxane (5 mL). Saturated aqueous NaHCO$_3$ (2.5 mL) was added and the reaction was irradiated at 130° C. for 30 minutes. SiliaBond® Thiol (3.25 g, 4.23 mmol) was added to the reaction mixture and it was stirred at room temperature for 2 hours, then filtered. The filtrate was then diluted with H$_2$O and extracted with EtOAc (2×). The organics were dried and concentrated to afford the crude title compound (0.412 g) as a dark brown oil. LC-MS (ES) m/z=461 [M+H]$^+$.

Example 174

(2S,5R)-4-[6-(3-Amino-1H-indazol-6-yl)-2-(methylamino)-4-pyrimidinyl]-5-ethyl-N-phenyl-2-morpholinecarboxamide

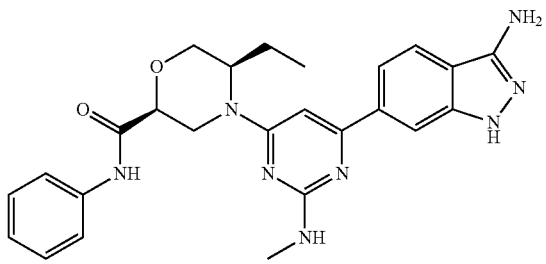 [SMILES: CC[C@@H]1CO[C@H](C(=O)Nc2ccccc2)CN1c1cc(-c2ccc3c(N)n[nH]c3c2)nc(NC)n1]

(2S,5R)-4-[6-(4-Cyano-3-fluorophenyl)-2-(methylamino)-4-pyrimidinyl]-5-ethyl-N-phenyl-2-morpholinecarboxamide (389 mg, 0.845 mmol) was taken up in CH$_3$CN (5 mL) and then added to a 20 mL microwave vessel followed by the addition of hydrazine (0.106 mL, 3.38 mmol) and Hunig's base (1.181 mL, 6.76 mmol). The reaction was irradiated at 150° C. for 15 minutes. The reaction was concentrated and purified via reverse phase HPLC (15-45% CH$_3$CN/H$_2$O, 0.1% TFA). Fractions were combined and concentrated to afford a TFA salt of the title compound (48.5 mg). LC-MS (ES) m/z=473 [M+H]$^+$. $^1$H NMR (400 MHz, DMSO-d$_6$): δ 0.92 (t, 3H), 1.74-1.86 (m, 2H), 3.34 (s, 3H), 3.71-3.74 (m, 1H), 3.74-3.77 (m, 1H), 4.03 (bs, 1H), 4.06 (bs, 1H), 4.10-4.16 (m, 1H), 4.64-4.85 (m, 1H), 5.39 (bs, 2H), 6.60-6.67 (m, 2H), 7.07-7.13 (m, 1H), 7.31-7.36 (m, 2H), 7.60-7.64 (m, 1H), 7.70-7.74 (m, 3H), 8.00 (s, 1H), 9.87 (bs, 1H), 11.50 (bs, 1H).

Intermediate 343

(2S,5R)-4-[6-Chloro-2-(methylamino)-4-pyrimidinyl]-N-cyclohexyl-5-ethyl-2-morpholinecarboxamide

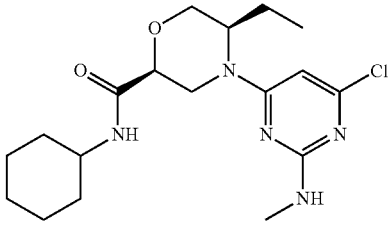 [SMILES: CC[C@@H]1CO[C@H](C(=O)NC2CCCCC2)CN1c1cc(Cl)nc(NC)n1]

4,6-Dichloro-N-methyl-2-pyrimidinamine (0.141 g, 0.791 mmol) was added to a 20 mL microwave vial followed by the addition of (2S,5R)—N-cyclohexyl-5-ethyl-2-morpholinecarboxamide (0.190 g, 0.791 mmol) in CH$_3$CN (5 mL) and Hunig's base (0.690 mL, 3.95 mmol). The reaction was irradiated at 150° C. for 10 minutes. The reaction was left in the 20 mL sealed microwave vessel and heated to 100° C. over the weekend. The reaction mixture was diluted with water and extracted with EtOAc (2×). The organic layers were combined and dried to afford the title compound (0.302 g). LC-MS (ES) m/z=382 [M+H]$^+$.

Intermediate 344

(2S,5R)-4-[6-(4-Cyano-3-fluorophenyl)-2-(methylamino)-4-pyrimidinyl]-N-cyclohexyl-5-ethyl-2-morpholinecarboxamide

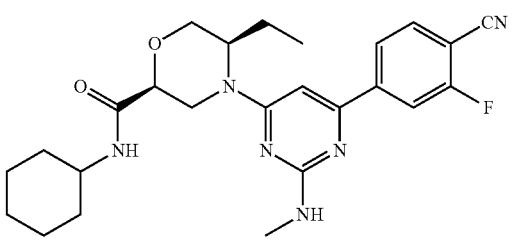 [SMILES: CC[C@@H]1CO[C@H](C(=O)NC2CCCCC2)CN1c1cc(-c2ccc(C#N)c(F)c2)nc(NC)n1]

(4-Cyano-3-fluorophenyl)boronic acid (0.261 g, 1.582 mmol) was added to a 20 mL microwave vessel followed by the addition of Pd(PPh$_3$)$_4$ (0.046 g, 0.040 mmol) and (2S,5R)-4-[6-chloro-2-(methylamino)-4-pyrimidinyl]-N-cyclohexyl-5-ethyl-2-morpholinecarboxamide (0.302 g, 0.791 mmol) dissolved in 1,4-dioxane (5 mL). Saturated aqueous NaHCO$_3$ (2.5 mL) was added and the reaction was irradiated at 130° C. for 30 minutes. SiliaBond® Thiol (3.04 g, 3.96 mmol) was added to the reaction and it was stirred at room temperature for 2 hours and then filtered. The filtrate was then diluted with H$_2$O and extracted with EtOAc (2×). The organics were dried

Example 175

(2S,5R)-4-[6-(3-amino-1H-indazol-6-yl)-2-(methylamino)-4-pyrimidinyl]-N-cyclohexyl-5-ethyl-2-morpholinecarboxamide

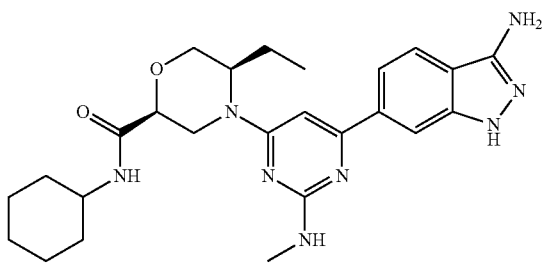 [SMILES: CC[C@@H]1CO[C@H](C(=O)NC2CCCCC2)CN1c1cc(-c2ccc3c(N)n[nH]c3c2)nc(NC)n1]

(2S,5R)-4-[6-(4-Cyano-3-fluorophenyl)-2-(methylamino)-4-pyrimidinyl]-N-cyclohexyl-5-ethyl-2-morpholinecarboxamide (369 mg, 0.791 mmol) was taken up in CH$_3$CN (5 mL) and then added to a 20 mL microwave vessel followed by the addition of hydrazine (0.099 mL, 3.16 mmol) and Hunig's base (1.105 mL, 6.33 mmol). The reaction was irradiated at 150° C. for 15 minutes. Solvent was removed from the reaction mixture via N$_2$ evaporator and the resulting residue was taken up in 5 mL DMSO for reverse phase purification (15-45% CH$_3$CN/H$_2$O, 0.1% TFA). Fractions were combined and concentrated to afford a TFA salt of the title compound (30.7 mg). LC-MS (ES) m/z=479 [M+H]$^+$. $^1$H NMR (400 MHz, DMSO-d$_6$): δ 0.85-0.92 (m, 3H), 1.07-1.15 (m, 2H), 1.20-1.35 (m, 4H), 1.52-1.61 (m, 2H), 1.65-1.80 (m, 4H), 2.81-2.88 (m, 5H), 3.56-3.63 (m, 1H), 3.63-3.69 (m, 1H), 3.86-3.92 (m, 1H), 3.93-3.99 (m, 1H), 4.57-4.83 (m, 2H), 5.38 (bs, 1H), 6.53-6.64 (m, 2H), 7.58-7.67 (m, 2H), 7.70-7.74 (m, 1H), 7.97 (bs, 1H), 11.49 (bs, 1H).

Intermediate 345

1,1-Dimethylethyl(2S,5R)-5-ethyl-2-{[(phenylmethyl)amino]carbonyl}-4-morpholinecarboxylate

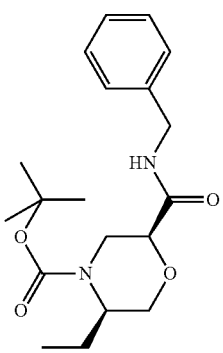 [SMILES: CC[C@@H]1CO[C@H](C(=O)NCc2ccccc2)CN1C(=O)OC(C)(C)C]

To (2S,5R)-4-{[(1,1-dimethylethyl)oxy]carbonyl}-5-ethyl-2-morpholinecarboxylic acid (0.390 g, 1.504 mmol) in CH$_2$Cl$_2$ (10 mL) were added benzylamine (0.164 mL, 1.504 mmol), HOAt (0.205 g, 1.504 mmol) and EDC (0.346 g, 1.805 mmol). The reaction was stirred at room temperature overnight. The reaction mixture was washed with H$_2$O (3×) and the organics were then dried over Na$_2$SO$_4$ and concentrated to afford the title compound (0.551 g). LC-MS (ES) m/z=249 [M+H-Boc]$^+$.

Intermediate 346

(2S,5R)-5-Ethyl-N-(phenylmethyl)-2-morpholinecarboxamide

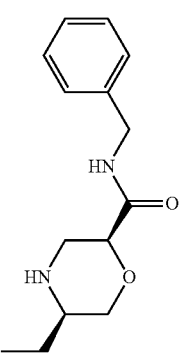 [SMILES: CC[C@@H]1CO[C@H](C(=O)NCc2ccccc2)CN1]

1,1-Dimethylethyl(2S,5R)-5-ethyl-2-{[(phenylmethyl)amino]carbonyl}-4-morpholinecarboxylate (0.551 g, 1.581 mmol) was taken up in HCl in 1,4-dioxane (4 M, 5 mL, 165 mmol) and was stirred at room temperature overnight. The reaction was concentrated to afford a HCl salt of the title compound (0.400 g) as a brown oil. LC-MS (ES) m/z=249 [M+H]$^+$.

Intermediate 347

(2S,5R)-4-[6-Chloro-2-(methylamino)-4-pyrimidinyl]-5-ethyl-N-(phenylmethyl)-2-morpholinecarboxamide

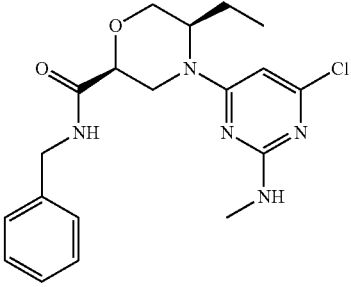 [SMILES: CC[C@@H]1CO[C@H](C(=O)NCc2ccccc2)CN1c1cc(Cl)nc(NC)n1]

4,6-Dichloro-N-methyl-2-pyrimidinamine (0.143 g, 0.805 mmol) was added to a 20 mL microwave vial followed by the addition of (2S,5R)-5-ethyl-N-(phenylmethyl)-2-morpholinecarboxamide (0.200 g, 0.805 mmol) in CH$_3$CN (5 mL) and Hunig's base (0.703 mL, 4.03 mmol). The reaction was irradiated at 150° C. for 10 minutes. The reaction was left in the 20 mL sealed microwave vessel and heated to 100° C. over the weekend. The reaction mixture was diluted with water and extracted with EtOAc (2×). The organic layers were combined and dried to afford the title compound (0.805 g) as an oil. LC-MS (ES) m/z=376 [M+H]$^+$.

Intermediate 348

(2S,5R)-4-[6-(4-Cyano-3-fluorophenyl)-2-(methylamino)-4-pyrimidinyl]-5-ethyl-N-(phenylmethyl)-2-morpholinecarboxamide

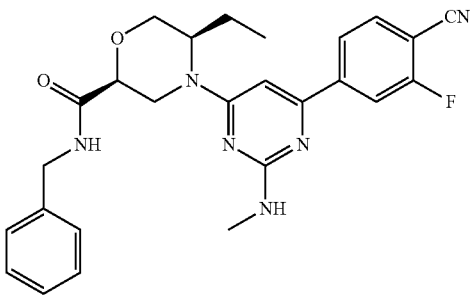 [SMILES: CC[C@@H]1CO[C@H](C(=O)NCc2ccccc2)CN1c1cc(-c2ccc(C#N)c(F)c2)nc(NC)n1]

(4-Cyano-3-fluorophenyl)boronic acid (0.266 g, 1.61 mmol) was added to a 20 mL microwave vessel followed by the addition of Pd(PPh$_3$)$_4$ (0.047 g, 0.040 mmol) and (2S,5R)-4-[6-chloro-2-(methylamino)-4-pyrimidinyl]-5-ethyl-N-(phenylmethyl)-2-morpholinecarboxamide (0.314 g, 0.805 mmol) dissolved in 1,4-dioxane (5 mL). Saturated aqueous NaHCO$_3$ (2.5 mL) was added and the reaction was irradiated at 130° C. for 30 minutes. SiliaBond® Thiol (3.10 g, 4.03 mmol) was added to the reaction and it was stirred at room temperature for 2 hours and then filtered. The filtrate was then diluted with H$_2$O and extracted with EtOAc (×2). The organics were dried and concentrated to afford the title compound (0.365 g) as a dark brown oil. LC-MS (ES) m/z=475 [M+H]$^+$.

Example 176

(2S,5R)-4-[6-(3-Amino-1H-indazol-6-yl)-2-(methylamino)-4-pyrimidinyl]-5-ethyl-N-(phenylmethyl)-2-morpholinecarboxamide

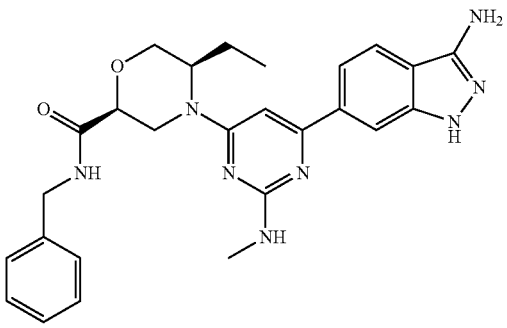 [SMILES: CC[C@@H]1CO[C@H](C(=O)NCc2ccccc2)CN1c1cc(-c2ccc3c(N)n[nH]c3c2)nc(NC)n1]

(2S,5R)-4-[6-(4-Cyano-3-fluorophenyl)-2-(methylamino)-4-pyrimidinyl]-5-ethyl-N-(phenylmethyl)-2-morpholinecarboxamide (382 mg, 0.805 mmol) was taken up in CH$_3$CN (5 mL) and then added to a 20 mL microwave vessel followed by the addition of hydrazine (0.101 mL, 3.22 mmol) and Hunig's base (1.125 mL, 6.44 mmol). The reaction was irradiated at 150° C. for 15 minutes. The reaction was concentrated and purified via reverse phase HPLC (15-45% CH$_3$CN/H$_2$O, 0.1% TFA). Fractions were combined and concentrated to afford a TFA salt the title compound (36.9 mg).

LC-MS (ES) m/z=487 [M+H]$^+$. $^1$H NMR (400 MHz, DMSO-d$_6$): δ 0.86-0.93 (m, 3H), 1.63-1.83 (m, 2H), 2.76-2.79 (m, 1H), 2.81-2.87 (m, 3H), 3.67-3.73 (m, 1H), 3.95-4.03 (m, 2H), 4.30-4.39 (m, 2H), 4.66 (s, 2H), 5.37-5.41 (m, 2H), 5.77 (s, 2H), 6.60 (bs, 2H), 7.22-7.36 (m, 5H), 7.59-7.63 (m, 1H), 7.70-7.74 (m, 1H), 7.98 (bs, 1H), 8.48-8.56 (m, 1H), 11.49 (bs, 1H).

Intermediate 349

4-Chloro-6-[(3R)-3-ethyl-4-morpholinyl]-N-methyl-2-pyrimidinamine

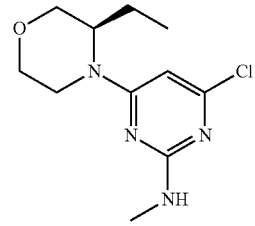 [SMILES: CC[C@@H]1COCCN1c1cc(Cl)nc(NC)n1]

(3R)-3-Ethylmorpholine (5 g, 43.4 mmol) was taken up in CH$_3$CN (100 mL) and Hunig's base (15.2 mL, 87 mmol), followed by the addition of 4,6-dichloro-N-methyl-2-pyrimidinamine (6.96 g, 39.1 mmol), and the reaction was heated to 130° C. overnight in a sealed tube. The reaction mixture was concentrated and then purified via flash chromatography (0-15% EtOAc/CHCl$_3$, 400 g). Fractions were combined and concentrated to afford the title compound (1.6 g) as a colorless oil. LC-MS (ES) m/z=257 [M+H]$^+$.

Intermediate 350

4-[6-[(3R)-3-Ethyl-4-morpholinyl]-2-(methylamino)-4-pyrimidinyl]-2-fluorobenzonitrile

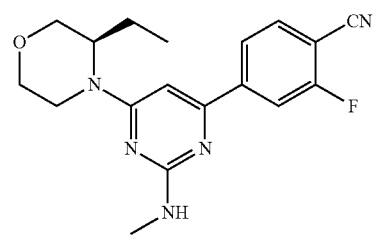 [SMILES: CC[C@@H]1COCCN1c1cc(-c2ccc(C#N)c(F)c2)nc(NC)n1]

4-Chloro-6-[(3R)-3-ethyl-4-morpholinyl]-N-methyl-2-pyrimidinamine (250 mg, 0.974 mmol) was added to a 20 mL microwave vial, followed by (4-cyano-3-fluorophenyl)boronic acid (209 mg, 1.266 mmol), PdCl$_2$(dppf).CH$_2$Cl$_2$ adduct (39.8 mg, 0.049 mmol), 2M K$_2$CO$_3$ (1.461 mL, 2.92 mmol) and 1,4-dioxane (4 mL). The mixture was heated to 140° C. for 10 minutes. The reaction mixture was filtered through a silica plug and washed with EtOAc (3×). The filtrate was then washed with H$_2$O (2×) and the organic layer was dried over Na$_2$SO$_4$ and concentrated to afford the title compound (464 mg) as a brown oil. LC-MS (ES) m/z=342 [M+H]$^+$.

Example 177

6-[6-[(3R)-3-Ethyl-4-morpholinyl]-2-(methylamino)-4-pyrimidinyl]-1H-indazol-3-amine

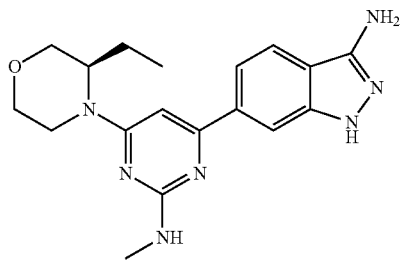 [SMILES: CC[C@@H]1COCCN1c1cc(-c2ccc3c(N)n[nH]c3c2)nc(NC)n1]

4-[6-[(3R)-3-Ethyl-4-morpholinyl]-2-(methylamino)-4-pyrimidinyl]-2-fluorobenzonitrile (0.464 g, 1.359 mmol) was taken up in $CH_3CN$ (5 mL) followed by the addition of hydrazine (0.171 mL, 5.44 mmol) and Hunig's (1.899 mL, 10.87 mmol) in a 20 mL microwave vial. The reaction was irradiated at 150° C. for 1 hour. The reaction mixture was then concentrated and the resulting residue was purified using reverse phase HPLC (5-30% $CH_3CN/H_2O$, 0.1% TFA). Fractions were combined and diluted with EtOAc. The organics were washed with saturated $NaHCO_3$ solution (2×) that was back extracted with EtOAc (×1). The organics were combined and dried over $Na_2SO_4$. The product was taken up in 2 mL $H_2O$ and lyophilized to afford the title compound (137 mg) as a white fluffy powder. LC-MS (ES) m/z=354 [M+H]$^+$. $^1$H NMR (400 MHz, DMSO-d$_6$): δ 0.89 (t, 3H), 1.60-1.82 (m, 2H), 2.83 (d, J=4.0 Hz, 3H), 3.10 (d, J=2.3 Hz, 1H), 3.43 (d, J=2.5 Hz, 1H), 3.52 (dd, J=11.5, 2.9 Hz, 1H), 3.84 (d, J=11.4 Hz, 1H), 3.89 (dd, J=11.2, 3.2 Hz, 1H), 4.03 (q, J=7.1 Hz, 1H), 4.14-4.26 (m, 1H), 4.29-4.38 (m, 1H), 5.38 (s, 2H), 6.55 (bs, 2H), 7.59 (d, J=8.6 Hz, 1H), 7.71 (d, J=8.6 Hz, 1H), 7.97 (bs, 1H), 11.50 (bs, 1H).

Intermediate 351

4-[6-[(3R)-3-Ethyl-4-morpholinyl]-2-(methylamino)-4-pyrimidinyl]-2,6-difluorobenzonitrile

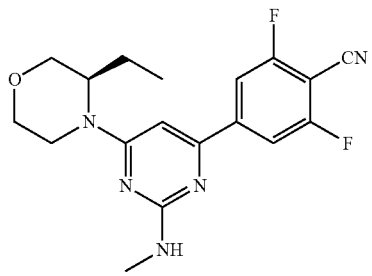 [SMILES: CC[C@@H]1COCCN1c1cc(-c2cc(F)c(C#N)c(F)c2)nc(NC)n1]

4-Chloro-6-[(3R)-3-ethyl-4-morpholinyl]-N-methyl-2-pyrimidinamine (250 mg, 0.974 mmol) was added to a 20 mL microwave vial, followed by (4-cyano-3,5-difluorophenyl)boronic acid (356 mg, 1.948 mmol), $PdCl_2(dppf) \cdot CH_2Cl_2$ adduct (39.8 mg, 0.049 mmol), 2M $K_2CO_3$ (1.461 mL, 2.92 mmol) and 1,4-dioxane (4 mL). The mixture was heated to 140° C. for 10 minutes. The reaction mixture was filtered through a silica plug and washed with EtOAc (3×). The filtrate was then washed with $H_2O$ (2×) and the organic layer was dried over $Na_2SO_4$ and concentrated to afford the title compound (453 mg) as a brown oil. LC-MS (ES) m/z=360 [M+H]$^+$.

Example 178

6-[6-[(3R)-3-Ethyl-4-morpholinyl]-2-(methylamino)-4-pyrimidinyl]-4-fluoro-1H-indazol-3-amine

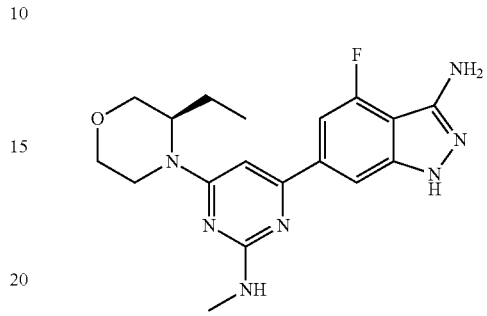

4-[6-[(3R)-3-Ethyl-4-morpholinyl]-2-(methylamino)-4-pyrimidinyl]-2-fluorobenzonitrile (0.453 g, 1.261 mmol) was taken up in $CH_3CN$ (5 mL) followed by the addition of hydrazine (0.158 mL, 5.04 mmol) and Hunig's base (1.76 mL, 10.1 mmol) in a 20 mL microwave vial. The reaction was irradiated at 150° C. for 1 hour. The reaction mixture was concentrated and purified by reverse phase HPLC (8-28% $CH_3CN/H_2O$, 0.1% TFA). Fractions were combined and diluted with EtOAc. The organics were washed with saturated $NaHCO_3$ solution (2×) that was back extracted with EtOAc. The organics were combined and dried over $Na_2SO_4$. The product was taken up in 2 mL $H_2O$ and lyophilized to afford the title compound (137 mg) as a white fluffy powder. LC-MS (ES) m/z=372 [M+H]$^+$. $^1$H NMR (400 MHz, DMSO-d$_6$): δ 0.88 (t, 3H), 1.60-1.81 (m, 2H), 2.82 (d, J=4.0 Hz, 3H), 3.05-3.16 (m, 1H), 3.43 (d, J=2.53 Hz, 1H), 3.51 (dd, J=11.5, 2.9 Hz, 1H), 3.83 (d, J=11.4 Hz, 1H), 3.89 (dd, J=11.1, 3.0 Hz, 1H), 4.03 (d, J=7.1 Hz, 1H), 4.16-4.28 (m, 1H), 4.30-4.43 (m, 1H), 5.26 (s, 2H), 6.58 (bs, 2H), 7.36 (d, J=12.4 Hz, 1H), 7.84 (bs, 1H), 11.89 (s, 1H).

Example 179

6-[6-[(3R)-3-Ethyl-4-morpholinyl]-2-(methylamino)-4-pyrimidinyl]-4-(methyloxy)-1H-indazol-3-amine

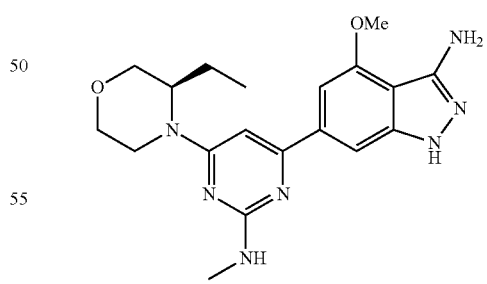

$CH_3OH$ (10 mL) was added dropwise to a 100 mL RBF at 0° C. charged with sodium hydride (66.8 mg, 2.78 mmol). The mixture was stirred for 10 minutes and then allowed to warm to room temperature for 10 minutes. To a 4 mL vial were added 4-[6-[(3R)-3-ethyl-4-morpholinyl]-2-(methylamino)-4-pyrimidinyl]-2,6-difluorobenzonitrile (100 mg, 0.278 mmol), DMF (1 mL) and 1.2 mL of sodium methoxide solution (1.2 eq). The reaction was stirred at room temperature overnight. An extra 0.5 eq of sodium methoxide was added to the reaction and it was heated to 40° C. for 3 hours. The reaction mixture was then poured into EtOAc (10 mL). The organics were washed with H$_2$O (2×) and then dried over Na$_2$SO$_4$ and concentrated to afford 4-[6-[(3R)-3-ethyl-4-morpholinyl]-2-(methylamino)-4-pyrimidinyl]-2-fluoro-6-(methyloxy)benzonitrile. This material was taken up in CH$_3$CN (1 mL) and added to a 5 mL microwave vial followed by the addition of hydrazine (0.035 mL, 1.113 mmol) and Hunig's base (0.39 mL, 2.23 mmol). The reaction was irradiated at 150° C. for 90 minutes. The reaction mixture was then concentrated and purified via reverse phase HPLC (10-30% CH$_3$CN/H$_2$O, 0.1% TFA). Fractions were combined and diluted with EtOAc. The organics were washed with saturated NaHCO$_3$ solution that was back extracted with EtOAc (×1). The organics were combined and dried over Na$_2$SO$_4$. The product was taken up in 2 mL H$_2$O and lyophilized to afford the title compound (34.8 mg) as a white fluffy powder. LC-MS (ES) m/z=384 [M+H]$^+$. $^1$H NMR (400 MHz, DMSO-d$_6$): δ 0.88 (t, 3H), 1.59-1.82 (m, 2H), 2.82 (d, J=3.8 Hz, 3H), 3.07-3.18 (m, 1H), 3.39-3.49 (m, 1H), 3.50-3.56 (m, 1H), 3.82-3.87 (m, 1H), 3.87-3.92 (m, 1H), 3.94 (s, 3H), 4.10-4.23 (m, 1H), 4.27-4.39 (m, 1H), 5.02 (s, 2H), 6.45-6.57 (m, 1H), 6.94 (bs, 1H), 7.52 (bs, 1H), 8.30-8.34 (bs, 1H), 11.53 (bs, 1H).

Example 180

6-[6-[(3R)-3-Ethyl-4-morpholinyl]-2-(methylamino)-4-pyrimidinyl]-4-(methylthio)-1H-indazol-3-amine

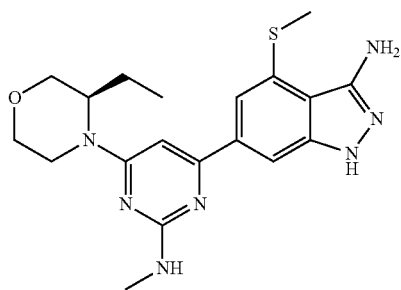 [SMILES: CC[C@@H]1COCCN1c1cc(-c2cc(SC)c3c(N)n[nH]c3c2)nc(NC)n1]

To a 4 mL vial was added 4-[6-[(3R)-3-ethyl-4-morpholinyl]-2-(methylamino)-4-pyrimidinyl]-2,6-difluorobenzonitrile (100 mg, 0.278 mmol), DMF (1 mL), and NaSMe (15 wt %, 117 mg, 0.250 mmol). The reaction was stirred at room temperature for 2 h. The reaction was poured into EtOAc (10 mL) followed by H$_2$O (10 mL). The aqueous was extracted with EtOAc (2×). The organics were then dried over Na$_2$SO$_4$ and concentrated to afford a yellow oil which was then taken up in CH$_3$CN (1.5 mL) and added to a 5 mL microwave vial followed by the addition of hydrazine (0.035 mL, 1.113 mmol) and Hunig's base (0.39 mL, 2.23 mmol). The reaction was irradiated at 150° C. for 90 minutes. The reaction mixture was then concentrated and purified via reverse phase HPLC (10-30% CH$_3$CN/H$_2$O, 0.1% TFA). Fractions were combined and diluted with EtOAc. The organics were washed with saturated NaHCO$_3$ solution that was back extracted with EtOAc. The organics were combined and dried over Na$_2$SO$_4$. The product was taken up in 2 mL H$_2$O and lyophilized to afford the title compound (28.8 mg) as a white fluffy powder. LC-MS (ES) m/z=400 [M+H]$^+$. $^1$H NMR (400 MHz, DMSO-d$_6$): δ 0.89 (t, 3H), 1.60-1.81 (m, 2H), 2.82 (d, J=3.3 Hz, 3H), 3.05-3.15 (m, 1H), 3.16-3.19 (m, 3H), 3.40-3.48 (m, 1H), 3.49-3.56 (m, 1H), 3.81-3.87 (m, 1H), 3.87-3.93 (m, 1H), 4.18 (bs, 1H), 4.33 (bs, 1H), 5.09 (s, 2H), 6.47-6.57 (m, 1H), 7.39-7.45 (m, 1H), 7.72-7.80 (m, 1H), 8.60-8.68 (m, 1H), 11.84 (bs, 1H).

Example 181

N$^4$-Cyclopentyl-6-[6-[(3R)-3-ethyl-4-morpholinyl]-2-(methylamino)-4-pyrimidinyl]-1H-indazole-3,4-diamine

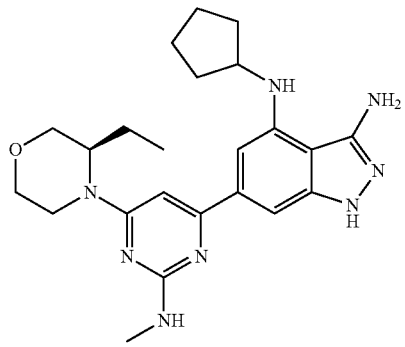 [SMILES: CC[C@@H]1COCCN1c1cc(-c2cc(NC3CCCC3)c3c(N)n[nH]c3c2)nc(NC)n1]

To a 4 mL vial was added 4-[6-[(3R)-3-ethyl-4-morpholinyl]-2-(methylamino)-4-pyrimidinyl]-2,6-difluorobenzonitrile (100 mg, 0.278 mmol), DMF (1 mL), and cyclopentyl amine (23.7 mg, 0.28 mmol). The reaction was stirred at room temperature for 2 hours. The reaction was poured into EtOAc (10 mL) and the aqueous was extracted with EtOAc (2×). The organics were then dried over Na$_2$SO$_4$ and concentrated to afford a yellow oil that was taken up in CH$_3$CN (1.5 mL) and added to a 5 mL microwave vial followed by the addition of hydrazine (0.035 mL, 1.113 mmol) and Hunig's base (0.39 mL, 2.23 mmol). The reaction was irradiated at 150° C. for 90 minutes. The reaction mixture was then concentrated and purified via reverse phase HPLC (20-40% CH$_3$CN/H$_2$O, 0.1% TFA). Fractions were combined and diluted with EtOAc. The organics were washed with saturated NaHCO$_3$ solution that was back extracted with EtOAc. The organics were combined and dried over Na$_2$SO$_4$. The product was taken up in 2 mL H$_2$O and lyophilized to afford the title compound (23 mg). LC-MS (ES) m/z=437 [M+H]$^+$. $^1$H NMR (400 MHz, DMSO-d$_6$): δ 0.89 (s, 3H), 1.53-1.82 (m, 8H), 2.00-2.09 (m, 2H), 2.79-2.85 (m, 3H), 3.03-3.13 (m, 1H), 3.39-3.48 (m, 1H), 3.49-3.55 (m, 1H), 3.82-3.86 (m, 1H), 3.87-3.92 (m, 1H), 4.11-4.19 (m, 1H), 4.20-4.28 (m, 1H), 5.03 (s, 2H), 5.32-5.37 (m, 1H), 6.35 (bs, 1H), 6.46 (bs, 1H), 6.55 (bs, 1H), 7.11 (bs, 1H), 11.38 (bs, 1H).

Example 182

6-[6-[(3R)-3-Ethyl-4-morpholinyl]-2-(methylamino)-4-pyrimidinyl]-N$^4$-methyl-1H-indazole-3,4-diamine

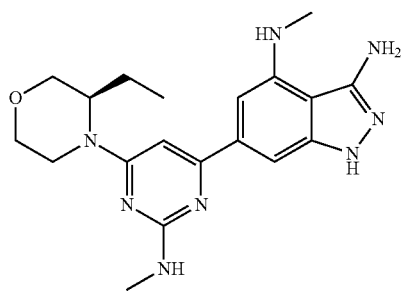 [SMILES: CC[C@@H]1COCCN1c1cc(-c2cc(NC)c3c(N)n[nH]c3c2)nc(NC)n1]

To a 4 mL vial was added 4-[6-[(3R)-3-ethyl-4-morpholinyl]-2-(methylamino)-4-pyrimidinyl]-2,6-difluorobenzonitrile (100 mg, 0.278 mmol), DMF (1 mL), and methylamine in THF (2 M, 0.14 mL, 0.28 mmol). The reaction was stirred at room temperature for 2 hours. The reaction was then poured into EtOAc (10 mL) and the aqueous was extracted with EtOAc (2×). The organics were then dried over Na₂SO₄ and concentrated to afford a yellow oil that was taken up in CH₃CN (1.5 mL) and added to a 5 mL microwave vial followed by the addition of hydrazine (0.035 mL, 1.113 mmol) and Hunig's base (0.39 mL, 2.23 mmol). The reaction was irradiated at 150° C. for 90 minutes. The reaction mixture was then concentrated and purified via reverse phase HPLC (10-30% CH₃CN/H₂O, 0.1% TFA). Fractions were combined and diluted with EtOAc. The organics were washed with saturated NaHCO₃ solution that was back extracted with EtOAc. The organics were combined and dried over Na₂SO₄. The product was taken up in 2 mL H₂O and lyophilized to afford the title compound (7 mg). LC-MS (ES) m/z=383 [M+H]⁺. ¹H NMR (400 MHz, DMSO-d₆): δ 0.85-0.91 (m, 3H), 1.58-1.82 (m, 2H), 2.79-2.84 (m, 3H), 3.05-3.14 (m, 1H), 3.22-3.28 (m, 3H), 3.39-3.48 (m, 1H), 3.49-3.55 (m, 1H), 3.81-3.86 (m, 1H), 3.87-3.92 (m, 1H), 4.12-4.20 (m, 1H), 4.31 (bs, 1H), 4.85 (s, 2H), 6.43 (bs, 1H), 6.51 (bs, 1H), 6.96 (bs, 1H), 7.48 (bs, 1H), 11.58 (bs, 1H).

Example 183

6-[6-[(3R)-3-Ethyl-4-morpholinyl]-2-(methylamino)-4-pyrimidinyl]-4-(1-pyrrolidinyl)-1H-indazol-3-amine

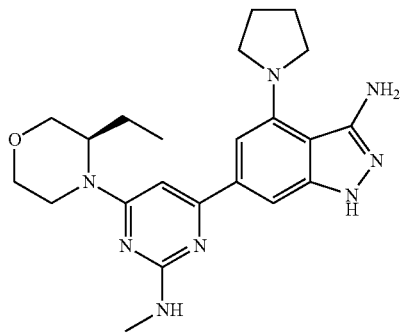 [SMILES: CC[C@@H]1COCCN1c1cc(-c2cc(N3CCCC3)c3c(N)n[nH]c3c2)nc(NC)n1]

To a 4 mL vial was added 4-[6-[(3R)-3-ethyl-4-morpholinyl]-2-(methylamino)-4-pyrimidinyl]-2,6-difluorobenzonitrile (100 mg, 0.278 mmol), DMF (1 mL), and pyrrolidine (19.8 mg, 0.28 mmol). The reaction was stirred at room temperature for 2 hours. The reaction was poured into EtOAc (10 mL) and the aqueous was extracted with EtOAc (2×). The organics were then dried over Na₂SO₄ and concentrated to afford a yellow oil that was taken up in CH₃CN (1.5 mL) and added to a 5 mL microwave vial followed by the addition of hydrazine (0.035 mL, 1.113 mmol) and Hunig's base (0.39 mL, 2.23 mmol). The reaction was irradiated at 150° C. for 90 minutes. The reaction mixture was then concentrated and purified via reverse phase HPLC (15-35% CH₃CN/H₂O, 0.1% TFA). Fractions were combined and diluted with EtOAc. The organics were washed with saturated sodium bicarbonate solution that was back extracted with EtOAc. The organics were combined and dried over Na₂SO₄. The product was taken up in 2 mL H₂O and lyophilized to afford the title compound (17.1 mg). LC-MS (ES) m/z=423 [M+H]⁺. ¹H NMR (400 MHz, DMSO-d₆): δ 0.88 (t, 3H), 1.57-1.82 (m, 4H), 2.81 (d, J=4.6 Hz, 3H), 2.84 (d, J=4.8 Hz, 4H), 3.04-3.14 (m, 1H), 3.40-3.48 (m, 1H), 3.49-3.55 (m, 1H), 3.81-3.86 (m, 1H), 3.86-3.92 (m, 1H), 4.11-4.20 (m, 1H), 4.29 (bs, 1H), 5.07 (s, 2H), 5.65-5.71 (m, 1H), 6.40 (bs, 2H), 6.44 (bs, 2H), 7.14 (bs, 1H), 11.34 (bs, 1H).

Example 184

6-[6-[(3R)-3-Ethyl-4-morpholinyl]-2-(methylamino)-4-pyrimidinyl]-4-(ethyloxy)-1H-indazol-3-amine

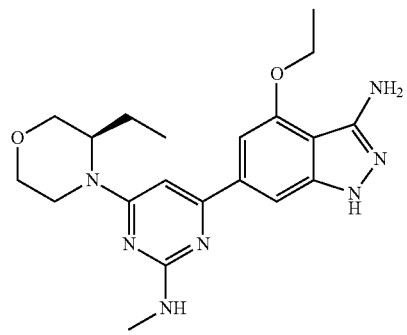 [SMILES: CCOc1cc(-c2cc(N3CCOC[C@H]3CC)nc(NC)n2)cc2[nH]nc(N)c12]

4-[6-[(3R)-3-Ethyl-4-morpholinyl]-2-(methylamino)-4-pyrimidinyl]-2,6-difluorobenzonitrile (690 mg, 1.92 mmol) was taken up in DMF (6 mL) followed by the addition of sodium ethoxide (1.1 M, 1.75 mL, 1.92 mmol). The reaction was then allowed to stir at room temperature. The reaction was diluted with EtOAc (20 mL) and washed with H₂O (25 mL). The H₂O was then back extracted with EtOAc (20 mL). The organics were dried and concentrated to afford a yellow oil that was then dissolved in CH₃CN (5 mL) and transferred to a 20 mL microwave vial, followed by the addition of hydrazine (0.241 mL, 7.68 mmol) and Hunig's base (2.68 mL, 15.36 mmol). The reaction was irradiated at 140° C. for 2 hours. Another equivalent of hydrazine (0.120 mL, 3.84 mmol) was added to the reaction and it was irradiated at 140° C. for 30 minutes. The reaction was concentrated and purified via flash chromatography (0-50%, 80:20:2 CH₂Cl₂:CH₃OH:NH₄OH, 60 g). Fractions were combined and concentrated to afford the title compound (398.8 mg) as a yellow solid. LC-MS (ES) m/z=398 [M+H]⁺. ¹H NMR (400 MHz, DMSO-d₆): δ 0.88 (t, J=7.5 Hz, 3H), 1.45 (t, J=7.0 Hz, 3H), 1.60-1.80 (m, 2H), 2.79-2.85 (m, 3H), 3.06-3.15 (m, 1H), 3.40-3.48 (m, 1H), 3.49-3.55 (m, 1H), 3.81-3.87 (m, 1H), 3.87-3.92 (m, 1H), 4.17-4.25 (m, 3H), 4.34 (bs, 1H), 4.99 (s, 2H), 6.50 (bs, 2H), 6.93 (bs, 1H), 7.52 (bs, 1H), 11.52 (bs, 1H).

Intermediate 352

2,6-Difluoro-4-{2-(methylamino)-6-[(2R)-2-methyl-1-pyrrolidinyl]-4-pyrimidinyl}benzonitrile

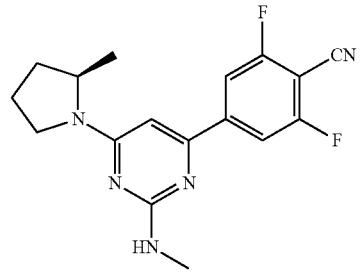 [SMILES: CNc1nc(-c2cc(F)c(C#N)c(F)c2)cc(N2CCC[C@H]2C)n1]

A mixture of 4,6-dichloro-N-methyl-2-pyrimidinamine (1.2 g, 6.74 mmol), (2R)-2-methylpyrrolidine (0.631 g, 7.41 mmol), and NaHCO₃ (2.83 g, 33.7 mmol) in dioxane (40 mL) and water (20 mL) was stirred overnight at 117° C. in a sealed tube. The reaction was allowed to cool to room temperature. LCMS showed most of the starting material 4,6-dichloro-2-pyrimidinamine had been consumed. Then (4-cyano-3,5-difluorophenyl)boronic acid (1.233 g, 6.74 mmol) and Pd(Ph₃P)₄ (0.156 g, 0.135 mmol) were added, and the reaction mixture was stirred for 24 hours at 117° C. The mixture was poured into water (30 mL) and EtOAc (100 mL). The compound stayed in the EtOAc layer. The organic layer was separated from the aqueous layer. There was some black colored suspension in the organic layer, which was filtered out. (they were not product). The organic layer was rotavaped to dryness to afford the title compound (0.8 g) as a light yellow solid. LC-MS (ES) m/z=330 [M+H]⁺.

Intermediate 353

2-Fluoro-4-{2-(methylamino)-6-[(2R)-2-methyl-1-pyrrolidinyl]-4-pyrimidinyl}-6-(methyloxy)benzonitrile

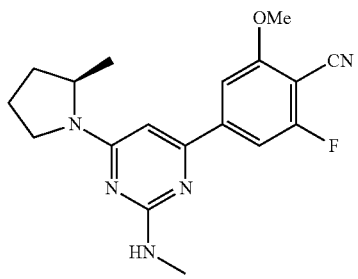 [SMILES: CNc1nc(-c2cc(F)c(C#N)c(OC)c2)cc(N2CCC[C@H]2C)n1]

A 1M solution of sodium methoxide in CH₃OH was prepared by addition of freshly cut sodium (50 mg, 2.17 mmol) to ice cold CH₃OH (2.17 mL). A portion of this solution (0.45 mL) was added to a solution of 2,6-difluoro-4-{2-(methylamino)-6-[(2R)-2-methyl-1-pyrrolidinyl]-4-pyrimidinyl}benzonitrile (134 mg, 0.407 mmol) in CH₃OH (1 mL). The suspension was stirred at room temperature overnight in a capped 10 mL vial. The mixture was poured into water (15 mL). A solid was formed which was filtered, washed by water and dried to afford the title compound (100 mg) as a light yellow solid. LC-MS (ES) m/z=342 [M+H]⁺.

Example 185

6-{2-(Methylamino)-6-[(2R)-2-methyl-1-pyrrolidinyl]-4-pyrimidinyl}-4-(methyloxy)-1H-indazol-3-amine

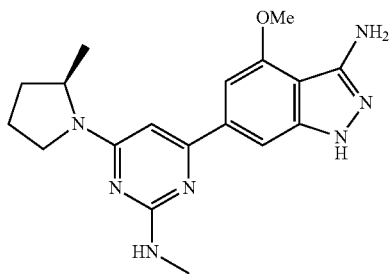 [SMILES: CNc1nc(-c2cc(OC)c3c(N)n[nH]c3c2)cc(N2CCC[C@H]2C)n1]

Into a sealable tube, 2-fluoro-4-{2-(methylamino)-6-[(2R)-2-methyl-1-pyrrolidinyl]-4-pyrimidinyl}-6-(methyloxy)benzonitrile (100 mg, 0.293 mmol), EtOH (5 mL), Hunig's base (0.05 mL, 0.29 mmol), and hydrazine anhydrous (0.055 mL, 1.76 mmol) were added, and the yellow suspension mixture was heated overnight at 110° C. in an oil bath. After overnight, there was yellow suspension as well as some black colored solid formed. LCMS showed mainly product. The reaction was cooled to room temperature. Water (20 mL) was added to the yellow solution, and a solid was formed. The solid was filtered, washed by water, and dried in vacuum. The solid was purified further by flash column chromatography. The fractions with product were combined, and the solvent was removed under reduced pressure to afford the title compound (23.7 mg) as a white solid. LC-MS (ES) m/z=354 [M+H]⁺. ¹H NMR (400 MHz, CDCl₃): δ 1.30 (d, J=6.3 Hz, 3H), 1.75-2.18 (m, 4H), 3.02 (s, 3H), 3.50-3.63 (m, 2H), 4.02 (s, 3H), 4.34 (m, 1H), 4.50 (m, 2H), 6.07 (s, 1H), 6.93 (s, 1H), 7.44 (s, 1H).

Intermediate 354

2-Fluoro-4-{2-(methylamino)-6-[(2R)-2-methyl-1-pyrrolidinyl]-4-pyrimidinyl}-6-(methylthio)benzonitrile

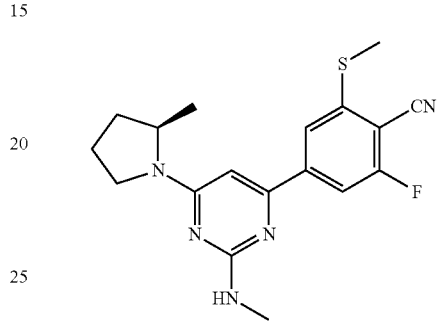

To a solution of 2,6-difluoro-4-{2-(methylamino)-6-[(2R)-2-methyl-1-pyrrolidinyl]-4-pyrimidinyl}benzonitrile (162 mg, 0.492 mmol) in DMF (4 mL), was added methyl mercaptan sodium salt (ca. 15% in water, 319 mg, 0.683 mmol). The solution was stirred at room temperature overnight in a capped 10 mL vial. The mixture was poured onto water (15 mL). The formed solid was filtered, washed by water and dried to afford the title compound (86 mg) as a light yellow solid. LC-MS (ES) m/z=358 [M+H]⁺.

Example 186

6-{2-(methylamino)-6-[(2R)-2-methyl-1-pyrrolidinyl]-4-pyrimidinyl}-4-(methylthio)-1H-indazol-3-amine

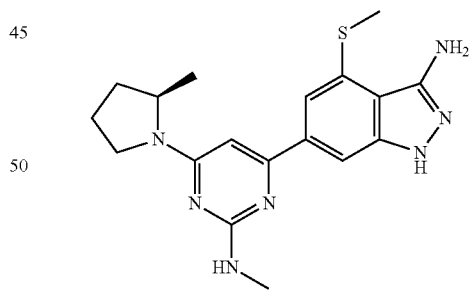

Into a sealable tube, 2-fluoro-4-{2-(methylamino)-6-[(2R)-2-methyl-1-pyrrolidinyl]-4-pyrimidinyl}-6-(methylthio)benzonitrile (86 mg, 0.241 mmol), EtOH (5 mL), Hunig's base (0.042 mL, 1.44 mmol), and hydrazine anhydrous (0.045 mL, 0.241 mmol) were added, and the yellow suspension mixture was heated overnight at 100° C. in an oil bath. After overnight, there was yellow solution as well as a little amount of white colored solid formed. LCMS showed no more starting material. The reaction was cooled to room temperature. Water (20 mL) was added to the yellow solution, and a solid was formed. The solid was filtered, washed by water, and dried in vacuum. The solid was further purified by flash column chromatography. The fractions containing product were combined, and the solvent was removed under reduced pressure to afford the title compound (20.5 mg) as a white solid. LC-MS (ES) m/z=370 [M+H]+. 1H NMR (400 MHz, DMSO-d6): δ 1.21 (d, J=6.1 Hz, 3H), 1.67 (m, 1H), 1.84-2.10 (m, 3H), 2.61 (s, 3H), 2.79-2.91 (m, 3H), 3.41-3.66 (m, 2H), 4.27 (m, 1H), 5.09 (s, 2H), 6.23 (s, 1H), 6.44 (s, 1H), 7.34-7.46 (m, 1H), 7.72 (s, 1H), 11.75 (s, 1H).

Intermediate 355

2-(Ethyloxy)-6-fluoro-4-{2-(methylamino)-6-[(2R)-2-methyl-1-pyrrolidinyl]-4-pyrimidinyl}benzonitrile

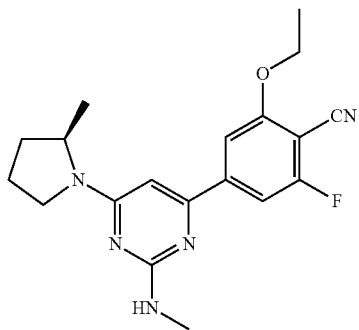 [SMILES: CCOc1cc(-c2cc(N3CCC[C@H]3C)nc(NC)n2)cc(F)c1C#N]

A 1M solution of sodium ethoxide in EtOH was prepared by addition of freshly cut sodium (55 mg, 2.4 mmol) to ice cold EtOH (2.4 mL). A portion of this solution (0.54 mL) was added to a solution of 2,6-difluoro-4-{2-(methylamino)-6-[(2R)-2-methyl-1-pyrrolidinyl]-4-pyrimidinyl}benzonitrile (161 mg, 0.489 mmol) in ethanol (6 mL). The suspension was stirred at room temperature overnight in a capped 10 mL vial. The mixture was poured into water (15 mL), and a solid was formed which was filtered, washed by water and dried to afford the title compound (87 mg) as a light yellow solid. LC-MS (ES) m/z=356 [M+H]+.

Example 187

4-(Ethyloxy)-6-{2-(methylamino)-6-[(2R)-2-methyl-1-pyrrolidinyl]-4-pyrimidinyl}-1H-indazol-3-amine

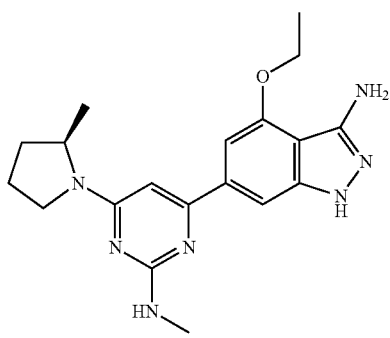 [SMILES: CCOc1cc(-c2cc(N3CCC[C@H]3C)nc(NC)n2)cc2[nH]nc(N)c12]

In a sealable tube, 2-(ethyloxy)-6-fluoro-4-{2-(methylamino)-6-[(2R)-2-methyl-1-pyrrolidinyl]-4-pyrimidinyl}benzonitrile (87 mg, 0.245 mmol), EtOH (5 mL), Hunig's base (0.046 mL, 1.469 mmol), and hydrazine anhydrous (0.043 mL, 0.245 mmol) were added, and the yellow suspension mixture was heated at 100° C. overnight in an oil bath. After overnight, there was a yellow solution as well as a little amount of white colored solid formed. LCMS showed no more starting material. The reaction was cooled to room temperature. Water (20 mL) was added to the yellow solution, and a solid was formed. The solid was filtered, washed by water, and dried in vacuum. The solid was purified by flash column chromatography. The fractions containing product were combined, and the solvent was removed under reduced pressure to afford the title compound (48 mg) as a white solid. LC-MS (ES) m/z=368 [M+H]+. 1H NMR (400 MHz, DMSO-d6): δ 1.21 (d, J=6.1 Hz, 3H), 1.44 (t, J=7.0 Hz, 3H), 1.66 (m, 1H), 2.02 (m, 3H), 2.82 (d, J=4.8 Hz, 3H), 3.56 (m, 1H), 4.12-4.24 (q, J=7.1 Hz, 2H), 4.99 (s, 2H), 6.19 (s, 1H), 6.32-6.51 (m, 1H), 6.87-6.98 (m, H), 7.41-7.56 (m, 1H), 11.50 (s, 1H).

Intermediate 356

(3S,6R)-1-[2-Amino-6-(4-cyano-3-fluorophenyl)-4-pyrimidinyl]-6-methyl-N-[(1S)-1-phenylethyl]-3-piperidinecarboxamide

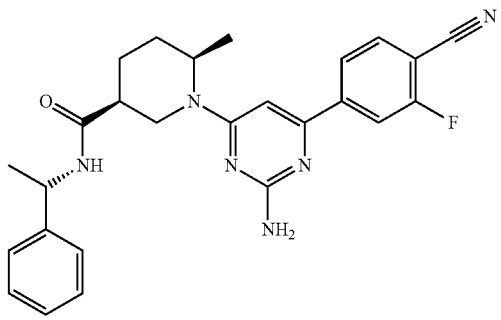

To a solution of (3S,6R)-1-[2-amino-6-(4-cyano-3-fluorophenyl)-4-pyrimidinyl]-6-methyl-3-piperidinecarboxylic acid (170 mg, 0.478 mmol) and HATU (218 mg, 0.574 mmol) in DMF (3 mL) was added Hunig's base (0.167 mL, 0.957 mmol), and the resulting mixture was stirred at room temperature for 15 minutes. (1S)-1-phenylethanamine (58 mg, 0.478 mmol) was added, and the reaction mixture was stirred at room temperature for 0.5 hours. LCMS showed reaction was completed. The reaction was poured into water, and EtOAc was added to extract the product. The product stayed in the EtOAc layer. The organic layer solution was concentrated, and the formed solid was recrystallized in CH3CN to afford the title compound (186 mg) as a light yellow solid. LC-MS (ES) m/z=459 [M+H]+.

Example 188

(3S,6R)-1-[2-Amino-6-(3-amino-1H-indazol-6-yl)-4-pyrimidinyl]-6-methyl-N-[(1S)-1-phenylethyl]-3-piperidinecarboxamide

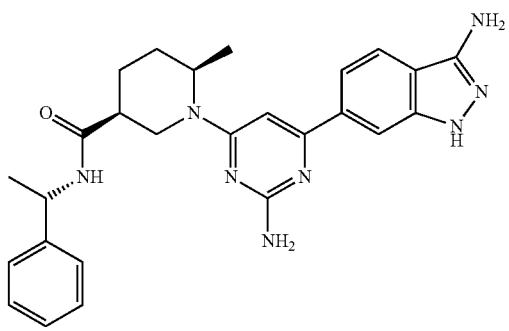

Into a sealable tube, (3S,6R)-1-[2-amino-6-(4-cyano-3-fluorophenyl)-4-pyrimidinyl]-6-methyl-N-[(1S)-1-phenyl ethyl]-3-piperidinecarboxamide (186 mg, 0.406 mmol), EtOH (5 mL), Hunig's base (0.071 ml, 0.406 mmol), and hydrazine anhydrous (0.076 mL, 2.434 mmol) were added, and the yellow suspension mixture was heated overnight at 110° C. in an oil bath. When the temperature of the reaction reached to 100° C., the solid in the mixture was all dissolved. After overnight, there was a yellow solution as well as a little amount of black colored solid formed. LCMS showed mainly product. CH$_3$OH (5 mL) was added to the solution. The black solid was filtered from the yellow solution. Water (20 mL) was added to the yellow solution, and a solid was formed. The solid was filtered, washed by water, and dried in vacuum. The solid was recrystallized from CH$_3$CN, and the solid was filtered, washed by CH$_3$CN, and dried in vacuum to afford the title compound (120 mg) as a light yellow solid. LC-MS (ES) m/z=471 [M+H]$^+$. $^1$H NMR (400 MHz, DMSO-d$_6$): δ 1.14 (d, J=6.8 Hz, 3H), 1.36 (d, J=7.1 Hz, 3H), 1.66 (m, 1H), 1.68 (m, 1H), 1.77 (m, 2H), 2.34 (m, 1H), 4.94 (m, 1H), 5.38 (s, 2H), 6.07 (s, 2H), 6.56 (s, 1H), 7.19-7.30 (m, 1H), 7.36 (m, 4H), 7.56 (dd, J=8.6, 1.5 Hz, 1H), 7.70 (d, J=8.34 Hz, 1H), 7.94 (s, 1H), 8.39 (d, J=8.1 Hz, 1H), 11.50 (s, 1H).

Intermediate 357

(3S,6R)-1-[2-Amino-6-(4-cyano-3-fluorophenyl)-4-pyrimidinyl]-6-methyl-N-{[2-(methyloxy)phenyl]methyl}-3-piperidinecarboxamide

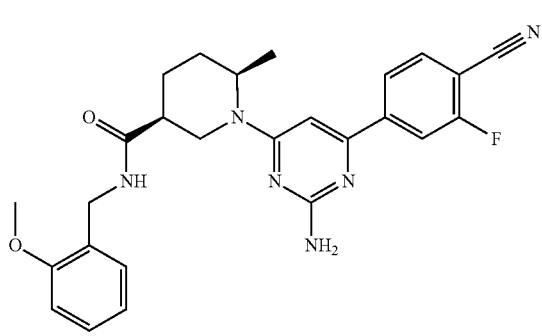 [SMILES: COc1ccccc1CNC(=O)[C@H]1CC[C@@H](C)N(c2cc(-c3ccc(C#N)c(F)c3)nc(N)n2)C1]

To a solution of (3S,6R)-1-[2-amino-6-(4-cyano-3-fluorophenyl)-4-pyrimidinyl]-6-methyl-3-piperidinecarboxylic acid (170 mg, 0.478 mmol) and HATU (218 mg, 0.574 mmol) in DMF (3 mL) was added Hunig's base (0.167 mL, 0.957 mmol), and the resulting mixture was stirred at room temperature for 15 minutes. 1-[2-(Methyloxy)phenyl]methanamine (65.6 mg, 0.478 mmol) was added, and the reaction mixture was stirred at room temperature for 0.5 hours. LCMS showed reaction was completed. The reaction was poured into water, and EtOAc was added to extract the product. The product stayed in the EtOAc layer. The organic layer solution was concentrated, and the formed solid was recrystallized from CH$_3$CN to afford the title compound (200 mg) as a light yellow solid. LC-MS (ES) m/z=475 [M+H]$^+$.

Example 189

(3S,6R)-1-[2-Amino-6-(3-amino-1H-indazol-6-yl)-4-pyrimidinyl]-6-methyl-N-{[2-(methyloxy)phenyl]methyl}-3-piperidinecarboxamide

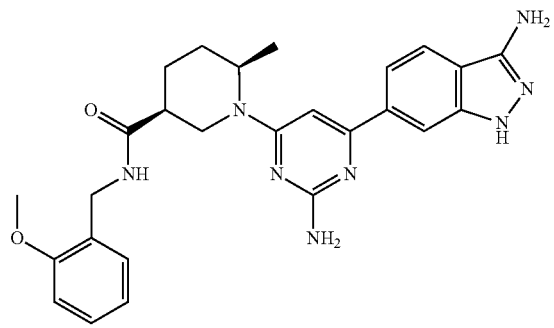 [SMILES: COc1ccccc1CNC(=O)[C@H]1CC[C@@H](C)N(c2cc(-c3ccc4c(N)n[nH]c4c3)nc(N)n2)C1]

Into a sealable tube, (3S,6R)-1-[2-amino-6-(4-cyano-3-fluorophenyl)-4-pyrimidinyl]-6-methyl-N-{[2-(methyloxy)phenyl]methyl}-3-piperidinecarboxamide (200 mg, 0.421 mmol), EtOH (5 mL), Hunig's base (0.074 mL, 0.421 mmol), and hydrazine anhydrous (0.08 mL, 2.5 mmol) were added, and the yellow suspension mixture was heated overnight at 110° C. in an oil bath. When the temperature of the reaction reached to 100° C., the solid in the mixture was all dissolved. After overnight, there was a yellow solution as well as a little amount of black colored solid formed. LCMS showed mainly product. CH$_3$OH (5 mL) was added to the solution. The black solid was filtered from the yellow solution. Water (20 mL) was added to the yellow solution, and a solid was formed. The solid was filtered, washed by water, and dried in vacuum. The solid was recrystallized from CH$_3$CN, and the solid was filtered, washed by CH$_3$CN, and dried in vacuum to afford the title compound (65 mg) as a light yellow solid. LC-MS (ES) m/z=487 [M+H]$^+$. $^1$H NMR (400 MHz, DMSO-d$_6$): δ 1.16 (d, J=6.82 Hz, 3H), 1.66 (m, 2H), 1.71-1.95 (m, 2H), 2.31-2.45 (m, 1H), 2.95 (m, 1H), 3.82 (s, 3H), 4.12-4.41 (m, 2H), 5.38 (s, 2H), 6.08 (s, 2H), 6.59 (s, 1H), 6.87-7.08 (m, 2H), 7.14-7.30 (m, 2H), 7.52-7.62 (m, 1H), 7.70 (m, 1H), 7.94 (s, 1H), 8.24-8.38 (m, 1), 11.50 (s, 1H).

Intermediate 358

(3S,6R)-1-[2-Amino-6-(4-cyano-3-fluorophenyl)-4-pyrimidinyl]-6-methyl-N-{[3-(methyloxy)phenyl]methyl}-3-piperidinecarboxamide

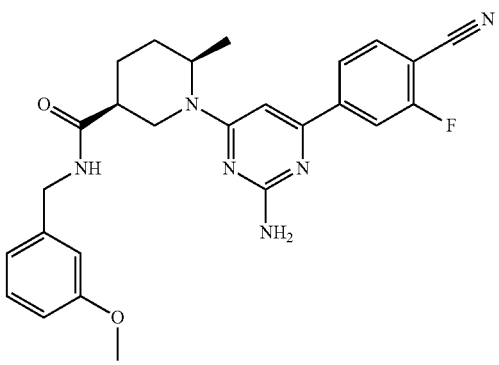 [SMILES: COc1cccc(CNC(=O)[C@H]2CC[C@@H](C)N(c3cc(-c4ccc(C#N)c(F)c4)nc(N)n3)C2)c1]

To a solution of (3S,6R)-1-[2-amino-6-(4-cyano-3-fluorophenyl)-4-pyrimidinyl]-6-methyl-3-piperidinecarboxylic acid (170 mg, 0.478 mmol) and HATU (218 mg, 0.574 mmol) in DMF (3 mL) was added Hunig's base (0.167 mL, 0.957 mmol), and the resulting mixture was stirred at room temperature for 15 minutes. 1-[3-(Methyloxy)phenyl]methanamine (65.6 mg, 0.478 mmol) was added, and the reaction mixture was stirred at room temperature for 0.5 hours. LCMS showed reaction was completed. The reaction was poured onto water, and EtOAc was added to extract the product. The product stayed in the EtOAc layer. The organic layer solution was concentrated, and the formed solid was recrystallized from $CH_3CN$ to afford the title compound (186 mg) as a light yellow solid. LC-MS (ES) m/z=475 [M+H]$^+$.

Example 190

(3S,6R)-1-[2-Amino-6-(3-amino-1H-indazol-6-yl)-4-pyrimidinyl]-6-methyl-N-{[3-(methyloxy)phenyl]methyl}-3-piperidinecarboxamide

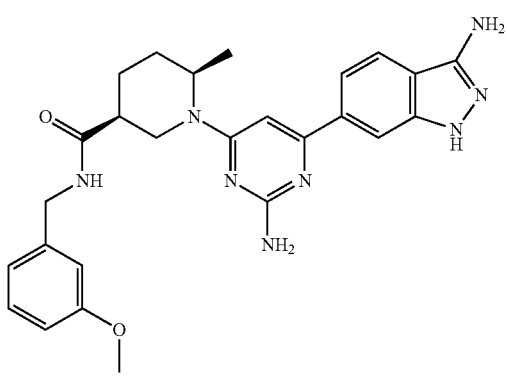 [SMILES: COc1cccc(CNC(=O)[C@H]2CC[C@@H](C)N(c3cc(-c4ccc5c(N)n[nH]c5c4)nc(N)n3)C2)c1]

Into a sealable tube, (3S,6R)-1-[2-amino-6-(4-cyano-3-fluorophenyl)-4-pyrimidinyl]-6-methyl-N-{[3-(methyloxy)phenyl]methyl}-3-piperidinecarboxamide (186 mg, 0.392 mmol), EtOH (5 mL), Hunig's base (0.068 ml, 0.392 mmol), and hydrazine anhydrous (0.074 mL, 2.35 mmol) were added, and the yellow suspension mixture was heated overnight at 110° C. in an oil bath. When the temperature of the reaction reached to 100° C., the solid in the mixture was all dissolved. After overnight, there was a yellow solution as well as a little amount of black colored solid formed. LCMS showed mainly product. $CH_3OH$ (5 mL) was added to the solution. The black solid was filtered from the yellow solution. Water (20 mL) was added to the yellow solution, and a solid was formed. The solid was filtered, washed by water, and dried in vacuum. The solid was recrystallized from $CH_3CN$, and the solid was filtered, washed by $CH_3CN$, and dried in vacuum to afford the title compound (31 mg) as a light yellow solid. LC-MS (ES) m/z=487 [M+H]$^+$. $^1$H NMR (400 MHz, DMSO-$d_6$): δ 1.16 (d, J=6.8 Hz, 3H), 1.58-1.71 (m, 2H), 1.76 (m, 1H), 1.86 (m, 1H), 2.36 (m, 1H), 3.75 (s, 3H), 4.19 (m, 1H), 4.23 (m, 1H), 4.33 (m, 1H), 4.37 (m, 1H), 5.38 (s, 2H), 6.08 (s, 2H), 6.59 (s, 1H), 6.81-6.91 (m, 3H), 7.26 (m, 1H), 7.52-7.63 (m, 1H), 7.70 (d, J=8.6 Hz, 1H), 7.94 (s, 1H), 8.48 (m, 1H), 11.50 (s, 1H).

Intermediate 359

(3S,6R)-1-[2-Amino-6-(4-cyano-3-fluorophenyl)-4-pyrimidinyl]-N-[(2-fluorophenyl)methyl]-6-methyl-3-piperidinecarboxamide

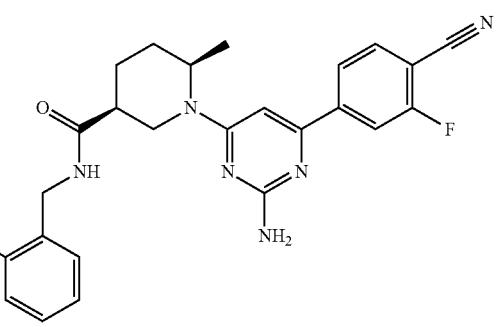

To a solution of (3S,6R)-1-[2-amino-6-(4-cyano-3-fluorophenyl)-4-pyrimidinyl]-6-methyl-3-piperidinecarboxylic acid (170 mg, 0.478 mmol) and HATU (218 mg, 0.574 mmol) in DMF (3 mL) was added Hunig's base (0.17 mL, 0.96 mmol), and the resulting mixture was stirred at room temperature for 15 minutes. 1-(2-Fluorophenyl)methanamine (60 mg, 0.48 mmol) was added, and the reaction mixture was stirred at room temperature for 0.5 hours. LCMS showed reaction was completed. The reaction was poured into water, and EtOAc was added to extract the product. The product stayed in the EtOAc layer. The organic layer solution was concentrated, and the formed solid was recrystallized from $CH_3CN$ to afford the title compound (189 mg) as a light yellow solid. LC-MS (ES) m/z=463 [M+H]$^+$.

Example 191

(3S,6R)-1-[2-Amino-6-(3-amino-1H-indazol-6-yl)-4-pyrimidinyl]-N-[(2-fluorophenyl)methyl]-6-methyl-3-piperidinecarboxamide

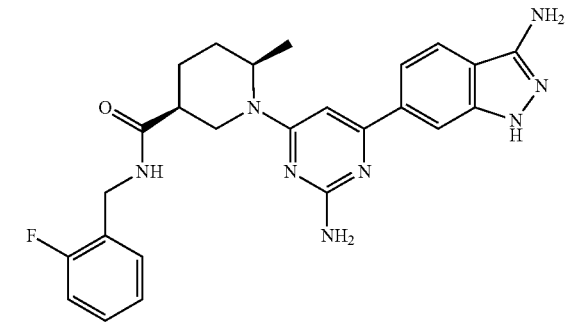 [SMILES: C[C@@H]1CC[C@H](C(=O)NCc2ccccc2F)CN1c1cc(-c2ccc3c(N)n[nH]c3c2)nc(N)n1]

Into a sealable vial, (3S,6R)-1-[2-amino-6-(4-cyano-3-fluorophenyl)-4-pyrimidinyl]-N-[(2-fluorophenyl)methyl]-6-methyl-3-piperidinecarboxamide (189 mg, 0.409 mmol), EtOH (5 mL), Hunig's base (0.071 ml, 0.409 mmol), and hydrazine anhydrous (0.077 mL, 2.452 mmol) were added, and the yellow suspension mixture was heated overnight at 110° C. in an oil bath. When the temperature of the reaction reached to 100° C., the solid in the mixture was all dissolved. After overnight, there was a yellow solution as well as a little amount of black colored solid formed. LCMS showed mainly product. $CH_3OH$ (5 mL) was added to the solution. The black solid was filtered from the yellow solution. Water (20 mL)

was added to the yellow solution, and a solid was formed. The solid was filtered, washed by water, and dried in vacuum. The solid was recrystallized from CH₃CN, and the solid was filtered, washed by CH₃CN, and dried in vacuum to afford the title compound (80 mg) as a light yellow solid. LC-MS (ES) m/z=475 [M+H]⁺. ¹H NMR (400 MHz, DMSO-d₆): δ 1.15 (d, J=6.8 Hz, 3H), 1.66 (m, 2H), 1.76 (m, 1H), 1.84 (m, 1H), 2.35 (m, 1H), 2.85 (m, 1H), 4.22-4.47 (m, 3H), 5.38 (s, 2H), 6.08 (s, 2H), 6.59 (s, 1H), 7.14-7.25 (m, 2H), 7.28-7.41 (m, 2H), 7.57 (m, 1H), 7.70 (d, J=8.3 Hz, 1H), 7.94 (s, 1H), 8.45-8.54 (m, 1H), 11.50 (s, 1H).

Intermediate 360

(3S,6R)-1-[2-Amino-6-(4-cyano-3-fluorophenyl)-4-pyrimidinyl]-6-methyl-N-[(1R)-1-phenylethyl]-3-piperidinecarboxamide

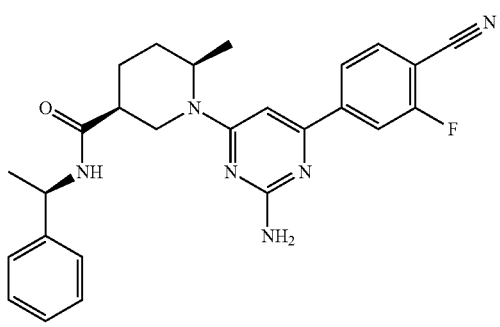 [SMILES: C[C@@H]1CC[C@H](C(=O)N[C@H](C)c2ccccc2)CN1c1cc(-c2ccc(C#N)c(F)c2)nc(N)n1]

To a solution of (3S,6R)-1-[2-amino-6-(4-cyano-3-fluorophenyl)-4-pyrimidinyl]-6-methyl-3-piperidinecarboxylic acid (170 mg, 0.478 mmol) and HATU (218 mg, 0.574 mmol) in DMF (3 mL) was added Hunig's base (0.167 mL, 0.957 mmol), and the resulting mixture was stirred at room temperature for 15 minutes. (1R)-1-Phenylethanamine (58 mg, 0.478 mmol) was added, and the reaction mixture was stirred at room temperature for 0.5 hours. LCMS showed reaction was completed. The reaction was poured onto water, and EtOAc was added to extract the product. The product stayed in the EtOAc layer. The organic layer solution was concentrated, and the formed solid was recrystallized from CH₃CN to afford the title compound (188 mg) as a light yellow solid. LC-MS (ES) m/z=459 [M+H]⁺.

Example 192

(3S,6R)-1-[2-Amino-6-(3-amino-1H-indazol-6-yl)-4-pyrimidinyl]-6-methyl-N-[(1R)-1-phenylethyl]-3-piperidinecarboxamide

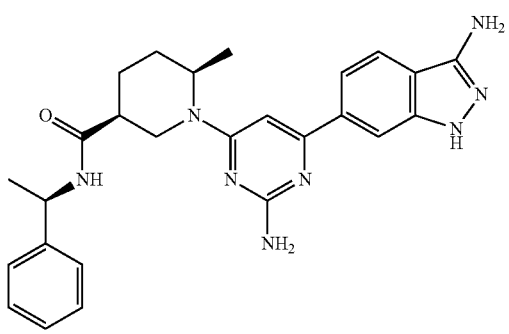 [SMILES: C[C@@H]1CC[C@H](C(=O)N[C@H](C)c2ccccc2)CN1c1cc(-c2ccc3c(N)n[nH]c3c2)nc(N)n1]

Into a sealable tube, (3S,6R)-1-[2-amino-6-(4-cyano-3-fluorophenyl)-4-pyrimidinyl]-6-methyl-N-[(1R)-1-phenylethyl]-3-piperidinecarboxamide (188 mg, 0.41 mmol), EtOH (5 ml), Hunig's base (0.072 ml, 0.41 mmol), and hydrazine anhydrous (0.077 mL, 2.46 mmol) were added, and the yellow suspension mixture was heated overnight at 110° C. in an oil bath. When the temperature of the reaction reached to 100° C., the solid in the mixture was all dissolved. After overnight, there was a yellow solution as well as a little amount of black colored solid formed. LCMS showed mainly product. CH₃OH (5 mL) was added to the solution. The black solid was filtered from the yellow solution. Water (20 mL) was added to the yellow solution, and a solid was formed. The solid was filtered, washed by water, and dried in vacuum. The solid was recrystallized from CH₃CN, and the solid was filtered, washed by CH₃CN, and dried in vacuum to afford the title compound (78 mg) as a light yellow solid. LC-MS (ES) m/z=471 [M+H]⁺. ¹H NMR (400 MHz, DMSO-d₆): δ 1.06-1.21 (m, 4H), 1.38 (m, 3H), 1.71 (m, 4H), 2.25-2.41 (m, 1H), 2.92 (m, 1H), 4.84-5.01 (m, 1H), 5.38 (s, H), 6.09 (s, 2H), 6.59 (s, 1H), 7.12-7.40 (m, 6H), 7.53-7.62 (m, 1H), 7.71 (d, J=8.6 Hz, 1H), 7.95 (s, 1H), 8.41 (d, J=8.1 Hz, 1H), 11.50 (s, 1H).

Intermediate 361

(3S,6R)-1-[2-Amino-6-(4-cyano-3-fluorophenyl)-4-pyrimidinyl]-6-methyl-N-(1-methyl-1-phenylethyl)-3-piperidinecarboxamide

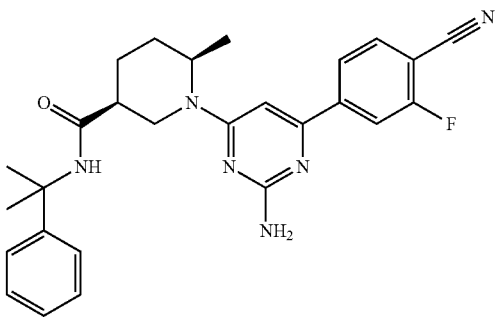 [SMILES: C[C@@H]1CC[C@H](C(=O)NC(C)(C)c2ccccc2)CN1c1cc(-c2ccc(C#N)c(F)c2)nc(N)n1]

To a solution of (3S,6R)-1-[2-amino-6-(4-cyano-3-fluorophenyl)-4-pyrimidinyl]-6-methyl-3-piperidinecarboxylic acid (170 mg, 0.478 mmol) and HATU (218 mg, 0.574 mmol) in DMF (3 mL) was added Hunig's base (0.167 mL, 0.957 mmol), and the resulting mixture was stirred at room temperature for 15 minutes. 2-Phenyl-2-propanamine (71 mg, 0.53 mmol) was added, and the reaction mixture was stirred at room temperature for 0.5 hours. LCMS showed reaction was completed. The reaction was poured onto water, and EtOAc was added to extract the product. The product stayed in the EtOAc layer. The organic layer solution was concentrated, and the formed solid was recrystallized from CH₃CN to afford the title compound (222 mg) as a light yellow solid. LC-MS (ES) m/z=473 [M+H]⁺.

Example 193

(3S,6R)-1-[2-Amino-6-(3-amino-1H-indazol-6-yl)-4-pyrimidinyl]-6-methyl-N-(1-methyl-1-phenyl-ethyl)-3-piperidinecarboxamide

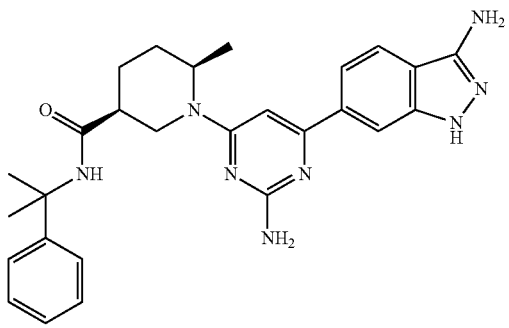 [SMILES: C[C@@H]1CC[C@H](C(=O)NC(C)(C)c2ccccc2)CN1c1cc(-c2ccc3c(N)n[nH]c3c2)nc(N)n1]

Into a sealable tube, (3S,6R)-1-[2-amino-6-(4-cyano-3-fluorophenyl)-4-pyrimidinyl]-6-methyl-N-(1-methyl-1-phenylethyl)-3-piperidinecarboxamide (222 mg, 0.47 mmol), EtOH (5 mL), Hunig's base (0.082 ml, 0.47 mmol), and hydrazine anhydrous (0.089 mL, 2.82 mmol) were added, and the yellow suspension mixture was heated overnight at 110° C. in an oil bath. When the temperature of the reaction reached to 100° C., the solid in the mixture was all dissolved. After overnight, there was a yellow solution as well as a little amount of black colored solid formed. LCMS showed mainly product. CH$_3$OH (5 mL) was added to the solution. The black solid was filtered from the yellow solution. Water (20 mL) was added to the yellow solution, and a solid was formed. The solid was filtered, washed by water, and dried in vacuum. The solid was recrystallized from CH$_3$CN, and the solid was filtered, washed by CH$_3$CN, and dried in vacuum to afford the title compound (101 mg) as a light yellow solid. LC-MS (ES) m/z=485 [M+H]$^+$. $^1$H NMR (400 MHz, DMSO-d$_6$): δ 1.11 (d, J=6.6 Hz, 3H), 1.53 (s, 3H), 1.62 (s, 3H), 1.71 (m, 4H), 2.32-2.44 (m, 2H), 2.84 (m, 1H), 5.38 (s, 2H), 6.09 (s, 2H), 6.57 (s, 1H), 7.11-7.22 (m, 1H), 7.30-7.42 (m, 4H), 7.52-7.60 (m, 1H), 7.71 (d, J=8.3 Hz, 1H), 7.94 (s, 1H), 8.16 (s, 1H), 11.50 (s, 1H).

Intermediate 362

(3S,6R)-1-[2-Amino-6-(4-cyano-3-fluorophenyl)-4-pyrimidinyl]-N-(4-ethylcyclohexyl)-6-methyl-3-piperidinecarboxamide

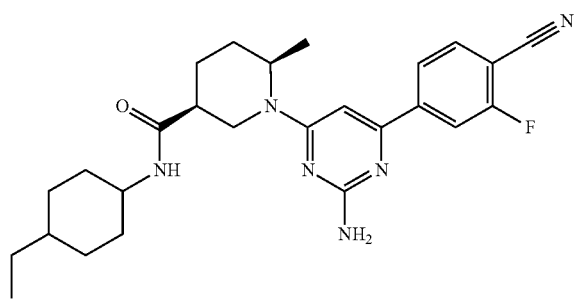 [SMILES: CCC1CCC(NC(=O)[C@H]2CC[C@@H](C)N(c3cc(-c4ccc(C#N)c(F)c4)nc(N)n3)C2)CC1]

To a solution of (3S,6R)-1-[2-amino-6-(4-cyano-3-fluorophenyl)-4-pyrimidinyl]-6-methyl-3-piperidinecarboxylic acid (170 mg, 0.478 mmol) and HATU (218 mg, 0.574 mmol) in DMF (3 mL) was added Hunig's base (0.167 mL, 0.957 mmol), and the resulting mixture was stirred at room temperature for 15 minutes. 4-Ethylcyclohexanamine (61 mg, 0.48 mmol) was added, and the reaction mixture was stirred at room temperature for 0.5 hours. LCMS showed reaction was completed. The reaction was poured into water, and EtOAc was added to extract the product. The product stayed in the EtOAc layer. The organic layer solution was concentrated, and the formed solid was recrystallized from CH$_3$CN to afford the title compound (187 mg) as a light yellow solid. LC-MS (ES) m/z=465 [M+H]$^+$.

Example 194

(3S,6R)-1-[2-Amino-6-(3-amino-1H-indazol-6-yl)-4-pyrimidinyl]-N-(4-ethylcyclohexyl)-6-methyl-3-piperidinecarboxamide

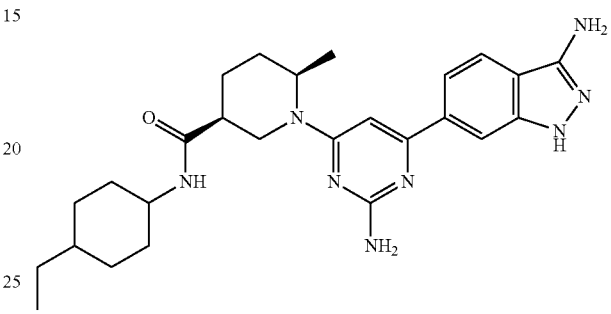

Into a sealable tube, (3S,6R)-1-[2-amino-6-(4-cyano-3-fluorophenyl)-4-pyrimidinyl]-N-(4-ethylcyclohexyl)-6-methyl-3-piperidinecarboxamide (187 mg, 0.403 mmol), EtOH (5 mL), Hunig's base (0.070 ml, 0.403 mmol), and hydrazine anhydrous (0.076 mL, 2.415 mmol) were added, and the yellow suspension mixture was heated overnight at 110° C. in an oil bath. When the temperature of the reaction reached to 100° C., the solid in the mixture was all dissolved. After overnight, there was a yellow solution as well as a little amount of black colored solid formed. LCMS showed mainly product. CH$_3$OH (5 mL) was added to the solution. The black solid was filtered from the yellow solution. Water (20 mL) was added to the yellow solution, and a solid was formed. The solid was filtered, washed by water, and dried in vacuum. The solid was recrystallized from CH$_3$CN, and the solid was filtered, washed by CH$_3$CN, and dried in vacuum to afford the title compound (50 mg) as a light yellow solid. LC-MS (ES) m/z=477 [M+H]$^+$. $^1$H NMR (400 MHz, DMSO-d$_6$): δ 0.79-1.25 (m, 14H), 1.64 (m, 3H), 1.68-1.88 (m, 5H), 2.22 (m, 1H), 2.90 (m, 1H), 3.41-3.58 (m, 1H), 5.38 (s, 2H), 6.07 (s, 2H), 6.57 (s, 1H), 7.58 (s, 1H), 7.65-7.84 (m, 2H), 7.94 (s, 1H), 11.49 (s, 1H).

Intermediate 363

(3S,6R)-1-[2-Amino-6-(4-cyano-3-fluorophenyl)-4-pyrimidinyl]-6-methyl-N-(2-methylcyclohexyl)-3-piperidinecarboxamide

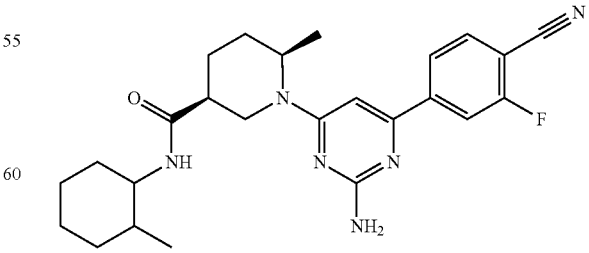

To a solution of (3S,6R)-1-[2-amino-6-(4-cyano-3-fluorophenyl)-4-pyrimidinyl]-6-methyl-3-piperidinecarboxylic acid (170 mg, 0.478 mmol) and HATU (218 mg, 0.574 mmol) in DMF (3 mL) was added Hunig's base (0.167 mL, 0.957 mmol), and the resulting mixture was stirred at room temperature for 15 minutes. 2-Methylcyclohexanamine (54.2 mg, 0.478 mmol) was added, and the reaction mixture was stirred at room temperature for 0.5 hours. LCMS showed reaction was completed. The reaction was poured into water, and EtOAc was added to extract the product. The product stayed in the EtOAc layer. The organic layer solution was concentrated, and the formed solid was recrystallized from $CH_3CN$ to afford the title compound (192 mg) as a light yellow solid. LC-MS (ES) m/z=451 [M+H]$^+$.

Example 195

(3S,6R)-1-[2-Amino-6-(3-amino-1H-indazol-6-yl)-4-pyrimidinyl]-6-methyl-N-(2-methylcyclohexyl)-3-piperidinecarboxamide

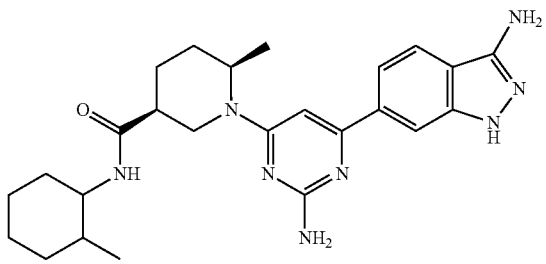 [SMILES: CC1CCCCC1NC(=O)[C@H]1CC[C@@H](C)N(c2cc(-c3ccc4c(N)n[nH]c4c3)nc(N)n2)C1]

Into a microwave tube, (3S,6R)-1-[2-amino-6-(4-cyano-3-fluorophenyl)-4-pyrimidinyl]-6-methyl-N-(2-methylcyclohexyl)-3-piperidinecarboxamide (192 mg, 0.426 mmol), EtOH (5 mL), Hunig's base (0.074 ml, 0.426 mmol), and hydrazine anhydrous (0.08 mL, 2.56 mmol) were added, and the yellow suspension mixture was heated overnight at 110° C. in an oil bath. When the temperature of the reaction reached to 100° C., the solid in the mixture was all dissolved. After overnight, there was a yellow solution as well as a little amount of black colored solid formed. LCMS showed mainly product. $CH_3OH$ (5 mL) was added to the solution. The black solid was filtered from the yellow solution. Water (20 mL) was added to the yellow solution, and a solid was formed. The solid was filtered, washed by water, and dried in vacuum. The solid was recrystallized from $CH_3CN$, and the solid was filtered, washed by $CH_3CN$, and dried in vacuum to afford the title compound (122 mg) as a light yellow solid. LC-MS (ES) m/z=463 [M+H]$^+$. $^1$H NMR (400 MHz, DMSO-d$_6$): δ 0.68-0.98 (m, 4H), 1.14 (m, 8H), 1.66 (m, 8H), 2.25 (m, 1H), 3.30 (m, 1H), 3.36 (m, 1H), 5.38 (s, 2H), 6.07 (s, 2H), 6.56 (d, J=3.5 Hz, 1H), 7.51-7.65 (m, 1H), 7.70 (s, 1H), 7.73 (s, H), 7.94 (d, J=2.8 Hz, 1H), 11.50 (s, 1H).

Intermediate 364

[(2S,5R)-5-Methyl-4-(phenylmethyl)-2-morpholinyl]methyl methanesulfonate

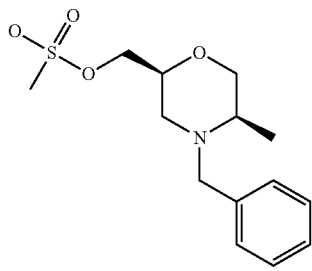

To a solution of [(2S,5R)-5-methyl-4-(phenylmethyl)-2-morpholinyl]methanol (5 g, 22.59 mmol) and triethylamine (9.45 mL, 67.8 mmol) in $CH_2Cl_2$ (50 mL) stirred under nitrogen at 0° C. was added a solution of methanesulfonyl chloride (4.37 mL, 56.5 mmol) in $CH_2Cl_2$ (15 mL) dropwise during 5 minutes. The reaction mixture was stirred at 25° C. for 2.5 hours. Then the reaction mixture was washed with saturated NaHCO$_3$ aqueous solution (2×25 mL). The organic layer was dried over Na$_2$SO$_4$, filtered and concentrated under reduced pressure to afford the title compound (8.0 g) as a yellow oil. LC-MS (ES) m/z=300 [M+H]$^+$.

Intermediate 365

(2S,5R)-2-(Iodomethyl)-5-methyl-4-(phenylmethyl)morpholine

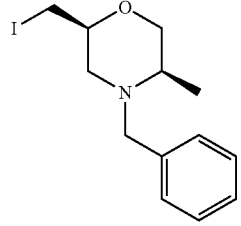 [SMILES: C[C@@H]1CO[C@H](CI)CN1Cc1ccccc1]

To a solution of [(2S,5R)-5-methyl-4-(phenylmethyl)-2-morpholinyl]methyl methanesulfonate (8.0 g, 26.7 mmol) in acetone (80 mL) stirred under nitrogen at room temp was added sodium iodide (20.03 g, 134 mmol), and the reaction mixture was stirred at reflux overnight. The reaction was cooled and concentrated under reduced pressure. Then to the residue was added water (50 mL) and $CH_2Cl_2$ (60 mL). The layers were separated, and the aqueous layer was extracted with $CH_2Cl_2$ (60 mL). The combined organic layers were washed with 1 M Na$_2$S$_2$O$_3$ (2×30 mL), then water (20 mL), dried (Na$_2$SO$_4$), and concentrated to afford the crude product. Purification by silica gel chromatography (300-400 mesh), eluting with Hex/EtOAc (2:1 to 3:2) and monitoring in iodine afforded the title compound (5.9 g) as a yellow oil. LC-MS (ES) m/z=332 [M+H]$^+$.

Intermediate 366

(2R,5R)-2,5-Dimethyl-4-(phenylmethyl)morpholine

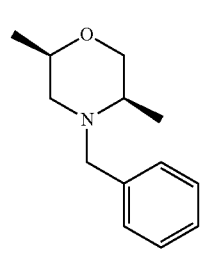

To a solution of (2S,5R)-2-(iodomethyl)-5-methyl-4-(phenylmethyl)morpholine (5.0 g, 15.10 mmol) in ethanol (120 mL) stirred under nitrogen at room temperature was added Pd/C (1.607 g, 1.510 mmol) in ethanol (120 mL). The reaction mixture was purged with hydrogen, and was stirred under hydrogen at 25° C. for 2 hours. After the completion (by LCMS), the mixture was filtered through a pad of celite, the filtrate was purified by silica gel chromatography (300-400 mesh), eluting with petroleum/EtOAc (1:1) to afford the desired title compound (2.5 g) as a white solid. LC-MS (ES) m/z=206 [M+H]$^+$. 1H NMR (CDCl3): δ 7.96-7.93 (m, 2H), 7.49-7.46 (m, 3H), 4.69-4.61 (m, 2H), 4.41-4.37 (m, 1H), 4.03-3.97 (m, 1H), 3.73-3.70 (d, J=12.8 Hz, 1H), 3.48-3.46

(d, J=6.4 Hz, 1H), 3.27-3.24 (d, J=12.4 Hz, 2H), 2.78-2.69 (m, 1H), 1.39-1.37 (d, J=6.4 Hz, 3H), 1.24-1.23 (d, J=12.4 Hz, 3H).

Intermediate 367

(2R,5R)-2,5-dimethylmorpholine

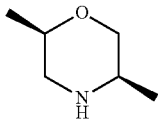

To a solution of ((2R,5R)-2,5-dimethyl-4-(phenylmethyl) morpholine (2.5 g, 12.18 mmol) and hydrochloric acid (0.740 mL, 24.36 mmol) in ethanol (80 mL) stirred under nitrogen at room temperature was added Pd/C (0.648 g, 6.09 mmol). Then the reaction mixture was purged with hydrogen and then stirred under hydrogen at 25° C. overnight. The mixture was filtered through a pad of silica gel, and the filtrate was concentrated under reduced pressure to afford the title compound (1.0 g) as a light yellow solid. LC-MS (ES) m/z=116 [M+H]$^+$. $^1$H NMR (400 MHz, DMSO-d$_6$): δ 1.14-1.14 (d, J=5.6 Hz, 3H), 1.32-1.33 (d, J=6.8 Hz, 3H), 2.81-2.84 (m, 1H), 2.96-2.99 (m, 1H), 3.60-3.63 (m, 2H), 3.82-3.85 (m, 2H), 9.42 (bs, 1H), 9.96 (bs, 1H).

Intermediate 368

4-Chloro-6-[(2R,5R)-2,5-dimethyl-4-morpholinyl]-N-methyl-2-pyrimidinamine

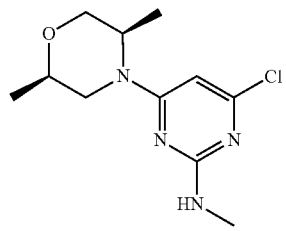 [SMILES: CNc1nc(Cl)cc(N2C[C@@H](C)OC[C@H]2C)n1]

To a solution of (2R,5R)-2,5-dimethylmorpholine (400 mg, 3.47 mmol) and 4,6-dichloro-N-methyl-2-pyrimidinamine (742 mg, 4.17 mmol) in CH$_3$CN (5 mL) stirred at room temperature was added Hunig's base (1.213 mL, 6.95 mmol). The reaction vessel was sealed and heated in Biotage Initiator using initial normal to 120° C. for 1 hour. After cooling the reaction, the mixture was concentrated under reduced pressure and the residue was added to a silica gel column and was eluted with Hex/EtOAc (10:1 to 3:1). Collected fractions:the first fraction was the starting material 4,6-dichloro-N-methyl-2-pyrimidinamine (300 mg), and the second fraction was the title compound (460 mg) as a light yellow solid. LC-MS (ES) m/z=257 [M+H]$^+$.

Intermediate 369

4-[6-[(2R,5R)-2,5-Dimethyl-4-morpholinyl]-2-(methylamino)-4-pyrimidinyl]-2-fluorobenzonitrile

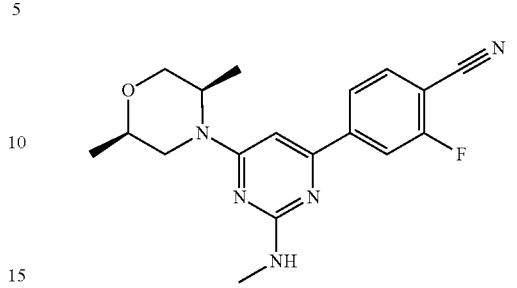

To a solution of 4-chloro-6-[(2R,5R)-2,5-dimethyl-4-morpholinyl]-N-methyl-2-pyrimidinamine (430 mg, 1.675 mmol) and 2-fluoro-4-(4,4,5,5-tetramethyl-1,3,2-dioxaborolan-2-yl)benzonitrile (621 mg, 2.51 mmol) in 1,4-dioxane (2 mL) and water (1.00 mL) in a microwave reaction vessel stirred under nitrogen at room temperature was added Na$_2$CO$_3$ (355 mg, 3.35 mmol) and Pd(Ph$_3$P)$_4$ (194 mg, 0.167 mmol). The reaction vessel was sealed and heated in Biotage Initiator using initial normal to 120° C. for 1 hour. After cooling the reaction to room temperature, the mixture was filtered through a pad of celite, and the filter cake was washed with THF (3×30 mL) and CH$_3$OH (3×30 mL). The filtrate was purified with a silica gel (300-400) column and was eluted with Hex/EtOAc (2:1 to 1:2) to afford the title compound (315 mg) as a light yellow solid. LC-MS (ES) m/z=342 [M+H]$^+$.

Example 196

6-[6-[(2R,5R)-2,5-Dimethyl-4-morpholinyl]-2-(methylamino)-4-pyrimidinyl]-1H-indazol-3-amine

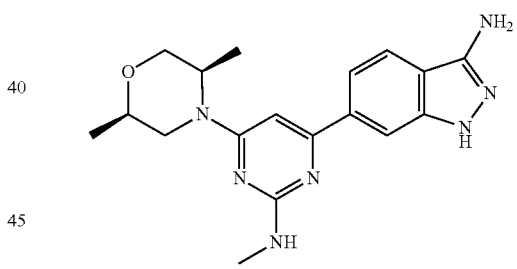

Run 1: To a solution of 4-[6-[(2R,5R)-2,5-dimethyl-4-morpholinyl]-2-(methylamino)-4-pyrimidinyl]-2-fluorobenzonitrile (315 mg, 0.923 mmol) in ethanol (2.5 mL) at room temperature was added hydrazine monohydrate (0.647 mL, 18.45 mmol). The reaction vessel was sealed and heated in Biotage Initiator using initial low to 120° C. for 1 hour. After cooling the reaction, the mixture was concentrated under reduced pressure, and then the crude product (300 mg, 0.740 mmol, 80% yield) was purified with another batch in later experiment. LC-MS (ES) m/z=354 [M+H]$^+$.

Run 2: To a solution of 4-[6-[(2R,5R)-2,5-dimethyl-4-morpholinyl]-2-(methylamino)-4-pyrimidinyl]-2-fluorobenzonitrile (300 mg, 0.879 mmol) in ethanol (2.5 mL) at room temperature was added hydrazine monohydrate (0.616 mL, 17.58 mmol). The reaction vessel was sealed and heated in Biotage Initiator using initial low to 120° C. for 1 hour. After cooling the reaction, the mixture was concentrated under reduced pressure, and then the crude product (250 mg, 0.626 mmol, 71.3% yield) was purified with the crude product from Run 1 by silica gel chromatography. LC-MS (ES) m/z=354 [M+H]$^+$.

Purification: The crude products from Run 1 (300 mg, 0.849 mmol) and Run 2 (250 mg, 0.707 mmol) were added to a silica gel column eluting with Hex/EtOAc (2:1 to 1:1) to afford the title compound (285 mg) as a white solid. LC-MS (ES) m/z=354 [M+H]+. 1H NMR (400 MHz, DMSO-$d_6$): δ 1.17-1.21 (m, 6H), 2.68-2.75 (t, J=10.0 Hz, 1H), 2.84-2.85 (d, J=4.8 Hz, 3H), 3.49-3.54 (m, 1H), 3.64-3.68 (dd, J=11.6 Hz, J=2.8 Hz, 1H), 3.72-3.75 (d, J=10.8 Hz, 1H), 4.17 (bs, 1H), 4.50 (bs, 1H), 5.37 (s, 2H), 6.53 (bs, 1H), 6.56 (s, 1H), 7.60-7.62 (d, J=8.0 Hz, 1H), 7.71-7.73 (d, J=8.8 Hz, 1H), 7.97 (s, 1H), 11.49 (s, 1H).

Intermediate 370

4-Chloro-6-[(3R)-3-(1-methylethyl)-4-morpholinyl]-2-pyrimidinamine

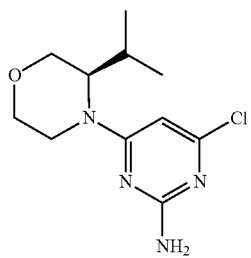 [SMILES: CC(C)[C@@H]1COCCN1c1cc(Cl)nc(N)n1]

(3R)-3-(1-Methylethyl)morpholine HCl salt (3.50 g, 21.1 mmol) and 4,6-dichloro-2-pyrimidinamine (3.81 g, 23.2 mmol, 1.1 equiv) were charged into a 60 mL sealable tube, followed with addition of 20 mL of propionitrile and Hunig's base (11.1 mL, 63.4 mmol, 3 equiv). The vessel was sealed and heated at 110° C. in an oil bath for 68 hours. The mixture was concentrated in vacuo, and the residue was partitioned between water (50 mL) and EtOAc (150 mL). The aqueous was extracted with another 100 mL of EtOAc. The combined organic was dried over $Na_2SO_4$, filtered, and concentrated in vacuo. The foamy residue was taken up in $CHCl_3$ with some EtOAc to give a suspension, which was filtered. The solids collected were mostly starting 4,6-dichloro-2-pyrimidinamine. The filtrate underwent silica gel column chromatography using gradient elution of 1% EtOAc in $CHCl_3$ to 80% EtOAc in $CHCl_3$ to afford the title compound (4.36 g) as a glassy foam. LC-MS (ES) m/z=257 [M+H]+.

Intermediate 371

4-{2-Amino-6-[(3R)-3-(1-methylethyl)-4-morpholinyl]-4-pyrimidinyl}-2-fluorobenzonitrile

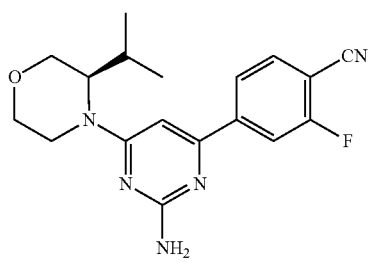 [SMILES: CC(C)[C@@H]1COCCN1c1cc(-c2ccc(C#N)c(F)c2)nc(N)n1]

4-Chloro-6-[(3R)-3-(1-methylethyl)-4-morpholinyl]-2-pyrimidinamine (350 mg, 1.36 mmol), (4-cyano-3-fluorophenyl)boronic acid (337 mg, 2.05 mmol, 1.5 equiv), tricyclohexylphosphine (57.3 mg, 0.20 mmol, 0.15 equiv), $Pd_2(dba)_3$ (94 mg, 0.10 mmol, 0.075 equiv) and $K_3PO_4$ (492 mg, 2.32 mmol, 1.7 equiv) were charged into a 30 mL microwave vial, followed by addition of 5 mL of 1,4-dioxane and 1.6 mL of water. The mixture was bubbled with argon for 10 minutes, followed by capping and heating in a oil bath at 100° C. for 20 hours. LCMS showed conversion complete. The mixture was filtered through celite and rinsed with EtOAc (40 mL). The filtrate was concentrated in vacuo. The residue was partitioned between EtOAc (50 mL) and brine (10 mL). The organic was dried over $Na_2SO_4$, filtered, and concentrated in vacuo. The residue was purified by silica gel column chromatography using gradient elution of 1% EtOAc in $CHCl_3$ to 80% EtOAc in $CHCl_3$ to afford the title compound (359 mg) as an off-white foam with a light yellow tint. LC-MS (ES) m/z=342 [M+H]+.

Example 197

6-{2-Amino-6-[(3R)-3-(1-methylethyl)-4-morpholinyl]-4-pyrimidinyl}-1H-indazol-3-amine

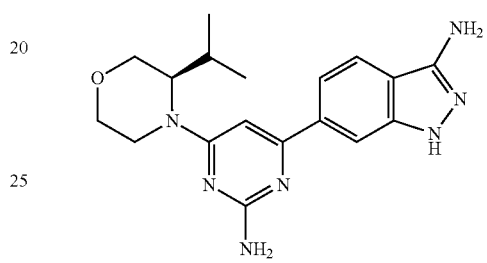

To a solution of 4-{2-amino-6-[(3R)-3-(1-methylethyl)-4-morpholinyl]-4-pyrimidinyl}-2-fluorobenzonitrile (355 mg, 1.04 mmol) in EtOH (10 mL) was added hydrazine monohydrate (2 mL) in one portion at room temperature. The mixture was heated in an oil bath at 100° C. under a gentle reflux for 18 hours. LCMS showed conversion complete. The mixture was cooled to room temperature, filtered through celite, and rinsed with EtOH (20 mL). The filtrate was concentrated in vacuo. The residue was suspended in water (10 mL). The suspension was sonicated briefly, and filtered. The solids were washed with water, dried under house vacuum at room temperature for 2 hours, and then under vacuum at room temperature over $P_2O_5$ for 20 hours. These solids were washed with hexane (2×3 mL), followed by drying under vacuum at 65° C. for 24 hours to give the title compound (256 mg) as a beige solid. LC-MS (ES) m/z=354 [M+H]+. 1H NMR (400 MHz, $CD_3OD$): δ 0.88 (d, J=6.8 Hz, 3H), 1.10 (d, J=6.6 Hz, 3H), 2.47-2.54 (m, 1H), 3.21-3.30 (m., 1H), 3.51-3.58 (m, 2H), 3.93 (dd, J=11.2, 3.41 Hz, 1H), 4.10 (d, J=11.6 Hz, 1H), 6.46 (s, 1H), 7.47 (dd, J=8.5, 1.4 Hz, 1H), 7.76 (d, J=8.6 Hz, 1H), 7.79 (s, 1H).

Intermediate 372

4-{2-Amino-6-[(3R)-3-(1-methylethyl)-4-morpholinyl]-4-pyrimidinyl}-2,6-difluorobenzonitrile

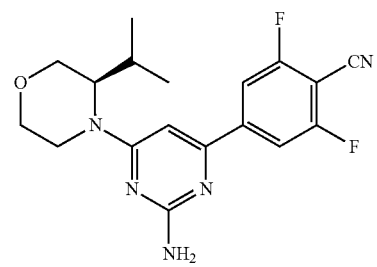 [SMILES: CC(C)[C@@H]1COCCN1c1cc(-c2cc(F)c(C#N)c(F)c2)nc(N)n1]

4-Chloro-6-[(3R)-3-(1-methylethyl)-4-morpholinyl]-2-pyrimidinamine (2.36 g, 9.19 mmol), (4-cyano-3,5-difluorophenyl)boronic acid (2.52 g, 13.19 mmol, 1.5 equiv), tricyclohexylphosphine (0.39 g, 1.38 mmol, 0.15 equiv), Pd$_2$(dba)$_3$ (0.63 g, 0.69 mmol, 0.075 equiv), and K$_3$PO$_4$ (3.32 g, 15.63 mmol, 1.7 equiv) were charged into a 250 mL RB flask, followed by addition of 1,4-dioxane (30 mL) and water (10 mL). The mixture was degassed and back flushed with nitrogen, which was repeated five times. The mixture was heated in an oil bath at 100° C. for 20 hours. LCMS showed conversion complete. The mixture was filtered through celite and rinsed with EtOAc (100 mL). The filtrate was concentrated in vacuo. The residue was partitioned between EtOAc (200 mL) and brine (50 mL). The organic was dried over Na$_2$SO$_4$, filtered, and concentrated in vacuo. The residue was purified by silica gel column chromatography using gradient elution of 1% EtOAc in CHCl$_3$ to 100% EtOAc, providing the title compound (2.92 g) as a yellowish foam. LC-MS (ES) m/z=360 [M+H]$^+$.

Intermediate 373

4-{2-Amino-6-[(3R)-3-(1-methylethyl)-4-morpholinyl]-4-pyrimidinyl}-2-fluoro-6-(methyloxy)benzonitrile

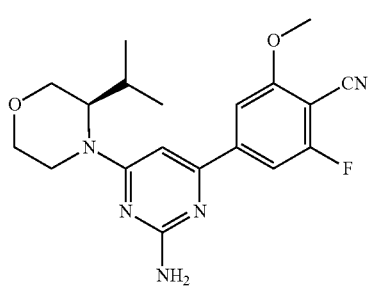 [SMILES: COc1cc(-c2cc(N3CCOC[C@H]3C(C)C)nc(N)n2)cc(F)c1C#N]

4-{2-Amino-6-[(3R)-3-(1-methylethyl)-4-morpholinyl]-4-pyrimidinyl}-2,6-difluorobenzonitrile (380 mg, 1.06 mmol) was azeotroped with toluene (2×12 mL). The residue was dissolved in 5 mL of DMF as a clear yellow solution, to which was added NaOMe (2.30 mL of a stock solution with concentration of 0.52 mmol/mL, 1.19 mmol, 1.12 equiv) at room temperature in one portion. The resulting mixture was stirred at room temperature for 18 hours. LCMS showed conversion complete. The mixture was concentrated in vacuo. The residue was purified by silica gel column chromatography using gradient elution of 1% EtOAc in CHCl$_3$ to 100% EtOAc, providing the title compound (276 mg) as a light yellow oily residue. LC-MS (ES) m/z=372 [M+H]$^+$.

Example 198

6-{2-Amino-6-[(3R)-3-(1-methylethyl)-4-morpholinyl]-4-pyrimidinyl}-4-(methyloxy)-1H-indazol-3-amine

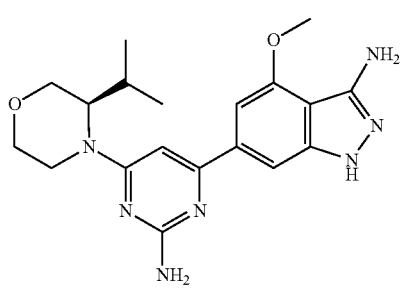 [SMILES: COc1cc(-c2cc(N3CCOC[C@H]3C(C)C)nc(N)n2)cc2[nH]nc(N)c12]

To a solution of 4-{2-amino-6-[(3R)-3-(1-methylethyl)-4-morpholinyl]-4-pyrimidinyl}-2-fluoro-6-(methyloxy)benzonitrile (276 mg, 0.74 mmol) in ethanol (10 mL) was added hydrazine monohydrate (2 mL) in one portion. The mixture was heated at 100° C. for 20 hours. LCMS showed conversion complete. The mixture was cooled to room temperature and concentrated in vacuo. The solid residue was partitioned between EtOAc (2×40 mL) and water (15 mL). The organic was concentrated in vacuo, and the residue was purified by silica gel column chromatography using gradient elution of 1% A in CHCl$_3$ to 75% A in CHCl$_3$, where A was a mixture of 800/80/3200 (v/v/v) CH$_3$OH/NH$_4$OH/CHCl$_3$. The collected fractions were concentrated in vacuo. The residue was redissolved in CHCl$_3$ and EtOAc, followed by filtration. The filtrate was concentrated in vacuo, and azeotroped with EtOH. The residue was taken up in water (8 mL) as a suspension. The solids were collected by filtration and washed with water (2×2 mL), followed with drying under house vacuum at room temperature for 1 hour and then vacuum at room temperature over P$_2$O$_5$ for 20 hours. The solids were washed with hexane (2×3 mL), and dried under vacuum at 65° C. for 20 hours to give the title compound (125 mg) as an off-white solid. LC-MS (ES) m/z=384 [M+H]$^+$. $^1$H NMR (400 MHz, CD$_3$OD): δ 0.88 (d, J=6.8 Hz, 3H), 1.10 (d, J=6.6 Hz, 3H), 2.45-2.55 (m, 1H), 3.20-3.30 (m, 1H), 3.48-3.60 (m, 2H), 3.93 (dd, J=11.4, 3.3 Hz, 1H), 4.04 (s, 3H), 4.10 (d, J=11.6 Hz, 1H), 6.43 (s, 1H), 6.85 (s, 1H), 7.31 (s, 1H).

Intermediate 374

4-{2-Amino-6-[(3R)-3-(1-methylethyl)-4-morpholinyl]-4-pyrimidinyl}-2-(ethyloxy)-6-fluorobenzonitrile

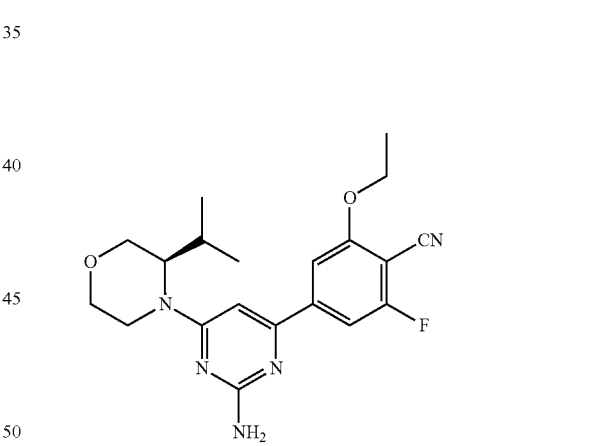

4-{2-Amino-6-[(3R)-3-(1-methylethyl)-4-morpholinyl]-4-pyrimidinyl}-2,6-difluorobenzonitrile (405 mg, 1.12 mmol) was azeotroped with toluene (2×15 mL). The residue was dissolved in 5 mL of DMF as a yellow clear solution, to which was added NaOEt (1.45 mL of a stock solution with concentration of 0.87 mmol/mL, 1.25 mmol, 1.12 equiv) at room temperature in one portion. The resulting light orange clear solution was stirred at room temperature for 20 hours. LCMS showed conversion complete. The mixture was concentrated in vacuo. The residue was purified by silica gel column chromatography using gradient elution of 1% EtOAc in CHCl$_3$ to 100% EtOAc, providing the title compound (310 mg) as a white solid residue. LC-MS (ES) m/z=386 [M+H]$^+$.

Example 199

6-{2-Amino-6-[(3R)-3-(1-methylethyl)-4-morpholinyl]-4-pyrimidinyl}-4-(ethyloxy)-1H-indazol-3-amine

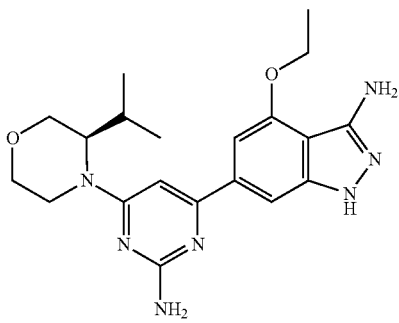 [SMILES: CCOc1cc(-c2cc(N3CCOC[C@H]3C(C)C)nc(N)n2)cc2[nH]nc(N)c12]

To a solution of 4-{2-amino-6-[(3R)-3-(1-methylethyl)-4-morpholinyl]-4-pyrimidinyl}-2-(ethyloxy)-6-fluorobenzonitrile (370 mg, 0.96 mmol) in ethanol (10 mL) was added hydrazine monohydrate (2.0 mL) in one portion. The mixture was heated at 100° C. for 20 hours. LCMS showed conversion complete. The mixture was cooled to room temperature and concentrated in vacuo. The solid residue was partitioned between EtOAc (2×40 mL) and water (15 mL). The organic was concentrated in vacuo, and the residue was purified by silica gel column chromatography using gradient elution of 1% A in CHCl₃ to 75% A in CHCl₃, where A was a mixture of 800/80/3200 (v/v/v) CH₃OH/NH₄OH/CHCl₃. The collected fractions were concentrated in vacuo. The residue was redissolved in CHCl₃ and EtOAc, followed by filtration. The filtrate was concentrated in vacuo, and azeotroped with EtOH. The residue was taken up in water (8 mL) as a suspension. The solids were collected by filtration and washed with water (2×2 mL), drying under house vacuum at room temperature for 1 hour and then drying under vacuum at room temperature over P₂O₅ for 20 hours. These solids were washed with hexane (2×3 mL), and dried under vacuum at 65° C. for 20 hours to afford the title compound (273 mg) as an off-white solid. LC-MS (ES) m/z=398 [M+H]$^+$. $^1$H NMR (400 MHz, CD₃OD): δ 0.87 (d, J=6.8 Hz, 3H), 1.10 (d, J=6.6 Hz, 3H), 1.54 (t, J=7.1 Hz, 3H), 2.44-2.54 (m, 1H), 3.21-3.30 (m, 1H), 3.50-3.59 (m, 2H), 3.92 (dd, J=11.2, 3.4 Hz, 1H), 4.09 (d, J=11.9 Hz, 1H), 4.30 (q, J=6.9 Hz, 2H), 6.41 (s, 1H), 6.83 (s, 1H), 7.30 (d, J=1.0 Hz, 1H).

Example 200

6-{2-Amino-6-[(3R)-3-methyl-4-morpholinyl]-4-pyrimidinyl}-4-(methyloxy)-1H-indazol-3-amine

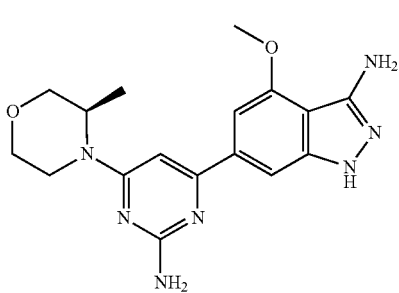 [SMILES: COc1cc(-c2cc(N3CCOC[C@H]3C)nc(N)n2)cc2[nH]nc(N)c12]

4-{2-Amino-6-[(3R)-3-methyl-4-morpholinyl]-4-pyrimidinyl}-2,6-difluorobenzonitrile (500 mg, 1.509 mmol) was suspended in CH₃OH (7 mL) with stirring in a 50 mL round bottom flask under nitrogen, and a solution of sodium methoxide in methanol (freshly prepared from sodium (41.6 mg, 1.811 mmol) and methanol (3 mL)) was added. The mixture was stirred at room temperature monitoring it by HPLC. After 4 hours, the reaction was not changing and seemed to stop. Since it was a suspension and solubility was poor, DMF (3 mL) was added to give a clear yellow solution. After another hour (5 hours total), HPLC showed some progression, so the reaction was left of stir overnight. HPLC indicated complete conversion. Acetic acid (5 drops) was added to quench any leftover methoxide, and the mixture was evaporated to dryness. The residue was suspended in ethanol (8 mL), and hydrazine monohydrate (1.464 mL, 30.2 mmol) was added. The mixture was refluxed under nitrogen in a 100° C. oil bath overnight. HPLC showed complete conversion to product. After concentrating to dryness, purification by silica gel chromatograpy (Analogix SF25-40 g cartridge) eluting with a gradient of CHCl₃ to 90:10:1 CHCl₃:CH₃OH: NH₄OH gave the title compound (491 mg) as a pale yellow solid. LC-MS (ES) m/z=356 [M+H]$^+$. $^1$H NMR (400 MHz, DMSO-d₆): δ 1.18 (d, J=6.6 Hz, 3H), 3.11 (td, J=12.8, 3.7 Hz, 1H), 3.44 (td, J=11.8, 2.9 Hz, 1H), 3.53-3.66 (m, 1H), 3.66-3.79 (m, 1H), 3.84-4.01 (m, 4H), 4.08 (d, J=12.6 Hz, 1H), 4.42-4.55 (m, 1H), 5.03 (s, 2H), 6.11 (s, 2H), 6.50 (s, 1H), 6.92 (s, 1H), 7.49 (s, 1H), 11.54 (s, 1H).

Intermediate 375

1,1-Dimethylethyl[(3R)-1-(2-amino-6-chloro-4-pyrimidinyl)-3-piperidinyl]carbamate

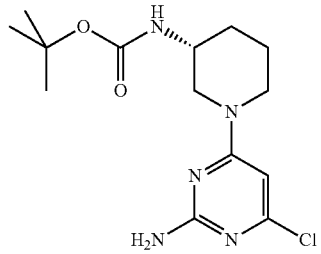 [SMILES: CC(C)(C)OC(=O)N[C@@H]1CCCN(c2cc(Cl)nc(N)n2)C1]

To a stirring mixture of 1,1-dimethylethyl(3R)-3-piperidinylcarbamate (10 g, 49.9 mmol) and K₂CO₃ (6.90 g, 49.9 mmol) in ethanol (100 mL) was added 4,6-dichloro-2-pyrimidinamine (7.78 g, 47.4 mmol), and the reaction mixture was refluxed for 1 hour. LCMS analysis indicated complete conversion. Water (150 mL) was slowly added to the hot mixture, which was then allowed to cool to room temperature with stirring. The precipitated product was collected by filtration, washed with 1:2 ethanol:water, and dried under vacuum at 45° C. to afford the title compound (14.98 g) as a tan solid. LC-MS (ES) m/z=328 [M+H]$^+$.

Intermediate 376

1,1-Dimethylethyl{(3R)-1-[2-amino-6-(4-cyano-3-fluorophenyl)-4-pyrimidinyl]-3-piperidinyl}carbamate

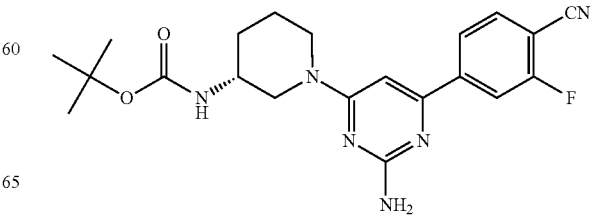

1,1-Dimethylethyl[(3R)-1-(2-amino-6-chloro-4-pyrimidinyl)-3-piperidinyl]carbamate (154 mg, 0.470 mmol) and (4-cyano-3-fluorophenyl)boronic acid (116 mg, 0.705 mmol) were dissolved in 1,4-dioxane (3 mL) in a 20 mL sealable vial. Saturated aqueous NaHCO$_3$ (1.5 mL) was added, and N$_2$ gas was bubbled through the mixture for 10 minutes. Then Pd(Ph$_3$P)$_4$ (81 mg, 0.070 mmol) was added, and N$_2$ gas was bubbled through the mixture for an additional 5 minutes. The reaction was then capped and heated at 100° C. overnight. The reaction was diluted with water (5 mL) and then extracted with EtOAc (3×10 mL). Organic was combined, dried over MgSO$_4$, filtered and concentrated. The yellow oil was then purified on a Biotage SNAP column (25 g) with a gradient of 0 to 45% EtOAc in Hexane over 30 minutes to afford the title compound (140 mg) as a yellow oil. LC-MS (ES) m/z=413 [M+H]$^+$.

Example 201

1,1-Dimethylethyl{(3R)-1-[2-amino-6-(3-amino-1H-indazol-6-yl)-4-pyrimidinyl]-3-piperidinyl}carbamate

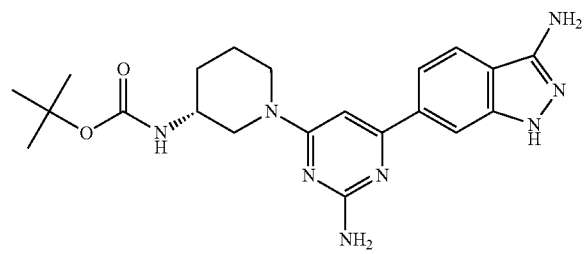 [SMILES: CC(C)(C)OC(=O)N[C@@H]1CCCN(c2cc(-c3ccc4c(N)n[nH]c4c3)nc(N)n2)C1]

1,1-Dimethylethyl{(3R)-1-[2-amino-6-(4-cyano-3-fluorophenyl)-4-pyrimidinyl]-3-piperidinyl}carbamate (140 mg, 0.339 mmol) was dissolved in ethanol (3 mL) in a 5 mL sealable vial. Then hydrazine monohydrate (0.499 mL, 10.18 mmol) was added, the vial was sealed, and the reaction was heated at 100° C. overnight. The reaction was then concentrated and dissolved in 2 mL of DMSO and purified on HPLC (HPLC condition: open-access Gilson using Trilution software with a Varian Polaris 5u C18(2) 100A. 50×30.00 mm 5 micron. 7.3-minute run (47 mL/min, 20% CH$_3$CN/H$_2$O, 0.1% TFA to 45% CH$_3$CN/H$_2$O, 0.1% TFA) with UV detection at 254 nm). Product fractions were combined and the volume was reduced to remove most of the CH$_3$CN. To the water left behind was then added saturated NaHCO$_3$ then extracted with EtOAc (3×15 mL). The organic was combined and washed with saturated NaCl, dried over MgSO$_4$, filtered, concentrated, and transferred to a haystack vial. Water (1 mL) was added, and the resulting mixture was freeze dried to afford the title compound (49 mg) as a light yellow solid. LC-MS (ES) m/z=425 [M+H]$^+$. $^1$H NMR (400 MHz, DMSO-d$_6$): δ 1.38 (s, 9H), 1.44 (bs, 2H), 1.73 (d, J=4.3 Hz, 1H), 1.86 (bs, 1H), 2.86 (bs, 1H), 3.02 (bs, 1H), 4.09 (bs, 1H), 4.26 (bs, 1H), 5.38 (s, 2H), 6.10 (bs, 2H), 6.57 (s, 1H), 6.94 (d, J=7.6 Hz, 1H), 7.54 (d, J=8.3 Hz, 1H), 7.70 (d, J=8.3 Hz, 1H), 7.92 (s, 1H), 11.51 (s, 1H).

Intermediate 377

1,1-Dimethylethyl{(3R)-1-[6-chloro-2-(methylamino)-4-pyrimidinyl]-3-piperidinyl}carbamate

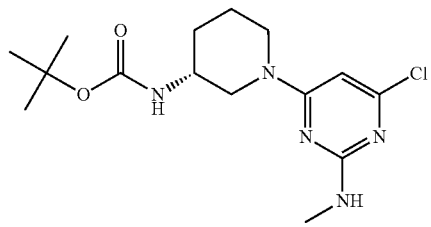 [SMILES: CNc1nc(Cl)cc(N2CCC[C@@H](NC(=O)OC(C)(C)C)C2)n1]

To a stirring mixture of 1,1-dimethylethyl(3R)-3-piperidinylcarbamate (4.8 g, 24.0 mmol) and K$_2$CO$_3$ (3.31 g, 24.0 mmol) in ethanol (50 mL) was added 4,6-dichloro-N-methyl-2-pyrimidinamine (4.05 g, 22.8 mmol), and the reaction mixture was refluxed for 1 hour. LCMS analysis indicated complete conversion. Water (50 mL) was slowly added to the hot mixture, which was then allowed to cool to room temperature with stirring. The precipitated product was collected by filtration, washed with 1:1 ethanol:water, and dried under vacuum at 45° C. to afford the title compound (7.07 g) as a white solid. LC-MS (ES) m/z=342 [M+H]$^+$.

Intermediate 378

1,1-Dimethylethyl{(3R)-1-[6-(4-cyano-3-fluorophenyl)-2-(methylamino)-4-pyrimidinyl]-3-piperidinyl}carbamate

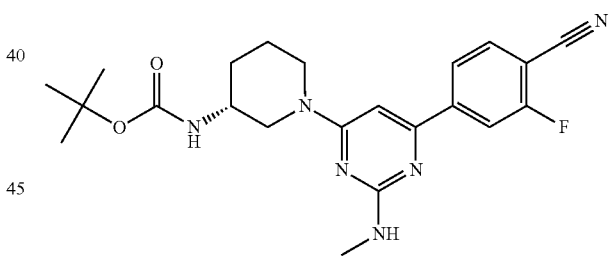

To 1,1-dimethylethyl{(3R)-1-[6-chloro-2-(methylamino)-4-pyrimidinyl]-3-piperidinyl}carbamate (3.0 g, 8.8 mmol) and (4-cyano-3-fluorophenyl)boronic acid (1.8 g, 10.9 mmol) were added 1,4-dioxane (50 mL) and sat. aq. NaHCO$_3$ (25 mL), and the resulting mixture was purged ("degassed") with N$_2$ into a sealable tube. Pd(Ph$_3$P)$_4$ (0.507 g, 0.439 mmol) was added, the tube was sealed, and the reaction mixture was stirred overnight at 95° C. The reaction was allowed to cool down to room temperature and poured onto water. A solid precipitated immediately. The mixture was sonicated and filtered to afford a yellow solid. This solid material was taken up into EtOAc (500 mL) and the resulting organic solution was dried (MgSO$_4$), filtered and concentrated until ~10 mL of solvent remained. This liquid was injected into a 400 g SiO$_2$ column and purified by flash chromatography (gradient: 100% Hexanes to 75% EtOAc/Hexanes) to afford the title compound (3.18 g) as a yellow solid. LC-MS (ES) m/z=427 [M+H]$^+$.

Example 202

1,1-Dimethylethyl{(3R)-1-[6-(3-amino-1H-indazol-6-yl)-2-(methylamino)-4-pyrimidinyl]-3-piperidinyl}carbamate

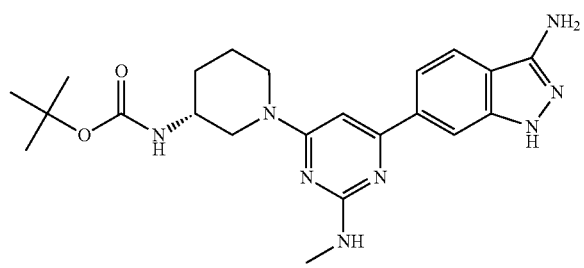 [SMILES: CNc1nc(-c2ccc3c(N)n[nH]c3c2)cc(N2CCC[C@@H](NC(=O)OC(C)(C)C)C2)n1]

1,1-Dimethylethyl{(3R)-1-[6-(4-cyano-3-fluorophenyl)-2-(methylamino)-4-pyrimidinyl]-3-piperidinyl}carbamate (162 mg, 0.380 mmol) was dissolved in ethanol (3 mL) in a 5 mL microwave vial. Then hydrazine monohydrate (0.559 mL, 11.40 mmol) was added, and the vial was capped and heated at 100° C. overnight. The reaction was then concentrated and dissolved in 2 mL of DMSO and purified on HPLC (HPLC condition: open-access Gilson using Trilution software with a Varian Polaris 5u C18(2) 100A. 50×30.00 mm 5 micron. 7.3-minute run (47 mL/min, 13% $CH_3CN/H_2O$, 0.1% TFA to 38% $CH_3CN/H_2O$, 0.1% TFA) with UV detection at 254 nm). Product fractions were combined and the volume was reduced to remove most of the $CH_3CN$. To the water left behind was then added saturated $NaHCO_3$, then extracted with EtOAc (3×15 mL). The organic was combined and washed with saturated NaCl, dried over $MgSO_4$, filtered, concentrated, and transferred to a haystack vial. Water (1 mL) was added, and the resulting mixture was freeze dried to afford the title compound (110 mg) as a light yellow solid. LC-MS (ES) m/z=439 [M+H]$^+$. $^1$H NMR (400 MHz, DMSO-$d_6$): δ 11.43 (s, 1H), 7.89 (br. s., 1H), 7.61-7.67 (m, 1H), 7.50 (d, J=8.34 Hz, 1H), 6.84 (d, J=7.58 Hz, 1H), 6.49 (br. s., 2H), 5.23-5.39 (m, 2H), 4.17 (br. s., 1H), 3.99-4.09 (m, 1H), 2.94-3.10 (m, 1H), 2.85 (br. s., 1H), 2.77 (d, J=4.39 Hz, 3H), 1.73-1.89 (m, 1H), 1.16-1.73 (m, 1H), 1.34-1.50 (m, 2H), 1.31 (s, 9H).

Intermediate 379

1,1-Dimethylethyl{(3R)-1-[6-(4-cyano-3,5-difluorophenyl)-2-(methylamino)-4-pyrimidinyl]-3-piperidinyl}carbamate

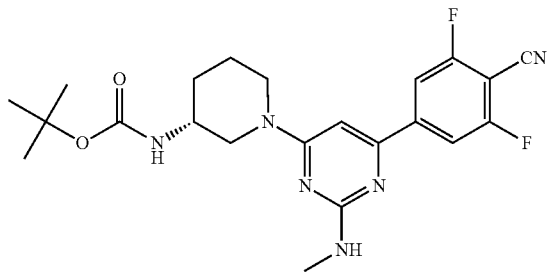 [SMILES: CNc1nc(-c2cc(F)c(C#N)c(F)c2)cc(N2CCC[C@@H](NC(=O)OC(C)(C)C)C2)n1]

1,1-Dimethylethyl{(3R)-1-[6-chloro-2-(methylamino)-4-pyrimidinyl]-3-piperidinyl}carbamate (150 mg, 0.439 mmol) and (4-cyano-3,5-difluorophenyl)boronic acid (120 mg, 0.658 mmol) were dissolved in 1,4-dioxane (3 mL) in a 20 mL sealable vial. Saturated $NaHCO_3$ (1.5 mL) was added, and $N_2$ gas was bubbled through the mixture for 10 minutes. Then $Pd(Ph_3P)_4$ (76 mg, 0.066 mmol) was added, and $N_2$ gas was bubbled through the mixture for an additional 5 minutes. The vial was capped, and the reaction was heated at 100° C. overnight. The reaction was diluted with water (5 mL) and then extracted with EtOAc (3×10 mL). Organic was the combined, dried over $MgSO_4$, filtered and concentrated. The yellow oil was then purified on Biotage SNAP column 25 g with a gradient of 0 to 55% EtOAc in Hexane over 35 minutes to afford the title compound (130 mg) as a yellow oil. LC-MS (ES) m/z=445 [M+H]$^+$.

Intermediate 380

1,1-Dimethylethyl{(3R)-1-[6-[4-cyano-3-fluoro-5-(methyloxy)phenyl]-2-(methylamino)-4-pyrimidinyl]-3-piperidinyl}carbamate

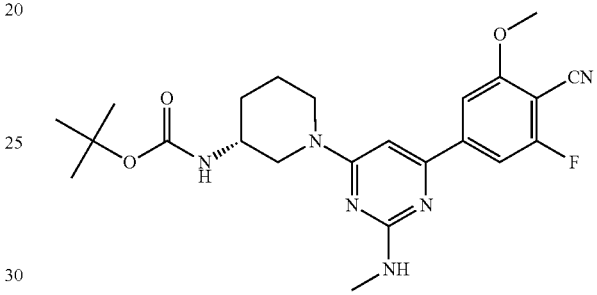

A solution of sodium methoxide was made from 65 mg of sodium dissolved in 2.8 mL of $CH_3OH$. From that solution, 0.35 mL was added to a pre-dissolved solution of 1,1-dimethylethyl{(3R)-1-[6-(4-cyano-3,5-difluorophenyl)-2-(methylamino)-4-pyrimidinyl]-3-piperidinyl}carbamate (130 mg, 0.292 mmol) in $CH_3OH$ (3 mL). The reaction was let stir at room temperature overnight. The reaction was concentrated, diluted with water (10 mL) and extracted with EtOAc (3×10 mL). The organic was combined, washed with saturated NaCl solution, dried over $MgSO_4$, filtered and concentrated to afford the crude title compound (118 mg). LC-MS (ES) m/z=457 [M+H]$^+$.

Example 203

1,1-Dimethylethyl{(3R)-1-[6-[3-amino-4-(methyloxy)-1H-indazol-6-yl]-2-(methylamino)-4-pyrimidinyl]-3-piperidinyl}carbamate

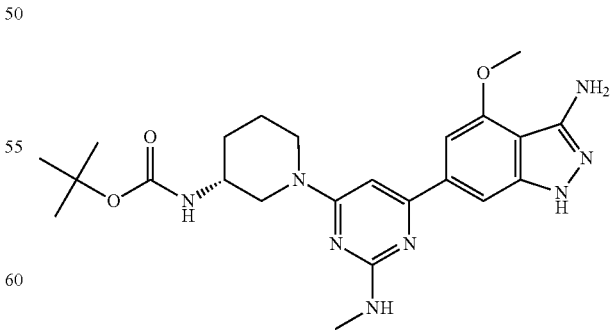

1,1-Dimethylethyl{(3S)-1-[2-amino-6-(4-cyano-3-fluorophenyl)-4-pyrimidinyl]-3-piperidinyl}carbamate (180 mg, 0.436 mmol) was dissolved in ethanol (3 mL) in a 5 mL sealable vial. Then hydrazine monohydrate (0.642 mL, 13.09 mmol) was added, the vial was capped, and the reaction was heated at 100° C. overnight. The reaction was then concentrated and dissolved in 2 mL of DMSO and purified on HPLC (HPLC condition: open-access Gilson using Trilution software with a Varian Polaris 5u C18(2) 100A. 50×30.00 mm 5 micron. 7.3-minute run (47 mL/min, 13% CH$_3$CN/H$_2$O, 0.1% TFA to 38% CH$_3$CN/H$_2$O, 0.1% TFA) with UV detection at 254 nm). Product fractions were combined and the volume was reduced to remove most of the CH$_3$CN. To the water left behind was then added saturated NaHCO$_3$, then extracted with EtOAc (3×15 mL). The organic was washed with saturated NaCl, dried over MgSO$_4$, filtered, concentrated, and transferred to a haystack vial. Water (1 mL) was added, and the resulting mixture was freeze dried to afford the title compound (63 mg) as a light yellow solid. LC-MS (ES) m/z=469 [M+H]$^+$. $^1$H NMR (400 MHz, DMSO-d$_6$): δ 1.31 (s, 9H), 1.34-1.46 (m, 2H), 1.61-1.71 (m, 1H), 1.74-1.84 (m, 1H), 2.68-2.88 (m, 4H), 2.89-3.07 (m, 1H), 3.88 (s, 3H), 4.05-4.30 (m, 2H), 4.96 (br. s, 2H), 6.49 (br. s, 2H), 6.81-6.90 (m, 2H), 7.45 (bs, 1H), 11.47 (s, 1H).

Intermediate 381

4-Chloro-2-(methylthio)-6-[(2S)-2-(trifluoromethyl)-1-pyrrolidinyl]pyrimidine

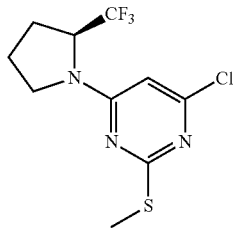 [SMILES: CSc1nc(Cl)cc(N2CCC[C@H]2C(F)(F)F)n1]

(2S)-2-(Trifluoromethyl)pyrrolidine (858 mg, 6.17 mmol) was dissolved in THF (10 mL) in a 250 mL RB flask. The mixture was cooled in an ice bath. Then molecular sieves were added and let stir for 5 minutes. LiHMDS (6.78 mL, 6.78 mmol) was added slowly followed by addition of 4,6-dichloro-2-(methylthio)pyrimidine (1.444 g, 7.40 mmol), and the reaction was stirred at 0° C. for an additional 10 minutes. Then water (10 mL) was added followed by dropwise addition of 6N HCl until pH was acidic. The mixture was then extracted with EtOAc (3×30 mL) and the organic was combined, washed with saturated NaCl, filtered and concentrated. The crude oil was purified on Biotage 25 g SNAP column with a gradient of 0 to 35% EtOAc in Hexane over 25 minutes to afford the title compound (1.42 g) as a clear oil. LC-MS (ES) m/z=298 [M+H]$^+$.

Intermediate 382

4-Chloro-2-(methylsulfonyl)-6-[(2S)-2-(trifluoromethyl)-1-pyrrolidinyl]pyrimidine

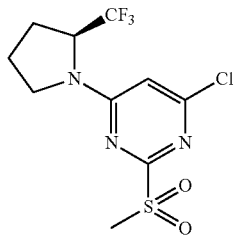 [SMILES: CS(=O)(=O)c1nc(Cl)cc(N2CCC[C@H]2C(F)(F)F)n1]

A suspension of 4-chloro-2-(methylthio)-6-[(2S)-2-(trifluoromethyl)-1-pyrrolidinyl]pyrimidine (1.45 g, 4.87 mmol) in CH$_3$OH (15 mL) was cooled in an ice bath and treated slowly with a premixed solution of oxone (3.89 g, 6.33 mmol) in water (5 mL). The reaction was let stir at room temperature overnight. The reaction was diluted with water (20 mL) followed by saturated NaHCO$_3$ (30 mL). The mixture was extracted with EtOAc (3×50 mL). The organic was combined, washed with saturated NaCl solution, dried over MgSO$_4$, filtered and concentrated to afford the crude title compound (1.55 g) as a yellowish oil. LC-MS (ES) m/z=330 [M+H]$^+$.

Intermediate 383

4-Chloro-N-methyl-6-[(2S)-2-(trifluoromethyl)-1-pyrrolidinyl]-2-pyrimidinamine

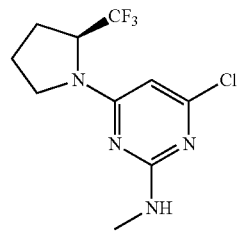 [SMILES: CNc1nc(Cl)cc(N2CCC[C@H]2C(F)(F)F)n1]

The crude 4-chloro-2-(methylsulfonyl)-6-[(2S)-2-(trifluoromethyl)-1-pyrrolidinyl]pyrimidine (1.09 g, 3.31 mmol) was dissolved 1,4-dioxane (30 mL). Hunig's base (2.88 mL, 16.53 mmol) and methylamine (6.61 mL, 13.22 mmol) were added, and the solution was stirred at room temperature overnight. Additional methylamine (2 mL) was added. The reaction was concentrated, then diluted with 30 mL EtOAc and washed with 0.1 N HCl (30 mL). The aqueous was back extracted with EtOAc and the organics were combined and washed with saturated NaCl, dried over MgSO$_4$, filtered and concentrated. Purfication on Biotage 25 g SNAP column with a gradient of 0 to 50% EtOAc in Hexane over 35 minutes afforded the title compound (760 mg) as a clear oil. LC-MS (ES) m/z=281 [M+H]$^+$.

Intermediate 384

2,6-Difluoro-4-{2-(methylamino)-6-[(2S)-2-(trifluoromethyl)-1-pyrrolidinyl]-4-pyrimidinyl}benzonitrile

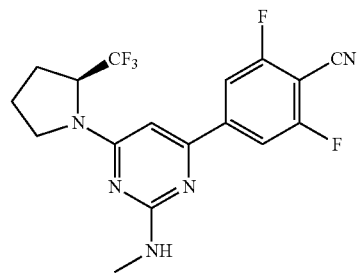 [SMILES: CNc1nc(-c2cc(F)c(C#N)c(F)c2)cc(N2CCC[C@H]2C(F)(F)F)n1]

4-Chloro-N-methyl-6-[(2S)-2-(trifluoromethyl)-1-pyrrolidinyl]-2-pyrimidinamine (600 mg, 2.138 mmol) and (4-cyano-3,5-difluorophenyl)boronic acid (587 mg, 3.21 mmol) were dissolved in 1,4-dioxane (10 mL) in a 20 mL sealable vial. Saturated NaHCO$_3$ solution (5 mL) was added, and N$_2$ gas was bubbled through the mixture for 10 minutes. Then Pd(Ph$_3$P)$_4$ (371 mg, 0.321 mmol) was added, and N$_2$ gas was bubbled through the mixture for an additional 5 minutes. The reaction vial was then capped and heated at 100° C. overnight. The reaction was diluted with water (10 mL) and then extracted with EtOAc (3×10 mL). Organic was then combined, dried over MgSO$_4$, filtered and concentrated. The yellow oil was then purified on Biotage SNAP 50 g column with a gradient of 0 to 35% EtOAc in Hexane over 30 minutes to isolated the title compound (452 mg). LC-MS (ES) m/z=384 [M+H]$^+$.

Intermediate 385

2-Fluoro-4-{2-(methylamino)-6-[(2S)-2-(trifluoromethyl)-1-pyrrolidinyl]-4-pyrimidinyl}-6-(methyloxy)benzonitrile

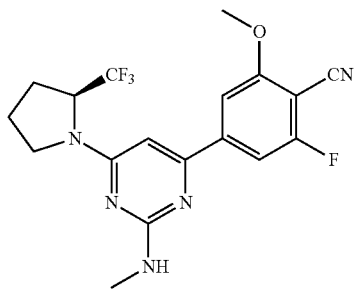 [SMILES: CNc1nc(-c2cc(F)c(C#N)c(OC)c2)cc(N2CCC[C@H]2C(F)(F)F)n1]

A solution of sodium methoxide was made from 65 mg of sodium dissolved in 2.8 mL of CH$_3$OH. From that solution 0.4 mL was added to a predissolved solution of 2,6-difluoro-4-{2-(methylamino)-6-[(2S)-2-(trifluoromethyl)-1-pyrrolidinyl]-4-pyrimidinyl}benzonitrile (127 mg, 0.331 mmol) in CH$_3$OH (3 mL). The reaction was stirred at room temperature overnight. The reaction was concentrated, then diluted with water (15 mL) and extracted with EtOAc (3×15 mL). The organic was combined, dried over MgSO$_4$, filtered and concentrated to afford the crude title compound (131 mg). LC-MS (ES) m/z=396 [M+H]$^+$.

Example 204

6-{2-(Methylamino)-6-[(2S)-2-(trifluoromethyl)-1-pyrrolidinyl]-4-pyrimidinyl}-4-(methyloxy)-1H-indazol-3-amine

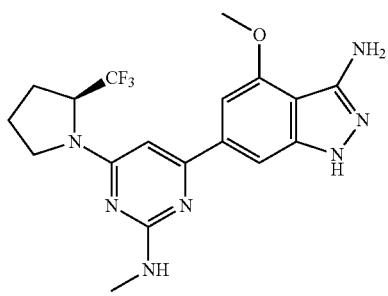 [SMILES: CNc1nc(-c2cc(OC)c3c(N)n[nH]c3c2)cc(N2CCC[C@H]2C(F)(F)F)n1]

2-Fluoro-4-{2-(methylamino)-6-[(2S)-2-(trifluoromethyl)-1-pyrrolidinyl]-4-pyrimidinyl}-6-(methyloxy)benzonitrile (131 mg, 0.331 mmol) was dissolved in ethanol (3 mL) in a 5 mL sealable vial. Hydrazine monohydrate (0.487 mL, 9.94 mmol) was added, the vial was capped, and the reaction was heated at 100° C. overnight. The reaction was concentrated, dissolved in 2 mL of DMSO and purified in HPLC (HPLC condition: open-access Gilson using Trilution software with a Sunfire 5u C18(2) 100A. 50×30.00 mm 5 micron. 7.3-minute run (47 mL/min, 18% CH$_3$CN/H$_2$O, 0.1% TFA to 43% CH$_3$CN/H$_2$O, 0.1% TFA) with UV detection at 254 nm). Product fractions were combined and the volume was reduced to remove most of the CH$_3$CN. To the water left behind was added saturated NaHCO$_3$, then extracted with EtOAc (3×15 mL). The organic was washed with brine, dried over MgSO$_4$, filtered, concentrated, and transferred to a haystack vial. Water (1 mL) was added, and the resulting mixture was freeze dried to afford the title compound (74 mg) as a light yellow solid. LC-MS (ES) m/z=408 [M+H]$^+$. $^1$H NMR (400 MHz, DMSO-d$_6$): δ 1.95-2.03 (m, 2H), 2.05 (bs, 2H), 2.77 (d, J=3.3 Hz, 3H) 3.47 (d, J=8.8 Hz, 1H) 3.62 (d, J=4.6 Hz, 1H), 3.87 (s, 3H), 4.98 (bs, 2H), 5.08 (bs, 1H), 6.39 (bs, 1H), 6.64 (bs, 1H), 6.88 (bs, 1H), 7.43 (bs, 1H), 11.50 (bs, 1H).

Intermediate 386

2-Fluoro-4-{2-(methylamino)-6-[(2S)-2-(trifluoromethyl)-1-pyrrolidinyl]-4-pyrimidinyl}benzonitrile

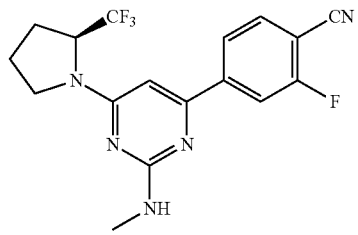 [SMILES: CNc1nc(-c2ccc(C#N)c(F)c2)cc(N2CCC[C@H]2C(F)(F)F)n1]

4-Chloro-N-methyl-6-[(2S)-2-(trifluoromethyl)-1-pyrrolidinyl]-2-pyrimidinamine (110 mg, 0.392 mmol) and (4-cyano-3-fluorophenyl)boronic acid (97 mg, 0.588 mmol) were dissolved in 1,4-dioxane (4 mL) in a 20 mL sealable vial. Saturated NaHCO$_3$ solution (5 mL) was added, and N$_2$ gas was bubbled through the mixture for 10 minutes. Then Pd(Ph$_3$P)$_4$ (371 mg, 0.321 mmol) was added, and N$_2$ gas was bubbled through the mixture for an additional 5 minutes. The reaction vial was then capped and heated at 100° C. overnight. The reaction was diluted with water (10 mL) and then extracted with EtOAc (3×10 mL). Organic was then combined, dried over MgSO$_4$, filtered and concentrated. The yellow oil was then purified on Biotage SNAP 10 g column with a gradient of 0 to 35% EtOAc in Hexane for 30 minutes to afford the title compouns (167 mg). LC-MS (ES) m/z=366 [M+H]$^+$.

Example 205

6-{2-(Methylamino)-6-[(2S)-2-(trifluoromethyl)-1-pyrrolidinyl]-4-pyrimidinyl}-1H-indazol-3-amine

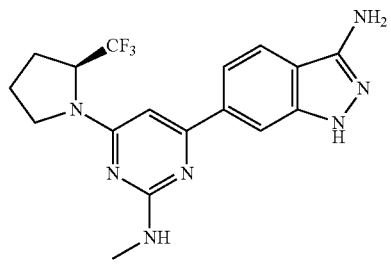 [SMILES: CNc1nc(-c2ccc3c(N)n[nH]c3c2)cc(N2CCC[C@H]2C(F)(F)F)n1]

2-Fluoro-4-{2-(methylamino)-6-[(2S)-2-(trifluoromethyl)-1-pyrrolidinyl]-4-pyrimidinyl}benzonitrile (166 mg, 0.454 mmol) was dissolved in ethanol (3 mL) in a 5 mL sealable vial. Hydrazine monohydrate (0.668 mL, 13.63 mmol) was added, the vial was capped, and the reaction was heated at 100° C. overnight. The reaction was concentrated, dissolved in 2 mL of DMSO and purified in HPLC (HPLC condition: open-access Gilson using Trilution software with a Sunfire 5u C18(2) 100A. 50×30.00 mm 5 micron. 7.3-minute run (47 ml/min, 1% $CH_3CN/H_2O$, 0.1% TFA to 42% $CH_3CN/H_2O$, 0.1% TFA) with UV detection at 254 nm). Product fractions were combined and the volume was reduced to remove most of the $CH_3CN$. To the water left behind was added saturated $NaHCO_3$, then extracted with EtOAc (3×15 mL). The organic was washed with brine, dried over $MgSO_4$, filtered, concentrated, and transferred to a haystack vial. Water (1 mL) was added, and the resulting mixture was freeze dried to afford the title compound (91 mg) as a light yellow solid. LC-MS (ES) m/z=377 [M+H]+. $^1$H NMR (400 MHz, DMSO-$d_6$): δ 2.01-2.22 (m, 4H), 2.85 (d, J=4.3 Hz, 3H), 3.48-3.61 (m, 1H), 3.68 (dt, J=10.1, 5.1 Hz, 1H), 5.14 (t, 1H), 5.40 (bs, 2H), 6.50 (bs, 1H), 6.68 (bs, 1H), 7.59 (d, J=8.3 Hz, 1H), 7.73 (d, J=8.3 Hz, 1H), 7.97 (bs, 1H), 11.54 (s, 1H).

Intermediate 387

4-[6-[(3R)-3-Amino-1-piperidinyl]-2-(methylamino)-4-pyrimidinyl]-2-fluorobenzonitrile

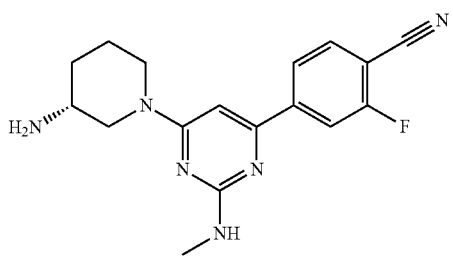 [SMILES: CNc1nc(-c2ccc(C#N)c(F)c2)cc(N2CCC[C@@H](N)C2)n1]

To 1,1-dimethylethyl{(3R)-1-[6-(4-cyano-3-fluorophenyl)-2-(methylamino)-4-pyrimidinyl]-3-piperidinyl}carbamate (0.544 g, 1.28 mmol) was added HCl in dioxane (4 mL, 16.00 mmol) at room temperature with stirring. A precipitate immediately formed. The mixture was stirred at room temperature overnight, and then concentrated to dryness to afford an HCl salt of the title compound (0.539 g) as an off-white solid. LC-MS (ES) m/z=327 [M+H]+.

Intermediate 388

N-{(3R)-1-[6-(4-Cyano-3-fluorophenyl)-2-(methylamino)-4-pyrimidinyl]-3-piperidinyl}benzamide

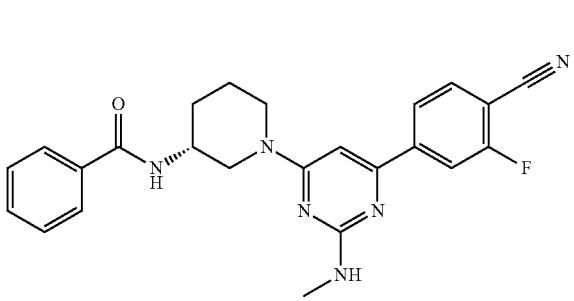 [SMILES: CNc1nc(-c2ccc(C#N)c(F)c2)cc(N2CCC[C@@H](NC(=O)c3ccccc3)C2)n1]

To benzoic acid (30.6 mg, 0.250 mmol) in DMF (2 mL) was added HATU (105 mg, 0.275 mmol) followed by Hunig's base (0.18 mL, 1.00 mmol). After 15 minutes, 4-[6-[(3R)-3-amino-1-piperidinyl]-2-(methylamino)-4-pyrimidinyl]-2-fluorobenzonitrile (100 mg, 0.250 mmol) was added, and the reaction mixture was stirred at room temperature for 30 minutes. Water was added (~10 mL), and a solid precipitated. The mixture was filtered, and the solid was washed with water and air dried to afford the crude title compound (83 mg) as a yellow solid. LC-MS (ES) m/z=431 [M+H]+.

Example 206

N-{(3R)-1-[6-(3-Amino-1H-indazol-6-yl)-2-(methylamino)-4-pyrimidinyl]-3-piperidinyl}benzamide

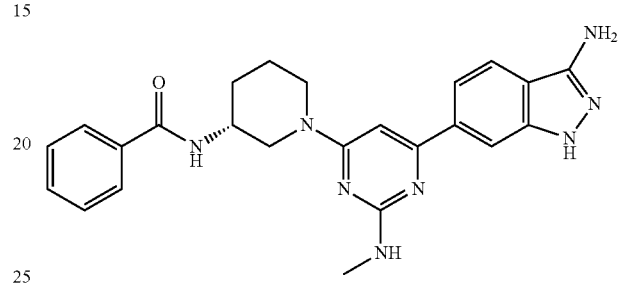

To N-{(3R)-1-[6-(4-cyano-3-fluorophenyl)-2-(methylamino)-4-pyrimidinyl]-3-piperidinyl}benzamide (83 mg, 0.19 mmol) in ethanol (2 mL) was added hydrazine monohydrate (0.5 mL, 10.2 mmol), and the reaction mixture was stirred overnight at 100° C. into a sealed tube. The solution was poured onto water (~50 mL) and a precipitate formed. The aqueous mixture was filtered, and the solid was further washed with water. The material was dried under vacuum overnight at 45° C. to afford the title compound (52 mg) as an off-white solid. LC-MS (ES) m/z=443 [M+H]+. $^1$H NMR (400 MHz, DMSO-$d_6$): δ 1.43-1.60 (m, 1H), 1.61-1.75 (m, 1H), 1.76-1.89 (m, 1H), 1.92-2.05 (m, 1H), 2.83 (d, J=4.0 Hz, 3H), 2.91-3.10 (m, 2H), 3.83-3.98 (m, 1H), 4.24-4.57 (m, 2H), 5.38 (s, 2H), 6.45-6.58 (m, 1H), 6.64 (s, 1H), 7.41-7.49 (m, 2H), 7.50-7.56 (m, 1H), 7.59 (d, J=8.6 Hz, 1H), 7.71 (d, J=8.34 Hz, 1H), 7.82-7.90 (m, 2H), 7.98 (bs, 1H), 8.37 (d, J=7.6 Hz, 1H), 11.50 (s, 1H).

Intermediate 389

4-{2-Amino-6-[(3R)-3-amino-1-piperidinyl]-4-pyrimidinyl}-2-fluorobenzonitrile

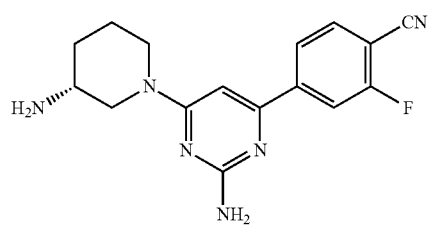 [SMILES: N#Cc1ccc(-c2cc(N3CCC[C@@H](N)C3)nc(N)n2)cc1F]

To 1,1-dimethylethyl{(3R)-1-[2-amino-6-(4-cyano-3-fluorophenyl)-4-pyrimidinyl]-3-piperidinyl}carbamate (1.02 g, 2.473 mmol) was added 4M HCl in 1,4-dioxane (6.18 mL, 24.73 mmol), and the resulting mixture was stirred at room temperature for 1.5 hours. The reaction was then concentrated to afford an HCl salt of the title compound (1.03 g) as a yellow solid. LC-MS (ES) m/z=313 [M+H]+.

Intermediate 390

Phenylmethyl{(3R)-1-[2-amino-6-(4-cyano-3-fluorophenyl)-4-pyrimidinyl]-3-piperidinyl}carbamate

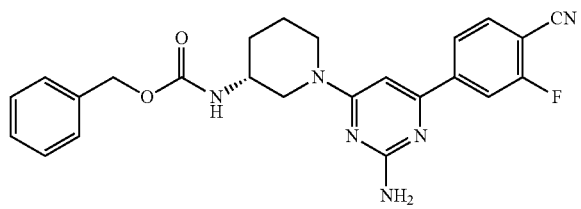 [SMILES: N#Cc1ccc(-c2cc(N3CCC[C@@H](NC(=O)OCc4ccccc4)C3)nc(N)n2)cc1F]

To 4-{2-amino-6-[(3R)-3-amino-1-piperidinyl]-4-pyrimidinyl}-2-fluorobenzonitrile (125 mg, 0.324 mmol) in THF (4 mL) and saturated NaHCO$_3$ (2 mL) was added phenylmethyl chloridocarbonate (0.055 mL, 0.389 mmol), and the resulting mixture was stirred at room temperature overnight. The reaction was diluted with water (10 mL), then extracted with EtOAc (3×10 mL). The organic was combined, washed with saturated NaCl solution, dried over MgSO$_4$, filtered and concentrated to afford the crude title compound (155 mg) as a yellow oil. LC-MS (ES) m/z=447 [M+H]$^+$.

Example 207

Phenylmethyl{(3R)-1-[2-amino-6-(3-amino-1H-indazol-6-yl)-4-pyrimidinyl]-3-piperidinyl}carbamate

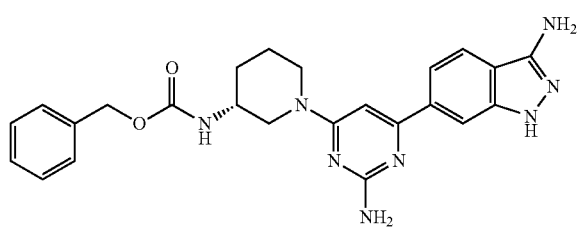 [SMILES: Nc1nc(-c2ccc3c(N)n[nH]c3c2)cc(N2CCC[C@@H](NC(=O)OCc3ccccc3)C2)n1]

Into a 5 sealable tube were added phenylmethyl{(3R)-1-[2-amino-6-(4-cyano-3-fluorophenyl)-4-pyrimidinyl]-3-piperidinyl}carbamate (155 mg, 0.347 mmol) and ethanol (3 mL) followed by hydrazine monohydrate (0.511 mL, 10.41 mmol). The mixture was then capped and heated at 100° C. overnight. The reaction was concentrated, then dissolved in 2 mL of DMSO and purified on HPLC (HPLC condition: open-access Gilson using Trilution software with a Sunfire 5u C18(2) 100A. 50×30.00 mm 5 micron. 7.3-minute run (47 mL/min, 10% CH$_3$CN/H$_2$O, 0.1% TFA to 35% CH$_3$CN/H$_2$O, 0.1% TFA) with UV detection at 254 nm). Product fractions were combined and the volume was reduced to remove most of the CH$_3$CN. To the water left behind was added saturated NaHCO$_3$, then extracted with EtOAc (3×15 mL). The organic was washed with brine, dried over MgSO$_4$, filtered, concentrated, and transferred to a haystack vial. Water (1 mL) was added, and the resulting mixture was freeze dried to afford the title compound (32 mg) as a light yellow solid. LC-MS (ES) m/z=459 [M+H]$^+$. $^1$H NMR (400 MHz, DMSO-d$_6$): δ 1.47 (bs, 2H), 1.71-1.78 (m, 1H), 1.87-1.94 (m, 1H), 2.92 (bs, 1H), 3.06 (bs, 1H), 3.40-3.48 (m, 1H), 4.12 (bs, 1H), 4.31 (bs, 1H), 4.96-5.08 (m, 2H), 5.40 (bs, 2H), 6.19 (bs, 2H), 6.61 (s, 1H), 7.29-7.37 (m, 5H), 7.43 (d, J=7.6 Hz, 1H), 7.54 (d, J=8.3 Hz, 1H), 7.72 (d, J=8.6 Hz, 1H), 7.93 (s, 1H), 11.55 (bs, 1H).

Intermediate 391

Cyclopentyl{(3R)-1-[2-amino-6-(4-cyano-3-fluorophenyl)-4-pyrimidinyl]-3-piperidinyl}carbamate

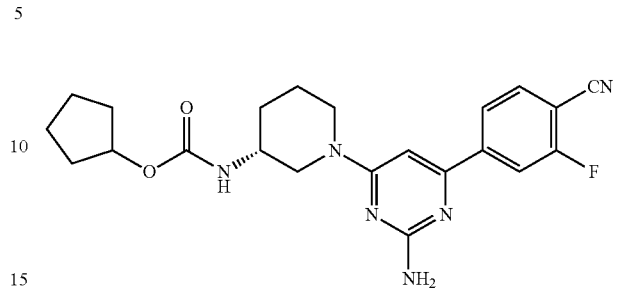

A premixed solution of cyclopentanol (33.5 mg, 0.389 mmol) and Hunig's base (57 uL) in CH$_2$Cl$_2$ (1 mL) was slowly added to a solution of triphosgene (38.5 mg, 0.130 mmol) in CH$_2$Cl$_2$ (1 mL), and the resulting solution was stirred for 1 hour. A premixed solution of 4-{2-amino-6-[(3R)-3-amino-1-piperidinyl]-4-pyrimidinyl}-2-fluorobenzonitrile (125 mg, 0.324 mmol) and Hunig's base (226 uL) in CH$_2$Cl$_2$ (5 mL) was added, and the reaction mixture was stirred at room temperature overnight. The reaction was concentrated, then loaded on a Biotage SNAP 10 g column and purified with a gradient of 0 to 55% EtOAc in Hexane over 25 min. LC-MS (ES) m/z=425 [M+H]$^+$.

Example 208

Cyclopentyl{(3R)-1-[2-amino-6-(3-amino-1H-indazol-6-yl)-4-pyrimidinyl]-3-piperidinyl}carbamate

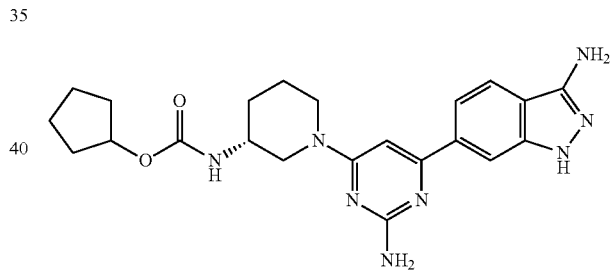

Into a 5 mL sealable vial were added cyclopentyl{(3R)-1-[2-amino-6-(4-cyano-3-fluorophenyl)-4-pyrimidinyl]-3-piperidinyl}carbamate (58 mg, 0.137 mmol) and ethanol (3 mL) followed by hydrazine monohydrate (0.201 mL, 4.10 mmol), and the resulting mixture was then capped and heated at 100° C. overnight. The reaction was concentrated, then dissolved in 2 mL of DMSO and purified on HPLC (HPLC condition: open-access Gilson using Trilution software with a Sunfire 5u C18(2) 100A. 50×30.00 mm 5 micron. 7.3-minute run (47 mL/min, 10% CH$_3$CN/H$_2$O, 0.1% TFA to 35% CH$_3$CN/H$_2$O, 0.1% TFA) with UV detection at 254 nm). Product fractions were combined and the volume was reduced to remove most of the CH$_3$CN. To the water left behind was added saturated NaHCO$_3$, then extracted with EtOAc (3×15 mL). The organic was washed with brine, dried over MgSO$_4$, filtered, concentrated, and transferred to a haystack vial. Water (1 mL) was added, and the resulting mixture was freeze dried to afford the title compound (39 mg) as a light yellow solid. LC-MS (ES) m/z=437 [M+H]$^+$. $^1$H NMR (400 MHz, DMSO-d$_6$): δ 1.40-1.63 (m, 8H), 1.70-1.82 (m, 3H), 1.85-1.92 (m, 1H), 2.83-2.93 (m, 1H), 3.05 (bs, 1H), 4.10 (m, 1H), 4.25 (bs, 1H), 4.94-5.01 (m, 1H), 5.38 (s, 2H), 6.09 (bs, 2H), 6.56 (s, 1H), 7.15 (d, J=7.6 Hz, 1H), 7.54 (d, J=8.3 Hz, 1H), 7.70 (d, J=8.3 Hz, 1H), 7.92 (s, 1H), 11.51 (s, 1H).

Intermediate 392

Cyclobutyl{(3R)-1-[2-amino-6-(4-cyano-3-fluorophenyl)-4-pyrimidinyl]-3-piperidinyl}carbamate

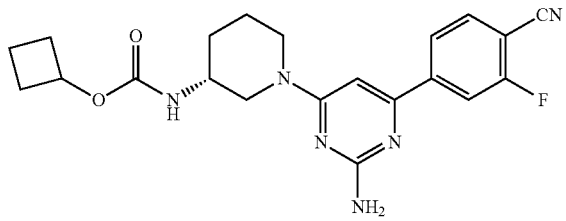 [SMILES: N#Cc1ccc(-c2cc(N3CCC[C@@H](NC(=O)OC4CCC4)C3)nc(N)n2)cc1F]

A premixed solution of cyclobutanol (30.5 µl, 0.389 mmol) and Hunig's base (57 uL) in CH$_2$Cl$_2$ (1 mL) was slowly added to a solution of triphosgene (38.5 mg, 0.130 mmol) in CH$_2$Cl$_2$ (1 mL), and the resulting solution was stirred for 1 hour. A premixed solution of 4-{2-amino-6-[(3R)-3-amino-1-piperidinyl]-4-pyrimidinyl}-2-fluorobenzonitrile (125 mg, 0.324 mmol) and Hunig's base (226 uL) in CH$_2$Cl$_2$ (5 mL) was added, and the reaction mixture was stirred at room temperature overnight. The reaction was concentrated, then loaded on a Biotage SNAP 10 g column and purified with a gradient of 0 to 55% EtOAc in Hexane over 25 min. LC-MS (ES) m/z=411 [M+H]$^+$.

Example 209

Cyclobutyl{(3R)-1-[2-amino-6-(3-amino-1H-indazol-6-yl)-4-pyrimidinyl]-3-piperidinyl}carbamate

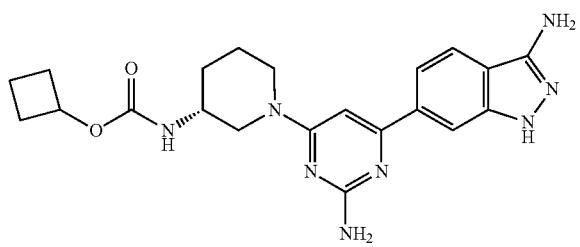 [SMILES: Nc1nc(-c2ccc3c(N)n[nH]c3c2)cc(N2CCC[C@@H](NC(=O)OC3CCC3)C2)n1]

Into a 5 mL sealable vial were added cyclobutyl{(3R)-1-[2-amino-6-(4-cyano-3-fluorophenyl)-4-pyrimidinyl]-3-piperidinyl}carbamate (49 mg, 0.119 mmol) and ethanol (3 mL) followed by hydrazine monohydrate (0.176 mL, 3.58 mmol), and the resulting mixture was then capped and heated at 100° C. overnight. The reaction was concentrated, and then dissolved in 2 mL of DMSO and purified on HPLC (HPLC condition: open-access Gilson using Trilution software with a Sunfire 5u C18(2) 100A. 50×30.00 mm 5 micron. 7.3-minute run (47 mL/min, 10% CH$_3$CN/H$_2$O, 0.1% TFA to 35% CH$_3$CN/H$_2$O, 0.1% TFA) with UV detection at 254 nm). Product fractions were combined and the volume was reduced to remove most of the CH$_3$CN. To the water left behind was added saturated NaHCO$_3$, and the resulting aqueous mixture was then extracted with EtOAc (3×15 mL). The organic was washed with brine, dried over MgSO$_4$, filtered, concentrated, and transferred to a haystack vial. Water (1 mL) was added, and the resulting mixture was freeze dried to afford the title compound (26 mg) as a light yellow solid. LC-MS (ES) m/z=423 [M+H]$^+$. $^1$H NMR (400 MHz, DMSO-d$_6$): δ 1.41-1.56 (m, 3H), 1.63-1.77 (m, 2H), 1.83-2.00 (m, 3H), 2.12-2.26 (m, 2H), 2.87 (bs, 1H), 3.03 (bs, 1H), 4.08-4.16 (m, 1H), 4.26 (bs, 1H), 4.83 (t, J=7.6 Hz, 1H), 5.38 (s, 2H), 6.06-6.13 (m, 2H), 6.56 (s, 1H), 7.25 (d, J=7.8 Hz, 1H), 7.54 (d, J=8.3 Hz, 1H), 7.71 (d, J=8.6 Hz, 1H), 7.92 (s, 1H), 11.52 (s, 1H).

Intermediate 393

Cyclohexyl{(3R)-1-[2-amino-6-(4-cyano-3-fluorophenyl)-4-pyrimidinyl]-3-piperidinyl}carbamate

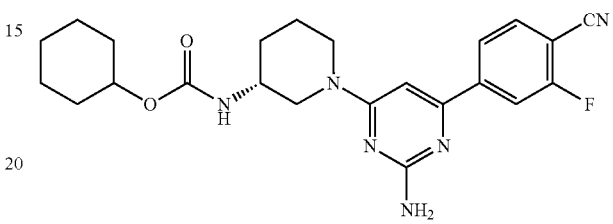

A premixed solution of cyclohexanol (40.7 µl, 0.389 mmol) and Hunig's base (57 uL) in CH$_2$Cl$_2$ (1 mL) was slowly added to a solution of triphosgene (38.5 mg, 0.130 mmol) in CH$_2$Cl$_2$ (1 mL), and the resulting mixture was stirred for 1 hr at room temperature. A premixed solution of 4-{2-amino-6-[(3R)-3-amino-1-piperidinyl]-4-pyrimidinyl}-2-fluorobenzonitrile (125 mg, 0.324 mmol) and Hunig's base (226 uL) in CH$_2$Cl$_2$ (5 mL) was added, and the reaction mixture was stirred at room temperature overnight. The reaction was concentrated, and then loaded on a Biotage SNAP 10 g column and purified with a gradient of 0 to 55% EtOAc in Hexane over 25 minutes to afford the title compound (45 mg) as a light yellow oil. LC-MS (ES) m/z=439 [M+H]$^+$.

Example 210

Cyclohexyl{(3R)-1-[2-amino-6-(3-amino-1H-indazol-6-yl)-4-pyrimidinyl]-3-piperidinyl}carbamate

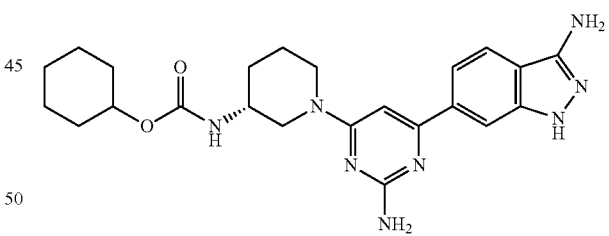

into a 5 mL sealable vial were added cyclohexyl{(3R)-1-[2-amino-6-(4-cyano-3-fluorophenyl)-4-pyrimidinyl]-3-piperidinyl}carbamate (45 mg, 0.103 mmol) and ethanol (3 mL) followed by hydrazine monohydrate (0.151 mL, 3.08 mmol), and the resulting mixture was then capped and heated at 100° C. overnight. The reaction was concentrated, then dissolved in 2 mL of DMSO and purified on HPLC (HPLC condition: open-access Gilson using Trilution software with a Sunfire 5u C18(2) 100A. 50×30.00 mm 5 micron. 7.3-minute run (47 mL/min, 10% CH$_3$CN/H$_2$O, 0.1% TFA to 35% CH$_3$CN/H$_2$O, 0.1% TFA) with UV detection at 254 nm). Product fractions were combined, and the volume was reduced to remove most of the CH$_3$CN. To the water left behind was added saturated NaHCO$_3$ and then it was extracted with EtOAc (3×15 mL). The organic was washed with brine, dried over MgSO$_4$, filtered, concentrated, and transferred to a haystack vial. Water (1 mL) was added, and the resulting mixture was freeze dried to afford the title compound (22 mg) as a light yellow solid. LC-MS (ES) m/z=451 [M+H]+. 1H NMR (400 MHz, DMSO-d6): δ 1.09-1.18 (m, 1H), 1.18-1.33 (m, 5H), 1.46 (bs, 3H), 1.53-1.92 (m, 7H), 2.95 (bs, 1H), 3.13 (bs, 1H), 4.00-4.08 (m, 1H), 4.48 (bs, 1H), 5.38 (s, 2H), 6.09 (bs, 2H), 6.55 (s, 1H), 7.17 (d, J=7.3 Hz, 1H), 7.53 (d, J=8.3 Hz, 1H), 7.70 (d, J=8.3 Hz, 1H), 7.91 (s, 1H), 11.52 (s, 1H).

Intermediate 394

4-{2-amino-6-[(3R)-3-(2-oxo-1,3-oxazolidin-3-yl)-1-piperidinyl]-4-pyrimidinyl}-2-fluorobenzonitrile

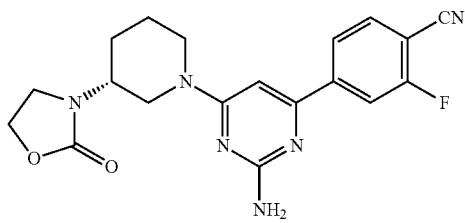 [SMILES: N#Cc1ccc(-c2cc(N3CCC[C@@H](N4CCOC4=O)C3)nc(N)n2)cc1F]

Into a 40 mL vial was added 4-{2-amino-6-[(3R)-3-amino-1-piperidinyl]-4-pyrimidinyl}-2-fluorobenzonitrile (100 mg, 0.260 mmol) followed by THF (3 mL) and saturated NaHCO3 (1.5 mL), and the resulting mixture was stirred for 5 minutes. Then 2-chloroethyl chloridocarbonate (0.032 mL, 0.311 mmol) was added, and the reaction mixture was capped and stirred at room temperature overnight. The reaction was then diluted with 5 mL of water and extracted with EtOAc (3×10 mL). The organic was combined and washed with saturated NaCl, dried over MgSO4, filtered and concentrated. The resulting light yellow solid (114 mg) was dissolved in DMF (3.00 mL), and then Cs2CO3 (127 mg, 0.389 mmol) was added, and the reaction was stirred at room temperature overnight. The reaction was incomplete. Additional 0.5 equiv of Cs2CO3 was added, and the reaction mixture was continue to stir at room temperature. After 5 hours, the reaction was completed, and then it was diluted with 10 mL water, and extracted with EtOAc (3×10 mL). The organics were combined, washed with saturated NaCl, dried over MgSO4, filtered and concentrated to afford the crude title compound (83 mg). LC-MS (ES) m/z=383 [M+H]+.

Example 211

3-{(3R)-1-[2-Amino-6-(3-amino-1H-indazol-6-yl)-4-pyrimidinyl]-3-piperidinyl}-1,3-oxazolidin-2-one

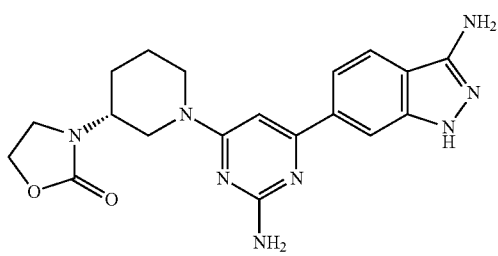 [SMILES: Nc1nc(-c2ccc3c(N)n[nH]c3c2)cc(N2CCC[C@@H](N3CCOC3=O)C2)n1]

Into a 5 mL sealable vial were added 4-{2-amino-6-[(3R)-3-(2-oxo-1,3-oxazolidin-3-yl)-1-piperidinyl]-4-pyrimidinyl}-2-fluorobenzonitrile (83 mg, 0.217 mmol) and ethanol (3 mL) followed by hydrazine monohydrate (0.319 mL, 6.51 mmol). The reaction vial was capped and was heated at 100° C. overnight. The reaction was concentrated, then dissolved in 2 mL of DMSO and purified on HPLC (HPLC condition: open-access Gilson using Trilution software with a Sunfire 5u C18(2) 100A. 50×30.00 mm 5 micron. 7.3-minute run (47 mL/min, 10% CH3CN/H2O, 0.1% TFA to 25% CH3CN/H2O, 0.1% TFA) with UV detection at 254 nm). Product fractions were combined and the volume was reduced to remove most of the CH3CN. To the water left behind was added saturated NaHCO3 and then extracted with EtOAc (5×100 mL). The organic was washed with brine, dried over MgSO4, filtered, concentrated, and transferred to a haystack vial. Water (1 mL) was added, and the resulting mixture was freeze dried to afford the title compound (37 mg) as a light yellow solid. LC-MS (ES) m/z=395 [M+H]+. 1H NMR (400 MHz, DMSO-d6): δ 1.45-1.58 (m, 1H), 1.68-1.89 (m, 3H), 2.82 (t, J=11.6 Hz, 1H), 2.99 (t, J=11.8 Hz, 1H), 3.54 (ddd, J=11.1, 7.0, 4.2 Hz, 1H), 3.60 (dd, J=9.6, 8.6 Hz, 2H), 4.29 (td, J=8.0, 2.2 Hz, 2H), 4.40 (dd, 2H), 5.38 (s, 2H), 6.14 (bs, 2H), 6.63 (s, 1H), 7.57 (dd, J=8.3, 1.3 Hz, 1H), 7.71 (d, J=8.3 Hz, 1H), 7.95 (s, 1H), 11.52 (s, 1H).

Intermediate 395

Dimethyl N-{[(1,1-dimethylethyl)oxy]carbonyl}-D-glutamate

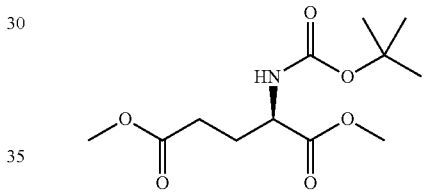

Into a 20 mL RB flask was dissolved dimethyl D-glutamate (25 g, 118 mmol) with CH3OH (150 mL). Triethylamine (36.2 mL, 260 mmol) was added followed by Boc2O (33.5 g, 154 mmol), and the reaction mixture was stirred at room temperature for 18 hours. The reaction was concentrated and then dissolved in 200 mL of CH2Cl2. The resulting organic solution was washed with 1N HCl (2×50 mL), saturated NaCl, dried over Na2SO4, filtered and concentrated. Purification was done on a 350 g Biotage SNAP column with gradient of 0 to 35% of EtOAc and Hexane over 35 minutes to isolated the title compound (30.7 g) as a clear oil. 1H NMR (400 MHz, DMSO-d6): δ 1.38 (s, 9H), 1.79 (ddd, J=14.5, 8.8, 6.1 Hz, 1H), 1.94 (t, J=13.4 Hz, 1H), 2.33-2.43 (m, 2H), 3.59 (s, 3H), 3.62 (s, 3H), 4.00 (dd, J=9.4, 7.6 Hz, 1H), 7.29 (d, J=7.8 Hz, 1H).

Intermediate 396

Dimethyl(4R)—N-{[(1,1-dimethylethyl)oxy]carbonyl}-4-methyl-D-glutamate

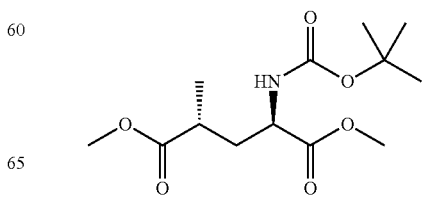

Into a 250 mL RB flask was added dimethyl N-{[(1,1-dimethylethyl)oxy]carbonyl}-D-glutamate (4 g, 14.53 mmol) and cool in Dry Ice/Aceton −78° C. bath. By cannulation was added by drop wise 1M LiHMDS in THF (30.5 mL, 30.5 mmol. After addition the mixture was let stir at −78° C. for 0.5 hours. Then methyl iodide (1.817 mL, 29.1 mmol) was added as rapidly as possible, and the solution was stirred at −78° C. for 4.5 hours. The reaction was then quenched with 1N HCl solution (40 mL), and extracted with EtOAc (3×50 mL). The organics were combined and washed with saturated NaHCO$_3$, brine, then dried over Na$_2$SO$_4$ and concentrated to give a red amber color oil. The oil was then purified on a Biotage SNAP 50 g column with a gradient of 0 to 35% gradient EtOAc in Hexane over 35 minutes. The fractions with product were combined to isolate the title compound (1.37 g) as a clear oil. $^1$H NMR (400 MHz, DMSO-d$_6$): δ 1.08 (d, J=7.1 Hz, 3H), 1.38 (s, 9H), 1.71 (ddd, J=13.6, 8.3, 5.1 Hz, 1H), 1.94 (ddd, J=13.9, 10.1, 6.1 Hz, 1H), 2.43-2.49 (m, 1H), 3.60 (s, 3H), 3.62 (s, 3H), 4.01 (ddd, J=9.9, 8.4, 5.2 Hz, 1H), 7.29 (d, J=8.3 Hz, 1H).

Intermediate 397

1,1-Dimethylethyl[(1R,3R)-4-hydroxy-1-(hydroxymethyl)-3-methylbutyl]carbamate

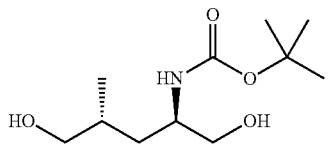 [SMILES: C[C@@H](CO)C[C@H](CO)NC(=O)OC(C)(C)C]

To a solution of dimethyl(4R)—N-{[(1,1-dimethylethyl)oxy]carbonyl}-4-methyl-D-glutamate (1.79 g, 6.19 mmol) in ethanol (15 mL) and THF (15 mL) cooled in an ice-bath, was added added sodium borohydride (1.873 g, 49.5 mmol) portiowise. The white cloudy mixture was stirred for 0.5 hours in an ice bath, then it was allowed to stir overnight at room temperature. A 10% Na$_2$CO$_3$ solution was added to quench the reaction, but the solution was too thick and an additional 20 mL of water was added. The white slurry was extracted with EtOAc (3×60 mL). The organic was combined and washed with saturated NaCl solution, dried over Na$_2$SO$_4$, filtered and concentrated to afford the crude title compound (1.56 g) as a clear oil. $^1$H NMR (400 MHz, DMSO-d$_6$): δ 0.82 (d, J=6.6 Hz, 3H), 1.18 (t, J=7.1 Hz, 1H), 1.31 (d, J=3.0 Hz, 1H), 1.37 (s, 9H), 1.49-1.60 (m, 1H), 3.09-3.33 (m, 4H), 3.45 (td, J=7.0, 5.1 Hz, 2H), 4.37 (dt, J=9.2, 5.2 Hz, 1H), 4.56 (t, J=5.7 Hz, 1H).

Intermediate 398

(2R,4R)-2-({[(1,1-Dimethylethyl)oxy]carbonyl}amino)-4-methyl-5-[(methylsulfonyl)oxy]pentyl methanesulfonate

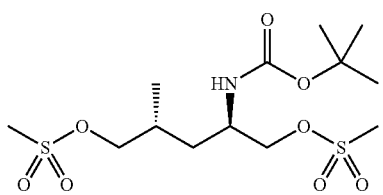

1,1-Dimethylethyl[(1R,3R)-4-hydroxy-1-(hydroxymethyl)-3-methylbutyl]carbamate (1.56 g, 6.69 mmol) was dissolved in CH$_2$Cl$_2$ (30 mL) in a 250 mL RB flask capped with a rubber septa. The reaction flask was charged with N$_2$ and cooled in an ice bath. Triethylamine (3.73 mL, 26.7 mmol) was added followed by the dropwise addition of methanesulfonyl chloride (1.563 mL, 20.06 mmol). After the addition, the reaction was allowed to stir at 0° C. for 1 hour. The reaction was then diluted with CH$_2$Cl$_2$ (30 mL) and washed with saturated NaHCO$_3$ (30 mL), then water, dried with Na$_2$SO$_4$, filtered and concentrated to afford the crude title compound (2.61 g). LC-MS (ES) m/z=390 [M+H]$^+$.

Intermediate 399

1,1-Dimethylethyl[(3R,5R)-5-methyl-1-(phenylmethyl)-3-piperidinyl]carbamate

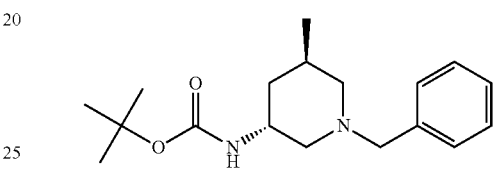

Into a 10 mL sealable vial was added (2R,4R)-2-({[(1,1-dimethylethyl)oxy]carbonyl}amino)-4-methyl-5-[(methylsulfonyl)oxy]pentyl methanesulfonate (1.05 g, 2.70 mmol) followed by benzylamine (5.88 mL, 53.9 mmol), and the reaction was capped and heated at 70° C. for 24 hours. The reaction was allowed to cool, and then it was transferred into a 1N NaOH solution (20 mL). The resulting oily mixture was then extracted with Hexane (3×20 mL). The combined extracts were washed with saturated NaCl solution, and then dried over MgSO$_4$, filtered, and concentrated. Purified was done on a 20 g Biotage SNAP column with gradient from 0 to 20% EtOAc in Hexane over 20 minutes to afford the title compound (452 mg) as a clear oil. LC-MS (ES) m/z=305 [M+H]$^+$.

Intermediate 400

1,1-Dimethylethyl[(3R,5R)-5-methyl-3-piperidinyl]carbamate

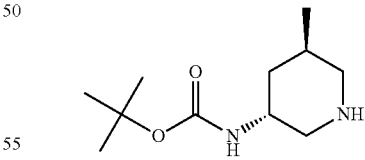

Into a Parr shaker jar was added Pd/C (316 mg, 0.148 mmol, Degussa type) followed by a premixed solution of 1,1-dimethylethyl[(3R,5R)-5-methyl-1-(phenylmethyl)-3-piperidinyl]carbamate (452 mg, 1.485 mmol) in ethanol (20 mL). The Parr shaker jar was then placed into the shaker, flushed with N$_2$, and then pressurized with hydrogen to 30 psi. The reaction was shaked at room temperature overnight. The reaction was filtered over syringe filter and concentrated to isolate the crude title compound (310 mg). LC-MS (ES) m/z=215 [M+H]$^+$.

Intermediate 401

1,1-Dimethylethyl[(3R,5R)-1-(2-amino-6-chloro-4-pyrimidinyl)-5-methyl-3-piperidinyl]carbamate

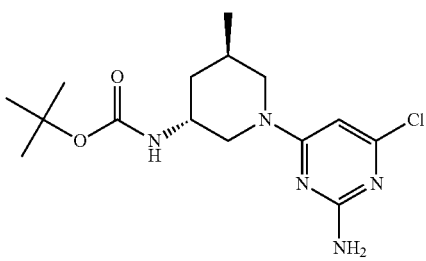 [SMILES: C[C@@H]1C[C@@H](NC(=O)OC(C)(C)C)CN(c2cc(Cl)nc(N)n2)C1]

Into a 20 mL sealable vial was dissolved 1,1-dimethylethyl [(3R,5R)-5-methyl-3-piperidinyl]carbamate (517 mg, 2.412 mmol) in ethanol (10 mL). Then 4,6-dichloro-2-pyrimidinamine (593 mg, 3.62 mmol) and triethylamine (0.672 mL, 4.82 mmol) were added, and the mixture was then capped and heated at 100° C. overnight. The reaction was then concentrated and loaded on to a Biotage SNAP 25 g column and purified with a gradient of 0 to 70% EtOAc in Hexane for 30 minutes to afford the title compound (720 mg) as a white solid. LC-MS (ES) m/z=342 [M+H]$^+$.

Intermediate 402

1,1-Dimethylethyl{(3R,5R)-1-[2-amino-6-(4-cyano-3-fluorophenyl)-4-pyrimidinyl]-5-methyl-3-piperidinyl}carbamate

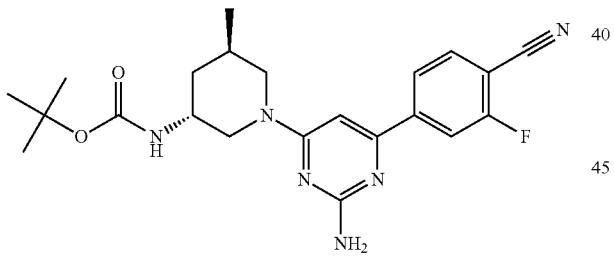

A mixture of 1,1-dimethylethyl[(3R,5R)-5-methyl-3-piperidinyl]carbamate (100 mg, 0.47 mmol) and 4,6-dichloro-2-pyrimidinamine (77 mg, 0.47 mmol) in 1,4-dioxane (6 mL) and sat. aq. NaHCO$_3$ (3 mL) was stirred for 3 hours at 80° C. into a sealed tube. The reaction was allowed to cool to room temperature. (4-Cyano-3-fluorophenyl)boronic acid (115 mg, 0.70 mmol) was added, and N$_2$ gas was bubbled through the resulting mixture for 10 minutes. Pd(Ph$_3$P)$_4$ (54 mg, 0.047 mmol) was added, the tube was resealed, and the reaction mixture was stirred overnight at 100° C. The mixture was poured onto water, and a precipitate was formed. The mixture was filtered. The resulting solid was taken up in EtOAc and filtered. The resulting organic filtrate was dried (MgSO$_4$), filtered, and concentrated until ~5 mL of solvent remained. This liquid was injected into a 40 g SiO$_2$ column and purified by flash chromatography (gradient: 100% Hexanes to 75% EtOAc/Hexanes) to afford the title compound (135 mg) as a yellow foam. LC-MS (ES) m/z=427 [M+H]$^+$.

Example 212

1,1-Dimethylethyl{(3R,5R)-1-[2-amino-6-(3-amino-1H-indazol-6-yl)-4-pyrimidinyl]-5-methyl-3-piperidinyl}carbamate

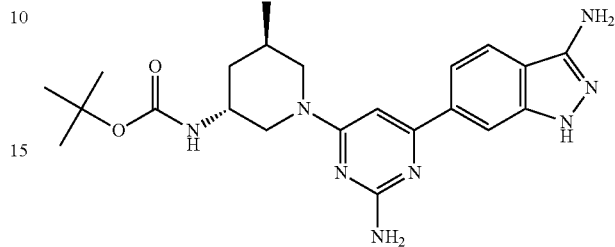

To 1,1-dimethylethyl{(3R,5R)-1-[2-amino-6-(4-cyano-3-fluorophenyl)-4-pyrimidinyl]-5-methyl-3-piperidinyl}carbamate (135 mg, 0.317 mmol) in ethanol (5 mL) was added hydrazine monohydrate (0.5 mL, 10.2 mmol), and the reaction mixture was stirred overnight at 100° C. into a sealed tube. The reaction was allowed to cool down to room temperature, and a precipitate was formed. Water was added (~5 mL), and the mixture was filtered. The off-white solid material was washed with water (2×20 mL). EtOAc (~25 mL) was added to the filter, and the mixture was shaken in an attempt to dissolve all the material. The mixture was filtered, and the process was repeated 2 more times. The combined filtrates were dried (MgSO$_4$), filtered, concentrated and dried in vacuo to afford the title compound (75 mg) as an off-white solid. LC-MS (ES) m/z=439 [M+H]$^+$. $^1$H NMR (400 MHz, DMSO-d$_6$): δ 0.88 (d, J=6.8 Hz, 3H), 1.29 (s, 9H), 1.37-1.52 (m, 2H), 1.68 (m, 1H), 1.93-2.07 (m, 1H), 2.83 (bs, 1H), 3.38 (bs, 1H), 3.63 (bs, 1H), 3.89 (m, 1H), 5.37 (s, 2H), 6.04 (bs, 2H), 6.49 (s, 1H), 6.82 (d, J=6.3 Hz, 1H), 7.50 (d, J=8.6 Hz, 1H), 7.69 (d, J=8.3 Hz, 1H), 7.89 (s, 1H), 11.49 (s, 1H).

Intermediate 403

4-{2-Amino-6-[(3R,5R)-3-amino-5-methyl-1-piperidinyl]-4-pyrimidinyl}-2-fluorobenzonitrile

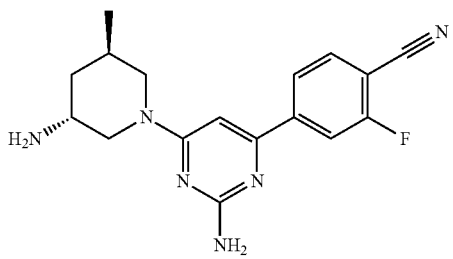 [SMILES: C[C@@H]1C[C@@H](N)CN(c2cc(-c3ccc(C#N)c(F)c3)nc(N)n2)C1]

To 1,1-dimethylethyl{(3R,5R)-1-[2-amino-6-(4-cyano-3-fluorophenyl)-4-pyrimidinyl]-5-methyl-3-piperidinyl}carbamate (127 mg, 0.298 mmol) in 1,4-dioxane (4 mL) was added 4M HCl in 1,4-dioxane (0.074 mL, 0.298 mmol), and the reaction was allowed to stir at room temperature for 3 hours. The reaction was concentrated to afford the bis HCl salt of the title compound (164 mg) as an off-white solid. LC-MS (ES) m/z=327 [M+H]$^+$.

Intermediate 404

4-{2-Amino-6-[(3R,5R)-3-methyl-5-(2-oxo-1,3-oxazolidin-3-yl)-1-piperidinyl]-4-pyrimidinyl}-2-fluorobenzonitrile

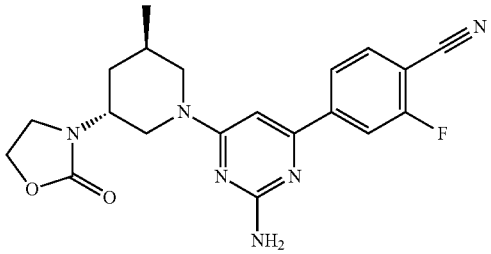 [SMILES: C[C@@H]1C[C@@H](N2CCOC2=O)CN(c2cc(-c3ccc(C#N)c(F)c3)nc(N)n2)C1]

Into a 40 mL vial was added 4-{2-amino-6-[(3R,5R)-3-amino-5-methyl-1-piperidinyl]-4-pyrimidinyl}-2-fluorobenzonitrile (164 mg, 0.411 mmol) followed by THF (5 mL) and saturated NaHCO$_3$ (2.5 mL), and the resulting mixture was stirred for 5 minutes. Then 2-chloroethyl chloridocarbonate (0.051 mL, 0.493 mmol) was added, and the mixture was then capped and stirred at room temperature overnight. The reaction was then diluted with 5 mL of water and extracted with EtOAc (3×10 mL). The organic was combined and washed with saturated NaCl, dried over MgSO$_4$, filtered and concentrated to yield 101 mg of a light yellow solid. Purification on a 10 g Biotage SNAp column with a gradient of 0 to 65% EtOAc in Hexane over 35 minutes yielded 101 mg of crude oil. The oil was dissolved in DMF (5.00 mL), and then Cs$_2$CO$_3$ (268 mg, 0.821 mmol) was added. The reaction was stirred at room temp overnight. The reaction was incomplete. Additional 0.5 equiv of Cs$_2$CO$_3$ was added and the reaction was continued to stir at room temperature. After 5 hours, the reaction was completed. The reaction was diluted with 10 mL water, and extracted with EtOAc (3×10 mL). The organics were combined, washed with saturated NaCl, dried over MgSO$_4$, filtered and concentrated to isolate the crude title compound (96 mg). LC-MS (ES) m/z=397 [M+H]$^+$.

Example 213

3-{(3R,5R)-1-[2-Amino-6-(3-amino-1H-indazol-6-yl)-4-pyrimidinyl]-5-methyl-3-piperidinyl}-1,3-oxazolidin-2-one

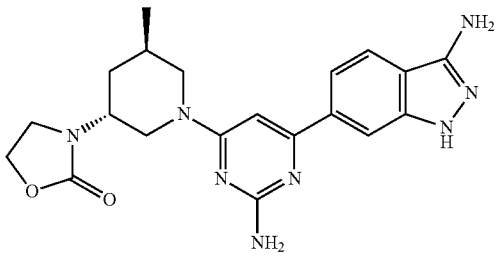 [SMILES: C[C@@H]1C[C@@H](N2CCOC2=O)CN(c2cc(-c3ccc4c(N)n[nH]c4c3)nc(N)n2)C1]

Into a 5 mL sealable vial were added 4-{2-amino-6-[(3R,5R)-3-methyl-5-(2-oxo-1,3-oxazolidin-3-yl)-1-piperidinyl]-4-pyrimidinyl}-2-fluorobenzonitrile (96 mg, 0.242 mmol) and ethanol (10 mL) followed by hydrazine monohydrate (0.356 mL, 7.27 mmol). The reaction vial was capped and was heated at 100° C. overnight. The reaction was concentrated, then dissolved in 2 mL of DMSO and purified on HPLC (HPLC condition: open-access Gilson using Trilution software with a Sunfire 5u C18(2) 100A. 50×30.00 mm 5 micron. 7.3-minute run (47 mL/min, 10% CH$_3$CN/H$_2$O, 0.1% TFA to 25% CH$_3$CN/H$_2$O, 0.1% TFA) with UV detection at 254 nm). Product fractions were combined and the volume was reduced to remove most of the CH$_3$CN. The water left behind was freeze dried, and the solid obtained was then dissolved in 2 mL of 9:1 CH$_2$Cl$_2$:CH$_3$OH and then loaded on to a 10 g Biotage SNAP column. The product was then eluded off the column with a gradient of 0 to 100% 95:5:1 CH$_2$Cl$_2$:CH$_3$OH:NH$_4$OH in CH$_2$Cl$_2$ over 25 minutes. The product fractions were combined, concentrated, and then transferred into haystack vial. Water (1 mL) was added, and the resulting mixture was freeze dried to afford the title compound (55 mg) as a light yellow solid. LC-MS (ES) m/z=409 [M+H]$^+$. $^1$H NMR (400 MHz, DMSO-d$_6$): δ 0.97 (d, J=6.6 Hz, 3H), 1.51-1.59 (m, 1H), 1.96 (ddd, J=12.8, 8.1, 4.4 Hz, 1H), 2.00-2.07 (m, 1H), 3.36-3.45 (m, 1H), 3.50-3.72 (m, 4H), 3.80-3.87 (m, 1H), 3.89-3.98 (m, 1H), 4.18-4.26 (m, 2H), 5.38 (s, 2H), 6.11 (s, 2H), 6.64 (s, 1H), 7.58 (dd, J=8.6, 1.3 Hz, 1H), 7.71 (d, J=8.3 Hz, 1H), 7.95 (s, 1H), 11.51 (s, 1H).

Intermediate 405

1,1-Dimethylethyl{(3R,5R)-1-[2-amino-6-(4-cyano-3,5-difluorophenyl)-4-pyrimidinyl]-5-methyl-3-piperidinyl}carbamate

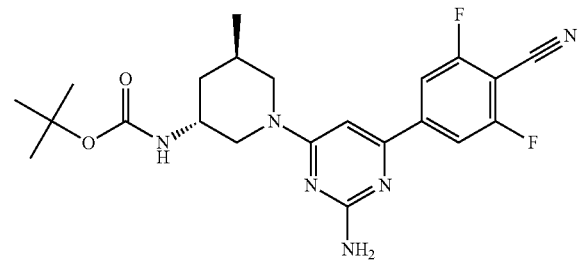 [SMILES: C[C@@H]1C[C@@H](NC(=O)OC(C)(C)C)CN(c2cc(-c3cc(F)c(C#N)c(F)c3)nc(N)n2)C1]

Into a 5 mL sealable vial were dissolved 1,1-dimethylethyl [(3R,5R)-1-(2-amino-6-chloro-4-pyrimidinyl)-5-methyl-3-piperidinyl]carbamate (100 mg, 0.293 mmol) and (4-cyano-3,5-difluorophenyl)boronic acid (80 mg, 0.439 mmol) with 1,4-dioxane (4 mL). Saturated NaHCO$_3$ (2 mL) was added, and N$_2$ gas was bubble through the mixture for 10 minutes. Then Pd(Ph$_3$P)$_4$ (33.8 mg, 0.029 mmol) was added, and N$_2$ gas was bubble through the mixture for an additional 5 minutes. The reaction was then capped and heated at 100° C. overnight. The reaction was diluted with water (10 mL) and then extracted with EtOAc (3×20 mL). The combined organics were dried over Mg$_2$SO$_4$, filtered and concentrated. The brown oil was then purified on Biotage SNAP column 10 g in a gradient of 0 to 45% EtOAc in Hexane to afford the title compound (128 mg) as a yellow oil. LC-MS (ES) m/z=445 [M+H]$^+$.

Intermediate 406

1,1-Dimethylethyl((3R,5R)-1-{2-amino-6-[4-cyano-3-fluoro-5-(methyloxy)phenyl]-4-pyrimidinyl}-5-methyl-3-piperidinyl)carbamate

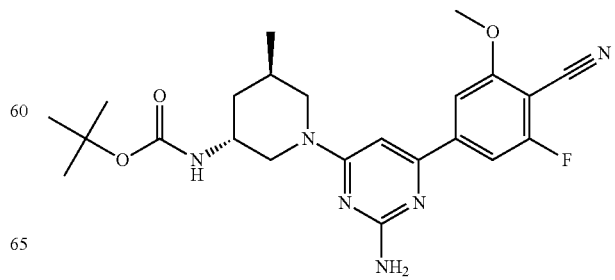

A solution of sodium methoxide was prepared from 50 mg of sodium metal dissolved in 2.1 mL of anhydrous $CH_3OH$. From that solution 0.32 mL was added to a predissolved solution of 1,1-dimethylethyl{(3R,5R)-1-[2-amino-6-(4-cyano-3,5-difluorophenyl)-4-pyrimidinyl]-5-methyl-3-piperidinyl}carbamate (120 mg, 0.270 mmol) in $CH_3OH$ (2 mL), and the reaction mixture was stirred at room temperature overnight. The reaction was concentrated, then diluted with water (10 mL) and extracted with EtOAc (3×10 mL). The organic was combined, washed with saturated NaCl solution, dried over $MgSO_4$, filtered and concentrated to afford the crude title compound (168 mg). LC-MS (ES) m/z=457 $[M+H]^+$.

Example 214

1,1-Dimethylethyl((3R,5R)-1-[2-amino-6-[3-amino-4-(methyloxy)-1H-indazol-6-yl]-4-pyrimidinyl]-5-methyl-3-piperidinyl)carbamate

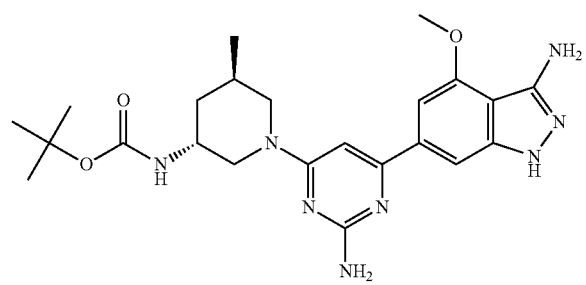 [SMILES: COc1cc(-c2cc(N3C[C@H](C)C[C@@H](NC(=O)OC(C)(C)C)C3)nc(N)n2)cc2[nH]nc(N)c12]

Into a sealable tube were added 1,1-dimethylethyl((3R,5R)-1-{2-amino-6-[4-cyano-3-fluoro-5-(methyloxy)phenyl]-4-pyrimidinyl}-5-methyl-3-piperidinyl)carbamate (168 mg, 0.368 mmol) and ethanol (3 mL) followed by hydrazine monohydrate (0.541 mL, 11.04 mmol). The solution was then capped and heated at 100° C. overnight. The reaction was concentrated, then dissolved in 2 mL of DMSO and purified on HPLC (HPLC condition: open-access Gilson using Trilution software with a Sunfire 5u C18(2) 100A. 50×30.00 mm 5 micron. 7.3-minute run (47 mL/min, 15% $CH_3CN/H_2O$, 0.1% TFA to 40% $CH_3CN/H_2O$, 0.1% TFA) with UV detection at 254 nm). Product fractions were combined, and the volume was reduced to remove most of the $CH_3CN$. To the water left behind was added saturated $NaHCO_3$. It was then extracted with EtOAc (3×50 mL). The organic was washed with brine, dried over $MgSO_4$, filtered, concentrated, and transferred to a haystack vial. Water (1 mL) was added, and the resulting mixture was freeze dried to afford the title compound (60 mg) as a light yellow solid. LC-MS (ES) m/z=469 $[M+H]^+$. $^1H$ NMR (400 MHz, DMSO-$d_6$): δ 0.88 (d, J=6.6 Hz, 3H), 1.29 (bs, 9H), 1.47 (d, J=12.88 Hz, 2H), 1.67 (bs, 1H), 1.95-2.03 (m, 1H), 2.92 (bs, 1H), 3.63 (bs, 1H), 3.82 (bs, 1H), 3.93 (s, 3H), 5.02 (bs, 2H), 6.05 (bs, 2H), 6.46 (s, 1H), 6.81 (d, J=6.1 Hz, 1H), 6.87 (s, 1H), 7.43 (s, 1H), 11.52 (s, 1H).

Intermediate 407

1,1-Dimethylethyl{(3R,5R)-1-[6-chloro-2-(methylamino)-4-pyrimidinyl]-5-methyl-3-piperidinyl}carbamate

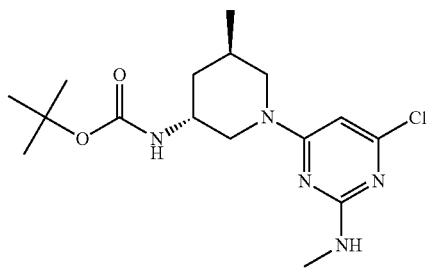 [SMILES: CNc1nc(Cl)cc(N2C[C@H](C)C[C@@H](NC(=O)OC(C)(C)C)C2)n1]

A mixture of 1,1-dimethylethyl[(3R,5R)-5-methyl-3-piperidinyl]carbamate (176 mg, 0.821 mmol) and 4,6-dichloro-N-methyl-2-pyrimidinamine (146 mg, 0.821 mmol) in 1,4-dioxane (4 mL) and saturated aqueous $NaHCO_3$ (2 mL) was stirred for 3 hours at 80° C. into a sealed tube. The reaction was allowed to cool to room temperature and diluted with water (~200 mL). A white precipitate formed which was filtered and washed with water (~50 mL). The white solid was dissolved in minimal $CH_2Cl_2$ and injected into a 40 g $SiO_2$ column. Flash chromatohraphy (gradient: 100% Hexanes to 40% EtOAc in Hexanes) afforded the title compound (234 mg) as a white solid. LC-MS (ES) m/z=356 $[M+H]^+$.

Intermediate 408

1,1-Dimethylethyl{(3R,5R)-1-[6-(4-cyano-3-fluorophenyl)-2-(methylamino)-4-pyrimidinyl]-5-methyl-3-piperidinyl}carbamate

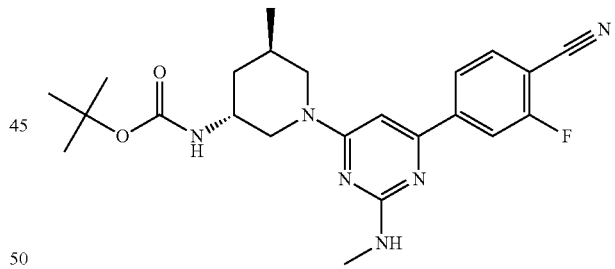

Into a sealable tube were dissolved 1,1-dimethylethyl{(3R,5R)-1-[6-chloro-2-(methylamino)-4-pyrimidinyl]-5-methyl-3-piperidinyl}carbamate (115 mg, 0.323 mmol) and (4-cyano-3-fluorophenyl)boronic acid (80 mg, 0.485 mmol) in 1,4-dioxane (4 mL). Saturated $NaHCO_3$ (2 mL) was added, and $N_2$ gas was bubble through the mixture for 10 minutes. Then $Pd(Ph_3P)_4$ (56.0 mg, 0.048 mmol) was added, and $N_2$ gas was bubble through the mixture for an additional 5 minutes. The reaction was then capped and heated at 100° C. overnight. The reaction was diluted with water (10 mL) and then extracted with EtOAc (3×20 mL). Organic was combined, dried over $MgSO_4$, filtered and concentrated.

The brown oil was then purified on Biotage SNAP 10 g column in a gradient of 0 to 35% EtOAc in Hexane. LC-MS (ES) m/z=441 $[M+H]^+$.

Example 215

1,1-Dimethylethyl{(3R,5R)-1-[6-(3-amino-1H-indazol-6-yl)-2-(methylamino)-4-pyrimidinyl]-5-methyl-3-piperidinyl}carbamate

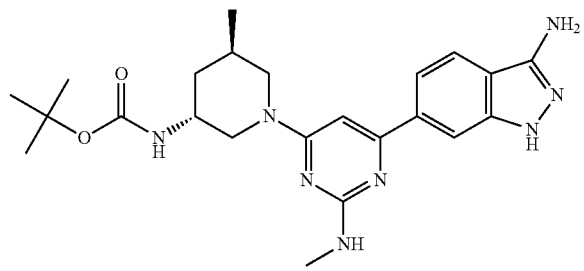 [SMILES: CNc1nc(-c2ccc3c(N)n[nH]c3c2)cc(N2C[C@H](C)C[C@@H](NC(=O)OC(C)(C)C)C2)n1]

Into a 5 mL sealable vial were added 1,1-dimethylethyl{(3R,5R)-1-[6-(4-cyano-3-fluorophenyl)-2-(methylamino)-4-pyrimidinyl]-5-methyl-3-piperidinyl}carbamate (121 mg, 0.275 mmol) and ethanol (3 mL) followed by hydrazine monohydrate (0.404 mL, 8.24 mmol). The reaction was capped and heated at 100° C. overnight. The reaction was concentrated, then dissolved in 2 mL of DMSO and purified on HPLC (HPLC condition: open-access Gilson using Trilution software with a Sunfire 5u C18(2) 100A. 50×30.00 mm 5 micron. 7.3-minute run (47 mL/min, 20% $CH_3CN/H_2O$, 0.1% TFA to 45% $CH_3CN/H_2O$, 0.1% TFA) with UV detection at 254 nm). Product fractions were combined and the volume was reduced to remove most of the $CH_3CN$. To the water left behind was added saturated $NaHCO_3$. It was then extracted with EtOAc (3×15 mL). The organic was washed with brine, dried over $MgSO_4$, filtered, concentrated, and transferred to a haystack vial. Water (1 mL) was added, and the resulting mixture was freeze dried to afford the title compound (87 mg) as a light yellow solid. LC-MS (ES) m/z=453 [M+H]$^+$. $^1$H NMR (400 MHz, DMSO-d$_6$): δ 0.88 (d, J=6.6 Hz, 3H,) 1.29 (s, 9H), 1.38-1.50 (m, 2H), 1.66-1.74 (m, 1H), 1.99 (s, 1H), 2.83 (d, J=4.6 Hz, 3H). 2.85-2.92 (m, 1H). 3.63 (bs, 1H), 3.96-4.08 (m, 1H), 4.07-4.22 (m, 1H), 5.37 (s, 2H), 6.50 (bs, 2H), 6.79 (d, J=6.6 Hz, 1H), 7.53 (d, J=8.3 Hz, 1H), 7.69 (d, J=8.6 Hz, 1H), 7.93 (bs, 1H).

Intermediate 409

1,1-Dimethylethyl{(3R,5R)-1-[6-(4-cyano-3,5-difluorophenyl)-2-(methylamino)-4-pyrimidinyl]-5-methyl-3-piperidinyl}carbamate

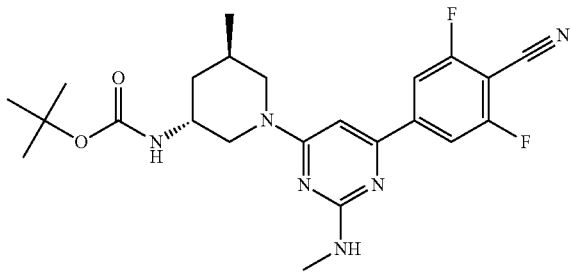 [SMILES: CNc1nc(-c2cc(F)c(C#N)c(F)c2)cc(N2C[C@H](C)C[C@@H](NC(=O)OC(C)(C)C)C2)n1]

Into a 5 mL sealable vial were dissolved 1,1-dimethylethyl{(3R,5R)-1-[6-chloro-2-(methylamino)-4-pyrimidinyl]-5-methyl-3-piperidinyl}carbamate (115 mg, 0.323 mmol) and (4-cyano-3,5-difluorophenyl)boronic acid (89 mg, 0.485 mmol) in 1,4-dioxane (4 mL). Saturated $NaHCO_3$ (2 mL) was added, and $N_2$ gas was bubbled through the mixture for 10 minutes. Then Pd(Ph$_3$P)$_4$ (56.0 mg, 0.048 mmol) was added, and $N_2$ gas was bubbled through the mixture for an additional 5 minutes. The reaction was then capped and heated at 100° C. overnight. The reaction was diluted with water (10 mL) and then extracted with EtOAc (3×20 mL). Organic was combined, dried over $Mg_2SO_4$, filtered and concentrated. The brown oil was then purified on Biotage SNAP column 25 g in a gradient of 0 to 35% EtOAc in Hexane to afford the title compound (128 mg) as a yellow oil. LC-MS (ES) m/z=459 [M+H]$^+$.

Intermediate 410

1,1-Dimethylethyl{(3R,5R)-1-[6-[4-cyano-3-fluoro-5-(methyloxy)phenyl]-2-(methylamino)-4-pyrimidinyl]-5-methyl-3-piperidinyl}carbamate

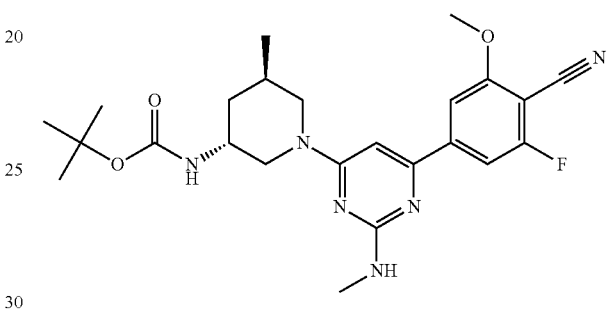

A solution of sodium methoxide was prepared from 60 mg of sodium metal dissolved in 2.6 mL of $CH_3OH$. From that solution 0.36 mL was added to a predissolved solution of 1,1-dimethylethyl{(3R,5R)-1-[6-(4-cyano-3,5-difluorophenyl)-2-(methylamino)-4-pyrimidinyl]-5-methyl-3-piperidinyl}carbamate (138 mg, 0.301 mmol) in $CH_3OH$ (3 mL). The reaction was stirred at room temperature overnight. The reaction observed about 5% of bis-OMe addition but no starting material. The reaction was concentrated, and then diluted with water (10 mL) and extracted with EtOAc (3×10 mL). The organic was combined, washed with saturated NaCl solution, dried over $MgSO_4$, filtered and concentrated to afford the crude title compound (109 mg). LC-MS (ES) m/z=471 [M+H]$^+$.

Example 216

1,1-Dimethylethyl{(3R,5R)-1-[6-[3-amino-4-(methyloxy)-1H-indazol-6-yl]-2-(methylamino)-4-pyrimidinyl]-5-methyl-3-piperidinyl}carbamate

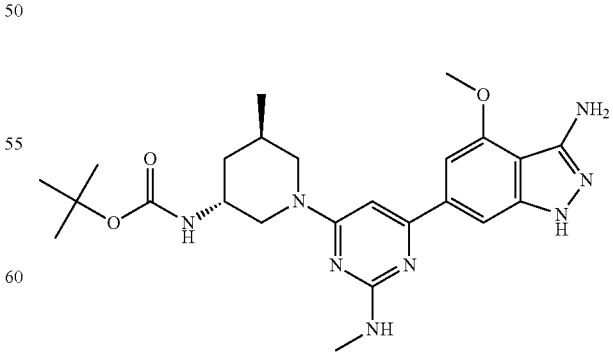

Into a sealable tube were added 1,1-dimethylethyl{(3R,5R)-1-[6-[4-cyano-3-fluoro-5-(methyloxy)phenyl]-2-(methylamino)-4-pyrimidinyl]-5-methyl-3-piperidinyl}carbamate (109 mg, 0.232 mmol) and ethanol (3 mL) followed by hydrazine monohydrate (0.341 mL, 6.95 mmol). The solution was then capped and heated at 100° C. overnight. The reaction was concentrated, then dissolved in 3 mL of DMSO and purified on HPLC (HPLC condition: open-access Gilson using Trilution software with a Sunfire 5u C18(2) 100A. 50×30.00 mm 5 micron. 7.3-minute run (47 mL/min, 20% CH$_3$CN/H$_2$O, 0.1% TFA to 45% CH$_3$CN/H$_2$O, 0.1% TFA) with UV detection at 254 nm). Product fractions were combined and the volume was reduced to remove most of the CH$_3$CN. To the water left behind was added saturated NaHCO$_3$. It was then extracted with EtOAc (3×15 mL). The organic was washed with brine, dried over MgSO$_4$, filtered, concentrated, and transferred to a haystack vial. Water (1 mL) was added, and the resulting mixture was freeze dried to afford the title compound (38 mg) as a light yellow solid. LC-MS (ES) m/z=483 [M+H]$^+$. $^1$H NMR (400 MHz, DMSO-d$_6$): δ 0.88 (d, J=6.6 Hz, 3H), 1.30 (s, 9H), 1.47 (d, J=5.1 Hz, 1H), 1.70 (d, J=12.9 Hz, 1H), 2.00 (bs, 1H) 2.82 (d, J=4.3 Hz, 3H), 2.97 (bs, 1H), 3.42 (bs, 1H), 3.62 (bs, 1H), 3.94 (s, 3H), 4.02 (bs, 1H), 5.02 (s, 2H), 6.47 (bs, 2H), 6.80 (d, J=6.3 Hz, 1H), 6.90 (bs, 1H), 7.46 (bs, 1H), 11.53 (s, 1H).

Intermediate 411

1-Methylethyl{(3R)-1-[2-amino-6-(4-cyano-3-fluorophenyl)-4-pyrimidinyl]-3-piperidinyl}carbamate

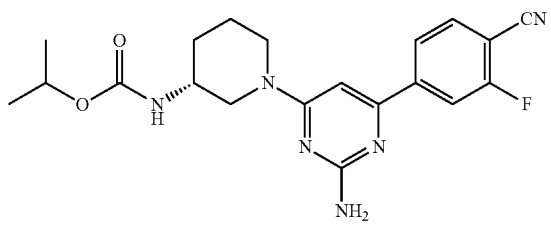 [SMILES: CC(C)OC(=O)N[C@@H]1CCCN(c2cc(-c3ccc(C#N)c(F)c3)nc(N)n2)C1]

To 4-{2-amino-6-[(3R)-3-amino-1-piperidinyl]-4-pyrimidinyl}-2-fluorobenzonitrile (125 mg, 0.324 mmol) in THF (4 mL) and saturated NaHCO$_3$ (2 mL) was added 1-methylethyl chloridocarbonate (0.389 mL, 0.389 mmol), and the mixture was stirred at room temperature overnight. The reaction was diluted with water (10 mL), then extracted with EtOAc (3×10 mL). The organic was combined, washed with saturated NaCl solution, dried over MgSO$_4$, filtered and concentrated to afford the crude title compound (116 mg) as a yellow oil. LC-MS (ES) m/z=399 [M+H]$^+$.

Example 217

1-Methylethyl{(3R)-1-[2-amino-6-(3-amino-1H-indazol-6-yl)-4-pyrimidinyl]-3-piperidinyl}carbamate

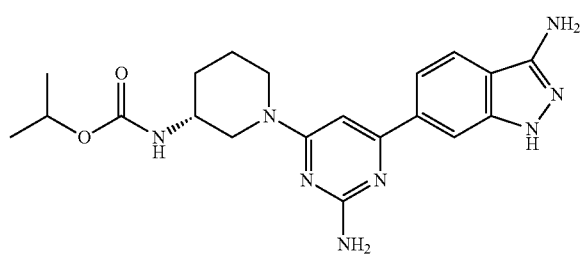 [SMILES: CC(C)OC(=O)N[C@@H]1CCCN(c2cc(-c3ccc4c(N)n[nH]c4c3)nc(N)n2)C1]

Into a 5 mL sealable vial was added 1-methylethyl{(3R)-1-[2-amino-6-(4-cyano-3-fluorophenyl)-4-pyrimidinyl]-3-piperidinyl}carbamate (116 mg, 0.291 mmol) followed by ethanol (3 mL) and hydrazine (0.428 mL, 8.73 mmol). The mixture was then capped and heated at 100° C. overnight. The reaction was concentrated, then dissolved in 2 mL of DMSO and purified on HPLC (HPLC condition: open-access Gilson using Trilution software with a Sunfire 5u C18(2) 100A. 50×30.00 mm 5 micron. 7.3-minute run (47 mL/min, 10% CH$_3$CN/H$_2$O, 0.1% TFA to 35% CH$_3$CN/H$_2$O, 0.1% TFA) with UV detection at 254 nm). Product fractions were combined and the volume was reduced to remove most of the CH$_3$CN. To the water left behind was added saturated NaHCO$_3$. It was then extracted with EtOAc (3×15 mL) and the organic fractions were combined and washed with saturated NaCl solution, dried over MgSO$_4$, filtered and concentrated. The product was then transferred to a haystack vial and 1 mL of water was added and freeze dried. LC-MS (ES) m/z=411 [M+H]$^+$. $^1$H NMR (400 MHz, DMSO-d$_6$): δ 1.13 (d, 3H), 1.16 (d, J=6.3 Hz, 3H), 1.39-1.49 (m, 2H), 1.70-1.77 (m, 1H), 1.85-1.93 (m, 1H), 2.87 (bs, 1H), 3.03 (bs, 1H), 4.06-4.16 (m, 1H), 4.28 (bs, 1H), 4.77 (ddd, J=12.51, 6.19, 6.06 Hz, 1H), 5.38 (s, 2H), 6.09 (bs, 2H), 6.56 (s, 1H), 7.16 (d, J=7.6 Hz, 1H), 7.54 (d, J=8.6 Hz, 1H), 7.70 (d, J=8.3 Hz, 1H), 7.92 (s, 1H), 11.52 (s, 1H).

Intermediate 412

4-Chloro-6-[(2R)-2-ethyl-1-pyrrolidinyl]-N-methyl-2-pyrimidinamine

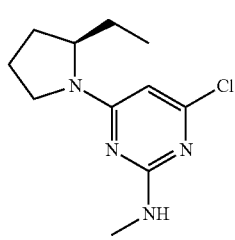 [SMILES: CC[C@@H]1CCCN1c1cc(Cl)nc(NC)n1]

A mixture of (2R)-2-ethylpyrrolidine (0.8 g, 5.90 mmol) and 4,6-dichloro-N-methyl-2-pyrimidinamine (0.997 g, 5.60 mmol) in 1,4-dioxane (40 mL) and saturated aqueous NaHCO$_3$ (20 mL) was stirred overnight at 100° C. into a sealed tube. The reaction mixture was poured onto water (~400 mL). A white precipitate was formed. The aqueous mixture was filtered, and the white solid was washed with water (~100 mL). The wet solid was dried overnight on vacuum at 40° C. to afford the title compound (1.19 g). LC-MS (ES) m/z=241 [M+H]$^+$.

Intermediate 413

4-[6-[(2R)-2-Ethyl-1-pyrrolidinyl]-2-(methylamino)-4-pyrimidinyl]-2,6-difluorobenzonitrile

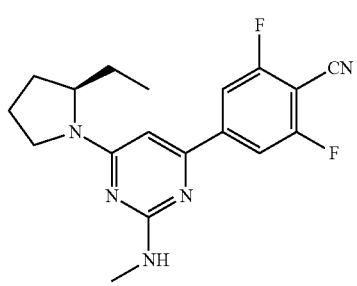 [SMILES: CC[C@@H]1CCCN1c1cc(-c2cc(F)c(C#N)c(F)c2)nc(NC)n1]

In a 150 mL microwave vial, 4-[6-[(2R)-2-ethyl-1-pyrrolidinyl]-2-(methylamino)-4-pyrimidinyl]-2,6-difluorobenzonitrile (1.18 g, 4.90 mmol) and (4-cyano-3,5-difluorophenyl)boronic acid (1.345 g, 7.35 mmol) were dissolved in 1,4-dioxane (40 mL) with stirring. Water (20 mL) was added followed by potassium phosphate tribasic monohydrate (3.05 g, 13.23 mmol), and the mixture was purged with $N_2$ to degass for 2 minutes. Tricyclohexylphosphine tetrafluoroborate (0.271 g, 0.735 mmol) and $Pd_2(dba)_3$ (0.337 g, 0.368 mmol) were added, and the mixture was sealed and heated at 100° C. overnight. LCMS indicated complete conversion. The mixture was diluted with EtOAc and washed with water, brine, dried ($MgSO_4$) filtered and evaporated. The product was purified further by chromatography (Analogix RS-90 g silica column) eluting with 0-20% EtOAc/hexane to give the title compound (1.4 g) as a yellow colored foam. LC-MS (ES) m/z=374 $[M+H]^+$.

Intermediate 414

4-[6-[(2R)-2-Ethyl-1-pyrrolidinyl]-2-(methylamino)-4-pyrimidinyl]-2-fluoro-6-(methyloxy)benzonitrile

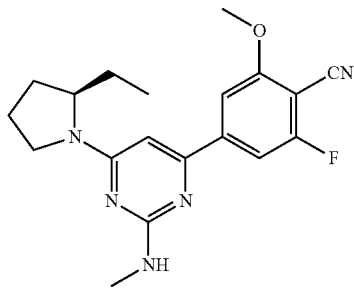 [SMILES: CC[C@@H]1CCCN1c1cc(-c2cc(F)c(C#N)c(OC)c2)nc(NC)n1]

A 1M solution of sodium methoxide in $CH_3OH$ was prepared by addition of 50 mg (2.17 mmol) of freshly cut sodium to ice cold $CH_3OH$ (2.17 mL). Of that, 0.489 mL was added to a solution of 4-[6-[(2R)-2-ethyl-1-pyrrolidinyl]-2-(methylamino)-4-pyrimidinyl]-2,6-difluorobenzonitrile (140 mg, 0.408 mmol) in $CH_3OH$/DMF (2 mL/0.2 mL). The yellow solution was stirred at room temperature overnight in a capped 10 mL vial. LCMS was very clean. The mixture was poured onto water (15 mL). The formed yellow solid was filtered, washed by water and dried to afford the title compound (129 mg) as a light yellow solid. LC-MS (ES) m/z=356 $[M+H]^+$.

Example 218

6-[6-[(2R)-2-Ethyl-1-pyrrolidinyl]-2-(methylamino)-4-pyrimidinyl]-4-(methyloxy)-1H-indazol-3-amine

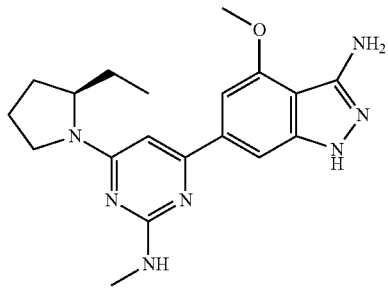 [SMILES: CC[C@@H]1CCCN1c1cc(-c2cc(OC)c3c(N)n[nH]c3c2)nc(NC)n1]

In a microwave tube, 4-[6-[(2R)-2-ethyl-1-pyrrolidinyl]-2-(methylamino)-4-pyrimidinyl]-2-fluoro-6-(methyloxy)benzonitrile (129 mg, 0.363 mmol), 5 mL of EtOH, Hunig's base (0.063 mL, 0.363 mmol), and hydrazine anhydrous (0.068 mL, 2.178 mmol) were added. The yellow suspension mixture was heated to 100° C. in an oil bath overnight. When the temperature of the reaction reached 100° C., the solid in the mixture was all dissolved. After overnight, there was a white colored solid formed. LCMS showed no more starting material. The reaction was cooled to room temperature, then the white solid was filtered from the yellow solution, washed by $CH_3CN$ (2 mL), and dried under reduced pressure to afford the title compound (70 mg) as a white solid. LC-MS (ES) m/z=368 $[M+H]^+$. $^1H$ NMR (400 MHz, DMSO-$d_6$): δ 0.90 (t, J=7.3 Hz, 3H), 1.37 (m, 1H), 1.80 (m, 2H), 1.93 (m, 3H), 2.82 (d, J=4.6 Hz, 3H), 3.39 (m, H), 3.47-3.63 (m, 1H), 3.93 (s, 3H), 4.05 (m, 1H), 5.02 (s, 2H), 6.19 (s, 1H), 6.41 (s, 1H), 6.92 (s, 1H), 7.46 (s, 1H), 11.51 (s, 1H).

Intermediate 415

4-[6-[(2R)-2-Ethyl-1-pyrrolidinyl]-2-(methylamino)-4-pyrimidinyl]-2-fluoro-6-(methylthio)benzonitrile

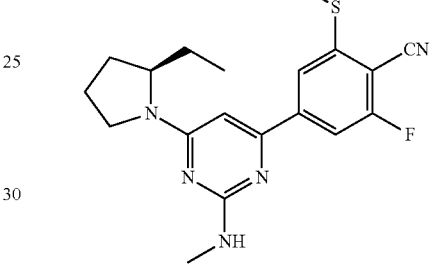

To a solution of 4-[6-[(2R)-2-ethyl-1-pyrrolidinyl]-2-(methylamino)-4-pyrimidinyl]-2,6-difluorobenzonitrile (140 mg, 0.408 mmol) in DMF (4 mL), was added methyl mercaptan sodium salt (ca. 15% in water) (252 mg, 0.543 mmol). The orange colored solution was stirred at room temperature overnight in a capped 10 mL vial. LCMS was very clean. The mixture was poured into water (15 mL). The formed solid was filtered, washed by water and dried to afford the title compound (136 mg) as a light yellow solid. LC-MS (ES) m/z=372 $[M+H]^+$.

Example 219

6-[6-[(2R)-2-Ethyl-1-pyrrolidinyl]-2-(methylamino)-4-pyrimidinyl]-4-(methylthio)-1H-indazol-3-amine

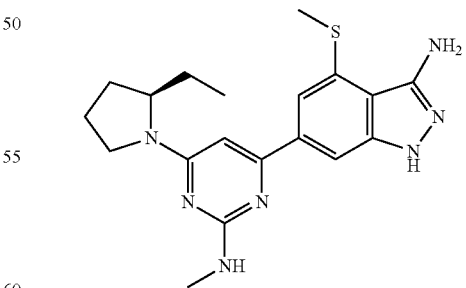

In a microwave tube, 4-[6-[(2R)-2-ethyl-1-pyrrolidinyl]-2-(methylamino)-4-pyrimidinyl]-2-fluoro-6-(methylthio)benzonitrile (136 mg, 0.366 mmol), 5 mL of EtOH, Hunig's base (0.064 mL, 0.366 mmol), and hydrazine anhydrous (0.069 mL, 2.197 mmol) were added. The yellow suspension mixture was heated to 100° C. in an oil bath overnight. When the temperature of the reaction reached 100° C., the solid in the mixture was all dissolved. After overnight, there was a white colored solid formed. LCMS showed no more starting material. The reaction was cooled to room temperature, then the white solid was filtered from the yellow solution, washed by CH$_3$CN (2 mL), dried under reduced pressure to afford the title compound (90 mg). LC-MS (ES) m/z=370 [M+H]$^+$. $^1$H NMR (400 MHz, DMSO-d$_6$): δ 0.91 (t, J=7.3 Hz, 3H), 1.36 (m, 1H), 1.80 (m, 2H), 1.93 (m, 3H), 2.59 (s, 3H), 2.83 (d, J=4.6 Hz, 3H), 3.53 (m, 1H), 4.06 (m, 1H), 5.08 (s, 2H), 6.22 (s, 1H), 6.44 (s, 1H), 7.38 (s, 1H), 7.71 (s, 1H), 11.75 (s, 1H).

Intermediate 416

2-(Ethyloxy)-4-[6-[(2R)-2-ethyl-1-pyrrolidinyl]-2-(methylamino)-4-pyrimidinyl]-6-fluorobenzonitrile

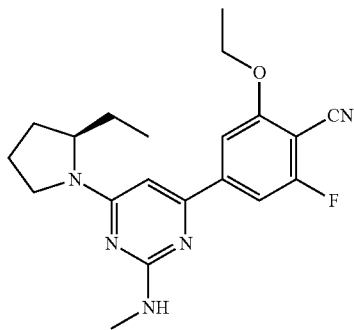 [SMILES: CCOc1cc(-c2cc(N3CCC[C@H]3CC)nc(NC)n2)cc(F)c1C#N]

A 1M solution of sodium ethoxide in EtOH was prepared by addition of 60 mg (2.61 mmol) of freshly cut sodium to ice cold EtOH (2.61 mL). Of that, 0.489 mL was added to a solution of 4-[6-[(2R)-2-ethyl-1-pyrrolidinyl]-2-(methylamino)-4-pyrimidinyl]-2,6-difluorobenzonitrile (140 mg, 0.408 mmol) in Ethanol/DMF (2 mL/0.2 mL). The yellow solution was stirred at room temperature overnight in a capped 10 mL vial. LCMS was very clean. The mixture was poured onto water (15 mL). The formed solid was filtered, washed by water and dried to afford the title compound (137 mg) as a light yellow solid. LC-MS (ES) m/z=370 [M+H]$^+$.

Example 220

4-(Ethyloxy)-6-[6-[(2R)-2-ethyl-1-pyrrolidinyl]-2-(methylamino)-4-pyrimidinyl]-1H-indazol-3-amine

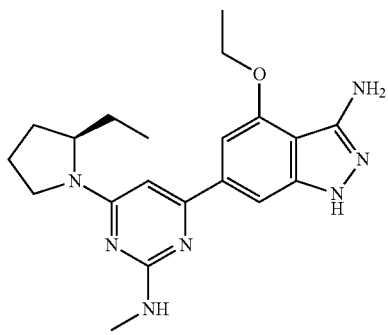 [SMILES: CCOc1cc(-c2cc(N3CCC[C@H]3CC)nc(NC)n2)cc2[nH]nc(N)c12]

In a microwave tube, 2-(ethyloxy)-4-[6-[(2R)-2-ethyl-1-pyrrolidinyl]-2-(methylamino)-4-pyrimidinyl]-6-fluorobenzonitrile (137 mg, 0.371 mmol), 5 mL of EtOH, Hunig's base (0.065 mL, 0.371 mmol), and hydrazine anhydrous (0.070 mL, 2.225 mmol) were added. The yellow suspension mixture was heated to 100° C. in an oil bath overnight. When the temperature of the reaction reached 100° C., the solid in the mixture was all dissolved. After overnight, there was a white colored solid formed. LCMS showed no more starting material. The reaction was cooled to room temperature, then the white solid was filtered from the yellow solution, washed by CH$_3$CN (2 mL), and dried under reduced pressure to afford the title compound (120 mg) as a white solid. LC-MS (ES) m/z=382 [M+H]$^+$. $^1$H NMR (400 MHz, DMSO-d$_6$): δ 0.90 (t, J=7.3 Hz, 3H), 1.35 (m, 1H), 1.44 (t, J=7.0 Hz, 3H), 1.80 (m, 2H), 1.93 (m, 3H), 2.82 (d, J=4.6 Hz, 3H), 3.39 (m, 1H), 3.40-3.45 (m, 1H), 3.48-3.62 (m, 1H), 4.05 (m, 1H), 4.13-4.25 (q, J=7.0 Hz, 2H), 4.99 (s, 2H), 6.17 (s, 1H), 6.40 (s, 1H), 6.92 (s, 1H), 7.44 (s, 1H), 11.50 (s, 1H).

Intermediate 416

1,1-Dimethylethyl methyl[(3R,5R)-5-methyl-1-(phenylmethyl)-3-piperidinyl]carbamate

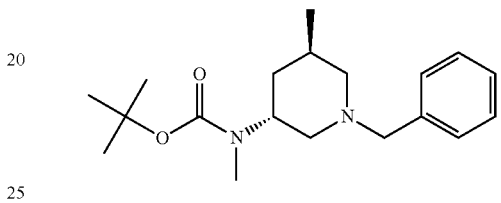

To 1,1-dimethylethyl[(3R,5R)-5-methyl-1-(phenylmethyl)-3-piperidinyl]carbamate (196 mg, 0.644 mmol) in DMF (3 mL) was added NaH (38.6 mg, 0.966 mmol), and the resulting mixture was vigorously stirred for 30 minutes. CH$_3$I (0.044 mL, 0.708 mmol) was added, and the reaction mixture was stirred for 3 hours at room temperature. Saturated aqueous NaHCO$_3$ was added carefully (~5 mL: initial vigorous bubbling), and the resulting mixture was poured onto water and EtOAc. The organic layer was separated, washed with brine, dried (MgSO$_4$), filtered and concentrated. Flash chromatography on SiO$_2$ (gradient: 100% Hexane to 30% EtOAc/Hexane) afforded the title compound (162 mg) as a colorless oil. LC-MS (ES) m/z=319 [M+H]$^+$.

Intermediate 417

1,1-Dimethylethyl{(3R,5R)-1-[2-amino-6-(4-cyano-3-fluorophenyl)-4-pyrimidinyl]-5-methyl-3-piperidinyl}methylcarbamate

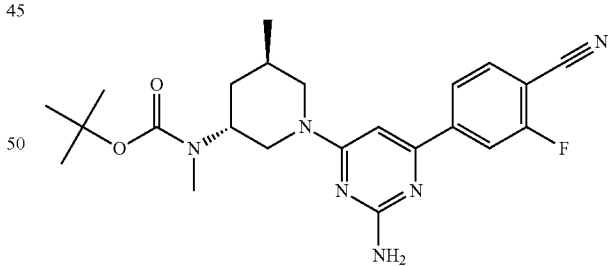

A solution of 1,1-dimethylethyl methyl[(3R,5R)-5-methyl-1-(phenylmethyl)-3-piperidinyl]carbamate (160 mg, 0.502 mmol) in ethanol (6 mL) was degassed with N$_2$ for 10 minutes. Pd/C degussa type (53.5 mg, 0.502 mmol) was added, and the resulting mixture was stirred for 3 days (probably the reaction is much quicker than that) at room temperature under a H$_2$ atmosphere (balloon setup). The mixture was degassed with N$_2$ and filtered through an Acrodisk, rinsing with ethanol (~15 mL). The mixture was concentrated under vacuum. The resulting residue was taken up into 1,4-dioxane (6.00 mL). To the resulting solution were added 4,6-dichloro-2-pyrimidinamine (79 mg, 0.477 mmol) and saturated aqueous NaHCO₃ (3 mL), and the resulting mixture was stirred overnight at 100° C. into a sealed tube. The reaction was allowed to cool to room temperature. (4-Cyano-3-fluorophenyl)boronic acid (124 mg, 0.754 mmol) was added, and N₂ gas was bubbled through the mixture for 10 minutes. Pd(Ph₃P)₄ (29 mg, 0.025 mmol) was added, the vessel was sealed, and the reaction mixture was stirred for 4 hours at 100° C. The mixture was poured onto water and EtOAc. The organic layer was separated, and the aqueous layer was further extracted with EtOAc. The combined organic layers were washed with brine, dried (MgSO₄), filtered and concentrated. Flash chromatography on SiO₂ (gradient: 100% Hexane to 70% EtOAc/Hexane) afforded the title compound (170 mg) as an thick oil. LC-MS (ES) m/z=441 [M+H]⁺.

Example 221

1,1-Dimethylethyl{(3R,5R)-1-[2-amino-6-(3-amino-1H-indazol-6-yl)-4-pyrimidinyl]-5-methyl-3-piperidinyl}methylcarbamate

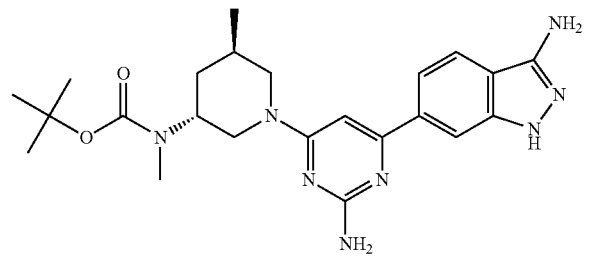 [SMILES: C[C@@H]1C[C@@H](N(C)C(=O)OC(C)(C)C)CN(c2cc(-c3ccc4c(N)n[nH]c4c3)nc(N)n2)C1]

To 1,1-dimethylethyl{(3R,5R)-1-[2-amino-6-(4-cyano-3-fluorophenyl)-4-pyrimidinyl]-5-methyl-3-piperidinyl}methylcarbamate (170 mg, 0.386 mmol) in ethanol (6 mL) was added hydrazine monohydrate (0.70 mL, 14.3 mmol), and the reaction mixture was stirred overnight at 100° C. into a sealed tube. The mixture was poured onto water (~150 mL) and a white precipitate was formed. The aqueous mixture was filtered, and the solid was air dried for 2 hours. The resulting white solid was dried under vacuum at 45° C. for 1 hour to afford the title compound (110 mg). LC-MS (ES) m/z=453 [M+H]⁺. ¹H NMR (400 MHz, DMSO-d₆): δ 0.92-1.02 (m, 3H), 1.41 (s, 9H), 1.46-1.55 (m, 1H), 1.85-1.99 (m, 1H), 2.07-2.19 (m, 1H), 2.76 (s, 3H), 3.02-3.14 (m, 1H), 3.12-3.23 (m, 1H), 3.90-4.15 (m, 2H), 4.35 (m, 1H), 5.38 (s, 2H), 6.07 (s, 2H), 6.60 (s, 1H), 7.57 (dd, J=8.6, 1.3 Hz, 1H), 7.70 (d, J=8.6 Hz, 1H), 7.95 (s, 1H), 11.50 (s, 1H).

Example 222

1-[2-amino-6-(3-amino-1H-indazol-6-yl)-4-pyrimidinyl]-L-prolinamide

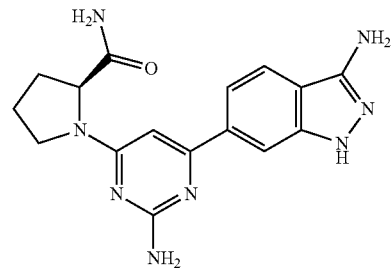 [SMILES: NC(=O)[C@@H]1CCCN1c1cc(-c2ccc3c(N)n[nH]c3c2)nc(N)n1]

In a 5 mL (max vol.) sealable tube, (3-(bis{[(1,1-dimethylethyl)oxy]carbonyl}amino)-1-{[(1,1-dimethylethyl)oxy]carbonyl}-1H-indazol-6-yl)(trifluoro)borate(1-) (335 mg, 0.621 mmol), 1-(2-amino-6-chloro-4-pyrimidinyl)-L-prolinamide (150 mg, 0.621 mmol), and potassium phosphate (224 mg, 1.055 mmol) were taken up in 4 mL of 3:1 dioxane-water. The contents were degassed by bubbling nitrogen through for 10 min. tricyclohexylphosphine (17.41 mg, 0.062 mmol) and Pd₂(dba)₃ (22.73 mg, 0.025 mmol) were added, contents degassed an additional 5 min. The vessel was sealed and heated to 100 C overnight (16 hrs). The contents were cooled to room temperature, and the dioxane layer was separated from the aqueous portion. The solids were filtered off and the crude dioxane layer was passed through a C18 filter cartridge. The filter cartridge was washed with 5 mL of acetonitrile, and the washings were combined with the crude dioxane solution. The crude material was then purified by RPHPLC using a 5-75% 0.1% TFA/ACN gradient over 10 min. The desired fractions were pooled and evaporated to dryness as the mono-Boc protected coupled product. This material was then treated with 10 mL of TFA for 30 min., evaporated to dryness, taken up in methanol and purified by RPHPLC as mentioned above and lyophilized to give a light yellow flocculent powder as the ditrifluoroacetate salt. LC-MS (ES) m/z=339 [M+H]⁺.

Example 223

6-{2-amino-6-[(3R)-3-ethyl-4-morpholinyl]-4-pyrimidinyl}-4-(ethyloxy)-1H-indazol-3-amine

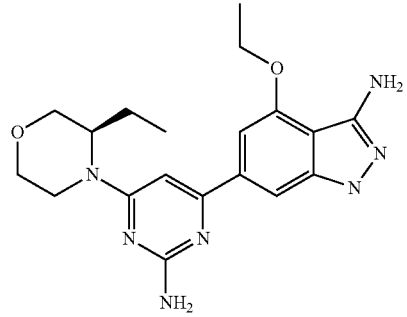 [SMILES: CCOc1cc(-c2cc(N3CCOC[C@H]3CC)nc(N)n2)cc2[nH]nc(N)c12]

To a 20 mL vial was added 4-{2-amino-6-[(3R)-3-ethyl-4-morpholinyl]-4-pyrimidinyl}-2,6-difluorobenzonitrile (850 mg, 2.461 mmol), N,N-dimethylformamide (DMF) (5 mL) and sodium ethoxide 1M (2.461 mL, 2.461 mmol). The reaction was stirred for 30 min at room temperature. The reaction was then poured into EtOAc (10 mL) followed by H₂O (15 mL). The aqueous was extracted with EtOAc (×1) and then dried over Na₂SO₄ and concentrated to a yellow solid that was taken up in acetonitrile (5 mL) and added to a 20 mL microwave vial followed by hydrazine (0.309 mL, 9.85 mmol) and DIEA (3.44 mL, 19.69 mmol). The reaction was sealed and heated in a microwave reactor at 150° C. for 3 h. The reaction mixture was concentrated to a yellow oil and purified via flash chromatography (120 g, 50-100%, DCM:MeOH:NH₄OH). Fractions were combined and concentrated to afford 6-{2-amino-6-[(3R)-3-ethyl-4-morpholinyl]-4-pyrimidinyl}-4-(ethyloxy)-1H-indazol-3-amine (514 mg) as a tan solid. LC-MS (ES) m/z=384 [M+H]⁺. ¹H NMR (400 MHz, DMSO-d₆) δ 0.87 (t, J=7.45 Hz, 3H), 1.45 (t, J=6.95 Hz, 3H), 1.58-1.80 (m, 2H), 3.01-3.14 (m, 1H), 3.37-3.47 (m, 1H), 3.46-3.56 (m, 1H), 3.83 (d, J=11.4 Hz, 2H), 3.85-3.91 (m, 1H), 4.21 (q, J=6.99 Hz, 3H), 4.25-4.39 (m, 1H), 5.00 (s, 2H), 6.07 (s, 2H), 6.49 (s, 1H), 6.90 (s, 1H), 7.47 (s, 1H), 11.53 (s, 1H).

Example 224

6-{2-amino-6-[(3R)-3-ethyl-4-morpholinyl]-4-pyrimidinyl}-4-(methyloxy)-1H-indazol-3-amine

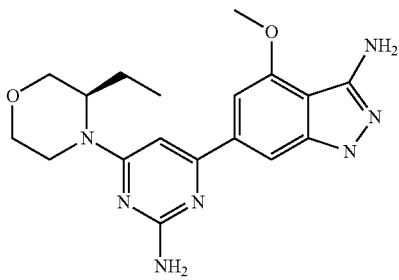 [SMILES: CC[C@@H]1COCCN1c1cc(-c2cc(OC)c3c(N)n[nH]c3c2)nc(N)n1]

To a 20 mL vial was added 4-{2-amino-6-[(3R)-3-ethyl-4-morpholinyl]-4-pyrimidinyl}-2,6-difluorobenzonitrile (850 mg, 2.461 mmol), N,N-dimethylformamide (DMF) (5 mL) and sodium methoxide 1M (2.461 mL, 2.461 mmol). The reaction was stirred for 30 min at room temperature. The reaction was then poured into EtOAc (10 mL) followed by H$_2$O (15 mL). The aqueous was extracted with EtOAc (×1) and then dried over Na$_2$SO$_4$ and concentrated to a yellow solid that was taken up in acetonitrile (5 mL) and added to a 20 mL microwave vial followed by hydrazine (0.309 mL, 9.85 mmol) and DIEA (3.44 mL, 19.69 mmol). The reaction was irradiated at 150° C. for 3 h. The reaction mixture was then concentrated for purification via flash chromatography (120 g, 50-100%, DCM:MeOH:NH$_4$OH). Fractions were combined and concentrated to afford 6-{2-amino-6-[(3R)-3-ethyl-4-morpholinyl]-4-pyrimidinyl}-4-(methyloxy)-1H-indazol-3-amine (421.5 mg, 1.084 mmol, 44% yield) as a tan solid. LC-MS (ES) m/z=370 [M+H]$^+$. $^1$H NMR (400 MHz, DMSO-d$_6$) δ 0.87 (t, J=7.45 Hz, 3H), 1.58-1.82 (m, 2H), 3.04-3.14 (m, 1H), 3.37-3.46 (m, 1H), 3.48-3.55 (m, 1H), 3.83 (d, J=11.62 Hz, 1H), 3.83 (d, J=11.6 Hz, 1H) 3.85-3.91 (m, 1H), 3.94 (s, 3H), 4.08-4.24 (m, 1H), 4.25-4.39 (m, 1H), 5.02 (s, 2H), 6.07 (s, 2H), 6.50 (s, 1H), 6.91 (s, 1H), 7.48 (s, 1H), 11.54 (s, 1H).

Intermediate 418

N-[(3R,5R)-1-(2-amino-6-chloro-4-pyrimidinyl)-5-methyl-3-piperidinyl]-N,3,3-trimethylbutanamide

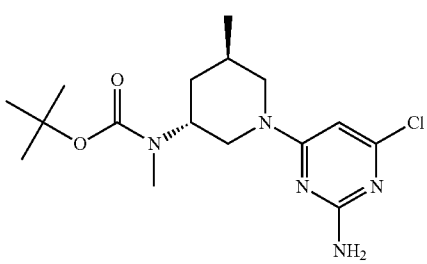 [SMILES: C[C@@H]1C[C@@H](N(C)C(=O)OC(C)(C)C)CN(c2cc(Cl)nc(N)n2)C1]

To 1,1-dimethylethyl[(3R,5R)-1-(2-amino-6-chloro-4-pyrimidinyl)-5-methyl-3-piperidinyl]methylcarbamate (75 mg, 0.211 mmol) in CH$_2$Cl$_2$ (2 mL) was added TFA (2 mL) and the reaction was let sit at room temperature for 2 hours. Toluene (~15 mL) was added, and the resulting mixture was evaporated under vacuum. To the resulting residue were added CH$_2$Cl$_2$ (2 mL) and Hunig's base (0.18 mL, 1.05 mmol) followed by 3,3-dimethylbutanoyl chloride (0.03 mL, 0.21 mmol), and the resulting mixture was stirred overnight at room temperature. Saturated aqueous NaHCO$_3$ (20 mL) was added, and the resulting mixture was extracted with EtOAc (~50 mL). The organic layer was separated, washed with brine, dried (MgSO$_4$), filtered, and concentrated to afford the title compound (80 mg). LC-MS (ES) m/z=354 [M+H]$^+$.

Intermediate 419

N-{(3R,5R)-1-[2-Amino-6-(4-cyano-3-fluorophenyl)-4-pyrimidinyl]-5-methyl-3-piperidinyl}-N,3,3-trimethylbutanamide

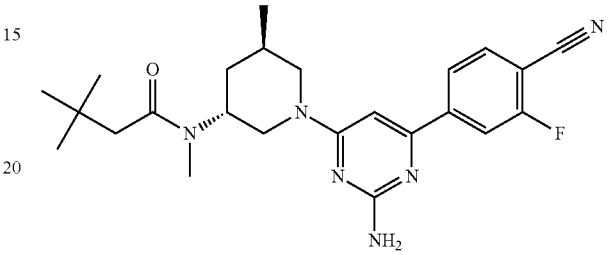

To N-[(3R,5R)-1-(2-amino-6-chloro-4-pyrimidinyl)-5-methyl-3-piperidinyl]-N,3,3-trimethylbutanamide (80 mg, 0.23 mmol) and (4-cyano-3-fluorophenyl)boronic acid (49 mg, 0.29 mmol) were added 1,4-dioxane (4 mL) and sat. aq. NaHCO$_3$ (2 mL), and the resulting mixture was purged ("degassed") with N$_2$ into a sealable tube. Pd(Ph$_3$P)$_4$ (26 mg, 0.023 mmol) was added, the tube was sealed, and the reaction mixture was stirred overnight at 100° C. The reaction was allowed to cool down to room temperature and poured onto water and EtOAc. The organic layer was separated, washed with brine, dried (MgSO$_4$), filtered and concentrated. Flash chromatography on SiO$_2$ (gradient: 100% Hexanes to 75% EtOAc/Hexanes) afforded the title compound (84 mg) as a solid. LC-MS (ES) m/z=439 [M+H]$^+$.

Example 225

N-{(3R,5R)-1-[2-amino-6-(3-amino-1H-indazol-6-yl)-4-pyrimidinyl]-5-methyl-3-piperidinyl}-N,3,3-trimethylbutanamide

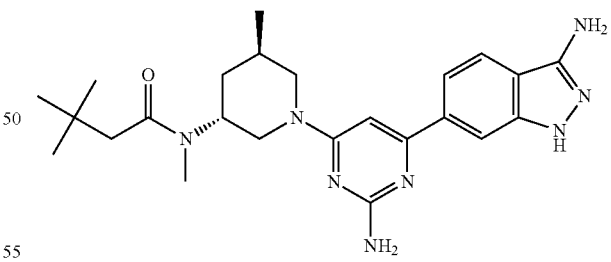

To N-{(3R,5R)-1-[2-amino-6-(4-cyano-3-fluorophenyl)-4-pyrimidinyl]-5-methyl-3-piperidinyl}-N,3,3-trimethylbutanamide (82 mg, 0.187 mmol) in ethanol (4 mL) was added hydrazine monohydrate (1 mL, 20.4 mmol), and the reaction mixture was stirred for 4 hours at 120° C. into a sealed vessel. The reaction was allowed to cool down to room temperature, and poured onto water (~120 mL). The resulting aqueous mixture was extracted with EtOAc (2×20 mL). The combined organic layers were washed with brine, dried (MgSO$_4$), filtered and concentrated to afford the title compound (36 mg) as an off-white solid as a 3:2 mixture of rotamers. LC-MS (ES) m/z=451 [M+H]$^+$. $^1$H NMR (400 MHz, DMSO-d$_6$+1 drop D₂O): δ 0.98 (m, 12H), 1.41 and 1.52 (m, 1H), 1.87-2.41 (m, 4H), 2.76 and 2.90 (s, 3H), 2.99-3.25 (m, 2H), 3.84-3.99 (m, 1H), 4.01-4.26 (m, 1H), 4.39-4.66 (m, 1H), 6.57-6.62 (s, 1H), 7.50-7.60 (m, 1H), 7.70 (m, 1H), 7.92 (s, 1H).

Intermediate 420

N-Cyclohexyl-1-(2,6-dichloro-4-pyrimidinyl)-6-(trifluoromethyl)-3-piperidinecarboxamide

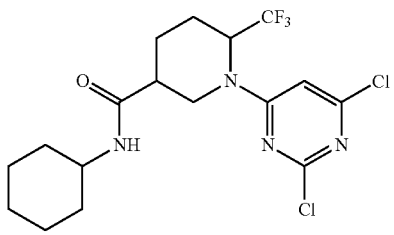 [SMILES: O=C(NC1CCCCC1)C1CCC(C(F)(F)F)N(c2cc(Cl)nc(Cl)n2)C1]

To a mixture of 2,4,6-trichloropyrimidine (0.18 mL, 1.59 mmol) and N-cyclohexyl-6-(trifluoromethyl)-3-piperidinecarboxamide (0.5 g, 1.588 mmol) in 1,4-dioxane (15 mL) was added Hunig's base (0.56 mL, 3.18 mmol), and the reaction mixture was stirred over the weekend (3 days) at 80° C. into a sealed tube. Approximately 35% starting material was remaining. The temperature was increased to 140° C., and the reaction mixture was stirred at this temperature for 3 hours. The reaction was then heated for 1 hour at 160° C. Since there was still remaining starting material, the reaction was stirred overnight at 140° C. The reaction mixture was poured onto water and EtOAc. The organic layer was separated, washed with brine, dried (MgSO₄), filtered and concentrated. Flash chromatography on SiO₂ (gradient: 100% Hexanes to 50% EtOAc in Hexanes) afforded the title compound (239 mg) as a white solid, and the corresponding regioisomer (196 mg) as a white solid. LC-MS (ES) m/z=425, 427 [M+H]⁺.

Intermediate 421

1-{6-[3-(Acetylamino)-4-fluoro-1H-indazol-6-yl]-2-chloro-4-pyrimidinyl}-N-cyclohexyl-6-(trifluoromethyl)-3-piperidinecarboxamide

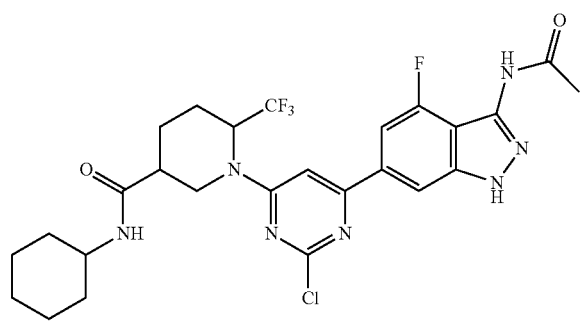 [SMILES: CC(=O)Nc1n[nH]c2cc(-c3cc(N4CC(C(=O)NC5CCCCC5)CCC4C(F)(F)F)nc(Cl)n3)cc(F)c12]

To N-cyclohexyl-1-(2,6-dichloro-4-pyrimidinyl)-6-(trifluoromethyl)-3-piperidinecarboxamide (150 mg, 0.353 mmol) and N-acetyl-N-[1-acetyl-4-fluoro-6-(4,4,5,5-tetramethyl-1,3,2-dioxaborolan-2-yl)-1H-indazol-3-yl]acetamide (142 mg, 0.353 mmol) were added to 1,4-dioxane (12 mL) and saturated aqueous NaHCO₃ (6 mL) in a sealable tube, and the resulting mixture was purged with N₂. Pd(Ph₃P)₄ (41 mg, 0.035 mmol) was added, the tube was sealed, and the reaction mixture was stirred overnight at 100° C. The reaction was allowed to cool down to room temperature and poured onto water. The resulting precipitate was filtered. EtOAc was added to the solid in the filter, and the organic solution was filtered. The filtrate was dried (MgSO₄), filtered and concentrated. Flash chromatography on SiO₂ (gradient: 100% CHCl₃ to 90:10:1 CHCl₃:CH₃OH:NH₄OH) afforded the product (93 mg) as a tan solid which contained a mixture of two regioisomers from cross-coupling at either chlorine of the starting material. The NMR analysis was inconclusive to determine the ratio of the two possible regioisomers. LC-MS (ES) m/z=582 [M+H]⁺.

Example 226

1-[2-Amino-6-(3-amino-4-fluoro-1H-indazol-6-yl)-4-pyrimidinyl]-N-cyclohexyl-6-(trifluoromethyl)-3-piperidinecarboxamide

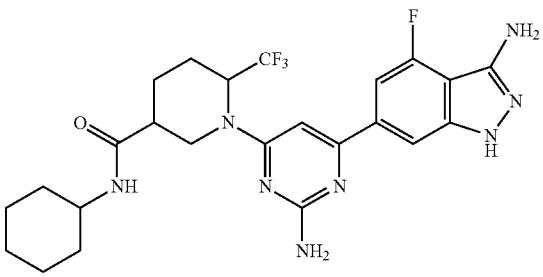 [SMILES: Nc1nc(-c2cc(F)c3c(N)n[nH]c3c2)cc(N2CC(C(=O)NC3CCCCC3)CCC2C(F)(F)F)n1]

A mixture of 1-{6-[3-(acetylamino)-4-fluoro-1H-indazol-6-yl]-2-chloro-4-pyrimidinyl}-N-cyclohexyl-6-(trifluoromethyl)-3-piperidinecarboxamide (mixture of regioisomers) (93 mg, 0.16 mmol) and 1-[2,4-bis(methyloxy)phenyl]methanamine (0.1 mL, 0.666 mmol) in 1,4-dioxane (6.00 mL) was stirred overnight at 120° C. into a sealed tube. Since there was still the presence of the chloropyrimidine intermediate, additional 1-[2,4-bis(methyloxy)phenyl]methanamine (0.1 mL, 0.666 mmol) was added, and the reaction mixture was stirred for 1 hour at 140° C. and for 2 hours at 160° C. The reaction mixture was concentrated under vacuum. To the resulting residue was added CH₃OH (6 mL) followed by conc. HCl (0.3 mL, 3.60 mmol), and the resulting mixture was stirred for 1 hour at 80° C. into a sealed tube. LCMS analysis indicated the complete acetate group removal. The mixture was concentrated, and the resulting residue was evaporated from toluene. To the residue was added TFA (6.00 mL). After 1 hour, the solution was poured onto a saturated aqueous solution of NaHCO₃. EtOAc was added, and the organic layer was separated. The aqueous layer was further extracted with EtOAc, and the combined organic layers were washed with brine, dried (MgSO₄), filtered and concentrated. Flash chromatography on SiO₂ (gradient: 100% CH₂Cl₂ to 80:20:2 CH₂Cl₂:CH₃OH:NH₄OH) afforded the product (49 mg) as a dark tan solid. This material was a ~2:1 mixture of regioisomers as a result of the starting material being a mixture of regioisomeric chloropyrimidine. This material was purified by HPLC purification to separate the regioisomers.

Prep HPLC
Luna C18(2) 5u 21.2×250 mm
A=300 mM Aqueous ammonium formate (pH 4)
B=acetonitrile
58:42—A:B
20 ml/min
uv 254 nm
sample 45 mg in 0.9 ml B+0.9 ml A (added a couple drops HCO₂H to give pH 4
single injection 45 mg Collected 2 main fractions @ 8, 16 min. Each fraction was worked up separately as follows: Conc. @ 45° C. to give a lt. tan suspension (10 mL). Adjusted pH of aqueous to 8.5 with conc. NH$_4$OH. Extracted aqueous with 3×EtOAc; washed with H$_2$O, Sat. NaCl; Dried over Na$_2$SO$_4$, filtered and conc. to a solid. Dried under high vac. @ 40° C., 1.5 hrs.

Recovery: Title compound; 25 mg tan solid; HPLC 98.4° A regioisomer; 15 mg tan solid; HPLC 99.5° A Data for title compound: LC-MS (ES) m/z=521 [M+H]$^+$. $^1$H NMR (400 MHz, CD$_3$OD): δ 1.14-1.46 (m, 5H), 1.59-1.72 (m, 1H), 1.72-2.11 (m, 7H), 2.14-2.26 (m, 1H), 2.37-2.50 (m, 1H), 3.18-3.30 (m, 1H), 3.58-3.73 (m, 1H), 6.63 (s, 1H), 7.22 (d, J=12.1 Hz, 1H), 7.68 (s, 1H).

Example 227

4-(ethyloxy)-6-{2-(methylamino)-6-[(3R)-3-methyl-4-morpholinyl]-4-pyrimidinyl}-1H-indazol-3-amine

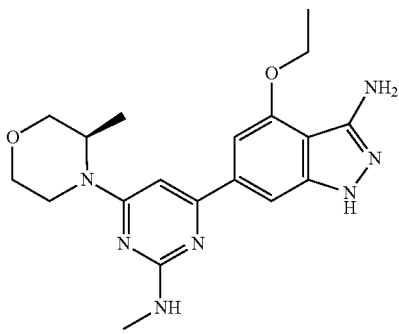 [SMILES: CCOc1cc(-c2cc(N3CCOC[C@H]3C)nc(NC)n2)cc2[nH]nc(N)c12]

A stock solution of sodium ethoxide in ethanol was generated by the addition of ethanol (10 mL) to NaH (204 mg, 8.48 mmol), followed by stirring at room temperature for 30 mins. To a 20-mL vial was added 2,6-difluoro-4-{2-(methylamino)-6-[(3R)-3-methyl-4-morpholinyl]-4-pyrimidinyl}benzonitrile (293 mg, 0.848 mmol), N,N-dimethylformamide (DMF) (1 mL) and ethanol (1.5 mL). The reaction was cooled to 0° C., and a solution of sodium ethoxide in ethanol (from 0.848 M stock solution) (1.101 mL, 0.933 mmol) was added dropwise. The reaction was stirred at room temperature for 90 min. Ammonium chloride (aq., sat., 2 mL) and water (2 mL) were added, and the mixture was extracted with ethyl acetate (3×10 mL). The combined organics were dried over sodium sulfate and concentrated. The residue was purified by flash chromatography (0-50% EtOAc in hexanes, 10-g column) to afford a white solid which was added to a 5-mL microwave vial with hydrazine (0.259 mL, 4.48 mmol), DIEA (0.391 mL, 2.239 mmol) and ethanol (3 mL). The resulting suspension was heated for 90 min at 150° C. in a microwave reactor. The reaction mixture was concentrated and dry-loaded onto silica and purified by flash chromatography (0-10% MeOH in DCM, 25-g column) to afford the title compound (175.4 mg, 0.457 mmol, 54% yield) as an off-white solid. LC-MS (ES) m/z=384 [M+H]$^+$. $^1$H NMR (400 MHz, DMSO-d$_6$) δ 1.19 (d, 3H), 1.45 (t, J=6.95 Hz, 3H), 2.83 (d, J=4.04 Hz, 3H), 3.05-3.18 (m, 1H), 3.45 (td, J=11.75, 2.53 Hz, 1H), 3.56-3.66 (m, 1H), 3.67-3.78 (m, 1H), 3.93 (dd, J=11.12, 3.03 Hz, 1H), 4.11 (d, J=12.88 Hz, 1H), 4.22 (q, J=6.99 Hz, 2H), 4.52 (d, J=4.80 Hz, 1H), 5.00 (s, 2H), 6.35-6.64 (m, 2H), 6.95 (s, 1H), 7.52 (br. s., 1H), 11.52 (s, 1H).

Intermediate 422

(3S,6R)-1-[6-(4-cyano-3,5-difluorophenyl)-2-(methylamino)-4-pyrimidinyl]-6-methyl-N-(phenylmethyl)-3-piperidinecarboxamide

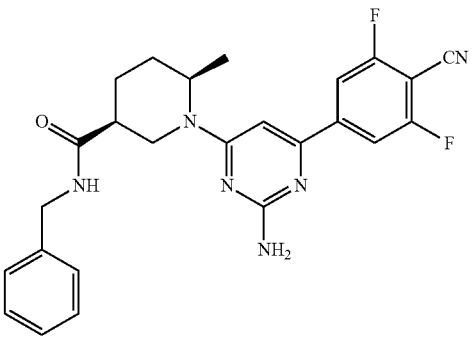 [SMILES: C[C@@H]1CC[C@H](C(=O)NCc2ccccc2)CN1c1cc(-c2cc(F)c(C#N)c(F)c2)nc(N)n1]

(3S,6R)-1-[6-chloro-2-(methylamino)-4-pyrimidinyl]-6-methyl-N-(phenylmethyl)-3-piperidinecarboxamide (100 mg, 0.267 mmol) and (4-cyano-3,5-difluorophenyl)boronic acid (73.4 mg, 0.401 mmol) were dissolved in 1,4-Dioxane (2 mL) in a 5 mL sealable vial then added saturated NaHCO$_3$ (1 mL). Nitrogen gas was bubbled through the mixture for 10 min. Then Pd(Ph$_3$P)$_4$ (37.1 mg, 0.032 mmol) was added and nitrogen gas bubbled for an additional 5 min. The vial was capped the reaction was heat at 100° C. overnight. The reaction was diluted with water (5 mL) and then extracted with EtOAc (3×10 mL). Organic were combined, dried over MgSO$_4$, filtered and concentrated. The yellow oil was then purified on a 10 g Biotage SNAP column with gradient of 0 to 40% EtOAc in Hexane. LC-MS (ES) m/z=477 [M+H]$^+$.

Intermediate 423

(3S,6R)-1-[6-[4-cyano-3-fluoro-5-(methyloxy)phenyl]-2-(methylamino)-4-pyrimidinyl]-6-methyl-N-(phenylmethyl)-3-piperidinecarboxamide

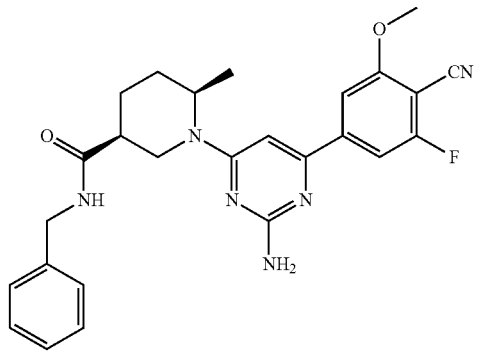 [SMILES: COc1cc(-c2cc(N3C[C@@H](C(=O)NCc4ccccc4)CC[C@H]3C)nc(N)n2)cc(F)c1C#N]

A 1M sodium methoxide solution was prepared from 55 mg (2.4 mmole) of freshly cut sodium and ice cooled 2.4 mL of MeOH. Of that, 0.176 mL was added to a solution of (3S,6R)-1-[6-(4-cyano-3,5-difluorophenyl)-2-(methylamino)-4-pyrimidinyl]-6-methyl-N-(phenylmethyl)-3-piperidinecarboxamide (84 mg, 0.176 mmol) in Methanol (1 mL). The solution was let stir overnight at room temperature. The reaction was concentrated and then diluted with water (10 ml) then extracted with EtOAc (3×10 mL). The organics were combined, washed with saturated NaCl solution, dried over MgSO₄, filtered and concentrated. The material was not purified further. LC-MS (ES) m/z=489 [M+H]⁺.

Example 228

(3S,6R)-1-[6-[3-amino-4-(methyloxy)-1H-indazol-6-yl]-2-(methylamino)-4-pyrimidinyl]-6-methyl-N-(phenylmethyl)-3-piperidinecarboxamide

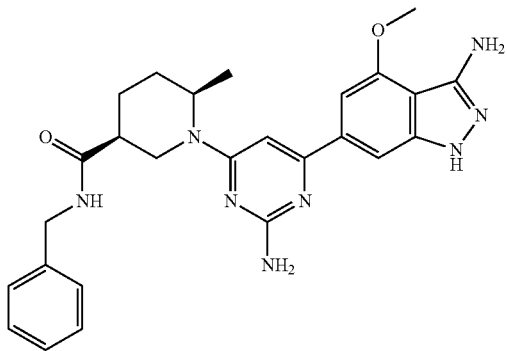 [SMILES: COc1cc(-c2cc(N3C[C@@H](C(=O)NCc4ccccc4)CC[C@H]3C)nc(N)n2)cc2[nH]nc(N)c12]

Dissolved (3S,6R)-1-[6-[4-cyano-3-fluoro-5-(methyloxy)phenyl]-2-(methylamino)-4-pyrimidinyl]-6-methyl-N-(phenylmethyl)-3-piperidinecarboxamide (96 mg, 0.196 mmol) with Ethanol (2 mL) in a 5 mL sealable vial then added hydrazine (0.185 mL, 5.89 mmol). The reaction was capped and heat overnight at 100° C. The reaction was concentrated then dissolved in 1 mL of DMSO and purified on HPLC (HPLC condition: open-access Gilson using Unipoint software with a Varian Polaris 5u C18(2) 100A, 50×30.00 mm 5 micron. 10-minute run (35 ml/min, 28% ACN/H₂O, 0.1% TFA to 53% ACN/H₂O, 0.1% TFA) with UV detection at 254 nm). Product fractions were pooled and the volume was reduced by reduce pressure until most of the MeCN was removed then the aqueous saturated NaHCO₃ (10 mL) added. The mixture was then extracted with EtOAc (3×10 mL). The organic was pooled, washed with saturated. NaCl, dried over MgSO₄, filtered, and concentrated. Then transferred in to 40 mL vial then water was added then freeze-dried to isolate 36 mg of off white solid. LC-MS (ES) m/z=501 [M+H]⁺. ¹H NMR (400 MHz, DMSO-d₆) d ppm 1.17 (d, J=7.07 Hz, 3H) 1.67 (d, J=3.54 Hz, 2H) 1.75 (dd, J=12.88, 3.03 Hz, 1H) 1.80-1.93 (m, 1H) 2.31-2.42 (m, 1H) 2.83 (d, J=4.55 Hz, 3H) 2.98 (br. s., 1H) 3.94 (s, 3H) 4.31 (dd, J=9.73, 5.94 Hz, 2H) 4.78 (br. s., 1H) 5.03 (br. s., 2H) 6.56 (br. s., 2H) 6.94 (br. s., 1H) 7.28 (d, J=7.07 Hz, 2H) 7.31-7.37 (m, 2H) 7.51 (br. s., 1H) 8.50 (t, J=5.94 Hz, 1H)

Intermediate 424

1,1-dimethylethyl methyl[(3R,5R)-5-methyl-3-piperidinyl]carbamate

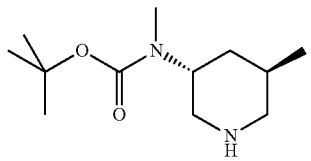 [SMILES: C[C@H]1CNC[C@H](N(C)C(=O)OC(C)(C)C)C1]

Into a Parr shaker jar was added Pd/C Deguessa type (0.922 g, 0.433 mmol) followed by a solution of 1,1-dimethylethyl methyl[(3R,5R)-5-methyl-1-(phenylmethyl)-3-piperidinyl] carbamate (1.38 g, 4.33 mmol) in Ethanol (20 mL). The Parr shaker jar was then placed on to the Parr Shaker machine and flushed the jar with N₂ then pressurized the jar with hydrogen to 30 psi. The reaction was let shake at room temperature overnight. The reaction was filtered and concentrated to isolate 860 mg of crude product as a clear oil, which was used without purification. LC-MS (ES) m/z=229 [M+H]⁺.

Intermediate 425

1,1-dimethylethyl[(3R,5R)-1-(2-amino-6-chloro-4-pyrimidinyl)-5-methyl-3-piperidinyl]methylcarbamate

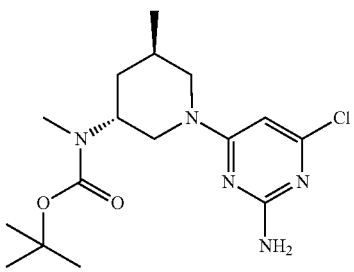 [SMILES: C[C@@H]1C[C@@H](N(C)C(=O)OC(C)(C)C)CN(c2cc(Cl)nc(N)n2)C1]

In to a 20 mL sealable vial was added 1,1-dimethylethyl methyl[(3R,5R)-5-methyl-3-piperidinyl]carbamate (443 mg, 1.940 mmol), 4,6-dichloro-2-pyrimidinamine (477 mg, 2.91 mmol), triethylamine (0.541 mL, 3.88 mmol) and Ethanol (10 mL) then capped. The mixture was then heated at 100° C. overnight. Upon heating the solid dissolved into solution. The reaction was concentrated then loaded on to 25 g Biotage SNAP column with gradient of 0 to 55% with EtOAc in Hexane. The fractions with the desired product were combined to isolated 678 mg of the desired product as a white solid. LC-MS (ES) m/z=356 [M+H]⁺.

Example 229

1,1-dimethylethyl{(3R,5R)-1-[2-amino-6-(3-methyl-1H-indazol-6-yl)-4-pyrimidinyl]-5-methyl-3-piperidinyl}methylcarbamate

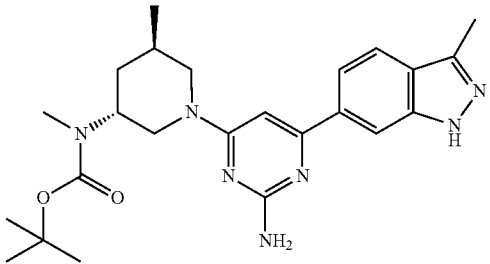 [SMILES: Cc1n[nH]c2cc(-c3cc(N4C[C@H](C)C[C@@H](N(C)C(=O)OC(C)(C)C)C4)nc(N)n3)ccc12]

Into a 5 mL sealable vial was added 1,1-dimethylethyl [(3R,5R)-1-(2-amino-6-chloro-4-pyrimidinyl)-5-methyl-3-piperidinyl]methylcarbamate (105 mg, 0.295 mmol), 3-methyl-6-(4,4,5,5-tetramethyl-1,3,2-dioxaborolan-2-yl)-1H-indazole (152 mg, 0.590 mmol), 1,4-Dioxane (2 mL) and saturated NaHCO₃ (1 mL). The mixture was then bubbled N₂ for 10 minutes then Pd(Ph₃P)₄ (34.1 mg, 0.030 mmol) was added and the mixture was bubbled for an additional 5 minutes. The mixture was then capped and heated at 100° C. overnight. The reaction was added water (5 mL) then extracted with EtOAc (3×10 ml). The organic was combined then dried over MgSO₄, filtered, conc. then dissolved in 2 mL of DMSO and purified on HPLC (HPLC condition: open-access Gilson using Trilution software with a Sunfire 5u C18(2) 100A. 50×30.00 mm 5 micron. 7.3-minute run (47 ml/min, 25% ACN/H₂O, 0.1% TFA to 50% ACN/H₂O, 0.1% TFA) with UV detection at 254 nm). Product fractions were pooled and the volume was reduced to remove most of the MeCN. The water left behind was added saturated NaHCO₃. It was then extracted with EtOAc (3×15 mL). The organic was combined and washed with saturated NaCl, dried over MgSO₄, filter and concentrated. Then transferred sample to a 40 mL vial with MeCN then water was added and freeze-dried to isolated 92 mg of an off white solid. LC-MS (ES) m/z=452 [M+H]+. ¹H NMR (400 MHz, DMSO-d₆) d ppm 0.97 (d, J=7.07 Hz, 3H) 1.41 (s, 9H) 1.46-1.55 (m, 1H) 1.88-1.98 (m, 1H) 2.09-2.18 (m, 1H) 2.51 (s, 3H) 2.76 (s, 3H) 3.09 (t, J=11.37 Hz, 1H) 3.18 (dd, J=12.88, 2.78 Hz, 1H) 3.94-4.13 (m, 2H) 4.37 (br. s., 1H) 6.14 (br. s., 2H) 6.65 (s, 1H) 7.67-7.80 (m, 2H) 8.15 (s, 1H) 12.77 (s, 1H)

Intermediate 426

1,1-dimethylethyl{(3R,5R)-1-[6-chloro-2-(methylamino)-4-pyrimidinyl]-5-methyl-3-piperidinyl}methylcarbamate

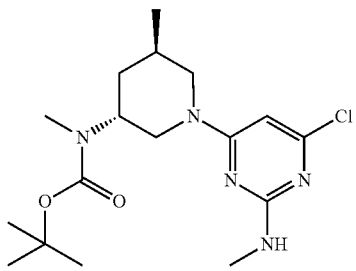 [SMILES: CNc1nc(Cl)cc(N2C[C@H](C)C[C@@H](N(C)C(=O)OC(C)(C)C)C2)n1]

In to a 20 mL sealable vial was added 1,1-dimethylethyl methyl[(3R,5R)-5-methyl-3-piperidinyl]carbamate (420 mg, 1.839 mmol), 4,6-dichloro-N-methyl-2-pyrimidinamine (491 mg, 2.76 mmol), triethylamine (0.513 mL, 3.68 mmol) and Ethanol (10 mL) then capped. The mixture was then heated at 100° C. overnight. Upon heating the solid dissolved into solution. The reaction was concentrated then loaded on to 25 g Biotage SNAP column with gradient of 0 to 45% with EtOAc in Hexane. The fractions with the desired product were combined to isolated 604 mg of a white solid. LC-MS (ES) m/z=370 [M+H]+.

Example 230

1,1-dimethylethyl methyl{(3R,5R)-5-methyl-1-[2-(methylamino)-6-(3-methyl-1H-indazol-6-yl)-4-pyrimidinyl]-3-piperidinyl}carbamate

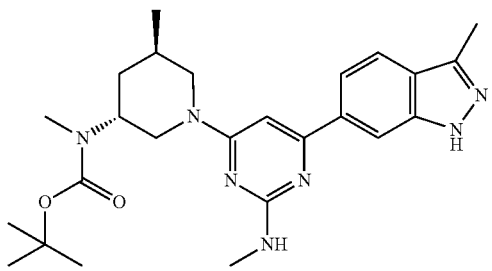 [SMILES: CNc1nc(-c2ccc3c(C)n[nH]c3c2)cc(N2C[C@H](C)C[C@@H](N(C)C(=O)OC(C)(C)C)C2)n1]

Into a 5 mL sealable vial was added 1,1-dimethylethyl{(3R,5R)-1-[6-chloro-2-(methylamino)-4-pyrimidinyl]-5-methyl-3-piperidinyl}methylcarbamate (113 mg, 0.305 mmol), 3-methyl-6-(4,4,5,5-tetramethyl-1,3,2-dioxaborolan-2-yl)-1H-indazole (158 mg, 0.611 mmol), 1,4-Dioxane (2 mL) and saturated NaHCO₃ (1 mL). The mixture was then bubbled N₂ for 10 minutes then Pd(Ph₃P)₄ (35.3 mg, 0.031 mmol) was added and the mixture was bubbled for an additional 5 minutes. The mixture was then capped and heated at 100° C. overnight. The reaction was concentrated then dissolved in 2 mL of DMSO and then purified on HPLC: (HPLC condition: open-access Gilson using Trilution software with a Sunfire 5u C18(2) 100A. 50×30.00 mm 5 micron. 7.3-minute run (47 ml/min, 20% ACN/H₂O, 0.1% TFA to 40% ACN/H₂O, 0.1% TFA) with UV detection at 254 nm). Product fractions were combined and the volume was reduced to remove most of the MeCN. The water left behind was added saturated NaHCO₃ and then extracted with EtOAc (3×15 mL). The organic was combined wash with saturated NaCl solution, dried over MgSO₄, filtered and concentrated. Then transferred into a 40 mL vial with MeCN then added water and freeze-dried to isolated 52 mg of pinkish white solid. LC-MS (ES) m/z=466 [M+H]+. ¹H NMR (400 MHz, DMSO-d₆) d ppm 0.97 (d, J=6.82 Hz, 3H) 1.40 (s, 9H) 1.47-1.57 (m, 1H) 1.90-2.01 (m, 1H) 2.10-2.18 (m, 1H) 2.50 (d, J=2.02 Hz, 3H) 2.76 (s, 3H) 2.84 (d, J=4.29 Hz, 3H) 3.08-3.23 (m, 2H) 3.98-4.12 (m, 2H) 4.36 (br. s., 1H) 6.55 (br. s., 1H) 6.65 (s, 1H) 7.70-7.75 (m, 1H) 7.75-7.81 (m, 1H) 8.18 (br. s., 1H) 12.76 (s, 1H)

Intermediate 427

1,1-dimethylethyl{(3R,5R)-1-[2-amino-6-(4-cyano-3,5-difluorophenyl)-4-pyrimidinyl]-5-methyl-3-piperidinyl}methylcarbamate

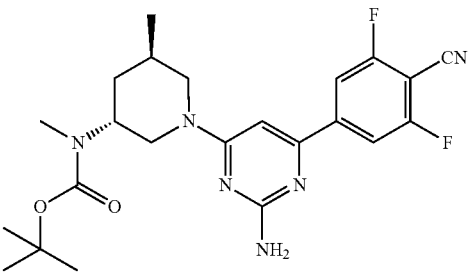 [SMILES: C[C@@H]1C[C@@H](N(C)C(=O)OC(C)(C)C)CN(c2cc(-c3cc(F)c(C#N)c(F)c3)nc(N)n2)C1]

Into a 5 mL sealable vial was added 1,1-dimethylethyl [(3R,5R)-1-(2-amino-6-chloro-4-pyrimidinyl)-5-methyl-3-piperidinyl]methylcarbamate (105 mg, 0.295 mmol), (4-cyano-3,5-difluorophenyl)boronic acid (108 mg, 0.590 mmol), 1,4-Dioxane (2 mL) and saturated NaHCO₃ (1 mL). The mixture was then bubbled N₂ for 10 minutes then Pd(Ph₃P)₄ (34.1 mg, 0.030 mmol) was added and the mixture was bubbled for an additional 5 minutes. The mixture was then capped and heated at 100° C. overnight. The reaction was added water (5 mL) then extracted with EtOAc (3×10 ml). The organic was combined then dried over MgSO₄, filtered, concentrated then loaded into a 10 g Biotage SNAP column with 0 to 50% gradient of EtOAc in Hexane over 30 minutes to isolated 106 mg of a yellow oil. LC-MS (ES) m/z=459 [M+H]+.

Example 231

1,1-dimethylethyl{(3R,5R)-1-[2-amino-6-(3-amino-4-fluoro-1H-indazol-6-yl)-4-pyrimidinyl]-5-methyl-3-piperidinyl}methylcarbamate

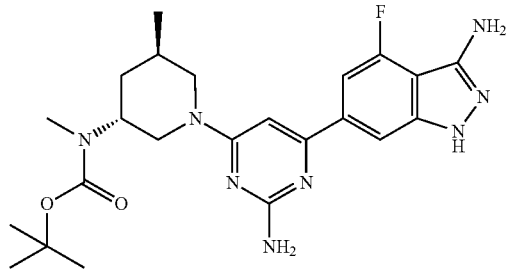 [SMILES: C[C@@H]1C[C@@H](N(C)C(=O)OC(C)(C)C)CN(c2cc(-c3cc(F)c4c(N)n[nH]c4c3)nc(N)n2)C1]

1,1-dimethylethyl{(3R,5R)-1-[2-amino-6-(4-cyano-3,5-difluorophenyl)-4-pyrimidinyl]-5-methyl-3-piperidinyl}methylcarbamate (106 mg, 0.231 mmol) was dissolved in Ethanol (3 mL) in a 5 mL sealable vial then added hydrazine monohydrate (0.340 mL, 6.94 mmol). The solution was then capped and heat at 100° C. overnight. The reaction was concentrated then dissolved in 2 mL of DMSO and then purified on HPLC: (HPLC condition: open-access Gilson using Trilution software with a Sunfire 5u C18(2) 100A. 50×30.00 mm 5 micron. 7.3-minute run (47 ml/min, 20% ACN/H$_2$O, 0.1% TFA to 40% ACN/H$_2$O, 0.1% TFA) with UV detection at 254 nm). Product fractions were combined and the volume was reduced to remove most of the MeCN. The water left behind was added saturated NaHCO$_3$ and then extracted with EtOAc (3×15 mL). The organics were combined and washed with saturated NaCl solution, dried over MgSO$_4$, filtered and concentrated. Then transferred into a 40 mL vial with MeCN then added water and freeze-dried to isolated 89 mg of an off white solid. LC-MS (ES) m/z=471 [M+H]+. $^1$H NMR (400 MHz, DMSO-d$_6$) dppm 0.96 (d, J=7.07 Hz, 3H) 1.41 (s, 9H) 1.50 (d, J=12.13 Hz, 1H) 1.88-1.97 (m, 1H) 2.08-2.17 (m, 1H) 2.76 (s, 3H) 3.04-3.13 (m, 1H) 3.17 (dd, J=13.01, 2.91 Hz, 1H) 3.96-4.10 (m, 2H) 4.36 (br. s., 1H) 5.26 (s, 2H) 6.12 (br. s., 2H) 6.64 (s, 1H) 7.35 (d, J=12.38 Hz, 1H) 7.82 (s, 1H) 11.90 (s, 1H).

Example 232

Capsule Composition

An oral dosage form for administering the present invention is produced by filing a standard two piece hard gelatin capsule with the ingredients in the proportions shown in Table I, below.

TABLE I

| INGREDIENTS | AMOUNTS |
| --- | --- |
| 6-(3-Amino-1H-indazol-6-yl)-N$^4$-phenyl-2,4-pyrimidinediamine (Compound of Example 1) | 7 mg |
| Lactose | 53 mg |
| Talc | 16 mg |
| Magnesium Stearate | 4 mg |

Example 233

Injectable Parenteral Composition

An injectable form for administering the present invention is produced by stirring 1.5% by weight of 6-[2-Amino-6-(4-thiomorpholinyl)-4-pyrimidinyl]-1H-indazol-3-amine (Compound of Example 4) in 10% by volume propylene glycol in water.

Example 234

Tablet Composition

The sucrose, calcium sulfate dihydrate and a PDK1 inhibitor as shown in Table II below, are mixed and granulated in the proportions shown with a 10% gelatin solution. The wet granules are screened, dried, mixed with the starch, talc and stearic acid; screened and compressed into a tablet.

TABLE II

| INGREDIENTS | AMOUNTS |
| --- | --- |
| 6-[2-Amino-6-(4-morpholinyl)-4-pyrimidinyl]-1H-indazol-3-amine (Compound of Example 6) | 12 mg |
| calcium sulfate dihydrate | 30 mg |
| sucrose | 4 mg |
| starch | 2 mg |
| talc | 1 mg |
| stearic acid | 0.5 mg |

Biological Activity

Substrate phosphorylation assays are carried out as follows:

The Source of Substrate Protein

Biotinylated-hAKT1: Human AKT1 (containing amino acid residues 136-480, as annotated by National Center for Biotechnology Information (NCBI) accession number AAL55732.1, with a MetLysLysHis$_6$ N-terminal addition) is purified to >90% from lysate of baculovirus expression by Nickel Chelating ProBond resin (InVitrogen), Q-Sepharose Fast Flow, and Superdex 200 size exclusion chromatography. Biotinylation is achieved using EZ-Link Sulfo-NHS-LC Biotin (Pierce). Samples, in 25 mM HEPES, pH 7.5, 200 mM NaCl, 2 mM DTT, and 30% glycerol are stored at −80C until use.

The Source of Enzyme:
PDK1:

Full-length human 3-Phosphoinositide Dependent protein Kinase-1 (hPDK1; National Center for Biotechnology Information (NCBI) accession number AAH39158.1 with a Met-GlyHis$_6$ N-terminal addition) is purified from baculovirus expression in Sf9 cells. Purity of approximately 80% is achieved by the use of chelation chromatography (Ni-NTA Superflow) and desalting columns. Samples, in 25 mM HEPES, 150 mM NaCl, 2.5 mM DTT, 0.05% Triton, 30% glycerol, pH 8.0, are stored at −80° C. until use.

The Source of Substrate Peptide:
Biotinylated-PDKtide:

The 39 amino acid biotinylated-PDKtide peptide Seq. ID No. 1: (Biotin-Ahx-KTFCGTPEYLAPEVRREPRILSEE-EQEMFRDFDYIADWC) was custom synthesized by 21$^{st}$ Century Biochemicals. The peptide was >95% pure and dissolved in HPLC grade water to give a final concentration of 1.1 mM. The concentration was confirmed by quantitative amino acid analysis.

Scintillation Proximity (LEADseeker) Kinase Assay of Purified hPDK1:

Assays are performed in 384-well microtiter plates (Greiner, Catalog No. 784075). The reaction volume (10 µl) contains, in final concentrations, 25 mM MOPS (pH 7.5), 10 mM MgCl2, 50 mM KCl, 0.1 mg/ml BSA, 1 μM ATP, 3 uCi/ml $^{33}$PγATP, 5 mM DTT, 1 mM CHAPS or 0.05% Tween20, 0.35 μM AKT1 biotinylated protein, and 10 nM hPDK1.

Compounds, titrated in DMSO, are evaluated at eleven concentrations ranging from 50 μM to 2 μM. Final assay concentrations of DMSO do not exceed 1%. No effect on activity relative to controls without DMSO is observed for hPDK1 at these DMSO amounts. hPDK1 is pre-incubated, 30 minutes at room temperature, with compounds before initiating phosphorylation of AKT1 by addition of substrate to hPDK1/compound. Reactions are stopped after 3 hours at room temperature by the addition of 50 mM EDTA, 5 mg/ml LEADseeker beads (GE Healthcare) in PBS (10 ul). Beads are allowed to settle overnight, and samples are imaged on Viewlux (PerkinElmer).

The data for compound concentration responses were plotted as % Inhibition, calculated with the data reduction formula $100*(1-[(U1-C2)/(C1-C2)])$, versus concentration of compound, where U is the unknown value, C1 is the average control value obtained for DMSO only, and C2 is the average control value obtained for reactions stopped with EDTA at t=0.

Data were fitted to the curve described by:

$y=((Vmax*x)/(K+x))$ where

Vmax is the upper asymptote and

K is the 1050.

The results for each compound were recorded as pIC50 calculated as follows:

pIC50=−Log 10(K).

TR-FRET Kinase Assay of Purified hPDK1:

Assays are performed in 384-well microtiter plates (Greiner, Catalog No. 784076). The reaction volume (10 μl) contains, in final concentrations, 25 mM MOPS (pH 7.5), 10 mM MgCl$_2$, 50 mM KCl, 0.1 mg/ml BSA, 5 μM ATP, 5 mM DTT, 1 mM CHAPS, 0.35 μM AKT1 biotinylated protein, and 0.6-0.9 nM hPDK1.

As previously described for the Scintillation Proximity protocol, hPDK1 is pre-incubated (30 minutes at room temperature) with compounds before initiating phosphorylation of AKT1 by addition of substrate to the hPDK1 and compound mix. Reactions are stopped after 4-6 hours at room temperature by the addition to final concentrations of 0.02 M EDTA, 0.0875 μM Streptavidin APC (PerkinElmer), 0.03 μM AKT1 (phospho T308) antibody (Abcam Inc.), 0.00375 μM Lance Eu-labeled anti rabbit IgG Antibody (PerkinElmer). Antibody binding reaches equilibrium in 30 minutes before signal is read on an EnVision™ 2103 Multilabel Reader (PerkinElmer). APC Signals are normalized to Europium signal. Data processing is the same as described for the Scintillation Proximity assay with the exception of the generation of the "C2" control by addition of buffer without hPDK1 to control wells at t=0 instead of EDTA.

Scintillation Proximity (LEADseeker) Kinase Assay of Purified hPDK1 using Biotinylated-PDKtide Peptide:

Assays are performed in 384-well microtiter plates (Greiner, Catalog No. 784075). The reaction volume (10 μl) contains, in final concentrations, 25 mM MOPS (pH 7.5), 10 mM MgCl2, 50 mM KCl, 0.1 mg/ml BSA, 1 μM ATP, 3 uCi/ml $^{33}$PγATP, 5 mM DTT, 0.5 mM CHAPS, 1 μM biotinylated-PDKtide peptide, and 0.5 nM hPDK1.

Compounds, titrated in DMSO, are evaluated at eleven concentrations ranging from 25 μM to 0.4 pM. Final assay concentrations of DMSO do not exceed 1%. No effect on activity relative to controls without DMSO is observed for hPDK1 at these DMSO amounts. hPDK1 is pre-incubated, 30 minutes at room temperature, with compounds before initiating phosphorylation of biotinylated-PDKtide peptide by addition of substrate to hPDK1/compound. Reactions are stopped after 4 hours at room temperature by the addition of 50 mM EDTA, 5 mg/ml LEADseeker beads (GE Healthcare) in PBS (10 ul). Beads are allowed to settle overnight, and samples are imaged on Viewlux (PerkinElmer).

The data for compound concentration responses were plotted as % Inhibition, calculated with the data reduction formula $100*(1-[(U1-C2)/(C1-C2)])$, versus concentration of compound, where U is the unknown value, C1 is the average control value obtained for DMSO only, and C2 is the average control value obtained for reactions stopped with EDTA at t=0.

Data were fitted to the curve described by:

$y=((Vmax*x)/(K+x))$ where

Vmax is the upper asymptote and

K is the IC50.

The results for each compound were recorded as pIC50 calculated as follows:

pIC50=−Log 10(K).

Abbreviations Used:

Ahx, aminohexanoic acid

APC, Allophycocyanin

ATP, adenosine triphosphate

BSA, bovine serum albumin

CHAPS, 3-[3-Cholamidopropyl)Dimethylammonio]-1-Propanesulfonate

DMSO, dimethyl sulfoxide

DTT, Dithiothreitol

EDTA, ethylenediaminetetraacetic acid

Eu, Europium

HEPES, N-(2-Hydroxyethyl)piperazine-N'-2-ethanesulfonic acid

HPLC, high performance/pressure liquid chromatography

KCl, Potassium chloride

M, molar mg, milligram

MgCl$_2$, magnesium chloride ml, milliliter mM, millimolar

MOPS, 3-morpholinopropanesulfonic acid

NaCl, Sodium chloride

NCBI, National Center for Biotechnology Information nM, nanomolar

PBS, phosphate buffered saline

PDK1, human 3-Phosphoinositide Dependent protein Kinase-1 pM, picomolar

Tris-HCl, Tris(hydroxymethyl)aminomethane hydrochloride

μM, micromolar

Phospho-AKT (S473, T308, Total AKT) and phospho-RSK ELISA

PC3 cells (ATCC, Manassas, Va.) were plated in 96-well flat bottom plates (Corning, Lowell, Mass.) at a density of 15,000 cells/well in RPMI 1640 medium supplemented with 10% FBS. Cells were incubated at 37° C., 5% CO$_2$ for 18-20 h. Compounds (dissolved in 100% DMSO) were diluted in an 11-point 3-fold dilution in DMSO. Compound dilution stocks were further diluted in RPMI 1640 with 10% FBS and added to each cell well. DMSO without compound was used in control wells. Final concentration of DMSO in each well was 0.15%. After 6 hours at 37° C. cells were washed with cold PBS (without calcium or magnesium) and lysed in lysis buffer (Meso Scale Discovery, Gaithersburg, Md.) supplemented with 1 protease inhibitor tablet/10 ml (Roche, Indianapolis, Ind.), 10 mM NaF, and 200 µl/10 ml Sigma phosphatase inhibitor 1 & 2 (Sigma Aldrich, St Louis, Mo.) for 30 min at 4° C. All washes were performed on a Bio Tek ELx405 plate washer (Bio Tek Instruments, Winooski, Vt.).

ELISA plates (Meso Scale Discovery; AKT Duplex, cat. N41100B-1; phospho AKT, cat. N411CAB-1; RSK, cat. N41ZB-1) were prepared by the addition of blocking buffer (3% Blocker A diluted in wash buffer (Meso Scale Discovery) for AKT duplex assay and phospho AKT assays; 5% Blocker A/1% Blocker B in Tris-buffered saline for RSK) for 1 hour and washed with wash buffer. Lysates were transferred to assay wells and incubated overnight at 4° C. Following washing with wash buffer, detection buffer (1% Blocker A in wash buffer for AKT duplex and phospho AKT or 1% Blocker A in TBS for RSK) with appropriate antibodies was added. Detection of AKT duplex and phospho AKT was carried out using a sulfo-tagged detection antibodies (Meso Scale Discovery). Detection of phospho-RSK was carried out sequentially with anti phospho-RSK1 (S221)/RSK2 (S227) (R&D systems, Minneapolis, Minn., cat. AF892) and goat anti-rabbit sulfo-tag antibody (cat R32AB-1; Meso Scale Discovery). Plates were incubated for 1 hour at room temperature and washed with wash buffer. Plates were read on a SECTOR™ Imager 6000 (Meso Scale Discovery) using Workbench software (Meso Scale Discovery) following addition of read buffer (Meso Scale Discovery) to each well. For analysis, phospho-AKT (S473) signals were normalized to total AKT, while phospho-AKT (T308) and phospho-RSK signals were analyzed without normalization. All values were expressed as percent of the DMSO-treated controls. $IC_{50}$s were determined from inhibition curves using XLfit4 software (IDBS, Guildford, UK).

Cell Proliferation Assays

Cells were plated at 5000 cells/well in complete growth medium in white, top-read capable, 96 well plates (Thermo-Fisher, Waltham, Mass.), and allowed to adhere overnight in an humidified incubator at 37° C. supplemented with 5% $CO_2$. Duplicate plates were used for each cell line. Compounds were diluted in dimethylsulfoxide (DMSO) and added directly to each well to yield a final compound concentration range of 10 pM to 30 µM in a 3-fold dilution series. The final concentration of DMSO was 0.3% per well. Cells were then returned to the incubator for 72 h. Cell Titer Glo reagent (Promega, Madison, Wis.) was added to each well and the plates rocked gently for 2 min. The chemiluminescent signal was allowed to develop at room temperature for 10 minutes following which luminescence was measured using in an Envision plate reader (Wallac/Perkin Elmer, Waltham, Mass.). Cell growth was expressed as a percentage of the cells in the DMSO control wells, and $IC_{50}$ for each compound was determined from the inhibition curves using the XLfit4 software (IDBS, Guildford, UK).

Compounds of the invention are tested for activity against PDK1 in one or more of the above assays.

The compounds of Examples 1 to 229 were tested generally according to the above PDK1 enzyme assays and in at least one experimental run exhibited an $IC_{50}$ value≤1.0 uM against full length PDK1.

The compounds of examples 14, 46, 71, 75, 177, 181, 184, 199 and 200 were tested generally according to the above PDK1 enzyme assays and in at least one experimental run exhibited an $IC_{50}$<150 nM against full length PDK1. In at least one experimental run Example 177 exhibited an $IC_{50}$ value equal to 25 nM against full length PDK1 using the PDKtide substrate assay.

The compounds of examples 2, 10, 38, 51, 61 and 74 were tested generally according to the above PDK1 enzyme assays and in at least one experimental run exhibited an $IC_{50}$<100 nM against full length PDK1. In at least one experimental run Example 61 exhibited an $IC_{50}$ value equal to 10 nM against full length PDK1 using the PDKtide substrate assay.

The compounds of examples 111, 120, 154, 203, 209, 211, 212, 214, 217 and 221 were tested generally according to the above PDK1 enzyme assays and in at least one experimental run exhibited an $IC_{50}$<50 nM against full length PDK1. In at least one experimental run Example 214 exhibited an $IC_{50}$ value equal to 2.0 nM against full length PDK1 using the PDKtide substrate assay.

The compounds of examples 67, 78, 80, 83, 85, 142, 149, 161 and 173 were tested generally according to the above PDK1 enzyme assays and in at least one experimental run exhibited an $IC_{50}$<20 nM against full length PDK1. In at least one experimental run Example 173 exhibited an $IC_{50}$ value equal to 7.9 nM against full length PDK1 using the PDKtide substrate assay.

Of Examples 1 to 229, 146 were generally tested in at least one experimental run for inhibition of AKT phosphorylation at T308 in PC-3 cells as described above. Of the 146 examples tested, 86 compounds exhibited an $IC_{50}$<5 uM. In at least one experimental run Examples 49, 67, 77, 78, 81, 83, 86, 121, 150, 161, 176, 212 and 221 exhibited an $IC_{50}$ value<1.0 uM.

While the preferred embodiments of the invention are illustrated by the above, it is to be understood that the invention is not limited to the precise instructions herein disclosed and that the right to all modifications coming within the scope of the following claims is reserved.

What is claimed is:

1. A compound according to Formula I:

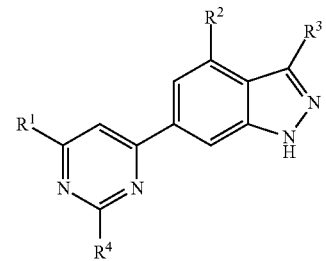

(I)

wherein:

$R^1$ is selected from: hydrogen, $C_1$-$C_6$alkyl, $C_3$-$C_7$cycloalkyl, $C_3$-$C_7$cycloalkyl substituted with from one to three $R^8$, $C_1$-$C_6$alkoxy, $C_1$-$C_6$mercapto, —N($R^5$)($R^6$), aryl, aryl substituted with from one to three $R^8$, heteroaryl, heteroaryl substituted with from one to three $R^8$, heterocycloalkyl and heterocycloalkyl substituted with from one to three $R^8$, where, $R^5$ is hydrogen or $C_1$-$C_3$alkyl, $R^6$ is selected from: hydrogen, aryl, aryl substituted with from one to three $R^7$, $C_3$-$C_7$cycloalkyl, $C_3$-$C_7$cycloalkyl substituted with from one to three $R^8$, $C_1$-$C_6$alkyl and $C_1$-$C_6$alkyl substituted with one $R^9$, where, $R^9$ is selected from: phenyl, phenyl substituted with from one to three $R^7$, heteroaryl, heteroaryl substituted with one to three $R^7$, $C_3$-$C_7$ cycloalkyl, $C_3$-$C_7$ cycloalkyl substituted with one or three $R^8$;

$R^2$ is selected from: hydrogen, halo, —N($R^{10}$)—($CH_2$)$_n$—$R^{11}$, —O—($CH_2$)$_n$—$R^{11}$, —S—($CH_2$)$_n$—$R^{11}$; aryl, aryl substituted with from one to three $R^7$, heteroaryl, heteroaryl substituted with from one to three $R^7$,
  $C_3$-$C_7$cycloalkyl, $C_3$-$C_7$cycloalkyl substituted with from one to three $R^7$, heterocycloalkyl, and heterocycloalkyl substituted with from one to three $R^7$, where,
  $R^{10}$ is hydrogen or $C_1$-$C_3$ alkyl,
  $R^{11}$ is selected from: hydrogen, $C_1$-$C_3$alkyl, $C_1$-$C_3$alkyl substituted with from one to three $R^7$, $C_3$-$C_7$cycloalkyl, $C_3$-$C_7$cycloalkyl substituted with from one to three $R^7$, aryl, aryl substituted with from one to three $R^7$, heteroaryl, heteroaryl substituted with one to three $R^7$, —O—$C_3$-$C_7$cycloalkyl, —O—$C_3$-$C_7$cycloalkyl substituted with from one to three $R^7$, —O-aryl, —O-aryl substituted with from one to three $R^7$,
    —O-heteroaryl and —O-heteroaryl substituted with one to three $R^7$, and
    n is 0, 1, 2, or 3
      provided that when $R^{11}$ is —O—$C_3$-$C_7$cycloalkyl, —O-aryl or —O-heteroaryl,
      n is not 0;
$R^3$ is selected from: hydrogen, —$NH_2$, $C_1$-$C_3$alkyl, and $C_3$-$C_7$cycloalkyl; and
$R^4$ is selected from: hydrogen, $NH_2$ and $NHC_1$-$C_3$alkyl; where,
each $R^8$ is independently selected from: hydroxy, $C_1$-$C_6$alkyl, $C_1$-$C_6$alkyl substituted with from one to three $R^7$, —C(O)$C_1$-$C_6$alkyl, $C_3$-$C_7$cycloalkyl, $C_1$-$C_6$alkoxy, amino, $C_1$-$C_4$alkylamino, di$C_1$-$C_4$alkylamino, —$C_1$-$C_4$alkylNR$^{200}$R$^{201}$, aryl, aryl substituted with from one to three $R^7$, —$C_1$-$C_4$alkylaryl, —$C_1$-$C_4$alkylaryl substituted with from one to three $R^7$, phenylheteroaryl, phenylheteroaryl substituted with from one to three $R^7$, heterocycloalkyl, heterocycloalkyl substituted with from one to three $R^7$, heteroaryl, heteroaryl substituted with from one to three $R^7$, nitro, cyano, oxo, halo, —CO$_2$R$^{120}$, —C(O)NR$^{200}$R$^{201}$, —$C_1$-$C_4$alkylOC(O)NR$^{200}$R$^{201}$, —OC(O)NR$^{200}$R$^{201}$, —OC(O)R$^{200}$, —NR$^{200}$C(O)OR$^{301}$, —$C_1$-$C_4$alkylNR$^{200}$C(O)OR$^{301}$, —NR$^{200}$C(O)R$^{302}$, —NR$^{200}$S(O)$_2$R$^{302}$, —$C_1$-$C_4$alkylNR$^{200}$C(O)R$^{302}$ and
—$C_1$-$C_4$alkylNR$^{200}$S(O)$_2$R$^{302}$,
where,
  $R^{120}$ is selected form: hydrogen, $C_1$-$C_4$alkyl and $C_3$-$C_7$cycloalkyl,
  $R^{200}$ is hydrogen or $C_1$-$C_3$alkyl,
  $R^{201}$ is selected from: hydrogen, $C_1$-$C_6$alkyl, $C_1$-$C_6$alkyl substituted with from one to three $R^7$, $C_3$-$C_7$cycloalkyl, $C_3$-$C_7$cycloalkyl substituted with from one to three $R^7$, —$C_1$-$C_4$alkyl$C_3$-$C_7$cycloalkyl,
    —$C_1$-$C_4$alkyl$C_3$-$C_7$cycloalkyl substituted with from one to three $R^7$, aryl, aryl substituted with from one to three $R^7$, —$C_1$-$C_4$alkylaryl,
    —$C_1$-$C_4$alkylaryl substituted with from one to three $R^7$, heteroaryl, heteroaryl substituted with from one to three $R^7$,
    —$C_1$-$C_4$alkylheteroaryl, —$C_1$-$C_4$alkylheteroaryl substituted with from one to three $R^7$, heterocycloalkyl, heterocycloalkyl substituted with from one to three $R^7$, —$C_1$-$C_4$alkylheterocycloalkyl,
    —$C_1$-$C_4$alkylheterocycloalkyl substituted with from one to three $R^7$,
  $R^{301}$ is selected from: $C_1$-$C_6$alkyl, $C_1$-$C_6$alkyl substituted with from one to three $R^7$, $C_3$-$C_7$cycloalkyl, $C_3$-$C_7$cycloalkyl substituted with from one to three $R^7$, —$C_1$-$C_4$alkylaryl,
    —$C_1$-$C_4$alkylaryl substituted with from one to three $R^7$, —$C_1$-$C_4$alkyl$C_3$-$C_7$cycloalkyl,
    —$C_1$-$C_4$alkyl$C_3$-$C_7$cycloalkyl substituted with from one to three $R^7$, and
  $R^{302}$ is selected from: hydrogen, $C_1$-$C_6$alkyl, $C_1$-$C_6$alkyl substituted with from one to three $R^7$, $C_3$-$C_7$cycloalkyl, $C_3$-$C_7$cycloalkyl substituted with from one to three $R^7$, —$C_1$-$C_4$alkyl$C_3$-$C_7$cycloalkyl,
    —$C_1$-$C_4$alkyl$C_3$-$C_7$cycloalkyl substituted with from one to three $R^7$, aryl, aryl substituted with from one to three $R^7$, —$C_1$-$C_4$alkylaryl,
    —$C_1$-$C_4$alkylaryl substituted with from one to three $R^7$, heteroaryl, heteroaryl substituted with from one to three $R^7$,
    —$C_1$-$C_4$alkylheteroaryl, —$C_1$-$C_4$alkylheteroaryl substituted with from one to three $R^7$, heterocycloalkyl, heterocycloalkyl substituted with from one to three $R^7$, —$C_1$-$C_4$alkylheterocycloalkyl,
    —$C_1$-$C_4$alkylheterocycloalkyl substituted with from one to three $R^7$; and
each $R^7$ is independently selected from: halo, cyano, hydroxy, amino, $C_1$-$C_4$alkylamino, di$C_1$-$C_4$alkylamino, $C_1$-$C_3$ alkyl and $C_1$-$C_3$ alkoxy;
or a salt thereof including a pharmaceutically acceptable salt thereof.

2. A compound of Formula (I), as described in claim 1, having the following Formula (II):

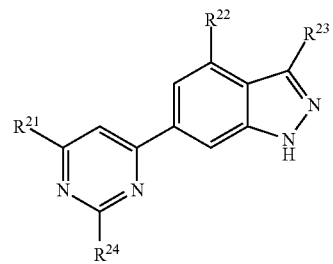

(II)

wherein:
$R^{21}$ is selected from: hydrogen, $C_1$-$C_6$alkyl, $C_3$-$C_7$cycloalkyl, $C_1$-$C_6$alkoxy, $C_1$-$C_6$mercapto, —N($R^{25}$)($R^{26}$), aryl, aryl substituted with from one to three $R^{28}$, heterocycloalkyl and heterocycloalkyl substituted with from one to three $R^{28}$,
where,
  $R^{25}$ is hydrogen or $C_1$-$C_3$alkyl,
  $R^{26}$ is selected from: hydrogen, aryl, aryl substituted with from one to three $R^{27}$, $C_3$-$C_7$cycloalkyl, $C_3$-$C_7$cycloalkyl substituted with from one to three $R^{28}$, $C_1$-$C_6$alkyl and $C_1$-$C_6$alkyl substituted with one $R^{29}$,
  where,
    $R^{29}$ is selected from: phenyl, phenyl substituted with from one to three $R^{27}$ and $C_3$-$C_7$ cycloalkyl;
$R^{22}$ is selected from: hydrogen, hydroxy, halo, —N($R^{30}$)—($CH_2$)$_n$—$R^{31}$, —O—($CH_2$)$_n$—$R^{31}$, —S—($CH_2$)$_n$—$R^{31}$; heteroaryl, heterocycloalkyl, and heterocycloalkyl substituted with from one to three $R^{27}$,
where,
  $R^{30}$ is hydrogen,
  $R^{31}$ is selected from: hydrogen, $C_1$-$C_3$alkyl, $C_1$-$C_3$alkyl substituted with from one to three $R^{27}$, $C_3$-$C_7$cycloalkyl, aryl, aryl substituted with from one to three $R^{27}$, heteroaryl, heteroaryl substituted with one to three $R^{27}$, —O-aryl and —O-aryl substituted with from one to three $R^{27}$, and
n is 0, 1, 2, or 3
provided that when $R^{31}$ is —O-aryl,
n is not 0;
$R^{23}$ is selected from: hydrogen, —$NH_2$ and $C_1$-$C_3$alkyl; and
$R^{24}$ is selected from: hydrogen, $NH_2$ and $NHC_1$-$C_3$alkyl;
where,
each $R^{28}$ is independently selected from: hydroxy, $C_1$-$C_6$alkyl, $C_1$-$C_6$alkyl substituted with from one to three $R^{27}$, $C_3$-$C_7$cycloalkyl, amino, $C_1$-$C_4$alkylamino, $diC_1$-$C_4$alkylamino, —$C_1$-$C_4$alkyl$NR^{500}R^{501}$,
—$C_1$-$C_4$alkylaryl, —$C_1$-$C_4$alkylaryl substituted with from one to three $R^{27}$, phenylheteroaryl, phenylheteroaryl substituted with from one to three $R^{27}$, heterocycloalkyl, heterocycloalkyl substituted with from one to three $R^{27}$, heteroaryl, heteroaryl substituted with from one to three $R^{27}$, nitro, cyano, oxo, halo, —$CO_2R^{420}$, —$C(O)NR^{500}R^{501}$,
—$C_1$-$C_4$alkylOC(O)$NR^{500}R^{501}$, —$OC(O)NR^{500}R^{501}$, —$OC(O)R^{500}$, —$NR^{500}C(O)OR^{601}$, —$C_1$-$C_4$alkyl$NR^{500}C(O)OR^{601}$, —$NR^{500}C(O)R^{602}$, —$NR^{500}S(O)_2R^{602}$, —$C_1$-$C_4$alkyl$NR^{500}C(O)R^{602}$ and —$C_1$-$C_4$alkyl$NR^{500}S(O)_2R^{602}$,
where,
$R^{420}$ is selected form: hydrogen, $C_1$-$C_4$alkyl and $C_3$-$C_7$cycloalkyl,
$R^{500}$ is hydrogen or $C_1$-$C_3$alkyl,
$R^{501}$ is selected from: hydrogen, $C_1$-$C_6$alkyl, $C_3$-$C_7$cycloalkyl, $C_3$-$C_7$cycloalkyl substituted with from one to three $R^{27}$,
—$C_1$-$C_4$alkyl$C_3$-$C_7$cycloalkyl, aryl, aryl substituted with from one to three $R^{27}$, —$C_1$-$C_4$alkylaryl, —$C_1$-$C_4$alkylaryl substituted with from one to three $R^{27}$, heteroaryl, heteroaryl substituted with from one to three $R^{27}$ and
—$C_1$-$C_4$alkylheteroaryl,
$R^{601}$ is selected from: $C_1$-$C_6$alkyl, $C_3$-$C_7$cycloalkyl, and —$C_1$-$C_4$alkylaryl, and
$R^{602}$ is selected from: hydrogen, $C_1$-$C_6$alkyl, $C_1$-$C_6$alkyl substituted with from one to three $R^{27}$, $C_3$-$C_7$cycloalkyl, $C_3$-$C_7$cycloalkyl substituted with from one to three $R^{27}$, —$C_1$-$C_4$alkyl$C_3$-$C_7$cycloalkyl, —$C_1$-$C_4$alkyl$C_3$-$C_7$cycloalkyl substituted with from one to three $R^{27}$, aryl, aryl substituted with from one to three $R^{27}$, —$C_1$-$C_4$alkylaryl, and —$C_1$-$C_4$alkylaryl substituted with from one to three $R^{27}$; and
each $R^{27}$ is independently selected from: halo, cyano, hydroxy, amino, $C_1$-$C_4$alkylamino, $diC_1$-$C_4$alkylamino, $C_1$-$C_3$ alkyl and $C_1$-$C_3$ alkoxy;
or a salt thereof including a pharmaceutically acceptable salt thereof.

3. A compound of Formula (I), as described in claim 1, having the following Formula (III):

(III)

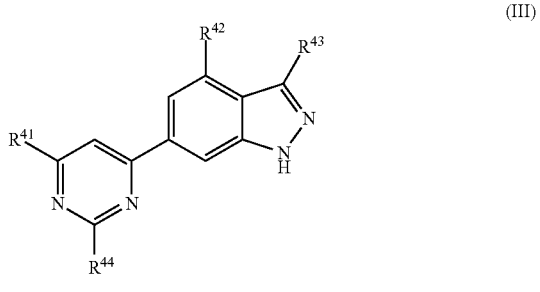

wherein:
$R^{41}$ is selected from the group consisting of:
hydrogen,
methyl,
trifluoromethyl,
ethyl,
propyl,
isopropyl,
tert-butyl,
sec-butyl,
cyclopropyl,
cyclobutyl,
cyclopentyl,
cyclohexyl,
methoxy,
ethoxy,
isopropoxy,
thiomethyl,
thio ethyl,
—$N(R^{55})(R^{56})$, where $R^{55}$ is H and $R^{56}$ are selected from: phenyl, ethyl, propyl, isopropyl, tert-butyl, cyclopropyl, cyclobutyl, cyclopentyl, cyclohexyl, $C_1$-$C_6$ alkyl, and $C_1$-$C_6$alkyl optionally substituted by phenyl or cyclohexyl,
amino,
phenyl,
phenyl substituted with one to three $R^{47}$,
thiazolyl,
thienyl,
furanyl,
pyridyl,
azetidinyl,
pyrrolidinyl,
piperidinyl,
morpholinyl,
thiomorpholinyl,
pyranyl,
hexahydro-1H-azepine, heterocycloalkyl substituted with one to three $R^{48}$, where heterocycloalkyl is selected from: azetidinyl, pyrrolidinyl, piperidinyl, morpholinyl, thiomorpholinyl, pyranyl and hexahydro-1H-azepine;
$R^{42}$ is selected from the group consisting of:
hydrogen,
halo,
furanyl,
—NH—$(CH_2)_n$—$R^{61}$, where $R^{61}$ is selected from: hydrogen, trifluoromethyl, phenyl, phenyl substituted with one to three $R^{47}$, phenoxy, phenoxy substituted with one to three $R^{47}$, heteroaryl and heteroaryl substituted with one to three $R^{47}$, and n is 1, 2, or 3, and
—O—$(CH_2)_n$—$R^{61}$, where $R^{61}$ is selected from: hydrogen, trifluoromethyl, phenyl, phenyl substituted with one to three $R^{47}$, phenoxy, phenoxy substituted with one to three $R^{47}$, heteroaryl and heteroaryl substituted with one to three $R^{47}$, and n is 1, 2, or 3,
$R^{43}$ is selected from: hydrogen, —$NH_2$ and $C_1$-$C_3$alkyl; and
$R^{44}$ is selected from: hydrogen, $NH_2$ and $NHC_1$-$C_3$alkyl;
where,
each $R^{48}$ is independently selected from:
hydroxy,
cyano,
oxo,
fluoro,
chloro,
trifluoromethyl,
$C_1$-$C_4$ alkyl,
$C_3$-$C_7$ cycloalkyl pyrazolyl,
imidazolyl,
azabenzimidazolyl,
benzimidazolyl,
benzimidazolyl substituted with one to three $R^{47}$,
1H-benzimidazol-2-yl,
4,5,6,7-tetrahydro-1H-benzimidazol-2-yl,
5-chloro-1H-benzimidazol-2-yl,
5-fluoro-1H-benzimidazol-2-yl,
5-methyl-1H-benzimidazol-2-yl,
5-methoxy-1H-benzimidazol-2-yl,
1H-imidazo[4,5-c]pyridin-2-yl,
1H-imidazo[4, 5-b]pyridin-2-yl,
4-(1,1-dimethylethyl)-1H-imidazol-2-yl,
4-phenyl-1H-imidazol-2-yl,
4-methyl-5-phenyl-1H-imidazol-2-yl,
4-(2-chlorophenyl)-1H-imidazol-2-yl,
4-(3-chlorophenyl)-1H-imidazol-2-yl,
4-(4-chlorophenyl)-1H-imidazol-2-yl,
4-(3-methoxyphenyl)-1H-imidazol-2-yl,
4-(4-methoxyphenyl)-1H-imidazol-2-yl,
hydroxy$C_1$-$C_4$alkyl,
—C(O)NH$_2$,
—C(O)NHCH$_3$,
—C(O)N(CH$_3$)$_2$,
—C(O)NR$^{800}$R$^{801}$, wherein R$^{800}$ is hydrogen and R$^{801}$ is selected from: ethyl, propyl, isopropyl, butyl, sec-butyl, isopentyl, cyclopentyl, cyclohexyl, 2-methylcyclohexyl, 3-methylcyclohexyl, 4-methylcyclohexyl, 4-ethylcycohexyl, 4-hydroxycyclohexyl, (1R)-1-cyclohexylethyl, phenyl, 4-fluorophenyl, 2-methylphenyl, 3-methylphenyl, 4-methylphenyl, -fluorophenyl, 3-fluorophenyl, 3,4-difluorophenyl, 4-chlorophenyl, 3-chlorophenyl, 3-methoxyphenyl, 4-methoxyphenyl, pyranyl, phenylethyl, benzyl, (1S)-1-phenylethyl, (1R)-1-phenylethyl, 1-methyl-1-phenylethyl, 2-methoxybenzyl, 3-methoxybenzyl, 4-methoxylbenzyl, 2-fluorobenzyl, 3-fluorobenzyl, 4-methylbenzyl, 4-fluorobenzyl, 4-pyridinylmethyl, 1-methyl-1H-pyrazol-5-yl and 1,3-dimethyl-1H-pyrazol-5-yl,
—OC(O)NHR$^{810}$, where R$^{810}$ is selected from: methyl, ethyl, isopropyl, cyclobutyl, tert-butyl, cyclopentyl, cyclohexyl, phenyl and benzyl, and
—NHC(O)OR$^{901}$, where R$^{901}$ is selected from: methyl, .ethyl. isopropyl, cyclobutyl, tert-butyl, cyclopentyl, cyclohexyl and benzyl; and
each $R^{47}$ is independently selected from:
halo,
cyano,
hydroxy,
amino,
$C_1$-$C_4$alkylamino,
di$C_1$-$C_4$alkylamino,
$C_1$-$C_3$ alkyl and
$C_1$-$C_3$ alkoxy;
or a salt thereof including a pharmaceutically acceptable salt thereof.
4. A compound of claim 1 selected from:
6-(3-Amino-1H-indazol-6-yl)-N$^4$-phenyl-2,4-pyrimidinediamine;
6-(3-Amino-1H-indazol-6-yl)-N$^4$-(phenylmethyl)-2,4-pyrimidinediamine;
6-[2-Amino-6-(methylthio)-4-pyrimidinyl]-1H-indazol-3-amine;
6-[2-Amino-6-(4-thiomorpholinyl)-4-pyrimidinyl]-1H-indazol-3-amine;
6-(3-Amino-1H-indazol-6-yl)-2,4-pyrimidinediamine;
6-[2-Amino-6-(4-morpholinyl)-4-pyrimidinyl]-1H-indazol-3-amine;
6-(3-Amino-1H-indazol-6-yl)-N$^4$-ethyl-2,4-pyrimidinediamine;
6-(3-Amino-1H-indazol-6-yl)-N$^4$-(1-methylethyl)-2,4-pyrimidinediamine;
6-[2-Amino-6-(1-piperidinyl)-4-pyrimidinyl]-1H-indazol-3-amine;
6-(3-Amino-1H-indazol-6-yl)-N$^4$-cyclopentyl-2,4-pyrimidinediamine;
6-(3-Amino-1H-indazol-6-yl)-N$^4$-cyclohexyl-2,4-pyrimidinediamine;
6-[2-Amino-6-(1-azetidinyl)-4-pyrimidinyl]-1H-indazol-3-amine;
6-[2-(Methylamino)-6-(1-piperidinyl)-4-pyrimidinyl]-1H-indazol-3-amine;
6-(2-Amino-6-methyl-4-pyrimidinyl)-1H-indazol-3-amine;
6-(2-Amino-6-phenyl-4-pyrimidinyl)-1H-indazol-3-amine;
6-(2-Amino-4-pyrimidinyl)-N$^4$-(2-phenylethyl)-1H-indazole-3,4-diamine;
6-(2-Amino-4-pyrimidinyl)-N$^4$-(3-phenylpropyl)-1H-indazole-3,4-diamine;
6-(2-Amino-4-pyrimidinyl)-N$^4$-[2-(phenyloxy)ethyl]-1H-indazole-3,4-diamine;
6-(2-Amino-4-pyrimidinyl)-N$^4$-[3-(5-methyl-1H-pyrazol-4-yl)propyl]-1H-indazole-3,4-diamine;
2-(3-{[3-Amino-6-(2-amino-4-pyrimidinyl)-1H-indazol-4-yl]amino}propyl)phenol;
6-(2-Amino-4-pyrimidinyl)-N$^4$-[3-(2-fluorophenyl)propyl]-1H-indazole-3,4-diamine;
6-(2-Amino-4-pyrimidinyl)-N$^4$-[3-(4-fluorophenyl)propyl]-1H-indazole-3,4-diamine;
6-(2-Amino-4-pyrimidinyl)-N$^4$-[3-(4-pyridinyl)propyl]-1H-indazole-3,4-diamine;
6-(2-Amino-4-pyrimidinyl)-N$^4$-[3-(3,5-dimethyl-1H-pyrazol-4-yl)propyl]-1H-indazole-3,4-diamine;
6-(2-Amino-4-pyrimidinyl)-N$^4$-[3-(phenyloxy)propyl]-1H-indazole-3,4-diamine;
6-(2-Amino-4-pyrimidinyl)-N$^4$-[3-(3-fluorophenyl)propyl]-1H-indazole-3,4-diamine;
6-(2-Amino-4-pyrimidinyl)-4-(methyloxy)-1H-indazol-3-amine;
6-(2-Amino-4-pyrimidinyl)-4-[(3-phenylpropyl)oxy]-1H-indazol-3-amine;
6-(2-Amino-4-pyrimidinyl)-4-{[3-(phenyloxy)propyl]oxy}-1H-indazol-3-amine;
6-(2-Amino-4-pyrimidinyl)-4-(ethyloxy)-1H-indazol-3-amine;
6-(2-Amino-4-pyrimidinyl)-4-[(2,2,2-trifluoroethyl)oxy]-1H-indazol-3-amine;
6-[2-Amino-6-(4-morpholinyl)-4-pyrimidinyl]-N$^4$-(2-phenylethyl)-1H-indazole-3,4-diamine;
6-[2-Amino-6-(4-morpholinyl)-4-pyrimidinyl]-4-(methyloxy)-1H-indazol-3-amine;
6-[2-Amino-6-(dimethylamino)-4-pyrimidinyl]-N$^4$-(2-phenylethyl)-1H-indazole-3,4-diamine;
6-[3-Amino-4-(methyloxy)-1H-indazol-6-yl]-N$^4$-ethyl-2,4-pyrimidinediamine;
6-(2-Amino-6-methyl-4-pyrimidinyl)-N$^4$-(3-phenylpropyl)-1H-indazole-3,4-diamine;
6-(2-amino-6-methyl-4-pyrimidinyl)-N$^4$-(2-phenylethyl)-1H-indazole-3,4-diamine;
6-(3-Amino-1H-indazol-6-yl)-N$^4$-(cyclohexylmethyl)-2,4-pyrimidinediamine;

6-{2-Amino-6-[2-(methyloxy)phenyl]-4-pyrimidinyl}-1H-indazol-3-amine;
6-{2-Amino-6-[2-(phenylmethyl)-1-pyrrolidinyl]-4-pyrimidinyl}-1H-indazol-3-amine;
6-{2-Amino-6-[2-(1-methylethyl)-1-pyrrolidinyl]-4-pyrimidinyl}-1H-indazol-3-amine;
6-[2-Amino-6-(2-methyl-1-pyrrolidinyl)-4-pyrimidinyl]-1H-indazol-3-amine;
6-(3-Amino-1H-indazol-6-yl)-$N^4$-(2-phenylethyl)-2,4-pyrimidinediamine'
6-[2-Amino-6-(hexahydro-1H-azepin-1-yl)-4-pyrimidinyl]-1H-indazol-3-amine;
6-[2-Amino-6-(methyloxy)-4-pyrimidinyl]-1H-indazol-3-amine;
6-{2-Amino-6-[(2R)-2-ethyl-1-pyrrolidinyl]-4-pyrimidinyl}-1H-indazol-3-amine;
6-[2-Amino-6-(2-cyclopropyl-1-pyrrolidinyl)-4-pyrimidinyl]-1H-indazol-3-amine;
Cis-1-[2-Amino-6-(3-amino-1H-indazol-6-yl)-4-pyrimidinyl]-N-cyclohexyl-6-(trifluoromethyl)-3-piperidinecarboxamide;
Cis-1-[6-(3-Amino-1H-indazol-6-yl)-2-(methylamino)-4-pyrimidinyl]-N-cyclohexyl-6-(trifluoromethyl)-3-piperidinecarboxamide;
6-(3-Amino-1H-indazol-6-yl)-$N^4$-[(2-chlorophenyl)methyl]-2,4-pyrimidinediamine;
6-(3-Amino-1H-indazol-6-yl)-$N^4$-cyclopropyl-2,4-pyrimidinediamine;
6-(3-Amino-1H-indazol-6-yl)-$N^4$-(3-phenylpropyl)-2,4-pyrimidinediamine;
6-(3-Amino-1H-indazol-6-yl)-$N^4$-[2-(2-fluorophenyl)ethyl]-2,4-pyrimidinediamine;
6-(3-Amino-1H-indazol-6-yl)-$N^4$-{2-[2-(methyloxy)phenyl]ethyl}-2,4-pyrimidinediamine;
6-(3-Amino-1H-indazol-6-yl)-$N^4$-[2-(3-chlorophenyl)ethyl]-2,4-pyrimidinediamine;
6-(3-Amino-1H-indazol-6-yl)-$N^4$-methyl-$N^4$-(2-phenylethyl)-2,4-pyrimidinediamine;
6-(3-Amino-1H-indazol-6-yl)-$N^4$-[2-(3-fluorophenyl)ethyl]-2,4-pyrimidinediamine;
6-(3-Amino-1H-indazol-6-yl)-$N^4$-[2-(2-chlorophenyl)ethyl]-2,4-pyrimidinediamine;
6-(3-Amino-1H-indazol-6-yl)-$N^4$-[2-(2-methylphenyl)ethyl]-2,4-pyrimidinediamine;
6-(3-Amino-1H-indazol-6-yl)-$N^4$-[2-(3-methylphenyl)ethyl]-2,4-pyrimidinediamine;
6-(3-Amino-1H-indazol-6-yl)-$N^4$-[1-(phenylmethyl)cyclopropyl]-2,4-pyrimidinediamine;
6-(3-Amino-1H-indazol-6-yl)-$N^4$-(1,1-dimethyl-2-phenylethyl)-2,4-pyrimidinediamine;
1-[2-Amino-6-(3-amino-1H-indazol-6-yl)-4-pyrimidinyl]-N-phenyl-3-pyrrolidinecarboxamide;
6-(3-Amino-1H-indazol-6-yl)-$N^4$-methyl-$N^4$-[(1R)-1-methyl-2-phenylethyl]-2,4-pyrimidinediamine;
6-(3-Amino-1H-indazol-6-yl)-$N^4$-(2,3-dihydro-1H-inden-1-yl)-2,4-pyrimidinediamine;
4-[2-Amino-6-(3-amino-1H-indazol-6-yl)-4-pyrimidinyl]benzamide;
(2S,5R)-4-[2-Amino-6-(3-amino-1H-indazol-6-yl)-4-pyrimidinyl]-5-methyl-N-phenyl-2-morpholinecarboxamide;
1,1-Dimethylethyl{1-[2-amino-6-(3-amino-1H-indazol-6-yl)-4-pyrimidinyl]-3-piperidinyl}carbamate;
N-{1-[2-Amino-6-(3-amino-1H-indazol-6-yl)-4-pyrimidinyl]-3-piperidinyl}benzamide;
6-{2-Amino-6-[2-(trifluoromethyl)-1-pyrrolidinyl]-4-pyrimidinyl}-1H-indazol-3-amine;
6-{2-Amino-6-[(3R)-3-ethyl-4-morpholinyl]-4-pyrimidinyl}-1H-indazol-3-amine;
6-(3-Amino-1H-indazol-6-yl)-$N^4$-(1,1-dimethylethyl)-2,4-pyrimidinediamine;
6-(3-Amino-1H-indazol-6-yl)-$N^4$-(2-methylpropyl)-2,4-pyrimidinediamine;
6-(3-Amino-1H-indazol-6-yl)-$N^4$-propyl-2,4-pyrimidinediamine;
6-{2-Amino-6-[(3R)-3-methyl-4-morpholinyl]-4-pyrimidinyl}-1H-indazol-3-amine;
4-[2-Amino-6-(3-amino-1H-indazol-6-yl)-4-pyrimidinyl]-N-phenyl-2-morpholinecarboxamide;
(3S,6R)-1-[6-(3-amino-1H-indazol-6-yl)-2-(methylamino)-4-pyrimidinyl]-6-methyl-N-phenyl-3-piperidinecarboxamide;
(3S,6R)-1-[6-(3-Amino-1H-indazol-6-yl)-2-(methylamino)-4-pyrimidinyl]-N-cyclohexyl-6-methyl-3-piperidinecarboxamide;
(3S,6R)—N-Cyclohexyl-1-[6-(1H-indazol-6-yl)-2-(methylamino)-4-pyrimidinyl]-6-methyl-3-piperidinecarboxamide;
(3S,6R)-1-[6-(3-Amino-1H-indazol-6-yl)-2-(methylamino)-4-pyrimidinyl]-6-methyl-N-(phenylmethyl)-3-piperidinecarboxamide;
(3S,6R)-1-[6-(1H-Indazol-6-yl)-2-(methylamino)-4-pyrimidinyl]-6-methyl-N-(phenylmethyl)-3-piperidinecarboxamide;
(3S,6R)-6-Methyl-1-[2-(methylamino)-6-(3-methyl-1H-indazol-6-yl)-4-pyrimidinyl]-N-phenyl-3-piperidinecarboxamide;
(3S,6R)—N-Cyclohexyl-6-methyl-1-[2-(methylamino)-6-(3-methyl-1H-indazol-6-yl)-4-pyrimidinyl]-3-piperidinecarboxamide;
(3S,6R)-6-Methyl-1-[2-(methylamino)-6-(3-methyl-1H-indazol-6-yl)-4-pyrimidinyl]-N-(phenylmethyl)-3-piperidinecarboxamide;
(3S,6R)-1-[6-(3-Amino-4-fluoro-1H-indazol-6-yl)-2-(methylamino)-4-pyrimidinyl]-N-cyclohexyl-6-methyl-3-piperidinecarboxamide;
(3S,6R)-1-[6-(3-Amino-4-fluoro-1H-indazol-6-yl)-2-(methylamino)-4-pyrimidinyl]-6-methyl-N-(phenylmethyl)-3-piperidinecarboxamide;
cis-1-[6-(3-amino-1H-indazol-6-yl)-2-(methylamino)-4-pyrimidinyl]-5-methyl-N-(phenylmethyl)-3-pyrrolidinecarboxamide;
4-[2-Amino-6-(3-amino-1H-indazol-6-yl)-4-pyrimidinyl]-3-morpholinecarboxamide;
N-({(2R,5R)-4-[2-Amino-6-(3-amino-1H-indazol-6-yl)-4-pyrimidinyl]-5-methyl-2-morpholinyl}methyl)benzamide;
N-({(2S,5R)-4-[2-Amino-6-(3-amino-1H-indazol-6-yl)-4-pyrimidinyl]-5-methyl-2-morpholinyl}methyl)benzenesulfonamide;
N-({(2R,5R)-4-[2-Amino-6-(3-amino-1H-indazol-6-yl)-4-pyrimidinyl]-5-methyl-2-morpholinyl}methyl)-2,2-dimethylpropanamide;
Methyl({(2R,5R)-4-[2-amino-6-(3-amino-1H-indazol-6-yl)-4-pyrimidinyl]-5-methyl-2-morpholinyl}methyl)carbamate;
N-({(2S,5R)-4-[2-Amino-6-(3-amino-1H-indazol-6-yl)-4-pyrimidinyl]-5-methyl-2-morpholinyl}methyl)methanesulfonamide;
N-({(2S,5R)-4-[2-Amino-6-(3-amino-1H-indazol-6-yl)-4-pyrimidinyl]-5-methyl-2-morpholinyl}methyl)cyclohexanesulfonamide;

6-(2-Amino-6-{2-[4-(4-chlorophenyl)-1H-imidazol-2-yl]-4-morpholinyl}-4-pyrimidinyl)-1H-indazol-3-amine;
6-{2-Amino-6-[2-(4,5,6,7-tetrahydro-1H-benzimidazol-2-yl)-4-morpholinyl]-4-pyrimidinyl}-1H-indazol-3-amine;
6-{2-Amino-6-[2-(4-phenyl-1H-imidazol-2-yl)-4-morpholinyl]-4-pyrimidinyl}-1H-indazol-3-amine;
6-(2-Amino-6-{2-[4-(3-chlorophenyl)-1H-imidazol-2-yl]-4-morpholinyl}-4-pyrimidinyl)-1H-indazol-3-amine;
6-[2-Amino-6-(2-{4-[4-(methyloxy)phenyl]-1H-imidazol-2-yl}-4-morpholinyl)-4-pyrimidinyl]-1H-indazol-3-amine;
(3S)-1-[2-Amino-6-(3-amino-4-fluoro-1H-indazol-6-yl)-4-pyrimidinyl]-N-phenyl-3-piperidinecarboxamide;
(3S)-1-[2-Amino-6-(3-amino-4-fluoro-1H-indazol-6-yl)-4-pyrimidinyl]-N-cyclohexyl-3-piperidinecarboxamide;
6-(3-Amino-1H-indazol-6-yl)-N$^4$-methyl-N$^4$-phenyl-2,4-pyrimidinediamine;
6-{2-Amino-6-[2-(1H-imidazo[4,5-c]pyridin-2-yl)-4-morpholinyl]-4-pyrimidinyl}-1H-indazol-3-amine;
6-[2-Amino-6-(2-{4-[3-(methyloxy)phenyl]-1H-imidazol-2-yl}-4-morpholinyl)-4-pyrimidinyl]-1H-indazol-3-amine;
6-(2-Amino-6-{2-[5-(methyloxy)-1H-benzimidazol-2-yl]-4-morpholinyl}-4-pyrimidinyl)-1H-indazol-3-amine;
{(2S,5R)-4-[2-Amino-6-(3-amino-1H-indazol-6-yl)-4-pyrimidinyl]-5-methyl-2-morpholinyl}methyl phenylcarbamate;
6-{2-Amino-6-[2-(4-methyl-5-phenyl-1H-imidazol-2-yl)-4-morpholinyl]-4-pyrimidinyl}-1H-indazol-3-amine;
6-{2-Amino-6-[2-(5-chloro-1H-benzimidazol-2-yl)-4-morpholinyl]-4-pyrimidinyl}-1H-indazol-3-amine;
6-{2-Amino-6-[2-(5-fluoro-1H-benzimidazol-2-yl)-4-morpholinyl]-4-pyrimidinyl}-1H-indazol-3-amine;
(3S,6R)-1-[2-Amino-6-(3-amino-1H-indazol-6-yl)-4-pyrimidinyl]-6-methyl-N-phenyl-3-piperidinecarboxamide;
Cis-1,1-dimethylethyl{(1-[2-amino-6-(3-amino-1H-indazol-6-yl)-4-pyrimidinyl]-6-methyl-3-piperidinyl}carbamate;
Phenylmethyl{(3S,6R)-1-[2-amino-6-(3-amino-1H-indazol-6-yl)-4-pyrimidinyl]-6-methyl-3-piperidinyl}carbamate;
N-{(3S,6R)-1-[2-Amino-6-(3-amino-1H-indazol-6-yl)-4-pyrimidinyl]-6-methyl-3-piperidinyl}benzamide;
N-{(3S,6R)-1-[2-Amino-6-(3-amino-1H-indazol-6-yl)-4-pyrimidinyl]-6-methyl-3-piperidinyl}-2-phenylacetamide;
cis-1-[6-(3-amino-1H-indazol-6-yl)-2-(methylamino)-4-pyrimidinyl]-N-cyclopentyl-6-(trifluoromethyl)-3-piperidinecarboxamide;
Cis-1-[6-(3-amino-1H-indazol-6-yl)-2-(methylamino)-4-pyrimidinyl]-N-(phenylmethyl)-6-(trifluoromethyl)-3-piperidinecarboxamide;
(3S)-1-[2-Amino-6-(3-amino-1H-indazol-6-yl)-4-pyrimidinyl]-N-cyclohexyl-3-piperidinecarboxamide;
(3S)-1-[2-Amino-6-(3-amino-1H-indazol-6-yl)-4-pyrimidinyl]-N-phenyl-3-piperidinecarboxamide;
(3R)-1-[2-Amino-6-(3-amino-1H-indazol-6-yl)-4-pyrimidinyl]-N-phenyl-3-piperidinecarboxamide;
Cis-cyclopentyl{1-[2-amino-6-(3-amino-1H-indazol-6-yl)-4-pyrimidinyl]-6-methyl-3-piperidinyl}carbamate;
(3S,6R)-1-[2-Amino-6-(3-amino-1H-indazol-6-yl)-4-pyrimidinyl]-N-cyclohexyl-6-methyl-3-piperidinecarboxamide;
(3S)-1-[2-Amino-6-(3-amino-1H-indazol-6-yl)-4-pyrimidinyl]-N-(4-fluorophenyl)-3-piperidinecarboxamide;
(3S)-1-[2-Amino-6-(3-amino-1H-indazol-6-yl)-4-pyrimidinyl]-N-(3-methylphenyl)-3-piperidinecarboxamide;
(3S)-1-[2-Amino-6-(3-amino-1H-indazol-6-yl)-4-pyrimidinyl]-N-(3,4-difluorophenyl)-3-piperidinecarboxamide;
(3S)-1-[2-Amino-6-(3-amino-1H-indazol-6-yl)-4-pyrimidinyl]-N-(4-methylphenyl)-3-piperidinecarboxamide;
(3S)-1-[2-Amino-6-(3-amino-1H-indazol-6-yl)-4-pyrimidinyl]-N-(2-fluorophenyl)-3-piperidinecarboxamide;
(3S)-1-[2-Amino-6-(3-amino-1H-indazol-6-yl)-4-pyrimidinyl]-N-(3-fluorophenyl)-3-piperidinecarboxamide;
(3S)-1-[2-Amino-6-(3-amino-1H-indazol-6-yl)-4-pyrimidinyl]-N-(2-methylphenyl)-3-piperidinecarboxamide;
(3S)-1-[2-Amino-6-(3-amino-1H-indazol-6-yl)-4-pyrimidinyl]-N-(4-chlorophenyl)-3-piperidinecarboxamide;
(3S)-1-[2-Amino-6-(3-amino-1H-indazol-6-yl)-4-pyrimidinyl]-N-[4-(methyloxy)phenyl]-3-piperidinecarboxamide;
(3S)-1-[2-Amino-6-(3-amino-1H-indazol-6-yl)-4-pyrimidinyl]-N-[3-(methyloxy)phenyl]-3-piperidinecarboxamide;
(3S)-1-[2-Amino-6-(3-amino-1H-indazol-6-yl)-4-pyrimidinyl]-N-(3-chlorophenyl)-3-piperidinecarboxamide;
(3S)-1-[2-Amino-6-(3-amino-1H-indazol-6-yl)-4-pyrimidinyl]-N-(phenylmethyl)-3-piperidinecarboxamide;
(3S)-1-[2-Amino-6-(3-amino-1H-indazol-6-yl)-4-pyrimidinyl]-N-(4-pyridinylmethyl)-3-piperidinecarboxamide;
(3S)-1-[2-Amino-6-(3-amino-1H-indazol-6-yl)-4-pyrimidinyl]-N-(4-methylcyclohexyl)-3-piperidinecarboxamide;
(3S)-1-[2-Amino-6-(3-amino-1H-indazol-6-yl)-4-pyrimidinyl]-N-(1-methyl-1H-pyrazol-5-yl)-3-piperidinecarboxamide;
(3S)-1-[2-Amino-6-(3-amino-1H-indazol-6-yl)-4-pyrimidinyl]-N-(1,3-dimethyl-1H-pyrazol-5-yl)-3-piperidinecarboxamide;
(3S,6R)-1-[2-Amino-6-(3-methyl-1H-indazol-6-yl)-4-pyrimidinyl]-6-methyl-N-(phenylmethyl)-3-piperidinecarboxamide;
(3S,6R)-1-[2-Amino-6-(1H-indazol-6-yl)-4-pyrimidinyl]-N-cyclohexyl-6-methyl-3-piperidinecarboxamide;
(3S,6R)-1-[2-amino-6-(3-amino-1H-indazol-6-yl)-4-pyrimidinyl]-N-(cyclohexylmethyl)-6-methyl-3-piperidinecarboxamide;
(3S,6R)-1-[2-amino-6-(3-amino-1H-indazol-6-yl)-4-pyrimidinyl]-6-methyl-N-{[4-(methyloxy)phenyl]methyl}-3-piperidinecarboxamide;
(3S,6R)-1-[2-amino-6-(3-amino-1H-indazol-6-yl)-4-pyrimidinyl]-N-cyclopentyl-6-methyl-3-piperidinecarboxamide;
(3S,6R)-1-[2-Amino-6-(3-amino-1H-indazol-6-yl)-4-pyrimidinyl]-N-[(1R)-1-cyclohexylethyl]-6-methyl-3-piperidinecarboxamide;
(3S,6R)-1-[2-Amino-6-(3-amino-1H-indazol-6-yl)-4-pyrimidinyl]-N-[(3-fluorophenyl)methyl]-6-methyl-3-piperidinecarboxamide;
(3S,6R)-1-[2-Amino-6-(3-amino-1H-indazol-6-yl)-4-pyrimidinyl]-6-methyl-N-(phenylmethyl)-3-piperidinecarboxamide;

(3S,6R)-1-[2-Amino-6-(3-amino-1H-indazol-6-yl)-4-pyrimidinyl]-6-methyl-N-[(4-methylphenyl)methyl]-3-piperidinecarboxamide;
(3S,6R)-1-[2-Amino-6-(3-amino-1H-indazol-6-yl)-4-pyrimidinyl]-N-[(4-fluorophenyl)methyl]-6-methyl-3-piperidinecarboxamide;
(3S,6R)-1-[2-Amino-6-(3-amino-1H-indazol-6-yl)-4-pyrimidinyl]-6-methyl-N-(3-methylcyclohexyl)-3-piperidinecarboxamide;
(3S,6R)-1-[2-Amino-6-(3-amino-1H-indazol-6-yl)-4-pyrimidinyl]-6-methyl-N-(2-phenylethyl)-3-piperidinecarboxamide;
(3S,6R)-1-[2-Amino-6-(3-amino-1H-indazol-6-yl)-4-pyrimidinyl]-6-methyl-N-(4-methylcyclohexyl)-3-piperidinecarboxamide;
6-{2-(Methylamino)-6-[(3R)-3-(1-methylethyl)-4-morpholinyl]-4-pyrimidinyl}-4-(methyloxy)-1H-indazol-3-amine;
4-(Ethyloxy)-6-{2-(methylamino)-6-[(3R)-3-(1-methylethyl)-4-morpholinyl]-4-pyrimidinyl}-1H-indazol-3-amine;
6-{2-(Methylamino)-6-[(3R)-3-(1-methylethyl)-4-morpholinyl]-4-pyrimidinyl}-4-(methylthio)-1H-indazol-3-amine;
1,1-Dimethylethyl{(3R,6S)-1-[2-amino-6-(3-amino-1H-indazol-6-yl)-4-pyrimidinyl]-6-methyl-3-piperidinyl}carbamate;
1,1-Dimethylethyl{(3R,6S)-1-[6-(3-amino-1H-indazol-6-yl)-2-(methylamino)-4-pyrimidinyl]-6-methyl-3-piperidinyl}carbamate;
6-{2-Amino-6-[(2R,5R)-2-(aminomethyl)-5-methyl-4-morpholinyl]-4-pyrimidinyl}-1H-indazol-3-amine;
6-[2-Amino-6-((2R,5R)-5-methyl-2-{[(phenylmethyl)amino]methyl}-4-morpholinyl)-4-pyrimidinyl]-1H-indazol-3-amine;
{(2S,5R)-4-[6-(3-Amino-1H-indazol-6-yl)-2-(methylamino)-4-pyrimidinyl]-5-methyl-2-morpholinyl}methanol;
(2S,5R)-4-[6-(3-amino-1H-indazol-6-yl)-2-(methylamino)-4-pyrimidinyl]-5-methyl-N-phenyl-2-morpholinecarboxamide;
(2S,5R)-4-[6-(3-amino-1H-indazol-6-yl)-2-(methylamino)-4-pyrimidinyl]-N-cyclohexyl-5-methyl-2-morpholinecarboxamide;
(2S,5R)-4-[6-(3-Amino-1H-indazol-6-yl)-2-(methylamino)-4-pyrimidinyl]-5-methyl-N-(phenylmethyl)-2-morpholinecarboxamide;
6-[6-{(2R,5R)-2-[(Dimethylamino)methyl]-5-methyl-4-morpholinyl}-2-(methylamino)-4-pyrimidinyl]-1H-indazol-3-amine;
6-(2-Amino-6-{2-[4-(2-chlorophenyl)-1H-imidazol-2-yl]-4-morpholinyl}-4-pyrimidinyl)-1H-indazol-3-amine;
4-Fluoro-6-{2-(methylamino)-6-[(3R)-3-methyl-4-morpholinyl]-4-pyrimidinyl}-1H-indazol-3-amine;
6-{2-(Methylamino)-6-[(3R)-3-methyl-4-morpholinyl]-4-pyrimidinyl}-1H-indazol-3-amine;
6-{2-(Methylamino)-6-[(3R)-3-methyl-4-morpholinyl]-4-pyrimidinyl}-4-(methyloxy)-1H-indazol-3-amine;
6-{2-(Methylamino)-6-[(3R)-3-methyl-4-morpholinyl]-4-pyrimidinyl}-4-(methylthio)-1H-indazol-3-amine;
$N^4$-Methyl-6-{2-(methylamino)-6-[(3R)-3-methyl-4-morpholinyl]-4-pyrimidinyl}-1H-indazole-3,4-diamine;
4-(2-Furanyl)-6-{2-(methylamino)-6-[(3R)-3-methyl-4-morpholinyl]-4-pyrimidinyl}-1H-indazol-3-amine;
6-{2-Amino-6-[(3R)-3-methyl-4-morpholinyl]-4-pyrimidinyl}-4-(ethyloxy)-1H-indazol-3-amine;
6-{2-Amino-6-[(3R)-3-methyl-4-morpholinyl]-4-pyrimidinyl}-4-[(1-methylethyl)oxy]-1H-indazol-3-amine;
(2S,5R)-4-[2-Amino-6-(3-amino-1H-indazol-6-yl)-4-pyrimidinyl]-5-ethyl-N-phenyl-2-morpholinecarboxamide;
(2S,5R)-4-[2-Amino-6-(3-amino-1H-indazol-6-yl)-4-pyrimidinyl]-N-cyclohexyl-5-ethyl-2-morpholinecarboxamide;
(2S,5R)-4-[6-(3-Amino-1H-indazol-6-yl)-2-(methylamino)-4-pyrimidinyl]-5-ethyl-N-phenyl-2-morpholinecarboxamide;
(2S,5R)-4-[6-(3-amino-1H-indazol-6-yl)-2-(methylamino)-4-pyrimidinyl]-N-cyclohexyl-5-ethyl-2-morpholinecarboxamide;
(2S,5R)-4-[6-(3-Amino-1H-indazol-6-yl)-2-(methylamino)-4-pyrimidinyl]-5-ethyl-N-(phenylmethyl)-2-morpholinecarboxamide;
6-[6-[(3R)-3-Ethyl-4-morpholinyl]-2-(methylamino)-4-pyrimidinyl]-1H-indazol-3-amine;
6-[6-[(3R)-3-Ethyl-4-morpholinyl]-2-(methylamino)-4-pyrimidinyl]-4-fluoro-1H-indazol-3-amine;
6-[6-[(3R)-3-Ethyl-4-morpholinyl]-2-(methylamino)-4-pyrimidinyl]-4-(methyloxy)-1H-indazol-3-amine;
6-[6-[(3R)-3-Ethyl-4-morpholinyl]-2-(methylamino)-4-pyrimidinyl]-4-(methylthio)-1H-indazol-3-amine;
$N^4$-Cyclopentyl-6-[6-[(3R)-3-ethyl-4-morpholinyl]-2-(methylamino)-4-pyrimidinyl]-1H-indazole-3,4-diamine;
6-[6-[(3R)-3-Ethyl-4-morpholinyl]-2-(methylamino)-4-pyrimidinyl]-$N^4$-methyl-1H-indazole-3,4-diamine;
6-[6-[(3R)-3-Ethyl-4-morpholinyl]-2-(methylamino)-4-pyrimidinyl]-4-(1-pyrrolidinyl)-1H-indazol-3-amine;
6-[6-[(3R)-3-Ethyl-4-morpholinyl]-2-(methylamino)-4-pyrimidinyl]-4-(ethyloxy)-1H-indazol-3-amine;
6-{2-(Methylamino)-6-[(2R)-2-methyl-1-pyrrolidinyl]-4-pyrimidinyl}-4-(methyloxy)-1H-indazol-3-amine;
6-{2-(methylamino)-6-[(2R)-2-methyl-1-pyrrolidinyl]-4-pyrimidinyl}-4-(methylthio)-1H-indazol-3-amine;
4-(Ethyloxy)-6-{2-(methylamino)-6-[(2R)-2-methyl-1-pyrrolidinyl]-4-pyrimidinyl}-1H-indazol-3-amine;
(3S,6R)-1-[2-Amino-6-(3-amino-1H-indazol-6-yl)-4-pyrimidinyl]-6-methyl-N-[(1S)-1-phenylethyl]-3-piperidinecarboxamide;
(3S,6R)-1-[2-Amino-6-(3-amino-1H-indazol-6-yl)-4-pyrimidinyl]-6-methyl-N-{[2-(methyloxy)phenyl]methyl}-3-piperidinecarboxamide;
(3S,6R)-1-[2-Amino-6-(3-amino-1H-indazol-6-yl)-4-pyrimidinyl]-6-methyl-N-{[3-(methyloxy)phenyl]methyl}-3-piperidinecarboxamide;
(3S,6R)-1-[2-Amino-6-(3-amino-1H-indazol-6-yl)-4-pyrimidinyl]-N-[(2-fluorophenyl)methyl]-6-methyl-3-piperidinecarboxamide;
(3S,6R)-1-[2-Amino-6-(3-amino-1H-indazol-6-yl)-4-pyrimidinyl]-6-methyl-N-[(1R)-1-phenylethyl]-3-piperidinecarboxamide;
(3S,6R)-1-[2-Amino-6-(3-amino-1H-indazol-6-yl)-4-pyrimidinyl]-6-methyl-N-(1-methyl-1-phenylethyl)-3-piperidinecarboxamide;
(3S,6R)-1-[2-Amino-6-(3-amino-1H-indazol-6-yl)-4-pyrimidinyl]-N-(4-ethylcyclohexyl)-6-methyl-3-piperidinecarboxamide;
(3S,6R)-1-[2-Amino-6-(3-amino-1H-indazol-6-yl)-4-pyrimidinyl]-6-methyl-N-(2-methylcyclohexyl)-3-piperidinecarboxamide;

6-[6-[(2R,5R)-2,5-Dimethyl-4-morpholinyl]-2-(methylamino)-4-pyrimidinyl]-1H-indazol-3-amine;
6-{2-Amino-6-[(3R)-3-(1-methylethyl)-4-morpholinyl]-4-pyrimidinyl}-1H-indazol-3-amine;
6-{2-Amino-6-[(3R)-3-(1-methylethyl)-4-morpholinyl]-4-pyrimidinyl}-4-(methyloxy)-1H-indazol-3-amine;
6-{2-Amino-6-[(3R)-3-(1-methylethyl)-4-morpholinyl]-4-pyrimidinyl}-4-(ethyloxy)-1H-indazol-3-amine;
6-{2-Amino-6-[(3R)-3-methyl-4-morpholinyl]-4-pyrimidinyl}-4-(methyloxy)-1H-indazol-3-amine;
1,1-Dimethylethyl{(3R)-1-[2-amino-6-(3-amino-1H-indazol-6-yl)-4-pyrimidinyl]-3-piperidinyl}carbamate;
1,1-Dimethylethyl{(3R)-1-[6-(3-amino-1H-indazol-6-yl)-2-(methylamino)-4-pyrimidinyl]-3-piperidinyl}carbamate;
1,1-Dimethylethyl{(3R)-1-[6-[3-amino-4-(methyloxy)-1H-indazol-6-yl]-2-(methylamino)-4-pyrimidinyl]-3-piperidinyl}carbamate;
6-{2-(Methylamino)-6-[(2S)-2-(trifluoromethyl)-1-pyrrolidinyl]-4-pyrimidinyl}-4-(methyloxy)-1H-indazol-3-amine;
6-{2-(Methylamino)-6-[(2S)-2-(trifluoromethyl)-1-pyrrolidinyl]-4-pyrimidinyl}-1H-indazol-3-amine;
N-{(3R)-1-[6-(3-Amino-1H-indazol-6-yl)-2-(methylamino)-4-pyrimidinyl]-3-piperidinyl}benzamide;
Phenylmethyl{(3R)-1-[2-amino-6-(3-amino-1H-indazol-6-yl)-4-pyrimidinyl]-3-piperidinyl}carbamate;
Cyclopentyl{(3R)-1-[2-amino-6-(3-amino-1H-indazol-6-yl)-4-pyrimidinyl]-3-piperidinyl}carbamate;
Cyclobutyl{(3R)-1-[2-amino-6-(3-amino-1H-indazol-6-yl)-4-pyrimidinyl]-3-piperidinyl}carbamate;
Cyclohexyl{(3R)-1-[2-amino-6-(3-amino-1H-indazol-6-yl)-4-pyrimidinyl]-3-piperidinyl}carbamate;
3-{(3R)-1-[2-Amino-6-(3-amino-1H-indazol-6-yl)-4-pyrimidinyl]-3-piperidinyl}-1,3-oxazolidin-2-one;
1,1-Dimethylethyl{(3R,5R)-1-[2-amino-6-(3-amino-1H-indazol-6-yl)-4-pyrimidinyl]-5-methyl-3-piperidinyl}carbamate;
3-{(3R,5R)-1-[2-Amino-6-(3-amino-1H-indazol-6-yl)-4-pyrimidinyl]-5-methyl-3-piperidinyl}-1,3-oxazolidin-2-one;
1,1-Dimethylethyl((3R,5R)-1-{2-amino-6-[3-amino-4-(methyloxy)-1H-indazol-6-yl]-4-pyrimidinyl}-5-methyl-3-piperidinyl)carbamate;
1,1-Dimethylethyl{(3R,5R)-1-[6-(3-amino-1H-indazol-6-yl)-2-(methylamino)-4-pyrimidinyl]-5-methyl-3-piperidinyl}carbamate;
1,1-Dimethylethyl{(3R,5R)-1-[6-[3-amino-4-(methyloxy)-1H-indazol-6-yl]-2-(methylamino)-4-pyrimidinyl]-5-methyl-3-piperidinyl}carbamate;
1-Methylethyl{(3R)-1-[2-amino-6-(3-amino-1H-indazol-6-yl)-4-pyrimidinyl]-3-piperidinyl}carbamate;
6-[6-[(2R)-2-Ethyl-1-pyrrolidinyl]-2-(methylamino)-4-pyrimidinyl]-4-(methyloxy)-1H-indazol-3-amine;
6-[6-[(2R)-2-Ethyl-1-pyrrolidinyl]-2-(methylamino)-4-pyrimidinyl]-4-(methylthio)-1H-indazol-3-amine;
4-(Ethyloxy)-6-[6-[(2R)-2-ethyl-1-pyrrolidinyl]-2-(methylamino)-4-pyrimidinyl]-1H-indazol-3-amine;
1,1-Dimethylethyl{(3R,5R)-1-[2-amino-6-(3-amino-1H-indazol-6-yl)-4-pyrimidinyl]-5-methyl-3-piperidinyl}methylcarbamate; and
1-[2-amino-6-(3-amino-1H-indazol-6-yl)-4-pyrimidinyl]-L-prolinamide;
or a salt thereof including a pharmaceutically acceptable salt thereof.

5. A compound of claim 1 selected from:
(2S,5R)-4-[2-Amino-6-(3-amino-1H-indazol-6-yl)-4-pyrimidinyl]-5-methyl-N-phenyl-2-morpholinecarboxamide;
6-{2-Amino-6-[(3R)-3-ethyl-4-morpholinyl]-4-pyrimidinyl}-1H-indazol-3-amine;
6-{2-Amino-6-[(3R)-3-methyl-4-morpholinyl]-4-pyrimidinyl}-1H-indazol-3-amine;
(3S,6R)-1-[6-(3-Amino-1H-indazol-6-yl)-2-(methylamino)-4-pyrimidinyl]-N-cyclohexyl-6-methyl-3-piperidinecarboxamide;
(3S,6R)-1-[6-(3-Amino-1H-indazol-6-yl)-2-(methylamino)-4-pyrimidinyl]-6-methyl-N-(phenylmethyl)-3-piperidinecarboxamide;
(3S,6R)—N-Cyclohexyl-6-methyl-1-[2-(methylamino)-6-(3-methyl-1H-indazol-6-yl)-4-pyrimidinyl]-3-piperidinecarboxamide;
(3S,6R)-1-[6-(3-Amino-4-fluoro-1H-indazol-6-yl)-2-(methylamino)-4-pyrimidinyl]-N-cyclohexyl-6-methyl-3-piperidinecarboxamide;
Cis-1,1-dimethylethyl{(1-[2-amino-6-(3-amino-1H-indazol-6-yl)-4-pyrimidinyl]-6-methyl-3-piperidinyl}carbamate;
Cis-cyclopentyl{1-[2-amino-6-(3-amino-1H-indazol-6-yl)-4-pyrimidinyl]-6-methyl-3-piperidinyl}carbamate;
(3S,6R)-1-[2-amino-6-(3-amino-1H-indazol-6-yl)-4-pyrimidinyl]-N-cyclopentyl-6-methyl-3-piperidinecarboxamide;
(3S,6R)-1-[2-Amino-6-(3-amino-1H-indazol-6-yl)-4-pyrimidinyl]-6-methyl-N-(2-phenylethyl)-3-piperidinecarboxamide;
1,1-Dimethylethyl{(3R,6S)-1-[2-amino-6-(3-amino-1H-indazol-6-yl)-4-pyrimidinyl]-6-methyl-3-piperidinyl}carbamate;
(2S,5R)-4-[6-(3-Amino-1H-indazol-6-yl)-2-(methylamino)-4-pyrimidinyl]-5-methyl-N-(phenylmethyl)-2-morpholinecarboxamide;
(2S,5R)-4-[2-Amino-6-(3-amino-1H-indazol-6-yl)-4-pyrimidinyl]-N-cyclohexyl-5-ethyl-2-morpholinecarboxamide;
6-[6-[(3R)-3-Ethyl-4-morpholinyl]-2-(methylamino)-4-pyrimidinyl]-1H-indazol-3-amine;
$N^4$-Cyclopentyl-6-[6-[(3R)-3-ethyl-4-morpholinyl]-2-(methylamino)-4-pyrimidinyl]-1H-indazole-3,4-diamine;
6-[6-[(3R)-3-Ethyl-4-morpholinyl]-2-(methylamino)-4-pyrimidinyl]-4-(ethyloxy)-1H-indazol-3-amine;
6-{2-Amino-6-[(3R)-3-(1-methylethyl)-4-morpholinyl]-4-pyrimidinyl}-4-(ethyloxy)-1H-indazol-3-amine;
6-{2-Amino-6-[(3R)-3-methyl-4-morpholinyl]-4-pyrimidinyl}-4-(methyloxy)-1H-indazol-3-amine;
1,1-Dimethylethyl{(3R)-1-[6-[3-amino-4-(methyloxy)-1H-indazol-6-yl]-2-(methylamino)-4-pyrimidinyl]-3-piperidinyl}carbamate;
Cyclobutyl{(3R)-1-[2-amino-6-(3-amino-1H-indazol-6-yl)-4-pyrimidinyl]-3-piperidinyl}carbamate;
3-{(3R)-1-[2-Amino-6-(3-amino-1H-indazol-6-yl)-4-pyrimidinyl]-3-piperidinyl}-1,3-oxazolidin-2-one;
1,1-Dimethylethyl{(3R,5R)-1-[2-amino-6-(3-amino-1H-indazol-6-yl)-4-pyrimidinyl]-5-methyl-3-piperidinyl}carbamate;
1,1-Dimethylethyl((3R,5R)-1-{2-amino-6-[3-amino-4-(methyloxy)-1H-indazol-6-yl]-4-pyrimidinyl}-5-methyl-3-piperidinyl)carbamate;
1-Methylethyl{(3R)-1-[2-amino-6-(3-amino-1H-indazol-6-yl)-4-pyrimidinyl]-3-piperidinyl}carbamate; and 1,1-Dimethylethyl{(3R,5R)-1-[2-amino-6-(3-amino-1H-indazol-6-yl)-4-pyrimidinyl]-5-methyl-3-piperidinyl}methylcarbamate;
or a salt thereof including a pharmaceutically acceptable salt thereof.

6. A pharmaceutical composition comprising a compound according to claim 1 or a pharmaceutically acceptable salt thereof and a pharmaceutically acceptable excipient.

7. A process for preparing a pharmaceutical composition containing a pharmaceutically acceptable excipient and an effective amount of a compound of Formula (I) as described in claim 1 or a pharmaceutically acceptable salt thereof, which process comprises bringing the compound of Formula (I) or a pharmaceutically acceptable salt thereof into association with a pharmaceutically acceptable excipient.

8. A compound of claim 1 selected from:
6-(2-Amino-6-methyl-4-pyrimidinyl)-1H-indazol-3-amine; and
6-{2-Amino-6-[(2R)-2-ethyl-1-pyrrolidinyl]-4-pyrimidinyl}-1H-indazol-3-amine;
or a salt thereof including a pharmaceutically acceptable salt thereof.

* * * * *